US010023633B2

(12) United States Patent
Laeremans et al.

(10) Patent No.: US 10,023,633 B2
(45) Date of Patent: *Jul. 17, 2018

(54) METHOD FOR GENERATION OF IMMUNOGLOBULIN SEQUENCES

(71) Applicant: Ablynx N.V., Zwijnaarde (BE)

(72) Inventors: Toon Laeremans, Dworp-Beersel (BE); Catelijne Stortelers, Ghent (BE); Friedrich Nolte, Hamburg (DE); Maria Gonzalez Pajuelo, Oporto (PT); Joana Assunção, Senhora Da Hora (PT); Philippe Van Rompaey, Melle (BE)

(73) Assignee: Ablynx N.V., Ghent-Zwijnaarde (BE)

( * ) Notice: Subject to any disclaimer, the term of this patent is extended or adjusted under 35 U.S.C. 154(b) by 0 days.

This patent is subject to a terminal disclaimer.

(21) Appl. No.: 15/040,323

(22) Filed: Feb. 10, 2016

(65) Prior Publication Data

US 2016/0264664 A1    Sep. 15, 2016

Related U.S. Application Data

(63) Continuation of application No. 12/643,286, filed on Dec. 21, 2009, now Pat. No. 9,260,508.

(60) Provisional application No. 61/203,188, filed on Dec. 19, 2008.

(51) Int. Cl.
*C07K 16/28* (2006.01)
*C07K 16/00* (2006.01)
*A61K 39/00* (2006.01)

(52) U.S. Cl.
CPC .............. *C07K 16/28* (2013.01); *C07K 16/00* (2013.01); *C07K 16/2866* (2013.01); *A61K 2039/505* (2013.01); *A61K 2039/53* (2013.01); *C07K 2317/22* (2013.01); *C07K 2317/34* (2013.01); *C07K 2317/56* (2013.01); *C07K 2317/565* (2013.01); *C07K 2317/567* (2013.01); *C07K 2317/569* (2013.01); *C07K 2317/75* (2013.01); *C07K 2317/92* (2013.01)

(58) Field of Classification Search
CPC ................................ C07K 16/00; C07K 16/28
USPC ....................................................... 424/184.1
See application file for complete search history.

(56) References Cited

U.S. PATENT DOCUMENTS

| 9,260,508 B2 | 2/2016 | Laeremans et al. |
| 2011/0206660 A1 | 8/2011 | Blanchetot et al. |

FOREIGN PATENT DOCUMENTS

| CA | 2724208 A1 | 11/2009 |
| CN | 1518559 A | 4/2004 |
| WO | WO 94/04678 A1 | 3/1994 |
| WO | WO 02/085945 A2 | 10/2002 |
| WO | WO 03/050531 A2 | 6/2003 |
| WO | WO 04/049794 A2 | 6/2004 |
| WO | WO 04/090097 A2 | 10/2004 |
| WO | WO 2005/044858 A1 | 5/2005 |
| WO | WO 2007/042289 A2 | 4/2007 |
| WO | WO 2008/043145 A1 | 4/2008 |
| WO | WO 2008/074839 A2 | 6/2008 |
| WO | WO 2009/068625 A2 | 6/2009 |
| WO | WO 2009/138519 A1 | 11/2009 |
| WO | WO 2013/178783 A1 | 12/2013 |

OTHER PUBLICATIONS

Rathanaswami et al. (Analytical Biochemistry, 2008, 373: 52-60, Available online Aug. 16, 2007).*
[No Author Listed], Ablynx presented at the 30th Annual J.P. morgan Healthcare Conference on Jan. 11, 2012. 1 page.
Adriouch et al., Probing the expression and function of the P2X7 purinoceptor with antibodies raised by genetic immunization. Cell Immunol. Jul.-Aug. 2005;236(1-2):72-7. Epub Sep. 12, 2005.
Bins et al., A rapid and potent DNA vaccination strategy defined by in vivo monitoring of antigen expression. Nat Med. Aug. 2005;11(8):899-904. Epub Jun. 19, 2005.
Bins et al., In vivo antigen stability affects DNA vaccine immunogenicity. J Immunol. Aug. 15, 2007;179(4):2126-33.
Buell et al., Blockade of human P2X7 receptor function with a monoclonal antibody. Blood. Nov. 15, 1998;92(10):3521-8.
Chowdhury, DNA immunization as a means to generate antibodies to proteins. Methods Mol Biol. 2003;207:57-62.
Dormitzer et al., Structure-based antigen design: a strategy for next generation vaccines. Trends Biotechnol. Dec. 2008;26(12):659-67. Epub Oct. 30, 2008.
Gurunathan et al., DNA vaccines: immunology, application, and optimization. Annu Rev Immunol. 2000;18:927-74.
Hamers-Casterman et al., Naturally occurring antibodies devoid of light chains. Nature. Jun. 3, 1993;363(6428):446-8.

(Continued)

*Primary Examiner* — Yan Xiao
(74) *Attorney, Agent, or Firm* — Wolf, Greenfield & Sacks, P.C.

(57) ABSTRACT

The present invention relates to a method for generating immunoglobulin sequences against cell-associated antigens, more particularly, antigens that are membrane-anchored. The invention also provides immunoglobulin sequences obtainable by the method of the invention. Specifically, the present invention relates to the generation of immunoglobulin sequences by use of DNA vaccination. More specifically, the present invention relates to generation of immunoglobulin sequences in camelids, preferably directed against cell-associated antigens, in particular antigens with multiple transmembrane spanning domains, including GPCRs and ion channels, by DNA vaccination. Furthermore, the present invention relates to said immunoglobulin sequences against cell-associated antigens, more particularly, antigens that are membrane-anchored, such as e.g. GPCRs and ion channels, more preferably ion channels.

11 Claims, 30 Drawing Sheets

(56) References Cited

OTHER PUBLICATIONS

Holt et al., Domain antibodies:proteins for therapy. Trends Biotechnol. Nov. 2003;21(11):484-90.

Kilpatrick et al., Gene gun delivered DNA-based immunizations mediate rapid production of murine monoclonal antibodies to the Flt-3 receptor. Hybridoma. Dec. 1998;17(6):569-76.

Kim et al., Differential assembly of rat purinergic P2X7 receptor in immune cells of the brain and periphery. J Biol Chem. Jun. 29, 2001;276(26):23262-7. Epub Apr. 19, 2001.

Koch-Nolte et al., Single domain antibodies from llama effectively and specifically block T cell ecto-ADP-ribosyltransferase ART2.2 in vivo. FASEB J. Nov. 2007;21(13):3490-8. Epub Jun. 15, 2007.

Li et al., Prime-Boost Immunization strategies in vaccine research. Prog in Microbiol Immunol. 2006;34(3):65-68.

Michel et al., How reliable are G-protein-coupled receptor antibodies? Naunyn Schmiedebergs Arch Pharmacol. Apr. 2009;379(4):385-8. Epub Jan. 27, 2009.

Muyldermans et al., Recognition of antigens by single-domain antibody fragments: the superfluous luxury of paired domains. Trends Biochem Sci. Apr. 2001;26(4):230-5.

Muyldermans, Single domain camel antibodies: current status. J Biotechnol. Jun. 2001;74(4):277-302.

Nagata et al., DNA immunization followed by a single boost with cells: a protein-free immunization protocol for production of monoclonal antibodies against the native form of membrane proteins. J Immunol Methods. Sep. 2003;280(1-2):59-72.

Pal et al., Immunization of rhesus macaques with a polyvalent DNA prime/protein boost human immunodeficiency virus type 1 vaccine elicits protective antibody response against simian human immunodeficiency virus of R5 phenotype. Virology. 2006;348:341-353.

Danquah et al., Nanobodies that block gating of the P2X7 ion channel ameliorate inflammation. Sci Transl Med. Nov. 23, 2016;8(366):366ra162.

Danquah et al.: Single domain antibodies as tools to block or enhance gating of P2X7. Purinergic Signalling. Mar. 2012; 8(1):116.

Pinto et al.: Tweaking the P2X7 ion channel with nanobodies. Purinergic Signalling. Dec. 2014; 10(4): 689-690.

Rissiek et al., Llama-derived nanobodies can act as P2X7 antagonists in vitro and in vivo. J Neuro. Oct. 15, 2014;275(1-2):70. Abstract 536.

Yang et al., Nanobody and Use thereof. J Cellular Molecular Immunology. Apr. 2008; 24(4):425-427.

\* cited by examiner

HEK293 WT
MCF:3918

HEK293/pVAX1-CXCR4
MCF:151547

CAKI WT
MCF:1089

CAKI/CXCR4
MCF:125290

2 µM NB:
- 14D5
- 13G9
- 7H6
- 13B5
- no NB
- Art2.2 NB

Figure 22

SEQUENCE LISTING

```
<160> NUMBER OF SEQ ID NOS: 793

<210> SEQ ID NO 1
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa can be any naturally occurring amino acid
<220> FEATURE:
<221> NAME/KEY: misc_feature
<222> LOCATION: (50)..(54)
<223> OTHER INFORMATION: Xaa can be any naturally occurring amino acid
<220> FEATURE:
<221> NAME/KEY: misc_feature
<222> LOCATION: (87)..(91)
<223> OTHER INFORMATION: Xaa can be any naturally occurring amino acid

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Pro Phe Ser Xaa Xaa
            20                  25                  30

Xaa Xaa Xaa Trp Phe Arg Gln Ala Pro Gly Lys Gln Arg Asp Ser Val
        35                  40                  45

Ala Xaa Xaa Xaa Xaa Xaa Arg Phe Thr Ile Ser Arg Asp Asn Ala Lys
```

```
                50                  55                  60
Asn Thr Val Tyr Leu Gln Met Asn Ser Leu Lys Pro Glu Asp Thr Ala
 65                  70                  75                  80

Val Tyr Arg Cys Tyr Phe Xaa Xaa Xaa Xaa Trp Gly Gln Gly Thr
                 85                  90                  95

Gln Val Thr Val Ser Ser
            100

<210> SEQ ID NO 2
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa can be any naturally occurring amino acid
<220> FEATURE:
<221> NAME/KEY: misc_feature
<222> LOCATION: (50)..(54)
<223> OTHER INFORMATION: Xaa can be any naturally occurring amino acid
<220> FEATURE:
<221> NAME/KEY: misc_feature
<222> LOCATION: (87)..(91)
<223> OTHER INFORMATION: Xaa can be any naturally occurring amino acid

<400> SEQUENCE: 2

Gln Val Lys Leu Glu Glu Ser Gly Gly Gly Leu Val Gln Ala Gly Gly
 1               5                  10                  15

Ser Leu Arg Leu Ser Cys Val Gly Ser Gly Arg Thr Phe Ser Xaa Xaa
                20                  25                  30

Xaa Xaa Xaa Trp Phe Arg Leu Ala Pro Gly Lys Glu Arg Glu Phe Val
            35                  40                  45

Ala Xaa Xaa Xaa Xaa Xaa Arg Phe Thr Ile Ser Arg Asp Thr Ala Ser
 50                  55                  60

Asn Arg Gly Tyr Leu His Met Asn Asn Leu Thr Pro Glu Asp Thr Ala
 65                  70                  75                  80

Val Tyr Tyr Cys Ala Ala Xaa Xaa Xaa Xaa Xaa Trp Gly Gln Gly Thr
                 85                  90                  95

Gln Val Thr Val Ser Ser
            100

<210> SEQ ID NO 3
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa can be any naturally occurring amino acid
<220> FEATURE:
<221> NAME/KEY: misc_feature
<222> LOCATION: (50)..(54)
<223> OTHER INFORMATION: Xaa can be any naturally occurring amino acid
<220> FEATURE:
<221> NAME/KEY: misc_feature
<222> LOCATION: (87)..(91)
<223> OTHER INFORMATION: Xaa can be any naturally occurring amino acid

<400> SEQUENCE: 3

Ala Val Gln Leu Val Asp Ser Gly Gly Gly Leu Val Gln Ala Gly Asp
 1               5                  10                  15
```

```
Ser Leu Lys Leu Ser Cys Ala Leu Thr Gly Gly Ala Phe Thr Xaa Xaa
            20                  25                  30

Xaa Xaa Xaa Trp Phe Arg Gln Thr Pro Gly Arg Glu Arg Glu Phe Val
        35                  40                  45

Ala Xaa Xaa Xaa Xaa Xaa Arg Phe Thr Ile Ser Arg Asp Asn Ala Lys
 50                  55                  60

Asn Met Val Tyr Leu Arg Met Asn Ser Leu Ile Pro Glu Asp Ala Ala
 65                  70                  75                  80

Val Tyr Ser Cys Ala Ala Xaa Xaa Xaa Xaa Xaa Trp Gly Gln Gly Thr
                 85                  90                  95

Leu Val Thr Val Ser Ser
            100

<210> SEQ ID NO 4
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa can be any naturally occurring amino acid
<220> FEATURE:
<221> NAME/KEY: misc_feature
<222> LOCATION: (50)..(54)
<223> OTHER INFORMATION: Xaa can be any naturally occurring amino acid
<220> FEATURE:
<221> NAME/KEY: misc_feature
<222> LOCATION: (87)..(91)
<223> OTHER INFORMATION: Xaa can be any naturally occurring amino acid

<400> SEQUENCE: 4

Gln Val Gln Leu Val Glu Ser Gly Gly Gly Leu Val Glu Ala Gly Gly
 1               5                  10                  15

Ser Leu Arg Leu Ser Cys Thr Ala Ser Glu Ser Pro Phe Arg Xaa Xaa
            20                  25                  30

Xaa Xaa Xaa Trp Phe Arg Gln Thr Ser Gly Gln Glu Arg Glu Phe Val
        35                  40                  45

Ala Xaa Xaa Xaa Xaa Xaa Arg Phe Thr Ile Ser Arg Asp Asp Ala Lys
 50                  55                  60

Asn Thr Val Trp Leu His Gly Ser Thr Leu Lys Pro Glu Asp Thr Ala
 65                  70                  75                  80

Val Tyr Tyr Cys Ala Ala Xaa Xaa Xaa Xaa Xaa Trp Gly Gln Gly Thr
                 85                  90                  95

Gln Val Thr Val Ser Ser
            100

<210> SEQ ID NO 5
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa can be any naturally occurring amino acid
<220> FEATURE:
<221> NAME/KEY: misc_feature
<222> LOCATION: (50)..(54)
<223> OTHER INFORMATION: Xaa can be any naturally occurring amino acid
<220> FEATURE:
<221> NAME/KEY: misc_feature
<222> LOCATION: (87)..(91)
```

<223> OTHER INFORMATION: Xaa can be any naturally occurring amino acid

<400> SEQUENCE: 5

```
Ala Val Gln Leu Val Glu Ser Gly Gly Gly Leu Val Gln Gly Gly Gly
1               5                   10                  15

Ser Leu Arg Leu Ala Cys Ala Ala Ser Glu Arg Ile Phe Asp Xaa Xaa
            20                  25                  30

Xaa Xaa Xaa Trp Tyr Arg Gln Gly Pro Gly Asn Glu Arg Glu Leu Val
        35                  40                  45

Ala Xaa Xaa Xaa Xaa Xaa Arg Phe Thr Ile Ser Met Asp Tyr Thr Lys
    50                  55                  60

Gln Thr Val Tyr Leu His Met Asn Ser Leu Arg Pro Glu Asp Thr Gly
65                  70                  75                  80

Leu Tyr Tyr Cys Lys Ile Xaa Xaa Xaa Xaa Xaa Trp Gly Gln Gly Thr
                85                  90                  95

Gln Val Thr Val Ser Ser
            100
```

<210> SEQ ID NO 6
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa can be any naturally occurring amino acid
<220> FEATURE:
<221> NAME/KEY: misc_feature
<222> LOCATION: (50)..(54)
<223> OTHER INFORMATION: Xaa can be any naturally occurring amino acid
<220> FEATURE:
<221> NAME/KEY: misc_feature
<222> LOCATION: (87)..(91)
<223> OTHER INFORMATION: Xaa can be any naturally occurring amino acid

<400> SEQUENCE: 6

```
Asp Val Lys Phe Val Glu Ser Gly Gly Gly Leu Val Gln Ala Gly Gly
1               5                   10                  15

Ser Leu Arg Leu Ser Cys Val Ala Ser Gly Phe Asn Phe Asp Xaa Xaa
            20                  25                  30

Xaa Xaa Xaa Trp Phe Arg Gln Ala Pro Gly Lys Glu Arg Glu Val
        35                  40                  45

Ala Xaa Xaa Xaa Xaa Xaa Arg Phe Thr Ile Ser Ser Glu Lys Asp Lys
    50                  55                  60

Asn Ser Val Tyr Leu Gln Met Asn Ser Leu Lys Pro Glu Asp Thr Ala
65                  70                  75                  80

Leu Tyr Ile Cys Ala Gly Xaa Xaa Xaa Xaa Xaa Trp Gly Arg Gly Thr
                85                  90                  95

Gln Val Thr Val Ser Ser
            100
```

<210> SEQ ID NO 7
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa can be any naturally occurring amino acid

```
<220> FEATURE:
<221> NAME/KEY: misc_feature
<222> LOCATION: (50)..(54)
<223> OTHER INFORMATION: Xaa can be any naturally occurring amino acid
<220> FEATURE:
<221> NAME/KEY: misc_feature
<222> LOCATION: (87)..(91)
<223> OTHER INFORMATION: Xaa can be any naturally occurring amino acid

<400> SEQUENCE: 7

Gln Val Arg Leu Ala Glu Ser Gly Gly Gly Leu Val Gln Ser Gly Gly
1               5                   10                  15

Ser Leu Arg Leu Ser Cys Val Ala Ser Gly Ser Thr Tyr Thr Xaa Xaa
            20                  25                  30

Xaa Xaa Xaa Trp Tyr Arg Gln Tyr Pro Gly Lys Gln Arg Ala Leu Val
        35                  40                  45

Ala Xaa Xaa Xaa Xaa Xaa Arg Phe Thr Ile Ala Arg Asp Ser Thr Lys
    50                  55                  60

Asp Thr Phe Cys Leu Gln Met Asn Asn Leu Lys Pro Glu Asp Thr Ala
65                  70                  75                  80

Val Tyr Tyr Cys Tyr Ala Xaa Xaa Xaa Xaa Xaa Trp Gly Gln Gly Thr
                85                  90                  95

Gln Val Thr Val Ser Ser
            100

<210> SEQ ID NO 8
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa can be any naturally occurring amino acid
<220> FEATURE:
<221> NAME/KEY: misc_feature
<222> LOCATION: (50)..(54)
<223> OTHER INFORMATION: Xaa can be any naturally occurring amino acid
<220> FEATURE:
<221> NAME/KEY: misc_feature
<222> LOCATION: (87)..(91)
<223> OTHER INFORMATION: Xaa can be any naturally occurring amino acid

<400> SEQUENCE: 8

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Ser Asp Xaa Xaa
            20                  25                  30

Xaa Xaa Xaa Trp Phe Arg Gln Ala Pro Gly Lys Pro Arg Glu Gly Val
        35                  40                  45

Ser Xaa Xaa Xaa Xaa Xaa Arg Phe Thr Ile Ser Thr Asp Asn Ala Lys
    50                  55                  60

Asn Thr Val His Leu Leu Met Asn Arg Val Asn Ala Glu Asp Thr Ala
65                  70                  75                  80

Leu Tyr Tyr Cys Ala Val Xaa Xaa Xaa Xaa Xaa Trp Gly Arg Gly Thr
                85                  90                  95

Arg Val Thr Val Ser Ser
            100

<210> SEQ ID NO 9
<211> LENGTH: 102
<212> TYPE: PRT
```

```
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa can be any naturally occurring amino acid
<220> FEATURE:
<221> NAME/KEY: misc_feature
<222> LOCATION: (50)..(54)
<223> OTHER INFORMATION: Xaa can be any naturally occurring amino acid
<220> FEATURE:
<221> NAME/KEY: misc_feature
<222> LOCATION: (87)..(91)
<223> OTHER INFORMATION: Xaa can be any naturally occurring amino acid

<400> SEQUENCE: 9

Gln Val Gln Leu Val Glu Ser Gly Gly Gly Leu Val Gln Pro Gly Gly
1               5                   10                  15

Ser Leu Arg Leu Ser Cys Gln Ala Ser Gly Asp Ile Ser Thr Xaa Xaa
            20                  25                  30

Xaa Xaa Xaa Trp Tyr Arg Gln Val Pro Gly Lys Leu Arg Glu Phe Val
        35                  40                  45

Ala Xaa Xaa Xaa Xaa Xaa Arg Phe Thr Ile Ser Gly Asp Asn Ala Lys
50                  55                  60

Arg Ala Ile Tyr Leu Gln Met Asn Asn Leu Lys Pro Asp Asp Thr Ala
65                  70                  75                  80

Val Tyr Tyr Cys Asn Arg Xaa Xaa Xaa Xaa Xaa Trp Gly Gln Gly Thr
                85                  90                  95

Gln Val Thr Val Ser Pro
            100

<210> SEQ ID NO 10
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa can be any naturally occurring amino acid
<220> FEATURE:
<221> NAME/KEY: misc_feature
<222> LOCATION: (50)..(54)
<223> OTHER INFORMATION: Xaa can be any naturally occurring amino acid
<220> FEATURE:
<221> NAME/KEY: misc_feature
<222> LOCATION: (87)..(91)
<223> OTHER INFORMATION: Xaa can be any naturally occurring amino acid

<400> SEQUENCE: 10

Gln Val Pro Val Val Glu Ser Gly Gly Gly Leu Val Gln Ala Gly Asp
1               5                   10                  15

Ser Leu Arg Leu Phe Cys Ala Val Pro Ser Phe Thr Ser Thr Xaa Xaa
            20                  25                  30

Xaa Xaa Xaa Trp Phe Arg Gln Ala Pro Gly Lys Glu Arg Glu Phe Val
        35                  40                  45

Ala Xaa Xaa Xaa Xaa Xaa Arg Phe Thr Ile Ser Arg Asn Ala Thr Lys
50                  55                  60

Asn Thr Leu Thr Leu Arg Met Asp Ser Leu Lys Pro Glu Asp Thr Ala
65                  70                  75                  80

Val Tyr Tyr Cys Ala Ala Xaa Xaa Xaa Xaa Xaa Trp Gly Gln Gly Thr
                85                  90                  95
```

Gln Val Thr Val Ser Ser
            100

<210> SEQ ID NO 11
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa can be any naturally occurring amino acid
<220> FEATURE:
<221> NAME/KEY: misc_feature
<222> LOCATION: (50)..(54)
<223> OTHER INFORMATION: Xaa can be any naturally occurring amino acid
<220> FEATURE:
<221> NAME/KEY: misc_feature
<222> LOCATION: (87)..(91)
<223> OTHER INFORMATION: Xaa can be any naturally occurring amino acid

<400> SEQUENCE: 11

Glu Val Gln Leu Val Glu Ser Gly Gly Gly Leu Val Gln Ala Gly Asp
1               5                   10                  15

Ser Leu Arg Leu Phe Cys Thr Val Ser Gly Gly Thr Ala Ser Xaa Xaa
            20                  25                  30

Xaa Xaa Xaa Trp Phe Arg Gln Ala Pro Gly Glu Lys Arg Glu Phe Val
        35                  40                  45

Ala Xaa Xaa Xaa Xaa Xaa Arg Phe Thr Ile Ala Arg Glu Asn Ala Gly
    50                  55                  60

Asn Met Val Tyr Leu Gln Met Asn Asn Leu Lys Pro Asp Asp Thr Ala
65                  70                  75                  80

Leu Tyr Thr Cys Ala Ala Xaa Xaa Xaa Xaa Xaa Trp Gly Arg Gly Thr
                85                  90                  95

Gln Val Thr Val Ser Ser
            100

<210> SEQ ID NO 12
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa can be any naturally occurring amino acid
<220> FEATURE:
<221> NAME/KEY: misc_feature
<222> LOCATION: (50)..(54)
<223> OTHER INFORMATION: Xaa can be any naturally occurring amino acid
<220> FEATURE:
<221> NAME/KEY: misc_feature
<222> LOCATION: (87)..(91)
<223> OTHER INFORMATION: Xaa can be any naturally occurring amino acid

<400> SEQUENCE: 12

Ala Val Gln Leu Val Glu Ser Gly Gly Asp Ser Val Gln Pro Gly Asp
1               5                   10                  15

Ser Gln Thr Leu Ser Cys Ala Ala Ser Gly Arg Thr Asn Ser Xaa Xaa
            20                  25                  30

Xaa Xaa Xaa Trp Phe Arg Gln Ala Pro Gly Lys Glu Arg Val Phe Leu
        35                  40                  45

Ala Xaa Xaa Xaa Xaa Xaa Arg Phe Thr Ile Ser Arg Asp Ser Ala Lys
    50                  55                  60

```
Asn Met Met Tyr Leu Gln Met Asn Asn Leu Lys Pro Gln Asp Thr Ala
65                  70                  75                  80

Val Tyr Tyr Cys Ala Ala Xaa Xaa Xaa Xaa Xaa Trp Gly Gln Gly Thr
                85                  90                  95

Gln Val Thr Val Ser Ser
            100

<210> SEQ ID NO 13
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa can be any naturally occurring amino acid
<220> FEATURE:
<221> NAME/KEY: misc_feature
<222> LOCATION: (50)..(54)
<223> OTHER INFORMATION: Xaa can be any naturally occurring amino acid
<220> FEATURE:
<221> NAME/KEY: misc_feature
<222> LOCATION: (87)..(91)
<223> OTHER INFORMATION: Xaa can be any naturally occurring amino acid

<400> SEQUENCE: 13

Ala Val Gln Leu Val Glu Ser Gly Gly Gly Leu Val Gln Ala Gly Gly
1               5                   10                  15

Ser Leu Arg Leu Ser Cys Val Val Ser Gly Leu Thr Ser Ser Xaa Xaa
            20                  25                  30

Xaa Xaa Xaa Trp Phe Arg Gln Thr Pro Trp Gln Glu Arg Asp Phe Val
        35                  40                  45

Ala Xaa Xaa Xaa Xaa Xaa Arg Phe Thr Ile Ser Arg Asp Asn Tyr Lys
    50                  55                  60

Asp Thr Val Leu Leu Glu Met Asn Phe Leu Lys Pro Glu Asp Thr Ala
65                  70                  75                  80

Ile Tyr Tyr Cys Ala Ala Xaa Xaa Xaa Xaa Xaa Trp Gly Gln Gly Thr
                85                  90                  95

Gln Val Thr Val Ser Ser
            100

<210> SEQ ID NO 14
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa can be any naturally occurring amino acid
<220> FEATURE:
<221> NAME/KEY: misc_feature
<222> LOCATION: (50)..(54)
<223> OTHER INFORMATION: Xaa can be any naturally occurring amino acid
<220> FEATURE:
<221> NAME/KEY: misc_feature
<222> LOCATION: (87)..(91)
<223> OTHER INFORMATION: Xaa can be any naturally occurring amino acid

<400> SEQUENCE: 14

Ala Val Gln Leu Val Glu Ser Gly Gly Gly Leu Val Gln Ala Gly Ala
1               5                   10                  15

Ser Leu Arg Leu Ser Cys Ala Thr Ser Thr Arg Thr Leu Asp Xaa Xaa
```

```
                   20                  25                  30
Xaa Xaa Xaa Trp Phe Arg Gln Ala Pro Gly Arg Asp Arg Glu Phe Val
            35                  40                  45

Ala Xaa Xaa Xaa Xaa Xaa Arg Phe Thr Val Ser Arg Asp Ser Ala Glu
    50                  55                  60

Asn Thr Val Ala Leu Gln Met Asn Ser Leu Lys Pro Glu Asp Thr Ala
65                  70                  75                  80

Val Tyr Tyr Cys Ala Ala Xaa Xaa Xaa Xaa Trp Gly Gln Gly Thr
                85                  90                  95

Arg Val Thr Val Ser Ser
            100

<210> SEQ ID NO 15
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa can be any naturally occurring amino acid
<220> FEATURE:
<221> NAME/KEY: misc_feature
<222> LOCATION: (50)..(54)
<223> OTHER INFORMATION: Xaa can be any naturally occurring amino acid
<220> FEATURE:
<221> NAME/KEY: misc_feature
<222> LOCATION: (87)..(91)
<223> OTHER INFORMATION: Xaa can be any naturally occurring amino acid

<400> SEQUENCE: 15

Gln Val Gln Leu Val Glu Ser Gly Gly Gly Leu Val Gln Pro Gly Gly
1               5                   10                  15

Ser Leu Arg Leu Ser Cys Thr Val Ser Arg Leu Thr Ala His Xaa Xaa
            20                  25                  30

Xaa Xaa Xaa Trp Phe Arg Gln Ala Pro Gly Lys Glu Arg Glu Ala Val
            35                  40                  45

Ser Xaa Xaa Xaa Xaa Xaa Arg Phe Thr Ile Ser Arg Asp Tyr Ala Gly
    50                  55                  60

Asn Thr Ala Phe Leu Gln Met Asp Ser Leu Lys Pro Glu Asp Thr Gly
65                  70                  75                  80

Val Tyr Tyr Cys Ala Thr Xaa Xaa Xaa Xaa Xaa Trp Gly Gln Gly Thr
                85                  90                  95

Gln Val Thr Val Ser Ser
            100

<210> SEQ ID NO 16
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa can be any naturally occurring amino acid
<220> FEATURE:
<221> NAME/KEY: misc_feature
<222> LOCATION: (50)..(54)
<223> OTHER INFORMATION: Xaa can be any naturally occurring amino acid
<220> FEATURE:
<221> NAME/KEY: misc_feature
<222> LOCATION: (87)..(91)
<223> OTHER INFORMATION: Xaa can be any naturally occurring amino acid
```

<400> SEQUENCE: 16

```
Glu Val Gln Leu Val Glu Ser Gly Gly Glu Leu Val Gln Ala Gly Gly
1               5                   10                  15

Ser Leu Lys Leu Ser Cys Thr Ala Ser Gly Arg Asn Phe Val Xaa Xaa
            20                  25                  30

Xaa Xaa Xaa Trp Phe Arg Arg Ala Pro Gly Lys Glu Arg Glu Phe Val
        35                  40                  45

Ala Xaa Xaa Xaa Xaa Arg Phe Thr Val Ser Arg Asp Asn Gly Lys
50                  55                  60

Asn Thr Ala Tyr Leu Arg Met Asn Ser Leu Lys Pro Glu Asp Thr Ala
65                  70                  75                  80

Asp Tyr Tyr Cys Ala Val Xaa Xaa Xaa Xaa Xaa Leu Gly Ser Gly Thr
            85                  90                  95

Gln Val Thr Val Ser Ser
            100
```

<210> SEQ ID NO 17
<211> LENGTH: 102
<212> TYPE: PRT
<213> ORGANISM: Artificial
<220> FEATURE:
<223> OTHER INFORMATION: GLEW-class Nanobody
<220> FEATURE:
<221> NAME/KEY: misc_feature
<222> LOCATION: (31)..(35)
<223> OTHER INFORMATION: Xaa can be any naturally occurring amino acid
<220> FEATURE:
<221> NAME/KEY: misc_feature
<222> LOCATION: (50)..(54)
<223> OTHER INFORMATION: Xaa can be any naturally occurring amino acid
<220> FEATURE:
<221> NAME/KEY: misc_feature
<222> LOCATION: (87)..(91)
<223> OTHER INFORMATION: Xaa can be any naturally occurring amino acid

<400> SEQUENCE: 17

```
Ala Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Xaa Xaa
            20                  25                  30

Xaa Xaa Xaa Trp Val Arg Gln Ala Pro Gly Lys Val Leu Glu Trp Val
        35                  40                  45

Ser Xaa Xaa Xaa Xaa Xaa Arg Phe Thr Ile Ser Arg Asp Asn Ala Lys
50                  55                  60

Asn Thr Leu Tyr Leu Gln Met Asn Ser Leu Lys Pro Glu Asp Thr Ala
65                  70                  75                  80

Val Tyr Tyr Cys Val Lys Xaa Xaa Xaa Xaa Xaa Gly Ser Gln Gly Thr
            85                  90                  95

Gln Val Thr Val Ser Ser
            100
```

<210> SEQ ID NO 18
<211> LENGTH: 102
<212> TYPE: PRT
<213> ORGANISM: Artificial
<220> FEATURE:
<223> OTHER INFORMATION: GLEW-class Nanobody
<220> FEATURE:
<221> NAME/KEY: misc_feature
<222> LOCATION: (31)..(35)
<223> OTHER INFORMATION: Xaa can be any naturally occurring amino acid
<220> FEATURE:

```
<221> NAME/KEY: misc_feature
<222> LOCATION: (50)..(54)
<223> OTHER INFORMATION: Xaa can be any naturally occurring amino acid
<220> FEATURE:
<221> NAME/KEY: misc_feature
<222> LOCATION: (87)..(91)
<223> OTHER INFORMATION: Xaa can be any naturally occurring amino acid

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Val Cys Val Ser Ser Gly Cys Thr Xaa Xaa
            20                  25                  30

Xaa Xaa Xaa Trp Val Arg Gln Ala Pro Gly Lys Ala Glu Trp Val
        35                  40                  45

Ser Xaa Xaa Xaa Xaa Xaa Arg Phe Lys Ile Ser Arg Asp Asn Ala Lys
    50                  55                  60

Lys Thr Leu Tyr Leu Gln Met Asn Ser Leu Gly Pro Glu Asp Thr Ala
65              70                  75                  80

Met Tyr Tyr Cys Gln Arg Xaa Xaa Xaa Xaa Xaa Arg Gly Gln Gly Thr
            85                  90                  95

Gln Val Thr Val Ser Ser
            100

<210> SEQ ID NO 19
<211> LENGTH: 102
<212> TYPE: PRT
<213> ORGANISM: Artificial
<220> FEATURE:
<223> OTHER INFORMATION: GLEW-class Nanobody
<220> FEATURE:
<221> NAME/KEY: misc_feature
<222> LOCATION: (31)..(35)
<223> OTHER INFORMATION: Xaa can be any naturally occurring amino acid
<220> FEATURE:
<221> NAME/KEY: misc_feature
<222> LOCATION: (50)..(54)
<223> OTHER INFORMATION: Xaa can be any naturally occurring amino acid
<220> FEATURE:
<221> NAME/KEY: misc_feature
<222> LOCATION: (87)..(91)
<223> OTHER INFORMATION: Xaa can be any naturally occurring amino acid

<400> SEQUENCE: 19

Glu Val Gln Leu Val Glu Ser Gly Gly Gly Leu Ala Leu Pro Gly Gly
1               5                   10                  15

Ser Leu Thr Leu Ser Cys Val Phe Ser Gly Ser Thr Phe Ser Xaa Xaa
            20                  25                  30

Xaa Xaa Xaa Trp Val Arg His Thr Pro Gly Lys Ala Glu Glu Trp Val
        35                  40                  45

Ser Xaa Xaa Xaa Xaa Xaa Arg Phe Thr Ile Ser Arg Asp Asn Ala Lys
    50                  55                  60

Asn Thr Leu Tyr Leu Glu Met Asn Ser Leu Ser Pro Glu Asp Thr Ala
65              70                  75                  80

Met Tyr Tyr Cys Gly Arg Xaa Xaa Xaa Xaa Xaa Arg Ser Lys Gly Ile
            85                  90                  95

Gln Val Thr Val Ser Ser
            100

<210> SEQ ID NO 20
<211> LENGTH: 102
<212> TYPE: PRT
<213> ORGANISM: Artificial
```

```
<220> FEATURE:
<223> OTHER INFORMATION: P,R,S 103-class Nanobody
<220> FEATURE:
<221> NAME/KEY: misc_feature
<222> LOCATION: (31)..(35)
<223> OTHER INFORMATION: Xaa can be any naturally occurring amino acid
<220> FEATURE:
<221> NAME/KEY: misc_feature
<222> LOCATION: (50)..(54)
<223> OTHER INFORMATION: Xaa can be any naturally occurring amino acid
<220> FEATURE:
<221> NAME/KEY: misc_feature
<222> LOCATION: (87)..(91)
<223> OTHER INFORMATION: Xaa can be any naturally occurring amino acid

<400> SEQUENCE: 20

Ala Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Xaa Xaa
            20                  25                  30

Xaa Xaa Xaa Trp Phe Arg Gln Ala Pro Gly Lys Glu Arg Glu Phe Val
        35                  40                  45

Ala Xaa Xaa Xaa Xaa Xaa Arg Phe Thr Ile Ser Arg Asp Asn Ala Lys
50                  55                  60

Asn Thr Val Tyr Leu Gln Met Asn Ser Leu Lys Pro Glu Asp Thr Ala
65                  70                  75                  80

Val Tyr Tyr Cys Ala Ala Xaa Xaa Xaa Xaa Xaa Arg Gly Gln Gly Thr
                85                  90                  95

Gln Val Thr Val Ser Ser
            100

<210> SEQ ID NO 21
<211> LENGTH: 102
<212> TYPE: PRT
<213> ORGANISM: Artificial
<220> FEATURE:
<223> OTHER INFORMATION: P,R,S 103-class Nanobody
<220> FEATURE:
<221> NAME/KEY: misc_feature
<222> LOCATION: (31)..(35)
<223> OTHER INFORMATION: Xaa can be any naturally occurring amino acid
<220> FEATURE:
<221> NAME/KEY: misc_feature
<222> LOCATION: (50)..(54)
<223> OTHER INFORMATION: Xaa can be any naturally occurring amino acid
<220> FEATURE:
<221> NAME/KEY: misc_feature
<222> LOCATION: (87)..(91)
<223> OTHER INFORMATION: Xaa can be any naturally occurring amino acid

<400> SEQUENCE: 21

Asp Val Gln Leu Val Glu Ser Gly Gly Asp Leu Val Gln Pro Gly Gly
1               5                   10                  15

Ser Leu Arg Leu Ser Cys Ala Ala Ser Gly Phe Ser Phe Asp Xaa Xaa
            20                  25                  30

Xaa Xaa Xaa Trp Leu Arg Gln Thr Pro Gly Lys Gly Leu Glu Trp Val
        35                  40                  45

Gly Xaa Xaa Xaa Xaa Xaa Arg Phe Thr Ile Ser Arg Asp Asn Ala Lys
50                  55                  60

Asn Met Leu Tyr Leu His Leu Asn Asn Leu Lys Ser Glu Asp Thr Ala
65                  70                  75                  80

Val Tyr Tyr Cys Arg Arg Xaa Xaa Xaa Xaa Xaa Leu Gly Gln Gly Thr
                85                  90                  95

Gln Val Thr Val Ser Ser
```

100

<210> SEQ ID NO 22
<211> LENGTH: 102
<212> TYPE: PRT
<213> ORGANISM: Artificial
<220> FEATURE:
<223> OTHER INFORMATION: P,R,S 103-class Nanobody
<220> FEATURE:
<221> NAME/KEY: misc_feature
<222> LOCATION: (31)..(35)
<223> OTHER INFORMATION: Xaa can be any naturally occurring amino acid
<220> FEATURE:
<221> NAME/KEY: misc_feature
<222> LOCATION: (50)..(54)
<223> OTHER INFORMATION: Xaa can be any naturally occurring amino acid
<220> FEATURE:
<221> NAME/KEY: misc_feature
<222> LOCATION: (87)..(91)
<223> OTHER INFORMATION: Xaa can be any naturally occurring amino acid

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Val Cys Val Ser Ser Gly Cys Thr Xaa Xaa
            20                  25                  30

Xaa Xaa Xaa Trp Val Arg Gln Ala Pro Gly Lys Ala Glu Glu Trp Val
        35                  40                  45

Ser Xaa Xaa Xaa Xaa Xaa Arg Phe Lys Ile Ser Arg Asp Asn Ala Lys
    50                  55                  60

Lys Thr Leu Tyr Leu Gln Met Asn Ser Leu Gly Pro Glu Asp Thr Ala
65                  70                  75                  80

Met Tyr Tyr Cys Gln Arg Xaa Xaa Xaa Xaa Xaa Arg Gly Gln Gly Thr
                85                  90                  95

Gln Val Thr Val Ser Ser
            100

<210> SEQ ID NO 23
<211> LENGTH: 30
<212> TYPE: PRT
<213> ORGANISM: Artificial
<220> FEATURE:
<223> OTHER INFORMATION: KERE-class Nanobody FW1 sequence

<400> SEQUENCE: 23

Gln Val Gln Arg Val Glu Ser Gly Gly Gly Leu Val Gln Ala Gly Gly
1               5                   10                  15

Ser Leu Arg Leu Ser Cys Ala Ala Ser Gly Arg Thr Ser Ser
            20                  25                  30

<210> SEQ ID NO 24
<211> LENGTH: 30
<212> TYPE: PRT
<213> ORGANISM: Artificial
<220> FEATURE:
<223> OTHER INFORMATION: KERE-class Nanobody FW1 sequence

<400> SEQUENCE: 24

Gln Val Gln Leu Val Glu Ser Gly Gly Gly Leu Val Gln Thr Gly Asp
1               5                   10                  15

Ser Leu Ser Leu Ser Cys Ser Ala Ser Gly Arg Thr Phe Ser
            20                  25                  30

<210> SEQ ID NO 25

```
<211> LENGTH: 30
<212> TYPE: PRT
<213> ORGANISM: Artificial
<220> FEATURE:
<223> OTHER INFORMATION: KERE-class Nanobody FW1 sequence

<400> SEQUENCE: 25

Gln Val Lys Leu Glu Glu Ser Gly Gly Gly Leu Val Gln Ala Gly Asp
1               5                   10                  15

Ser Leu Arg Leu Ser Cys Ala Ala Thr Gly Arg Ala Phe Gly
            20                  25                  30

<210> SEQ ID NO 26
<211> LENGTH: 30
<212> TYPE: PRT
<213> ORGANISM: Artificial
<220> FEATURE:
<223> OTHER INFORMATION: KERE-class Nanobody FW1 sequence

<400> SEQUENCE: 26

Ala Val Gln Leu Val Glu Ser Gly Gly Gly Leu Val Gln Pro Gly Glu
1               5                   10                  15

Ser Leu Gly Leu Ser Cys Val Ala Ser Gly Arg Asp Phe Val
            20                  25                  30

<210> SEQ ID NO 27
<211> LENGTH: 30
<212> TYPE: PRT
<213> ORGANISM: Artificial
<220> FEATURE:
<223> OTHER INFORMATION: KERE-class Nanobody FW1 sequence

<400> SEQUENCE: 27

Glu Val Gln Leu Val Glu Ser Gly Gly Gly Leu Val Gln Ala Gly Gly
1               5                   10                  15

Ser Leu Arg Leu Ser Cys Glu Val Leu Gly Arg Thr Ala Gly
            20                  25                  30

<210> SEQ ID NO 28
<211> LENGTH: 30
<212> TYPE: PRT
<213> ORGANISM: Artificial
<220> FEATURE:
<223> OTHER INFORMATION: KERE-class Nanobody FW1 sequence

<400> SEQUENCE: 28

Gln Val Gln Leu Val Glu Ser Gly Gly Gly Trp Val Gln Pro Gly Gly
1               5                   10                  15

Ser Leu Arg Leu Ser Cys Ala Ala Ser Glu Thr Ile Leu Ser
            20                  25                  30

<210> SEQ ID NO 29
<211> LENGTH: 30
<212> TYPE: PRT
<213> ORGANISM: Artificial
<220> FEATURE:
<223> OTHER INFORMATION: KERE-class Nanobody FW1 sequence

<400> SEQUENCE: 29

Gln Val Gln Leu Val Glu Ser Gly Gly Gly Thr Val Gln Pro Gly Gly
1               5                   10                  15

Ser Leu Asn Leu Ser Cys Val Ala Ser Gly Asn Thr Phe Asn
            20                  25                  30
```

```
<210> SEQ ID NO 30
<211> LENGTH: 30
<212> TYPE: PRT
<213> ORGANISM: Artificial
<220> FEATURE:
<223> OTHER INFORMATION: KERE-class Nanobody FW1 sequence

<400> SEQUENCE: 30

Glu Val Gln Leu Val Glu Ser Gly Gly Gly Leu Ala Gln Pro Gly Gly
1               5                   10                  15

Ser Leu Gln Leu Ser Cys Ser Ala Pro Gly Phe Thr Leu Asp
            20                  25                  30

<210> SEQ ID NO 31
<211> LENGTH: 30
<212> TYPE: PRT
<213> ORGANISM: Artificial
<220> FEATURE:
<223> OTHER INFORMATION: KERE-class Nanobody FW1 sequence

<400> SEQUENCE: 31

Ala Gln Glu Leu Glu Glu Ser Gly Gly Gly Leu Val Gln Ala Gly Gly
1               5                   10                  15

Ser Leu Arg Leu Ser Cys Ala Ala Ser Gly Arg Thr Phe Asn
            20                  25                  30

<210> SEQ ID NO 32
<211> LENGTH: 22
<212> TYPE: PRT
<213> ORGANISM: Artificial
<220> FEATURE:
<223> OTHER INFORMATION: KERE-class Nanobody FW1 sequence

<400> SEQUENCE: 32

Val Glu Ser Gly Gly Gly Leu Val Gln Pro Gly Gly Ser Leu Arg Leu
1               5                   10                  15

Ser Cys Ala Ala Ser Gly
            20

<210> SEQ ID NO 33
<211> LENGTH: 22
<212> TYPE: PRT
<213> ORGANISM: Artificial
<220> FEATURE:
<223> OTHER INFORMATION: KERE-class Nanobody FW1 sequence

<400> SEQUENCE: 33

Val Asp Ser Gly Gly Gly Leu Val Gln Ala Gly Asp Ser Leu Lys Leu
1               5                   10                  15

Ser Cys Ala Leu Thr Gly
            20

<210> SEQ ID NO 34
<211> LENGTH: 22
<212> TYPE: PRT
<213> ORGANISM: Artificial
<220> FEATURE:
<223> OTHER INFORMATION: KERE-class Nanobody FW1 sequence

<400> SEQUENCE: 34

Val Asp Ser Gly Gly Gly Leu Val Gln Ala Gly Asp Ser Leu Arg Leu
1               5                   10                  15

Ser Cys Ala Ala Ser Gly
            20
```

```
<210> SEQ ID NO 35
<211> LENGTH: 22
<212> TYPE: PRT
<213> ORGANISM: Artificial
<220> FEATURE:
<223> OTHER INFORMATION: KERE-class Nanobody FW1 sequence

<400> SEQUENCE: 35

Val Asp Ser Gly Gly Gly Leu Val Glu Ala Gly Gly Ser Leu Arg Leu
1               5                   10                  15

Ser Cys Gln Val Ser Glu
            20

<210> SEQ ID NO 36
<211> LENGTH: 22
<212> TYPE: PRT
<213> ORGANISM: Artificial
<220> FEATURE:
<223> OTHER INFORMATION: KERE-class Nanobody FW1 sequence

<400> SEQUENCE: 36

Gln Asp Ser Gly Gly Gly Ser Val Gln Ala Gly Gly Ser Leu Lys Leu
1               5                   10                  15

Ser Cys Ala Ala Ser Gly
            20

<210> SEQ ID NO 37
<211> LENGTH: 22
<212> TYPE: PRT
<213> ORGANISM: Artificial
<220> FEATURE:
<223> OTHER INFORMATION: KERE-class Nanobody FW1 sequence

<400> SEQUENCE: 37

Val Gln Ser Gly Gly Arg Leu Val Gln Ala Gly Asp Ser Leu Arg Leu
1               5                   10                  15

Ser Cys Ala Ala Ser Glu
            20

<210> SEQ ID NO 38
<211> LENGTH: 22
<212> TYPE: PRT
<213> ORGANISM: Artificial
<220> FEATURE:
<223> OTHER INFORMATION: KERE-class Nanobody FW1 sequence

<400> SEQUENCE: 38

Val Glu Ser Gly Gly Thr Leu Val Gln Ser Gly Asp Ser Leu Lys Leu
1               5                   10                  15

Ser Cys Ala Ser Ser Thr
            20

<210> SEQ ID NO 39
<211> LENGTH: 22
<212> TYPE: PRT
<213> ORGANISM: Artificial
<220> FEATURE:
<223> OTHER INFORMATION: KERE-class Nanobody FW1 sequence

<400> SEQUENCE: 39

Met Glu Ser Gly Gly Asp Ser Val Gln Ser Gly Gly Ser Leu Thr Leu
1               5                   10                  15

Ser Cys Val Ala Ser Gly
            20
```

<210> SEQ ID NO 40
<211> LENGTH: 22
<212> TYPE: PRT
<213> ORGANISM: Artificial
<220> FEATURE:
<223> OTHER INFORMATION: KERE-class Nanobody FW1 sequence

<400> SEQUENCE: 40

Gln Ala Ser Gly Gly Gly Leu Val Gln Ala Gly Gly Ser Leu Arg Leu
1               5                   10                  15

Ser Cys Ser Ala Ser Val
            20

<210> SEQ ID NO 41
<211> LENGTH: 14
<212> TYPE: PRT
<213> ORGANISM: Artificial
<220> FEATURE:
<223> OTHER INFORMATION: KERE-class Nanobody FW2 sequence

<400> SEQUENCE: 41

Trp Phe Arg Gln Ala Pro Gly Lys Glu Arg Glu Phe Val Ala
1               5                   10

<210> SEQ ID NO 42
<211> LENGTH: 14
<212> TYPE: PRT
<213> ORGANISM: Artificial
<220> FEATURE:
<223> OTHER INFORMATION: KERE-class Nanobody FW2 sequence

<400> SEQUENCE: 42

Trp Phe Arg Gln Thr Pro Gly Arg Glu Arg Glu Phe Val Ala
1               5                   10

<210> SEQ ID NO 43
<211> LENGTH: 14
<212> TYPE: PRT
<213> ORGANISM: Artificial
<220> FEATURE:
<223> OTHER INFORMATION: KERE-class Nanobody FW2 sequence

<400> SEQUENCE: 43

Trp Tyr Arg Gln Ala Pro Gly Lys Gln Arg Glu Met Val Ala
1               5                   10

<210> SEQ ID NO 44
<211> LENGTH: 14
<212> TYPE: PRT
<213> ORGANISM: Artificial
<220> FEATURE:
<223> OTHER INFORMATION: KERE-class Nanobody FW2 sequence

<400> SEQUENCE: 44

Trp Tyr Arg Gln Gly Pro Gly Lys Gln Arg Glu Leu Val Ala
1               5                   10

<210> SEQ ID NO 45
<211> LENGTH: 14
<212> TYPE: PRT
<213> ORGANISM: Artificial
<220> FEATURE:
<223> OTHER INFORMATION: KERE-class Nanobody FW2 sequence

<400> SEQUENCE: 45

Trp Ile Arg Gln Ala Pro Gly Lys Glu Arg Glu Gly Val Ser
1               5                   10

<210> SEQ ID NO 46
<211> LENGTH: 14
<212> TYPE: PRT
<213> ORGANISM: Artificial
<220> FEATURE:
<223> OTHER INFORMATION: KERE-class Nanobody FW2 sequence

<400> SEQUENCE: 46

Trp Phe Arg Glu Ala Pro Gly Lys Glu Arg Glu Gly Ile Ser
1               5                   10

<210> SEQ ID NO 47
<211> LENGTH: 14
<212> TYPE: PRT
<213> ORGANISM: Artificial
<220> FEATURE:
<223> OTHER INFORMATION: KERE-class Nanobody FW2 sequence

<400> SEQUENCE: 47

Trp Tyr Arg Gln Ala Pro Gly Lys Glu Arg Asp Leu Val Ala
1               5                   10

<210> SEQ ID NO 48
<211> LENGTH: 14
<212> TYPE: PRT
<213> ORGANISM: Artificial
<220> FEATURE:
<223> OTHER INFORMATION: KERE-class Nanobody FW2 sequence

<400> SEQUENCE: 48

Trp Phe Arg Gln Ala Pro Gly Lys Gln Arg Glu Glu Val Ser
1               5                   10

<210> SEQ ID NO 49
<211> LENGTH: 14
<212> TYPE: PRT
<213> ORGANISM: Artificial
<220> FEATURE:
<223> OTHER INFORMATION: KERE-class Nanobody FW2 sequence

<400> SEQUENCE: 49

Trp Phe Arg Gln Pro Pro Gly Lys Val Arg Glu Phe Val Gly
1               5                   10

<210> SEQ ID NO 50
<211> LENGTH: 32
<212> TYPE: PRT
<213> ORGANISM: Artificial
<220> FEATURE:
<223> OTHER INFORMATION: KERE-class Nanobody FW3 sequence

<400> SEQUENCE: 50

Arg Phe Thr Ile Ser Arg Asp Asn Ala Lys Asn Thr Val Tyr Leu Gln
1               5                   10                  15

Met Asn Ser Leu Lys Pro Glu Asp Thr Ala Val Tyr Arg Cys Tyr Phe
                20                  25                  30

<210> SEQ ID NO 51
<211> LENGTH: 32
<212> TYPE: PRT
<213> ORGANISM: Artificial
<220> FEATURE:
<223> OTHER INFORMATION: KERE-class Nanobody FW3 sequence -continued

```
<400> SEQUENCE: 51

Arg Phe Ala Ile Ser Arg Asp Asn Asn Lys Asn Thr Gly Tyr Leu Gln
1               5                   10                  15

Met Asn Ser Leu Glu Pro Glu Asp Thr Ala Val Tyr Tyr Cys Ala Ala
                20                  25                  30

<210> SEQ ID NO 52
<211> LENGTH: 32
<212> TYPE: PRT
<213> ORGANISM: Artificial
<220> FEATURE:
<223> OTHER INFORMATION: KERE-class Nanobody FW3 sequence

<400> SEQUENCE: 52

Arg Phe Thr Val Ala Arg Asn Asn Ala Lys Asn Thr Val Asn Leu Glu
1               5                   10                  15

Met Asn Ser Leu Lys Pro Glu Asp Thr Ala Val Tyr Tyr Cys Ala Ala
                20                  25                  30

<210> SEQ ID NO 53
<211> LENGTH: 32
<212> TYPE: PRT
<213> ORGANISM: Artificial
<220> FEATURE:
<223> OTHER INFORMATION: KERE-class Nanobody FW3 sequence

<400> SEQUENCE: 53

Arg Phe Thr Ile Ser Arg Asp Ile Ala Lys Asn Thr Val Asp Leu Leu
1               5                   10                  15

Met Asn Asn Leu Glu Pro Glu Asp Thr Ala Val Tyr Tyr Cys Ala Ala
                20                  25                  30

<210> SEQ ID NO 54
<211> LENGTH: 32
<212> TYPE: PRT
<213> ORGANISM: Artificial
<220> FEATURE:
<223> OTHER INFORMATION: KERE-class Nanobody FW3 sequence

<400> SEQUENCE: 54

Arg Leu Thr Ile Ser Arg Asp Asn Ala Val Asp Thr Met Tyr Leu Gln
1               5                   10                  15

Met Asn Ser Leu Lys Pro Glu Asp Thr Ala Val Tyr Tyr Cys Ala Ala
                20                  25                  30

<210> SEQ ID NO 55
<211> LENGTH: 32
<212> TYPE: PRT
<213> ORGANISM: Artificial
<220> FEATURE:
<223> OTHER INFORMATION: KERE-class Nanobody FW3 sequence

<400> SEQUENCE: 55

Arg Phe Thr Ile Ser Arg Asp Asn Ala Lys Asn Thr Val Tyr Leu Gln
1               5                   10                  15

Met Asp Asn Val Lys Pro Glu Asp Thr Ala Ile Tyr Tyr Cys Ala Ala
                20                  25                  30

<210> SEQ ID NO 56
<211> LENGTH: 32
<212> TYPE: PRT
<213> ORGANISM: Artificial
<220> FEATURE:
<223> OTHER INFORMATION: KERE-class Nanobody FW3 sequence
```

```
<400> SEQUENCE: 56

Arg Phe Thr Ile Ser Lys Asp Ser Gly Lys Asn Thr Val Tyr Leu Gln
1               5                   10                  15

Met Thr Ser Leu Lys Pro Glu Asp Thr Ala Val Tyr Tyr Cys Ala Thr
            20                  25                  30

<210> SEQ ID NO 57
<211> LENGTH: 32
<212> TYPE: PRT
<213> ORGANISM: Artificial
<220> FEATURE:
<223> OTHER INFORMATION: KERE-class Nanobody FW3 sequence

<400> SEQUENCE: 57

Arg Phe Thr Ile Ser Arg Asp Ser Ala Lys Asn Met Met Tyr Leu Gln
1               5                   10                  15

Met Asn Asn Leu Lys Pro Gln Asp Thr Ala Val Tyr Tyr Cys Ala Ala
            20                  25                  30

<210> SEQ ID NO 58
<211> LENGTH: 32
<212> TYPE: PRT
<213> ORGANISM: Artificial
<220> FEATURE:
<223> OTHER INFORMATION: KERE-class Nanobody FW3 sequence

<400> SEQUENCE: 58

Arg Phe Thr Ile Ser Arg Glu Asn Asp Lys Ser Thr Val Tyr Leu Gln
1               5                   10                  15

Leu Asn Ser Leu Lys Pro Glu Asp Thr Ala Val Tyr Tyr Cys Ala Ala
            20                  25                  30

<210> SEQ ID NO 59
<211> LENGTH: 32
<212> TYPE: PRT
<213> ORGANISM: Artificial
<220> FEATURE:
<223> OTHER INFORMATION: KERE-class Nanobody FW3 sequence

<400> SEQUENCE: 59

Arg Phe Thr Ile Ser Arg Asp Tyr Ala Gly Asn Thr Ala Tyr Leu Gln
1               5                   10                  15

Met Asn Ser Leu Lys Pro Glu Asp Thr Gly Val Tyr Tyr Cys Ala Thr
            20                  25                  30

<210> SEQ ID NO 60
<211> LENGTH: 11
<212> TYPE: PRT
<213> ORGANISM: Artificial
<220> FEATURE:
<223> OTHER INFORMATION: KERE-class Nanobody FW4 sequence

<400> SEQUENCE: 60

Trp Gly Gln Gly Thr Gln Val Thr Val Ser Ser
1               5                   10

<210> SEQ ID NO 61
<211> LENGTH: 11
<212> TYPE: PRT
<213> ORGANISM: Artificial
<220> FEATURE:
<223> OTHER INFORMATION: KERE-class Nanobody FW4 sequence

<400> SEQUENCE: 61
```

```
Trp Gly Lys Gly Thr Leu Val Thr Val Ser Ser
1               5                   10
```

<210> SEQ ID NO 62
<211> LENGTH: 11
<212> TYPE: PRT
<213> ORGANISM: Artificial
<220> FEATURE:
<223> OTHER INFORMATION: KERE-class Nanobody FW4 sequence

<400> SEQUENCE: 62

```
Arg Gly Gln Gly Thr Arg Val Thr Val Ser Ser
1               5                   10
```

<210> SEQ ID NO 63
<211> LENGTH: 11
<212> TYPE: PRT
<213> ORGANISM: Artificial
<220> FEATURE:
<223> OTHER INFORMATION: KERE-class Nanobody FW4 sequence

<400> SEQUENCE: 63

```
Trp Gly Leu Gly Thr Gln Val Thr Ile Ser Ser
1               5                   10
```

<210> SEQ ID NO 64
<211> LENGTH: 30
<212> TYPE: PRT
<213> ORGANISM: Artificial
<220> FEATURE:
<223> OTHER INFORMATION: GLEW-class Nanobody FW1 sequence

<400> SEQUENCE: 64

```
Gln Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser
                20                  25                  30
```

<210> SEQ ID NO 65
<211> LENGTH: 30
<212> TYPE: PRT
<213> ORGANISM: Artificial
<220> FEATURE:
<223> OTHER INFORMATION: GLEW-class Nanobody FW1 sequence

<400> SEQUENCE: 65

```
Glu Val His Leu Val Glu Ser Gly Gly Gly Leu Val Arg Pro Gly Gly
1               5                   10                  15

Ser Leu Arg Leu Ser Cys Ala Ala Phe Gly Phe Ile Phe Lys
                20                  25                  30
```

<210> SEQ ID NO 66
<211> LENGTH: 30
<212> TYPE: PRT
<213> ORGANISM: Artificial
<220> FEATURE:
<223> OTHER INFORMATION: GLEW-class Nanobody FW1 sequence

<400> SEQUENCE: 66

```
Gln Val Lys Leu Glu Glu Ser Gly Gly Gly Leu Ala Gln Pro Gly Gly
1               5                   10                  15

Ser Leu Arg Leu Ser Cys Val Ala Ser Gly Phe Thr Phe Ser
                20                  25                  30
```

```
<210> SEQ ID NO 67
<211> LENGTH: 30
<212> TYPE: PRT
<213> ORGANISM: Artificial
<220> FEATURE:
<223> OTHER INFORMATION: GLEW-class Nanobody FW1 sequence

<400> SEQUENCE: 67

Glu Val Gln Leu Val Glu Ser Gly Gly Gly Leu Val Gln Pro Gly Gly
1               5                   10                  15

Ser Leu Arg Leu Ser Cys Val Cys Val Ser Ser Gly Cys Thr
            20                  25                  30

<210> SEQ ID NO 68
<211> LENGTH: 30
<212> TYPE: PRT
<213> ORGANISM: Artificial
<220> FEATURE:
<223> OTHER INFORMATION: GLEW-class Nanobody FW1 sequence

<400> SEQUENCE: 68

Glu Val Gln Leu Val Glu Ser Gly Gly Gly Leu Ala Leu Pro Gly Gly
1               5                   10                  15

Ser Leu Thr Leu Ser Cys Val Phe Ser Gly Ser Thr Phe Ser
            20                  25                  30

<210> SEQ ID NO 69
<211> LENGTH: 22
<212> TYPE: PRT
<213> ORGANISM: Artificial
<220> FEATURE:
<223> OTHER INFORMATION: GLEW-class Nanobody FW1 sequence

<400> SEQUENCE: 69

Val Glu Ser Gly Gly Gly Leu Val Gln Pro Gly Gly Ser Leu Arg Leu
1               5                   10                  15

Ser Cys Ala Ala Ser Gly
            20

<210> SEQ ID NO 70
<211> LENGTH: 22
<212> TYPE: PRT
<213> ORGANISM: Artificial
<220> FEATURE:
<223> OTHER INFORMATION: GLEW-class Nanobody FW1 sequence

<400> SEQUENCE: 70

Glu Glu Ser Gly Gly Gly Leu Ala Gln Pro Gly Gly Ser Leu Arg Leu
1               5                   10                  15

Ser Cys Val Ala Ser Gly
            20

<210> SEQ ID NO 71
<211> LENGTH: 22
<212> TYPE: PRT
<213> ORGANISM: Artificial
<220> FEATURE:
<223> OTHER INFORMATION: GLEW-class Nanobody FW1 sequence

<400> SEQUENCE: 71

Val Glu Ser Gly Gly Gly Leu Ala Leu Pro Gly Gly Ser Leu Thr Leu
1               5                   10                  15

Ser Cys Val Phe Ser Gly
            20
```

<210> SEQ ID NO 72
<211> LENGTH: 14
<212> TYPE: PRT
<213> ORGANISM: Artificial
<220> FEATURE:
<223> OTHER INFORMATION: GLEW-class Nanobody FW2 sequence

<400> SEQUENCE: 72

Trp Val Arg Gln Ala Pro Gly Lys Val Leu Glu Trp Val Ser
1               5                   10

<210> SEQ ID NO 73
<211> LENGTH: 14
<212> TYPE: PRT
<213> ORGANISM: Artificial
<220> FEATURE:
<223> OTHER INFORMATION: GLEW-class Nanobody FW2 sequence

<400> SEQUENCE: 73

Trp Val Arg Arg Pro Pro Gly Lys Gly Leu Glu Trp Val Ser
1               5                   10

<210> SEQ ID NO 74
<211> LENGTH: 14
<212> TYPE: PRT
<213> ORGANISM: Artificial
<220> FEATURE:
<223> OTHER INFORMATION: GLEW-class Nanobody FW2 sequence

<400> SEQUENCE: 74

Trp Val Arg Gln Ala Pro Gly Met Gly Leu Glu Trp Val Ser
1               5                   10

<210> SEQ ID NO 75
<211> LENGTH: 14
<212> TYPE: PRT
<213> ORGANISM: Artificial
<220> FEATURE:
<223> OTHER INFORMATION: GLEW-class Nanobody FW2 sequence

<400> SEQUENCE: 75

Trp Val Arg Gln Ala Pro Gly Lys Glu Pro Glu Trp Val Ser
1               5                   10

<210> SEQ ID NO 76
<211> LENGTH: 14
<212> TYPE: PRT
<213> ORGANISM: Artificial
<220> FEATURE:
<223> OTHER INFORMATION: GLEW-class Nanobody FW2 sequence

<400> SEQUENCE: 76

Trp Val Arg Gln Ala Pro Gly Lys Asp Gln Glu Trp Val Ser
1               5                   10

<210> SEQ ID NO 77
<211> LENGTH: 14
<212> TYPE: PRT
<213> ORGANISM: Artificial
<220> FEATURE:
<223> OTHER INFORMATION: GLEW-class Nanobody FW2 sequence

<400> SEQUENCE: 77

Trp Val Arg Gln Ala Pro Gly Lys Ala Glu Glu Trp Val Ser
1               5                   10

```
<210> SEQ ID NO 78
<211> LENGTH: 14
<212> TYPE: PRT
<213> ORGANISM: Artificial
<220> FEATURE:
<223> OTHER INFORMATION: GLEW-class Nanobody FW2 sequence

<400> SEQUENCE: 78

Trp Val Arg Gln Ala Pro Gly Lys Gly Leu Glu Trp Val Ala
1               5                   10

<210> SEQ ID NO 79
<211> LENGTH: 14
<212> TYPE: PRT
<213> ORGANISM: Artificial
<220> FEATURE:
<223> OTHER INFORMATION: GLEW-class Nanobody FW2 sequence

<400> SEQUENCE: 79

Trp Val Arg Gln Ala Pro Gly Arg Ala Thr Glu Trp Val Ser
1               5                   10

<210> SEQ ID NO 80
<211> LENGTH: 32
<212> TYPE: PRT
<213> ORGANISM: Artificial
<220> FEATURE:
<223> OTHER INFORMATION: GLEW-class Nanobody FW3 sequence

<400> SEQUENCE: 80

Arg Phe Thr Ile Ser Arg Asp Asn Ala Lys Asn Thr Leu Tyr Leu Gln
1               5                   10                  15

Met Asn Ser Leu Lys Pro Glu Asp Thr Ala Val Tyr Tyr Cys Val Lys
            20                  25                  30

<210> SEQ ID NO 81
<211> LENGTH: 32
<212> TYPE: PRT
<213> ORGANISM: Artificial
<220> FEATURE:
<223> OTHER INFORMATION: GLEW-class Nanobody FW3 sequence

<400> SEQUENCE: 81

Arg Phe Thr Ile Ser Arg Asp Asn Ala Arg Asn Thr Leu Tyr Leu Gln
1               5                   10                  15

Met Asp Ser Leu Ile Pro Glu Asp Thr Ala Leu Tyr Tyr Cys Ala Arg
            20                  25                  30

<210> SEQ ID NO 82
<211> LENGTH: 32
<212> TYPE: PRT
<213> ORGANISM: Artificial
<220> FEATURE:
<223> OTHER INFORMATION: GLEW-class Nanobody FW3 sequence

<400> SEQUENCE: 82

Arg Phe Thr Ser Ser Arg Asp Asn Ala Lys Ser Thr Leu Tyr Leu Gln
1               5                   10                  15

Met Asn Asp Leu Lys Pro Glu Asp Thr Ala Leu Tyr Tyr Cys Ala Arg
            20                  25                  30

<210> SEQ ID NO 83
<211> LENGTH: 32
<212> TYPE: PRT
<213> ORGANISM: Artificial
<220> FEATURE:
```

<223> OTHER INFORMATION: GLEW-class Nanobody FW3 sequence

<400> SEQUENCE: 83

Arg Phe Ile Ile Ser Arg Asp Asn Ala Lys Asn Thr Leu Tyr Leu Gln
1               5                   10                  15
Met Asn Ser Leu Gly Pro Glu Asp Thr Ala Met Tyr Tyr Cys Gln Arg
            20                  25                  30

<210> SEQ ID NO 84
<211> LENGTH: 32
<212> TYPE: PRT
<213> ORGANISM: Artificial
<220> FEATURE:
<223> OTHER INFORMATION: GLEW-class Nanobody FW3 sequence

<400> SEQUENCE: 84

Arg Phe Thr Ala Ser Arg Asp Asn Ala Lys Asn Thr Leu Tyr Leu Gln
1               5                   10                  15
Met Asn Ser Leu Lys Ser Glu Asp Thr Ala Arg Tyr Tyr Cys Ala Arg
            20                  25                  30

<210> SEQ ID NO 85
<211> LENGTH: 32
<212> TYPE: PRT
<213> ORGANISM: Artificial
<220> FEATURE:
<223> OTHER INFORMATION: GLEW-class Nanobody FW3 sequence

<400> SEQUENCE: 85

Arg Phe Thr Ile Ser Arg Asp Asn Ala Lys Asn Thr Leu Tyr Leu Gln
1               5                   10                  15
Met Asp Asp Leu Gln Ser Glu Asp Thr Ala Met Tyr Tyr Cys Gly Arg
            20                  25                  30

<210> SEQ ID NO 86
<211> LENGTH: 11
<212> TYPE: PRT
<213> ORGANISM: Artificial
<220> FEATURE:
<223> OTHER INFORMATION: GLEW-class Nanobody FW4 sequence

<400> SEQUENCE: 86

Gly Ser Gln Gly Thr Gln Val Thr Val Ser Ser
1               5                   10

<210> SEQ ID NO 87
<211> LENGTH: 11
<212> TYPE: PRT
<213> ORGANISM: Artificial
<220> FEATURE:
<223> OTHER INFORMATION: GLEW-class Nanobody FW4 sequence

<400> SEQUENCE: 87

Leu Arg Gly Gly Thr Gln Val Thr Val Ser Ser
1               5                   10

<210> SEQ ID NO 88
<211> LENGTH: 11
<212> TYPE: PRT
<213> ORGANISM: Artificial
<220> FEATURE:
<223> OTHER INFORMATION: GLEW-class Nanobody FW4 sequence

<400> SEQUENCE: 88

Arg Gly Gln Gly Thr Leu Val Thr Val Ser Ser

```
1               5                  10
```

<210> SEQ ID NO 89
<211> LENGTH: 11
<212> TYPE: PRT
<213> ORGANISM: Artificial
<220> FEATURE:
<223> OTHER INFORMATION: GLEW-class Nanobody FW4 sequence

<400> SEQUENCE: 89

```
Arg Ser Arg Gly Ile Gln Val Thr Val Ser Ser
1               5                  10
```

<210> SEQ ID NO 90
<211> LENGTH: 11
<212> TYPE: PRT
<213> ORGANISM: Artificial
<220> FEATURE:
<223> OTHER INFORMATION: GLEW-class Nanobody FW4 sequence

<400> SEQUENCE: 90

```
Trp Gly Lys Gly Thr Gln Val Thr Val Ser Ser
1               5                  10
```

<210> SEQ ID NO 91
<211> LENGTH: 11
<212> TYPE: PRT
<213> ORGANISM: Artificial
<220> FEATURE:
<223> OTHER INFORMATION: GLEW-class Nanobody FW4 sequence

<400> SEQUENCE: 91

```
Trp Gly Gln Gly Thr Gln Val Thr Val Ser Ser
1               5                  10
```

<210> SEQ ID NO 92
<211> LENGTH: 30
<212> TYPE: PRT
<213> ORGANISM: Artificial
<220> FEATURE:
<223> OTHER INFORMATION: P,R,S 103-class Nanobody FW1 sequence

<400> SEQUENCE: 92

```
Ala Val Gln Leu Val Glu Ser Gly Gly Gly Leu Val Gln Ala Gly Gly
1               5                  10                  15

Ser Leu Arg Leu Ser Cys Ala Ala Ser Gly Arg Thr Phe Ser
            20                  25                  30
```

<210> SEQ ID NO 93
<211> LENGTH: 30
<212> TYPE: PRT
<213> ORGANISM: Artificial
<220> FEATURE:
<223> OTHER INFORMATION: P,R,S 103-class Nanobody FW1 sequence

<400> SEQUENCE: 93

```
Gln Val Gln Leu Gln Glu Ser Gly Gly Gly Met Val Gln Pro Gly Gly
1               5                  10                  15

Ser Leu Arg Leu Ser Cys Ala Ala Ser Gly Phe Asp Phe Gly
            20                  25                  30
```

<210> SEQ ID NO 94
<211> LENGTH: 30
<212> TYPE: PRT
<213> ORGANISM: Artificial
<220> FEATURE:

<223> OTHER INFORMATION: P,R,S 103-class Nanobody FW1 sequence

<400> SEQUENCE: 94

```
Glu Val His Leu Val Glu Ser Gly Gly Gly Leu Val Arg Pro Gly Gly
1               5                   10                  15
Ser Leu Arg Leu Ser Cys Ala Ala Phe Gly Phe Ile Phe Lys
            20                  25                  30
```

<210> SEQ ID NO 95
<211> LENGTH: 30
<212> TYPE: PRT
<213> ORGANISM: Artificial
<220> FEATURE:
<223> OTHER INFORMATION: P,R,S 103-class Nanobody FW1 sequence

<400> SEQUENCE: 95

```
Gln Val Gln Leu Ala Glu Ser Gly Gly Gly Leu Val Gln Pro Gly Gly
1               5                   10                  15
Ser Leu Lys Leu Ser Cys Ala Ala Ser Arg Thr Ile Val Ser
            20                  25                  30
```

<210> SEQ ID NO 96
<211> LENGTH: 30
<212> TYPE: PRT
<213> ORGANISM: Artificial
<220> FEATURE:
<223> OTHER INFORMATION: P,R,S 103-class Nanobody FW1 sequence

<400> SEQUENCE: 96

```
Gln Glu His Leu Val Glu Ser Gly Gly Gly Leu Val Asp Ile Gly Gly
1               5                   10                  15
Ser Leu Arg Leu Ser Cys Ala Ala Ser Glu Arg Ile Phe Ser
            20                  25                  30
```

<210> SEQ ID NO 97
<211> LENGTH: 30
<212> TYPE: PRT
<213> ORGANISM: Artificial
<220> FEATURE:
<223> OTHER INFORMATION: P,R,S 103-class Nanobody FW1 sequence

<400> SEQUENCE: 97

```
Gln Val Lys Leu Glu Glu Ser Gly Gly Gly Leu Ala Gln Pro Gly Gly
1               5                   10                  15
Ser Leu Arg Leu Ser Cys Val Ala Ser Gly Phe Thr Phe Ser
            20                  25                  30
```

<210> SEQ ID NO 98
<211> LENGTH: 30
<212> TYPE: PRT
<213> ORGANISM: Artificial
<220> FEATURE:
<223> OTHER INFORMATION: P,R,S 103-class Nanobody FW1 sequence

<400> SEQUENCE: 98

```
Glu Val Gln Leu Val Glu Ser Gly Gly Gly Leu Val Gln Pro Gly Gly
1               5                   10                  15
Ser Leu Arg Leu Ser Cys Val Cys Val Ser Ser Gly Cys Thr
            20                  25                  30
```

<210> SEQ ID NO 99
<211> LENGTH: 30
<212> TYPE: PRT
<213> ORGANISM: Artificial

```
<220> FEATURE:
<223> OTHER INFORMATION: P,R,S 103-class Nanobody FW1 sequence

<400> SEQUENCE: 99

Glu Val Gln Leu Val Glu Ser Gly Gly Gly Leu Ala Leu Pro Gly Gly
1               5                   10                  15
Ser Leu Thr Leu Ser Cys Val Phe Ser Gly Ser Thr Phe Ser
            20                  25                  30

<210> SEQ ID NO 100
<211> LENGTH: 22
<212> TYPE: PRT
<213> ORGANISM: Artificial
<220> FEATURE:
<223> OTHER INFORMATION: P,R,S 103-class Nanobody FW1 sequence

<400> SEQUENCE: 100

Val Glu Ser Gly Gly Gly Leu Val Gln Ala Gly Gly Ser Leu Arg Leu
1               5                   10                  15
Ser Cys Ala Ala Ser Gly
            20

<210> SEQ ID NO 101
<211> LENGTH: 22
<212> TYPE: PRT
<213> ORGANISM: Artificial
<220> FEATURE:
<223> OTHER INFORMATION: P,R,S 103-class Nanobody FW1 sequence

<400> SEQUENCE: 101

Ala Glu Ser Gly Gly Gly Leu Val Gln Pro Gly Gly Ser Leu Lys Leu
1               5                   10                  15
Ser Cys Ala Ala Ser Arg
            20

<210> SEQ ID NO 102
<211> LENGTH: 14
<212> TYPE: PRT
<213> ORGANISM: Artificial
<220> FEATURE:
<223> OTHER INFORMATION: P,R,S 103-class Nanobody FW2 sequence

<400> SEQUENCE: 102

Trp Phe Arg Gln Ala Pro Gly Lys Glu Arg Glu Phe Val Ala
1               5                   10

<210> SEQ ID NO 103
<211> LENGTH: 14
<212> TYPE: PRT
<213> ORGANISM: Artificial
<220> FEATURE:
<223> OTHER INFORMATION: P,R,S 103-class Nanobody FW2 sequence

<400> SEQUENCE: 103

Trp Val Arg Gln Ala Pro Gly Lys Val Leu Glu Trp Val Ser
1               5                   10

<210> SEQ ID NO 104
<211> LENGTH: 14
<212> TYPE: PRT
<213> ORGANISM: Artificial
<220> FEATURE:
<223> OTHER INFORMATION: P,R,S 103-class Nanobody FW2 sequence

<400> SEQUENCE: 104
```

Trp Val Arg Arg Pro Gly Lys Gly Leu Glu Trp Val Ser
1               5                   10

<210> SEQ ID NO 105
<211> LENGTH: 14
<212> TYPE: PRT
<213> ORGANISM: Artificial
<220> FEATURE:
<223> OTHER INFORMATION: P,R,S 103-class Nanobody FW2 sequence

<400> SEQUENCE: 105

Trp Ile Arg Gln Ala Pro Gly Lys Glu Arg Glu Gly Val Ser
1               5                   10

<210> SEQ ID NO 106
<211> LENGTH: 14
<212> TYPE: PRT
<213> ORGANISM: Artificial
<220> FEATURE:
<223> OTHER INFORMATION: P,R,S 103-class Nanobody FW2 sequence

<400> SEQUENCE: 106

Trp Val Arg Gln Tyr Pro Gly Lys Glu Pro Glu Trp Val Ser
1               5                   10

<210> SEQ ID NO 107
<211> LENGTH: 14
<212> TYPE: PRT
<213> ORGANISM: Artificial
<220> FEATURE:
<223> OTHER INFORMATION: P,R,S 103-class Nanobody FW2 sequence

<400> SEQUENCE: 107

Trp Phe Arg Gln Pro Pro Gly Lys Glu His Glu Phe Val Ala
1               5                   10

<210> SEQ ID NO 108
<211> LENGTH: 14
<212> TYPE: PRT
<213> ORGANISM: Artificial
<220> FEATURE:
<223> OTHER INFORMATION: P,R,S 103-class Nanobody FW2 sequence

<400> SEQUENCE: 108

Trp Tyr Arg Gln Ala Pro Gly Lys Arg Thr Glu Leu Val Ala
1               5                   10

<210> SEQ ID NO 109
<211> LENGTH: 14
<212> TYPE: PRT
<213> ORGANISM: Artificial
<220> FEATURE:
<223> OTHER INFORMATION: P,R,S 103-class Nanobody FW2 sequence

<400> SEQUENCE: 109

Trp Leu Arg Gln Ala Pro Gly Gln Gly Leu Glu Trp Val Ser
1               5                   10

<210> SEQ ID NO 110
<211> LENGTH: 14
<212> TYPE: PRT
<213> ORGANISM: Artificial
<220> FEATURE:
<223> OTHER INFORMATION: P,R,S 103-class Nanobody FW2 sequence

<400> SEQUENCE: 110

Trp Leu Arg Gln Thr Pro Gly Lys Gly Leu Glu Trp Val Gly

```
<210> SEQ ID NO 111
<211> LENGTH: 14
<212> TYPE: PRT
<213> ORGANISM: Artificial
<220> FEATURE:
<223> OTHER INFORMATION: P,R,S 103-class Nanobody FW2 sequence

<400> SEQUENCE: 111

Trp Val Arg Gln Ala Pro Gly Lys Ala Glu Glu Phe Val Ser
1               5                   10

<210> SEQ ID NO 112
<211> LENGTH: 32
<212> TYPE: PRT
<213> ORGANISM: Artificial
<220> FEATURE:
<223> OTHER INFORMATION: P,R,S 103-class Nanobody FW3 sequence

<400> SEQUENCE: 112

Arg Phe Thr Ile Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Ala Ala
            20                  25                  30

<210> SEQ ID NO 113
<211> LENGTH: 32
<212> TYPE: PRT
<213> ORGANISM: Artificial
<220> FEATURE:
<223> OTHER INFORMATION: P,R,S 103-class Nanobody FW3 sequence

<400> SEQUENCE: 113

Arg Phe Thr Ile Ser Arg Asp Asn Ala Arg Asn Thr Leu Tyr Leu Gln
1               5                   10                  15

Met Asp Ser Leu Ile Pro Glu Asp Thr Ala Leu Tyr Tyr Cys Ala Arg
            20                  25                  30

<210> SEQ ID NO 114
<211> LENGTH: 32
<212> TYPE: PRT
<213> ORGANISM: Artificial
<220> FEATURE:
<223> OTHER INFORMATION: P,R,S 103-class Nanobody FW3 sequence

<400> SEQUENCE: 114

Arg Phe Thr Ile Ser Arg Asp Asn Ala Lys Asn Glu Met Tyr Leu Gln
1               5                   10                  15

Met Asn Asn Leu Lys Thr Glu Asp Thr Gly Val Tyr Trp Cys Gly Ala
            20                  25                  30

<210> SEQ ID NO 115
<211> LENGTH: 32
<212> TYPE: PRT
<213> ORGANISM: Artificial
<220> FEATURE:
<223> OTHER INFORMATION: P,R,S 103-class Nanobody FW3 sequence

<400> SEQUENCE: 115

Arg Phe Thr Ile Ser Ser Asp Ser Asn Arg Asn Met Ile Tyr Leu Gln
1               5                   10                  15

Met Asn Asn Leu Lys Pro Glu Asp Thr Ala Val Tyr Tyr Cys Ala Ala
            20                  25                  30
```

<210> SEQ ID NO 116
<211> LENGTH: 32
<212> TYPE: PRT
<213> ORGANISM: Artificial
<220> FEATURE:
<223> OTHER INFORMATION: P,R,S 103-class Nanobody FW3 sequence

<400> SEQUENCE: 116

Arg Phe Thr Ile Ser Arg Asp Asn Ala Lys Asn Met Leu Tyr Leu His
1               5                   10                  15

Leu Asn Asn Leu Lys Ser Glu Asp Thr Ala Val Tyr Tyr Cys Arg Arg
            20                  25                  30

<210> SEQ ID NO 117
<211> LENGTH: 32
<212> TYPE: PRT
<213> ORGANISM: Artificial
<220> FEATURE:
<223> OTHER INFORMATION: P,R,S 103-class Nanobody FW3 sequence

<400> SEQUENCE: 117

Arg Phe Thr Ile Ser Arg Asp Asn Ala Lys Lys Thr Val Tyr Leu Arg
1               5                   10                  15

Leu Asn Ser Leu Asn Pro Glu Asp Thr Ala Val Tyr Ser Cys Asn Leu
            20                  25                  30

<210> SEQ ID NO 118
<211> LENGTH: 32
<212> TYPE: PRT
<213> ORGANISM: Artificial
<220> FEATURE:
<223> OTHER INFORMATION: P,R,S 103-class Nanobody FW3 sequence

<400> SEQUENCE: 118

Arg Phe Lys Ile Ser Arg Asp Asn Ala Lys Lys Thr Leu Tyr Leu Gln
1               5                   10                  15

Met Asn Ser Leu Gly Pro Glu Asp Thr Ala Met Tyr Tyr Cys Gln Arg
            20                  25                  30

<210> SEQ ID NO 119
<211> LENGTH: 32
<212> TYPE: PRT
<213> ORGANISM: Artificial
<220> FEATURE:
<223> OTHER INFORMATION: P,R,S 103-class Nanobody FW3 sequence

<400> SEQUENCE: 119

Arg Phe Thr Val Ser Arg Asp Asn Gly Lys Asn Thr Ala Tyr Leu Arg
1               5                   10                  15

Met Asn Ser Leu Lys Pro Glu Asp Thr Ala Asp Tyr Tyr Cys Ala Val
            20                  25                  30

<210> SEQ ID NO 120
<211> LENGTH: 11
<212> TYPE: PRT
<213> ORGANISM: Artificial
<220> FEATURE:
<223> OTHER INFORMATION: P,R,S 103-class Nanobody FW4 sequence

<400> SEQUENCE: 120

Arg Gly Gln Gly Thr Gln Val Thr Val Ser Ser
1               5                   10

<210> SEQ ID NO 121

```
<211> LENGTH: 11
<212> TYPE: PRT
<213> ORGANISM: Artificial
<220> FEATURE:
<223> OTHER INFORMATION: P,R,S 103-class Nanobody FW4 sequence

<400> SEQUENCE: 121

Leu Arg Gly Gly Thr Gln Val Thr Val Ser Ser
1               5                   10

<210> SEQ ID NO 122
<211> LENGTH: 11
<212> TYPE: PRT
<213> ORGANISM: Artificial
<220> FEATURE:
<223> OTHER INFORMATION: P,R,S 103-class Nanobody FW4 sequence

<400> SEQUENCE: 122

Gly Asn Lys Gly Thr Leu Val Thr Val Ser Ser
1               5                   10

<210> SEQ ID NO 123
<211> LENGTH: 11
<212> TYPE: PRT
<213> ORGANISM: Artificial
<220> FEATURE:
<223> OTHER INFORMATION: P,R,S 103-class Nanobody FW4 sequence

<400> SEQUENCE: 123

Ser Ser Pro Gly Thr Gln Val Thr Val Ser Ser
1               5                   10

<210> SEQ ID NO 124
<211> LENGTH: 11
<212> TYPE: PRT
<213> ORGANISM: Artificial
<220> FEATURE:
<223> OTHER INFORMATION: P,R,S 103-class Nanobody FW4 sequence

<400> SEQUENCE: 124

Ser Ser Gln Gly Thr Leu Val Thr Val Ser Ser
1               5                   10

<210> SEQ ID NO 125
<211> LENGTH: 11
<212> TYPE: PRT
<213> ORGANISM: Artificial
<220> FEATURE:
<223> OTHER INFORMATION: P,R,S 103-class Nanobody FW4 sequence

<400> SEQUENCE: 125

Arg Ser Arg Gly Ile Gln Val Thr Val Ser Ser
1               5                   10

<210> SEQ ID NO 126
<211> LENGTH: 30
<212> TYPE: PRT
<213> ORGANISM: Artificial
<220> FEATURE:
<223> OTHER INFORMATION: Nanobody or nanobody construct

<400> SEQUENCE: 126

Glu Val Gln Leu Val Glu Ser Gly Gly Asp Val Val Gln Ala Gly Gly
1               5                   10                  15

Ser Leu Arg Leu Ser Cys Leu Ala Ser Gly Phe Thr Phe Asp
            20                  25                  30
```

<210> SEQ ID NO 127
<211> LENGTH: 30
<212> TYPE: PRT
<213> ORGANISM: Artificial
<220> FEATURE:
<223> OTHER INFORMATION: Nanobody or nanobody construct

<400> SEQUENCE: 127

Glu Val Gln Leu Val Glu Ser Gly Gly Asp Val Val Gln Ala Gly Gly
1               5                   10                  15

Ser Leu Arg Leu Ser Cys Leu Ala Ser Gly Phe Thr Phe Asp
            20                  25                  30

<210> SEQ ID NO 128
<211> LENGTH: 30
<212> TYPE: PRT
<213> ORGANISM: Artificial
<220> FEATURE:
<223> OTHER INFORMATION: Nanobody or nanobody construct

<400> SEQUENCE: 128

Glu Met Gln Leu Val Glu Ser Gly Gly Asp Val Val Gln Ala Gly Gly
1               5                   10                  15

Ser Leu Arg Leu Ser Cys Leu Ala Ser Gly Phe Thr Phe Asp
            20                  25                  30

<210> SEQ ID NO 129
<211> LENGTH: 30
<212> TYPE: PRT
<213> ORGANISM: Artificial
<220> FEATURE:
<223> OTHER INFORMATION: Nanobody or nanobody construct

<400> SEQUENCE: 129

Glu Val Gln Leu Val Glu Ser Gly Gly Asp Val Val Gln Ala Gly Gly
1               5                   10                  15

Ser Leu Arg Leu Ser Cys Leu Ala Ser Gly Phe Thr Phe Asp
            20                  25                  30

<210> SEQ ID NO 130
<211> LENGTH: 30
<212> TYPE: PRT
<213> ORGANISM: Artificial
<220> FEATURE:
<223> OTHER INFORMATION: Nanobody or nanobody construct

<400> SEQUENCE: 130

Glu Val Gln Leu Val Glu Ser Gly Gly Asp Val Val Gln Ala Gly Gly
1               5                   10                  15

Ser Leu Arg Leu Ser Cys Leu Ala Ser Gly Phe Thr Phe Asp
            20                  25                  30

<210> SEQ ID NO 131
<211> LENGTH: 30
<212> TYPE: PRT
<213> ORGANISM: Artificial
<220> FEATURE:
<223> OTHER INFORMATION: Nanobody or nanobody construct

<400> SEQUENCE: 131

Glu Val Gln Leu Val Glu Ser Gly Gly Asp Val Val Gln Ala Gly Gly
1               5                   10                  15

Ser Leu Arg Leu Ser Cys Leu Ala Ser Gly Phe Thr Phe Asp
            20                  25                  30

```
<210> SEQ ID NO 132
<211> LENGTH: 30
<212> TYPE: PRT
<213> ORGANISM: Artificial
<220> FEATURE:
<223> OTHER INFORMATION: Nanobody or nanobody construct

<400> SEQUENCE: 132

Glu Val Gln Leu Val Glu Ser Gly Gly Asp Val Val Gln Ala Gly Gly
1               5                   10                  15

Ser Leu Arg Leu Ser Cys Leu Ala Ser Gly Phe Thr Phe Asp
            20                  25                  30

<210> SEQ ID NO 133
<211> LENGTH: 30
<212> TYPE: PRT
<213> ORGANISM: Artificial
<220> FEATURE:
<223> OTHER INFORMATION: Nanobody or nanobody construct

<400> SEQUENCE: 133

Glu Val Gln Leu Val Glu Ser Gly Gly Gly Leu Val Gln Thr Gly Gly
1               5                   10                  15

Ser Leu Arg Leu Ser Cys Ala Ala Ser Gly Phe Thr Leu Asp
            20                  25                  30

<210> SEQ ID NO 134
<211> LENGTH: 30
<212> TYPE: PRT
<213> ORGANISM: Artificial
<220> FEATURE:
<223> OTHER INFORMATION: Nanobody or nanobody construct

<400> SEQUENCE: 134

Glu Val Gln Leu Val Glu Ser Gly Gly Gly Leu Val Gln Thr Gly Gly
1               5                   10                  15

Ser Leu Arg Leu Ser Cys Ala Ala Ser Gly Phe Thr Leu Asp
            20                  25                  30

<210> SEQ ID NO 135
<211> LENGTH: 30
<212> TYPE: PRT
<213> ORGANISM: Artificial
<220> FEATURE:
<223> OTHER INFORMATION: Nanobody or nanobody construct

<400> SEQUENCE: 135

Glu Val Gln Leu Val Glu Ser Gly Gly Gly Leu Val Gln Thr Gly Gly
1               5                   10                  15

Ser Leu Arg Leu Ser Cys Ala Ala Ser Gly Phe Thr Leu Asp
            20                  25                  30

<210> SEQ ID NO 136
<211> LENGTH: 30
<212> TYPE: PRT
<213> ORGANISM: Artificial
<220> FEATURE:
<223> OTHER INFORMATION: Nanobody or nanobody construct

<400> SEQUENCE: 136

Glu Val Gln Leu Val Glu Ser Gly Gly Gly Leu Val Gln Thr Gly Gly
1               5                   10                  15

Ser Leu Arg Leu Ser Cys Ala Ala Ser Gly Phe Thr Leu Asp
```

```
                 20                  25                  30

<210> SEQ ID NO 137
<211> LENGTH: 30
<212> TYPE: PRT
<213> ORGANISM: Artificial
<220> FEATURE:
<223> OTHER INFORMATION: Nanobody or nanobody construct

<400> SEQUENCE: 137

Glu Val Gln Leu Val Glu Ser Gly Gly Gly Leu Val Gln Ala Gly Gly
1               5                   10                  15

Ser Leu Arg Leu Ser Cys Ala Ala Ser Glu Arg Thr Tyr Ser
            20                  25                  30

<210> SEQ ID NO 138
<211> LENGTH: 30
<212> TYPE: PRT
<213> ORGANISM: Artificial
<220> FEATURE:
<223> OTHER INFORMATION: Nanobody or nanobody construct

<400> SEQUENCE: 138

Glu Val Gln Leu Val Glu Ser Gly Gly Gly Leu Val Gln Ala Gly Gly
1               5                   10                  15

Ser Leu Arg Leu Ser Cys Ala Ala Ser Glu Arg Thr Tyr Ser
            20                  25                  30

<210> SEQ ID NO 139
<211> LENGTH: 30
<212> TYPE: PRT
<213> ORGANISM: Artificial
<220> FEATURE:
<223> OTHER INFORMATION: Nanobody or nanobody construct

<400> SEQUENCE: 139

Glu Val Gln Leu Val Glu Ser Gly Gly Gly Leu Val Gln Ala Gly Gly
1               5                   10                  15

Ser Leu Arg Leu Ser Cys Ala Ala Ser Glu Arg Thr Tyr Ser
            20                  25                  30

<210> SEQ ID NO 140
<211> LENGTH: 30
<212> TYPE: PRT
<213> ORGANISM: Artificial
<220> FEATURE:
<223> OTHER INFORMATION: Nanobody or nanobody construct

<400> SEQUENCE: 140

Glu Val Gln Leu Val Glu Ser Gly Gly Gly Leu Val Gln Ala Gly Gly
1               5                   10                  15

Ser Leu Arg Leu Ser Cys Ala Ala Pro Glu Arg Thr Tyr Ser
            20                  25                  30

<210> SEQ ID NO 141
<211> LENGTH: 30
<212> TYPE: PRT
<213> ORGANISM: Artificial
<220> FEATURE:
<223> OTHER INFORMATION: Nanobody or nanobody construct

<400> SEQUENCE: 141

Glu Val Gln Leu Val Glu Ser Gly Gly Gly Leu Val Gln Ala Gly Gly
1               5                   10                  15
```

Ser Leu Arg Leu Ser Cys Ala Ala Ser Glu Arg Thr Tyr Ser
            20                  25                  30

<210> SEQ ID NO 142
<211> LENGTH: 30
<212> TYPE: PRT
<213> ORGANISM: Artificial
<220> FEATURE:
<223> OTHER INFORMATION: Nanobody or nanobody construct

<400> SEQUENCE: 142

Glu Val Gln Leu Val Glu Ser Arg Gly Gly Leu Val Gln Ala Gly Gly
1               5                   10                  15

Ser Leu Arg Leu Ser Cys Ala Ala Ser Glu Arg Thr Tyr Ser
            20                  25                  30

<210> SEQ ID NO 143
<211> LENGTH: 30
<212> TYPE: PRT
<213> ORGANISM: Artificial
<220> FEATURE:
<223> OTHER INFORMATION: Nanobody or nanobody construct

<400> SEQUENCE: 143

Glu Val Gln Leu Val Glu Ser Gly Gly Gly Leu Val Gln Ala Gly Gly
1               5                   10                  15

Ser Leu Arg Leu Ser Cys Ala Ala Ser Glu Arg Thr Tyr Ser
            20                  25                  30

<210> SEQ ID NO 144
<211> LENGTH: 30
<212> TYPE: PRT
<213> ORGANISM: Artificial
<220> FEATURE:
<223> OTHER INFORMATION: Nanobody or nanobody construct

<400> SEQUENCE: 144

Glu Val Gln Leu Val Glu Ser Gly Gly Gly Leu Val Gln Pro Gly Gly
1               5                   10                  15

Ser Leu Arg Leu Ser Cys Ala Ala Ser Glu Arg Thr Tyr Ser
            20                  25                  30

<210> SEQ ID NO 145
<211> LENGTH: 30
<212> TYPE: PRT
<213> ORGANISM: Artificial
<220> FEATURE:
<223> OTHER INFORMATION: Nanobody or nanobody construct

<400> SEQUENCE: 145

Glu Val Gln Leu Val Glu Ser Gly Gly Gly Leu Val Gln Ala Gly Gly
1               5                   10                  15

Ser Leu Arg Leu Ser Cys Ala Ala Ser Glu Arg Thr Tyr Ser
            20                  25                  30

<210> SEQ ID NO 146
<211> LENGTH: 30
<212> TYPE: PRT
<213> ORGANISM: Artificial
<220> FEATURE:
<223> OTHER INFORMATION: Nanobody or nanobody construct

<400> SEQUENCE: 146

Lys Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Val Ser
            20                  25                  30

<210> SEQ ID NO 147
<211> LENGTH: 30
<212> TYPE: PRT
<213> ORGANISM: Artificial
<220> FEATURE:
<223> OTHER INFORMATION: Nanobody or nanobody construct

<400> SEQUENCE: 147

Glu Val Gln Leu Met Glu Ser Gly Gly Gly Leu Val Gln Ala Gly Gly
1               5                   10                  15

Ser Leu Arg Leu Ser Cys Ala Ala Ser Gly Arg Thr Val Ser
            20                  25                  30

<210> SEQ ID NO 148
<211> LENGTH: 30
<212> TYPE: PRT
<213> ORGANISM: Artificial
<220> FEATURE:
<223> OTHER INFORMATION: Nanobody or nanobody construct

<400> SEQUENCE: 148

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Val Ser
            20                  25                  30

<210> SEQ ID NO 149
<211> LENGTH: 30
<212> TYPE: PRT
<213> ORGANISM: Artificial
<220> FEATURE:
<223> OTHER INFORMATION: Nanobody or nanobody construct

<400> SEQUENCE: 149

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Val Ser
            20                  25                  30

<210> SEQ ID NO 150
<211> LENGTH: 30
<212> TYPE: PRT
<213> ORGANISM: Artificial
<220> FEATURE:
<223> OTHER INFORMATION: Nanobody or nanobody construct

<400> SEQUENCE: 150

Glu Val Gln Leu Met Glu Ser Gly Gly Gly Leu Val Gln Ala Gly Gly
1               5                   10                  15

Pro Leu Arg Leu Ser Cys Ala Ala Ser Gly Arg Thr Val Ser
            20                  25                  30

<210> SEQ ID NO 151
<211> LENGTH: 30
<212> TYPE: PRT
<213> ORGANISM: Artificial
<220> FEATURE:
<223> OTHER INFORMATION: Nanobody or nanobody construct

<400> SEQUENCE: 151

Ala Val Gln Leu Val Glu Ser Gly Gly Gly Leu Val Gln Ala Gly Gly

```
                1               5                  10                  15
Ser Leu Arg Leu Ser Cys Ala Ala Ser Gly Asn Phe Phe Arg
            20                  25                  30

<210> SEQ ID NO 152
<211> LENGTH: 30
<212> TYPE: PRT
<213> ORGANISM: Artificial
<220> FEATURE:
<223> OTHER INFORMATION: Nanobody or nanobody construct

<400> SEQUENCE: 152

Glu Val Gln Leu Val Glu Ser Gly Gly Gly Leu Val Gln Ala Gly Gly
1               5                  10                  15

Ser Leu Arg Leu Ser Cys Ala Ala Ser Gly Asn Phe Phe Arg
            20                  25                  30

<210> SEQ ID NO 153
<211> LENGTH: 30
<212> TYPE: PRT
<213> ORGANISM: Artificial
<220> FEATURE:
<223> OTHER INFORMATION: Nanobody or nanobody construct

<400> SEQUENCE: 153

Glu Val Gln Leu Val Glu Ser Gly Gly Gly Leu Val Gln Ala Gly Gly
1               5                  10                  15

Pro Leu Arg Leu Ser Cys Ala Ala Ser Gly Asn Phe Phe Arg
            20                  25                  30

<210> SEQ ID NO 154
<211> LENGTH: 30
<212> TYPE: PRT
<213> ORGANISM: Artificial
<220> FEATURE:
<223> OTHER INFORMATION: Nanobody or nanobody construct

<400> SEQUENCE: 154

Glu Val Gln Leu Val Glu Ser Gly Gly Gly Leu Val Gln Ala Gly Gly
1               5                  10                  15

Ser Leu Arg Leu Ser Cys Ala Ala Ser Gly Ser Phe Phe Arg
            20                  25                  30

<210> SEQ ID NO 155
<211> LENGTH: 30
<212> TYPE: PRT
<213> ORGANISM: Artificial
<220> FEATURE:
<223> OTHER INFORMATION: Nanobody or nanobody construct

<400> SEQUENCE: 155

Glu Val Gln Leu Val Glu Ser Gly Gly Gly Leu Val Gln Ala Gly Gly
1               5                  10                  15

Pro Leu Arg Leu Ser Cys Ala Ala Ser Gly Ser Phe Phe Arg
            20                  25                  30

<210> SEQ ID NO 156
<211> LENGTH: 30
<212> TYPE: PRT
<213> ORGANISM: Artificial
<220> FEATURE:
<223> OTHER INFORMATION: Nanobody or nanobody construct

<400> SEQUENCE: 156
```

Glu Val Gln Leu Val Glu Ser Gly Gly Gly Leu Val Gln Ala Gly Gly
1               5                   10                  15

Ser Leu Arg Leu Ser Cys Ala Ala Ser Gly Asn Phe Phe Arg
            20                  25                  30

<210> SEQ ID NO 157
<211> LENGTH: 30
<212> TYPE: PRT
<213> ORGANISM: Artificial
<220> FEATURE:
<223> OTHER INFORMATION: Nanobody or nanobody construct

<400> SEQUENCE: 157

Glu Val Gln Leu Val Glu Ser Gly Gly Gly Leu Val Gln Ala Gly Gly
1               5                   10                  15

Ser Leu Gly Leu Ser Cys Ala Ala Ser Gly Asn Phe Phe Arg
            20                  25                  30

<210> SEQ ID NO 158
<211> LENGTH: 30
<212> TYPE: PRT
<213> ORGANISM: Artificial
<220> FEATURE:
<223> OTHER INFORMATION: Nanobody or nanobody construct

<400> SEQUENCE: 158

Glu Met Gln Leu Val Glu Ser Gly Gly Gly Leu Val Gln Ala Gly Gly
1               5                   10                  15

Ser Leu Arg Leu Ser Cys Ala Ala Ser Gly Asn Phe Phe Arg
            20                  25                  30

<210> SEQ ID NO 159
<211> LENGTH: 30
<212> TYPE: PRT
<213> ORGANISM: Artificial
<220> FEATURE:
<223> OTHER INFORMATION: Nanobody or nanobody construct

<400> SEQUENCE: 159

Glu Val Gln Leu Val Glu Ser Gly Gly Gly Leu Val Gln Ala Gly Gly
1               5                   10                  15

Ser Leu Arg Leu Leu Cys Ala Ala Ser Gly Ser Phe Phe Arg
            20                  25                  30

<210> SEQ ID NO 160
<211> LENGTH: 30
<212> TYPE: PRT
<213> ORGANISM: Artificial
<220> FEATURE:
<223> OTHER INFORMATION: Nanobody or nanobody construct

<400> SEQUENCE: 160

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Phe Phe Arg
            20                  25                  30

<210> SEQ ID NO 161
<211> LENGTH: 30
<212> TYPE: PRT
<213> ORGANISM: Artificial
<220> FEATURE:
<223> OTHER INFORMATION: Nanobody or nanobody construct

<400> SEQUENCE: 161

Glu Val Gln Leu Val Glu Ser Gly Gly Gly Leu Val Gln Ala Gly
1               5                   10                  15

Ser Leu Arg Leu Ser Cys Ala Ala Ser Gly Ser Phe Phe Arg
            20                  25                  30

<210> SEQ ID NO 162
<211> LENGTH: 30
<212> TYPE: PRT
<213> ORGANISM: Artificial
<220> FEATURE:
<223> OTHER INFORMATION: Nanobody or nanobody construct

<400> SEQUENCE: 162

Glu Val Gln Leu Val Lys Ser Gly Gly Gly Leu Val Gln Ala Gly Gly
1               5                   10                  15

Ser Leu Arg Leu Ser Cys Ala Ala Ser Gly Ser Phe Phe Arg
            20                  25                  30

<210> SEQ ID NO 163
<211> LENGTH: 30
<212> TYPE: PRT
<213> ORGANISM: Artificial
<220> FEATURE:
<223> OTHER INFORMATION: Nanobody or nanobody construct

<400> SEQUENCE: 163

Lys Val Gln Leu Val Glu Ser Gly Gly Gly Leu Val Gln Ala Gly Gly
1               5                   10                  15

Ser Leu Arg Leu Ser Cys Ala Ala Ser Gly Ser Phe Phe Arg
            20                  25                  30

<210> SEQ ID NO 164
<211> LENGTH: 30
<212> TYPE: PRT
<213> ORGANISM: Artificial
<220> FEATURE:
<223> OTHER INFORMATION: Nanobody or nanobody construct

<400> SEQUENCE: 164

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Phe Phe Arg
            20                  25                  30

<210> SEQ ID NO 165
<211> LENGTH: 30
<212> TYPE: PRT
<213> ORGANISM: Artificial
<220> FEATURE:
<223> OTHER INFORMATION: Nanobody or nanobody construct

<400> SEQUENCE: 165

Glu Val Gln Leu Val Glu Ser Gly Gly Gly Leu Val Lys Pro Gly Gly
1               5                   10                  15

Ser Leu Arg Leu Ser Cys Ala Ala Ser Gly Ser Phe Phe Arg
            20                  25                  30

<210> SEQ ID NO 166
<211> LENGTH: 30
<212> TYPE: PRT
<213> ORGANISM: Artificial
<220> FEATURE:
<223> OTHER INFORMATION: Nanobody or nanobody construct

```
<400> SEQUENCE: 166

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Phe Phe Arg
            20                  25                  30

<210> SEQ ID NO 167
<211> LENGTH: 30
<212> TYPE: PRT
<213> ORGANISM: Artificial
<220> FEATURE:
<223> OTHER INFORMATION: Nanobody or nanobody construct

<400> SEQUENCE: 167

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Phe Phe Arg
            20                  25                  30

<210> SEQ ID NO 168
<211> LENGTH: 30
<212> TYPE: PRT
<213> ORGANISM: Artificial
<220> FEATURE:
<223> OTHER INFORMATION: Nanobody or nanobody construct

<400> SEQUENCE: 168

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Phe Phe Arg
            20                  25                  30

<210> SEQ ID NO 169
<211> LENGTH: 30
<212> TYPE: PRT
<213> ORGANISM: Artificial
<220> FEATURE:
<223> OTHER INFORMATION: Nanobody or nanobody construct

<400> SEQUENCE: 169

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Phe Phe Arg
            20                  25                  30

<210> SEQ ID NO 170
<211> LENGTH: 30
<212> TYPE: PRT
<213> ORGANISM: Artificial
<220> FEATURE:
<223> OTHER INFORMATION: Nanobody or nanobody construct

<400> SEQUENCE: 170

Glu Val Gln Leu Val Glu Ser Gly Gly Asp Leu Val Gln Ala Gly Gly
1               5                   10                  15

Ser Leu Lys Leu Ser Cys Val Val Ser Gly Val Thr Phe Asp
            20                  25                  30

<210> SEQ ID NO 171
<211> LENGTH: 30
<212> TYPE: PRT
<213> ORGANISM: Artificial
<220> FEATURE:
<223> OTHER INFORMATION: Nanobody or nanobody construct
```

<400> SEQUENCE: 171

Glu Val Gln Leu Val Glu Ser Gly Gly Asp Leu Val Gln Ala Gly Gly
1               5                   10                  15

Ser Leu Lys Leu Ser Cys Val Val Ser Gly Val Thr Phe Asp
            20                  25                  30

<210> SEQ ID NO 172
<211> LENGTH: 30
<212> TYPE: PRT
<213> ORGANISM: Artificial
<220> FEATURE:
<223> OTHER INFORMATION: Nanobody or nanobody construct

<400> SEQUENCE: 172

Glu Met Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser
            20                  25                  30

<210> SEQ ID NO 173
<211> LENGTH: 30
<212> TYPE: PRT
<213> ORGANISM: Artificial
<220> FEATURE:
<223> OTHER INFORMATION: Nanobody or nanobody construct

<400> SEQUENCE: 173

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser
            20                  25                  30

<210> SEQ ID NO 174
<211> LENGTH: 30
<212> TYPE: PRT
<213> ORGANISM: Artificial
<220> FEATURE:
<223> OTHER INFORMATION: Nanobody or nanobody construct

<400> SEQUENCE: 174

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser
            20                  25                  30

<210> SEQ ID NO 175
<211> LENGTH: 30
<212> TYPE: PRT
<213> ORGANISM: Artificial
<220> FEATURE:
<223> OTHER INFORMATION: Nanobody or nanobody construct

<400> SEQUENCE: 175

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Gly
            20                  25                  30

<210> SEQ ID NO 176
<211> LENGTH: 30
<212> TYPE: PRT
<213> ORGANISM: Artificial
<220> FEATURE:

<223> OTHER INFORMATION: Nanobody or nanobody construct

<400> SEQUENCE: 176

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser
            20                  25                  30

<210> SEQ ID NO 177
<211> LENGTH: 30
<212> TYPE: PRT
<213> ORGANISM: Artificial
<220> FEATURE:
<223> OTHER INFORMATION: Nanobody or nanobody construct

<400> SEQUENCE: 177

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser
            20                  25                  30

<210> SEQ ID NO 178
<211> LENGTH: 30
<212> TYPE: PRT
<213> ORGANISM: Artificial
<220> FEATURE:
<223> OTHER INFORMATION: Nanobody or nanobody construct

<400> SEQUENCE: 178

Glu Val Gln Leu Val Glu Ser Gly Gly Gly Leu Val Gln Ala Gly Ala
1               5                   10                  15

Ser Leu Arg Val Ser Cys Ala Ala Ser Ala Arg Thr Gly Ser
            20                  25                  30

<210> SEQ ID NO 179
<211> LENGTH: 30
<212> TYPE: PRT
<213> ORGANISM: Artificial
<220> FEATURE:
<223> OTHER INFORMATION: Nanobody or nanobody construct

<400> SEQUENCE: 179

Glu Val Gln Leu Val Glu Ser Gly Gly Gly Leu Val Gln Ala Gly Gly
1               5                   10                  15

Ser Leu Arg Val Ser Cys Ala Ala Ser Ala Arg Thr Gly Ser
            20                  25                  30

<210> SEQ ID NO 180
<211> LENGTH: 30
<212> TYPE: PRT
<213> ORGANISM: Artificial
<220> FEATURE:
<223> OTHER INFORMATION: Nanobody or nanobody construct

<400> SEQUENCE: 180

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Asn Phe Gly
            20                  25                  30

<210> SEQ ID NO 181
<211> LENGTH: 30
<212> TYPE: PRT
<213> ORGANISM: Artificial

```
<220> FEATURE:
<223> OTHER INFORMATION: Nanobody or nanobody construct

<400> SEQUENCE: 181

Glu Val Gln Leu Val Glu Ser Gly Gly Gly Leu Val Gln Pro Gly Gly
1               5                   10                  15

Ser Leu Arg Leu Ser Cys Val Val Ser Gly Ser Met Tyr Arg
            20                  25                  30

<210> SEQ ID NO 182
<211> LENGTH: 30
<212> TYPE: PRT
<213> ORGANISM: Artificial
<220> FEATURE:
<223> OTHER INFORMATION: Nanobody or nanobody construct

<400> SEQUENCE: 182

Glu Val Gln Leu Val Glu Ser Gly Gly Gly Leu Val Gln Ser Gly Gly
1               5                   10                  15

Ser Leu Arg Leu Ser Cys Ala Gly Ser Gly Phe Ser Tyr Tyr
            20                  25                  30

<210> SEQ ID NO 183
<211> LENGTH: 30
<212> TYPE: PRT
<213> ORGANISM: Artificial
<220> FEATURE:
<223> OTHER INFORMATION: Nanobody or nanobody construct

<400> SEQUENCE: 183

Glu Val Gln Leu Val Glu Ser Gly Gly Gly Leu Val Gln Ser Gly Gly
1               5                   10                  15

Ser Leu Arg Leu Ser Cys Ala Gly Ser Gly Phe Ser Tyr Tyr
            20                  25                  30

<210> SEQ ID NO 184
<211> LENGTH: 30
<212> TYPE: PRT
<213> ORGANISM: Artificial
<220> FEATURE:
<223> OTHER INFORMATION: Nanobody or nanobody construct

<400> SEQUENCE: 184

Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Leu Glu
            20                  25                  30

<210> SEQ ID NO 185
<211> LENGTH: 30
<212> TYPE: PRT
<213> ORGANISM: Artificial
<220> FEATURE:
<223> OTHER INFORMATION: Nanobody or nanobody construct

<400> SEQUENCE: 185

Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Leu Thr
            20                  25                  30

<210> SEQ ID NO 186
<211> LENGTH: 30
<212> TYPE: PRT
```

-continued

```
<213> ORGANISM: Artificial
<220> FEATURE:
<223> OTHER INFORMATION: Nanobody or nanobody construct

<400> SEQUENCE: 186

Glu Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Ser
            20                  25                  30

<210> SEQ ID NO 187
<211> LENGTH: 30
<212> TYPE: PRT
<213> ORGANISM: Artificial
<220> FEATURE:
<223> OTHER INFORMATION: Nanobody or nanobody construct

<400> SEQUENCE: 187

Glu Val Gln Leu Val Glu Ser Gly Gly Gly Leu Val Gln Ala Gly Gly
1               5                   10                  15

Ser Leu Arg Leu Ser Cys Ala Ala Ser Pro Gly Thr Phe Ser
            20                  25                  30

<210> SEQ ID NO 188
<211> LENGTH: 30
<212> TYPE: PRT
<213> ORGANISM: Artificial
<220> FEATURE:
<223> OTHER INFORMATION: Nanobody or nanobody construct

<400> SEQUENCE: 188

Glu Val Gln Leu Val Glu Ser Gly Gly Gly Leu Val Gln Ala Gly Gly
1               5                   10                  15

Ser Leu Arg Leu Ser Cys Ala Ala Ser Pro Gly Ala Phe Ser
            20                  25                  30

<210> SEQ ID NO 189
<211> LENGTH: 30
<212> TYPE: PRT
<213> ORGANISM: Artificial
<220> FEATURE:
<223> OTHER INFORMATION: Nanobody or nanobody construct

<400> SEQUENCE: 189

Glu Met Gln Leu Val Glu Ser Gly Gly Gly Leu Val Gln Ala Gly Gly
1               5                   10                  15

Ser Leu Arg Leu Ser Cys Ala Ala Ser Pro Gly Thr Phe Ser
            20                  25                  30

<210> SEQ ID NO 190
<211> LENGTH: 30
<212> TYPE: PRT
<213> ORGANISM: Artificial
<220> FEATURE:
<223> OTHER INFORMATION: Nanobody or nanobody construct

<400> SEQUENCE: 190

Glu Val Gln Leu Val Lys Ser Gly Gly Gly Leu Val Gln Ala Gly Gly
1               5                   10                  15

Ser Leu Arg Leu Ser Cys Ala Ala Ser Pro Gly Thr Phe Ser
            20                  25                  30

<210> SEQ ID NO 191
<211> LENGTH: 30
```

```
<212> TYPE: PRT
<213> ORGANISM: Artificial
<220> FEATURE:
<223> OTHER INFORMATION: Nanobody or nanobody construct

<400> SEQUENCE: 191

Glu Val Gln Leu Val Glu Ser Gly Gly Gly Leu Val Gln Ala Gly Gly
1               5                   10                  15

Ser Leu Arg Leu Ser Cys Val Val Ser Gly Arg Thr Phe Ser
            20                  25                  30

<210> SEQ ID NO 192
<211> LENGTH: 30
<212> TYPE: PRT
<213> ORGANISM: Artificial
<220> FEATURE:
<223> OTHER INFORMATION: Nanobody or nanobody construct

<400> SEQUENCE: 192

Lys Val Gln Leu Val Glu Ser Gly Gly Gly Leu Val Gln Ala Gly Gly
1               5                   10                  15

Ser Leu Arg Leu Ser Cys Ala Ala Ser Gly Ser Pro Ile Ser
            20                  25                  30

<210> SEQ ID NO 193
<211> LENGTH: 30
<212> TYPE: PRT
<213> ORGANISM: Artificial
<220> FEATURE:
<223> OTHER INFORMATION: Nanobody or nanobody construct

<400> SEQUENCE: 193

Glu Val Gln Leu Val Glu Ser Gly Gly Gly Leu Val Gln Ala Gly Gly
1               5                   10                  15

Ser Leu Arg Leu Ser Cys Ala Ala Ser Asp Arg Thr Phe Gly
            20                  25                  30

<210> SEQ ID NO 194
<211> LENGTH: 30
<212> TYPE: PRT
<213> ORGANISM: Artificial
<220> FEATURE:
<223> OTHER INFORMATION: Nanobody or nanobody construct

<400> SEQUENCE: 194

Glu Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Ser
            20                  25                  30

<210> SEQ ID NO 195
<211> LENGTH: 30
<212> TYPE: PRT
<213> ORGANISM: Artificial
<220> FEATURE:
<223> OTHER INFORMATION: Nanobody or nanobody construct

<400> SEQUENCE: 195

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 196
```

```
<211> LENGTH: 30
<212> TYPE: PRT
<213> ORGANISM: Artificial
<220> FEATURE:
<223> OTHER INFORMATION: Nanobody or nanobody construct

<400> SEQUENCE: 196

Glu Val Gln Leu Val Glu Ser Gly Gly Gly Leu Val Gln Ala Gly Gly
1               5                   10                  15

Ser Leu Arg Leu Ser Cys Ala Ala Ser Asp Arg Thr Phe Gly
            20                  25                  30

<210> SEQ ID NO 197
<211> LENGTH: 30
<212> TYPE: PRT
<213> ORGANISM: Artificial
<220> FEATURE:
<223> OTHER INFORMATION: Nanobody or nanobody construct

<400> SEQUENCE: 197

Glu Val Gln Leu Val Glu Ser Gly Gly Gly Leu Val Gln Pro Gly Glu
1               5                   10                  15

Ser Leu Arg Leu Ser Cys Thr Ala Ser Arg Phe Met Leu Asp
            20                  25                  30

<210> SEQ ID NO 198
<211> LENGTH: 30
<212> TYPE: PRT
<213> ORGANISM: Artificial
<220> FEATURE:
<223> OTHER INFORMATION: Nanobody or nanobody construct

<400> SEQUENCE: 198

Glu Val Gln Leu Val Glu Ser Gly Gly Gly Leu Val Gln Pro Gly Glu
1               5                   10                  15

Ser Leu Arg Leu Ser Cys Thr Ala Ser Arg Phe Asp Leu Asp
            20                  25                  30

<210> SEQ ID NO 199
<211> LENGTH: 30
<212> TYPE: PRT
<213> ORGANISM: Artificial
<220> FEATURE:
<223> OTHER INFORMATION: Nanobody or nanobody construct

<400> SEQUENCE: 199

Glu Val Gln Leu Val Glu Ser Gly Gly Gly Leu Val Gln Ala Gly Gly
1               5                   10                  15

Ser Leu Arg Leu Ser Cys Val Ala Ser Gly Arg Thr Phe Ser
            20                  25                  30

<210> SEQ ID NO 200
<211> LENGTH: 30
<212> TYPE: PRT
<213> ORGANISM: Artificial
<220> FEATURE:
<223> OTHER INFORMATION: Nanobody or nanobody construct

<400> SEQUENCE: 200

Glu Val Gln Leu Val Glu Ser Gly Gly Arg Val Met Gln Thr Gly Gly
1               5                   10                  15

Ser Leu Arg Leu Ser Cys Ala Ala Ser Gly His Thr Phe Asn
            20                  25                  30
```

```
<210> SEQ ID NO 201
<211> LENGTH: 30
<212> TYPE: PRT
<213> ORGANISM: Artificial
<220> FEATURE:
<223> OTHER INFORMATION: Nanobody or nanobody construct

<400> SEQUENCE: 201

Glu Val Gln Leu Val Glu Ser Gly Gly Arg Val Met Gln Thr Gly Gly
1               5                   10                  15

Ser Leu Arg Leu Ser Cys Ala Ala Ser Gly His Thr Phe Asn
            20                  25                  30

<210> SEQ ID NO 202
<211> LENGTH: 30
<212> TYPE: PRT
<213> ORGANISM: Artificial
<220> FEATURE:
<223> OTHER INFORMATION: Nanobody or nanobody construct

<400> SEQUENCE: 202

Glu Val Gln Leu Val Glu Ser Gly Gly Asp Leu Val Gln Pro Gly Gly
1               5                   10                  15

Ser Leu Arg Leu Ser Cys Val Ala Ser Gly Phe Ala Leu Glu
            20                  25                  30

<210> SEQ ID NO 203
<211> LENGTH: 30
<212> TYPE: PRT
<213> ORGANISM: Artificial
<220> FEATURE:
<223> OTHER INFORMATION: Nanobody or nanobody construct

<400> SEQUENCE: 203

Glu Val Gln Leu Val Glu Ser Gly Gly Asp Leu Val Gln Pro Gly Gly
1               5                   10                  15

Ser Leu Arg Leu Ser Cys Val Ala Ser Gly Phe Ala Leu Glu
            20                  25                  30

<210> SEQ ID NO 204
<211> LENGTH: 30
<212> TYPE: PRT
<213> ORGANISM: Artificial
<220> FEATURE:
<223> OTHER INFORMATION: Nanobody or nanobody construct

<400> SEQUENCE: 204

Glu Val Gln Leu Val Glu Ser Gly Gly Gly Leu Val Gln Ala Gly Gly
1               5                   10                  15

Ser Leu Arg Leu Ser Cys Val Ala Ser Gly Arg Thr Leu Ser
            20                  25                  30

<210> SEQ ID NO 205
<211> LENGTH: 30
<212> TYPE: PRT
<213> ORGANISM: Artificial
<220> FEATURE:
<223> OTHER INFORMATION: Nanobody or nanobody construct

<400> SEQUENCE: 205

Glu Val Gln Leu Val Glu Ser Gly Gly Gly Leu Val Gln Ala Gly Gly
1               5                   10                  15

Ser Leu Arg Leu Ser Cys Ala Ala Ser Gly Asn Asp Phe Ala
            20                  25                  30
```

<210> SEQ ID NO 206
<211> LENGTH: 30
<212> TYPE: PRT
<213> ORGANISM: Artificial
<220> FEATURE:
<223> OTHER INFORMATION: Nanobody or nanobody construct

<400> SEQUENCE: 206

Glu Met Gln Leu Val Glu Ser Gly Gly Gly Trp Val Gln Ala Gly Gly
1               5                   10                  15

Ser Leu Arg Leu Ser Cys Ala Ser Ser Gly Ser Ile Phe Ser
            20                  25                  30

<210> SEQ ID NO 207
<211> LENGTH: 30
<212> TYPE: PRT
<213> ORGANISM: Artificial
<220> FEATURE:
<223> OTHER INFORMATION: Nanobody or nanobody construct

<400> SEQUENCE: 207

Glu Val Gln Leu Val Glu Ser Gly Gly Gly Leu Val Gln Ala Gly Gly
1               5                   10                  15

Ser Leu Arg Leu Ser Cys Ala Ala Ser Gly Pro Thr Thr Phe
            20                  25                  30

<210> SEQ ID NO 208
<211> LENGTH: 5
<212> TYPE: PRT
<213> ORGANISM: Artificial
<220> FEATURE:
<223> OTHER INFORMATION: Nanobody or nanobody construct

<400> SEQUENCE: 208

Asp Tyr Ala Ile Gly
1               5

<210> SEQ ID NO 209
<211> LENGTH: 5
<212> TYPE: PRT
<213> ORGANISM: Artificial
<220> FEATURE:
<223> OTHER INFORMATION: Nanobody or nanobody construct

<400> SEQUENCE: 209

Asp Tyr Ala Ile Gly
1               5

<210> SEQ ID NO 210
<211> LENGTH: 5
<212> TYPE: PRT
<213> ORGANISM: Artificial
<220> FEATURE:
<223> OTHER INFORMATION: Nanobody or nanobody construct

<400> SEQUENCE: 210

Asp Tyr Ala Ile Gly
1               5

<210> SEQ ID NO 211
<211> LENGTH: 5
<212> TYPE: PRT
<213> ORGANISM: Artificial
<220> FEATURE:
<223> OTHER INFORMATION: Nanobody or nanobody construct

```
<400> SEQUENCE: 211

Asp Tyr Ala Ile Gly
1               5

<210> SEQ ID NO 212
<211> LENGTH: 5
<212> TYPE: PRT
<213> ORGANISM: Artificial
<220> FEATURE:
<223> OTHER INFORMATION: Nanobody or nanobody construct

<400> SEQUENCE: 212

Asp Tyr Ala Ile Gly
1               5

<210> SEQ ID NO 213
<211> LENGTH: 5
<212> TYPE: PRT
<213> ORGANISM: Artificial
<220> FEATURE:
<223> OTHER INFORMATION: Nanobody or nanobody construct

<400> SEQUENCE: 213

Asp Tyr Ala Ile Gly
1               5

<210> SEQ ID NO 214
<211> LENGTH: 5
<212> TYPE: PRT
<213> ORGANISM: Artificial
<220> FEATURE:
<223> OTHER INFORMATION: Nanobody or nanobody construct

<400> SEQUENCE: 214

Asp Tyr Ala Ile Gly
1               5

<210> SEQ ID NO 215
<211> LENGTH: 5
<212> TYPE: PRT
<213> ORGANISM: Artificial
<220> FEATURE:
<223> OTHER INFORMATION: Nanobody or nanobody construct

<400> SEQUENCE: 215

Asp Tyr Ala Ile Ala
1               5

<210> SEQ ID NO 216
<211> LENGTH: 5
<212> TYPE: PRT
<213> ORGANISM: Artificial
<220> FEATURE:
<223> OTHER INFORMATION: Nanobody or nanobody construct

<400> SEQUENCE: 216

Asp Tyr Ala Ile Ala
1               5

<210> SEQ ID NO 217
<211> LENGTH: 5
<212> TYPE: PRT
<213> ORGANISM: Artificial
<220> FEATURE:
<223> OTHER INFORMATION: Nanobody or nanobody construct

<400> SEQUENCE: 217
```

Asp Tyr Ala Ile Ala
1               5

<210> SEQ ID NO 218
<211> LENGTH: 5
<212> TYPE: PRT
<213> ORGANISM: Artificial
<220> FEATURE:
<223> OTHER INFORMATION: Nanobody or nanobody construct

<400> SEQUENCE: 218

Asp Tyr Ala Ile Ala
1               5

<210> SEQ ID NO 219

<400> SEQUENCE: 219

000

<210> SEQ ID NO 220

<400> SEQUENCE: 220

000

<210> SEQ ID NO 221

<400> SEQUENCE: 221

000

<210> SEQ ID NO 222

<400> SEQUENCE: 222

000

<210> SEQ ID NO 223

<400> SEQUENCE: 223

000

<210> SEQ ID NO 224

<400> SEQUENCE: 224

000

<210> SEQ ID NO 225

<400> SEQUENCE: 225

000

<210> SEQ ID NO 226

<400> SEQUENCE: 226

000

<210> SEQ ID NO 227

<400> SEQUENCE: 227

000

```
<210> SEQ ID NO 228
<211> LENGTH: 5
<212> TYPE: PRT
<213> ORGANISM: Artificial
<220> FEATURE:
<223> OTHER INFORMATION: Nanobody or nanobody construct

<400> SEQUENCE: 228

Asp Tyr Gly Met Gly
1               5

<210> SEQ ID NO 229
<211> LENGTH: 5
<212> TYPE: PRT
<213> ORGANISM: Artificial
<220> FEATURE:
<223> OTHER INFORMATION: Nanobody or nanobody construct

<400> SEQUENCE: 229

Asp Tyr Gly Met Gly
1               5

<210> SEQ ID NO 230
<211> LENGTH: 5
<212> TYPE: PRT
<213> ORGANISM: Artificial
<220> FEATURE:
<223> OTHER INFORMATION: Nanobody or nanobody construct

<400> SEQUENCE: 230

Asp Tyr Gly Met Gly
1               5

<210> SEQ ID NO 231
<211> LENGTH: 5
<212> TYPE: PRT
<213> ORGANISM: Artificial
<220> FEATURE:
<223> OTHER INFORMATION: Nanobody or nanobody construct

<400> SEQUENCE: 231

Asp Tyr Gly Met Gly
1               5

<210> SEQ ID NO 232
<211> LENGTH: 5
<212> TYPE: PRT
<213> ORGANISM: Artificial
<220> FEATURE:
<223> OTHER INFORMATION: Nanobody or nanobody construct

<400> SEQUENCE: 232

Asp Tyr Gly Met Gly
1               5

<210> SEQ ID NO 233
<211> LENGTH: 5
<212> TYPE: PRT
<213> ORGANISM: Artificial
<220> FEATURE:
<223> OTHER INFORMATION: Nanobody or nanobody construct

<400> SEQUENCE: 233

Val Asn Thr Met Ala
1               5
```

```
<210> SEQ ID NO 234
<211> LENGTH: 5
<212> TYPE: PRT
<213> ORGANISM: Artificial
<220> FEATURE:
<223> OTHER INFORMATION: Nanobody or nanobody construct

<400> SEQUENCE: 234

Val Asn Thr Met Ala
1               5

<210> SEQ ID NO 235
<211> LENGTH: 5
<212> TYPE: PRT
<213> ORGANISM: Artificial
<220> FEATURE:
<223> OTHER INFORMATION: Nanobody or nanobody construct

<400> SEQUENCE: 235

Val Asn Thr Met Ala
1               5

<210> SEQ ID NO 236
<211> LENGTH: 5
<212> TYPE: PRT
<213> ORGANISM: Artificial
<220> FEATURE:
<223> OTHER INFORMATION: Nanobody or nanobody construct

<400> SEQUENCE: 236

Val Asn Asn Met Ala
1               5

<210> SEQ ID NO 237
<211> LENGTH: 5
<212> TYPE: PRT
<213> ORGANISM: Artificial
<220> FEATURE:
<223> OTHER INFORMATION: Nanobody or nanobody construct

<400> SEQUENCE: 237

Val Asn Asn Met Ala
1               5

<210> SEQ ID NO 238
<211> LENGTH: 5
<212> TYPE: PRT
<213> ORGANISM: Artificial
<220> FEATURE:
<223> OTHER INFORMATION: Nanobody or nanobody construct

<400> SEQUENCE: 238

Val Asn Thr Met Ala
1               5

<210> SEQ ID NO 239
<211> LENGTH: 5
<212> TYPE: PRT
<213> ORGANISM: Artificial
<220> FEATURE:
<223> OTHER INFORMATION: Nanobody or nanobody construct

<400> SEQUENCE: 239

Val Asn Thr Met Ala
1               5
```

-continued

```
<210> SEQ ID NO 240
<211> LENGTH: 5
<212> TYPE: PRT
<213> ORGANISM: Artificial
<220> FEATURE:
<223> OTHER INFORMATION: Nanobody or nanobody construct

<400> SEQUENCE: 240

Val Asn Thr Met Ala
1               5

<210> SEQ ID NO 241
<211> LENGTH: 5
<212> TYPE: PRT
<213> ORGANISM: Artificial
<220> FEATURE:
<223> OTHER INFORMATION: Nanobody or nanobody construct

<400> SEQUENCE: 241

Val Asn Asn Met Ala
1               5

<210> SEQ ID NO 242
<211> LENGTH: 5
<212> TYPE: PRT
<213> ORGANISM: Artificial
<220> FEATURE:
<223> OTHER INFORMATION: Nanobody or nanobody construct

<400> SEQUENCE: 242

Val Asn Asn Met Ala
1               5

<210> SEQ ID NO 243
<211> LENGTH: 5
<212> TYPE: PRT
<213> ORGANISM: Artificial
<220> FEATURE:
<223> OTHER INFORMATION: Nanobody or nanobody construct

<400> SEQUENCE: 243

Val Asn Asn Met Ala
1               5

<210> SEQ ID NO 244
<211> LENGTH: 5
<212> TYPE: PRT
<213> ORGANISM: Artificial
<220> FEATURE:
<223> OTHER INFORMATION: Nanobody or nanobody construct

<400> SEQUENCE: 244

Val Asn Asn Met Ala
1               5

<210> SEQ ID NO 245
<211> LENGTH: 5
<212> TYPE: PRT
<213> ORGANISM: Artificial
<220> FEATURE:
<223> OTHER INFORMATION: Nanobody or nanobody construct

<400> SEQUENCE: 245

Val Asn Asn Met Ala
1               5

<210> SEQ ID NO 246
```

```
<211> LENGTH: 5
<212> TYPE: PRT
<213> ORGANISM: Artificial
<220> FEATURE:
<223> OTHER INFORMATION: Nanobody or nanobody construct

<400> SEQUENCE: 246

Val Asn Val Met Ala
1               5

<210> SEQ ID NO 247
<211> LENGTH: 5
<212> TYPE: PRT
<213> ORGANISM: Artificial
<220> FEATURE:
<223> OTHER INFORMATION: Nanobody or nanobody construct

<400> SEQUENCE: 247

Val Asn Asn Met Ala
1               5

<210> SEQ ID NO 248
<211> LENGTH: 5
<212> TYPE: PRT
<213> ORGANISM: Artificial
<220> FEATURE:
<223> OTHER INFORMATION: Nanobody or nanobody construct

<400> SEQUENCE: 248

Val Asn Asn Met Ala
1               5

<210> SEQ ID NO 249
<211> LENGTH: 5
<212> TYPE: PRT
<213> ORGANISM: Artificial
<220> FEATURE:
<223> OTHER INFORMATION: Nanobody or nanobody construct

<400> SEQUENCE: 249

Val Asn Asn Met Ala
1               5

<210> SEQ ID NO 250
<211> LENGTH: 5
<212> TYPE: PRT
<213> ORGANISM: Artificial
<220> FEATURE:
<223> OTHER INFORMATION: Nanobody or nanobody construct

<400> SEQUENCE: 250

Val Asn Asn Met Ala
1               5

<210> SEQ ID NO 251
<211> LENGTH: 5
<212> TYPE: PRT
<213> ORGANISM: Artificial
<220> FEATURE:
<223> OTHER INFORMATION: Nanobody or nanobody construct

<400> SEQUENCE: 251

Val Asn Asn Met Ala
1               5

<210> SEQ ID NO 252
<211> LENGTH: 5
```

```
<212> TYPE: PRT
<213> ORGANISM: Artificial
<220> FEATURE:
<223> OTHER INFORMATION: Nanobody or nanobody construct

<400> SEQUENCE: 252

Asp Gly Thr Ile Gly
1               5

<210> SEQ ID NO 253
<211> LENGTH: 5
<212> TYPE: PRT
<213> ORGANISM: Artificial
<220> FEATURE:
<223> OTHER INFORMATION: Nanobody or nanobody construct

<400> SEQUENCE: 253

Asp Gly Thr Ile Gly
1               5

<210> SEQ ID NO 254
<211> LENGTH: 5
<212> TYPE: PRT
<213> ORGANISM: Artificial
<220> FEATURE:
<223> OTHER INFORMATION: Nanobody or nanobody construct

<400> SEQUENCE: 254

Ser Leu Ala Met Gly
1               5

<210> SEQ ID NO 255
<211> LENGTH: 5
<212> TYPE: PRT
<213> ORGANISM: Artificial
<220> FEATURE:
<223> OTHER INFORMATION: Nanobody or nanobody construct

<400> SEQUENCE: 255

Ser Leu Ala Met Gly
1               5

<210> SEQ ID NO 256
<211> LENGTH: 5
<212> TYPE: PRT
<213> ORGANISM: Artificial
<220> FEATURE:
<223> OTHER INFORMATION: Nanobody or nanobody construct

<400> SEQUENCE: 256

Ser Leu Ala Met Gly
1               5

<210> SEQ ID NO 257
<211> LENGTH: 5
<212> TYPE: PRT
<213> ORGANISM: Artificial
<220> FEATURE:
<223> OTHER INFORMATION: Nanobody or nanobody construct

<400> SEQUENCE: 257

Ser Ser Pro Val Gly
1               5

<210> SEQ ID NO 258
<211> LENGTH: 5
<212> TYPE: PRT
```

<213> ORGANISM: Artificial
<220> FEATURE:
<223> OTHER INFORMATION: Nanobody or nanobody construct

<400> SEQUENCE: 258

Ser Ser Pro Val Gly
1               5

<210> SEQ ID NO 259
<211> LENGTH: 5
<212> TYPE: PRT
<213> ORGANISM: Artificial
<220> FEATURE:
<223> OTHER INFORMATION: Nanobody or nanobody construct

<400> SEQUENCE: 259

Ser Ser Pro Val Gly
1               5

<210> SEQ ID NO 260
<211> LENGTH: 4
<212> TYPE: PRT
<213> ORGANISM: Artificial
<220> FEATURE:
<223> OTHER INFORMATION: Nanobody or nanobody construct

<400> SEQUENCE: 260

Tyr Thr Met Gly
1

<210> SEQ ID NO 261
<211> LENGTH: 4
<212> TYPE: PRT
<213> ORGANISM: Artificial
<220> FEATURE:
<223> OTHER INFORMATION: Nanobody or nanobody construct

<400> SEQUENCE: 261

Tyr Ser Met Gly
1

<210> SEQ ID NO 262
<211> LENGTH: 5
<212> TYPE: PRT
<213> ORGANISM: Artificial
<220> FEATURE:
<223> OTHER INFORMATION: Nanobody or nanobody construct

<400> SEQUENCE: 262

Ser Tyr Thr Met Ala
1               5

<210> SEQ ID NO 263
<211> LENGTH: 5
<212> TYPE: PRT
<213> ORGANISM: Artificial
<220> FEATURE:
<223> OTHER INFORMATION: Nanobody or nanobody construct

<400> SEQUENCE: 263

Ile Asp Asn Met Gly
1               5

<210> SEQ ID NO 264

<400> SEQUENCE: 264

```
<210> SEQ ID NO 265

<400> SEQUENCE: 265

000

<210> SEQ ID NO 266
<211> LENGTH: 5
<212> TYPE: PRT
<213> ORGANISM: Artificial
<220> FEATURE:
<223> OTHER INFORMATION: Nanobody or nanobody construct

<400> SEQUENCE: 266

Tyr Tyr Asn Ile Gly
1               5

<210> SEQ ID NO 267
<211> LENGTH: 5
<212> TYPE: PRT
<213> ORGANISM: Artificial
<220> FEATURE:
<223> OTHER INFORMATION: Nanobody or nanobody construct

<400> SEQUENCE: 267

Tyr Tyr Asn Ile Gly
1               5

<210> SEQ ID NO 268
<211> LENGTH: 5
<212> TYPE: PRT
<213> ORGANISM: Artificial
<220> FEATURE:
<223> OTHER INFORMATION: Nanobody or nanobody construct

<400> SEQUENCE: 268

Ser Val Ala Val Gly
1               5

<210> SEQ ID NO 269
<211> LENGTH: 5
<212> TYPE: PRT
<213> ORGANISM: Artificial
<220> FEATURE:
<223> OTHER INFORMATION: Nanobody or nanobody construct

<400> SEQUENCE: 269

Ser Phe Asn Met Gly
1               5

<210> SEQ ID NO 270
<211> LENGTH: 5
<212> TYPE: PRT
<213> ORGANISM: Artificial
<220> FEATURE:
<223> OTHER INFORMATION: Nanobody or nanobody construct

<400> SEQUENCE: 270

Ser Phe Asn Met Gly
1               5

<210> SEQ ID NO 271
<211> LENGTH: 5
<212> TYPE: PRT
<213> ORGANISM: Artificial
```

```
<220> FEATURE:
<223> OTHER INFORMATION: Nanobody or nanobody construct

<400> SEQUENCE: 271

Ser Phe Asn Met Gly
1               5

<210> SEQ ID NO 272
<211> LENGTH: 5
<212> TYPE: PRT
<213> ORGANISM: Artificial
<220> FEATURE:
<223> OTHER INFORMATION: Nanobody or nanobody construct

<400> SEQUENCE: 272

Ser Phe Asn Met Gly
1               5

<210> SEQ ID NO 273

<400> SEQUENCE: 273

000

<210> SEQ ID NO 274
<211> LENGTH: 5
<212> TYPE: PRT
<213> ORGANISM: Artificial
<220> FEATURE:
<223> OTHER INFORMATION: Nanobody or nanobody construct

<400> SEQUENCE: 274

Ser Tyr Ala Met Gly
1               5

<210> SEQ ID NO 275
<211> LENGTH: 5
<212> TYPE: PRT
<213> ORGANISM: Artificial
<220> FEATURE:
<223> OTHER INFORMATION: Nanobody or nanobody construct

<400> SEQUENCE: 275

Ser Ser Ala Met Gly
1               5

<210> SEQ ID NO 276
<211> LENGTH: 5
<212> TYPE: PRT
<213> ORGANISM: Artificial
<220> FEATURE:
<223> OTHER INFORMATION: Nanobody or nanobody construct

<400> SEQUENCE: 276

Ser Tyr Ala Met Gly
1               5

<210> SEQ ID NO 277
<211> LENGTH: 5
<212> TYPE: PRT
<213> ORGANISM: Artificial
<220> FEATURE:
<223> OTHER INFORMATION: Nanobody or nanobody construct

<400> SEQUENCE: 277

Thr Asn Ile Met Thr
1               5
```

<210> SEQ ID NO 278
<211> LENGTH: 5
<212> TYPE: PRT
<213> ORGANISM: Artificial
<220> FEATURE:
<223> OTHER INFORMATION: Nanobody or nanobody construct

<400> SEQUENCE: 278

Ser Ser Thr Met Gly
1               5

<210> SEQ ID NO 279
<211> LENGTH: 5
<212> TYPE: PRT
<213> ORGANISM: Artificial
<220> FEATURE:
<223> OTHER INFORMATION: Nanobody or nanobody construct

<400> SEQUENCE: 279

Tyr Tyr Asp Ile Gly
1               5

<210> SEQ ID NO 280
<211> LENGTH: 5
<212> TYPE: PRT
<213> ORGANISM: Artificial
<220> FEATURE:
<223> OTHER INFORMATION: Nanobody or nanobody construct

<400> SEQUENCE: 280

Tyr Tyr Asp Ile Ala
1               5

<210> SEQ ID NO 281
<211> LENGTH: 5
<212> TYPE: PRT
<213> ORGANISM: Artificial
<220> FEATURE:
<223> OTHER INFORMATION: Nanobody or nanobody construct

<400> SEQUENCE: 281

Ile Leu Thr Met Gly
1               5

<210> SEQ ID NO 282
<211> LENGTH: 5
<212> TYPE: PRT
<213> ORGANISM: Artificial
<220> FEATURE:
<223> OTHER INFORMATION: Nanobody or nanobody construct

<400> SEQUENCE: 282

Asp Tyr Ser Met Gly
1               5

<210> SEQ ID NO 283
<211> LENGTH: 5
<212> TYPE: PRT
<213> ORGANISM: Artificial
<220> FEATURE:
<223> OTHER INFORMATION: Nanobody or nanobody construct

<400> SEQUENCE: 283

Asp Tyr Asn Met Gly
1               5

<210> SEQ ID NO 284
<211> LENGTH: 5
<212> TYPE: PRT
<213> ORGANISM: Artificial
<220> FEATURE:
<223> OTHER INFORMATION: Nanobody or nanobody construct

<400> SEQUENCE: 284

Glu His Ala Ile Gly
1               5

<210> SEQ ID NO 285
<211> LENGTH: 5
<212> TYPE: PRT
<213> ORGANISM: Artificial
<220> FEATURE:
<223> OTHER INFORMATION: Nanobody or nanobody construct

<400> SEQUENCE: 285

Glu His Ala Ile Gly
1               5

<210> SEQ ID NO 286
<211> LENGTH: 5
<212> TYPE: PRT
<213> ORGANISM: Artificial
<220> FEATURE:
<223> OTHER INFORMATION: Nanobody or nanobody construct

<400> SEQUENCE: 286

Thr Ala Val Met Gly
1               5

<210> SEQ ID NO 287
<211> LENGTH: 8
<212> TYPE: PRT
<213> ORGANISM: Artificial
<220> FEATURE:
<223> OTHER INFORMATION: Nanobody or nanobody construct

<400> SEQUENCE: 287

Arg Phe Ser Ile Asp Ala Met Gly
1               5

<210> SEQ ID NO 288
<211> LENGTH: 5
<212> TYPE: PRT
<213> ORGANISM: Artificial
<220> FEATURE:
<223> OTHER INFORMATION: Nanobody or nanobody construct

<400> SEQUENCE: 288

Ala Gly Ala Met Gly
1               5

<210> SEQ ID NO 289
<211> LENGTH: 6
<212> TYPE: PRT
<213> ORGANISM: Artificial
<220> FEATURE:
<223> OTHER INFORMATION: Nanobody or nanobody construct

<400> SEQUENCE: 289

Gly Arg Tyr Thr Met Gly
1               5

```
<210> SEQ ID NO 290
<211> LENGTH: 14
<212> TYPE: PRT
<213> ORGANISM: Artificial
<220> FEATURE:
<223> OTHER INFORMATION: Nanobody or nanobody construct

<400> SEQUENCE: 290

Trp Phe Arg Gln Ala Pro Gly Lys Glu Arg Glu Gly Ile Ser
1               5                   10

<210> SEQ ID NO 291
<211> LENGTH: 14
<212> TYPE: PRT
<213> ORGANISM: Artificial
<220> FEATURE:
<223> OTHER INFORMATION: Nanobody or nanobody construct

<400> SEQUENCE: 291

Trp Phe Arg Gln Ala Pro Gly Lys Glu Arg Glu Gly Ile Ser
1               5                   10

<210> SEQ ID NO 292
<211> LENGTH: 14
<212> TYPE: PRT
<213> ORGANISM: Artificial
<220> FEATURE:
<223> OTHER INFORMATION: Nanobody or nanobody construct

<400> SEQUENCE: 292

Trp Phe Arg Gln Ala Pro Gly Lys Glu Arg Glu Gly Ile Ser
1               5                   10

<210> SEQ ID NO 293
<211> LENGTH: 14
<212> TYPE: PRT
<213> ORGANISM: Artificial
<220> FEATURE:
<223> OTHER INFORMATION: Nanobody or nanobody construct

<400> SEQUENCE: 293

Trp Phe Arg Gln Ala Pro Gly Lys Glu Arg Glu Gly Ile Ser
1               5                   10

<210> SEQ ID NO 294
<211> LENGTH: 14
<212> TYPE: PRT
<213> ORGANISM: Artificial
<220> FEATURE:
<223> OTHER INFORMATION: Nanobody or nanobody construct

<400> SEQUENCE: 294

Trp Phe Arg Gln Ala Pro Gly Lys Glu Arg Glu Gly Ile Ser
1               5                   10

<210> SEQ ID NO 295
<211> LENGTH: 14
<212> TYPE: PRT
<213> ORGANISM: Artificial
<220> FEATURE:
<223> OTHER INFORMATION: Nanobody or nanobody construct

<400> SEQUENCE: 295

Trp Phe Arg Gln Ala Pro Gly Lys Glu Arg Glu Gly Ile Ser
1               5                   10

<210> SEQ ID NO 296
```

-continued

<211> LENGTH: 14
<212> TYPE: PRT
<213> ORGANISM: Artificial
<220> FEATURE:
<223> OTHER INFORMATION: Nanobody or nanobody construct

<400> SEQUENCE: 296

Trp Phe Arg Gln Ala Pro Gly Lys Glu Arg Glu Gly Ile Ser
1               5                   10

<210> SEQ ID NO 297
<211> LENGTH: 14
<212> TYPE: PRT
<213> ORGANISM: Artificial
<220> FEATURE:
<223> OTHER INFORMATION: Nanobody or nanobody construct

<400> SEQUENCE: 297

Trp Phe Arg Gln Ala Pro Gly Lys Glu Arg Glu Gly Val Ser
1               5                   10

<210> SEQ ID NO 298
<211> LENGTH: 14
<212> TYPE: PRT
<213> ORGANISM: Artificial
<220> FEATURE:
<223> OTHER INFORMATION: Nanobody or nanobody construct

<400> SEQUENCE: 298

Trp Phe Arg Gln Ala Pro Gly Lys Glu Arg Glu Gly Val Ser
1               5                   10

<210> SEQ ID NO 299
<211> LENGTH: 14
<212> TYPE: PRT
<213> ORGANISM: Artificial
<220> FEATURE:
<223> OTHER INFORMATION: Nanobody or nanobody construct

<400> SEQUENCE: 299

Trp Phe Arg Gln Ala Pro Gly Lys Glu Arg Glu Gly Val Ser
1               5                   10

<210> SEQ ID NO 300
<211> LENGTH: 14
<212> TYPE: PRT
<213> ORGANISM: Artificial
<220> FEATURE:
<223> OTHER INFORMATION: Nanobody or nanobody construct

<400> SEQUENCE: 300

Trp Phe Arg Gln Ala Pro Gly Lys Glu Arg Glu Gly Val Ser
1               5                   10

<210> SEQ ID NO 301
<211> LENGTH: 14
<212> TYPE: PRT
<213> ORGANISM: Artificial
<220> FEATURE:
<223> OTHER INFORMATION: Nanobody or nanobody construct

<400> SEQUENCE: 301

Trp Phe Arg Gln Ala Pro Gly Lys Glu Arg Glu Phe Val Ala
1               5                   10

<210> SEQ ID NO 302
<211> LENGTH: 14

-continued

```
<212> TYPE: PRT
<213> ORGANISM: Artificial
<220> FEATURE:
<223> OTHER INFORMATION: Nanobody or nanobody construct

<400> SEQUENCE: 302

Trp Phe Arg Arg Ala Pro Gly Lys Glu Arg Glu Phe Val Ala
1               5                   10

<210> SEQ ID NO 303
<211> LENGTH: 14
<212> TYPE: PRT
<213> ORGANISM: Artificial
<220> FEATURE:
<223> OTHER INFORMATION: Nanobody or nanobody construct

<400> SEQUENCE: 303

Trp Phe Arg Gln Ala Pro Gly Lys Glu Arg Glu Phe Val Ala
1               5                   10

<210> SEQ ID NO 304
<211> LENGTH: 14
<212> TYPE: PRT
<213> ORGANISM: Artificial
<220> FEATURE:
<223> OTHER INFORMATION: Nanobody or nanobody construct

<400> SEQUENCE: 304

Trp Phe Arg Gln Ala Pro Gly Lys Glu Arg Glu Phe Val Ala
1               5                   10

<210> SEQ ID NO 305
<211> LENGTH: 14
<212> TYPE: PRT
<213> ORGANISM: Artificial
<220> FEATURE:
<223> OTHER INFORMATION: Nanobody or nanobody construct

<400> SEQUENCE: 305

Trp Phe Arg Gln Ala Pro Gly Lys Glu Arg Glu Phe Val Ala
1               5                   10

<210> SEQ ID NO 306
<211> LENGTH: 14
<212> TYPE: PRT
<213> ORGANISM: Artificial
<220> FEATURE:
<223> OTHER INFORMATION: Nanobody or nanobody construct

<400> SEQUENCE: 306

Trp Phe Arg Gln Ala Pro Gly Lys Glu Arg Glu Phe Val Ala
1               5                   10

<210> SEQ ID NO 307
<211> LENGTH: 14
<212> TYPE: PRT
<213> ORGANISM: Artificial
<220> FEATURE:
<223> OTHER INFORMATION: Nanobody or nanobody construct

<400> SEQUENCE: 307

Trp Phe Arg Gln Ala Pro Gly Lys Glu Arg Glu Phe Val Ala
1               5                   10

<210> SEQ ID NO 308
<211> LENGTH: 14
<212> TYPE: PRT
```

<210> SEQ ID NO 308
<211> LENGTH: 14
<212> TYPE: PRT
<213> ORGANISM: Artificial
<220> FEATURE:
<223> OTHER INFORMATION: Nanobody or nanobody construct

<400> SEQUENCE: 308

Trp Phe Arg Gln Ala Pro Gly Lys Glu Arg Glu Phe Val Ala
1               5                   10

<210> SEQ ID NO 309
<211> LENGTH: 14
<212> TYPE: PRT
<213> ORGANISM: Artificial
<220> FEATURE:
<223> OTHER INFORMATION: Nanobody or nanobody construct

<400> SEQUENCE: 309

Trp Phe Arg Gln Ala Pro Gly Lys Glu Arg Glu Phe Val Ala
1               5                   10

<210> SEQ ID NO 310
<211> LENGTH: 14
<212> TYPE: PRT
<213> ORGANISM: Artificial
<220> FEATURE:
<223> OTHER INFORMATION: Nanobody or nanobody construct

<400> SEQUENCE: 310

Trp Phe Arg Gln Ala Pro Gly Lys Leu Arg Glu Phe Val Ala
1               5                   10

<210> SEQ ID NO 311
<211> LENGTH: 14
<212> TYPE: PRT
<213> ORGANISM: Artificial
<220> FEATURE:
<223> OTHER INFORMATION: Nanobody or nanobody construct

<400> SEQUENCE: 311

Trp Phe Arg Gln Ala Pro Gly Lys Leu Arg Glu Phe Val Ala
1               5                   10

<210> SEQ ID NO 312
<211> LENGTH: 14
<212> TYPE: PRT
<213> ORGANISM: Artificial
<220> FEATURE:
<223> OTHER INFORMATION: Nanobody or nanobody construct

<400> SEQUENCE: 312

Trp Phe Arg Gln Ala Pro Gly Lys Leu Arg Glu Phe Val Ala
1               5                   10

<210> SEQ ID NO 313
<211> LENGTH: 14
<212> TYPE: PRT
<213> ORGANISM: Artificial
<220> FEATURE:
<223> OTHER INFORMATION: Nanobody or nanobody construct

<400> SEQUENCE: 313

Trp Phe Arg Gln Ala Pro Gly Lys Glu Cys Glu Phe Val Ala
1               5                   10

<210> SEQ ID NO 314
<211> LENGTH: 14
<212> TYPE: PRT
<213> ORGANISM: Artificial

-continued

```
<220> FEATURE:
<223> OTHER INFORMATION: Nanobody or nanobody construct

<400> SEQUENCE: 314

Trp Phe Arg Gln Ala Pro Gly Lys Glu Arg Glu Phe Val Ala
1               5                   10

<210> SEQ ID NO 315
<211> LENGTH: 14
<212> TYPE: PRT
<213> ORGANISM: Artificial
<220> FEATURE:
<223> OTHER INFORMATION: Nanobody or nanobody construct

<400> SEQUENCE: 315

Trp Tyr Arg Gln Ala Pro Gly Lys Gln Arg Glu Leu Val Ala
1               5                   10

<210> SEQ ID NO 316
<211> LENGTH: 14
<212> TYPE: PRT
<213> ORGANISM: Artificial
<220> FEATURE:
<223> OTHER INFORMATION: Nanobody or nanobody construct

<400> SEQUENCE: 316

Trp Tyr Arg Gln Ala Pro Gly Lys Gln Arg Glu Leu Val Ala
1               5                   10

<210> SEQ ID NO 317
<211> LENGTH: 14
<212> TYPE: PRT
<213> ORGANISM: Artificial
<220> FEATURE:
<223> OTHER INFORMATION: Nanobody or nanobody construct

<400> SEQUENCE: 317

Trp Tyr Arg Gln Ala Pro Gly Lys Gln Arg Glu Leu Val Ala
1               5                   10

<210> SEQ ID NO 318
<211> LENGTH: 14
<212> TYPE: PRT
<213> ORGANISM: Artificial
<220> FEATURE:
<223> OTHER INFORMATION: Nanobody or nanobody construct

<400> SEQUENCE: 318

Trp Tyr Arg Gln Ala Pro Gly Lys Gln Arg Glu Leu Val Ala
1               5                   10

<210> SEQ ID NO 319
<211> LENGTH: 14
<212> TYPE: PRT
<213> ORGANISM: Artificial
<220> FEATURE:
<223> OTHER INFORMATION: Nanobody or nanobody construct

<400> SEQUENCE: 319

Trp Tyr Arg Gln Ala Pro Gly Lys Gln Arg Glu Leu Val Ala
1               5                   10

<210> SEQ ID NO 320
<211> LENGTH: 14
<212> TYPE: PRT
<213> ORGANISM: Artificial
<220> FEATURE:
```

```
<223> OTHER INFORMATION: Nanobody or nanobody construct

<400> SEQUENCE: 320

Trp Tyr Arg Gln Ala Pro Gly Lys Gln Arg Glu Leu Val Ala
1               5                   10

<210> SEQ ID NO 321
<211> LENGTH: 14
<212> TYPE: PRT
<213> ORGANISM: Artificial
<220> FEATURE:
<223> OTHER INFORMATION: Nanobody or nanobody construct

<400> SEQUENCE: 321

Trp Tyr Arg Gln Ala Pro Gly Lys Gln Arg Glu Leu Val Ala
1               5                   10

<210> SEQ ID NO 322
<211> LENGTH: 14
<212> TYPE: PRT
<213> ORGANISM: Artificial
<220> FEATURE:
<223> OTHER INFORMATION: Nanobody or nanobody construct

<400> SEQUENCE: 322

Trp Tyr Arg Gln Ala Pro Gly Lys Gln Arg Glu Leu Val Ala
1               5                   10

<210> SEQ ID NO 323
<211> LENGTH: 14
<212> TYPE: PRT
<213> ORGANISM: Artificial
<220> FEATURE:
<223> OTHER INFORMATION: Nanobody or nanobody construct

<400> SEQUENCE: 323

Trp Tyr Arg Gln Ala Pro Gly Lys Gln Arg Glu Leu Val Ala
1               5                   10

<210> SEQ ID NO 324
<211> LENGTH: 14
<212> TYPE: PRT
<213> ORGANISM: Artificial
<220> FEATURE:
<223> OTHER INFORMATION: Nanobody or nanobody construct

<400> SEQUENCE: 324

Trp Tyr Arg Gln Ala Pro Gly Lys Gln Arg Glu Leu Val Ala
1               5                   10

<210> SEQ ID NO 325
<211> LENGTH: 14
<212> TYPE: PRT
<213> ORGANISM: Artificial
<220> FEATURE:
<223> OTHER INFORMATION: Nanobody or nanobody construct

<400> SEQUENCE: 325

Trp Tyr Arg Gln Ala Pro Gly Lys Gln Arg Glu Leu Val Ala
1               5                   10

<210> SEQ ID NO 326
<211> LENGTH: 14
<212> TYPE: PRT
<213> ORGANISM: Artificial
<220> FEATURE:
<223> OTHER INFORMATION: Nanobody or nanobody construct
```

```
<400> SEQUENCE: 326

Trp Tyr Arg Gln Ala Pro Gly Lys Gln Arg Glu Leu Val Ala
1               5                   10

<210> SEQ ID NO 327
<211> LENGTH: 14
<212> TYPE: PRT
<213> ORGANISM: Artificial
<220> FEATURE:
<223> OTHER INFORMATION: Nanobody or nanobody construct

<400> SEQUENCE: 327

Trp Tyr Arg Gln Gly Pro Gly Lys Gln Arg Glu Leu Val Ala
1               5                   10

<210> SEQ ID NO 328
<211> LENGTH: 14
<212> TYPE: PRT
<213> ORGANISM: Artificial
<220> FEATURE:
<223> OTHER INFORMATION: Nanobody or nanobody construct

<400> SEQUENCE: 328

Trp Tyr Arg Gln Gly Pro Gly Lys Gln Arg Glu Leu Val Ala
1               5                   10

<210> SEQ ID NO 329
<211> LENGTH: 14
<212> TYPE: PRT
<213> ORGANISM: Artificial
<220> FEATURE:
<223> OTHER INFORMATION: Nanobody or nanobody construct

<400> SEQUENCE: 329

Trp Tyr Arg Gln Gly Pro Gly Lys Gln Arg Glu Leu Val Ala
1               5                   10

<210> SEQ ID NO 330
<211> LENGTH: 14
<212> TYPE: PRT
<213> ORGANISM: Artificial
<220> FEATURE:
<223> OTHER INFORMATION: Nanobody or nanobody construct

<400> SEQUENCE: 330

Trp Tyr Arg Gln Ala Pro Gly Lys Gln Arg Glu Leu Val Ala
1               5                   10

<210> SEQ ID NO 331
<211> LENGTH: 14
<212> TYPE: PRT
<213> ORGANISM: Artificial
<220> FEATURE:
<223> OTHER INFORMATION: Nanobody or nanobody construct

<400> SEQUENCE: 331

Trp Tyr Arg Gln Gly Pro Gly Lys Gln Arg Glu Leu Val Ala
1               5                   10

<210> SEQ ID NO 332
<211> LENGTH: 14
<212> TYPE: PRT
<213> ORGANISM: Artificial
<220> FEATURE:
<223> OTHER INFORMATION: Nanobody or nanobody construct
```

<400> SEQUENCE: 332

Trp Tyr Arg Gln Ala Pro Gly Lys Gln Arg Glu Leu Val Ala
1               5                   10

<210> SEQ ID NO 333
<211> LENGTH: 14
<212> TYPE: PRT
<213> ORGANISM: Artificial
<220> FEATURE:
<223> OTHER INFORMATION: Nanobody or nanobody construct

<400> SEQUENCE: 333

Trp Tyr Arg Gln Gly Pro Gly Lys Gln Arg Glu Leu Val Ala
1               5                   10

<210> SEQ ID NO 334
<211> LENGTH: 14
<212> TYPE: PRT
<213> ORGANISM: Artificial
<220> FEATURE:
<223> OTHER INFORMATION: Nanobody or nanobody construct

<400> SEQUENCE: 334

Trp Phe Arg Gln Ala Pro Gly Lys Glu Arg Glu Gly Ile Ala
1               5                   10

<210> SEQ ID NO 335
<211> LENGTH: 14
<212> TYPE: PRT
<213> ORGANISM: Artificial
<220> FEATURE:
<223> OTHER INFORMATION: Nanobody or nanobody construct

<400> SEQUENCE: 335

Trp Phe Arg Gln Ala Pro Gly Lys Glu Arg Glu Gly Ile Ala
1               5                   10

<210> SEQ ID NO 336
<211> LENGTH: 14
<212> TYPE: PRT
<213> ORGANISM: Artificial
<220> FEATURE:
<223> OTHER INFORMATION: Nanobody or nanobody construct

<400> SEQUENCE: 336

Trp Leu Arg Gln Ala Pro Gly Lys Glu Arg Glu Phe Val Ser
1               5                   10

<210> SEQ ID NO 337
<211> LENGTH: 14
<212> TYPE: PRT
<213> ORGANISM: Artificial
<220> FEATURE:
<223> OTHER INFORMATION: Nanobody or nanobody construct

<400> SEQUENCE: 337

Trp Leu Arg Gln Ala Pro Gly Lys Glu Arg Glu Phe Val Ser
1               5                   10

<210> SEQ ID NO 338
<211> LENGTH: 14
<212> TYPE: PRT
<213> ORGANISM: Artificial
<220> FEATURE:
<223> OTHER INFORMATION: Nanobody or nanobody construct

<400> SEQUENCE: 338

Trp Leu Arg Gln Ala Pro Gly Lys Glu Arg Glu Phe Val Ser
1               5                   10

<210> SEQ ID NO 339
<211> LENGTH: 14
<212> TYPE: PRT
<213> ORGANISM: Artificial
<220> FEATURE:
<223> OTHER INFORMATION: Nanobody or nanobody construct

<400> SEQUENCE: 339

Trp Phe Arg Gln Ala Pro Gly Lys Glu Arg Asp Phe Val Ala
1               5                   10

<210> SEQ ID NO 340
<211> LENGTH: 14
<212> TYPE: PRT
<213> ORGANISM: Artificial
<220> FEATURE:
<223> OTHER INFORMATION: Nanobody or nanobody construct

<400> SEQUENCE: 340

Trp Phe Arg Gln Ala Pro Gly Lys Glu Arg Asp Phe Val Ala
1               5                   10

<210> SEQ ID NO 341
<211> LENGTH: 14
<212> TYPE: PRT
<213> ORGANISM: Artificial
<220> FEATURE:
<223> OTHER INFORMATION: Nanobody or nanobody construct

<400> SEQUENCE: 341

Trp Phe Arg Gln Ala Pro Gly Lys Glu Arg Asp Phe Val Ala
1               5                   10

<210> SEQ ID NO 342
<211> LENGTH: 14
<212> TYPE: PRT
<213> ORGANISM: Artificial
<220> FEATURE:
<223> OTHER INFORMATION: Nanobody or nanobody construct

<400> SEQUENCE: 342

Trp Phe Arg Gln Ala Pro Gly Lys Glu Arg Glu Phe Val Ser
1               5                   10

<210> SEQ ID NO 343
<211> LENGTH: 14
<212> TYPE: PRT
<213> ORGANISM: Artificial
<220> FEATURE:
<223> OTHER INFORMATION: Nanobody or nanobody construct

<400> SEQUENCE: 343

Trp Phe Arg Gln Ala Pro Gly Lys Glu Arg Glu Phe Val Ser
1               5                   10

<210> SEQ ID NO 344
<211> LENGTH: 14
<212> TYPE: PRT
<213> ORGANISM: Artificial
<220> FEATURE:
<223> OTHER INFORMATION: Nanobody or nanobody construct

<400> SEQUENCE: 344

```
Trp Phe Arg Gln Ala Pro Gly Lys Gly Arg Glu Phe Val Ser
1               5                   10
```

<210> SEQ ID NO 345
<211> LENGTH: 14
<212> TYPE: PRT
<213> ORGANISM: Artificial
<220> FEATURE:
<223> OTHER INFORMATION: Nanobody or nanobody construct

<400> SEQUENCE: 345

```
Trp Tyr Arg Gln Ala Pro Gly Lys Gln Arg Glu Leu Val Ala
1               5                   10
```

<210> SEQ ID NO 346
<211> LENGTH: 14
<212> TYPE: PRT
<213> ORGANISM: Artificial
<220> FEATURE:
<223> OTHER INFORMATION: Nanobody or nanobody construct

<400> SEQUENCE: 346

```
Trp Phe Arg Gln Ala Pro Gly Lys Glu Arg Glu Glu Val Ser
1               5                   10
```

<210> SEQ ID NO 347
<211> LENGTH: 14
<212> TYPE: PRT
<213> ORGANISM: Artificial
<220> FEATURE:
<223> OTHER INFORMATION: Nanobody or nanobody construct

<400> SEQUENCE: 347

```
Trp Phe Arg Gln Ala Pro Gly Lys Glu Arg Glu Glu Val Ser
1               5                   10
```

<210> SEQ ID NO 348
<211> LENGTH: 14
<212> TYPE: PRT
<213> ORGANISM: Artificial
<220> FEATURE:
<223> OTHER INFORMATION: Nanobody or nanobody construct

<400> SEQUENCE: 348

```
Trp Phe Arg Gln Ala Pro Gly Lys Glu Arg Glu Gly Val Ala
1               5                   10
```

<210> SEQ ID NO 349
<211> LENGTH: 14
<212> TYPE: PRT
<213> ORGANISM: Artificial
<220> FEATURE:
<223> OTHER INFORMATION: Nanobody or nanobody construct

<400> SEQUENCE: 349

```
Trp Phe Arg Gln Ala Pro Gly Lys Glu Arg Glu Gly Val Ser
1               5                   10
```

<210> SEQ ID NO 350
<211> LENGTH: 14
<212> TYPE: PRT
<213> ORGANISM: Artificial
<220> FEATURE:
<223> OTHER INFORMATION: Nanobody or nanobody construct

<400> SEQUENCE: 350

```
Trp Phe Arg Gln Ala Pro Gly Lys Glu Arg Asp Phe Val Ala
```

```
1               5                   10
```

<210> SEQ ID NO 351
<211> LENGTH: 14
<212> TYPE: PRT
<213> ORGANISM: Artificial
<220> FEATURE:
<223> OTHER INFORMATION: Nanobody or nanobody construct

<400> SEQUENCE: 351

```
Trp Phe Arg Gln Thr Pro Gly Lys Glu Arg Glu Phe Val Ala
1               5                   10
```

<210> SEQ ID NO 352
<211> LENGTH: 14
<212> TYPE: PRT
<213> ORGANISM: Artificial
<220> FEATURE:
<223> OTHER INFORMATION: Nanobody or nanobody construct

<400> SEQUENCE: 352

```
Trp Phe Arg Gln Thr Pro Gly Lys Glu Arg Glu Phe Val Ala
1               5                   10
```

<210> SEQ ID NO 353
<211> LENGTH: 14
<212> TYPE: PRT
<213> ORGANISM: Artificial
<220> FEATURE:
<223> OTHER INFORMATION: Nanobody or nanobody construct

<400> SEQUENCE: 353

```
Trp Phe Arg Gln Thr Pro Gly Lys Glu Arg Glu Phe Val Ala
1               5                   10
```

<210> SEQ ID NO 354
<211> LENGTH: 14
<212> TYPE: PRT
<213> ORGANISM: Artificial
<220> FEATURE:
<223> OTHER INFORMATION: Nanobody or nanobody construct

<400> SEQUENCE: 354

```
Trp Phe Arg Gln Thr Pro Gly Lys Glu Arg Glu Phe Val Ala
1               5                   10
```

<210> SEQ ID NO 355
<211> LENGTH: 14
<212> TYPE: PRT
<213> ORGANISM: Artificial
<220> FEATURE:
<223> OTHER INFORMATION: Nanobody or nanobody construct

<400> SEQUENCE: 355

```
Trp Phe Arg Gln Ala Pro Gly Lys Glu Arg Glu Phe Val Ala
1               5                   10
```

<210> SEQ ID NO 356
<211> LENGTH: 14
<212> TYPE: PRT
<213> ORGANISM: Artificial
<220> FEATURE:
<223> OTHER INFORMATION: Nanobody or nanobody construct

<400> SEQUENCE: 356

```
Trp Tyr Arg Gln Ala Pro Gly Lys Pro Arg Glu Leu Val Ala
1               5                   10
```

```
<210> SEQ ID NO 357
<211> LENGTH: 14
<212> TYPE: PRT
<213> ORGANISM: Artificial
<220> FEATURE:
<223> OTHER INFORMATION: Nanobody or nanobody construct

<400> SEQUENCE: 357

Trp Phe Arg Gln Ala Pro Gly Lys Asp Arg Asp Phe Val Ala
1               5                   10

<210> SEQ ID NO 358
<211> LENGTH: 14
<212> TYPE: PRT
<213> ORGANISM: Artificial
<220> FEATURE:
<223> OTHER INFORMATION: Nanobody or nanobody construct

<400> SEQUENCE: 358

Trp Phe Arg Gln Ala Pro Gly Lys Glu Arg Glu Phe Val Ala
1               5                   10

<210> SEQ ID NO 359
<211> LENGTH: 14
<212> TYPE: PRT
<213> ORGANISM: Artificial
<220> FEATURE:
<223> OTHER INFORMATION: Nanobody or nanobody construct

<400> SEQUENCE: 359

Trp Val Arg Gln Ala Pro Gly Lys Gly Leu Glu Trp Ile Ser
1               5                   10

<210> SEQ ID NO 360
<211> LENGTH: 14
<212> TYPE: PRT
<213> ORGANISM: Artificial
<220> FEATURE:
<223> OTHER INFORMATION: Nanobody or nanobody construct

<400> SEQUENCE: 360

Trp Phe Arg Gln Pro Pro Gly Lys Asn Arg Glu Phe Val Ala
1               5                   10

<210> SEQ ID NO 361
<211> LENGTH: 14
<212> TYPE: PRT
<213> ORGANISM: Artificial
<220> FEATURE:
<223> OTHER INFORMATION: Nanobody or nanobody construct

<400> SEQUENCE: 361

Trp Phe Arg Gln Ala Pro Gly Lys Glu Arg Glu Gly Val Ser
1               5                   10

<210> SEQ ID NO 362
<211> LENGTH: 14
<212> TYPE: PRT
<213> ORGANISM: Artificial
<220> FEATURE:
<223> OTHER INFORMATION: Nanobody or nanobody construct

<400> SEQUENCE: 362

Trp Phe Arg Gln Ala Pro Gly Lys Glu Arg Glu Gly Val Ser
1               5                   10
```

<210> SEQ ID NO 363
<211> LENGTH: 14
<212> TYPE: PRT
<213> ORGANISM: Artificial
<220> FEATURE:
<223> OTHER INFORMATION: Nanobody or nanobody construct

<400> SEQUENCE: 363

Trp Phe Arg Gln Ala Pro Gly Lys Glu Arg Glu Phe Val Ala
1               5                   10

<210> SEQ ID NO 364
<211> LENGTH: 14
<212> TYPE: PRT
<213> ORGANISM: Artificial
<220> FEATURE:
<223> OTHER INFORMATION: Nanobody or nanobody construct

<400> SEQUENCE: 364

Trp Phe Arg Gln Ala Pro Gly Lys Glu Leu Glu Phe Leu Ala
1               5                   10

<210> SEQ ID NO 365
<211> LENGTH: 14
<212> TYPE: PRT
<213> ORGANISM: Artificial
<220> FEATURE:
<223> OTHER INFORMATION: Nanobody or nanobody construct

<400> SEQUENCE: 365

Trp Phe Arg Gln Ala Pro Gly Lys Glu Leu Glu Phe Leu Ala
1               5                   10

<210> SEQ ID NO 366
<211> LENGTH: 14
<212> TYPE: PRT
<213> ORGANISM: Artificial
<220> FEATURE:
<223> OTHER INFORMATION: Nanobody or nanobody construct

<400> SEQUENCE: 366

Trp Phe Arg Gln Ala Pro Gly Lys Glu Arg Glu Gly Val Ser
1               5                   10

<210> SEQ ID NO 367
<211> LENGTH: 14
<212> TYPE: PRT
<213> ORGANISM: Artificial
<220> FEATURE:
<223> OTHER INFORMATION: Nanobody or nanobody construct

<400> SEQUENCE: 367

Trp Phe Arg Gln Ala Pro Gly Lys Glu Arg Glu Gly Val Ser
1               5                   10

<210> SEQ ID NO 368
<211> LENGTH: 14
<212> TYPE: PRT
<213> ORGANISM: Artificial
<220> FEATURE:
<223> OTHER INFORMATION: Nanobody or nanobody construct

<400> SEQUENCE: 368

Trp Phe Arg Gln Ala Pro Gly Lys Glu Arg Gly Leu Val Ala
1               5                   10

-continued

```
<210> SEQ ID NO 369
<211> LENGTH: 14
<212> TYPE: PRT
<213> ORGANISM: Artificial
<220> FEATURE:
<223> OTHER INFORMATION: Nanobody or nanobody construct

<400> SEQUENCE: 369

Trp Tyr Arg Gln Ala Pro Gly Lys Gln Arg Glu Leu Val Ala
1               5                   10

<210> SEQ ID NO 370
<211> LENGTH: 14
<212> TYPE: PRT
<213> ORGANISM: Artificial
<220> FEATURE:
<223> OTHER INFORMATION: Nanobody or nanobody construct

<400> SEQUENCE: 370

Trp Tyr Arg Gln Pro Ala Gly Lys Gln Arg Glu Leu Val Ala
1               5                   10

<210> SEQ ID NO 371
<211> LENGTH: 14
<212> TYPE: PRT
<213> ORGANISM: Artificial
<220> FEATURE:
<223> OTHER INFORMATION: Nanobody or nanobody construct

<400> SEQUENCE: 371

Trp Phe Arg Gln Ala Pro Gly Arg Glu Arg Glu Phe Val Ala
1               5                   10

<210> SEQ ID NO 372
<211> LENGTH: 16
<212> TYPE: PRT
<213> ORGANISM: Artificial
<220> FEATURE:
<223> OTHER INFORMATION: Nanobody or nanobody construct

<400> SEQUENCE: 372

Cys Ile Ser Ser Thr Gly Asn Val Phe Tyr Ala Asp Ser Val Lys Gly
1               5                   10                  15

<210> SEQ ID NO 373
<211> LENGTH: 16
<212> TYPE: PRT
<213> ORGANISM: Artificial
<220> FEATURE:
<223> OTHER INFORMATION: Nanobody or nanobody construct

<400> SEQUENCE: 373

Cys Ile Ser Ser Thr Gly Asn Val Phe Tyr Ala Asp Ser Val Lys Gly
1               5                   10                  15

<210> SEQ ID NO 374
<211> LENGTH: 16
<212> TYPE: PRT
<213> ORGANISM: Artificial
<220> FEATURE:
<223> OTHER INFORMATION: Nanobody or nanobody construct

<400> SEQUENCE: 374

Cys Ile Ser Ser Thr Gly Asn Val Phe Tyr Ala Asp Ser Val Lys Gly
1               5                   10                  15

<210> SEQ ID NO 375
```

```
<211> LENGTH: 16
<212> TYPE: PRT
<213> ORGANISM: Artificial
<220> FEATURE:
<223> OTHER INFORMATION: Nanobody or nanobody construct

<400> SEQUENCE: 375

Cys Ile Ser Ser Thr Gly Asn Val Phe Tyr Ala Asp Ser Val Lys Gly
1               5                   10                  15

<210> SEQ ID NO 376
<211> LENGTH: 16
<212> TYPE: PRT
<213> ORGANISM: Artificial
<220> FEATURE:
<223> OTHER INFORMATION: Nanobody or nanobody construct

<400> SEQUENCE: 376

Cys Ile Ser Ser Thr Gly Asn Val Phe Tyr Ala Asp Ser Val Lys Gly
1               5                   10                  15

<210> SEQ ID NO 377
<211> LENGTH: 16
<212> TYPE: PRT
<213> ORGANISM: Artificial
<220> FEATURE:
<223> OTHER INFORMATION: Nanobody or nanobody construct

<400> SEQUENCE: 377

Cys Ile Ser Ser Thr Gly Asn Val Phe Tyr Ala Asp Ser Val Lys Gly
1               5                   10                  15

<210> SEQ ID NO 378
<211> LENGTH: 16
<212> TYPE: PRT
<213> ORGANISM: Artificial
<220> FEATURE:
<223> OTHER INFORMATION: Nanobody or nanobody construct

<400> SEQUENCE: 378

Cys Ile Ser Ser Thr Gly Asn Val Phe Tyr Ala Asp Ser Val Lys Gly
1               5                   10                  15

<210> SEQ ID NO 379
<211> LENGTH: 16
<212> TYPE: PRT
<213> ORGANISM: Artificial
<220> FEATURE:
<223> OTHER INFORMATION: Nanobody or nanobody construct

<400> SEQUENCE: 379

Ile Leu Ser Ser Ile Gly Lys Thr Phe Tyr Ala Asp Ser Val Lys Asp
1               5                   10                  15

<210> SEQ ID NO 380
<211> LENGTH: 16
<212> TYPE: PRT
<213> ORGANISM: Artificial
<220> FEATURE:
<223> OTHER INFORMATION: Nanobody or nanobody construct

<400> SEQUENCE: 380

Ile Leu Ser Ser Ile Gly Lys Thr Phe Tyr Ala Asp Ser Val Lys Asp
1               5                   10                  15

<210> SEQ ID NO 381
<211> LENGTH: 16
```

```
<212> TYPE: PRT
<213> ORGANISM: Artificial
<220> FEATURE:
<223> OTHER INFORMATION: Nanobody or nanobody construct

<400> SEQUENCE: 381

Ile Leu Ser Ser Ile Gly Lys Thr Phe Tyr Ala Asp Ser Val Lys Asp
1               5                   10                  15

<210> SEQ ID NO 382
<211> LENGTH: 16
<212> TYPE: PRT
<213> ORGANISM: Artificial
<220> FEATURE:
<223> OTHER INFORMATION: Nanobody or nanobody construct

<400> SEQUENCE: 382

Ile Leu Ser Ser Ile Gly Lys Thr Phe Tyr Ala Asp Ser Ala Lys Asp
1               5                   10                  15

<210> SEQ ID NO 383
<211> LENGTH: 17
<212> TYPE: PRT
<213> ORGANISM: Artificial
<220> FEATURE:
<223> OTHER INFORMATION: Nanobody or nanobody construct

<400> SEQUENCE: 383

Gly Ser Gly Trp Asp Gly Ile Pro Thr Arg Tyr Ala Asp Ser Val Lys
1               5                   10                  15

Gly

<210> SEQ ID NO 384
<211> LENGTH: 17
<212> TYPE: PRT
<213> ORGANISM: Artificial
<220> FEATURE:
<223> OTHER INFORMATION: Nanobody or nanobody construct

<400> SEQUENCE: 384

Gly Ser Gly Trp Asp Gly Ile Pro Thr Arg Tyr Ala Asp Ser Val Lys
1               5                   10                  15

Gly

<210> SEQ ID NO 385
<211> LENGTH: 17
<212> TYPE: PRT
<213> ORGANISM: Artificial
<220> FEATURE:
<223> OTHER INFORMATION: Nanobody or nanobody construct

<400> SEQUENCE: 385

Gly Ser Gly Trp Asp Gly Thr Pro Thr Arg Tyr Ala Asp Ser Val Lys
1               5                   10                  15

Gly

<210> SEQ ID NO 386
<211> LENGTH: 17
<212> TYPE: PRT
<213> ORGANISM: Artificial
<220> FEATURE:
<223> OTHER INFORMATION: Nanobody or nanobody construct

<400> SEQUENCE: 386

Gly Ser Gly Trp Asp Gly Ile Pro Thr Arg Tyr Ala Asp Ser Val Lys
```

```
1               5                  10                 15

Gly

<210> SEQ ID NO 387
<211> LENGTH: 17
<212> TYPE: PRT
<213> ORGANISM: Artificial
<220> FEATURE:
<223> OTHER INFORMATION: Nanobody or nanobody construct

<400> SEQUENCE: 387

Gly Ser Gly Trp Asp Gly Ile Pro Thr Arg Tyr Ala Asp Ser Val Lys
1               5                  10                 15

Gly

<210> SEQ ID NO 388
<211> LENGTH: 17
<212> TYPE: PRT
<213> ORGANISM: Artificial
<220> FEATURE:
<223> OTHER INFORMATION: Nanobody or nanobody construct

<400> SEQUENCE: 388

Gly Ser Gly Trp Asp Gly Ile Pro Thr Arg Tyr Ala Asp Ser Val Lys
1               5                  10                 15

Ser

<210> SEQ ID NO 389
<211> LENGTH: 17
<212> TYPE: PRT
<213> ORGANISM: Artificial
<220> FEATURE:
<223> OTHER INFORMATION: Nanobody or nanobody construct

<400> SEQUENCE: 389

Gly Ser Gly Trp Asp Gly Ile Pro Thr Arg Tyr Ala Asp Ser Val Lys
1               5                  10                 15

Gly

<210> SEQ ID NO 390
<211> LENGTH: 17
<212> TYPE: PRT
<213> ORGANISM: Artificial
<220> FEATURE:
<223> OTHER INFORMATION: Nanobody or nanobody construct

<400> SEQUENCE: 390

Gly Ser Gly Trp Asp Gly Ile Pro Thr Arg Tyr Ala Asp Ser Val Lys
1               5                  10                 15

Gly

<210> SEQ ID NO 391
<211> LENGTH: 17
<212> TYPE: PRT
<213> ORGANISM: Artificial
<220> FEATURE:
<223> OTHER INFORMATION: Nanobody or nanobody construct

<400> SEQUENCE: 391

Gly Ser Gly Trp Asp Gly Ile Pro Thr Arg Tyr Ala Asp Ser Val Lys
1               5                  10                 15

Gly
```

<210> SEQ ID NO 392
<211> LENGTH: 17
<212> TYPE: PRT
<213> ORGANISM: Artificial
<220> FEATURE:
<223> OTHER INFORMATION: Nanobody or nanobody construct

<400> SEQUENCE: 392

Ser Ile Asn Trp Ser Gly Ile Tyr Thr Arg Tyr Ile Asp Ser Val Glu
1               5                   10                  15
Gly

<210> SEQ ID NO 393
<211> LENGTH: 17
<212> TYPE: PRT
<213> ORGANISM: Artificial
<220> FEATURE:
<223> OTHER INFORMATION: Nanobody or nanobody construct

<400> SEQUENCE: 393

Ser Ile Asn Trp Ser Gly Ile Tyr Thr Arg Tyr Ile Asp Ser Val Glu
1               5                   10                  15
Gly

<210> SEQ ID NO 394
<211> LENGTH: 17
<212> TYPE: PRT
<213> ORGANISM: Artificial
<220> FEATURE:
<223> OTHER INFORMATION: Nanobody or nanobody construct

<400> SEQUENCE: 394

Ser Ile Asn Trp Ser Gly Ile Tyr Thr Arg Tyr Ile Asp Ser Val Glu
1               5                   10                  15
Gly

<210> SEQ ID NO 395
<211> LENGTH: 17
<212> TYPE: PRT
<213> ORGANISM: Artificial
<220> FEATURE:
<223> OTHER INFORMATION: Nanobody or nanobody construct

<400> SEQUENCE: 395

Ser Ile Asn Trp Ser Gly Thr Tyr Thr Arg Tyr Ile Asp Ser Val Glu
1               5                   10                  15
Gly

<210> SEQ ID NO 396
<211> LENGTH: 17
<212> TYPE: PRT
<213> ORGANISM: Artificial
<220> FEATURE:
<223> OTHER INFORMATION: Nanobody or nanobody construct

<400> SEQUENCE: 396

Ser Ile Asn Trp Ser Gly Thr Tyr Thr Arg Tyr Ile Asp Ser Val Glu
1               5                   10                  15
Gly

<210> SEQ ID NO 397
<211> LENGTH: 16
<212> TYPE: PRT

<210> SEQ ID NO 397
<211> LENGTH: 16
<212> TYPE: PRT
<213> ORGANISM: Artificial
<220> FEATURE:
<223> OTHER INFORMATION: Nanobody or nanobody construct

<400> SEQUENCE: 397

Asp Ile Thr Arg Gly Asp Arg Thr Asn Tyr Ala Asp Thr Val Asn Gly
1               5                   10                  15

<210> SEQ ID NO 398
<211> LENGTH: 16
<212> TYPE: PRT
<213> ORGANISM: Artificial
<220> FEATURE:
<223> OTHER INFORMATION: Nanobody or nanobody construct

<400> SEQUENCE: 398

Asp Ile Thr Arg Gly Asp Arg Thr Asn Tyr Ala Asp Thr Val Asn Gly
1               5                   10                  15

<210> SEQ ID NO 399
<211> LENGTH: 16
<212> TYPE: PRT
<213> ORGANISM: Artificial
<220> FEATURE:
<223> OTHER INFORMATION: Nanobody or nanobody construct

<400> SEQUENCE: 399

Asp Ile Thr Arg Gly Asp Arg Thr Asn Tyr Ala Asp Thr Val Asn Gly
1               5                   10                  15

<210> SEQ ID NO 400
<211> LENGTH: 16
<212> TYPE: PRT
<213> ORGANISM: Artificial
<220> FEATURE:
<223> OTHER INFORMATION: Nanobody or nanobody construct

<400> SEQUENCE: 400

Asp Ile Thr Arg Gly Asp Arg Thr Asn Tyr Ala Asp Ser Val Asn Gly
1               5                   10                  15

<210> SEQ ID NO 401
<211> LENGTH: 16
<212> TYPE: PRT
<213> ORGANISM: Artificial
<220> FEATURE:
<223> OTHER INFORMATION: Nanobody or nanobody construct

<400> SEQUENCE: 401

Asp Ile Thr Arg Gly Asp Arg Thr Asn Tyr Ala Asp Ser Val Asn Gly
1               5                   10                  15

<210> SEQ ID NO 402
<211> LENGTH: 16
<212> TYPE: PRT
<213> ORGANISM: Artificial
<220> FEATURE:
<223> OTHER INFORMATION: Nanobody or nanobody construct

<400> SEQUENCE: 402

Asp Ile Thr Arg Gly Asp Arg Thr Asn Tyr Ala Asp Thr Val Asn Gly
1               5                   10                  15

<210> SEQ ID NO 403
<211> LENGTH: 16
<212> TYPE: PRT
<213> ORGANISM: Artificial

```
<220> FEATURE:
<223> OTHER INFORMATION: Nanobody or nanobody construct

<400> SEQUENCE: 403

Asp Ile Thr Arg Gly Asp Arg Thr Asn Tyr Ala Asp Thr Val Asn Gly
1               5                   10                  15

<210> SEQ ID NO 404
<211> LENGTH: 16
<212> TYPE: PRT
<213> ORGANISM: Artificial
<220> FEATURE:
<223> OTHER INFORMATION: Nanobody or nanobody construct

<400> SEQUENCE: 404

Asp Ile Thr Arg Gly Asp Arg Thr Asn Tyr Ala Asp Thr Val Asn Gly
1               5                   10                  15

<210> SEQ ID NO 405
<211> LENGTH: 16
<212> TYPE: PRT
<213> ORGANISM: Artificial
<220> FEATURE:
<223> OTHER INFORMATION: Nanobody or nanobody construct

<400> SEQUENCE: 405

Asp Ile Thr Arg Gly Asp Arg Thr Asn Tyr Ala Asp Ser Val Asn Gly
1               5                   10                  15

<210> SEQ ID NO 406
<211> LENGTH: 16
<212> TYPE: PRT
<213> ORGANISM: Artificial
<220> FEATURE:
<223> OTHER INFORMATION: Nanobody or nanobody construct

<400> SEQUENCE: 406

Asp Ile Thr Arg Gly Asp Arg Thr Asn Tyr Ala Asp Ser Val Asn Gly
1               5                   10                  15

<210> SEQ ID NO 407
<211> LENGTH: 16
<212> TYPE: PRT
<213> ORGANISM: Artificial
<220> FEATURE:
<223> OTHER INFORMATION: Nanobody or nanobody construct

<400> SEQUENCE: 407

Asp Ile Thr Arg Gly Asp Arg Thr Asn Tyr Ala Asp Ser Val Asn Gly
1               5                   10                  15

<210> SEQ ID NO 408
<211> LENGTH: 16
<212> TYPE: PRT
<213> ORGANISM: Artificial
<220> FEATURE:
<223> OTHER INFORMATION: Nanobody or nanobody construct

<400> SEQUENCE: 408

Asp Ile Thr Arg Gly Asp Arg Thr Asn Tyr Ala Asp Ser Val Asn Gly
1               5                   10                  15

<210> SEQ ID NO 409
<211> LENGTH: 16
<212> TYPE: PRT
<213> ORGANISM: Artificial
<220> FEATURE:
```

<223> OTHER INFORMATION: Nanobody or nanobody construct

<400> SEQUENCE: 409

Asp Ile Thr Arg Gly Asp Arg Thr Asn Tyr Ala Asp Ser Val Asn Gly
1               5                   10                  15

<210> SEQ ID NO 410
<211> LENGTH: 16
<212> TYPE: PRT
<213> ORGANISM: Artificial
<220> FEATURE:
<223> OTHER INFORMATION: Nanobody or nanobody construct

<400> SEQUENCE: 410

Asp Ile Thr Arg Gly Asp Arg Thr Asn Tyr Ala Asp Ser Val Asn Gly
1               5                   10                  15

<210> SEQ ID NO 411
<211> LENGTH: 16
<212> TYPE: PRT
<213> ORGANISM: Artificial
<220> FEATURE:
<223> OTHER INFORMATION: Nanobody or nanobody construct

<400> SEQUENCE: 411

Asp Ile Thr Arg Gly Asp Arg Thr Asn Tyr Ala Asp Ser Val Asn Gly
1               5                   10                  15

<210> SEQ ID NO 412
<211> LENGTH: 16
<212> TYPE: PRT
<213> ORGANISM: Artificial
<220> FEATURE:
<223> OTHER INFORMATION: Nanobody or nanobody construct

<400> SEQUENCE: 412

Asp Ile Thr Arg Gly Asp Arg Thr Asn Tyr Ala Asp Ser Val Asn Gly
1               5                   10                  15

<210> SEQ ID NO 413
<211> LENGTH: 16
<212> TYPE: PRT
<213> ORGANISM: Artificial
<220> FEATURE:
<223> OTHER INFORMATION: Nanobody or nanobody construct

<400> SEQUENCE: 413

Asp Ile Thr Arg Gly Asp Arg Thr Asn Tyr Ala Asp Ser Val Asn Gly
1               5                   10                  15

<210> SEQ ID NO 414
<211> LENGTH: 16
<212> TYPE: PRT
<213> ORGANISM: Artificial
<220> FEATURE:
<223> OTHER INFORMATION: Nanobody or nanobody construct

<400> SEQUENCE: 414

Asp Ile Thr Arg Gly Asp Arg Thr Asn Tyr Ala Asp Ser Val Asn Gly
1               5                   10                  15

<210> SEQ ID NO 415
<211> LENGTH: 16
<212> TYPE: PRT
<213> ORGANISM: Artificial
<220> FEATURE:
<223> OTHER INFORMATION: Nanobody or nanobody construct

<400> SEQUENCE: 415

Asp Ile Thr Arg Gly Asp Arg Thr Asn Tyr Ala Asp Ser Val Asn Gly
1               5                   10                  15

<210> SEQ ID NO 416
<211> LENGTH: 17
<212> TYPE: PRT
<213> ORGANISM: Artificial
<220> FEATURE:
<223> OTHER INFORMATION: Nanobody or nanobody construct

<400> SEQUENCE: 416

Cys Ile Ser Arg Val Asp Gly Thr Thr Tyr Tyr Arg Asp Ser Val Lys
1               5                   10                  15

Gly

<210> SEQ ID NO 417
<211> LENGTH: 17
<212> TYPE: PRT
<213> ORGANISM: Artificial
<220> FEATURE:
<223> OTHER INFORMATION: Nanobody or nanobody construct

<400> SEQUENCE: 417

Cys Ile Ser Arg Val Asp Gly Thr Thr Tyr Tyr Arg Asp Ser Val Lys
1               5                   10                  15

Gly

<210> SEQ ID NO 418
<211> LENGTH: 17
<212> TYPE: PRT
<213> ORGANISM: Artificial
<220> FEATURE:
<223> OTHER INFORMATION: Nanobody or nanobody construct

<400> SEQUENCE: 418

Gly Ile Ser Arg Gly Gly Thr Ser Thr Tyr Tyr Ala Asp Ser Val Lys
1               5                   10                  15

Gly

<210> SEQ ID NO 419
<211> LENGTH: 17
<212> TYPE: PRT
<213> ORGANISM: Artificial
<220> FEATURE:
<223> OTHER INFORMATION: Nanobody or nanobody construct

<400> SEQUENCE: 419

Gly Ile Ser Arg Gly Gly Thr Ser Thr Tyr Tyr Ala Asp Ser Val Lys
1               5                   10                  15

Gly

<210> SEQ ID NO 420
<211> LENGTH: 17
<212> TYPE: PRT
<213> ORGANISM: Artificial
<220> FEATURE:
<223> OTHER INFORMATION: Nanobody or nanobody construct

<400> SEQUENCE: 420

Gly Ile Ser Arg Gly Gly Thr Ser Thr Tyr Tyr Ala Asp Ser Val Lys
1               5                   10                  15

-continued

Gly

<210> SEQ ID NO 421
<211> LENGTH: 17
<212> TYPE: PRT
<213> ORGANISM: Artificial
<220> FEATURE:
<223> OTHER INFORMATION: Nanobody or nanobody construct

<400> SEQUENCE: 421

Thr Ile Ser Trp Asn Gly Val Asp Thr His Tyr Leu Asp Ser Val Lys
1               5                   10                  15
Gly

<210> SEQ ID NO 422
<211> LENGTH: 17
<212> TYPE: PRT
<213> ORGANISM: Artificial
<220> FEATURE:
<223> OTHER INFORMATION: Nanobody or nanobody construct

<400> SEQUENCE: 422

Thr Ile Ser Trp Asn Gly Val Asp Thr His Tyr Leu Asp Ser Val Lys
1               5                   10                  15
Gly

<210> SEQ ID NO 423
<211> LENGTH: 17
<212> TYPE: PRT
<213> ORGANISM: Artificial
<220> FEATURE:
<223> OTHER INFORMATION: Nanobody or nanobody construct

<400> SEQUENCE: 423

Thr Ile Ser Trp Asn Gly Val Asp Thr His Tyr Leu Asp Ser Val Lys
1               5                   10                  15
Gly

<210> SEQ ID NO 424
<211> LENGTH: 17
<212> TYPE: PRT
<213> ORGANISM: Artificial
<220> FEATURE:
<223> OTHER INFORMATION: Nanobody or nanobody construct

<400> SEQUENCE: 424

Thr Ile Ser Trp Asn Gly Ala Ser Thr Val Tyr Ala Asp Ser Val Lys
1               5                   10                  15
Gly

<210> SEQ ID NO 425
<211> LENGTH: 17
<212> TYPE: PRT
<213> ORGANISM: Artificial
<220> FEATURE:
<223> OTHER INFORMATION: Nanobody or nanobody construct

<400> SEQUENCE: 425

Thr Ile Ser Trp Asn Gly Ala Asp Thr Val Tyr Ala Asp Ser Val Lys
1               5                   10                  15
Gly

<210> SEQ ID NO 426

```
<211> LENGTH: 17
<212> TYPE: PRT
<213> ORGANISM: Artificial
<220> FEATURE:
<223> OTHER INFORMATION: Nanobody or nanobody construct

<400> SEQUENCE: 426

Thr Ile Asn Trp Ser Gly Gly Asp Thr Asp Tyr Ala Asp Ser Val Lys
1               5                   10                  15
Gly

<210> SEQ ID NO 427
<211> LENGTH: 16
<212> TYPE: PRT
<213> ORGANISM: Artificial
<220> FEATURE:
<223> OTHER INFORMATION: Nanobody or nanobody construct

<400> SEQUENCE: 427

Thr Val Thr Arg Gly Asp Ile Thr Asn Tyr Ala Asp Ser Val Lys Gly
1               5                   10                  15

<210> SEQ ID NO 428
<211> LENGTH: 17
<212> TYPE: PRT
<213> ORGANISM: Artificial
<220> FEATURE:
<223> OTHER INFORMATION: Nanobody or nanobody construct

<400> SEQUENCE: 428

Cys Ile Arg Val Thr Asp Gly Ser Thr Tyr Tyr Thr Asn Ser Val Lys
1               5                   10                  15
Gly

<210> SEQ ID NO 429
<211> LENGTH: 17
<212> TYPE: PRT
<213> ORGANISM: Artificial
<220> FEATURE:
<223> OTHER INFORMATION: Nanobody or nanobody construct

<400> SEQUENCE: 429

Cys Ile Arg Val Thr Asp Gly Ser Thr Tyr His Thr Asn Ser Val Lys
1               5                   10                  15
Gly

<210> SEQ ID NO 430
<211> LENGTH: 17
<212> TYPE: PRT
<213> ORGANISM: Artificial
<220> FEATURE:
<223> OTHER INFORMATION: Nanobody or nanobody construct

<400> SEQUENCE: 430

Cys Ile Asp Trp Thr Glu Gly Ser Thr Phe Tyr Val Asp Ser Val Lys
1               5                   10                  15
Gly

<210> SEQ ID NO 431
<211> LENGTH: 17
<212> TYPE: PRT
<213> ORGANISM: Artificial
<220> FEATURE:
<223> OTHER INFORMATION: Nanobody or nanobody construct
```

<400> SEQUENCE: 431

Cys Ile Asp Trp Thr Asp Gly Thr Thr Phe Tyr Ala Asp Ser Val Lys
1               5                   10                  15

Gly

<210> SEQ ID NO 432
<211> LENGTH: 17
<212> TYPE: PRT
<213> ORGANISM: Artificial
<220> FEATURE:
<223> OTHER INFORMATION: Nanobody or nanobody construct

<400> SEQUENCE: 432

Trp Ile Ser Trp Ser Gly Asp Ser Thr Tyr Tyr Ala Asp Ser Val Lys
1               5                   10                  15

Gly

<210> SEQ ID NO 433
<211> LENGTH: 17
<212> TYPE: PRT
<213> ORGANISM: Artificial
<220> FEATURE:
<223> OTHER INFORMATION: Nanobody or nanobody construct

<400> SEQUENCE: 433

Ala Thr Ser Trp Ser Asp Ile Ser Thr Tyr Tyr Ala Asp Ser Val Lys
1               5                   10                  15

Gly

<210> SEQ ID NO 434
<211> LENGTH: 17
<212> TYPE: PRT
<213> ORGANISM: Artificial
<220> FEATURE:
<223> OTHER INFORMATION: Nanobody or nanobody construct

<400> SEQUENCE: 434

Ala Thr Ser Trp Ser Asp Ile Ser Thr Tyr Tyr Ala Asp Ser Val Lys
1               5                   10                  15

Gly

<210> SEQ ID NO 435
<211> LENGTH: 17
<212> TYPE: PRT
<213> ORGANISM: Artificial
<220> FEATURE:
<223> OTHER INFORMATION: Nanobody or nanobody construct

<400> SEQUENCE: 435

Ala Thr Ser Trp Ser Asp Ile Ser Thr Tyr Tyr Ala Asp Ser Val Lys
1               5                   10                  15

Gly

<210> SEQ ID NO 436
<211> LENGTH: 17
<212> TYPE: PRT
<213> ORGANISM: Artificial
<220> FEATURE:
<223> OTHER INFORMATION: Nanobody or nanobody construct

<400> SEQUENCE: 436

Ala Thr Ser Trp Ser Asp Ile Ser Thr Tyr Tyr Ala Asp Ser Val Lys
1               5                   10                  15

Gly

<210> SEQ ID NO 437
<211> LENGTH: 17
<212> TYPE: PRT
<213> ORGANISM: Artificial
<220> FEATURE:
<223> OTHER INFORMATION: Nanobody or nanobody construct

<400> SEQUENCE: 437

Thr Val Gly Trp Asn Pro Met Asn Ser Tyr Tyr Gly Asp Ser Val Lys
1               5                   10                  15
Gly

<210> SEQ ID NO 438
<211> LENGTH: 16
<212> TYPE: PRT
<213> ORGANISM: Artificial
<220> FEATURE:
<223> OTHER INFORMATION: Nanobody or nanobody construct

<400> SEQUENCE: 438

Arg Ile Tyr Thr Gly Gly Thr Ala Trp Tyr Glu Asp Ser Val Lys Gly
1               5                   10                  15

<210> SEQ ID NO 439
<211> LENGTH: 17
<212> TYPE: PRT
<213> ORGANISM: Artificial
<220> FEATURE:
<223> OTHER INFORMATION: Nanobody or nanobody construct

<400> SEQUENCE: 439

Ala Ile Ser Trp Ser Gly Ser Ser Thr His Tyr Ala Asp Ser Val Lys
1               5                   10                  15
Gly

<210> SEQ ID NO 440
<211> LENGTH: 17
<212> TYPE: PRT
<213> ORGANISM: Artificial
<220> FEATURE:
<223> OTHER INFORMATION: Nanobody or nanobody construct

<400> SEQUENCE: 440

Ala Ile Ser Leu Ser Gly Ser Met Thr Tyr Tyr Ala Asp Ser Met Lys
1               5                   10                  15
Gly

<210> SEQ ID NO 441
<211> LENGTH: 17
<212> TYPE: PRT
<213> ORGANISM: Artificial
<220> FEATURE:
<223> OTHER INFORMATION: Nanobody or nanobody construct

<400> SEQUENCE: 441

Thr Ile Asn Ser Gly Gly Gly Thr Thr Tyr Ala Asp Ser Val Arg
1               5                   10                  15
Gly

<210> SEQ ID NO 442
<211> LENGTH: 17

```
<212> TYPE: PRT
<213> ORGANISM: Artificial
<220> FEATURE:
<223> OTHER INFORMATION: Nanobody or nanobody construct

<400> SEQUENCE: 442

Thr Ile Ala Trp Ser Ala Thr Thr Thr His Tyr Ala Asp Ala Val Lys
1               5                   10                  15

Gly

<210> SEQ ID NO 443
<211> LENGTH: 17
<212> TYPE: PRT
<213> ORGANISM: Artificial
<220> FEATURE:
<223> OTHER INFORMATION: Nanobody or nanobody construct

<400> SEQUENCE: 443

Cys Arg Phe Thr Asn Asp Gly Ser Thr Ala Tyr Ala Asp Ser Val Lys
1               5                   10                  15

Gly

<210> SEQ ID NO 444
<211> LENGTH: 17
<212> TYPE: PRT
<213> ORGANISM: Artificial
<220> FEATURE:
<223> OTHER INFORMATION: Nanobody or nanobody construct

<400> SEQUENCE: 444

Cys Ser Phe Thr Asn Asp Gly Ser Thr Tyr Tyr Ala Asp Ser Val Lys
1               5                   10                  15

Gly

<210> SEQ ID NO 445
<211> LENGTH: 16
<212> TYPE: PRT
<213> ORGANISM: Artificial
<220> FEATURE:
<223> OTHER INFORMATION: Nanobody or nanobody construct

<400> SEQUENCE: 445

Ala Ile Ser Gly Ile Gly Ala Ile His Tyr Ala Asp Ser Val Lys Gly
1               5                   10                  15

<210> SEQ ID NO 446
<211> LENGTH: 17
<212> TYPE: PRT
<213> ORGANISM: Artificial
<220> FEATURE:
<223> OTHER INFORMATION: Nanobody or nanobody construct

<400> SEQUENCE: 446

Gly Ile Asn Trp Ser Gly Met Ser Thr Trp Tyr Ala Asp Ser Val Lys
1               5                   10                  15

Asp

<210> SEQ ID NO 447
<211> LENGTH: 17
<212> TYPE: PRT
<213> ORGANISM: Artificial
<220> FEATURE:
<223> OTHER INFORMATION: Nanobody or nanobody construct

<400> SEQUENCE: 447
```

```
Gly Ile Asn Trp Ser Gly Met Ser Thr Trp Tyr Ala Asp Ser Val Lys
1               5                   10                  15
Asp
```

<210> SEQ ID NO 448
<211> LENGTH: 16
<212> TYPE: PRT
<213> ORGANISM: Artificial
<220> FEATURE:
<223> OTHER INFORMATION: Nanobody or nanobody construct

<400> SEQUENCE: 448

```
Leu Ser Ser Tyr Leu Gly Ala Ala Tyr Tyr Ala Thr Ser Val Lys Gly
1               5                   10                  15
```

<210> SEQ ID NO 449
<211> LENGTH: 16
<212> TYPE: PRT
<213> ORGANISM: Artificial
<220> FEATURE:
<223> OTHER INFORMATION: Nanobody or nanobody construct

<400> SEQUENCE: 449

```
Leu Ser Ser Tyr Val Gly Ala Val Tyr Tyr Ala Thr Ser Val Lys Gly
1               5                   10                  15
```

<210> SEQ ID NO 450
<211> LENGTH: 17
<212> TYPE: PRT
<213> ORGANISM: Artificial
<220> FEATURE:
<223> OTHER INFORMATION: Nanobody or nanobody construct

<400> SEQUENCE: 450

```
Met Ile Ser Trp Ser Gly Ser Met Thr Tyr Tyr Ala Lys Ser Val Lys
1               5                   10                  15
Gly
```

<210> SEQ ID NO 451
<211> LENGTH: 16
<212> TYPE: PRT
<213> ORGANISM: Artificial
<220> FEATURE:
<223> OTHER INFORMATION: Nanobody or nanobody construct

<400> SEQUENCE: 451

```
Thr Val Thr Glu Asp Gly Thr Lys Asn Tyr Ala Asp Ser Val Lys Gly
1               5                   10                  15
```

<210> SEQ ID NO 452
<211> LENGTH: 16
<212> TYPE: PRT
<213> ORGANISM: Artificial
<220> FEATURE:
<223> OTHER INFORMATION: Nanobody or nanobody construct

<400> SEQUENCE: 452

```
Asp Ile Thr Leu Gly Gly Ser Thr Asn Tyr Ala Asp Ser Val Lys Gly
1               5                   10                  15
```

<210> SEQ ID NO 453
<211> LENGTH: 17
<212> TYPE: PRT
<213> ORGANISM: Artificial
<220> FEATURE:

<223> OTHER INFORMATION: Nanobody or nanobody construct

<400> SEQUENCE: 453

Ala Ile Ser Trp Ile Gly Gly Arg Thr Tyr Tyr Val Asp Val Val Lys
1               5                   10                  15

Gly

<210> SEQ ID NO 454
<211> LENGTH: 32
<212> TYPE: PRT
<213> ORGANISM: Artificial
<220> FEATURE:
<223> OTHER INFORMATION: Nanobody or nanobody construct

<400> SEQUENCE: 454

Arg Phe Thr Ile Ser Ser Asp Lys Glu Lys Asn Thr Leu Tyr Leu Gln
1               5                   10                  15

Met Asn Ser Leu Lys Pro Glu Asp Thr Ala Val Tyr His Cys Ala Ala
                20                  25                  30

<210> SEQ ID NO 455
<211> LENGTH: 32
<212> TYPE: PRT
<213> ORGANISM: Artificial
<220> FEATURE:
<223> OTHER INFORMATION: Nanobody or nanobody construct

<400> SEQUENCE: 455

Arg Phe Thr Ile Ser Ser Asp Lys Glu Lys Asn Thr Leu Tyr Leu Gln
1               5                   10                  15

Met Asn Ser Leu Glu Pro Glu Asp Thr Ala Val Tyr His Cys Ala Ala
                20                  25                  30

<210> SEQ ID NO 456
<211> LENGTH: 32
<212> TYPE: PRT
<213> ORGANISM: Artificial
<220> FEATURE:
<223> OTHER INFORMATION: Nanobody or nanobody construct

<400> SEQUENCE: 456

Arg Phe Thr Ile Ser Ser Asp Lys Glu Lys Asn Thr Leu Tyr Leu Gln
1               5                   10                  15

Met Asn Ser Leu Lys Pro Glu Asp Thr Ala Val Tyr His Cys Ala Ala
                20                  25                  30

<210> SEQ ID NO 457
<211> LENGTH: 32
<212> TYPE: PRT
<213> ORGANISM: Artificial
<220> FEATURE:
<223> OTHER INFORMATION: Nanobody or nanobody construct

<400> SEQUENCE: 457

Arg Phe Thr Ile Ser Ser Asp Lys Glu Lys Asn Thr Leu Tyr Leu Gln
1               5                   10                  15

Met Asn Ser Leu Lys Pro Gly Asp Thr Ala Val Tyr His Cys Ala Ala
                20                  25                  30

<210> SEQ ID NO 458
<211> LENGTH: 32
<212> TYPE: PRT
<213> ORGANISM: Artificial
<220> FEATURE:

<223> OTHER INFORMATION: Nanobody or nanobody construct

<400> SEQUENCE: 458

Arg Leu Thr Ile Ser Ser Asp Lys Glu Lys Asn Thr Leu Tyr Leu Gln
1               5                   10                  15
Met Asn Ser Leu Lys Pro Glu Asp Thr Ala Val Tyr His Cys Ala Ala
            20                  25                  30

<210> SEQ ID NO 459
<211> LENGTH: 32
<212> TYPE: PRT
<213> ORGANISM: Artificial
<220> FEATURE:
<223> OTHER INFORMATION: Nanobody or nanobody construct

<400> SEQUENCE: 459

Arg Phe Thr Ile Ser Ser Asp Lys Glu Lys Asn Thr Leu Tyr Leu Gln
1               5                   10                  15
Met Asp Ser Leu Lys Pro Glu Asp Thr Ala Val Tyr His Cys Ala Ala
            20                  25                  30

<210> SEQ ID NO 460
<211> LENGTH: 32
<212> TYPE: PRT
<213> ORGANISM: Artificial
<220> FEATURE:
<223> OTHER INFORMATION: Nanobody or nanobody construct

<400> SEQUENCE: 460

Arg Phe Thr Ile Ser Ser Asp Lys Glu Lys Asn Thr Leu Tyr Leu Gln
1               5                   10                  15
Met Asn Ser Leu Lys Pro Glu Asp Thr Ala Val Tyr His Cys Ala Ala
            20                  25                  30

<210> SEQ ID NO 461
<211> LENGTH: 32
<212> TYPE: PRT
<213> ORGANISM: Artificial
<220> FEATURE:
<223> OTHER INFORMATION: Nanobody or nanobody construct

<400> SEQUENCE: 461

Arg Phe Ser Ile Thr Ala Asp Gly Ala Lys Thr Thr Val Phe Leu Gln
1               5                   10                  15
Met Asn Ser Leu Lys Pro Gly Asp Thr Ala Ile Tyr Tyr Cys Val Ala
            20                  25                  30

<210> SEQ ID NO 462
<211> LENGTH: 32
<212> TYPE: PRT
<213> ORGANISM: Artificial
<220> FEATURE:
<223> OTHER INFORMATION: Nanobody or nanobody construct

<400> SEQUENCE: 462

Arg Phe Ser Ile Thr Ala Asp Gly Ala Lys Thr Thr Val Phe Leu Gln
1               5                   10                  15
Met Asn Ser Leu Lys Pro Glu Asp Thr Ala Ile Tyr Tyr Cys Val Ala
            20                  25                  30

<210> SEQ ID NO 463
<211> LENGTH: 32
<212> TYPE: PRT
<213> ORGANISM: Artificial

```
<220> FEATURE:
<223> OTHER INFORMATION: Nanobody or nanobody construct

<400> SEQUENCE: 463

Arg Phe Ser Ile Thr Ala Asp Gly Ala Lys Thr Thr Val Phe Leu Gln
1               5                   10                  15

Met Asn Ser Leu Lys Pro Glu Asp Thr Ala Ile Tyr Tyr Cys Val Ala
            20                  25                  30

<210> SEQ ID NO 464
<211> LENGTH: 32
<212> TYPE: PRT
<213> ORGANISM: Artificial
<220> FEATURE:
<223> OTHER INFORMATION: Nanobody or nanobody construct

<400> SEQUENCE: 464

Arg Phe Ser Ile Thr Ala Asp Gly Ala Lys Thr Thr Val Phe Leu Gln
1               5                   10                  15

Met Asn Ser Leu Lys Pro Glu Asp Thr Ala Ile Tyr Tyr Cys Val Ala
            20                  25                  30

<210> SEQ ID NO 465
<211> LENGTH: 32
<212> TYPE: PRT
<213> ORGANISM: Artificial
<220> FEATURE:
<223> OTHER INFORMATION: Nanobody or nanobody construct

<400> SEQUENCE: 465

Arg Leu Thr Ile Ser Arg Asp Asn Ala Lys Asn Thr Val Ser Leu Gln
1               5                   10                  15

Met Ser Gly Leu Lys Pro Glu Asp Thr Ala Ile Tyr Tyr Cys Ala Thr
            20                  25                  30

<210> SEQ ID NO 466
<211> LENGTH: 32
<212> TYPE: PRT
<213> ORGANISM: Artificial
<220> FEATURE:
<223> OTHER INFORMATION: Nanobody or nanobody construct

<400> SEQUENCE: 466

Arg Phe Thr Ile Ser Arg Asp Asn Ala Lys Asn Thr Val Ser Leu Gln
1               5                   10                  15

Met Ser Gly Leu Lys Pro Glu Asp Thr Ala Ile Tyr Tyr Cys Ala Thr
            20                  25                  30

<210> SEQ ID NO 467
<211> LENGTH: 32
<212> TYPE: PRT
<213> ORGANISM: Artificial
<220> FEATURE:
<223> OTHER INFORMATION: Nanobody or nanobody construct

<400> SEQUENCE: 467

Arg Phe Thr Ile Ser Arg Asp Asn Ala Lys Asn Thr Val Ser Leu Gln
1               5                   10                  15

Met Ser Gly Leu Lys Pro Glu Asp Thr Ala Ile Tyr Tyr Cys Ala Thr
            20                  25                  30

<210> SEQ ID NO 468
<211> LENGTH: 32
<212> TYPE: PRT
```

<213> ORGANISM: Artificial
<220> FEATURE:
<223> OTHER INFORMATION: Nanobody or nanobody construct

<400> SEQUENCE: 468

Arg Phe Thr Ile Ser Arg Asp Asn Ala Lys Asn Thr Val Ser Leu Gln
1               5                   10                  15

Met Ser Gly Leu Lys Pro Glu Asp Thr Ala Ile Tyr Tyr Cys Ala Thr
            20                  25                  30

<210> SEQ ID NO 469
<211> LENGTH: 32
<212> TYPE: PRT
<213> ORGANISM: Artificial
<220> FEATURE:
<223> OTHER INFORMATION: Nanobody or nanobody construct

<400> SEQUENCE: 469

Arg Phe Thr Ile Ser Arg Asp Asn Ala Lys Asn Thr Val Ser Leu Gln
1               5                   10                  15

Met Ser Gly Leu Lys Pro Glu Asp Thr Ala Ile Tyr Tyr Cys Ala Thr
            20                  25                  30

<210> SEQ ID NO 470
<211> LENGTH: 32
<212> TYPE: PRT
<213> ORGANISM: Artificial
<220> FEATURE:
<223> OTHER INFORMATION: Nanobody or nanobody construct

<400> SEQUENCE: 470

Arg Phe Thr Ile Ser Arg Asp Asn Ala Lys Asn Thr Val Ser Leu Gln
1               5                   10                  15

Met Ser Gly Leu Lys Pro Glu Asp Thr Ala Ile Tyr Tyr Cys Ala Thr
            20                  25                  30

<210> SEQ ID NO 471
<211> LENGTH: 32
<212> TYPE: PRT
<213> ORGANISM: Artificial
<220> FEATURE:
<223> OTHER INFORMATION: Nanobody or nanobody construct

<400> SEQUENCE: 471

Arg Phe Thr Ile Ser Arg Asp Asn Ala Lys Asn Ala Val Ser Leu Gln
1               5                   10                  15

Met Ser Gly Leu Lys Pro Glu Asp Thr Ala Ile Tyr Tyr Cys Ala Thr
            20                  25                  30

<210> SEQ ID NO 472
<211> LENGTH: 32
<212> TYPE: PRT
<213> ORGANISM: Artificial
<220> FEATURE:
<223> OTHER INFORMATION: Nanobody or nanobody construct

<400> SEQUENCE: 472

Arg Phe Thr Ile Ser Arg Asp Asn Ala Lys Asn Thr Val Ser Leu Gln
1               5                   10                  15

Met Ser Gly Leu Lys Pro Glu Asp Thr Ala Ile Tyr Tyr Cys Ala Thr
            20                  25                  30

<210> SEQ ID NO 473
<211> LENGTH: 32

<212> TYPE: PRT
<213> ORGANISM: Artificial
<220> FEATURE:
<223> OTHER INFORMATION: Nanobody or nanobody construct

<400> SEQUENCE: 473

Arg Phe Thr Ile Ser Arg Asp Asn Ala Lys Ser Thr Val Ser Leu Gln
1               5                   10                  15
Met Ser Gly Leu Lys Pro Glu Asp Thr Ala Ile Tyr Tyr Cys Ala Thr
            20                  25                  30

<210> SEQ ID NO 474
<211> LENGTH: 32
<212> TYPE: PRT
<213> ORGANISM: Artificial
<220> FEATURE:
<223> OTHER INFORMATION: Nanobody or nanobody construct

<400> SEQUENCE: 474

Arg Phe Thr Ile Ser Arg Asp Asn Thr Lys Asn Thr Leu Tyr Leu Gln
1               5                   10                  15
Met Asn Asn Leu Arg Ala Glu Asp Thr Ala Val Tyr Tyr Cys Ala Tyr
            20                  25                  30

<210> SEQ ID NO 475
<211> LENGTH: 32
<212> TYPE: PRT
<213> ORGANISM: Artificial
<220> FEATURE:
<223> OTHER INFORMATION: Nanobody or nanobody construct

<400> SEQUENCE: 475

Arg Phe Thr Ile Ser Arg Asp Asn Thr Lys Asn Thr Leu Tyr Leu Gln
1               5                   10                  15
Met Asn Asn Leu Lys Ala Glu Asp Thr Ala Val Tyr Tyr Cys Ala Tyr
            20                  25                  30

<210> SEQ ID NO 476
<211> LENGTH: 32
<212> TYPE: PRT
<213> ORGANISM: Artificial
<220> FEATURE:
<223> OTHER INFORMATION: Nanobody or nanobody construct

<400> SEQUENCE: 476

Arg Phe Thr Ile Ser Arg Asp Asn Thr Lys Asn Thr Leu Tyr Leu Gln
1               5                   10                  15
Met Asn Asn Leu Lys Ala Glu Asp Thr Ala Val Tyr Tyr Cys Ala Tyr
            20                  25                  30

<210> SEQ ID NO 477
<211> LENGTH: 32
<212> TYPE: PRT
<213> ORGANISM: Artificial
<220> FEATURE:
<223> OTHER INFORMATION: Nanobody or nanobody construct

<400> SEQUENCE: 477

Arg Phe Thr Ile Ser Arg Asp Asn Thr Glu Asn Thr Leu Tyr Leu Gln
1               5                   10                  15
Met Asn Asn Leu Lys Ala Glu Asp Thr Ala Val Tyr Tyr Cys Ala Tyr
            20                  25                  30

<210> SEQ ID NO 478

-continued

```
<211> LENGTH: 32
<212> TYPE: PRT
<213> ORGANISM: Artificial
<220> FEATURE:
<223> OTHER INFORMATION: Nanobody or nanobody construct

<400> SEQUENCE: 478

Arg Phe Thr Ile Ser Arg Asp Asn Thr Glu Asn Thr Leu Tyr Leu Gln
1               5                   10                  15

Met Asn Asn Leu Lys Ala Glu Asp Thr Ala Val Tyr Tyr Cys Ala Tyr
            20                  25                  30

<210> SEQ ID NO 479
<211> LENGTH: 32
<212> TYPE: PRT
<213> ORGANISM: Artificial
<220> FEATURE:
<223> OTHER INFORMATION: Nanobody or nanobody construct

<400> SEQUENCE: 479

Arg Phe Thr Ile Ser Arg Asp Asn Val Arg Asn Thr Val Tyr Leu Gln
1               5                   10                  15

Met Asn Gly Leu Arg Pro Glu Asp Thr Ala Ala Tyr Tyr Cys Tyr Ala
            20                  25                  30

<210> SEQ ID NO 480
<211> LENGTH: 32
<212> TYPE: PRT
<213> ORGANISM: Artificial
<220> FEATURE:
<223> OTHER INFORMATION: Nanobody or nanobody construct

<400> SEQUENCE: 480

Arg Phe Thr Ile Ser Arg Asp Asn Val Arg Asn Thr Val Tyr Leu Gln
1               5                   10                  15

Met Asn Gly Leu Lys Pro Glu Asp Thr Ala Ala Tyr Tyr Cys Tyr Ala
            20                  25                  30

<210> SEQ ID NO 481
<211> LENGTH: 32
<212> TYPE: PRT
<213> ORGANISM: Artificial
<220> FEATURE:
<223> OTHER INFORMATION: Nanobody or nanobody construct

<400> SEQUENCE: 481

Arg Phe Thr Ile Ser Arg Asp Asn Val Arg Asn Thr Val Tyr Leu Gln
1               5                   10                  15

Met Asn Gly Leu Lys Pro Glu Asp Thr Ala Ala Tyr Tyr Cys Tyr Ala
            20                  25                  30

<210> SEQ ID NO 482
<211> LENGTH: 32
<212> TYPE: PRT
<213> ORGANISM: Artificial
<220> FEATURE:
<223> OTHER INFORMATION: Nanobody or nanobody construct

<400> SEQUENCE: 482

Arg Phe Thr Ile Ser Arg Asp Asn Val Arg Asn Thr Val Tyr Leu Gln
1               5                   10                  15

Met Asn Gly Leu Lys Pro Glu Asp Thr Ala Val Tyr Tyr Cys Tyr Ala
            20                  25                  30
```

```
<210> SEQ ID NO 483
<211> LENGTH: 32
<212> TYPE: PRT
<213> ORGANISM: Artificial
<220> FEATURE:
<223> OTHER INFORMATION: Nanobody or nanobody construct

<400> SEQUENCE: 483

Arg Phe Thr Ile Ser Arg Asp Asn Val Arg Asn Thr Val Tyr Leu Gln
1               5                   10                  15
Met Asn Gly Leu Lys Pro Glu Asp Thr Ala Val Tyr Tyr Cys Tyr Ala
            20                  25                  30

<210> SEQ ID NO 484
<211> LENGTH: 32
<212> TYPE: PRT
<213> ORGANISM: Artificial
<220> FEATURE:
<223> OTHER INFORMATION: Nanobody or nanobody construct

<400> SEQUENCE: 484

Arg Phe Thr Ile Ser Arg Asp Asn Val Arg Asn Thr Val Tyr Leu Gln
1               5                   10                  15
Met Asn Ser Leu Lys Pro Glu Asp Thr Ala Ala Tyr Tyr Cys Tyr Ala
            20                  25                  30

<210> SEQ ID NO 485
<211> LENGTH: 32
<212> TYPE: PRT
<213> ORGANISM: Artificial
<220> FEATURE:
<223> OTHER INFORMATION: Nanobody or nanobody construct

<400> SEQUENCE: 485

Arg Phe Thr Ile Ser Arg Asp Asn Val Arg Asn Thr Val Tyr Leu Gln
1               5                   10                  15
Met Asn Gly Leu Lys Pro Glu Asp Thr Ala Ala Tyr Tyr Cys Tyr Ala
            20                  25                  30

<210> SEQ ID NO 486
<211> LENGTH: 32
<212> TYPE: PRT
<213> ORGANISM: Artificial
<220> FEATURE:
<223> OTHER INFORMATION: Nanobody or nanobody construct

<400> SEQUENCE: 486

Arg Phe Thr Ile Ser Arg Asp Asn Val Arg Asn Thr Val Tyr Leu Gln
1               5                   10                  15
Met Asn Gly Leu Lys Pro Glu Asp Thr Ala Ala Tyr Tyr Cys Tyr Ala
            20                  25                  30

<210> SEQ ID NO 487
<211> LENGTH: 32
<212> TYPE: PRT
<213> ORGANISM: Artificial
<220> FEATURE:
<223> OTHER INFORMATION: Nanobody or nanobody construct

<400> SEQUENCE: 487

Arg Phe Thr Ile Ser Arg Asp Asn Val Arg Asn Thr Val Tyr Leu Gln
1               5                   10                  15
Met Asn Gly Leu Lys Pro Glu Asp Thr Ala Val Tyr Ser Cys Tyr Ala
            20                  25                  30
```

<210> SEQ ID NO 488
<211> LENGTH: 32
<212> TYPE: PRT
<213> ORGANISM: Artificial
<220> FEATURE:
<223> OTHER INFORMATION: Nanobody or nanobody construct

<400> SEQUENCE: 488

Arg Phe Thr Ile Ser Arg Asp Asn Val Arg Asn Thr Val Tyr Leu Gln
1               5                   10                  15

Met Asp Gly Leu Lys Pro Glu Asp Thr Ala Val Tyr Tyr Cys Tyr Ala
            20                  25                  30

<210> SEQ ID NO 489
<211> LENGTH: 32
<212> TYPE: PRT
<213> ORGANISM: Artificial
<220> FEATURE:
<223> OTHER INFORMATION: Nanobody or nanobody construct

<400> SEQUENCE: 489

Arg Phe Thr Ile Ser Arg Asp Asn Val Arg Asn Thr Val Tyr Leu Gln
1               5                   10                  15

Met Asn Gly Leu Lys Pro Glu Asp Thr Ala Val Tyr Tyr Cys Tyr Ala
            20                  25                  30

<210> SEQ ID NO 490
<211> LENGTH: 32
<212> TYPE: PRT
<213> ORGANISM: Artificial
<220> FEATURE:
<223> OTHER INFORMATION: Nanobody or nanobody construct

<400> SEQUENCE: 490

Arg Phe Thr Ile Ser Arg Asp Asn Val Arg Asn Thr Val Tyr Leu Gln
1               5                   10                  15

Met Asn Gly Leu Lys Pro Glu Asp Thr Ala Val Tyr Tyr Cys Tyr Ala
            20                  25                  30

<210> SEQ ID NO 491
<211> LENGTH: 32
<212> TYPE: PRT
<213> ORGANISM: Artificial
<220> FEATURE:
<223> OTHER INFORMATION: Nanobody or nanobody construct

<400> SEQUENCE: 491

Arg Phe Thr Ile Ser Arg Asp Asn Val Arg Asn Thr Val Tyr Leu Gln
1               5                   10                  15

Met Asn Gly Leu Lys Pro Glu Asp Thr Ala Val Tyr Tyr Cys Tyr Ala
            20                  25                  30

<210> SEQ ID NO 492
<211> LENGTH: 32
<212> TYPE: PRT
<213> ORGANISM: Artificial
<220> FEATURE:
<223> OTHER INFORMATION: Nanobody or nanobody construct

<400> SEQUENCE: 492

Arg Phe Thr Ile Ser Arg Asp Asn Val Arg Asn Thr Val Tyr Leu Gln
1               5                   10                  15

Met Asn Gly Leu Lys Pro Glu Asp Thr Ala Val Tyr Tyr Cys Tyr Ala
            20                  25                  30

<210> SEQ ID NO 493
<211> LENGTH: 32
<212> TYPE: PRT
<213> ORGANISM: Artificial
<220> FEATURE:
<223> OTHER INFORMATION: Nanobody or nanobody construct

<400> SEQUENCE: 493

Arg Phe Thr Ile Ser Arg Asp Asn Val Arg Asn Thr Val Tyr Leu Gln
1               5                   10                  15

Met Asn Gly Leu Lys Pro Glu Asp Thr Ala Val Tyr Tyr Cys Tyr Ala
            20                  25                  30

<210> SEQ ID NO 494
<211> LENGTH: 32
<212> TYPE: PRT
<213> ORGANISM: Artificial
<220> FEATURE:
<223> OTHER INFORMATION: Nanobody or nanobody construct

<400> SEQUENCE: 494

Arg Phe Thr Ile Ser Arg Asp Asn Val Arg Asn Thr Val Tyr Leu Gln
1               5                   10                  15

Met Asn Gly Leu Lys Pro Glu Asp Thr Ala Val Tyr Tyr Cys Tyr Ala
            20                  25                  30

<210> SEQ ID NO 495
<211> LENGTH: 32
<212> TYPE: PRT
<213> ORGANISM: Artificial
<220> FEATURE:
<223> OTHER INFORMATION: Nanobody or nanobody construct

<400> SEQUENCE: 495

Arg Phe Thr Ile Ser Arg Asp Asn Val Arg Asn Thr Val Tyr Leu Gln
1               5                   10                  15

Met Asn Gly Leu Lys Pro Glu Asp Thr Ala Val Tyr Tyr Cys Tyr Ala
            20                  25                  30

<210> SEQ ID NO 496
<211> LENGTH: 32
<212> TYPE: PRT
<213> ORGANISM: Artificial
<220> FEATURE:
<223> OTHER INFORMATION: Nanobody or nanobody construct

<400> SEQUENCE: 496

Arg Phe Thr Ile Ser Arg Asp Asn Val Arg Asn Thr Val Tyr Leu Gln
1               5                   10                  15

Met Asn Gly Leu Lys Pro Glu Asp Thr Ala Val Tyr Tyr Cys Tyr Ala
            20                  25                  30

<210> SEQ ID NO 497
<211> LENGTH: 32
<212> TYPE: PRT
<213> ORGANISM: Artificial
<220> FEATURE:
<223> OTHER INFORMATION: Nanobody or nanobody construct

<400> SEQUENCE: 497

Arg Phe Thr Ile Ser Arg Asp Asn Val Arg Asn Thr Val Tyr Leu Gln
1               5                   10                  15

Met Asp Gly Leu Lys Pro Glu Asp Thr Ala Val Tyr Tyr Cys Tyr Ala

```
                20                  25                  30
```

<210> SEQ ID NO 498
<211> LENGTH: 32
<212> TYPE: PRT
<213> ORGANISM: Artificial
<220> FEATURE:
<223> OTHER INFORMATION: Nanobody or nanobody construct

<400> SEQUENCE: 498

```
Arg Phe Thr Val Ser Ser Asp Ser Ala Lys Thr Thr Val Asn Leu Gln
1               5                   10                  15

Met Asn Ser Leu Lys Pro Glu Asp Thr Ala Val Tyr Tyr Cys Ala Ala
                20                  25                  30
```

<210> SEQ ID NO 499
<211> LENGTH: 32
<212> TYPE: PRT
<213> ORGANISM: Artificial
<220> FEATURE:
<223> OTHER INFORMATION: Nanobody or nanobody construct

<400> SEQUENCE: 499

```
Arg Phe Thr Val Ser Ser Asp Ser Ala Lys Thr Thr Val Asn Leu Gln
1               5                   10                  15

Met Asn Ser Leu Lys Pro Glu Asp Thr Ala Val Tyr Tyr Cys Ala Ala
                20                  25                  30
```

<210> SEQ ID NO 500
<211> LENGTH: 32
<212> TYPE: PRT
<213> ORGANISM: Artificial
<220> FEATURE:
<223> OTHER INFORMATION: Nanobody or nanobody construct

<400> SEQUENCE: 500

```
Arg Phe Thr Ile Ser Arg Asp Asn Ala Lys Asn Thr Met Tyr Leu Gln
1               5                   10                  15

Met Asn Ser Leu Lys Pro Glu Asp Thr Ala Val Tyr Tyr Cys Ala Gly
                20                  25                  30
```

<210> SEQ ID NO 501
<211> LENGTH: 32
<212> TYPE: PRT
<213> ORGANISM: Artificial
<220> FEATURE:
<223> OTHER INFORMATION: Nanobody or nanobody construct

<400> SEQUENCE: 501

```
Arg Phe Thr Ile Ser Arg Asp Asn Ala Lys Asn Thr Met Tyr Leu Gln
1               5                   10                  15

Met Asn Ser Leu Lys Pro Glu Asp Thr Ala Val Tyr Tyr Cys Ala Gly
                20                  25                  30
```

<210> SEQ ID NO 502
<211> LENGTH: 32
<212> TYPE: PRT
<213> ORGANISM: Artificial
<220> FEATURE:
<223> OTHER INFORMATION: Nanobody or nanobody construct

<400> SEQUENCE: 502

```
Arg Leu Thr Ile Ser Arg Asp Asn Ala Lys Asn Thr Met Tyr Leu Gln
1               5                   10                  15
```

Met Asn Ser Leu Lys Pro Glu Asp Thr Ala Val Tyr Tyr Cys Ala Gly
            20                  25                  30

<210> SEQ ID NO 503
<211> LENGTH: 32
<212> TYPE: PRT
<213> ORGANISM: Artificial
<220> FEATURE:
<223> OTHER INFORMATION: Nanobody or nanobody construct

<400> SEQUENCE: 503

Arg Phe Thr Ile Ser Arg Asp Asn Ala Lys Asn Thr Val His Leu Gln
1               5                   10                  15

Met His Ile Leu Lys Pro Glu Asp Thr Ala Leu Tyr Tyr Cys Ala Ala
            20                  25                  30

<210> SEQ ID NO 504
<211> LENGTH: 32
<212> TYPE: PRT
<213> ORGANISM: Artificial
<220> FEATURE:
<223> OTHER INFORMATION: Nanobody or nanobody construct

<400> SEQUENCE: 504

Arg Phe Thr Ile Ser Arg Asp Asn Ala Leu Asn Thr Val His Leu Gln
1               5                   10                  15

Met His Ile Leu Lys Pro Glu Asp Thr Ala Leu Tyr Tyr Cys Ala Ala
            20                  25                  30

<210> SEQ ID NO 505
<211> LENGTH: 32
<212> TYPE: PRT
<213> ORGANISM: Artificial
<220> FEATURE:
<223> OTHER INFORMATION: Nanobody or nanobody construct

<400> SEQUENCE: 505

Arg Phe Thr Ile Ser Arg Asp Asn Ala Leu Asn Thr Val His Leu Gln
1               5                   10                  15

Met His Ile Leu Lys Pro Glu Asp Thr Ala Leu Tyr Tyr Cys Ala Ala
            20                  25                  30

<210> SEQ ID NO 506
<211> LENGTH: 32
<212> TYPE: PRT
<213> ORGANISM: Artificial
<220> FEATURE:
<223> OTHER INFORMATION: Nanobody or nanobody construct

<400> SEQUENCE: 506

Arg Phe Thr Ile Ser Arg Asp Asn Ala Lys Asn Thr Val Ser Leu Gln
1               5                   10                  15

Met Asn Ser Leu Lys Pro Glu Asp Thr Ala Val Tyr Tyr Cys Ala Gly
            20                  25                  30

<210> SEQ ID NO 507
<211> LENGTH: 32
<212> TYPE: PRT
<213> ORGANISM: Artificial
<220> FEATURE:
<223> OTHER INFORMATION: Nanobody or nanobody construct

<400> SEQUENCE: 507

Arg Phe Thr Ile Ser Arg Asp Asn Ala Lys Asp Thr Val Tyr Leu Gln
1               5                   10                  15

```
Met Asn Ser Leu Lys Pro Glu Asp Thr Ala Val Tyr Tyr Cys Ala Gly
            20                  25                  30
```

<210> SEQ ID NO 508
<211> LENGTH: 32
<212> TYPE: PRT
<213> ORGANISM: Artificial
<220> FEATURE:
<223> OTHER INFORMATION: Nanobody or nanobody construct

<400> SEQUENCE: 508

```
Arg Phe Thr Ile Ser Arg Asp Asn Ala Lys Asn Thr Val Tyr Leu Gln
1               5                   10                  15
Met Asp Ser Leu Lys Pro Glu Asp Thr Ala Val Tyr Tyr Cys Ala Ala
            20                  25                  30
```

<210> SEQ ID NO 509
<211> LENGTH: 32
<212> TYPE: PRT
<213> ORGANISM: Artificial
<220> FEATURE:
<223> OTHER INFORMATION: Nanobody or nanobody construct

<400> SEQUENCE: 509

```
Arg Phe Thr Ile Gly Arg Asp Asn Ala Lys Asn Thr Val Tyr Leu Gln
1               5                   10                  15
Met Asn Ser Leu Lys Pro Ala Asp Thr Ala Val Tyr Tyr Cys Asn Ile
            20                  25                  30
```

<210> SEQ ID NO 510
<211> LENGTH: 32
<212> TYPE: PRT
<213> ORGANISM: Artificial
<220> FEATURE:
<223> OTHER INFORMATION: Nanobody or nanobody construct

<400> SEQUENCE: 510

```
Arg Phe Thr Met Ser Arg Asp Asn Ala Glu Asn Thr Val Tyr Leu Gln
1               5                   10                  15
Met Asn Ser Leu Lys Pro Glu Asp Thr Ala Val Tyr Ser Cys Ala Thr
            20                  25                  30
```

<210> SEQ ID NO 511
<211> LENGTH: 32
<212> TYPE: PRT
<213> ORGANISM: Artificial
<220> FEATURE:
<223> OTHER INFORMATION: Nanobody or nanobody construct

<400> SEQUENCE: 511

```
Arg Phe Thr Met Ser Arg Asp Asn Ala Glu Asn Thr Val Tyr Leu Gln
1               5                   10                  15
Met Asn Ser Leu Lys Pro Glu Asp Thr Ala Val Tyr Ser Cys Ala Thr
            20                  25                  30
```

<210> SEQ ID NO 512
<211> LENGTH: 32
<212> TYPE: PRT
<213> ORGANISM: Artificial
<220> FEATURE:
<223> OTHER INFORMATION: Nanobody or nanobody construct

<400> SEQUENCE: 512

```
Arg Phe Thr Ile Ser Thr Asp Asn Ala Lys Asn Thr Val Tyr Leu His
```

```
                1               5                   10                  15
            Met Asn Ser Leu Glu Pro Glu Asp Thr Ala Val Tyr Tyr Cys Ala Ala
                        20                  25                  30
```

<210> SEQ ID NO 513
<211> LENGTH: 32
<212> TYPE: PRT
<213> ORGANISM: Artificial
<220> FEATURE:
<223> OTHER INFORMATION: Nanobody or nanobody construct

<400> SEQUENCE: 513

```
Arg Phe Thr Ile Ser Thr Asp Asn Ala Lys Asn Thr Val Tyr Leu His
1               5                   10                  15

Leu Asn Ser Leu Glu Pro Glu Asp Thr Ala Val Tyr Tyr Cys Ala Ala
            20                  25                  30
```

<210> SEQ ID NO 514
<211> LENGTH: 32
<212> TYPE: PRT
<213> ORGANISM: Artificial
<220> FEATURE:
<223> OTHER INFORMATION: Nanobody or nanobody construct

<400> SEQUENCE: 514

```
Arg Phe Thr Ala Ser Arg Asp Asn Val Asn Asn Thr Val Tyr Leu Gln
1               5                   10                  15

Met Asn Ser Leu Lys Pro Glu Asp Thr Ala Asp Tyr Tyr Cys Ala Ala
            20                  25                  30
```

<210> SEQ ID NO 515
<211> LENGTH: 32
<212> TYPE: PRT
<213> ORGANISM: Artificial
<220> FEATURE:
<223> OTHER INFORMATION: Nanobody or nanobody construct

<400> SEQUENCE: 515

```
Arg Phe Thr Ile Ser Arg Asp Asn Ala Lys Asn Thr Val Thr Leu Glu
1               5                   10                  15

Met Asn Ser Leu Lys Pro Glu Asp Thr Ala Val Tyr Tyr Cys Ala Ala
            20                  25                  30
```

<210> SEQ ID NO 516
<211> LENGTH: 32
<212> TYPE: PRT
<213> ORGANISM: Artificial
<220> FEATURE:
<223> OTHER INFORMATION: Nanobody or nanobody construct

<400> SEQUENCE: 516

```
Arg Phe Thr Ile Ser Arg Asp Asn Ala Lys Asn Thr Val Thr Leu Glu
1               5                   10                  15

Met Asn Ser Leu Lys Pro Glu Asp Thr Ala Val Tyr Tyr Cys Ala Ala
            20                  25                  30
```

<210> SEQ ID NO 517
<211> LENGTH: 32
<212> TYPE: PRT
<213> ORGANISM: Artificial
<220> FEATURE:
<223> OTHER INFORMATION: Nanobody or nanobody construct

<400> SEQUENCE: 517

Arg Phe Thr Ile Ser Arg Asp Asn Ala Lys Asn Thr Val Thr Leu Glu
1               5                   10                  15

Met Asn Ser Leu Lys Pro Glu Asp Thr Ala Val Tyr Tyr Cys Ala Ala
            20                  25                  30

<210> SEQ ID NO 518
<211> LENGTH: 32
<212> TYPE: PRT
<213> ORGANISM: Artificial
<220> FEATURE:
<223> OTHER INFORMATION: Nanobody or nanobody construct

<400> SEQUENCE: 518

Arg Phe Thr Ile Ser Arg Asp Asn Ala Lys Asn Thr Val Thr Leu Glu
1               5                   10                  15

Met Asn Ser Leu Lys Pro Glu Asp Thr Ala Val Tyr Tyr Cys Ala Ala
            20                  25                  30

<210> SEQ ID NO 519
<211> LENGTH: 32
<212> TYPE: PRT
<213> ORGANISM: Artificial
<220> FEATURE:
<223> OTHER INFORMATION: Nanobody or nanobody construct

<400> SEQUENCE: 519

Arg Phe Thr Ile Phe Arg Asp Asn Ala Lys Asn Thr Val Tyr Leu Gln
1               5                   10                  15

Met Asn Ser Leu Lys Pro Glu Asp Thr Ala Val Tyr Tyr Cys Ala Gly
            20                  25                  30

<210> SEQ ID NO 520
<211> LENGTH: 32
<212> TYPE: PRT
<213> ORGANISM: Artificial
<220> FEATURE:
<223> OTHER INFORMATION: Nanobody or nanobody construct

<400> SEQUENCE: 520

Arg Phe Thr Ile Ser Arg Asp Asn Ala Gln Asn Thr Val Tyr Leu Gln
1               5                   10                  15

Met Asn Ser Leu Lys Ser Glu Asp Thr Ala Val Tyr Tyr Cys His Gly
            20                  25                  30

<210> SEQ ID NO 521
<211> LENGTH: 32
<212> TYPE: PRT
<213> ORGANISM: Artificial
<220> FEATURE:
<223> OTHER INFORMATION: Nanobody or nanobody construct

<400> SEQUENCE: 521

Arg Phe Thr Ile Ser Arg Asp Asn Ala Lys Asn Thr Met Tyr Leu Gln
1               5                   10                  15

Met Asn Ser Leu Lys Pro Ala Asp Thr Ala Val Tyr Thr Cys Ala Ala
            20                  25                  30

<210> SEQ ID NO 522
<211> LENGTH: 32
<212> TYPE: PRT
<213> ORGANISM: Artificial
<220> FEATURE:
<223> OTHER INFORMATION: Nanobody or nanobody construct

<400> SEQUENCE: 522

```
Arg Phe Thr Ile Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Ala Ala
            20                  25                  30
```

<210> SEQ ID NO 523
<211> LENGTH: 32
<212> TYPE: PRT
<213> ORGANISM: Artificial
<220> FEATURE:
<223> OTHER INFORMATION: Nanobody or nanobody construct

<400> SEQUENCE: 523

```
Arg Phe Thr Ile Ser Arg Asp Asn Ala Lys Asn Met Leu Tyr Leu Gln
1               5                   10                  15

Met Ser Ser Leu Lys Pro Glu Asp Thr Ala Leu Tyr Tyr Cys Ile Thr
            20                  25                  30
```

<210> SEQ ID NO 524
<211> LENGTH: 32
<212> TYPE: PRT
<213> ORGANISM: Artificial
<220> FEATURE:
<223> OTHER INFORMATION: Nanobody or nanobody construct

<400> SEQUENCE: 524

```
Arg Phe Thr Val Ser Arg Asp Asn Ala Leu Asn Thr Val Tyr Leu Gln
1               5                   10                  15

Met Asn Ser Leu Lys Pro Glu Asp Thr Ala Val Tyr Tyr Cys Ala Ala
            20                  25                  30
```

<210> SEQ ID NO 525
<211> LENGTH: 32
<212> TYPE: PRT
<213> ORGANISM: Artificial
<220> FEATURE:
<223> OTHER INFORMATION: Nanobody or nanobody construct

<400> SEQUENCE: 525

```
Arg Phe Thr Ile Ser Arg Asp Ile Val Lys His Thr Val Tyr Leu Gln
1               5                   10                  15

Met Asn Ser Leu Gln Pro Glu Asp Thr Ala Val Tyr Tyr Cys Ala Ala
            20                  25                  30
```

<210> SEQ ID NO 526
<211> LENGTH: 32
<212> TYPE: PRT
<213> ORGANISM: Artificial
<220> FEATURE:
<223> OTHER INFORMATION: Nanobody or nanobody construct

<400> SEQUENCE: 526

```
Arg Phe Thr Met Ser Arg Asn Asn Asp His Arg Thr Val Tyr Leu Gln
1               5                   10                  15

Met Thr Ser Leu Gln Pro Glu Asp Thr Ala Val Tyr Thr Cys Ala Val
            20                  25                  30
```

<210> SEQ ID NO 527
<211> LENGTH: 32
<212> TYPE: PRT
<213> ORGANISM: Artificial
<220> FEATURE:
<223> OTHER INFORMATION: Nanobody or nanobody construct

```
<400> SEQUENCE: 527

Arg Phe Thr Leu Ser Arg Asp Asn Ala Arg Asn Thr Val Ser Leu His
1               5                   10                  15

Met Asn Ser Leu Lys Pro Glu Asp Thr Ala Val Tyr Tyr Cys Ala Ala
                20                  25                  30

<210> SEQ ID NO 528
<211> LENGTH: 32
<212> TYPE: PRT
<213> ORGANISM: Artificial
<220> FEATURE:
<223> OTHER INFORMATION: Nanobody or nanobody construct

<400> SEQUENCE: 528

Arg Phe Thr Ile Ser Arg Asp Asn Asn Lys Asn Thr Val Phe Leu Gln
1               5                   10                  15

Met Asn Ser Leu Glu Pro Gly Asp Thr Ala Val Tyr Tyr Cys Ala Ala
                20                  25                  30

<210> SEQ ID NO 529
<211> LENGTH: 32
<212> TYPE: PRT
<213> ORGANISM: Artificial
<220> FEATURE:
<223> OTHER INFORMATION: Nanobody or nanobody construct

<400> SEQUENCE: 529

Arg Phe Thr Ile Ser Arg Asp Asn Asn Lys Asn Thr Val Phe Leu Gln
1               5                   10                  15

Met Asn Ser Leu Glu Pro Gly Asp Thr Ala Val Tyr Tyr Cys Ala Ala
                20                  25                  30

<210> SEQ ID NO 530
<211> LENGTH: 32
<212> TYPE: PRT
<213> ORGANISM: Artificial
<220> FEATURE:
<223> OTHER INFORMATION: Nanobody or nanobody construct

<400> SEQUENCE: 530

Arg Phe Thr Ile Ser Arg Asp Asn Ala Lys Asn Thr Val Thr Leu Gln
1               5                   10                  15

Met Asn Ser Leu Lys Pro Glu Asp Thr Ala Val Tyr Tyr Cys Ala Arg
                20                  25                  30

<210> SEQ ID NO 531
<211> LENGTH: 32
<212> TYPE: PRT
<213> ORGANISM: Artificial
<220> FEATURE:
<223> OTHER INFORMATION: Nanobody or nanobody construct

<400> SEQUENCE: 531

Arg Phe Thr Ile Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Ala Arg
                20                  25                  30

<210> SEQ ID NO 532
<211> LENGTH: 32
<212> TYPE: PRT
<213> ORGANISM: Artificial
<220> FEATURE:
<223> OTHER INFORMATION: Nanobody or nanobody construct
```

<400> SEQUENCE: 532

Arg Phe Thr Ile Ser Arg Asp Asn Ala Lys Asn Thr Met Tyr Leu Gln
1               5                   10                  15

Met Asn Ser Leu Lys Pro Glu Asp Thr Ala Val Tyr Tyr Cys Ala Ala
            20                  25                  30

<210> SEQ ID NO 533
<211> LENGTH: 32
<212> TYPE: PRT
<213> ORGANISM: Artificial
<220> FEATURE:
<223> OTHER INFORMATION: Nanobody or nanobody construct

<400> SEQUENCE: 533

Arg Ala Thr Ile Ser Arg Asp Asp Ala Asn Asn Ser Met Tyr Leu Glu
1               5                   10                  15

Met Asn Thr Leu Lys Pro Glu Asp Thr Ala Val Tyr Tyr Cys Lys Met
            20                  25                  30

<210> SEQ ID NO 534
<211> LENGTH: 32
<212> TYPE: PRT
<213> ORGANISM: Artificial
<220> FEATURE:
<223> OTHER INFORMATION: Nanobody or nanobody construct

<400> SEQUENCE: 534

Arg Phe Thr Ile Ser Arg Asp Asn Ala Lys Asn Ala Val Phe Leu Gln
1               5                   10                  15

Met Asn Ser Leu Lys Pro Glu Asp Thr Ala Val Tyr Tyr Cys Asn Gly
            20                  25                  30

<210> SEQ ID NO 535
<211> LENGTH: 32
<212> TYPE: PRT
<213> ORGANISM: Artificial
<220> FEATURE:
<223> OTHER INFORMATION: Nanobody or nanobody construct

<400> SEQUENCE: 535

Arg Phe Thr Ile Ser Arg Asp Asn Ala Lys Lys Met Val Tyr Leu Gln
1               5                   10                  15

Met Asn Ser Leu Lys Pro Asp Asp Thr Ala Val Tyr His Cys Ala Ala
            20                  25                  30

<210> SEQ ID NO 536
<211> LENGTH: 18
<212> TYPE: PRT
<213> ORGANISM: Artificial
<220> FEATURE:
<223> OTHER INFORMATION: Nanobody or nanobody construct

<400> SEQUENCE: 536

Gly His Phe Thr Val Asp Ser Gly Lys Val Leu Leu Arg Thr Asp Ile
1               5                   10                  15

Ser Ser

<210> SEQ ID NO 537
<211> LENGTH: 18
<212> TYPE: PRT
<213> ORGANISM: Artificial
<220> FEATURE:
<223> OTHER INFORMATION: Nanobody or nanobody construct

```
<400> SEQUENCE: 537

Gly His Phe Thr Val Asp Ser Gly Lys Val Leu Leu Arg Thr Asp Ile
1               5                   10                  15

Ser Ser

<210> SEQ ID NO 538
<211> LENGTH: 18
<212> TYPE: PRT
<213> ORGANISM: Artificial
<220> FEATURE:
<223> OTHER INFORMATION: Nanobody or nanobody construct

<400> SEQUENCE: 538

Gly His Phe Thr Val Asp Ser Gly Lys Val Leu Leu Arg Thr Asp Ile
1               5                   10                  15

Ser Ser

<210> SEQ ID NO 539
<211> LENGTH: 18
<212> TYPE: PRT
<213> ORGANISM: Artificial
<220> FEATURE:
<223> OTHER INFORMATION: Nanobody or nanobody construct

<400> SEQUENCE: 539

Gly His Phe Thr Val Asp Ser Gly Lys Val Leu Leu Arg Thr Asp Ile
1               5                   10                  15

Ser Ser

<210> SEQ ID NO 540
<211> LENGTH: 18
<212> TYPE: PRT
<213> ORGANISM: Artificial
<220> FEATURE:
<223> OTHER INFORMATION: Nanobody or nanobody construct

<400> SEQUENCE: 540

Gly His Phe Thr Val Asp Ser Gly Lys Val Leu Leu Arg Thr Asp Ile
1               5                   10                  15

Ser Ser

<210> SEQ ID NO 541
<211> LENGTH: 18
<212> TYPE: PRT
<213> ORGANISM: Artificial
<220> FEATURE:
<223> OTHER INFORMATION: Nanobody or nanobody construct

<400> SEQUENCE: 541

Gly His Phe Thr Val Asp Ser Gly Lys Val Leu Leu Arg Thr Asp Ile
1               5                   10                  15

Ser Ser

<210> SEQ ID NO 542
<211> LENGTH: 18
<212> TYPE: PRT
<213> ORGANISM: Artificial
<220> FEATURE:
<223> OTHER INFORMATION: Nanobody or nanobody construct

<400> SEQUENCE: 542

Gly His Phe Thr Val Asp Ser Gly Lys Val Leu Leu Arg Thr Asp Val
```

Ser Ser

<210> SEQ ID NO 543
<211> LENGTH: 20
<212> TYPE: PRT
<213> ORGANISM: Artificial
<220> FEATURE:
<223> OTHER INFORMATION: Nanobody or nanobody construct

<400> SEQUENCE: 543

Gly His Phe Val Tyr Asn Asp Gly Ala Ile Ser Leu Asn Thr Ala Arg
1               5                   10                  15

Gly Ser Gly Phe
            20

<210> SEQ ID NO 544
<211> LENGTH: 20
<212> TYPE: PRT
<213> ORGANISM: Artificial
<220> FEATURE:
<223> OTHER INFORMATION: Nanobody or nanobody construct

<400> SEQUENCE: 544

Gly His Phe Val Tyr Asn Asp Gly Ala Ile Ser Leu Asn Thr Ala Arg
1               5                   10                  15

Gly Ser Gly Phe
            20

<210> SEQ ID NO 545
<211> LENGTH: 20
<212> TYPE: PRT
<213> ORGANISM: Artificial
<220> FEATURE:
<223> OTHER INFORMATION: Nanobody or nanobody construct

<400> SEQUENCE: 545

Gly His Phe Val Tyr Asn Asp Gly Ala Ile Ser Leu Asn Thr Ala Arg
1               5                   10                  15

Gly Ser Gly Phe
            20

<210> SEQ ID NO 546
<211> LENGTH: 20
<212> TYPE: PRT
<213> ORGANISM: Artificial
<220> FEATURE:
<223> OTHER INFORMATION: Nanobody or nanobody construct

<400> SEQUENCE: 546

Gly His Phe Val Tyr Asn Asp Gly Ala Ile Ser Leu Asn Thr Ala Arg
1               5                   10                  15

Gly Ser Gly Phe
            20

<210> SEQ ID NO 547
<211> LENGTH: 9
<212> TYPE: PRT
<213> ORGANISM: Artificial
<220> FEATURE:
<223> OTHER INFORMATION: Nanobody or nanobody construct

<400> SEQUENCE: 547

Gly Thr Ser Val Tyr His Tyr Gln Tyr

```
1               5

<210> SEQ ID NO 548
<211> LENGTH: 9
<212> TYPE: PRT
<213> ORGANISM: Artificial
<220> FEATURE:
<223> OTHER INFORMATION: Nanobody or nanobody construct

<400> SEQUENCE: 548

Gly Thr Ser Val Tyr His Tyr Gln Tyr
1               5

<210> SEQ ID NO 549
<211> LENGTH: 9
<212> TYPE: PRT
<213> ORGANISM: Artificial
<220> FEATURE:
<223> OTHER INFORMATION: Nanobody or nanobody construct

<400> SEQUENCE: 549

Gly Thr Ser Val Tyr His Tyr Gln Tyr
1               5

<210> SEQ ID NO 550
<211> LENGTH: 9
<212> TYPE: PRT
<213> ORGANISM: Artificial
<220> FEATURE:
<223> OTHER INFORMATION: Nanobody or nanobody construct

<400> SEQUENCE: 550

Gly Thr Ser Val Tyr His Tyr Gln Tyr
1               5

<210> SEQ ID NO 551
<211> LENGTH: 9
<212> TYPE: PRT
<213> ORGANISM: Artificial
<220> FEATURE:
<223> OTHER INFORMATION: Nanobody or nanobody construct

<400> SEQUENCE: 551

Gly Thr Ser Val Tyr His Tyr Gln Tyr
1               5

<210> SEQ ID NO 552
<211> LENGTH: 9
<212> TYPE: PRT
<213> ORGANISM: Artificial
<220> FEATURE:
<223> OTHER INFORMATION: Nanobody or nanobody construct

<400> SEQUENCE: 552

Gly Thr Ser Val Tyr His Tyr Gln Tyr
1               5

<210> SEQ ID NO 553
<211> LENGTH: 9
<212> TYPE: PRT
<213> ORGANISM: Artificial
<220> FEATURE:
<223> OTHER INFORMATION: Nanobody or nanobody construct

<400> SEQUENCE: 553

Gly Thr Ser Val Tyr His Tyr Gln Tyr
1               5
```

```
<210> SEQ ID NO 554
<211> LENGTH: 9
<212> TYPE: PRT
<213> ORGANISM: Artificial
<220> FEATURE:
<223> OTHER INFORMATION: Nanobody or nanobody construct

<400> SEQUENCE: 554

Gly Thr Ser Val Tyr His Tyr Gln Tyr
1               5

<210> SEQ ID NO 555
<211> LENGTH: 9
<212> TYPE: PRT
<213> ORGANISM: Artificial
<220> FEATURE:
<223> OTHER INFORMATION: Nanobody or nanobody construct

<400> SEQUENCE: 555

Gly Thr Ser Val Tyr His Tyr Gln Tyr
1               5

<210> SEQ ID NO 556
<211> LENGTH: 18
<212> TYPE: PRT
<213> ORGANISM: Artificial
<220> FEATURE:
<223> OTHER INFORMATION: Nanobody or nanobody construct

<400> SEQUENCE: 556

Phe Leu Gly Pro Asn Trp Tyr Ser Asn Tyr Gly Arg Pro Ser Ser Tyr
1               5                   10                  15

Asp Phe

<210> SEQ ID NO 557
<211> LENGTH: 18
<212> TYPE: PRT
<213> ORGANISM: Artificial
<220> FEATURE:
<223> OTHER INFORMATION: Nanobody or nanobody construct

<400> SEQUENCE: 557

Phe Leu Gly Pro Asn Trp Tyr Ser Asn Tyr Gly Arg Pro Ser Ser Tyr
1               5                   10                  15

Asp Phe

<210> SEQ ID NO 558
<211> LENGTH: 18
<212> TYPE: PRT
<213> ORGANISM: Artificial
<220> FEATURE:
<223> OTHER INFORMATION: Nanobody or nanobody construct

<400> SEQUENCE: 558

Phe Leu Gly Pro Asn Trp Tyr Ser Asn Tyr Gly Arg Pro Ser Ser Tyr
1               5                   10                  15

Gly Phe

<210> SEQ ID NO 559
<211> LENGTH: 18
<212> TYPE: PRT
<213> ORGANISM: Artificial
<220> FEATURE:
<223> OTHER INFORMATION: Nanobody or nanobody construct
```

```
<400> SEQUENCE: 559

Phe Leu Gly Pro Asn Trp Tyr Ser Asp Tyr Gly Arg Pro Ser Ser Tyr
1               5                   10                  15
Asp Phe

<210> SEQ ID NO 560
<211> LENGTH: 18
<212> TYPE: PRT
<213> ORGANISM: Artificial
<220> FEATURE:
<223> OTHER INFORMATION: Nanobody or nanobody construct

<400> SEQUENCE: 560

Phe Leu Gly Pro Asn Trp Tyr Ser Asp Tyr Gly Arg Pro Ser Ser Tyr
1               5                   10                  15
Asp Phe

<210> SEQ ID NO 561
<211> LENGTH: 12
<212> TYPE: PRT
<213> ORGANISM: Artificial
<220> FEATURE:
<223> OTHER INFORMATION: Nanobody or nanobody construct

<400> SEQUENCE: 561

Val Ile Glu Leu Gly Val Leu Glu Pro Arg Asp Tyr
1               5                   10

<210> SEQ ID NO 562
<211> LENGTH: 12
<212> TYPE: PRT
<213> ORGANISM: Artificial
<220> FEATURE:
<223> OTHER INFORMATION: Nanobody or nanobody construct

<400> SEQUENCE: 562

Arg Ile Glu Leu Gly Val Leu Glu Pro Arg Asp Tyr
1               5                   10

<210> SEQ ID NO 563
<211> LENGTH: 12
<212> TYPE: PRT
<213> ORGANISM: Artificial
<220> FEATURE:
<223> OTHER INFORMATION: Nanobody or nanobody construct

<400> SEQUENCE: 563

Arg Ile Glu Leu Gly Val Leu Glu Pro Arg Asp Tyr
1               5                   10

<210> SEQ ID NO 564
<211> LENGTH: 12
<212> TYPE: PRT
<213> ORGANISM: Artificial
<220> FEATURE:
<223> OTHER INFORMATION: Nanobody or nanobody construct

<400> SEQUENCE: 564

Arg Ile Glu Leu Gly Val Leu Glu Pro Arg Asp Tyr
1               5                   10

<210> SEQ ID NO 565
<211> LENGTH: 12
<212> TYPE: PRT
```

-continued

<213> ORGANISM: Artificial
<220> FEATURE:
<223> OTHER INFORMATION: Nanobody or nanobody construct

<400> SEQUENCE: 565

Arg Ile Glu Leu Gly Val Leu Glu Pro Arg Asp Tyr
1               5                   10

<210> SEQ ID NO 566
<211> LENGTH: 12
<212> TYPE: PRT
<213> ORGANISM: Artificial
<220> FEATURE:
<223> OTHER INFORMATION: Nanobody or nanobody construct

<400> SEQUENCE: 566

Arg Ile Glu Leu Gly Val Leu Glu Pro Arg Asp Tyr
1               5                   10

<210> SEQ ID NO 567
<211> LENGTH: 12
<212> TYPE: PRT
<213> ORGANISM: Artificial
<220> FEATURE:
<223> OTHER INFORMATION: Nanobody or nanobody construct

<400> SEQUENCE: 567

Arg Ile Glu Leu Gly Val Leu Glu Pro Arg Asp Tyr
1               5                   10

<210> SEQ ID NO 568
<211> LENGTH: 12
<212> TYPE: PRT
<213> ORGANISM: Artificial
<220> FEATURE:
<223> OTHER INFORMATION: Nanobody or nanobody construct

<400> SEQUENCE: 568

Arg Ile Glu Leu Gly Val Leu Glu Pro Arg Asp Tyr
1               5                   10

<210> SEQ ID NO 569
<211> LENGTH: 12
<212> TYPE: PRT
<213> ORGANISM: Artificial
<220> FEATURE:
<223> OTHER INFORMATION: Nanobody or nanobody construct

<400> SEQUENCE: 569

Arg Ile Glu Leu Gly Ile Leu Glu Pro Arg Asp Tyr
1               5                   10

<210> SEQ ID NO 570
<211> LENGTH: 12
<212> TYPE: PRT
<213> ORGANISM: Artificial
<220> FEATURE:
<223> OTHER INFORMATION: Nanobody or nanobody construct

<400> SEQUENCE: 570

Arg Ile Glu Leu Gly Val Leu Val Pro Arg Asp Tyr
1               5                   10

<210> SEQ ID NO 571
<211> LENGTH: 12
<212> TYPE: PRT
<213> ORGANISM: Artificial

<220> FEATURE:
<223> OTHER INFORMATION: Nanobody or nanobody construct

<400> SEQUENCE: 571

Arg Ile Glu Leu Gly Pro Leu Val Pro Arg Asp Tyr
1               5                   10

<210> SEQ ID NO 572
<211> LENGTH: 12
<212> TYPE: PRT
<213> ORGANISM: Artificial
<220> FEATURE:
<223> OTHER INFORMATION: Nanobody or nanobody construct

<400> SEQUENCE: 572

Arg Ile Glu Leu Gly Pro Leu Val Pro Arg Asp Tyr
1               5                   10

<210> SEQ ID NO 573
<211> LENGTH: 12
<212> TYPE: PRT
<213> ORGANISM: Artificial
<220> FEATURE:
<223> OTHER INFORMATION: Nanobody or nanobody construct

<400> SEQUENCE: 573

Thr Ile Glu Leu Gly Val Leu Glu Pro Arg Asp Tyr
1               5                   10

<210> SEQ ID NO 574
<211> LENGTH: 12
<212> TYPE: PRT
<213> ORGANISM: Artificial
<220> FEATURE:
<223> OTHER INFORMATION: Nanobody or nanobody construct

<400> SEQUENCE: 574

Thr Ile Glu Leu Gly Val Leu Glu Pro Arg Asp Tyr
1               5                   10

<210> SEQ ID NO 575
<211> LENGTH: 12
<212> TYPE: PRT
<213> ORGANISM: Artificial
<220> FEATURE:
<223> OTHER INFORMATION: Nanobody or nanobody construct

<400> SEQUENCE: 575

Thr Ile Glu Leu Gly Val Leu Glu Pro Arg Asp Tyr
1               5                   10

<210> SEQ ID NO 576
<211> LENGTH: 12
<212> TYPE: PRT
<213> ORGANISM: Artificial
<220> FEATURE:
<223> OTHER INFORMATION: Nanobody or nanobody construct

<400> SEQUENCE: 576

Thr Ile Glu Leu Gly Val Leu Glu Pro Arg Asp Tyr
1               5                   10

<210> SEQ ID NO 577
<211> LENGTH: 12
<212> TYPE: PRT
<213> ORGANISM: Artificial
<220> FEATURE:

<223> OTHER INFORMATION: Nanobody or nanobody construct

<400> SEQUENCE: 577

Thr Ile Glu Leu Gly Val Leu Glu Pro Arg Asp Tyr
1               5                   10

<210> SEQ ID NO 578
<211> LENGTH: 12
<212> TYPE: PRT
<213> ORGANISM: Artificial
<220> FEATURE:
<223> OTHER INFORMATION: Nanobody or nanobody construct

<400> SEQUENCE: 578

Thr Ile Glu Leu Gly Val Leu Glu Pro Arg Asp Tyr
1               5                   10

<210> SEQ ID NO 579
<211> LENGTH: 12
<212> TYPE: PRT
<213> ORGANISM: Artificial
<220> FEATURE:
<223> OTHER INFORMATION: Nanobody or nanobody construct

<400> SEQUENCE: 579

Thr Ile Glu Leu Gly Val Leu Val Pro Arg Asp Tyr
1               5                   10

<210> SEQ ID NO 580
<211> LENGTH: 18
<212> TYPE: PRT
<213> ORGANISM: Artificial
<220> FEATURE:
<223> OTHER INFORMATION: Nanobody or nanobody construct

<400> SEQUENCE: 580

Asp Tyr Ala Ser Leu Cys Thr Ile Glu Thr Gly Tyr Gly Ser Leu Tyr
1               5                   10                  15

Asp Tyr

<210> SEQ ID NO 581
<211> LENGTH: 18
<212> TYPE: PRT
<213> ORGANISM: Artificial
<220> FEATURE:
<223> OTHER INFORMATION: Nanobody or nanobody construct

<400> SEQUENCE: 581

Asp Tyr Ala Ser Leu Cys Thr Ile Glu Thr Gly Tyr Gly Ser Leu Tyr
1               5                   10                  15

Asp Tyr

<210> SEQ ID NO 582
<211> LENGTH: 15
<212> TYPE: PRT
<213> ORGANISM: Artificial
<220> FEATURE:
<223> OTHER INFORMATION: Nanobody or nanobody construct

<400> SEQUENCE: 582

Ser Pro Val Leu Ser Ile Val Leu Asp Thr Arg Gly Leu Glu Tyr
1               5                   10                  15

<210> SEQ ID NO 583
<211> LENGTH: 15

```
<212> TYPE: PRT
<213> ORGANISM: Artificial
<220> FEATURE:
<223> OTHER INFORMATION: Nanobody or nanobody construct

<400> SEQUENCE: 583

Ser Pro Val Leu Ser Ile Val Leu Asp Thr Arg Gly Leu Glu Tyr
 1               5                  10                  15

<210> SEQ ID NO 584
<211> LENGTH: 15
<212> TYPE: PRT
<213> ORGANISM: Artificial
<220> FEATURE:
<223> OTHER INFORMATION: Nanobody or nanobody construct

<400> SEQUENCE: 584

Ser Pro Val Leu Ser Ile Val Leu Asp Thr Arg Gly Leu Glu Tyr
 1               5                  10                  15

<210> SEQ ID NO 585
<211> LENGTH: 17
<212> TYPE: PRT
<213> ORGANISM: Artificial
<220> FEATURE:
<223> OTHER INFORMATION: Nanobody or nanobody construct

<400> SEQUENCE: 585

Ser Thr Ser Gly Ser Val Tyr Leu Pro Tyr Arg Val Tyr Gln Tyr Asp
 1               5                  10                  15

Ser

<210> SEQ ID NO 586
<211> LENGTH: 17
<212> TYPE: PRT
<213> ORGANISM: Artificial
<220> FEATURE:
<223> OTHER INFORMATION: Nanobody or nanobody construct

<400> SEQUENCE: 586

Ser Thr Ser Gly Ser Ala Tyr Leu Pro Tyr Arg Val Tyr Gln Tyr Asp
 1               5                  10                  15

Ser

<210> SEQ ID NO 587
<211> LENGTH: 17
<212> TYPE: PRT
<213> ORGANISM: Artificial
<220> FEATURE:
<223> OTHER INFORMATION: Nanobody or nanobody construct

<400> SEQUENCE: 587

Ser Thr Ser Gly Ser Ala Tyr Leu Pro Tyr Arg Val His Gln Tyr Asp
 1               5                  10                  15

Ser

<210> SEQ ID NO 588
<211> LENGTH: 15
<212> TYPE: PRT
<213> ORGANISM: Artificial
<220> FEATURE:
<223> OTHER INFORMATION: Nanobody or nanobody construct

<400> SEQUENCE: 588

Ser Ile Ser Ser Tyr Ser Ser Arg Trp Gln Asp Asp Tyr Glu Tyr
```

```
<210> SEQ ID NO 589
<211> LENGTH: 15
<212> TYPE: PRT
<213> ORGANISM: Artificial
<220> FEATURE:
<223> OTHER INFORMATION: Nanobody or nanobody construct

<400> SEQUENCE: 589

Ser Ile Thr Ser Tyr Val Ser Thr Trp Gln His Asp Tyr Glu Tyr
1               5                   10                  15

<210> SEQ ID NO 590
<211> LENGTH: 14
<212> TYPE: PRT
<213> ORGANISM: Artificial
<220> FEATURE:
<223> OTHER INFORMATION: Nanobody or nanobody construct

<400> SEQUENCE: 590

Gly Leu Glu Tyr Met Ser Thr Ile Arg Tyr Thr Tyr Glu Tyr
1               5                   10

<210> SEQ ID NO 591
<211> LENGTH: 12
<212> TYPE: PRT
<213> ORGANISM: Artificial
<220> FEATURE:
<223> OTHER INFORMATION: Nanobody or nanobody construct

<400> SEQUENCE: 591

Asp Ser Tyr Ile Ile Gly Ala Gly Val Arg Asp Tyr
1               5                   10

<210> SEQ ID NO 592
<211> LENGTH: 13
<212> TYPE: PRT
<213> ORGANISM: Artificial
<220> FEATURE:
<223> OTHER INFORMATION: Nanobody or nanobody construct

<400> SEQUENCE: 592

Glu Cys Gln Arg Trp Ala Tyr Pro Asn Arg Ile Gly Ala
1               5                   10

<210> SEQ ID NO 593
<211> LENGTH: 13
<212> TYPE: PRT
<213> ORGANISM: Artificial
<220> FEATURE:
<223> OTHER INFORMATION: Nanobody or nanobody construct

<400> SEQUENCE: 593

Glu Cys Gln Arg Trp Ala Tyr Pro Asn Arg Ile Gly Ala
1               5                   10

<210> SEQ ID NO 594
<211> LENGTH: 20
<212> TYPE: PRT
<213> ORGANISM: Artificial
<220> FEATURE:
<223> OTHER INFORMATION: Nanobody or nanobody construct

<400> SEQUENCE: 594

Gly Trp Gly Arg Val Ile Thr Val Gln His Met Cys Ala Asp Arg Ser
1               5                   10                  15
```

Leu Phe Thr Ser
            20

<210> SEQ ID NO 595
<211> LENGTH: 20
<212> TYPE: PRT
<213> ORGANISM: Artificial
<220> FEATURE:
<223> OTHER INFORMATION: Nanobody or nanobody construct

<400> SEQUENCE: 595

Gly Trp Gly Arg Val Met Thr Val Gln His Met Cys Ala Asp Arg Ser
1               5                   10                  15

Leu Phe Thr Ser
            20

<210> SEQ ID NO 596
<211> LENGTH: 17
<212> TYPE: PRT
<213> ORGANISM: Artificial
<220> FEATURE:
<223> OTHER INFORMATION: Nanobody or nanobody construct

<400> SEQUENCE: 596

Ala Trp Lys Tyr Asp Arg Ala Ser Tyr Asp Phe Pro Glu Ala Tyr Asp
1               5                   10                  15

Tyr

<210> SEQ ID NO 597
<211> LENGTH: 20
<212> TYPE: PRT
<213> ORGANISM: Artificial
<220> FEATURE:
<223> OTHER INFORMATION: Nanobody or nanobody construct

<400> SEQUENCE: 597

Gly Tyr Tyr Arg Gly Gly Tyr Leu Gly Tyr Arg Leu Thr Leu Glu Gly
1               5                   10                  15

Ser Tyr Asp Val
            20

<210> SEQ ID NO 598
<211> LENGTH: 20
<212> TYPE: PRT
<213> ORGANISM: Artificial
<220> FEATURE:
<223> OTHER INFORMATION: Nanobody or nanobody construct

<400> SEQUENCE: 598

Gly Tyr Tyr Arg Gly Gly Tyr Leu Gly Tyr Arg Leu Thr Leu Glu Gly
1               5                   10                  15

Ser Tyr Asp Val
            20

<210> SEQ ID NO 599
<211> LENGTH: 20
<212> TYPE: PRT
<213> ORGANISM: Artificial
<220> FEATURE:
<223> OTHER INFORMATION: Nanobody or nanobody construct

<400> SEQUENCE: 599

Gly Tyr Tyr Arg Gly Gly Tyr Leu Gly Tyr Arg Leu Thr Leu Glu Gly
1               5                   10                  15

Ser Tyr Asp Val
        20

<210> SEQ ID NO 600
<211> LENGTH: 20
<212> TYPE: PRT
<213> ORGANISM: Artificial
<220> FEATURE:
<223> OTHER INFORMATION: Nanobody or nanobody construct

<400> SEQUENCE: 600

Gly Tyr Tyr Arg Gly Gly Tyr Leu Gly Tyr Arg Leu Thr Leu Glu Gly
1               5                   10                  15

Ser Tyr Asp Val
        20

<210> SEQ ID NO 601
<211> LENGTH: 15
<212> TYPE: PRT
<213> ORGANISM: Artificial
<220> FEATURE:
<223> OTHER INFORMATION: Nanobody or nanobody construct

<400> SEQUENCE: 601

Ser Gly Ser Leu Leu Asp Val Thr Ser Glu Ala Val Tyr Thr Asp
1               5                   10                  15

<210> SEQ ID NO 602
<211> LENGTH: 6
<212> TYPE: PRT
<213> ORGANISM: Artificial
<220> FEATURE:
<223> OTHER INFORMATION: Nanobody or nanobody construct

<400> SEQUENCE: 602

Arg Val Arg Tyr Asp Tyr
1               5

<210> SEQ ID NO 603
<211> LENGTH: 15
<212> TYPE: PRT
<213> ORGANISM: Artificial
<220> FEATURE:
<223> OTHER INFORMATION: Nanobody or nanobody construct

<400> SEQUENCE: 603

Ser Arg Arg Ala Tyr Leu Pro Ala Lys Val Gly Glu Tyr Asp Phe
1               5                   10                  15

<210> SEQ ID NO 604
<211> LENGTH: 16
<212> TYPE: PRT
<213> ORGANISM: Artificial
<220> FEATURE:
<223> OTHER INFORMATION: Nanobody or nanobody construct

<400> SEQUENCE: 604

Glu Glu Leu Gly Asp Gly Leu Gly Tyr Leu Ala Tyr Arg Tyr Asp Tyr
1               5                   10                  15

<210> SEQ ID NO 605
<211> LENGTH: 4
<212> TYPE: PRT
<213> ORGANISM: Artificial
<220> FEATURE:
<223> OTHER INFORMATION: Nanobody or nanobody construct

```
<400> SEQUENCE: 605

Pro Arg Gly Val
1

<210> SEQ ID NO 606
<211> LENGTH: 14
<212> TYPE: PRT
<213> ORGANISM: Artificial
<220> FEATURE:
<223> OTHER INFORMATION: Nanobody or nanobody construct

<400> SEQUENCE: 606

Thr Leu Thr Trp Leu Gly Ile His Glu Tyr Glu Tyr Asn Thr
1               5                   10

<210> SEQ ID NO 607
<211> LENGTH: 18
<212> TYPE: PRT
<213> ORGANISM: Artificial
<220> FEATURE:
<223> OTHER INFORMATION: Nanobody or nanobody construct

<400> SEQUENCE: 607

Gly Pro Leu Thr Lys Arg Arg Gln Cys Val Pro Gly Asp Phe Ser Met
1               5                   10                  15

Asp Phe

<210> SEQ ID NO 608
<211> LENGTH: 18
<212> TYPE: PRT
<213> ORGANISM: Artificial
<220> FEATURE:
<223> OTHER INFORMATION: Nanobody or nanobody construct

<400> SEQUENCE: 608

Gly Pro Leu Thr Arg Arg Arg Gln Cys Val Pro Gly Asp Phe Ser Met
1               5                   10                  15

Asp Phe

<210> SEQ ID NO 609
<211> LENGTH: 15
<212> TYPE: PRT
<213> ORGANISM: Artificial
<220> FEATURE:
<223> OTHER INFORMATION: Nanobody or nanobody construct

<400> SEQUENCE: 609

Lys Ala Asn Tyr Glu Ser Pro Ser Arg Glu Thr Ser Tyr Ala Tyr
1               5                   10                  15

<210> SEQ ID NO 610
<211> LENGTH: 17
<212> TYPE: PRT
<213> ORGANISM: Artificial
<220> FEATURE:
<223> OTHER INFORMATION: Nanobody or nanobody construct

<400> SEQUENCE: 610

Arg Gln Trp Ile Ser Thr Ile Ile Leu Thr Ala Pro Ser Gln Tyr Asp
1               5                   10                  15

Tyr

<210> SEQ ID NO 611
```

```
<211> LENGTH: 17
<212> TYPE: PRT
<213> ORGANISM: Artificial
<220> FEATURE:
<223> OTHER INFORMATION: Nanobody or nanobody construct

<400> SEQUENCE: 611

Arg Gln Trp Ile Ser Thr Ile Ile Leu Thr Ala Pro Ser Gln Tyr Asp
1               5                   10                  15

Tyr

<210> SEQ ID NO 612
<211> LENGTH: 17
<212> TYPE: PRT
<213> ORGANISM: Artificial
<220> FEATURE:
<223> OTHER INFORMATION: Nanobody or nanobody construct

<400> SEQUENCE: 612

Gly His Phe Thr Tyr Asp Asp Gly Arg Ile Thr Ile Arg Ser Val Asp
1               5                   10                  15

Tyr

<210> SEQ ID NO 613
<211> LENGTH: 17
<212> TYPE: PRT
<213> ORGANISM: Artificial
<220> FEATURE:
<223> OTHER INFORMATION: Nanobody or nanobody construct

<400> SEQUENCE: 613

Gly His Phe Thr Tyr Asp Asp Gly Arg Ile Ser Ile Arg Ser Val Asp
1               5                   10                  15

His

<210> SEQ ID NO 614
<211> LENGTH: 21
<212> TYPE: PRT
<213> ORGANISM: Artificial
<220> FEATURE:
<223> OTHER INFORMATION: Nanobody or nanobody construct

<400> SEQUENCE: 614

Asp Met Gly Gly Gly Pro Pro Asp Gly Asp Ala Met Pro Arg Leu Ser
1               5                   10                  15

Ser Gly Met Asp Tyr
            20

<210> SEQ ID NO 615
<211> LENGTH: 12
<212> TYPE: PRT
<213> ORGANISM: Artificial
<220> FEATURE:
<223> OTHER INFORMATION: Nanobody or nanobody construct

<400> SEQUENCE: 615

Gly Gly Leu Ile Asp Gly Ala Ala Pro Tyr Glu Phe
1               5                   10

<210> SEQ ID NO 616
<211> LENGTH: 13
<212> TYPE: PRT
<213> ORGANISM: Artificial
<220> FEATURE:
<223> OTHER INFORMATION: Nanobody or nanobody construct
```

```
<400> SEQUENCE: 616

Leu Ile Asn Thr Phe Ala Arg Lys Ile Pro Arg Tyr Ala
1               5                   10

<210> SEQ ID NO 617
<211> LENGTH: 13
<212> TYPE: PRT
<213> ORGANISM: Artificial
<220> FEATURE:
<223> OTHER INFORMATION: Nanobody or nanobody construct

<400> SEQUENCE: 617

Ala Phe Gln Ala Leu Gly Ser Pro Arg Glu Tyr Asp Tyr
1               5                   10

<210> SEQ ID NO 618
<211> LENGTH: 11
<212> TYPE: PRT
<213> ORGANISM: Artificial
<220> FEATURE:
<223> OTHER INFORMATION: Nanobody or nanobody construct

<400> SEQUENCE: 618

Trp Gly Gln Gly Thr Gln Val Thr Val Ser Ser
1               5                   10

<210> SEQ ID NO 619
<211> LENGTH: 11
<212> TYPE: PRT
<213> ORGANISM: Artificial
<220> FEATURE:
<223> OTHER INFORMATION: Nanobody or nanobody construct

<400> SEQUENCE: 619

Trp Gly Gln Gly Thr Gln Val Thr Val Ser Ser
1               5                   10

<210> SEQ ID NO 620
<211> LENGTH: 11
<212> TYPE: PRT
<213> ORGANISM: Artificial
<220> FEATURE:
<223> OTHER INFORMATION: Nanobody or nanobody construct

<400> SEQUENCE: 620

Trp Gly Gln Gly Thr Gln Val Thr Val Ser Ser
1               5                   10

<210> SEQ ID NO 621
<211> LENGTH: 11
<212> TYPE: PRT
<213> ORGANISM: Artificial
<220> FEATURE:
<223> OTHER INFORMATION: Nanobody or nanobody construct

<400> SEQUENCE: 621

Trp Gly Gln Gly Thr Gln Val Thr Val Ser Ser
1               5                   10

<210> SEQ ID NO 622
<211> LENGTH: 11
<212> TYPE: PRT
<213> ORGANISM: Artificial
<220> FEATURE:
<223> OTHER INFORMATION: Nanobody or nanobody construct
```

```
<400> SEQUENCE: 622

Trp Gly Gln Gly Thr Gln Val Thr Val Ser Ser
1               5                   10

<210> SEQ ID NO 623
<211> LENGTH: 11
<212> TYPE: PRT
<213> ORGANISM: Artificial
<220> FEATURE:
<223> OTHER INFORMATION: Nanobody or nanobody construct

<400> SEQUENCE: 623

Trp Gly Gln Gly Thr Gln Val Thr Val Ser Ser
1               5                   10

<210> SEQ ID NO 624
<211> LENGTH: 11
<212> TYPE: PRT
<213> ORGANISM: Artificial
<220> FEATURE:
<223> OTHER INFORMATION: Nanobody or nanobody construct

<400> SEQUENCE: 624

Trp Gly Gln Gly Thr Gln Val Thr Val Ser Ser
1               5                   10

<210> SEQ ID NO 625
<211> LENGTH: 11
<212> TYPE: PRT
<213> ORGANISM: Artificial
<220> FEATURE:
<223> OTHER INFORMATION: Nanobody or nanobody construct

<400> SEQUENCE: 625

Trp Gly Gln Gly Ala Gln Val Thr Val Ser Ser
1               5                   10

<210> SEQ ID NO 626
<211> LENGTH: 11
<212> TYPE: PRT
<213> ORGANISM: Artificial
<220> FEATURE:
<223> OTHER INFORMATION: Nanobody or nanobody construct

<400> SEQUENCE: 626

Trp Gly Gln Gly Ala Gln Val Thr Val Ser Ser
1               5                   10

<210> SEQ ID NO 627
<211> LENGTH: 11
<212> TYPE: PRT
<213> ORGANISM: Artificial
<220> FEATURE:
<223> OTHER INFORMATION: Nanobody or nanobody construct

<400> SEQUENCE: 627

Trp Gly Gln Gly Thr Gln Val Thr Val Ser Ser
1               5                   10

<210> SEQ ID NO 628
<211> LENGTH: 11
<212> TYPE: PRT
<213> ORGANISM: Artificial
<220> FEATURE:
<223> OTHER INFORMATION: Nanobody or nanobody construct

<400> SEQUENCE: 628
```

Trp Gly Gln Gly Thr Gln Val Thr Val Ser Ser
1               5                   10

<210> SEQ ID NO 629
<211> LENGTH: 11
<212> TYPE: PRT
<213> ORGANISM: Artificial
<220> FEATURE:
<223> OTHER INFORMATION: Nanobody or nanobody construct

<400> SEQUENCE: 629

Trp Gly Gln Gly Thr Gln Val Thr Val Ser Ser
1               5                   10

<210> SEQ ID NO 630
<211> LENGTH: 11
<212> TYPE: PRT
<213> ORGANISM: Artificial
<220> FEATURE:
<223> OTHER INFORMATION: Nanobody or nanobody construct

<400> SEQUENCE: 630

Trp Gly Gln Gly Thr Gln Val Thr Val Ser Ser
1               5                   10

<210> SEQ ID NO 631
<211> LENGTH: 11
<212> TYPE: PRT
<213> ORGANISM: Artificial
<220> FEATURE:
<223> OTHER INFORMATION: Nanobody or nanobody construct

<400> SEQUENCE: 631

Trp Gly Gln Gly Thr Gln Val Thr Val Ser Ser
1               5                   10

<210> SEQ ID NO 632
<211> LENGTH: 11
<212> TYPE: PRT
<213> ORGANISM: Artificial
<220> FEATURE:
<223> OTHER INFORMATION: Nanobody or nanobody construct

<400> SEQUENCE: 632

Trp Gly Gln Gly Thr Gln Val Thr Val Ser Ser
1               5                   10

<210> SEQ ID NO 633
<211> LENGTH: 11
<212> TYPE: PRT
<213> ORGANISM: Artificial
<220> FEATURE:
<223> OTHER INFORMATION: Nanobody or nanobody construct

<400> SEQUENCE: 633

Trp Gly Gln Gly Thr Gln Val Thr Val Ser Ser
1               5                   10

<210> SEQ ID NO 634
<211> LENGTH: 11
<212> TYPE: PRT
<213> ORGANISM: Artificial
<220> FEATURE:
<223> OTHER INFORMATION: Nanobody or nanobody construct

<400> SEQUENCE: 634

Trp Gly Gln Gly Thr Gln Val Thr Val Ser Ser
1               5                   10

<210> SEQ ID NO 635
<211> LENGTH: 11
<212> TYPE: PRT
<213> ORGANISM: Artificial
<220> FEATURE:
<223> OTHER INFORMATION: Nanobody or nanobody construct

<400> SEQUENCE: 635

Trp Gly Gln Gly Thr Gln Val Thr Val Ser Ser
1               5                   10

<210> SEQ ID NO 636
<211> LENGTH: 11
<212> TYPE: PRT
<213> ORGANISM: Artificial
<220> FEATURE:
<223> OTHER INFORMATION: Nanobody or nanobody construct

<400> SEQUENCE: 636

Trp Gly Gln Gly Thr Gln Val Thr Val Ser Ser
1               5                   10

<210> SEQ ID NO 637
<211> LENGTH: 11
<212> TYPE: PRT
<213> ORGANISM: Artificial
<220> FEATURE:
<223> OTHER INFORMATION: Nanobody or nanobody construct

<400> SEQUENCE: 637

Trp Gly Gln Gly Thr Gln Val Thr Val Ser Ser
1               5                   10

<210> SEQ ID NO 638
<211> LENGTH: 11
<212> TYPE: PRT
<213> ORGANISM: Artificial
<220> FEATURE:
<223> OTHER INFORMATION: Nanobody or nanobody construct

<400> SEQUENCE: 638

Tyr Gly Gln Gly Thr Gln Val Thr Val Ser Ser
1               5                   10

<210> SEQ ID NO 639
<211> LENGTH: 11
<212> TYPE: PRT
<213> ORGANISM: Artificial
<220> FEATURE:
<223> OTHER INFORMATION: Nanobody or nanobody construct

<400> SEQUENCE: 639

Tyr Gly Gln Gly Thr Gln Val Thr Val Ser Ser
1               5                   10

<210> SEQ ID NO 640
<211> LENGTH: 11
<212> TYPE: PRT
<213> ORGANISM: Artificial
<220> FEATURE:
<223> OTHER INFORMATION: Nanobody or nanobody construct

<400> SEQUENCE: 640

Tyr Gly Gln Gly Thr Gln Val Thr Val Ser Ser

```
1               5                  10
```

<210> SEQ ID NO 641
<211> LENGTH: 11
<212> TYPE: PRT
<213> ORGANISM: Artificial
<220> FEATURE:
<223> OTHER INFORMATION: Nanobody or nanobody construct

<400> SEQUENCE: 641

```
Tyr Gly Gln Gly Thr Gln Val Thr Val Ser Ser
1               5                  10
```

<210> SEQ ID NO 642
<211> LENGTH: 11
<212> TYPE: PRT
<213> ORGANISM: Artificial
<220> FEATURE:
<223> OTHER INFORMATION: Nanobody or nanobody construct

<400> SEQUENCE: 642

```
Tyr Gly Gln Gly Thr Gln Val Thr Val Ser Ser
1               5                  10
```

<210> SEQ ID NO 643
<211> LENGTH: 11
<212> TYPE: PRT
<213> ORGANISM: Artificial
<220> FEATURE:
<223> OTHER INFORMATION: Nanobody or nanobody construct

<400> SEQUENCE: 643

```
Trp Gly Gln Gly Thr Gln Val Thr Val Ser Ser
1               5                  10
```

<210> SEQ ID NO 644
<211> LENGTH: 11
<212> TYPE: PRT
<213> ORGANISM: Artificial
<220> FEATURE:
<223> OTHER INFORMATION: Nanobody or nanobody construct

<400> SEQUENCE: 644

```
Trp Gly Gln Gly Thr Gln Val Thr Val Ser Ser
1               5                  10
```

<210> SEQ ID NO 645
<211> LENGTH: 11
<212> TYPE: PRT
<213> ORGANISM: Artificial
<220> FEATURE:
<223> OTHER INFORMATION: Nanobody or nanobody construct

<400> SEQUENCE: 645

```
Trp Gly Gln Gly Thr Gln Val Thr Val Ser Ser
1               5                  10
```

<210> SEQ ID NO 646
<211> LENGTH: 11
<212> TYPE: PRT
<213> ORGANISM: Artificial
<220> FEATURE:
<223> OTHER INFORMATION: Nanobody or nanobody construct

<400> SEQUENCE: 646

```
Trp Gly Gln Gly Thr Gln Val Thr Val Ser Ser
1               5                  10
```

```
<210> SEQ ID NO 647
<211> LENGTH: 11
<212> TYPE: PRT
<213> ORGANISM: Artificial
<220> FEATURE:
<223> OTHER INFORMATION: Nanobody or nanobody construct

<400> SEQUENCE: 647

Trp Gly Gln Gly Thr Gln Val Thr Val Ser Ser
1               5                   10

<210> SEQ ID NO 648
<211> LENGTH: 11
<212> TYPE: PRT
<213> ORGANISM: Artificial
<220> FEATURE:
<223> OTHER INFORMATION: Nanobody or nanobody construct

<400> SEQUENCE: 648

Trp Gly Gln Gly Thr Gln Val Thr Val Ser Ser
1               5                   10

<210> SEQ ID NO 649
<211> LENGTH: 11
<212> TYPE: PRT
<213> ORGANISM: Artificial
<220> FEATURE:
<223> OTHER INFORMATION: Nanobody or nanobody construct

<400> SEQUENCE: 649

Trp Gly Gln Gly Thr Gln Val Thr Val Ser Ser
1               5                   10

<210> SEQ ID NO 650
<211> LENGTH: 11
<212> TYPE: PRT
<213> ORGANISM: Artificial
<220> FEATURE:
<223> OTHER INFORMATION: Nanobody or nanobody construct

<400> SEQUENCE: 650

Trp Gly Gln Gly Thr Gln Val Thr Val Ser Ser
1               5                   10

<210> SEQ ID NO 651
<211> LENGTH: 11
<212> TYPE: PRT
<213> ORGANISM: Artificial
<220> FEATURE:
<223> OTHER INFORMATION: Nanobody or nanobody construct

<400> SEQUENCE: 651

Trp Gly Gln Gly Thr Gln Val Thr Val Ser Ser
1               5                   10

<210> SEQ ID NO 652
<211> LENGTH: 11
<212> TYPE: PRT
<213> ORGANISM: Artificial
<220> FEATURE:
<223> OTHER INFORMATION: Nanobody or nanobody construct

<400> SEQUENCE: 652

Trp Gly Gln Gly Thr Gln Val Thr Val Ser Ser
1               5                   10
```

<210> SEQ ID NO 653
<211> LENGTH: 11
<212> TYPE: PRT
<213> ORGANISM: Artificial
<220> FEATURE:
<223> OTHER INFORMATION: Nanobody or nanobody construct

<400> SEQUENCE: 653

Trp Gly Gln Gly Thr Gln Val Thr Val Ser Ser
1               5                   10

<210> SEQ ID NO 654
<211> LENGTH: 11
<212> TYPE: PRT
<213> ORGANISM: Artificial
<220> FEATURE:
<223> OTHER INFORMATION: Nanobody or nanobody construct

<400> SEQUENCE: 654

Trp Gly Gln Gly Thr Gln Val Thr Val Ser Ser
1               5                   10

<210> SEQ ID NO 655
<211> LENGTH: 11
<212> TYPE: PRT
<213> ORGANISM: Artificial
<220> FEATURE:
<223> OTHER INFORMATION: Nanobody or nanobody construct

<400> SEQUENCE: 655

Trp Gly Gln Gly Thr Gln Val Thr Val Ser Ser
1               5                   10

<210> SEQ ID NO 656
<211> LENGTH: 11
<212> TYPE: PRT
<213> ORGANISM: Artificial
<220> FEATURE:
<223> OTHER INFORMATION: Nanobody or nanobody construct

<400> SEQUENCE: 656

Trp Gly Gln Gly Thr Gln Val Thr Val Ser Ser
1               5                   10

<210> SEQ ID NO 657
<211> LENGTH: 11
<212> TYPE: PRT
<213> ORGANISM: Artificial
<220> FEATURE:
<223> OTHER INFORMATION: Nanobody or nanobody construct

<400> SEQUENCE: 657

Trp Gly Gln Gly Thr Gln Val Thr Val Ser Ser
1               5                   10

<210> SEQ ID NO 658
<211> LENGTH: 11
<212> TYPE: PRT
<213> ORGANISM: Artificial
<220> FEATURE:
<223> OTHER INFORMATION: Nanobody or nanobody construct

<400> SEQUENCE: 658

Trp Gly Gln Gly Thr Gln Val Thr Val Ser Ser
1               5                   10

```
<210> SEQ ID NO 659
<211> LENGTH: 11
<212> TYPE: PRT
<213> ORGANISM: Artificial
<220> FEATURE:
<223> OTHER INFORMATION: Nanobody or nanobody construct

<400> SEQUENCE: 659

Trp Gly Gln Gly Thr Gln Val Thr Val Ser Ser
1               5                   10

<210> SEQ ID NO 660
<211> LENGTH: 11
<212> TYPE: PRT
<213> ORGANISM: Artificial
<220> FEATURE:
<223> OTHER INFORMATION: Nanobody or nanobody construct

<400> SEQUENCE: 660

Trp Gly Gln Gly Thr Gln Val Thr Val Ser Ser
1               5                   10

<210> SEQ ID NO 661
<211> LENGTH: 11
<212> TYPE: PRT
<213> ORGANISM: Artificial
<220> FEATURE:
<223> OTHER INFORMATION: Nanobody or nanobody construct

<400> SEQUENCE: 661

Trp Gly Gln Gly Thr Gln Val Thr Val Ser Ser
1               5                   10

<210> SEQ ID NO 662
<211> LENGTH: 11
<212> TYPE: PRT
<213> ORGANISM: Artificial
<220> FEATURE:
<223> OTHER INFORMATION: Nanobody or nanobody construct

<400> SEQUENCE: 662

Trp Gly Arg Gly Thr Gln Val Thr Val Ser Ser
1               5                   10

<210> SEQ ID NO 663
<211> LENGTH: 11
<212> TYPE: PRT
<213> ORGANISM: Artificial
<220> FEATURE:
<223> OTHER INFORMATION: Nanobody or nanobody construct

<400> SEQUENCE: 663

Trp Gly Lys Gly Thr Gln Val Thr Val Ser Ser
1               5                   10

<210> SEQ ID NO 664
<211> LENGTH: 11
<212> TYPE: PRT
<213> ORGANISM: Artificial
<220> FEATURE:
<223> OTHER INFORMATION: Nanobody or nanobody construct

<400> SEQUENCE: 664

Trp Gly Gln Gly Thr Gln Val Thr Val Ser Ser
1               5                   10

<210> SEQ ID NO 665
```

<210> SEQ ID NO 665
<211> LENGTH: 11
<212> TYPE: PRT
<213> ORGANISM: Artificial
<220> FEATURE:
<223> OTHER INFORMATION: Nanobody or nanobody construct

<400> SEQUENCE: 665

Trp Gly Gln Gly Thr Gln Val Thr Val Ser Ser
1               5                   10

<210> SEQ ID NO 666
<211> LENGTH: 11
<212> TYPE: PRT
<213> ORGANISM: Artificial
<220> FEATURE:
<223> OTHER INFORMATION: Nanobody or nanobody construct

<400> SEQUENCE: 666

Trp Gly Gln Gly Thr Gln Val Thr Val Ser Ser
1               5                   10

<210> SEQ ID NO 667
<211> LENGTH: 11
<212> TYPE: PRT
<213> ORGANISM: Artificial
<220> FEATURE:
<223> OTHER INFORMATION: Nanobody or nanobody construct

<400> SEQUENCE: 667

Trp Gly Gln Gly Thr Gln Val Thr Val Ser Ser
1               5                   10

<210> SEQ ID NO 668
<211> LENGTH: 11
<212> TYPE: PRT
<213> ORGANISM: Artificial
<220> FEATURE:
<223> OTHER INFORMATION: Nanobody or nanobody construct

<400> SEQUENCE: 668

Trp Gly Gln Gly Thr Gln Val Thr Val Ser Ser
1               5                   10

<210> SEQ ID NO 669
<211> LENGTH: 11
<212> TYPE: PRT
<213> ORGANISM: Artificial
<220> FEATURE:
<223> OTHER INFORMATION: Nanobody or nanobody construct

<400> SEQUENCE: 669

Trp Gly Gln Gly Thr Gln Val Thr Val Ser Ser
1               5                   10

<210> SEQ ID NO 670
<211> LENGTH: 11
<212> TYPE: PRT
<213> ORGANISM: Artificial
<220> FEATURE:
<223> OTHER INFORMATION: Nanobody or nanobody construct

<400> SEQUENCE: 670

Trp Gly Gln Gly Thr Gln Val Thr Val Ser Ser
1               5                   10

<210> SEQ ID NO 671
<211> LENGTH: 11

<212> TYPE: PRT
<213> ORGANISM: Artificial
<220> FEATURE:
<223> OTHER INFORMATION: Nanobody or nanobody construct

<400> SEQUENCE: 671

Trp Gly Gln Gly Thr Gln Val Thr Val Ser Ser
1               5                   10

<210> SEQ ID NO 672
<211> LENGTH: 11
<212> TYPE: PRT
<213> ORGANISM: Artificial
<220> FEATURE:
<223> OTHER INFORMATION: Nanobody or nanobody construct

<400> SEQUENCE: 672

Trp Gly Gln Gly Thr Gln Val Thr Val Ser Ser
1               5                   10

<210> SEQ ID NO 673
<211> LENGTH: 11
<212> TYPE: PRT
<213> ORGANISM: Artificial
<220> FEATURE:
<223> OTHER INFORMATION: Nanobody or nanobody construct

<400> SEQUENCE: 673

Trp Gly Arg Gly Thr Gln Val Thr Val Ser Ser
1               5                   10

<210> SEQ ID NO 674
<211> LENGTH: 11
<212> TYPE: PRT
<213> ORGANISM: Artificial
<220> FEATURE:
<223> OTHER INFORMATION: Nanobody or nanobody construct

<400> SEQUENCE: 674

Arg Gly Gln Gly Thr Gln Val Thr Val Ser Ser
1               5                   10

<210> SEQ ID NO 675
<211> LENGTH: 11
<212> TYPE: PRT
<213> ORGANISM: Artificial
<220> FEATURE:
<223> OTHER INFORMATION: Nanobody or nanobody construct

<400> SEQUENCE: 675

Arg Gly Gln Gly Thr Gln Val Thr Val Ser Ser
1               5                   10

<210> SEQ ID NO 676
<211> LENGTH: 11
<212> TYPE: PRT
<213> ORGANISM: Artificial
<220> FEATURE:
<223> OTHER INFORMATION: Nanobody or nanobody construct

<400> SEQUENCE: 676

Trp Gly Gln Gly Thr Gln Val Thr Val Ser Ser
1               5                   10

<210> SEQ ID NO 677
<211> LENGTH: 11
<212> TYPE: PRT

<213> ORGANISM: Artificial
<220> FEATURE:
<223> OTHER INFORMATION: Nanobody or nanobody construct

<400> SEQUENCE: 677

Trp Gly Gln Gly Thr Gln Val Thr Val Ser Ser
1               5                   10

<210> SEQ ID NO 678
<211> LENGTH: 11
<212> TYPE: PRT
<213> ORGANISM: Artificial
<220> FEATURE:
<223> OTHER INFORMATION: Nanobody or nanobody construct

<400> SEQUENCE: 678

Trp Gly Gln Gly Thr Gln Val Thr Val Ser Ser
1               5                   10

<210> SEQ ID NO 679
<211> LENGTH: 11
<212> TYPE: PRT
<213> ORGANISM: Artificial
<220> FEATURE:
<223> OTHER INFORMATION: Nanobody or nanobody construct

<400> SEQUENCE: 679

Trp Gly Gln Gly Thr Gln Val Thr Val Ser Ser
1               5                   10

<210> SEQ ID NO 680
<211> LENGTH: 11
<212> TYPE: PRT
<213> ORGANISM: Artificial
<220> FEATURE:
<223> OTHER INFORMATION: Nanobody or nanobody construct

<400> SEQUENCE: 680

Trp Gly Gln Gly Thr Gln Val Thr Val Ser Ser
1               5                   10

<210> SEQ ID NO 681
<211> LENGTH: 11
<212> TYPE: PRT
<213> ORGANISM: Artificial
<220> FEATURE:
<223> OTHER INFORMATION: Nanobody or nanobody construct

<400> SEQUENCE: 681

Trp Gly Gln Gly Thr Gln Val Thr Val Ser Ser
1               5                   10

<210> SEQ ID NO 682
<211> LENGTH: 11
<212> TYPE: PRT
<213> ORGANISM: Artificial
<220> FEATURE:
<223> OTHER INFORMATION: Nanobody or nanobody construct

<400> SEQUENCE: 682

Trp Gly Gln Gly Thr Gln Val Thr Val Ser Ser
1               5                   10

<210> SEQ ID NO 683
<211> LENGTH: 11
<212> TYPE: PRT
<213> ORGANISM: Artificial

<220> FEATURE:
<223> OTHER INFORMATION: Nanobody or nanobody construct

<400> SEQUENCE: 683

Trp Gly Gln Gly Thr Gln Val Thr Val Ser Ser
1               5                   10

<210> SEQ ID NO 684
<211> LENGTH: 11
<212> TYPE: PRT
<213> ORGANISM: Artificial
<220> FEATURE:
<223> OTHER INFORMATION: Nanobody or nanobody construct

<400> SEQUENCE: 684

Trp Gly Gln Gly Thr Gln Val Thr Val Ser Ser
1               5                   10

<210> SEQ ID NO 685
<211> LENGTH: 11
<212> TYPE: PRT
<213> ORGANISM: Artificial
<220> FEATURE:
<223> OTHER INFORMATION: Nanobody or nanobody construct

<400> SEQUENCE: 685

Trp Gly Gln Gly Thr Gln Val Thr Val Ser Ser
1               5                   10

<210> SEQ ID NO 686
<211> LENGTH: 11
<212> TYPE: PRT
<213> ORGANISM: Artificial
<220> FEATURE:
<223> OTHER INFORMATION: Nanobody or nanobody construct

<400> SEQUENCE: 686

Trp Gly Gln Gly Thr Gln Val Thr Val Ser Ser
1               5                   10

<210> SEQ ID NO 687
<211> LENGTH: 11
<212> TYPE: PRT
<213> ORGANISM: Artificial
<220> FEATURE:
<223> OTHER INFORMATION: Nanobody or nanobody construct

<400> SEQUENCE: 687

Lys Gly Arg Gly Thr Gln Val Thr Val Ser Ser
1               5                   10

<210> SEQ ID NO 688
<211> LENGTH: 11
<212> TYPE: PRT
<213> ORGANISM: Artificial
<220> FEATURE:
<223> OTHER INFORMATION: Nanobody or nanobody construct

<400> SEQUENCE: 688

Trp Gly Gln Gly Thr Gln Val Thr Val Ser Ser
1               5                   10

<210> SEQ ID NO 689
<211> LENGTH: 11
<212> TYPE: PRT
<213> ORGANISM: Artificial
<220> FEATURE:

<223> OTHER INFORMATION: Nanobody or nanobody construct

<400> SEQUENCE: 689

Trp Gly Glu Gly Thr Leu Val Thr Val Ser Ser
1               5                   10

<210> SEQ ID NO 690
<211> LENGTH: 11
<212> TYPE: PRT
<213> ORGANISM: Artificial
<220> FEATURE:
<223> OTHER INFORMATION: Nanobody or nanobody construct

<400> SEQUENCE: 690

Trp Gly Glu Gly Thr Leu Val Thr Val Ser Ser
1               5                   10

<210> SEQ ID NO 691
<211> LENGTH: 11
<212> TYPE: PRT
<213> ORGANISM: Artificial
<220> FEATURE:
<223> OTHER INFORMATION: Nanobody or nanobody construct

<400> SEQUENCE: 691

Trp Gly Gln Gly Thr Gln Val Thr Val Ser Ser
1               5                   10

<210> SEQ ID NO 692
<211> LENGTH: 11
<212> TYPE: PRT
<213> ORGANISM: Artificial
<220> FEATURE:
<223> OTHER INFORMATION: Nanobody or nanobody construct

<400> SEQUENCE: 692

Trp Gly Gln Gly Thr Gln Val Thr Val Ser Ser
1               5                   10

<210> SEQ ID NO 693
<211> LENGTH: 11
<212> TYPE: PRT
<213> ORGANISM: Artificial
<220> FEATURE:
<223> OTHER INFORMATION: Nanobody or nanobody construct

<400> SEQUENCE: 693

Trp Gly Gln Gly Thr Gln Val Thr Val Ser Ser
1               5                   10

<210> SEQ ID NO 694
<211> LENGTH: 11
<212> TYPE: PRT
<213> ORGANISM: Artificial
<220> FEATURE:
<223> OTHER INFORMATION: Nanobody or nanobody construct

<400> SEQUENCE: 694

Trp Gly Lys Gly Thr Leu Val Thr Val Ser Ser
1               5                   10

<210> SEQ ID NO 695
<211> LENGTH: 11
<212> TYPE: PRT
<213> ORGANISM: Artificial
<220> FEATURE:
<223> OTHER INFORMATION: Nanobody or nanobody construct -continued

```
<400> SEQUENCE: 695

Trp Gly Lys Gly Thr Leu Val Thr Val Ser Ser
1               5                  10

<210> SEQ ID NO 696
<211> LENGTH: 11
<212> TYPE: PRT
<213> ORGANISM: Artificial
<220> FEATURE:
<223> OTHER INFORMATION: Nanobody or nanobody construct

<400> SEQUENCE: 696

Trp Gly Lys Gly Thr Leu Val Thr Val Ser Ser
1               5                  10

<210> SEQ ID NO 697
<211> LENGTH: 11
<212> TYPE: PRT
<213> ORGANISM: Artificial
<220> FEATURE:
<223> OTHER INFORMATION: Nanobody or nanobody construct

<400> SEQUENCE: 697

Trp Gly Arg Gly Thr Gln Val Thr Val Ser Ser
1               5                  10

<210> SEQ ID NO 698
<211> LENGTH: 11
<212> TYPE: PRT
<213> ORGANISM: Artificial
<220> FEATURE:
<223> OTHER INFORMATION: Nanobody or nanobody construct

<400> SEQUENCE: 698

Trp Gly Gln Gly Thr Gln Val Thr Val Ser Ser
1               5                  10

<210> SEQ ID NO 699
<211> LENGTH: 11
<212> TYPE: PRT
<213> ORGANISM: Artificial
<220> FEATURE:
<223> OTHER INFORMATION: Nanobody or nanobody construct

<400> SEQUENCE: 699

Trp Gly Gln Gly Thr Gln Val Thr Val Ser Ser
1               5                  10

<210> SEQ ID NO 700
<211> LENGTH: 121
<212> TYPE: PRT
<213> ORGANISM: Artificial
<220> FEATURE:
<223> OTHER INFORMATION: Nanobody or nanobody construct

<400> SEQUENCE: 700

Glu Val Gln Leu Val Glu Ser Gly Gly Gly Leu Leu Gln Ala Gly Gly
1               5                  10                  15

Ser Leu Arg Leu Ser Cys Ala Ala Ser Glu Arg Ala Phe Ile Ile Tyr
            20                  25                  30

Gly Lys Ala Trp Phe Arg Gln Ala Pro Gly Lys Glu Arg Glu Phe Val
        35                  40                  45

Ala Gly Ile Asn Trp Asn Gly Gly Asp Leu His Tyr Ala Asp Ser Val
    50                  55                  60
```

```
Lys Gly Arg Phe Thr Ile Ser Arg Asp Asn Thr Asn Asn Val Val Tyr
 65                  70                  75                  80

Leu Gln Met Asn Ser Leu Lys Ser Glu Asp Thr Ala Val Tyr Tyr Cys
                 85                  90                  95

Ala Val Arg Arg Gly Thr Ala Tyr Glu Thr Asp Val Ser Tyr Glu
            100                 105                 110

Trp Gly Thr Gln Val Thr Val Ser Ser
            115                 120

<210> SEQ ID NO 701
<211> LENGTH: 123
<212> TYPE: PRT
<213> ORGANISM: Artificial
<220> FEATURE:
<223> OTHER INFORMATION: Nanobody or nanobody construct

<400> SEQUENCE: 701

Glu Val Gln Leu Val Glu Ser Gly Gly Leu Val Gln Ala Gly Gly
 1               5                  10                  15

Ser Leu Arg Leu Ser Cys Ala Ala Ser Gly Arg Ser Ile Ser Glu Tyr
                 20                  25                  30

Ala Met Gly Trp Phe Arg Gln Ala Pro Gly Gln Glu Arg Glu Phe Val
             35                  40                  45

Ala Ser Ile Ser Thr Ser Gly Gly Ser Thr Thr Tyr Ala Asp Ser Val
         50                  55                  60

Lys Gly Arg Phe Ile Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Ala Arg Tyr Asn Gly Trp Met Tyr Ala Gly Thr Met Gly Val His
            100                 105                 110

Phe Gly Gln Gly Thr Gln Val Thr Val Ser Ser
            115                 120

<210> SEQ ID NO 702
<211> LENGTH: 119
<212> TYPE: PRT
<213> ORGANISM: Artificial
<220> FEATURE:
<223> OTHER INFORMATION: Nanobody or nanobody construct

<400> SEQUENCE: 702

Glu Val Gln Leu Val Glu Ser Gly Gly Gly Leu Val Gln Pro Gly Gly
 1               5                  10                  15

Ser Leu Arg Leu Ser Cys Ala Ala Ser Gly Ser Ile Asp Ser Ile Asn
                 20                  25                  30

Arg Met Gly Trp Tyr Arg Gln Ala Pro Gly Lys Gln Arg Glu Leu Val
             35                  40                  45

Ala Ser Ser Thr Ser Gly Gly Ser Thr Asp Tyr Ala Asp Ser Val Lys
         50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Asn
                 85                  90                  95

Phe Arg Gly Ser Tyr Tyr Ser Gly Tyr Gly Asp Tyr Trp Gly Lys Gly
            100                 105                 110

Thr Leu Val Thr Val Ser Ser
```

115

<210> SEQ ID NO 703
<211> LENGTH: 124
<212> TYPE: PRT
<213> ORGANISM: Artificial
<220> FEATURE:
<223> OTHER INFORMATION: Nanobody or nanobody construct

<400> SEQUENCE: 703

Lys Val Gln Leu Val Glu Ser Gly Gly Gly Trp Val Arg Thr Gly Gly
1               5                   10                  15

Ser Met Arg Leu Ser Cys Ala Ala Ser Gly Arg Thr Ser Ser Gly Ser
                20                  25                  30

Ala Met Gly Trp Phe Arg Gln Ala Pro Gly Lys Glu Arg Val Phe Val
            35                  40                  45

Ala Ala Ile Ser Trp Gly Gly Ala Tyr Thr Asp Tyr Ala Asp Ser Val
        50                  55                  60

Lys Gly Arg Phe Thr Ile Ser Arg Asp Asn Trp Arg Asn Thr Val Asp
65                  70                  75                  80

Leu Gln Met Asn Asn Leu Lys Pro Glu Asp Thr Ala Val Tyr Tyr Cys
                85                  90                  95

Ala Asp Gly Gly Ser Thr Trp Tyr Glu Pro Thr Glu Ser Asp Phe Gly
            100                 105                 110

Ser Trp Gly Gln Gly Thr Gln Val Thr Val Ser Ser
        115                 120

<210> SEQ ID NO 704
<211> LENGTH: 122
<212> TYPE: PRT
<213> ORGANISM: Artificial
<220> FEATURE:
<223> OTHER INFORMATION: Nanobody or nanobody construct

<400> SEQUENCE: 704

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Arg Asp Arg Leu Asn
                20                  25                  30

Val Met Gly Trp Tyr Arg Gln Ala Pro Gly Lys Glu Arg Asp Leu Val
            35                  40                  45

Ala Thr Met Thr Ala Gly Gly Ser Thr Asn Tyr Ala Asp Ser Val Lys
        50                  55                  60

Gly Arg Phe Thr Ile Ser Arg Asp Ile Ala Asn Met Val Tyr Leu Gln
65                  70                  75                  80

Met Asn Ser Leu Lys Pro Glu Asp Thr Ala Val Tyr Tyr Cys Asn Gly
                85                  90                  95

Ile Thr Ala Ser Trp Tyr Ser Gly Ser Tyr Asn Tyr Asn Asn Tyr Trp
            100                 105                 110

Gly Gln Gly Thr Gln Val Thr Val Ser Ser
        115                 120

<210> SEQ ID NO 705
<211> LENGTH: 126
<212> TYPE: PRT
<213> ORGANISM: Artificial
<220> FEATURE:
<223> OTHER INFORMATION: Nanobody or nanobody construct

<400> SEQUENCE: 705

```
Glu Val Gln Leu Val Glu Ser Gly Gly Asp Val Val Gln Ala Gly Gly
1               5                   10                  15

Ser Leu Arg Leu Ser Cys Leu Ala Ser Gly Phe Thr Phe Asp Asp Tyr
            20                  25                  30

Ala Ile Gly Trp Phe Arg Gln Ala Pro Gly Lys Glu Arg Glu Gly Ile
            35                  40                  45

Ser Cys Ile Ser Ser Thr Gly Asn Val Phe Tyr Ala Asp Ser Val Lys
            50                  55                  60

Gly Arg Phe Thr Ile Ser Ser Asp Lys Glu Lys Asn Thr Leu Tyr Leu
65                  70                  75                  80

Gln Met Asn Ser Leu Lys Pro Glu Asp Thr Ala Val Tyr His Cys Ala
            85                  90                  95

Ala Gly His Phe Thr Val Asp Ser Gly Lys Val Leu Leu Arg Thr Asp
            100                 105                 110

Ile Ser Ser Trp Gly Gln Gly Thr Gln Val Thr Val Ser Ser
            115                 120                 125
```

<210> SEQ ID NO 706
<211> LENGTH: 126
<212> TYPE: PRT
<213> ORGANISM: Artificial
<220> FEATURE:
<223> OTHER INFORMATION: Nanobody or nanobody construct

<400> SEQUENCE: 706

```
Glu Val Gln Leu Val Glu Ser Gly Gly Asp Val Val Gln Ala Gly Gly
1               5                   10                  15

Ser Leu Arg Leu Ser Cys Leu Ala Ser Gly Phe Thr Phe Asp Asp Tyr
            20                  25                  30

Ala Ile Gly Trp Phe Arg Gln Ala Pro Gly Lys Glu Arg Glu Gly Ile
            35                  40                  45

Ser Cys Ile Ser Ser Thr Gly Asn Val Phe Tyr Ala Asp Ser Val Lys
            50                  55                  60

Gly Arg Phe Thr Ile Ser Ser Asp Lys Glu Lys Asn Thr Leu Tyr Leu
65                  70                  75                  80

Gln Met Asn Ser Leu Glu Pro Glu Asp Thr Ala Val Tyr His Cys Ala
            85                  90                  95

Ala Gly His Phe Thr Val Asp Ser Gly Lys Val Leu Leu Arg Thr Asp
            100                 105                 110

Ile Ser Ser Trp Gly Gln Gly Thr Gln Val Thr Val Ser Ser
            115                 120                 125
```

<210> SEQ ID NO 707
<211> LENGTH: 126
<212> TYPE: PRT
<213> ORGANISM: Artificial
<220> FEATURE:
<223> OTHER INFORMATION: Nanobody or nanobody construct

<400> SEQUENCE: 707

```
Glu Met Gln Leu Val Glu Ser Gly Gly Asp Val Val Gln Ala Gly Gly
1               5                   10                  15

Ser Leu Arg Leu Ser Cys Leu Ala Ser Gly Phe Thr Phe Asp Asp Tyr
            20                  25                  30

Ala Ile Gly Trp Phe Arg Gln Ala Pro Gly Lys Glu Arg Glu Gly Ile
            35                  40                  45

Ser Cys Ile Ser Ser Thr Gly Asn Val Phe Tyr Ala Asp Ser Val Lys
```

Gly Arg Phe Thr Ile Ser Ser Asp Lys Glu Lys Asn Thr Leu Tyr Leu
65                  70                  75                  80

Gln Met Asn Ser Leu Lys Pro Glu Asp Thr Ala Val Tyr His Cys Ala
                85                  90                  95

Ala Gly His Phe Thr Val Asp Ser Gly Lys Val Leu Leu Arg Thr Asp
            100                 105                 110

Ile Ser Ser Trp Gly Gln Gly Thr Gln Val Thr Val Ser Ser
        115                 120                 125

<210> SEQ ID NO 708
<211> LENGTH: 126
<212> TYPE: PRT
<213> ORGANISM: Artificial
<220> FEATURE:
<223> OTHER INFORMATION: Nanobody or nanobody construct

<400> SEQUENCE: 708

Glu Val Gln Leu Val Glu Ser Gly Gly Asp Val Val Gln Ala Gly Gly
1               5                   10                  15

Ser Leu Arg Leu Ser Cys Leu Ala Ser Gly Phe Thr Phe Asp Asp Tyr
            20                  25                  30

Ala Ile Gly Trp Phe Arg Gln Ala Pro Gly Lys Glu Arg Glu Gly Ile
        35                  40                  45

Ser Cys Ile Ser Ser Thr Gly Asn Val Phe Tyr Ala Asp Ser Val Lys
    50                  55                  60

Gly Arg Phe Thr Ile Ser Ser Asp Lys Glu Lys Asn Thr Leu Tyr Leu
65                  70                  75                  80

Gln Met Asn Ser Leu Lys Pro Gly Asp Thr Ala Val Tyr His Cys Ala
                85                  90                  95

Ala Gly His Phe Thr Val Asp Ser Gly Lys Val Leu Leu Arg Thr Asp
            100                 105                 110

Ile Ser Ser Trp Gly Gln Gly Thr Gln Val Thr Val Ser Ser
        115                 120                 125

<210> SEQ ID NO 709
<211> LENGTH: 126
<212> TYPE: PRT
<213> ORGANISM: Artificial
<220> FEATURE:
<223> OTHER INFORMATION: Nanobody or nanobody construct

<400> SEQUENCE: 709

Glu Val Gln Leu Val Glu Ser Gly Gly Asp Val Val Gln Ala Gly Gly
1               5                   10                  15

Ser Leu Arg Leu Ser Cys Leu Ala Ser Gly Phe Thr Phe Asp Asp Tyr
            20                  25                  30

Ala Ile Gly Trp Phe Arg Gln Ala Pro Gly Lys Glu Arg Glu Gly Ile
        35                  40                  45

Ser Cys Ile Ser Ser Thr Gly Asn Val Phe Tyr Ala Asp Ser Val Lys
    50                  55                  60

Gly Arg Leu Thr Ile Ser Ser Asp Lys Glu Lys Asn Thr Leu Tyr Leu
65                  70                  75                  80

Gln Met Asn Ser Leu Lys Pro Glu Asp Thr Ala Val Tyr His Cys Ala
                85                  90                  95

Ala Gly His Phe Thr Val Asp Ser Gly Lys Val Leu Leu Arg Thr Asp
            100                 105                 110

```
Ile Ser Ser Trp Gly Gln Gly Thr Gln Val Thr Val Ser Ser
        115                 120                 125
```

```
<210> SEQ ID NO 710
<211> LENGTH: 126
<212> TYPE: PRT
<213> ORGANISM: Artificial
<220> FEATURE:
<223> OTHER INFORMATION: Nanobody or nanobody construct

<400> SEQUENCE: 710
```

```
Glu Val Gln Leu Val Glu Ser Gly Gly Asp Val Val Gln Ala Gly Gly
1               5                   10                  15

Ser Leu Arg Leu Ser Cys Leu Ala Ser Gly Phe Thr Phe Asp Asp Tyr
            20                  25                  30

Ala Ile Gly Trp Phe Arg Gln Ala Pro Gly Lys Glu Arg Glu Gly Ile
        35                  40                  45

Ser Cys Ile Ser Ser Thr Gly Asn Val Phe Tyr Ala Asp Ser Val Lys
    50                  55                  60

Gly Arg Phe Thr Ile Ser Ser Asp Lys Glu Lys Asn Thr Leu Tyr Leu
65                  70                  75                  80

Gln Met Asp Ser Leu Lys Pro Glu Asp Thr Ala Val Tyr His Cys Ala
                85                  90                  95

Ala Gly His Phe Thr Val Asp Ser Gly Lys Val Leu Leu Arg Thr Asp
            100                 105                 110

Ile Ser Ser Trp Gly Gln Gly Thr Gln Val Thr Val Ser Ser
        115                 120                 125
```

```
<210> SEQ ID NO 711
<211> LENGTH: 126
<212> TYPE: PRT
<213> ORGANISM: Artificial
<220> FEATURE:
<223> OTHER INFORMATION: Nanobody or nanobody construct

<400> SEQUENCE: 711
```

```
Glu Val Gln Leu Val Glu Ser Gly Gly Asp Val Val Gln Ala Gly Gly
1               5                   10                  15

Ser Leu Arg Leu Ser Cys Leu Ala Ser Gly Phe Thr Phe Asp Asp Tyr
            20                  25                  30

Ala Ile Gly Trp Phe Arg Gln Ala Pro Gly Lys Glu Arg Glu Gly Ile
        35                  40                  45

Ser Cys Ile Ser Ser Thr Gly Asn Val Phe Tyr Ala Asp Ser Val Lys
    50                  55                  60

Gly Arg Phe Thr Ile Ser Ser Asp Lys Glu Lys Asn Thr Leu Tyr Leu
65                  70                  75                  80

Gln Met Asn Ser Leu Lys Pro Glu Asp Thr Ala Val Tyr His Cys Ala
                85                  90                  95

Ala Gly His Phe Thr Val Asp Ser Gly Lys Val Leu Leu Arg Thr Asp
            100                 105                 110

Val Ser Ser Trp Gly Gln Gly Thr Gln Val Thr Val Ser Ser
        115                 120                 125
```

```
<210> SEQ ID NO 712
<211> LENGTH: 128
<212> TYPE: PRT
<213> ORGANISM: Artificial
<220> FEATURE:
<223> OTHER INFORMATION: Nanobody or nanobody construct
```

<400> SEQUENCE: 712

Glu Val Gln Leu Val Glu Ser Gly Gly Gly Leu Val Gln Thr Gly Gly
1               5                   10                  15

Ser Leu Arg Leu Ser Cys Ala Ala Ser Gly Phe Thr Leu Asp Asp Tyr
            20                  25                  30

Ala Ile Ala Trp Phe Arg Gln Ala Pro Gly Lys Glu Arg Glu Gly Val
        35                  40                  45

Ser Ile Leu Ser Ser Ile Gly Lys Thr Phe Tyr Ala Asp Ser Val Lys
    50                  55                  60

Asp Arg Phe Ser Ile Thr Ala Asp Gly Ala Lys Thr Thr Val Phe Leu
65                  70                  75                  80

Gln Met Asn Ser Leu Lys Pro Gly Asp Thr Ala Ile Tyr Tyr Cys Val
                85                  90                  95

Ala Gly His Phe Val Tyr Asn Asp Gly Ala Ile Ser Leu Asn Thr Ala
            100                 105                 110

Arg Gly Ser Gly Phe Trp Gly Gln Gly Ala Gln Val Thr Val Ser Ser
        115                 120                 125

<210> SEQ ID NO 713
<211> LENGTH: 128
<212> TYPE: PRT
<213> ORGANISM: Artificial
<220> FEATURE:
<223> OTHER INFORMATION: Nanobody or nanobody construct

<400> SEQUENCE: 713

Glu Val Gln Leu Val Glu Ser Gly Gly Gly Leu Val Gln Thr Gly Gly
1               5                   10                  15

Ser Leu Arg Leu Ser Cys Ala Ala Ser Gly Phe Thr Leu Asp Asp Tyr
            20                  25                  30

Ala Ile Ala Trp Phe Arg Gln Ala Pro Gly Lys Glu Arg Glu Gly Val
        35                  40                  45

Ser Ile Leu Ser Ser Ile Gly Lys Thr Phe Tyr Ala Asp Ser Val Lys
    50                  55                  60

Asp Arg Phe Ser Ile Thr Ala Asp Gly Ala Lys Thr Thr Val Phe Leu
65                  70                  75                  80

Gln Met Asn Ser Leu Lys Pro Glu Asp Thr Ala Ile Tyr Tyr Cys Val
                85                  90                  95

Ala Gly His Phe Val Tyr Asn Asp Gly Ala Ile Ser Leu Asn Thr Ala
            100                 105                 110

Arg Gly Ser Gly Phe Trp Gly Gln Gly Ala Gln Val Thr Val Ser Ser
        115                 120                 125

<210> SEQ ID NO 714
<211> LENGTH: 128
<212> TYPE: PRT
<213> ORGANISM: Artificial
<220> FEATURE:
<223> OTHER INFORMATION: Nanobody or nanobody construct

<400> SEQUENCE: 714

Glu Val Gln Leu Val Glu Ser Gly Gly Gly Leu Val Gln Thr Gly Gly
1               5                   10                  15

Ser Leu Arg Leu Ser Cys Ala Ala Ser Gly Phe Thr Leu Asp Asp Tyr
            20                  25                  30

Ala Ile Ala Trp Phe Arg Gln Ala Pro Gly Lys Glu Arg Glu Gly Val
        35                  40                  45

```
Ser Ile Leu Ser Ser Ile Gly Lys Thr Phe Tyr Ala Asp Ser Val Lys
        50                  55                  60

Asp Arg Phe Ser Ile Thr Ala Asp Gly Ala Lys Thr Thr Val Phe Leu
 65                  70                  75                  80

Gln Met Asn Ser Leu Lys Pro Glu Asp Thr Ala Ile Tyr Tyr Cys Val
                85                  90                  95

Ala Gly His Phe Val Tyr Asn Asp Gly Ala Ile Ser Leu Asn Thr Ala
               100                 105                 110

Arg Gly Ser Gly Phe Trp Gly Gln Gly Thr Gln Val Thr Val Ser Ser
               115                 120                 125

<210> SEQ ID NO 715
<211> LENGTH: 128
<212> TYPE: PRT
<213> ORGANISM: Artificial
<220> FEATURE:
<223> OTHER INFORMATION: Nanobody or nanobody construct

<400> SEQUENCE: 715

Glu Val Gln Leu Val Glu Ser Gly Gly Gly Leu Val Gln Thr Gly Gly
  1               5                  10                  15

Ser Leu Arg Leu Ser Cys Ala Ala Ser Gly Phe Thr Leu Asp Asp Tyr
                20                  25                  30

Ala Ile Ala Trp Phe Arg Gln Ala Pro Gly Lys Glu Arg Glu Gly Val
                35                  40                  45

Ser Ile Leu Ser Ser Ile Gly Lys Thr Phe Tyr Ala Asp Ser Ala Lys
        50                  55                  60

Asp Arg Phe Ser Ile Thr Ala Asp Gly Ala Lys Thr Thr Val Phe Leu
 65                  70                  75                  80

Gln Met Asn Ser Leu Lys Pro Glu Asp Thr Ala Ile Tyr Tyr Cys Val
                85                  90                  95

Ala Gly His Phe Val Tyr Asn Asp Gly Ala Ile Ser Leu Asn Thr Ala
               100                 105                 110

Arg Gly Ser Gly Phe Trp Gly Gln Gly Thr Gln Val Thr Val Ser Ser
               115                 120                 125

<210> SEQ ID NO 716
<211> LENGTH: 115
<212> TYPE: PRT
<213> ORGANISM: Artificial
<220> FEATURE:
<223> OTHER INFORMATION: Nanobody or nanobody construct

<400> SEQUENCE: 716

Glu Val Gln Leu Val Glu Ser Gly Gly Gly Leu Val Gln Ala Gly Gly
  1               5                  10                  15

Ser Leu Arg Leu Ser Cys Ala Ala Ser Glu Arg Thr Tyr Ser Met Gly
                20                  25                  30

Trp Phe Arg Gln Ala Pro Gly Lys Glu Arg Glu Phe Val Ala Gly Ser
                35                  40                  45

Gly Trp Asp Gly Ile Pro Thr Arg Tyr Ala Asp Ser Val Lys Gly Arg
        50                  55                  60

Leu Thr Ile Ser Arg Asp Asn Ala Lys Asn Thr Val Ser Leu Gln Met
 65                  70                  75                  80

Ser Gly Leu Lys Pro Glu Asp Thr Ala Ile Tyr Tyr Cys Ala Thr Gly
                85                  90                  95

Thr Ser Val Tyr His Tyr Gln Tyr Trp Gly Gln Gly Thr Gln Val Thr
               100                 105                 110
```

Val Ser Ser
        115

<210> SEQ ID NO 717
<211> LENGTH: 115
<212> TYPE: PRT
<213> ORGANISM: Artificial
<220> FEATURE:
<223> OTHER INFORMATION: Nanobody or nanobody construct

<400> SEQUENCE: 717

Glu Val Gln Leu Val Glu Ser Gly Gly Gly Leu Val Gln Ala Gly Gly
1               5                   10                  15

Ser Leu Arg Leu Ser Cys Ala Ala Ser Glu Arg Thr Tyr Ser Met Gly
            20                  25                  30

Trp Phe Arg Gln Ala Pro Gly Lys Glu Arg Glu Phe Val Ala Gly Ser
        35                  40                  45

Gly Trp Asp Gly Ile Pro Thr Arg Tyr Ala Asp Ser Val Lys Gly Arg
    50                  55                  60

Phe Thr Ile Ser Arg Asp Asn Ala Lys Asn Thr Val Ser Leu Gln Met
65                  70                  75                  80

Ser Gly Leu Lys Pro Glu Asp Thr Ala Ile Tyr Tyr Cys Ala Thr Gly
                85                  90                  95

Thr Ser Val Tyr His Tyr Gln Tyr Arg Gly Gln Gly Thr Gln Val Thr
            100                 105                 110

Val Ser Ser
        115

<210> SEQ ID NO 718
<211> LENGTH: 115
<212> TYPE: PRT
<213> ORGANISM: Artificial
<220> FEATURE:
<223> OTHER INFORMATION: Nanobody or nanobody construct

<400> SEQUENCE: 718

Glu Val Gln Leu Val Glu Ser Gly Gly Gly Leu Val Gln Ala Gly Gly
1               5                   10                  15

Ser Leu Arg Leu Ser Cys Ala Ala Ser Glu Arg Thr Tyr Ser Met Gly
            20                  25                  30

Trp Phe Arg Arg Ala Pro Gly Lys Glu Arg Glu Phe Val Ala Gly Ser
        35                  40                  45

Gly Trp Asp Gly Ile Pro Thr Arg Tyr Ala Asp Ser Val Lys Gly Arg
    50                  55                  60

Phe Thr Ile Ser Arg Asp Asn Ala Lys Asn Thr Val Ser Leu Gln Met
65                  70                  75                  80

Ser Gly Leu Lys Pro Glu Asp Thr Ala Ile Tyr Tyr Cys Ala Thr Gly
                85                  90                  95

Thr Ser Val Tyr His Tyr Gln Tyr Trp Gly Gln Gly Thr Gln Val Thr
            100                 105                 110

Val Ser Ser
        115

<210> SEQ ID NO 719
<211> LENGTH: 115
<212> TYPE: PRT
<213> ORGANISM: Artificial
<220> FEATURE:
<223> OTHER INFORMATION: Nanobody or nanobody construct

<400> SEQUENCE: 719

Glu Val Gln Leu Val Glu Ser Gly Gly Gly Leu Val Gln Ala Gly Gly
1               5                   10                  15

Ser Leu Arg Leu Ser Cys Ala Ala Ser Glu Arg Thr Tyr Ser Val Gly
            20                  25                  30

Trp Phe Arg Gln Ala Pro Gly Lys Glu Arg Glu Phe Val Ala Gly Ser
        35                  40                  45

Gly Trp Asp Gly Thr Pro Thr Arg Tyr Ala Asp Ser Val Lys Gly Arg
    50                  55                  60

Phe Thr Ile Ser Arg Asp Asn Ala Lys Asn Thr Val Ser Leu Gln Met
65                  70                  75                  80

Ser Gly Leu Lys Pro Glu Asp Thr Ala Ile Tyr Tyr Cys Ala Thr Gly
                85                  90                  95

Thr Ser Val Tyr His Tyr Gln Tyr Trp Gly Gln Gly Thr Gln Val Thr
            100                 105                 110

Val Ser Ser
        115

<210> SEQ ID NO 720
<211> LENGTH: 115
<212> TYPE: PRT
<213> ORGANISM: Artificial
<220> FEATURE:
<223> OTHER INFORMATION: Nanobody or nanobody construct

<400> SEQUENCE: 720

Glu Val Gln Leu Val Glu Ser Gly Gly Gly Leu Val Gln Ala Gly Gly
1               5                   10                  15

Ser Leu Arg Leu Ser Cys Ala Ala Pro Glu Arg Thr Tyr Ser Met Gly
            20                  25                  30

Trp Phe Arg Gln Ala Pro Gly Lys Glu Arg Glu Phe Val Ala Gly Ser
        35                  40                  45

Gly Trp Asp Gly Ile Pro Thr Arg Tyr Ala Asp Ser Val Lys Gly Arg
    50                  55                  60

Phe Thr Ile Ser Arg Asp Asn Ala Lys Asn Thr Val Ser Leu Gln Met
65                  70                  75                  80

Ser Gly Leu Lys Pro Glu Asp Thr Ala Ile Tyr Tyr Cys Ala Thr Gly
                85                  90                  95

Thr Ser Val Tyr His Tyr Gln Tyr Trp Gly Gln Gly Thr Gln Val Thr
            100                 105                 110

Val Ser Ser
        115

<210> SEQ ID NO 721
<211> LENGTH: 115
<212> TYPE: PRT
<213> ORGANISM: Artificial
<220> FEATURE:
<223> OTHER INFORMATION: Nanobody or nanobody construct

<400> SEQUENCE: 721

Glu Val Gln Leu Val Glu Ser Gly Gly Gly Leu Val Gln Ala Gly Gly
1               5                   10                  15

Ser Leu Arg Leu Ser Cys Ala Ala Ser Glu Arg Thr Tyr Ser Met Gly
            20                  25                  30

Trp Phe Arg Gln Ala Pro Gly Lys Glu Arg Glu Phe Val Ala Gly Ser
        35                  40                  45

Gly Trp Asp Gly Ile Pro Thr Arg Tyr Ala Asp Ser Val Lys Gly Arg
            50                  55                  60

Phe Thr Ile Ser Arg Asp Asn Ala Lys Asn Thr Val Ser Leu Gln Met
65                  70                  75                  80

Ser Gly Leu Lys Pro Glu Asp Thr Ala Ile Tyr Tyr Cys Ala Thr Gly
                85                  90                  95

Thr Ser Val Tyr His Tyr Gln Tyr Trp Gly Gln Gly Thr Gln Val Thr
            100                 105                 110

Val Ser Ser
        115

<210> SEQ ID NO 722
<211> LENGTH: 115
<212> TYPE: PRT
<213> ORGANISM: Artificial
<220> FEATURE:
<223> OTHER INFORMATION: Nanobody or nanobody construct

<400> SEQUENCE: 722

Glu Val Gln Leu Val Glu Ser Arg Gly Gly Leu Val Gln Ala Gly Gly
1               5                   10                  15

Ser Leu Arg Leu Ser Cys Ala Ala Ser Glu Arg Thr Tyr Ser Met Gly
            20                  25                  30

Trp Phe Arg Gln Ala Pro Gly Lys Glu Arg Glu Phe Val Ala Gly Ser
        35                  40                  45

Gly Trp Asp Gly Ile Pro Thr Arg Tyr Ala Asp Ser Val Lys Ser Arg
            50                  55                  60

Phe Thr Ile Ser Arg Asp Asn Ala Lys Asn Thr Val Ser Leu Gln Met
65                  70                  75                  80

Ser Gly Leu Lys Pro Glu Asp Thr Ala Ile Tyr Tyr Cys Ala Thr Gly
                85                  90                  95

Thr Ser Val Tyr His Tyr Gln Tyr Trp Gly Gln Gly Thr Gln Val Thr
            100                 105                 110

Val Ser Ser
        115

<210> SEQ ID NO 723
<211> LENGTH: 115
<212> TYPE: PRT
<213> ORGANISM: Artificial
<220> FEATURE:
<223> OTHER INFORMATION: Nanobody or nanobody construct

<400> SEQUENCE: 723

Glu Val Gln Leu Val Glu Ser Gly Gly Gly Leu Val Gln Ala Gly Gly
1               5                   10                  15

Ser Leu Arg Leu Ser Cys Ala Ala Ser Glu Arg Thr Tyr Ser Met Gly
            20                  25                  30

Trp Phe Arg Gln Ala Pro Gly Lys Glu Arg Glu Phe Val Ala Gly Ser
        35                  40                  45

Gly Trp Asp Gly Ile Pro Thr Arg Tyr Ala Asp Ser Val Lys Gly Arg
            50                  55                  60

Phe Thr Ile Ser Arg Asp Asn Ala Lys Asn Ala Val Ser Leu Gln Met
65                  70                  75                  80

Ser Gly Leu Lys Pro Glu Asp Thr Ala Ile Tyr Tyr Cys Ala Thr Gly
                85                  90                  95

Thr Ser Val Tyr His Tyr Gln Tyr Trp Gly Gln Gly Thr Gln Val Thr

-continued

<210> SEQ ID NO 724
<211> LENGTH: 115
<212> TYPE: PRT
<213> ORGANISM: Artificial
<220> FEATURE:
<223> OTHER INFORMATION: Nanobody or nanobody construct

<400> SEQUENCE: 724

Glu Val Gln Leu Val Glu Ser Gly Gly Gly Leu Val Gln Pro Gly Gly
1               5                   10                  15

Ser Leu Arg Leu Ser Cys Ala Ala Ser Glu Arg Thr Tyr Ser Met Gly
            20                  25                  30

Trp Phe Arg Gln Ala Pro Gly Lys Glu Arg Glu Phe Val Ala Gly Ser
        35                  40                  45

Gly Trp Asp Gly Ile Pro Thr Arg Tyr Ala Asp Ser Val Lys Gly Arg
    50                  55                  60

Phe Thr Ile Ser Arg Asp Asn Ala Lys Asn Thr Val Ser Leu Gln Met
65                  70                  75                  80

Ser Gly Leu Lys Pro Glu Asp Thr Ala Ile Tyr Tyr Cys Ala Thr Gly
                85                  90                  95

Thr Ser Val Tyr His Tyr Gln Tyr Trp Gly Gln Gly Thr Gln Val Thr
            100                 105                 110

Val Ser Ser
        115

<210> SEQ ID NO 725
<211> LENGTH: 115
<212> TYPE: PRT
<213> ORGANISM: Artificial
<220> FEATURE:
<223> OTHER INFORMATION: Nanobody or nanobody construct

<400> SEQUENCE: 725

Glu Val Gln Leu Val Glu Ser Gly Gly Gly Leu Val Gln Ala Gly Gly
1               5                   10                  15

Ser Leu Arg Leu Ser Cys Ala Ala Ser Glu Arg Thr Tyr Ser Met Gly
            20                  25                  30

Trp Phe Arg Gln Ala Pro Gly Lys Glu Arg Glu Phe Val Ala Gly Ser
        35                  40                  45

Gly Trp Asp Gly Ile Pro Thr Arg Tyr Ala Asp Ser Val Lys Gly Arg
    50                  55                  60

Phe Thr Ile Ser Arg Asp Asn Ala Lys Ser Thr Val Ser Leu Gln Met
65                  70                  75                  80

Ser Gly Leu Lys Pro Glu Asp Thr Ala Ile Tyr Tyr Cys Ala Thr Gly
                85                  90                  95

Thr Ser Val Tyr His Tyr Gln Tyr Trp Gly Gln Gly Thr Gln Val Thr
            100                 105                 110

Val Ser Ser
        115

<210> SEQ ID NO 726
<211> LENGTH: 127
<212> TYPE: PRT
<213> ORGANISM: Artificial
<220> FEATURE:

<223> OTHER INFORMATION: Nanobody or nanobody construct

<400> SEQUENCE: 726

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Val Ser Asp Tyr
            20                  25                  30

Gly Met Gly Trp Phe Arg Gln Ala Pro Gly Lys Leu Arg Glu Phe Val
        35                  40                  45

Ala Ser Ile Asn Trp Ser Gly Ile Tyr Thr Arg Tyr Ile Asp Ser Val
    50                  55                  60

Glu Gly Arg Phe Thr Ile Ser Arg Asp Asn Thr Lys Asn Thr Leu Tyr
65                  70                  75                  80

Leu Gln Met Asn Asn Leu Lys Ala Glu Asp Thr Ala Val Tyr Tyr Cys
                85                  90                  95

Ala Tyr Phe Leu Gly Pro Asn Trp Tyr Ser Asn Tyr Gly Arg Pro Ser
            100                 105                 110

Ser Tyr Asp Phe Tyr Gly Gln Gly Thr Gln Val Thr Val Ser Ser
        115                 120                 125

<210> SEQ ID NO 727
<211> LENGTH: 127
<212> TYPE: PRT
<213> ORGANISM: Artificial
<220> FEATURE:
<223> OTHER INFORMATION: Nanobody or nanobody construct

<400> SEQUENCE: 727

Lys Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Val Ser Asp Tyr
            20                  25                  30

Gly Met Gly Trp Phe Arg Gln Ala Pro Gly Lys Leu Arg Glu Phe Val
        35                  40                  45

Ala Ser Ile Asn Trp Ser Gly Ile Tyr Thr Arg Tyr Ile Asp Ser Val
    50                  55                  60

Glu Gly Arg Phe Thr Ile Ser Arg Asp Asn Thr Lys Asn Thr Leu Tyr
65                  70                  75                  80

Leu Gln Met Asn Asn Leu Arg Ala Glu Asp Thr Ala Val Tyr Tyr Cys
                85                  90                  95

Ala Tyr Phe Leu Gly Pro Asn Trp Tyr Ser Asn Tyr Gly Arg Pro Ser
            100                 105                 110

Ser Tyr Asp Phe Tyr Gly Gln Gly Thr Gln Val Thr Val Ser Ser
        115                 120                 125

<210> SEQ ID NO 728
<211> LENGTH: 127
<212> TYPE: PRT
<213> ORGANISM: Artificial
<220> FEATURE:
<223> OTHER INFORMATION: Nanobody or nanobody construct

<400> SEQUENCE: 728

Glu Val Gln Leu Met Glu Ser Gly Gly Gly Leu Val Gln Ala Gly Gly
1               5                   10                  15

Ser Leu Arg Leu Ser Cys Ala Ala Ser Gly Arg Thr Val Ser Asp Tyr
            20                  25                  30

Gly Met Gly Trp Phe Arg Gln Ala Pro Gly Lys Leu Arg Glu Phe Val

```
                35                  40                  45
Ala Ser Ile Asn Trp Ser Gly Ile Tyr Thr Arg Tyr Ile Asp Ser Val
     50                  55                  60
Glu Gly Arg Phe Thr Ile Ser Arg Asp Asn Thr Lys Asn Thr Leu Tyr
 65                  70                  75                  80
Leu Gln Met Asn Asn Leu Lys Ala Glu Asp Thr Ala Val Tyr Tyr Cys
                 85                  90                  95
Ala Tyr Phe Leu Gly Pro Asn Trp Tyr Ser Asn Tyr Gly Arg Pro Ser
                100                 105                 110
Ser Tyr Asp Phe Tyr Gly Gln Gly Thr Gln Val Thr Val Ser Ser
            115                 120                 125
```

<210> SEQ ID NO 729
<211> LENGTH: 127
<212> TYPE: PRT
<213> ORGANISM: Artificial
<220> FEATURE:
<223> OTHER INFORMATION: Nanobody or nanobody construct

<400> SEQUENCE: 729

```
Glu Val Gln Leu Val Glu Ser Gly Gly Gly Leu Val Gln Ala Gly Gly
 1               5                  10                  15
Ser Leu Arg Leu Ser Cys Ala Ala Ser Gly Arg Thr Val Ser Asp Tyr
             20                  25                  30
Gly Met Gly Trp Phe Arg Gln Ala Pro Gly Lys Leu Arg Glu Phe Val
                35                  40                  45
Ala Ser Ile Asn Trp Ser Gly Ile Tyr Thr Arg Tyr Ile Asp Ser Val
     50                  55                  60
Glu Gly Arg Phe Thr Ile Ser Arg Asp Asn Thr Lys Asn Thr Leu Tyr
 65                  70                  75                  80
Leu Gln Met Asn Asn Leu Lys Ala Glu Asp Thr Ala Val Tyr Tyr Cys
                 85                  90                  95
Ala Tyr Phe Leu Gly Pro Asn Trp Tyr Ser Asn Tyr Gly Arg Pro Ser
                100                 105                 110
Ser Tyr Gly Phe Tyr Gly Gln Gly Thr Gln Val Thr Val Ser Ser
            115                 120                 125
```

<210> SEQ ID NO 730
<211> LENGTH: 127
<212> TYPE: PRT
<213> ORGANISM: Artificial
<220> FEATURE:
<223> OTHER INFORMATION: Nanobody or nanobody construct

<400> SEQUENCE: 730

```
Glu Val Gln Leu Val Glu Ser Gly Gly Gly Leu Val Gln Ala Gly Gly
 1               5                  10                  15
Ser Leu Arg Leu Ser Cys Ala Ala Ser Gly Arg Thr Val Ser Asp Tyr
             20                  25                  30
Gly Met Gly Trp Phe Arg Gln Ala Pro Gly Lys Glu Cys Glu Phe Val
                35                  40                  45
Ala Ser Ile Asn Trp Ser Gly Thr Tyr Thr Arg Tyr Ile Asp Ser Val
     50                  55                  60
Glu Gly Arg Phe Thr Ile Ser Arg Asp Asn Thr Glu Asn Thr Leu Tyr
 65                  70                  75                  80
Leu Gln Met Asn Asn Leu Lys Ala Glu Asp Thr Ala Val Tyr Tyr Cys
                 85                  90                  95
```

```
Ala Tyr Phe Leu Gly Pro Asn Trp Tyr Ser Asp Tyr Gly Arg Pro Ser
            100                 105                 110

Ser Tyr Asp Phe Tyr Gly Gln Gly Thr Gln Val Thr Val Ser Ser
            115                 120                 125

<210> SEQ ID NO 731
<211> LENGTH: 127
<212> TYPE: PRT
<213> ORGANISM: Artificial
<220> FEATURE:
<223> OTHER INFORMATION: Nanobody or nanobody construct

<400> SEQUENCE: 731

Glu Val Gln Leu Met Glu Ser Gly Gly Gly Leu Val Gln Ala Gly Gly
1               5                   10                  15

Pro Leu Arg Leu Ser Cys Ala Ala Ser Gly Arg Thr Val Ser Asp Tyr
            20                  25                  30

Gly Met Gly Trp Phe Arg Gln Ala Pro Gly Lys Glu Arg Glu Phe Val
            35                  40                  45

Ala Ser Ile Asn Trp Ser Gly Thr Tyr Thr Arg Tyr Ile Asp Ser Val
        50                  55                  60

Glu Gly Arg Phe Thr Ile Ser Arg Asp Asn Thr Glu Asn Thr Leu Tyr
65                  70                  75                  80

Leu Gln Met Asn Asn Leu Lys Ala Glu Asp Thr Ala Val Tyr Tyr Cys
                85                  90                  95

Ala Tyr Phe Leu Gly Pro Asn Trp Tyr Ser Asp Tyr Gly Arg Pro Ser
            100                 105                 110

Ser Tyr Asp Phe Tyr Gly Gln Gly Thr Gln Val Thr Val Ser Ser
            115                 120                 125

<210> SEQ ID NO 732
<211> LENGTH: 120
<212> TYPE: PRT
<213> ORGANISM: Artificial
<220> FEATURE:
<223> OTHER INFORMATION: Nanobody or nanobody construct

<400> SEQUENCE: 732

Ala Val Gln Leu Val Glu Ser Gly Gly Gly Leu Val Gln Ala Gly Gly
1               5                   10                  15

Ser Leu Arg Leu Ser Cys Ala Ala Ser Gly Asn Phe Phe Arg Val Asn
            20                  25                  30

Thr Met Ala Trp Tyr Arg Gln Ala Pro Gly Lys Gln Arg Glu Leu Val
            35                  40                  45

Ala Asp Ile Thr Arg Gly Asp Arg Thr Asn Tyr Ala Asp Thr Val Asn
        50                  55                  60

Gly Arg Phe Thr Ile Ser Arg Asp Asn Val Arg Asn Thr Val Tyr Leu
65                  70                  75                  80

Gln Met Asn Gly Leu Arg Pro Glu Asp Thr Ala Ala Tyr Tyr Cys Tyr
                85                  90                  95

Ala Val Ile Glu Leu Gly Val Leu Glu Pro Arg Asp Tyr Trp Gly Gln
            100                 105                 110

Gly Thr Gln Val Thr Val Ser Ser
            115                 120

<210> SEQ ID NO 733
<211> LENGTH: 120
<212> TYPE: PRT
<213> ORGANISM: Artificial
```

-continued

```
<220> FEATURE:
<223> OTHER INFORMATION: Nanobody or nanobody construct

<400> SEQUENCE: 733
```

| Glu | Val | Gln | Leu | Val | Glu | Ser | Gly | Gly | Gly | Leu | Val | Gln | Ala | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Asn | Phe | Phe | Arg | Val | Asn |
|---|---|---|---|---|---|---|---|---|---|---|---|---|---|---|---|
| | | | 20 | | | | | 25 | | | | | 30 | | |

| Thr | Met | Ala | Trp | Tyr | Arg | Gln | Ala | Pro | Gly | Lys | Gln | Arg | Glu | Leu | Val |
|---|---|---|---|---|---|---|---|---|---|---|---|---|---|---|---|
| | | 35 | | | | | 40 | | | | | 45 | | | |

| Ala | Asp | Ile | Thr | Arg | Gly | Asp | Arg | Thr | Asn | Tyr | Ala | Asp | Thr | Val | Asn |
|---|---|---|---|---|---|---|---|---|---|---|---|---|---|---|---|
| 50 | | | | | 55 | | | | | 60 | | | | | |

| Gly | Arg | Phe | Thr | Ile | Ser | Arg | Asp | Asn | Val | Arg | Asn | Thr | Val | Tyr | Leu |
|---|---|---|---|---|---|---|---|---|---|---|---|---|---|---|---|
| 65 | | | | | 70 | | | | | 75 | | | | | 80 |

| Gln | Met | Asn | Gly | Leu | Lys | Pro | Glu | Asp | Thr | Ala | Ala | Tyr | Tyr | Cys | Tyr |
|---|---|---|---|---|---|---|---|---|---|---|---|---|---|---|---|
| | | | | 85 | | | | | 90 | | | | | 95 | |

| Ala | Arg | Ile | Glu | Leu | Gly | Val | Leu | Glu | Pro | Arg | Asp | Tyr | Trp | Gly | Gln |
|---|---|---|---|---|---|---|---|---|---|---|---|---|---|---|---|
| | | | 100 | | | | | 105 | | | | | 110 | | |

| Gly | Thr | Gln | Val | Thr | Val | Ser | Ser |
|---|---|---|---|---|---|---|---|
| | | 115 | | | | | 120 |

```
<210> SEQ ID NO 734
<211> LENGTH: 120
<212> TYPE: PRT
<213> ORGANISM: Artificial
<220> FEATURE:
<223> OTHER INFORMATION: Nanobody or nanobody construct

<400> SEQUENCE: 734
```

| Glu | Val | Gln | Leu | Val | Glu | Ser | Gly | Gly | Gly | Leu | Val | Gln | Ala | Gly | Gly |
|---|---|---|---|---|---|---|---|---|---|---|---|---|---|---|---|
| 1 | | | | 5 | | | | | 10 | | | | | 15 | |

| Pro | Leu | Arg | Leu | Ser | Cys | Ala | Ala | Ser | Gly | Asn | Phe | Phe | Arg | Val | Asn |
|---|---|---|---|---|---|---|---|---|---|---|---|---|---|---|---|
| | | | 20 | | | | | 25 | | | | | 30 | | |

| Thr | Met | Ala | Trp | Tyr | Arg | Gln | Ala | Pro | Gly | Lys | Gln | Arg | Glu | Leu | Val |
|---|---|---|---|---|---|---|---|---|---|---|---|---|---|---|---|
| | | 35 | | | | | 40 | | | | | 45 | | | |

| Ala | Asp | Ile | Thr | Arg | Gly | Asp | Arg | Thr | Asn | Tyr | Ala | Asp | Thr | Val | Asn |
|---|---|---|---|---|---|---|---|---|---|---|---|---|---|---|---|
| 50 | | | | | 55 | | | | | 60 | | | | | |

| Gly | Arg | Phe | Thr | Ile | Ser | Arg | Asp | Asn | Val | Arg | Asn | Thr | Val | Tyr | Leu |
|---|---|---|---|---|---|---|---|---|---|---|---|---|---|---|---|
| 65 | | | | | 70 | | | | | 75 | | | | | 80 |

| Gln | Met | Asn | Gly | Leu | Lys | Pro | Glu | Asp | Thr | Ala | Ala | Tyr | Tyr | Cys | Tyr |
|---|---|---|---|---|---|---|---|---|---|---|---|---|---|---|---|
| | | | | 85 | | | | | 90 | | | | | 95 | |

| Ala | Arg | Ile | Glu | Leu | Gly | Val | Leu | Glu | Pro | Arg | Asp | Tyr | Trp | Gly | Gln |
|---|---|---|---|---|---|---|---|---|---|---|---|---|---|---|---|
| | | | 100 | | | | | 105 | | | | | 110 | | |

| Gly | Thr | Gln | Val | Thr | Val | Ser | Ser |
|---|---|---|---|---|---|---|---|
| | | 115 | | | | | 120 |

```
<210> SEQ ID NO 735
<211> LENGTH: 120
<212> TYPE: PRT
<213> ORGANISM: Artificial
<220> FEATURE:
<223> OTHER INFORMATION: Nanobody or nanobody construct

<400> SEQUENCE: 735
```

| Glu | Val | Gln | Leu | Val | Glu | Ser | Gly | Gly | Gly | Leu | Val | Gln | Ala | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Ser | Phe | Phe | Arg | Val | Asn |
|---|---|---|---|---|---|---|---|---|---|---|---|---|---|---|---|
| | | | 20 | | | | | 25 | | | | | 30 | | |

```
Asn Met Ala Trp Tyr Arg Gln Ala Pro Gly Lys Gln Arg Glu Leu Val
        35                  40                  45

Ala Asp Ile Thr Arg Gly Asp Arg Thr Asn Tyr Ala Asp Ser Val Asn
 50                  55                  60

Gly Arg Phe Thr Ile Ser Arg Asp Asn Val Arg Asn Thr Val Tyr Leu
 65                  70                  75                  80

Gln Met Asn Gly Leu Lys Pro Glu Asp Thr Ala Val Tyr Tyr Cys Tyr
            85                  90                  95

Ala Arg Ile Glu Leu Gly Val Leu Glu Pro Arg Asp Tyr Trp Gly Gln
            100                 105                 110

Gly Thr Gln Val Thr Val Ser Ser
        115                 120

<210> SEQ ID NO 736
<211> LENGTH: 120
<212> TYPE: PRT
<213> ORGANISM: Artificial
<220> FEATURE:
<223> OTHER INFORMATION: Nanobody or nanobody construct

<400> SEQUENCE: 736

Glu Val Gln Leu Val Glu Ser Gly Gly Gly Leu Val Gln Ala Gly Gly
 1               5                  10                  15

Pro Leu Arg Leu Ser Cys Ala Ala Ser Gly Ser Phe Phe Arg Val Asn
            20                  25                  30

Asn Met Ala Trp Tyr Arg Gln Ala Pro Gly Lys Gln Arg Glu Leu Val
        35                  40                  45

Ala Asp Ile Thr Arg Gly Asp Arg Thr Asn Tyr Ala Asp Ser Val Asn
 50                  55                  60

Gly Arg Phe Thr Ile Ser Arg Asp Asn Val Arg Asn Thr Val Tyr Leu
 65                  70                  75                  80

Gln Met Asn Gly Leu Lys Pro Glu Asp Thr Ala Val Tyr Tyr Cys Tyr
            85                  90                  95

Ala Arg Ile Glu Leu Gly Val Leu Glu Pro Arg Asp Tyr Trp Gly Gln
            100                 105                 110

Gly Thr Gln Val Thr Val Ser Ser
        115                 120

<210> SEQ ID NO 737
<211> LENGTH: 120
<212> TYPE: PRT
<213> ORGANISM: Artificial
<220> FEATURE:
<223> OTHER INFORMATION: Nanobody or nanobody construct

<400> SEQUENCE: 737

Glu Val Gln Leu Val Glu Ser Gly Gly Gly Leu Val Gln Ala Gly Gly
 1               5                  10                  15

Ser Leu Arg Leu Ser Cys Ala Ser Gly Asn Phe Phe Arg Val Asn
            20                  25                  30

Thr Met Ala Trp Tyr Arg Gln Ala Pro Gly Lys Gln Arg Glu Leu Val
        35                  40                  45

Ala Asp Ile Thr Arg Gly Asp Arg Thr Asn Tyr Ala Asp Thr Val Asn
 50                  55                  60

Gly Arg Phe Thr Ile Ser Arg Asp Asn Val Arg Asn Thr Val Tyr Leu
 65                  70                  75                  80

Gln Met Asn Ser Leu Lys Pro Glu Asp Thr Ala Ala Tyr Tyr Cys Tyr
            85                  90                  95
```

Ala Arg Ile Glu Leu Gly Val Leu Glu Pro Arg Asp Tyr Trp Gly Gln
            100                 105                 110

Gly Thr Gln Val Thr Val Ser Ser
        115                 120

<210> SEQ ID NO 738
<211> LENGTH: 120
<212> TYPE: PRT
<213> ORGANISM: Artificial
<220> FEATURE:
<223> OTHER INFORMATION: Nanobody or nanobody construct

<400> SEQUENCE: 738

Glu Val Gln Leu Val Glu Ser Gly Gly Gly Leu Val Gln Ala Gly Gly
1               5                   10                  15

Ser Leu Gly Leu Ser Cys Ala Ala Ser Gly Asn Phe Phe Arg Val Asn
            20                  25                  30

Thr Met Ala Trp Tyr Arg Gln Ala Pro Gly Lys Gln Arg Glu Leu Val
        35                  40                  45

Ala Asp Ile Thr Arg Gly Asp Arg Thr Asn Tyr Ala Asp Thr Val Asn
    50                  55                  60

Gly Arg Phe Thr Ile Ser Arg Asp Asn Val Arg Asn Thr Val Tyr Leu
65                  70                  75                  80

Gln Met Asn Gly Leu Lys Pro Glu Asp Thr Ala Ala Tyr Tyr Cys Tyr
                85                  90                  95

Ala Arg Ile Glu Leu Gly Val Leu Glu Pro Arg Asp Tyr Trp Gly Gln
            100                 105                 110

Gly Thr Gln Val Thr Val Ser Ser
        115                 120

<210> SEQ ID NO 739
<211> LENGTH: 120
<212> TYPE: PRT
<213> ORGANISM: Artificial
<220> FEATURE:
<223> OTHER INFORMATION: Nanobody or nanobody construct

<400> SEQUENCE: 739

Glu Met Gln Leu Val Glu Ser Gly Gly Gly Leu Val Gln Ala Gly Gly
1               5                   10                  15

Ser Leu Arg Leu Ser Cys Ala Ala Ser Gly Asn Phe Phe Arg Val Asn
            20                  25                  30

Thr Met Ala Trp Tyr Arg Gln Ala Pro Gly Lys Gln Arg Glu Leu Val
        35                  40                  45

Ala Asp Ile Thr Arg Gly Asp Arg Thr Asn Tyr Ala Asp Thr Val Asn
    50                  55                  60

Gly Arg Phe Thr Ile Ser Arg Asp Asn Val Arg Asn Thr Val Tyr Leu
65                  70                  75                  80

Gln Met Asn Gly Leu Lys Pro Glu Asp Thr Ala Ala Tyr Tyr Cys Tyr
                85                  90                  95

Ala Arg Ile Glu Leu Gly Val Leu Glu Pro Arg Asp Tyr Trp Gly Gln
            100                 105                 110

Gly Thr Gln Val Thr Val Ser Ser
        115                 120

<210> SEQ ID NO 740
<211> LENGTH: 120
<212> TYPE: PRT

<213> ORGANISM: Artificial
<220> FEATURE:
<223> OTHER INFORMATION: Nanobody or nanobody construct

<400> SEQUENCE: 740

Glu Val Gln Leu Val Glu Ser Gly Gly Gly Leu Val Gln Ala Gly Gly
1               5                   10                  15

Ser Leu Arg Leu Leu Cys Ala Ala Ser Gly Ser Phe Phe Arg Val Asn
            20                  25                  30

Asn Met Ala Trp Tyr Arg Gln Ala Pro Gly Lys Gln Arg Glu Leu Val
        35                  40                  45

Ala Asp Ile Thr Arg Gly Asp Arg Thr Asn Tyr Ala Asp Ser Val Asn
    50                  55                  60

Gly Arg Phe Thr Ile Ser Arg Asp Asn Val Arg Asn Thr Val Tyr Leu
65                  70                  75                  80

Gln Met Asn Gly Leu Lys Pro Glu Asp Thr Ala Val Tyr Ser Cys Tyr
                85                  90                  95

Ala Arg Ile Glu Leu Gly Ile Leu Glu Pro Arg Asp Tyr Trp Gly Gln
            100                 105                 110

Gly Thr Gln Val Thr Val Ser Ser
        115                 120

<210> SEQ ID NO 741
<211> LENGTH: 120
<212> TYPE: PRT
<213> ORGANISM: Artificial
<220> FEATURE:
<223> OTHER INFORMATION: Nanobody or nanobody construct

<400> SEQUENCE: 741

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Phe Phe Arg Val Asn
            20                  25                  30

Asn Met Ala Trp Tyr Arg Gln Ala Pro Gly Lys Gln Arg Glu Leu Val
        35                  40                  45

Ala Asp Ile Thr Arg Gly Asp Arg Thr Asn Tyr Ala Asp Ser Val Asn
    50                  55                  60

Gly Arg Phe Thr Ile Ser Arg Asp Asn Val Arg Asn Thr Val Tyr Leu
65                  70                  75                  80

Gln Met Asp Gly Leu Lys Pro Glu Asp Thr Ala Val Tyr Tyr Cys Tyr
                85                  90                  95

Ala Arg Ile Glu Leu Gly Val Leu Val Pro Arg Asp Tyr Trp Gly Gln
            100                 105                 110

Gly Thr Gln Val Thr Val Ser Ser
        115                 120

<210> SEQ ID NO 742
<211> LENGTH: 120
<212> TYPE: PRT
<213> ORGANISM: Artificial
<220> FEATURE:
<223> OTHER INFORMATION: Nanobody or nanobody construct

<400> SEQUENCE: 742

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Phe Phe Arg Val Asn
            20                  25                  30

```
Asn Met Ala Trp Tyr Arg Gln Ala Pro Gly Lys Gln Arg Glu Leu Val
         35                  40                  45

Ala Asp Ile Thr Arg Gly Asp Arg Thr Asn Tyr Ala Asp Ser Val Asn
     50                  55                  60

Gly Arg Phe Thr Ile Ser Arg Asp Asn Val Arg Asn Thr Val Tyr Leu
 65                  70                  75                  80

Gln Met Asn Gly Leu Lys Pro Glu Asp Thr Ala Val Tyr Tyr Cys Tyr
                 85                  90                  95

Ala Arg Ile Glu Leu Gly Pro Leu Val Pro Arg Asp Tyr Trp Gly Gln
             100                 105                 110

Gly Thr Gln Val Thr Val Ser Ser
         115                 120

<210> SEQ ID NO 743
<211> LENGTH: 120
<212> TYPE: PRT
<213> ORGANISM: Artificial
<220> FEATURE:
<223> OTHER INFORMATION: Nanobody or nanobody construct

<400> SEQUENCE: 743

Glu Val Gln Leu Val Lys Ser Gly Gly Gly Leu Val Gln Ala Gly Gly
 1               5                  10                  15

Ser Leu Arg Leu Ser Cys Ala Ala Ser Gly Ser Phe Phe Arg Val Asn
             20                  25                  30

Asn Met Ala Trp Tyr Arg Gln Ala Pro Gly Lys Gln Arg Glu Leu Val
         35                  40                  45

Ala Asp Ile Thr Arg Gly Asp Arg Thr Asn Tyr Ala Asp Ser Val Asn
     50                  55                  60

Gly Arg Phe Thr Ile Ser Arg Asp Asn Val Arg Asn Thr Val Tyr Leu
 65                  70                  75                  80

Gln Met Asn Gly Leu Lys Pro Glu Asp Thr Ala Val Tyr Tyr Cys Tyr
                 85                  90                  95

Ala Arg Ile Glu Leu Gly Pro Leu Val Pro Arg Asp Tyr Trp Gly Gln
             100                 105                 110

Gly Thr Gln Val Thr Val Ser Ser
         115                 120

<210> SEQ ID NO 744
<211> LENGTH: 120
<212> TYPE: PRT
<213> ORGANISM: Artificial
<220> FEATURE:
<223> OTHER INFORMATION: Nanobody or nanobody construct

<400> SEQUENCE: 744

Lys Val Gln Leu Val Glu Ser Gly Gly Gly Leu Val Gln Ala Gly Gly
 1               5                  10                  15

Ser Leu Arg Leu Ser Cys Ala Ala Ser Gly Ser Phe Phe Arg Val Asn
             20                  25                  30

Asn Met Ala Trp Tyr Arg Gln Gly Pro Gly Lys Gln Arg Glu Leu Val
         35                  40                  45

Ala Asp Ile Thr Arg Gly Asp Arg Thr Asn Tyr Ala Asp Ser Val Asn
     50                  55                  60

Gly Arg Phe Thr Ile Ser Arg Asp Asn Val Arg Asn Thr Val Tyr Leu
 65                  70                  75                  80

Gln Met Asn Gly Leu Lys Pro Glu Asp Thr Ala Val Tyr Tyr Cys Tyr
```

```
                    85                  90                  95

Ala Thr Ile Glu Leu Gly Val Leu Glu Pro Arg Asp Tyr Trp Gly Gln
                100                 105                 110

Gly Thr Gln Val Thr Val Ser Ser
        115                 120

<210> SEQ ID NO 745
<211> LENGTH: 120
<212> TYPE: PRT
<213> ORGANISM: Artificial
<220> FEATURE:
<223> OTHER INFORMATION: Nanobody or nanobody construct

<400> SEQUENCE: 745

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Phe Phe Arg Val Asn
                20                  25                  30

Val Met Ala Trp Tyr Arg Gln Gly Pro Gly Lys Gln Arg Glu Leu Val
                35                  40                  45

Ala Asp Ile Thr Arg Gly Asp Arg Thr Asn Tyr Ala Asp Ser Val Asn
    50                  55                  60

Gly Arg Phe Thr Ile Ser Arg Asp Asn Val Arg Asn Thr Val Tyr Leu
65                  70                  75                  80

Gln Met Asn Gly Leu Lys Pro Glu Asp Thr Ala Val Tyr Tyr Cys Tyr
                85                  90                  95

Ala Thr Ile Glu Leu Gly Val Leu Glu Pro Arg Asp Tyr Trp Gly Gln
                100                 105                 110

Gly Thr Gln Val Thr Val Ser Ser
        115                 120

<210> SEQ ID NO 746
<211> LENGTH: 120
<212> TYPE: PRT
<213> ORGANISM: Artificial
<220> FEATURE:
<223> OTHER INFORMATION: Nanobody or nanobody construct

<400> SEQUENCE: 746

Glu Val Gln Leu Val Glu Ser Gly Gly Gly Leu Val Lys Pro Gly Gly
1               5                   10                  15

Ser Leu Arg Leu Ser Cys Ala Ala Ser Gly Ser Phe Phe Arg Val Asn
                20                  25                  30

Asn Met Ala Trp Tyr Arg Gln Gly Pro Gly Lys Gln Arg Glu Leu Val
                35                  40                  45

Ala Asp Ile Thr Arg Gly Asp Arg Thr Asn Tyr Ala Asp Ser Val Asn
    50                  55                  60

Gly Arg Phe Thr Ile Ser Arg Asp Asn Val Arg Asn Thr Val Tyr Leu
65                  70                  75                  80

Gln Met Asn Gly Leu Lys Pro Glu Asp Thr Ala Val Tyr Tyr Cys Tyr
                85                  90                  95

Ala Thr Ile Glu Leu Gly Val Leu Glu Pro Arg Asp Tyr Trp Gly Gln
                100                 105                 110

Gly Thr Gln Val Thr Val Ser Ser
        115                 120

<210> SEQ ID NO 747
<211> LENGTH: 120
```

```
<212> TYPE: PRT
<213> ORGANISM: Artificial
<220> FEATURE:
<223> OTHER INFORMATION: Nanobody or nanobody construct

<400> SEQUENCE: 747

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Phe Phe Arg Val Asn
            20                  25                  30

Asn Met Ala Trp Tyr Arg Gln Ala Pro Gly Lys Gln Arg Glu Leu Val
        35                  40                  45

Ala Asp Ile Thr Arg Gly Asp Arg Thr Asn Tyr Ala Asp Ser Val Asn
    50                  55                  60

Gly Arg Phe Thr Ile Ser Arg Asp Asn Val Arg Asn Thr Val Tyr Leu
65                  70                  75                  80

Gln Met Asn Gly Leu Lys Pro Glu Asp Thr Ala Val Tyr Tyr Cys Tyr
                85                  90                  95

Ala Thr Ile Glu Leu Gly Val Leu Glu Pro Arg Asp Tyr Trp Gly Gln
            100                 105                 110

Gly Thr Gln Val Thr Val Ser Ser
        115                 120

<210> SEQ ID NO 748
<211> LENGTH: 120
<212> TYPE: PRT
<213> ORGANISM: Artificial
<220> FEATURE:
<223> OTHER INFORMATION: Nanobody or nanobody construct

<400> SEQUENCE: 748

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Phe Phe Arg Val Asn
            20                  25                  30

Asn Met Ala Trp Tyr Arg Gln Gly Pro Gly Lys Gln Arg Glu Leu Val
        35                  40                  45

Ala Asp Ile Thr Arg Gly Asp Arg Thr Asn Tyr Ala Asp Ser Val Asn
    50                  55                  60

Gly Arg Phe Thr Ile Ser Arg Asp Asn Val Arg Asn Thr Val Tyr Leu
65                  70                  75                  80

Gln Met Asn Gly Leu Lys Pro Glu Asp Thr Ala Val Tyr Tyr Cys Tyr
                85                  90                  95

Ala Thr Ile Glu Leu Gly Val Leu Glu Pro Arg Asp Tyr Trp Gly Gln
            100                 105                 110

Gly Thr Gln Val Thr Val Ser Ser
        115                 120

<210> SEQ ID NO 749
<211> LENGTH: 120
<212> TYPE: PRT
<213> ORGANISM: Artificial
<220> FEATURE:
<223> OTHER INFORMATION: Nanobody or nanobody construct

<400> SEQUENCE: 749

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Phe Phe Arg Val Asn
```

```
                    20                  25                  30

Asn Met Ala Trp Tyr Arg Gln Ala Pro Gly Lys Gln Arg Glu Leu Val
            35                  40                  45

Ala Asp Ile Thr Arg Gly Asp Arg Thr Asn Tyr Ala Asp Ser Val Asn
    50                  55                  60

Gly Arg Phe Thr Ile Ser Arg Asp Asn Val Arg Asn Thr Val Tyr Leu
65                  70                  75                  80

Gln Met Asn Gly Leu Lys Pro Glu Asp Thr Ala Val Tyr Tyr Cys Tyr
            85                  90                  95

Ala Thr Ile Glu Leu Gly Val Leu Gly Pro Arg Asp Tyr Trp Gly Gln
            100                 105                 110

Gly Thr Gln Val Thr Val Ser Ser
            115                 120

<210> SEQ ID NO 750
<211> LENGTH: 120
<212> TYPE: PRT
<213> ORGANISM: Artificial
<220> FEATURE:
<223> OTHER INFORMATION: Nanobody or nanobody construct

<400> SEQUENCE: 750

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Phe Phe Arg Val Asn
            20                  25                  30

Asn Met Ala Trp Tyr Arg Gln Gly Pro Gly Lys Gln Arg Glu Leu Val
            35                  40                  45

Ala Asp Ile Thr Arg Gly Asp Arg Thr Asn Tyr Ala Asp Ser Val Asn
    50                  55                  60

Gly Arg Phe Thr Ile Ser Arg Asp Asn Val Arg Asn Thr Val Tyr Leu
65                  70                  75                  80

Gln Met Asp Gly Leu Lys Pro Glu Asp Thr Ala Val Tyr Tyr Cys Tyr
            85                  90                  95

Ala Thr Ile Glu Leu Gly Val Leu Val Pro Arg Asp Tyr Trp Gly Gln
            100                 105                 110

Gly Thr Gln Val Thr Val Ser Ser
            115                 120

<210> SEQ ID NO 751
<211> LENGTH: 127
<212> TYPE: PRT
<213> ORGANISM: Artificial
<220> FEATURE:
<223> OTHER INFORMATION: Nanobody or nanobody construct

<400> SEQUENCE: 751

Glu Val Gln Leu Val Glu Ser Gly Gly Asp Leu Val Gln Ala Gly Gly
1               5                   10                  15

Ser Leu Lys Leu Ser Cys Val Val Ser Gly Val Thr Phe Asp Asp Gly
            20                  25                  30

Thr Ile Gly Trp Phe Arg Gln Ala Pro Gly Lys Glu Arg Glu Gly Ile
            35                  40                  45

Ala Cys Ile Ser Arg Val Asp Gly Thr Thr Tyr Tyr Arg Asp Ser Val
    50                  55                  60

Lys Gly Arg Phe Thr Val Ser Ser Asp Ser Ala Lys Thr Thr Val Asn
65                  70                  75                  80
```

-continued

Leu Gln Met Asn Ser Leu Lys Pro Glu Asp Thr Ala Val Tyr Tyr Cys
                85                  90                  95

Ala Ala Asp Tyr Ala Ser Leu Cys Thr Ile Glu Thr Gly Tyr Gly Ser
            100                 105                 110

Leu Tyr Asp Tyr Trp Gly Arg Gly Thr Gln Val Thr Val Ser Ser
        115                 120                 125

<210> SEQ ID NO 752
<211> LENGTH: 127
<212> TYPE: PRT
<213> ORGANISM: Artificial
<220> FEATURE:
<223> OTHER INFORMATION: Nanobody or nanobody construct

<400> SEQUENCE: 752

Glu Val Gln Leu Val Glu Ser Gly Gly Asp Leu Val Gln Ala Gly Gly
1               5                   10                  15

Ser Leu Lys Leu Ser Cys Val Val Ser Gly Val Thr Phe Asp Asp Gly
                20                  25                  30

Thr Ile Gly Trp Phe Arg Gln Ala Pro Gly Lys Glu Arg Glu Gly Ile
            35                  40                  45

Ala Cys Ile Ser Arg Val Asp Gly Thr Thr Tyr Arg Asp Ser Val
        50                  55                  60

Lys Gly Arg Phe Thr Val Ser Ser Asp Ser Ala Lys Thr Thr Val Asn
65                  70                  75                  80

Leu Gln Met Asn Ser Leu Lys Pro Glu Asp Thr Ala Val Tyr Tyr Cys
                85                  90                  95

Ala Ala Asp Tyr Ala Ser Leu Cys Thr Ile Glu Thr Gly Tyr Gly Ser
            100                 105                 110

Leu Tyr Asp Tyr Trp Gly Lys Gly Thr Gln Val Thr Val Ser Ser
        115                 120                 125

<210> SEQ ID NO 753
<211> LENGTH: 124
<212> TYPE: PRT
<213> ORGANISM: Artificial
<220> FEATURE:
<223> OTHER INFORMATION: Nanobody or nanobody construct

<400> SEQUENCE: 753

Glu Met Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Leu
                20                  25                  30

Ala Met Gly Trp Leu Arg Gln Ala Pro Gly Lys Glu Arg Glu Phe Val
            35                  40                  45

Ser Gly Ile Ser Arg Gly Gly Ser Thr Tyr Tyr Ala Asp Ser Val
        50                  55                  60

Lys Gly Arg Phe Thr Ile Ser Arg Asp Asn Ala Lys Asn Thr Met Tyr
65                  70                  75                  80

Leu Gln Met Asn Ser Leu Lys Pro Glu Asp Thr Ala Val Tyr Tyr Cys
                85                  90                  95

Ala Gly Ser Pro Val Leu Ser Ile Val Leu Asp Thr Arg Gly Leu Glu
            100                 105                 110

Tyr Trp Gly Gln Gly Thr Gln Val Thr Val Ser Ser
        115                 120

<210> SEQ ID NO 754

```
<211> LENGTH: 124
<212> TYPE: PRT
<213> ORGANISM: Artificial
<220> FEATURE:
<223> OTHER INFORMATION: Nanobody or nanobody construct

<400> SEQUENCE: 754

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Leu
            20                  25                  30

Ala Met Gly Trp Leu Arg Gln Ala Pro Gly Lys Glu Arg Glu Phe Val
        35                  40                  45

Ser Gly Ile Ser Arg Gly Gly Thr Ser Thr Tyr Tyr Ala Asp Ser Val
    50                  55                  60

Lys Gly Arg Phe Thr Ile Ser Arg Asp Asn Ala Lys Asn Thr Met Tyr
65                  70                  75                  80

Leu Gln Met Asn Ser Leu Lys Pro Glu Asp Thr Ala Val Tyr Tyr Cys
                85                  90                  95

Ala Gly Ser Pro Val Leu Ser Ile Val Leu Asp Thr Arg Gly Leu Glu
            100                 105                 110

Tyr Trp Gly Gln Gly Thr Gln Val Thr Val Ser Ser
        115                 120

<210> SEQ ID NO 755
<211> LENGTH: 124
<212> TYPE: PRT
<213> ORGANISM: Artificial
<220> FEATURE:
<223> OTHER INFORMATION: Nanobody or nanobody construct

<400> SEQUENCE: 755

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Leu
            20                  25                  30

Ala Met Gly Trp Leu Arg Gln Ala Pro Gly Lys Glu Arg Glu Phe Val
        35                  40                  45

Ser Gly Ile Ser Arg Gly Gly Thr Ser Thr Tyr Tyr Ala Asp Ser Val
    50                  55                  60

Lys Gly Arg Leu Thr Ile Ser Arg Asp Asn Ala Lys Asn Thr Met Tyr
65                  70                  75                  80

Leu Gln Met Asn Ser Leu Lys Pro Glu Asp Thr Ala Val Tyr Tyr Cys
                85                  90                  95

Ala Gly Ser Pro Val Leu Ser Ile Val Leu Asp Thr Arg Gly Leu Glu
            100                 105                 110

Tyr Trp Gly Gln Gly Thr Gln Val Thr Val Ser Ser
        115                 120

<210> SEQ ID NO 756
<211> LENGTH: 126
<212> TYPE: PRT
<213> ORGANISM: Artificial
<220> FEATURE:
<223> OTHER INFORMATION: Nanobody or nanobody construct

<400> SEQUENCE: 756

Glu Val Gln Leu Val Glu Ser Gly Gly Gly Leu Val Gln Ala Gly Gly
1               5                   10                  15
```

-continued

Ser Leu Arg Leu Ser Cys Ala Ala Ser Gly Arg Thr Phe Ser Ser
        20                  25                  30

Pro Val Gly Trp Phe Arg Gln Ala Pro Gly Lys Glu Arg Asp Phe Val
        35                  40                  45

Ala Thr Ile Ser Trp Asn Gly Val Asp Thr His Tyr Leu Asp Ser Val
    50                  55                  60

Lys Gly Arg Phe Thr Ile Ser Arg Asp Asn Ala Lys Asn Thr Val His
65                  70                  75                  80

Leu Gln Met His Ile Leu Lys Pro Glu Asp Thr Ala Leu Tyr Tyr Cys
                85                  90                  95

Ala Ala Ser Thr Ser Gly Ser Val Tyr Leu Pro Tyr Arg Val Tyr Gln
            100                 105                 110

Tyr Asp Ser Trp Gly Gln Gly Thr Gln Val Thr Val Ser Ser
        115                 120                 125

<210> SEQ ID NO 757
<211> LENGTH: 126
<212> TYPE: PRT
<213> ORGANISM: Artificial
<220> FEATURE:
<223> OTHER INFORMATION: Nanobody or nanobody construct

<400> SEQUENCE: 757

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser
        20                  25                  30

Pro Val Gly Trp Phe Arg Gln Ala Pro Gly Lys Glu Arg Asp Phe Val
        35                  40                  45

Ala Thr Ile Ser Trp Asn Gly Val Asp Thr His Tyr Leu Asp Ser Val
    50                  55                  60

Lys Gly Arg Phe Thr Ile Ser Arg Asp Asn Ala Leu Asn Thr Val His
65                  70                  75                  80

Leu Gln Met His Ile Leu Lys Pro Glu Asp Thr Ala Leu Tyr Tyr Cys
                85                  90                  95

Ala Ala Ser Thr Ser Gly Ser Ala Tyr Leu Pro Tyr Arg Val Tyr Gln
            100                 105                 110

Tyr Asp Ser Trp Gly Gln Gly Thr Gln Val Thr Val Ser Ser
        115                 120                 125

<210> SEQ ID NO 758
<211> LENGTH: 126
<212> TYPE: PRT
<213> ORGANISM: Artificial
<220> FEATURE:
<223> OTHER INFORMATION: Nanobody or nanobody construct

<400> SEQUENCE: 758

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser
        20                  25                  30

Pro Val Gly Trp Phe Arg Gln Ala Pro Gly Lys Glu Arg Asp Phe Val
        35                  40                  45

Ala Thr Ile Ser Trp Asn Gly Val Asp Thr His Tyr Leu Asp Ser Val
    50                  55                  60

Lys Gly Arg Phe Thr Ile Ser Arg Asp Asn Ala Leu Asn Thr Val His
65                  70                  75                  80

Leu Gln Met His Ile Leu Lys Pro Glu Asp Thr Ala Leu Tyr Tyr Cys
            85                  90                  95

Ala Ala Ser Thr Ser Gly Ser Ala Tyr Leu Pro Tyr Arg Val His Gln
            100                 105                 110

Tyr Asp Ser Trp Gly Gln Gly Thr Gln Val Thr Val Ser Ser
            115                 120                 125

<210> SEQ ID NO 759
<211> LENGTH: 123
<212> TYPE: PRT
<213> ORGANISM: Artificial
<220> FEATURE:
<223> OTHER INFORMATION: Nanobody or nanobody construct

<400> SEQUENCE: 759

Glu Val Gln Leu Val Glu Ser Gly Gly Gly Leu Val Gln Ala Gly Ala
1               5                   10                  15

Ser Leu Arg Val Ser Cys Ala Ala Ser Ala Arg Thr Gly Ser Tyr Thr
            20                  25                  30

Met Gly Trp Phe Arg Gln Ala Pro Gly Lys Glu Arg Glu Phe Val Ser
            35                  40                  45

Thr Ile Ser Trp Asn Gly Ala Ser Thr Val Tyr Ala Asp Ser Val Lys
        50                  55                  60

Gly Arg Phe Thr Ile Ser Arg Asp Asn Ala Lys Asn Thr Val Ser Leu
65                  70                  75                  80

Gln Met Asn Ser Leu Lys Pro Glu Asp Thr Ala Val Tyr Tyr Cys Ala
            85                  90                  95

Gly Ser Ile Ser Ser Tyr Ser Ser Arg Trp Gln Asp Asp Tyr Glu Tyr
            100                 105                 110

Trp Gly Gln Gly Thr Gln Val Thr Val Ser Ser
            115                 120

<210> SEQ ID NO 760
<211> LENGTH: 123
<212> TYPE: PRT
<213> ORGANISM: Artificial
<220> FEATURE:
<223> OTHER INFORMATION: Nanobody or nanobody construct

<400> SEQUENCE: 760

Glu Val Gln Leu Val Glu Ser Gly Gly Gly Leu Val Gln Ala Gly Gly
1               5                   10                  15

Ser Leu Arg Val Ser Cys Ala Ala Ser Ala Arg Thr Gly Ser Tyr Ser
            20                  25                  30

Met Gly Trp Phe Arg Gln Ala Pro Gly Lys Glu Arg Glu Phe Val Ser
            35                  40                  45

Thr Ile Ser Trp Asn Gly Ala Asp Thr Val Tyr Ala Asp Ser Val Lys
        50                  55                  60

Gly Arg Phe Thr Ile Ser Arg Asp Asn Ala Lys Asp Thr Val Tyr Leu
65                  70                  75                  80

Gln Met Asn Ser Leu Lys Pro Glu Asp Thr Ala Val Tyr Tyr Cys Ala
            85                  90                  95

Gly Ser Ile Thr Ser Tyr Val Ser Thr Trp Gln His Asp Tyr Glu Tyr
            100                 105                 110

Trp Gly Gln Gly Thr Gln Val Thr Val Ser Ser
            115                 120

```
<210> SEQ ID NO 761
<211> LENGTH: 123
<212> TYPE: PRT
<213> ORGANISM: Artificial
<220> FEATURE:
<223> OTHER INFORMATION: Nanobody or nanobody construct

<400> SEQUENCE: 761

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Asn Phe Gly Ser Tyr
            20                  25                  30

Thr Met Ala Trp Phe Arg Gln Ala Pro Gly Lys Gly Arg Glu Phe Val
        35                  40                  45

Ser Thr Ile Asn Trp Ser Gly Gly Asp Thr Asp Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asp Ser Leu Lys Pro Glu Asp Thr Ala Val Tyr Tyr Cys
                85                  90                  95

Ala Ala Gly Leu Glu Tyr Met Ser Thr Ile Arg Tyr Thr Tyr Glu Tyr
            100                 105                 110

Trp Gly Gln Gly Thr Gln Val Thr Val Ser Ser
        115                 120

<210> SEQ ID NO 762
<211> LENGTH: 120
<212> TYPE: PRT
<213> ORGANISM: Artificial
<220> FEATURE:
<223> OTHER INFORMATION: Nanobody or nanobody construct

<400> SEQUENCE: 762

Glu Val Gln Leu Val Glu Ser Gly Gly Gly Leu Val Gln Pro Gly Gly
1               5                   10                  15

Ser Leu Arg Leu Ser Cys Val Val Ser Gly Ser Met Tyr Arg Ile Asp
            20                  25                  30

Asn Met Gly Trp Tyr Arg Gln Ala Pro Gly Lys Gln Arg Glu Leu Val
        35                  40                  45

Ala Thr Val Thr Arg Gly Asp Ile Thr Asn Tyr Ala Asp Ser Val Lys
    50                  55                  60

Gly Arg Phe Thr Ile Gly Arg Asp Asn Ala Lys Asn Thr Val Tyr Leu
65                  70                  75                  80

Gln Met Asn Ser Leu Lys Pro Ala Asp Thr Ala Val Tyr Tyr Cys Asn
                85                  90                  95

Ile Asp Ser Tyr Ile Ile Gly Ala Gly Val Arg Asp Tyr Trp Gly Arg
            100                 105                 110

Gly Thr Gln Val Thr Val Ser Ser
        115                 120

<210> SEQ ID NO 763
<211> LENGTH: 120
<212> TYPE: PRT
<213> ORGANISM: Artificial
<220> FEATURE:
<223> OTHER INFORMATION: Nanobody or nanobody construct

<400> SEQUENCE: 763

Glu Val Gln Leu Val Glu Ser Gly Gly Gly Leu Val Gln Ser Gly Gly
1               5                   10                  15
```

```
Ser Leu Arg Leu Ser Cys Ala Gly Ser Gly Phe Ser Tyr Tyr Ile Ile
            20                  25                  30

Gly Trp Phe Arg Gln Ala Pro Gly Lys Glu Arg Glu Val Ser Cys
        35                  40                  45

Ile Arg Val Thr Asp Gly Ser Thr Tyr Tyr Asn Ser Val Lys Gly
    50                  55                  60

Arg Phe Thr Met Ser Arg Asp Asn Ala Glu Asn Thr Val Tyr Leu Gln
65                  70                  75                  80

Met Asn Ser Leu Lys Pro Glu Asp Thr Ala Val Tyr Ser Cys Ala Thr
                85                  90                  95

Glu Cys Gln Arg Trp Ala Tyr Pro Asn Arg Ile Gly Ala Arg Gly Gln
            100                 105                 110

Gly Thr Gln Val Thr Val Ser Ser
        115                 120
```

<210> SEQ ID NO 764
<211> LENGTH: 120
<212> TYPE: PRT
<213> ORGANISM: Artificial
<220> FEATURE:
<223> OTHER INFORMATION: Nanobody or nanobody construct

<400> SEQUENCE: 764

```
Glu Val Gln Leu Val Glu Ser Gly Gly Gly Leu Val Gln Ser Gly Gly
1               5                   10                  15

Ser Leu Arg Leu Ser Cys Ala Gly Ser Gly Phe Ser Tyr Tyr Ile Ile
            20                  25                  30

Gly Trp Phe Arg Gln Ala Pro Gly Lys Glu Arg Glu Val Ser Cys
        35                  40                  45

Ile Arg Val Thr Asp Gly Ser Thr Tyr His Thr Asn Ser Val Lys Gly
    50                  55                  60

Arg Phe Thr Met Ser Arg Asp Asn Ala Glu Asn Thr Val Tyr Leu Gln
65                  70                  75                  80

Met Asn Ser Leu Lys Pro Glu Asp Thr Ala Val Tyr Ser Cys Ala Thr
                85                  90                  95

Glu Cys Gln Arg Trp Ala Tyr Pro Asn Arg Ile Gly Ala Arg Gly Gln
            100                 105                 110

Gly Thr Gln Val Thr Val Ser Ser
        115                 120
```

<210> SEQ ID NO 765
<211> LENGTH: 129
<212> TYPE: PRT
<213> ORGANISM: Artificial
<220> FEATURE:
<223> OTHER INFORMATION: Nanobody or nanobody construct

<400> SEQUENCE: 765

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Leu Glu Tyr Tyr
            20                  25                  30

Asn Ile Gly Trp Phe Arg Gln Ala Pro Gly Lys Glu Arg Glu Gly Val
        35                  40                  45

Ala Cys Ile Asp Trp Thr Glu Gly Ser Thr Phe Tyr Val Asp Ser Val
    50                  55                  60

Lys Gly Arg Phe Thr Ile Ser Thr Asp Asn Ala Lys Asn Thr Val Tyr
```

```
                65                  70                  75                  80
Leu His Met Asn Ser Leu Glu Pro Glu Asp Thr Ala Val Tyr Tyr Cys
                    85                  90                  95

Ala Ala Gly Trp Gly Arg Val Ile Thr Val Gln His Met Cys Ala Asp
                100                 105                 110

Arg Ser Leu Phe Thr Ser Trp Gly Gln Gly Thr Gln Val Thr Val Ser
            115                 120                 125

Ser

<210> SEQ ID NO 766
<211> LENGTH: 129
<212> TYPE: PRT
<213> ORGANISM: Artificial
<220> FEATURE:
<223> OTHER INFORMATION: Nanobody or nanobody construct

<400> SEQUENCE: 766

Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Leu Thr Tyr Tyr
            20                  25                  30

Asn Ile Gly Trp Phe Arg Gln Ala Pro Gly Lys Glu Arg Glu Gly Val
        35                  40                  45

Ser Cys Ile Asp Trp Thr Asp Gly Thr Thr Phe Tyr Ala Asp Ser Val
    50                  55                  60

Lys Gly Arg Phe Thr Ile Ser Thr Asp Asn Ala Lys Asn Thr Val Tyr
65                  70                  75                  80

Leu His Leu Asn Ser Leu Glu Pro Glu Asp Thr Ala Val Tyr Tyr Cys
                85                  90                  95

Ala Ala Gly Trp Gly Arg Val Met Thr Val Gln His Met Cys Ala Asp
                100                 105                 110

Arg Ser Leu Phe Thr Ser Trp Gly Gln Gly Thr Gln Val Thr Val Ser
            115                 120                 125

Ser

<210> SEQ ID NO 767
<211> LENGTH: 126
<212> TYPE: PRT
<213> ORGANISM: Artificial
<220> FEATURE:
<223> OTHER INFORMATION: Nanobody or nanobody construct

<400> SEQUENCE: 767

Glu Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Ser Ser Val
            20                  25                  30

Ala Val Gly Trp Phe Arg Gln Ala Pro Gly Lys Glu Arg Asp Phe Val
        35                  40                  45

Ala Trp Ile Ser Trp Ser Gly Asp Ser Thr Tyr Tyr Ala Asp Ser Val
    50                  55                  60

Lys Gly Arg Phe Thr Ala Ser Arg Asp Asn Val Asn Asn Thr Val Tyr
65                  70                  75                  80

Leu Gln Met Asn Ser Leu Lys Pro Glu Asp Thr Ala Asp Tyr Tyr Cys
                85                  90                  95

Ala Ala Ala Trp Lys Tyr Asp Arg Ala Ser Tyr Asp Phe Pro Glu Ala
                100                 105                 110
```

```
Tyr Asp Tyr Trp Gly Gln Gly Thr Gln Val Thr Val Ser Ser
        115                 120                 125

<210> SEQ ID NO 768
<211> LENGTH: 129
<212> TYPE: PRT
<213> ORGANISM: Artificial
<220> FEATURE:
<223> OTHER INFORMATION: Nanobody or nanobody construct

<400> SEQUENCE: 768

Glu Val Gln Leu Val Glu Ser Gly Gly Leu Val Gln Ala Gly Gly
1               5                   10                  15

Ser Leu Arg Leu Ser Cys Ala Ala Ser Pro Gly Thr Phe Ser Ser Phe
            20                  25                  30

Asn Met Gly Trp Phe Arg Gln Thr Pro Gly Lys Glu Arg Glu Phe Val
        35                  40                  45

Ala Ala Thr Ser Trp Ser Asp Ile Ser Thr Tyr Tyr Ala Asp Ser Val
    50                  55                  60

Lys Gly Arg Phe Thr Ile Ser Arg Asp Asn Ala Lys Asn Thr Val Thr
65                  70                  75                  80

Leu Glu Met Asn Ser Leu Lys Pro Glu Asp Thr Ala Val Tyr Tyr Cys
                85                  90                  95

Ala Ala Gly Tyr Tyr Arg Gly Gly Tyr Leu Gly Tyr Arg Leu Thr Leu
            100                 105                 110

Glu Gly Ser Tyr Asp Val Trp Gly Gln Gly Thr Gln Val Thr Val Ser
        115                 120                 125

Ser

<210> SEQ ID NO 769
<211> LENGTH: 129
<212> TYPE: PRT
<213> ORGANISM: Artificial
<220> FEATURE:
<223> OTHER INFORMATION: Nanobody or nanobody construct

<400> SEQUENCE: 769

Glu Val Gln Leu Val Glu Ser Gly Gly Gly Leu Val Gln Ala Gly Gly
1               5                   10                  15

Ser Leu Arg Leu Ser Cys Ala Ala Ser Pro Gly Ala Phe Ser Ser Phe
            20                  25                  30

Asn Met Gly Trp Phe Arg Gln Thr Pro Gly Lys Glu Arg Glu Phe Val
        35                  40                  45

Ala Ala Thr Ser Trp Ser Asp Ile Ser Thr Tyr Tyr Ala Asp Ser Val
    50                  55                  60

Lys Gly Arg Phe Thr Ile Ser Arg Asp Asn Ala Lys Asn Thr Val Thr
65                  70                  75                  80

Leu Glu Met Asn Ser Leu Lys Pro Glu Asp Thr Ala Val Tyr Tyr Cys
                85                  90                  95

Ala Ala Gly Tyr Tyr Arg Gly Gly Tyr Leu Gly Tyr Arg Leu Thr Leu
            100                 105                 110

Glu Gly Ser Tyr Asp Val Trp Gly Gln Gly Thr Gln Val Thr Val Ser
        115                 120                 125

Ser

<210> SEQ ID NO 770
<211> LENGTH: 129
```

<212> TYPE: PRT
<213> ORGANISM: Artificial
<220> FEATURE:
<223> OTHER INFORMATION: Nanobody or nanobody construct

<400> SEQUENCE: 770

Glu Met Gln Leu Val Glu Ser Gly Gly Gly Leu Val Gln Ala Gly Gly
1               5                   10                  15

Ser Leu Arg Leu Ser Cys Ala Ala Ser Pro Gly Thr Phe Ser Ser Phe
            20                  25                  30

Asn Met Gly Trp Phe Arg Gln Thr Pro Gly Lys Glu Arg Glu Phe Val
        35                  40                  45

Ala Ala Thr Ser Trp Ser Asp Ile Ser Thr Tyr Tyr Ala Asp Ser Val
    50                  55                  60

Lys Gly Arg Phe Thr Ile Ser Arg Asp Asn Ala Lys Asn Thr Val Thr
65                  70                  75                  80

Leu Glu Met Asn Ser Leu Lys Pro Glu Asp Thr Ala Val Tyr Tyr Cys
                85                  90                  95

Ala Ala Gly Tyr Tyr Arg Gly Gly Tyr Leu Gly Tyr Arg Leu Thr Leu
            100                 105                 110

Glu Gly Ser Tyr Asp Val Trp Gly Gln Gly Thr Gln Val Thr Val Ser
        115                 120                 125

Ser

<210> SEQ ID NO 771
<211> LENGTH: 129
<212> TYPE: PRT
<213> ORGANISM: Artificial
<220> FEATURE:
<223> OTHER INFORMATION: Nanobody or nanobody construct

<400> SEQUENCE: 771

Glu Val Gln Leu Val Lys Ser Gly Gly Gly Leu Val Gln Ala Gly Gly
1               5                   10                  15

Ser Leu Arg Leu Ser Cys Ala Ala Ser Pro Gly Thr Phe Ser Ser Phe
            20                  25                  30

Asn Met Gly Trp Phe Arg Gln Thr Pro Gly Lys Glu Arg Glu Phe Val
        35                  40                  45

Ala Ala Thr Ser Trp Ser Asp Ile Ser Thr Tyr Tyr Ala Asp Ser Val
    50                  55                  60

Lys Gly Arg Phe Thr Ile Ser Arg Asp Asn Ala Lys Asn Thr Val Thr
65                  70                  75                  80

Leu Glu Met Asn Ser Leu Lys Pro Glu Asp Thr Ala Val Tyr Tyr Cys
                85                  90                  95

Ala Ala Gly Tyr Tyr Arg Gly Gly Tyr Leu Gly Tyr Arg Leu Thr Leu
            100                 105                 110

Glu Gly Ser Tyr Asp Val Trp Gly Gln Gly Thr Gln Val Thr Val Ser
        115                 120                 125

Ser

<210> SEQ ID NO 772
<211> LENGTH: 122
<212> TYPE: PRT
<213> ORGANISM: Artificial
<220> FEATURE:
<223> OTHER INFORMATION: Nanobody or nanobody construct

<400> SEQUENCE: 772

-continued

```
Glu Val Gln Leu Val Glu Ser Gly Gly Gly Leu Val Gln Ala Gly Gly
1               5                   10                  15

Ser Leu Arg Leu Ser Cys Val Val Ser Gly Arg Thr Phe Ser Ala Met
            20                  25                  30

Gly Trp Phe Arg Gln Ala Pro Gly Lys Glu Arg Glu Phe Val Ala Thr
        35                  40                  45

Val Gly Trp Asn Pro Met Asn Ser Tyr Tyr Gly Asp Ser Val Lys Gly
    50                  55                  60

Arg Phe Thr Ile Phe Arg Asp Asn Ala Lys Asn Thr Val Tyr Leu Gln
65                  70                  75                  80

Met Asn Ser Leu Lys Pro Glu Asp Thr Ala Val Tyr Tyr Cys Ala Gly
            85                  90                  95

Ser Gly Ser Leu Leu Asp Val Thr Ser Glu Ala Val Tyr Thr Asp Trp
        100                 105                 110

Gly Gln Gly Thr Gln Val Thr Val Ser Ser
        115                 120
```

<210> SEQ ID NO 773
<211> LENGTH: 114
<212> TYPE: PRT
<213> ORGANISM: Artificial
<220> FEATURE:
<223> OTHER INFORMATION: Nanobody or nanobody construct

<400> SEQUENCE: 773

```
Lys Val Gln Leu Val Glu Ser Gly Gly Gly Leu Val Gln Ala Gly Gly
1               5                   10                  15

Ser Leu Arg Leu Ser Cys Ala Ala Ser Gly Ser Pro Ile Ser Ser Tyr
            20                  25                  30

Ala Met Gly Trp Tyr Arg Gln Ala Pro Gly Lys Pro Arg Glu Leu Val
        35                  40                  45

Ala Arg Ile Tyr Thr Gly Gly Thr Ala Trp Tyr Glu Asp Ser Val Lys
    50                  55                  60

Gly Arg Phe Thr Ile Ser Arg Asp Asn Ala Gln Asn Thr Val Tyr Leu
65                  70                  75                  80

Gln Met Asn Ser Leu Lys Ser Glu Asp Thr Ala Val Tyr Tyr Cys His
            85                  90                  95

Gly Arg Val Arg Tyr Asp Tyr Trp Gly Gln Gly Thr Gln Val Thr Val
        100                 105                 110

Ser Ser
```

<210> SEQ ID NO 774
<211> LENGTH: 124
<212> TYPE: PRT
<213> ORGANISM: Artificial
<220> FEATURE:
<223> OTHER INFORMATION: Nanobody or nanobody construct

<400> SEQUENCE: 774

```
Glu Val Gln Leu Val Glu Ser Gly Gly Gly Leu Val Gln Ala Gly Gly
1               5                   10                  15

Ser Leu Arg Leu Ser Cys Ala Ala Ser Asp Arg Thr Phe Gly Ser Ser
            20                  25                  30

Ala Met Gly Trp Phe Arg Gln Ala Pro Gly Lys Asp Arg Asp Phe Val
        35                  40                  45

Ala Ala Ile Ser Trp Ser Gly Ser Thr His Tyr Ala Asp Ser Val
    50                  55                  60
```

```
Lys Gly Arg Phe Thr Ile Ser Arg Asp Asn Ala Lys Asn Thr Met Tyr
 65                  70                  75                  80

Leu Gln Met Asn Ser Leu Lys Pro Ala Asp Thr Ala Val Tyr Thr Cys
                 85                  90                  95

Ala Ala Ser Arg Arg Ala Tyr Leu Pro Ala Lys Val Gly Glu Tyr Asp
            100                 105                 110

Phe Trp Gly Gln Gly Thr Gln Val Thr Val Ser Ser
            115                 120
```

<210> SEQ ID NO 775
<211> LENGTH: 125
<212> TYPE: PRT
<213> ORGANISM: Artificial
<220> FEATURE:
<223> OTHER INFORMATION: Nanobody or nanobody construct

<400> SEQUENCE: 775

```
Glu Val Gln Leu Val Glu Ser Gly Gly Gly Leu Val Gln Ala Gly Asp
  1               5                  10                  15

Ser Leu Arg Leu Ser Cys Ala Ala Ser Gly Arg Thr Phe Ser Ser Tyr
                 20                  25                  30

Ala Met Gly Trp Phe Arg Gln Ala Pro Gly Lys Glu Arg Glu Phe Val
             35                  40                  45

Ala Ala Ile Ser Leu Ser Gly Ser Met Thr Tyr Tyr Ala Asp Ser Met
         50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Ala Ala Glu Glu Leu Gly Asp Gly Leu Gly Tyr Leu Ala Tyr Arg Tyr
            100                 105                 110

Asp Tyr Trp Gly Gln Gly Thr Gln Val Thr Val Ser Ser
            115                 120                 125
```

<210> SEQ ID NO 776
<211> LENGTH: 113
<212> TYPE: PRT
<213> ORGANISM: Artificial
<220> FEATURE:
<223> OTHER INFORMATION: Nanobody or nanobody construct

<400> SEQUENCE: 776

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Thr Asn
                 20                  25                  30

Ile Met Thr Trp Val Arg Gln Ala Pro Gly Lys Gly Leu Glu Trp Ile
             35                  40                  45

Ser Thr Ile Asn Ser Gly Gly Gly Thr Thr Tyr Ala Asp Ser Val
         50                  55                  60

Arg Gly Arg Phe Thr Ile Ser Arg Asp Asn Ala Lys Asn Met Leu Tyr
 65                  70                  75                  80

Leu Gln Met Ser Ser Leu Lys Pro Glu Asp Thr Ala Leu Tyr Tyr Cys
                 85                  90                  95

Ile Thr Pro Arg Gly Val Lys Gly Arg Gly Thr Gln Val Thr Val Ser
            100                 105                 110

Ser
```

-continued

<210> SEQ ID NO 777
<211> LENGTH: 123
<212> TYPE: PRT
<213> ORGANISM: Artificial
<220> FEATURE:
<223> OTHER INFORMATION: Nanobody or nanobody construct

<400> SEQUENCE: 777

Glu Val Gln Leu Val Glu Ser Gly Gly Gly Leu Val Gln Ala Gly Gly
1               5                   10                  15

Ser Leu Arg Leu Ser Cys Ala Ala Ser Asp Arg Thr Phe Gly Ser Ser
            20                  25                  30

Thr Met Gly Trp Phe Arg Gln Pro Pro Gly Lys Asn Arg Glu Phe Val
        35                  40                  45

Ala Thr Ile Ala Trp Ser Ala Thr Thr His Tyr Ala Asp Ala Val
    50                  55                  60

Lys Gly Arg Phe Thr Val Ser Arg Asp Asn Ala Leu Asn Thr Val Tyr
65                  70                  75                  80

Leu Gln Met Asn Ser Leu Lys Pro Glu Asp Thr Ala Val Tyr Tyr Cys
                85                  90                  95

Ala Ala Thr Leu Thr Trp Leu Gly Ile His Glu Tyr Gly Tyr Asn Thr
            100                 105                 110

Trp Gly Gln Gly Thr Gln Val Thr Val Ser Ser
        115                 120

<210> SEQ ID NO 778
<211> LENGTH: 127
<212> TYPE: PRT
<213> ORGANISM: Artificial
<220> FEATURE:
<223> OTHER INFORMATION: Nanobody or nanobody construct

<400> SEQUENCE: 778

Glu Val Gln Leu Val Glu Ser Gly Gly Gly Leu Val Gln Pro Gly Glu
1               5                   10                  15

Ser Leu Arg Leu Ser Cys Thr Ala Ser Arg Phe Met Leu Asp Tyr Tyr
            20                  25                  30

Asp Ile Gly Trp Phe Arg Gln Ala Pro Gly Lys Glu Arg Glu Gly Val
        35                  40                  45

Ser Cys Arg Phe Thr Asn Asp Gly Ser Thr Ala Tyr Ala Asp Ser Val
    50                  55                  60

Lys Gly Arg Phe Thr Ile Ser Arg Asp Ile Val Lys His Thr Val Tyr
65                  70                  75                  80

Leu Gln Met Asn Ser Leu Gln Pro Glu Asp Thr Ala Val Tyr Tyr Cys
                85                  90                  95

Ala Ala Gly Pro Leu Thr Lys Arg Arg Gln Cys Val Pro Gly Asp Phe
            100                 105                 110

Ser Met Asp Phe Trp Gly Glu Gly Thr Leu Val Thr Val Ser Ser
        115                 120                 125

<210> SEQ ID NO 779
<211> LENGTH: 127
<212> TYPE: PRT
<213> ORGANISM: Artificial
<220> FEATURE:
<223> OTHER INFORMATION: Nanobody or nanobody construct

<400> SEQUENCE: 779

Glu Val Gln Leu Val Glu Ser Gly Gly Gly Leu Val Gln Pro Gly Glu

-continued

```
                1               5                  10                  15
Ser Leu Arg Leu Ser Cys Thr Ala Ser Arg Phe Asp Leu Asp Tyr Tyr
                20                  25                  30

Asp Ile Ala Trp Phe Arg Gln Ala Pro Gly Lys Glu Arg Glu Gly Val
            35                  40                  45

Ser Cys Ser Phe Thr Asn Asp Gly Ser Thr Tyr Tyr Ala Asp Ser Val
    50                  55                  60

Lys Gly Arg Phe Thr Met Ser Arg Asn Asn Asp His Arg Thr Val Tyr
65                  70                  75                  80

Leu Gln Met Thr Ser Leu Gln Pro Glu Asp Thr Ala Val Tyr Thr Cys
                85                  90                  95

Ala Val Gly Pro Leu Thr Arg Arg Gln Cys Val Pro Gly Asp Phe
                100                 105                 110

Ser Met Asp Phe Trp Gly Glu Gly Thr Leu Val Thr Val Ser Ser
            115                 120                 125
```

<210> SEQ ID NO 780
<211> LENGTH: 123
<212> TYPE: PRT
<213> ORGANISM: Artificial
<220> FEATURE:
<223> OTHER INFORMATION: Nanobody or nanobody construct

<400> SEQUENCE: 780

```
Glu Val Gln Leu Val Glu Ser Gly Gly Gly Leu Val Gln Ala Gly Gly
1               5                   10                  15

Ser Leu Arg Leu Ser Cys Val Ala Ser Gly Arg Thr Phe Ser Ile Leu
                20                  25                  30

Thr Met Gly Trp Phe Arg Gln Ala Pro Gly Lys Glu Arg Glu Phe Val
            35                  40                  45

Ala Ala Ile Ser Gly Ile Gly Ala Ile His Tyr Ala Asp Ser Val Lys
    50                  55                  60

Gly Arg Phe Thr Leu Ser Arg Asp Asn Ala Arg Asn Thr Val Ser Leu
65                  70                  75                  80

His Met Asn Ser Leu Lys Pro Glu Asp Thr Ala Val Tyr Tyr Cys Ala
                85                  90                  95

Ala Lys Ala Asn Tyr Glu Ser Pro Ser Arg Glu Thr Ser Tyr Ala Tyr
                100                 105                 110

Trp Gly Gln Gly Thr Gln Val Thr Val Ser Ser
            115                 120
```

<210> SEQ ID NO 781
<211> LENGTH: 126
<212> TYPE: PRT
<213> ORGANISM: Artificial
<220> FEATURE:
<223> OTHER INFORMATION: Nanobody or nanobody construct

<400> SEQUENCE: 781

```
Glu Val Gln Leu Val Glu Ser Gly Gly Arg Val Met Gln Thr Gly Gly
1               5                   10                  15

Ser Leu Arg Leu Ser Cys Ala Ala Ser Gly His Thr Phe Asn Asp Tyr
                20                  25                  30

Ser Met Gly Trp Phe Arg Gln Ala Pro Gly Lys Glu Leu Glu Phe Leu
            35                  40                  45

Ala Gly Ile Asn Trp Ser Gly Met Ser Thr Trp Tyr Ala Asp Ser Val
    50                  55                  60
```

```
Lys Asp Arg Phe Thr Ile Ser Arg Asp Asn Lys Asn Thr Val Phe
 65                  70                  75                  80

Leu Gln Met Asn Ser Leu Glu Pro Gly Asp Thr Ala Val Tyr Tyr Cys
                 85                  90                  95

Ala Ala Arg Gln Trp Ile Ser Thr Ile Ile Leu Thr Ala Pro Ser Gln
            100                 105                 110

Tyr Asp Tyr Trp Gly Gln Gly Thr Gln Val Thr Val Ser Ser
        115                 120                 125

<210> SEQ ID NO 782
<211> LENGTH: 126
<212> TYPE: PRT
<213> ORGANISM: Artificial
<220> FEATURE:
<223> OTHER INFORMATION: Nanobody or nanobody construct

<400> SEQUENCE: 782

Glu Val Gln Leu Val Glu Ser Gly Gly Arg Val Met Gln Thr Gly Gly
 1               5                  10                  15

Ser Leu Arg Leu Ser Cys Ala Ala Ser Gly His Thr Phe Asn Asp Tyr
                20                  25                  30

Asn Met Gly Trp Phe Arg Gln Ala Pro Gly Lys Glu Leu Glu Phe Leu
            35                  40                  45

Ala Gly Ile Asn Trp Ser Gly Met Ser Thr Trp Tyr Ala Asp Ser Val
 50                  55                  60

Lys Asp Arg Phe Thr Ile Ser Arg Asp Asn Lys Asn Thr Val Phe
 65                  70                  75                  80

Leu Gln Met Asn Ser Leu Glu Pro Gly Asp Thr Ala Val Tyr Tyr Cys
                 85                  90                  95

Ala Ala Arg Gln Trp Ile Ser Thr Ile Ile Leu Thr Ala Pro Ser Gln
            100                 105                 110

Tyr Asp Tyr Trp Gly Gln Gly Thr Gln Val Thr Val Ser Ser
        115                 120                 125

<210> SEQ ID NO 783
<211> LENGTH: 125
<212> TYPE: PRT
<213> ORGANISM: Artificial
<220> FEATURE:
<223> OTHER INFORMATION: Nanobody or nanobody construct

<400> SEQUENCE: 783

Glu Val Gln Leu Val Glu Ser Gly Gly Asp Leu Val Gln Pro Gly Gly
 1               5                  10                  15

Ser Leu Arg Leu Ser Cys Val Ala Ser Gly Phe Ala Leu Glu Glu His
                20                  25                  30

Ala Ile Gly Trp Phe Arg Gln Ala Pro Gly Lys Glu Arg Glu Gly Val
            35                  40                  45

Ser Leu Ser Ser Tyr Leu Gly Ala Ala Tyr Tyr Ala Thr Ser Val Lys
 50                  55                  60

Gly Arg Phe Thr Ile Ser Arg Asp Asn Ala Lys Asn Thr Val Thr Leu
 65                  70                  75                  80

Gln Met Asn Ser Leu Lys Pro Glu Asp Thr Ala Val Tyr Tyr Cys Ala
                 85                  90                  95

Arg Gly His Phe Thr Tyr Asp Asp Gly Arg Ile Thr Ile Arg Ser Val
            100                 105                 110

Asp Tyr Trp Gly Lys Gly Thr Leu Val Thr Val Ser Ser
        115                 120                 125
```

```
<210> SEQ ID NO 784
<211> LENGTH: 125
<212> TYPE: PRT
<213> ORGANISM: Artificial
<220> FEATURE:
<223> OTHER INFORMATION: Nanobody or nanobody construct

<400> SEQUENCE: 784
```

Glu Val Gln Leu Val Glu Ser Gly Gly Asp Leu Val Gln Pro Gly Gly
1               5                   10                  15

Ser Leu Arg Leu Ser Cys Val Ala Ser Gly Phe Ala Leu Glu Glu His
            20                  25                  30

Ala Ile Gly Trp Phe Arg Gln Ala Pro Gly Lys Glu Arg Glu Gly Val
        35                  40                  45

Ser Leu Ser Ser Tyr Val Gly Ala Val Tyr Tyr Ala Thr Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Arg Gly His Phe Thr Tyr Asp Asp Gly Arg Ile Ser Ile Arg Ser Val
            100                 105                 110

Asp His Trp Gly Lys Gly Thr Leu Val Thr Val Ser Ser
        115                 120                 125

```
<210> SEQ ID NO 785
<211> LENGTH: 130
<212> TYPE: PRT
<213> ORGANISM: Artificial
<220> FEATURE:
<223> OTHER INFORMATION: Nanobody or nanobody construct

<400> SEQUENCE: 785
```

Glu Val Gln Leu Val Glu Ser Gly Gly Gly Leu Val Gln Ala Gly Gly
1               5                   10                  15

Ser Leu Arg Leu Ser Cys Val Ala Ser Gly Arg Thr Leu Ser Thr Ala
            20                  25                  30

Val Met Gly Trp Phe Arg Gln Ala Pro Gly Lys Glu Arg Gly Leu Val
        35                  40                  45

Ala Met Ile Ser Trp Ser Gly Ser Met Thr Tyr Tyr Ala Lys Ser Val
    50                  55                  60

Lys Gly Arg Phe Thr Ile Ser Arg Asp Asn Ala Lys Asn Thr Met Tyr
65                  70                  75                  80

Leu Gln Met Asn Ser Leu Lys Pro Glu Asp Thr Ala Val Tyr Tyr Cys
                85                  90                  95

Ala Ala Asp Met Gly Gly Pro Pro Asp Gly Asp Ala Met Pro Arg
            100                 105                 110

Leu Ser Ser Gly Met Asp Tyr Trp Gly Lys Gly Thr Leu Val Thr Val
        115                 120                 125

Ser Ser
    130

```
<210> SEQ ID NO 786
<211> LENGTH: 123
<212> TYPE: PRT
<213> ORGANISM: Artificial
<220> FEATURE:
<223> OTHER INFORMATION: Nanobody or nanobody construct
```

<400> SEQUENCE: 786

Glu Val Gln Leu Val Glu Ser Gly Gly Gly Leu Val Gln Ala Gly Gly
1               5                   10                  15

Ser Leu Arg Leu Ser Cys Ala Ala Ser Gly Asn Asp Phe Ala Arg Phe
            20                  25                  30

Ser Ile Asp Ala Met Gly Trp Tyr Arg Gln Ala Pro Gly Lys Gln Arg
        35                  40                  45

Glu Leu Val Ala Thr Val Thr Glu Asp Gly Thr Lys Asn Tyr Ala Asp
    50                  55                  60

Ser Val Lys Gly Arg Ala Thr Ile Ser Arg Asp Asp Ala Asn Asn Ser
65                  70                  75                  80

Met Tyr Leu Glu Met Asn Thr Leu Lys Pro Glu Asp Thr Ala Val Tyr
                85                  90                  95

Tyr Cys Lys Met Gly Gly Leu Ile Asp Gly Ala Ala Pro Tyr Glu Phe
            100                 105                 110

Trp Gly Arg Gly Thr Gln Val Thr Val Ser Ser
        115                 120

<210> SEQ ID NO 787
<211> LENGTH: 121
<212> TYPE: PRT
<213> ORGANISM: Artificial
<220> FEATURE:
<223> OTHER INFORMATION: Nanobody or nanobody construct

<400> SEQUENCE: 787

Glu Met Gln Leu Val Glu Ser Gly Gly Gly Trp Val Gln Ala Gly Gly
1               5                   10                  15

Ser Leu Arg Leu Ser Cys Ala Ser Ser Gly Ser Ile Phe Ser Ala Gly
            20                  25                  30

Ala Met Gly Trp Tyr Arg Gln Pro Ala Gly Lys Gln Arg Glu Leu Val
        35                  40                  45

Ala Asp Ile Thr Leu Gly Gly Ser Thr Asn Tyr Ala Asp Ser Val Lys
    50                  55                  60

Gly Arg Phe Thr Ile Ser Arg Asp Asn Ala Lys Asn Ala Val Phe Leu
65                  70                  75                  80

Gln Met Asn Ser Leu Lys Pro Glu Asp Thr Ala Val Tyr Tyr Cys Asn
                85                  90                  95

Gly Leu Ile Asn Thr Phe Ala Arg Lys Ile Pro Arg Tyr Ala Trp Gly
            100                 105                 110

Gln Gly Thr Gln Val Thr Val Ser Ser
        115                 120

<210> SEQ ID NO 788
<211> LENGTH: 123
<212> TYPE: PRT
<213> ORGANISM: Artificial
<220> FEATURE:
<223> OTHER INFORMATION: Nanobody or nanobody construct

<400> SEQUENCE: 788

Glu Val Gln Leu Val Glu Ser Gly Gly Gly Leu Val Gln Ala Gly Gly
1               5                   10                  15

Ser Leu Arg Leu Ser Cys Ala Ala Ser Gly Pro Thr Thr Phe Gly Arg
            20                  25                  30

Tyr Thr Met Gly Trp Phe Arg Gln Ala Pro Gly Arg Glu Arg Glu Phe
        35                  40                  45

```
Val Ala Ala Ile Ser Trp Ile Gly Gly Arg Thr Tyr Tyr Val Asp Val
    50                  55                  60

Val Lys Gly Arg Phe Thr Ile Ser Arg Asp Asn Ala Lys Lys Met Val
65                  70                  75                  80

Tyr Leu Gln Met Asn Ser Leu Lys Pro Asp Asp Thr Ala Val Tyr His
                85                  90                  95

Cys Ala Ala Ala Phe Gln Ala Leu Gly Ser Pro Arg Glu Tyr Asp Tyr
                100                 105                 110

Trp Gly Gln Gly Thr Gln Val Thr Val Ser Ser
            115                 120

<210> SEQ ID NO 789
<211> LENGTH: 263
<212> TYPE: PRT
<213> ORGANISM: Artificial
<220> FEATURE:
<223> OTHER INFORMATION: Nanobody or nanobody construct

<400> SEQUENCE: 789

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Pro Ile Ser Ser Tyr
                20                  25                  30

Ala Met Gly Trp Tyr Arg Gln Ala Pro Gly Lys Pro Arg Glu Leu Val
            35                  40                  45

Ala Arg Ile Tyr Thr Gly Gly Thr Ala Trp Tyr Glu Asp Ser Val Lys
    50                  55                  60

Gly Arg Phe Thr Ile Ser Arg Asp Asn Ala Gln Asn Thr Val Tyr Leu
65                  70                  75                  80

Gln Met Asn Ser Leu Lys Ser Glu Asp Thr Ala Val Tyr Tyr Cys His
                85                  90                  95

Gly Arg Val Arg Tyr Asp Tyr Trp Gly Gln Gly Thr Gln Val Thr Val
                100                 105                 110

Ser Ser Gly Gly Gly Gly Ser Gly Gly Gly Gly Ser Gly Gly Gly Gly
            115                 120                 125

Ser Gly Gly Gly Gly Ser Gly Gly Gly Gly Ser Gly Gly Gly Gly Ser
    130                 135                 140

Gly Gly Gly Gly Ser Glu Val Gln Leu Val Glu Ser Gly Gly Gly Leu
145                 150                 155                 160

Val Gln Ala Gly Gly Ser Leu Arg Leu Ser Cys Ala Ala Ser Gly Ser
                165                 170                 175

Pro Ile Ser Ser Tyr Ala Met Gly Trp Tyr Arg Gln Ala Pro Gly Lys
            180                 185                 190

Pro Arg Glu Leu Val Ala Arg Ile Tyr Thr Gly Gly Thr Ala Trp Tyr
        195                 200                 205

Glu Asp Ser Val Lys Gly Arg Phe Thr Ile Ser Arg Asp Asn Ala Gln
    210                 215                 220

Asn Thr Val Tyr Leu Gln Met Asn Ser Leu Lys Ser Glu Asp Thr Ala
225                 230                 235                 240

Val Tyr Tyr Cys His Gly Arg Val Arg Tyr Asp Tyr Trp Gly Gln Gly
                245                 250                 255

Thr Gln Val Thr Val Ser Ser
            260

<210> SEQ ID NO 790
```

<211> LENGTH: 289
<212> TYPE: PRT
<213> ORGANISM: Artificial
<220> FEATURE:
<223> OTHER INFORMATION: Nanobody or nanobody construct

<400> SEQUENCE: 790

Glu Val Gln Leu Val Glu Ser Gly Gly Gly Leu Val Gln Pro Gly Glu
1               5                   10                  15

Ser Leu Arg Leu Ser Cys Thr Ala Ser Arg Phe Met Leu Asp Tyr Tyr
            20                  25                  30

Asp Ile Gly Trp Phe Arg Gln Ala Pro Gly Lys Glu Arg Glu Gly Val
        35                  40                  45

Ser Cys Arg Phe Thr Asn Asp Gly Ser Thr Ala Tyr Ala Asp Ser Val
    50                  55                  60

Lys Gly Arg Phe Thr Ile Ser Arg Asp Ile Val Lys His Thr Val Tyr
65                  70                  75                  80

Leu Gln Met Asn Ser Leu Gln Pro Glu Asp Thr Ala Val Tyr Tyr Cys
                85                  90                  95

Ala Ala Gly Pro Leu Thr Lys Arg Arg Gln Cys Val Pro Gly Asp Phe
            100                 105                 110

Ser Met Asp Phe Trp Gly Glu Gly Thr Leu Val Thr Val Ser Ser Gly
        115                 120                 125

Gly Gly Gly Ser Gly Gly Gly Ser Gly Gly Gly Ser Gly Gly
130                 135                 140

Gly Gly Ser Gly Gly Gly Ser Gly Gly Gly Ser Gly Gly Gly
145                 150                 155                 160

Gly Ser Glu Val Gln Leu Val Glu Ser Gly Gly Gly Leu Val Gln Pro
            165                 170                 175

Gly Glu Ser Leu Arg Leu Ser Cys Thr Ala Ser Arg Phe Met Leu Asp
            180                 185                 190

Tyr Tyr Asp Ile Gly Trp Phe Arg Gln Ala Pro Gly Lys Glu Arg Glu
        195                 200                 205

Gly Val Ser Cys Arg Phe Thr Asn Asp Gly Ser Thr Ala Tyr Ala Asp
    210                 215                 220

Ser Val Lys Gly Arg Phe Thr Ile Ser Arg Asp Ile Val Lys His Thr
225                 230                 235                 240

Val Tyr Leu Gln Met Asn Ser Leu Gln Pro Glu Asp Thr Ala Val Tyr
                245                 250                 255

Tyr Cys Ala Ala Gly Pro Leu Thr Lys Arg Arg Gln Cys Val Pro Gly
            260                 265                 270

Asp Phe Ser Met Asp Phe Trp Gly Glu Gly Thr Leu Val Thr Val Ser
        275                 280                 285

Ser

<210> SEQ ID NO 791
<211> LENGTH: 275
<212> TYPE: PRT
<213> ORGANISM: Artificial
<220> FEATURE:
<223> OTHER INFORMATION: Nanobody or nanobody construct

<400> SEQUENCE: 791

Glu Val Gln Leu Val Glu Ser Gly Gly Gly Leu Val Gln Ala Gly Gly
1               5                   10                  15

Ser Leu Arg Leu Ser Cys Ala Ala Ser Gly Asn Phe Phe Arg Val Asn
            20                  25                  30

```
Thr Met Ala Trp Tyr Arg Gln Ala Pro Gly Lys Gln Arg Glu Leu Val
        35                  40                  45

Ala Asp Ile Thr Arg Gly Asp Arg Thr Asn Tyr Ala Asp Thr Val Asn
 50                  55                  60

Gly Arg Phe Thr Ile Ser Arg Asp Asn Val Arg Asn Thr Val Tyr Leu
 65                  70                  75                  80

Gln Met Asn Gly Leu Arg Pro Glu Asp Thr Ala Ala Tyr Tyr Cys Tyr
                 85                  90                  95

Ala Val Ile Glu Leu Gly Val Leu Glu Pro Arg Asp Tyr Trp Gly Gln
            100                 105                 110

Gly Thr Gln Val Thr Val Ser Ser Gly Gly Gly Gly Ser Gly Gly Gly
            115                 120                 125

Gly Ser Gly Gly Gly Gly Ser Gly Gly Gly Ser Gly Gly Gly Gly
            130                 135                 140

Ser Gly Gly Gly Gly Ser Gly Gly Gly Ser Glu Val Gln Leu Val
145                 150                 155                 160

Glu Ser Gly Gly Gly Leu Val Gln Ala Gly Gly Ser Leu Arg Leu Ser
                165                 170                 175

Cys Ala Ala Ser Gly Asn Phe Phe Arg Val Asn Thr Met Ala Trp Tyr
            180                 185                 190

Arg Gln Ala Pro Gly Lys Gln Arg Glu Leu Val Ala Asp Ile Thr Arg
        195                 200                 205

Gly Asp Arg Thr Asn Tyr Ala Asp Thr Val Asn Gly Arg Phe Thr Ile
        210                 215                 220

Ser Arg Asp Asn Val Arg Asn Thr Val Tyr Leu Gln Met Asn Gly Leu
225                 230                 235                 240

Arg Pro Glu Asp Thr Ala Ala Tyr Tyr Cys Tyr Ala Val Ile Glu Leu
                245                 250                 255

Gly Val Leu Glu Pro Arg Asp Tyr Trp Gly Gln Gly Thr Gln Val Thr
            260                 265                 270

Val Ser Ser
        275

<210> SEQ ID NO 792
<211> LENGTH: 595
<212> TYPE: PRT
<213> ORGANISM: Homo sapiens

<400> SEQUENCE: 792

Met Pro Ala Cys Cys Ser Cys Ser Asp Val Phe Gln Tyr Glu Thr Asn
1               5                  10                  15

Lys Val Thr Arg Ile Gln Ser Met Asn Tyr Gly Thr Ile Lys Trp Phe
            20                  25                  30

Phe His Val Ile Ile Phe Ser Tyr Val Cys Phe Ala Leu Val Ser Asp
            35                  40                  45

Lys Leu Tyr Gln Arg Lys Glu Pro Val Ile Ser Ser Val His Thr Lys
        50                  55                  60

Val Lys Gly Ile Ala Glu Val Lys Glu Ile Val Glu Asn Gly Val
 65                  70                  75                  80

Lys Lys Leu Val His Ser Val Phe Asp Thr Ala Asp Tyr Thr Phe Pro
                 85                  90                  95

Leu Gln Gly Asn Ser Phe Phe Val Met Thr Asn Phe Leu Lys Thr Glu
            100                 105                 110

Gly Gln Glu Gln Arg Leu Cys Pro Glu Tyr Pro Thr Arg Arg Thr Leu
```

```
            115                 120                 125
Cys Ser Ser Asp Arg Gly Cys Lys Lys Gly Trp Met Asp Pro Gln Ser
130                 135                 140
Lys Gly Ile Gln Thr Gly Arg Cys Val Val Tyr Glu Gly Asn Gln Lys
145                 150                 155                 160
Thr Cys Glu Val Ser Ala Trp Cys Pro Ile Glu Ala Val Glu Glu Ala
                    165                 170                 175
Pro Arg Pro Ala Leu Leu Asn Ser Ala Glu Asn Phe Thr Val Leu Ile
                180                 185                 190
Lys Asn Asn Ile Asp Phe Pro Gly His Asn Tyr Thr Thr Arg Asn Ile
            195                 200                 205
Leu Pro Gly Leu Asn Ile Thr Cys Thr Phe His Lys Thr Gln Asn Pro
        210                 215                 220
Gln Cys Pro Ile Phe Arg Leu Gly Asp Ile Phe Arg Glu Thr Gly Asp
225                 230                 235                 240
Asn Phe Ser Asp Val Ala Ile Gln Gly Gly Ile Met Gly Ile Glu Ile
                    245                 250                 255
Tyr Trp Asp Cys Asn Leu Asp Arg Trp Phe His His Cys Arg Pro Lys
                260                 265                 270
Tyr Ser Phe Arg Arg Leu Asp Asp Lys Thr Thr Asn Val Ser Leu Tyr
            275                 280                 285
Pro Gly Tyr Asn Phe Arg Tyr Ala Lys Tyr Tyr Lys Glu Asn Asn Val
        290                 295                 300
Glu Lys Arg Thr Leu Ile Lys Val Phe Gly Ile Arg Phe Asp Ile Leu
305                 310                 315                 320
Val Phe Gly Thr Gly Gly Lys Phe Asp Ile Ile Gln Leu Val Val Tyr
                    325                 330                 335
Ile Gly Ser Thr Leu Ser Tyr Phe Gly Leu Ala Ala Val Phe Ile Asp
                340                 345                 350
Phe Leu Ile Asp Thr Tyr Ser Ser Asn Cys Cys Arg Ser His Ile Tyr
            355                 360                 365
Pro Trp Cys Lys Cys Gln Pro Cys Val Val Asn Glu Tyr Tyr Tyr
        370                 375                 380
Arg Lys Lys Cys Glu Ser Ile Val Glu Pro Lys Pro Thr Leu Lys Tyr
385                 390                 395                 400
Val Ser Phe Val Asp Glu Ser His Ile Arg Met Val Asn Gln Gln Leu
                    405                 410                 415
Leu Gly Arg Ser Leu Gln Asp Val Lys Gly Gln Glu Val Pro Arg Pro
                420                 425                 430
Ala Met Asp Phe Thr Asp Leu Ser Arg Leu Pro Leu Ala Leu His Asp
            435                 440                 445
Thr Pro Pro Ile Pro Gly Gln Pro Glu Glu Ile Gln Leu Leu Arg Lys
        450                 455                 460
Glu Ala Thr Pro Arg Ser Arg Asp Ser Pro Val Trp Cys Gln Cys Gly
465                 470                 475                 480
Ser Cys Leu Pro Ser Gln Leu Pro Glu Ser His Arg Cys Leu Glu Glu
                    485                 490                 495
Leu Cys Cys Arg Lys Lys Pro Gly Ala Cys Ile Thr Thr Ser Glu Leu
                500                 505                 510
Phe Arg Lys Leu Val Leu Ser Arg His Val Leu Gln Phe Leu Leu Leu
            515                 520                 525
Tyr Gln Glu Pro Leu Leu Ala Leu Asp Val Asp Ser Thr Asn Ser Arg
        530                 535                 540
```

```
Leu Arg His Cys Ala Tyr Arg Cys Tyr Ala Thr Trp Arg Phe Gly Ser
545                 550                 555                 560

Gln Asp Met Ala Asp Phe Ala Asn Leu Pro Ser Cys Cys Arg Trp Arg
                565                 570                 575

Ile Arg Lys Glu Phe Pro Lys Ser Glu Gly Gln Tyr Ser Gly Phe Lys
            580                 585                 590

Ser Pro Tyr
        595

<210> SEQ ID NO 793
<211> LENGTH: 595
<212> TYPE: PRT
<213> ORGANISM: Mus musculus

<400> SEQUENCE: 793

Met Pro Ala Cys Cys Ser Trp Asn Asp Val Leu Gln Tyr Glu Thr Asn
1               5                   10                  15

Lys Val Thr Arg Ile Gln Ser Thr Asn Tyr Gly Thr Val Lys Trp Val
            20                  25                  30

Leu His Met Ile Val Phe Ser Tyr Ile Ser Phe Ala Leu Val Ser Asp
        35                  40                  45

Lys Leu Tyr Gln Arg Lys Glu Pro Val Ile Ser Ser Val His Thr Lys
50                  55                  60

Val Lys Gly Ile Ala Glu Val Thr Glu Asn Val Thr Glu Gly Gly Val
65                  70                  75                  80

Thr Lys Leu Gly His Ser Ile Phe Asp Thr Ala Asp Tyr Thr Phe Pro
                85                  90                  95

Leu Gln Gly Asn Ser Phe Phe Val Met Thr Asn Tyr Val Lys Ser Glu
            100                 105                 110

Gly Gln Val Gln Thr Leu Cys Pro Glu Tyr Pro Arg Arg Gly Ala Gln
        115                 120                 125

Cys Ser Ser Asp Arg Arg Cys Lys Lys Gly Trp Met Asp Pro Gln Ser
130                 135                 140

Lys Gly Ile Gln Thr Gly Arg Cys Val Pro Tyr Asp Lys Thr Arg Lys
145                 150                 155                 160

Thr Cys Glu Val Ser Ala Trp Cys Pro Thr Glu Glu Glu Lys Glu Ala
                165                 170                 175

Pro Arg Pro Ala Leu Leu Arg Ser Ala Glu Asn Phe Thr Val Leu Ile
            180                 185                 190

Lys Asn Asn Ile His Phe Pro Gly His Asn Tyr Thr Thr Arg Asn Ile
        195                 200                 205

Leu Pro Thr Met Asn Gly Ser Cys Thr Phe His Lys Thr Trp Asp Pro
210                 215                 220

Gln Cys Ser Ile Phe Arg Leu Gly Asp Ile Phe Gln Glu Ala Gly Glu
225                 230                 235                 240

Asn Phe Thr Glu Val Ala Val Gln Gly Gly Ile Met Gly Ile Glu Ile
                245                 250                 255

Tyr Trp Asp Cys Asn Leu Asp Ser Trp Ser His His Cys Arg Pro Arg
            260                 265                 270

Tyr Ser Phe Arg Arg Leu Asp Asp Lys Asn Met Asp Glu Ser Phe Val
        275                 280                 285

Pro Gly Tyr Asn Phe Arg Tyr Ala Lys Tyr Tyr Lys Glu Asn Asn Val
    290                 295                 300

Glu Lys Arg Thr Leu Ile Lys Ala Phe Gly Ile Arg Phe Asp Ile Leu
```

-continued

```
305                 310                 315                 320
Val Phe Gly Thr Gly Gly Lys Phe Asp Ile Ile Gln Leu Val Val Tyr
            325                 330                 335

Ile Gly Ser Thr Leu Ser Tyr Phe Gly Leu Ala Thr Val Cys Ile Asp
            340                 345                 350

Leu Leu Ile Asn Thr Tyr Ser Ser Ala Phe Cys Arg Ser Gly Val Tyr
            355                 360                 365

Pro Tyr Cys Lys Cys Cys Glu Pro Cys Thr Val Asn Glu Tyr Tyr Tyr
            370                 375                 380

Arg Lys Lys Cys Glu Ser Ile Met Glu Pro Lys Pro Thr Leu Lys Tyr
385                 390                 395                 400

Val Ser Phe Val Asp Glu Pro His Ile Arg Met Val Asp Gln Gln Leu
                405                 410                 415

Leu Gly Lys Ser Leu Gln Val Val Lys Gly Gln Glu Val Pro Arg Pro
            420                 425                 430

Gln Met Asp Phe Ser Asp Leu Ser Arg Leu Ser Leu Ser Leu His Asp
            435                 440                 445

Ser Pro Leu Thr Pro Gly Gln Ser Glu Glu Ile Gln Leu Leu His Glu
    450                 455                 460

Glu Val Ala Pro Lys Ser Gly Asp Ser Pro Ser Trp Cys Gln Cys Gly
465                 470                 475                 480

Asn Cys Leu Pro Ser Arg Leu Pro Glu Gln Arg Arg Ala Leu Glu Glu
            485                 490                 495

Leu Cys Cys Arg Arg Lys Pro Gly Arg Cys Ile Thr Thr Ser Lys Leu
            500                 505                 510

Phe His Lys Leu Val Leu Ser Arg Asp Thr Leu Gln Leu Leu Leu Leu
        515                 520                 525

Tyr Gln Asp Pro Leu Leu Val Leu Gly Glu Glu Ala Thr Asn Ser Arg
        530                 535                 540

Leu Arg His Arg Ala Tyr Arg Cys Tyr Ala Thr Trp Arg Phe Gly Ser
545                 550                 555                 560

Gln Asp Met Ala Asp Phe Ala Ile Leu Pro Ser Cys Cys Arg Trp Arg
                565                 570                 575

Ile Arg Lys Glu Phe Pro Lys Thr Glu Gly Gln Tyr Ser Gly Phe Lys
            580                 585                 590

Tyr Pro Tyr
    595
```

METHOD FOR GENERATION OF IMMUNOGLOBULIN SEQUENCES

RELATED APPLICATIONS

This application is a continuation of Ser. No. 12/643,286, filed on Dec. 21, 2009, which claims the benefit under 35 U.S.C. 119(e) of U.S. provisional application Ser. No. 61/203,188, filed Dec. 19, 2008, the entire contents of each of which are incorporated herein by reference.

FIELD OF THE INVENTION

The present invention relates to a method for generating immunoglobulin sequences against cell-associated antigens, more particularly, antigens that are membrane-anchored. The invention also provides immunoglobulin sequences obtainable by the method of the invention. Specifically, the present invention relates to the generation of immunoglobulin sequences by use of DNA vaccination. More specifically, the present invention relates to generation of immunoglobulin sequences in camelids, preferably directed against cell-associated antigens, in particular antigens with multiple transmembrane spanning domains, including GPCRs and ion channels, by DNA vaccination. Furthermore, the present invention relates to said immunoglobulin sequences against cell-associated antigens, more particularly, antigens that are membrane-anchored, such as e.g. GPCRs and ion channels, more preferably ion channels.

BACKGROUND OF THE INVENTION

Cell-associated antigens, more specifically those with single or multiple transmembrane domains, are difficult to purify in their native conformation. In order to identify antibodies (or antibody fragments such as Nanobodies) against native epitopes which are able to modify the function of the target in vivo, it is crucial to administer the target antigen in its native conformation to the camelid [Dormitz et al. (2008). Trends in Biotechnology 26: 659-667]. In absence of purified native protein of these cell-associated antigens, the most applied immunization strategy consists of repetitive injections of whole cells functionally expressing the antigen of choice at regular intervals. Examples of targets for which such immunization strategy has been executed successfully (i.e. resulting in the identification of neutralizing, in vivo matured Nanobodies) are described in WO 05/044858 and WO 07/042289). Repeated booster injections of target expressing cells, however, often result in diluted or non-detectable target specific immune responses, especially when the expression level of the target is low and the host cell background is highly immunogenic. The humoral response can be focused more towards the target by using a cell line of camelid origin, which is less immunogenic to llama. Nevertheless, repeated injections of (quasi) self-surface markers also result in a response against the camelid cell line surface markers.

The identification of (neutralizing) selective antibodies against GPCRs, Ion channels or any other type of multispanning cell surface marker is challenging [Michel et al. (2009). Naunyn-Schmied Archives Pharmacology 379:385-388], since i) most often no native protein is available for immunization or subsequent antibody identification, ii) multispanners often show low immunogenicity (due to a limited number of extracellular surface exposed amino acid residues compared to most single transmembrane receptors) and iii) multispanning surface molecules are often expressed at low densities.

SUMMARY OF THE INVENTION

Immunoglobulin sequences, such as antibodies and antigen binding fragments derived therefrom are widely used to specifically target their respective antigens in research and therapeutic applications. Typically, the generation of antibodies involves the immunization of experimental animals, fusion of antibody producing cells to create hybridomas and screening for the desired specificities. Alternatively, antibodies can be generated by screening of naïve or synthetic libraries e.g. by phage display.

The generation of immunoglobulin sequences, such as Nanobodies, has been described extensively in various publications, among which WO 94/04678, Hamers-Casterman et al. 1993 and Muyldermans et al. 2001 can be exemplified. In these methods, camelids are immunized with the target antigen in order to induce an immune response against said target antigen. The repertoire of Nanobodies obtained from said immunization is further screened for Nanobodies that bind the target antigen.

In these instances, the generation of antibodies requires purified antigen for immunization and/or screening. Antigens can be purified from natural sources, or in the course of recombinant production.

An important class of potential therapeutic targets are cell associated antigens, including transmembrane antigens, in particular transmembrane antigens with multiple membrane spanning domains. Cell-associated, and especially membrane bound antigens, however, are difficult to obtain in their natural conformation because they are embedded within, or anchored in the cell membrane. In order to obtain immunoglobulin sequences against epitopes present in the natural conformation, i.e. conformational epitopes, which are present in vivo, it is however essential to immunize with the target antigen in the correct conformation. Such conformational epitopes are of paramount importance for creating pharmaceutically active immunoglobulin sequences. For example, an immunoglobulin sequence specifically interacting with the pore region of an ion channel will affect its conductivity, and thus provide a pharmacological effect.

Immunization and/or screening for immunoglobulin sequences can be performed using peptide fragments of such antigens. However, such an approach will not provide antibodies to conformation dependent epitopes, as such epitopes cannot be reproduced by short synthetic peptides.

Therefore, for these cell-associated antigens, immunization with whole cells carrying the antigen and subsequent screening of the repertoire of Nanobodies induced in this way for Nanobodies that bind the cell-associated antigen is an option (as was done e.g. in WO 2005/044858; WO 2007/042289; WO 2008/074839; WO 2009/068625; WO 2009/138519). However, such cells express a multitude of antigens, resulting in an antibody response that is largely directed to antigens of no interest. Hence, the antibody response obtainable by this approach is characterized by a low specificity, and in particular by a very low frequency of the antibodies of interest amongst all antibodies generated. Hence this approach precludes the efficient generation of antibodies to the target antigen of interest.

Hence, the art provides no satisfactory method to generate specific antibody responses of suitable breadth against conformational epitopes, in particular of membrane associated antigens.

It is the objective of the present invention to overcome these shortcomings of the art. In particular it is an objective of the present invention to provide a method for creating immunoglobulin sequences against complex antigens, like cell associated antigens that exhibit conformational epitopes.

The above mentioned problems are overcome by the present invention. It has been found that genetic vaccination can result in an antibody response of good specificity and acceptable breadth against conformational epitopes, i.e. against cell associated antigens in their natural conformation.

The present invention relates to the following.

A method for the generation of immunoglobulin sequences that can bind to and/or have affinity for a cell-associated antigen comprising the steps of:
a) genetic vaccination of a non-human animal with a nucleic acid encoding said cell-associated antigen or a domain or specific part of said cell associated antigen; and
b) optionally boosting the animal with said antigen in its natural conformation selected from cells comprising natural or transfected cells expressing the cell-associated antigen, cell derived membrane extracts, vesicles or any other membrane derivative harbouring enriched antigen, liposomes, or virus particles expressing the cell associated antigen
c) screening a set, collection or library of immunoglobulin sequences derived from said non-human animal for immunoglobulin sequences that can bind to and/or have affinity for said cell-associated antigen. In a particular embodiment of the invention, said cell-associated antigen is selected from transmembrane antigens, transmembrane antigens with multiple spanning domains, such as GPCRs or ion channels. According to the invention said non-human animal can be selected from vertebrate, shark, mammal, lizard, camelid, llama, preferably camelids and llama.

In one embodiment of the invention, the immunoglobulin sequences are light chain variable domain sequences (e.g. a $V_L$-sequence), or heavy chain variable domain sequences (e.g. a $V_H$-sequence); more specifically, the immunoglobulin sequences can be heavy chain variable domain sequences that are derived from a conventional four-chain antibody or heavy chain variable domain sequences that are derived from a heavy chain antibody.

According to the invention, the immunoglobulin sequences can be domain antibodies, or immunoglobulin sequences that are suitable for use as domain antibodies, single domain antibodies, or immunoglobulin sequences that are suitable for use as single domain antibodies, "dAbs", or immunoglobulin sequences that are suitable for use as dAbs, or Nanobodies, including but not limited to $V_{HH}$ sequences, and preferably are Nanobodies.

According to the invention, vaccination can be performed by a needle-free jet injection, by a ballistic method, by needle-mediated injections such as Tattoo, by topical application of the DNA onto the skin in patches or by any of these administration methods followed by in vivo electroporation, and furthermore includes vaccination performed by intradermal, intramuscular or subcutaneous administration of DNA.

The set, collection or library of immunoglobulin sequences can be obtained from the blood of said non-human mammal.

In the present invention, said cell-associated antigen can be expressed on any cell background which allows expression of the native conformation of the antigen. Examples of such cell backgrounds are Cho, Cos7, Hek293, or cells of camelid origin. Preferably, said cell-associated antigen is a membrane-spanning antigen, including but not limited to an antigen selected from CXCR7, CXCR4 and P2X7.

The set, collection or library of immunoglobulin sequences can be expressed on a set, collection or sample of cells or viruses and said set, collection or sample of cells or viruses is screened for cells or viruses that express an immunoglobulin sequence that can bind to and/or have affinity for said cell-associated antigen, more specifically, a nucleic acid sequence that encodes the immunoglobulin sequence that can bind to and/or has affinity for said cell-associated antigen can be purified and/or isolated from the cell or virus, followed by expression of said immunoglobulin sequence.

According to the invention, the set, collection or library of immunoglobulin sequences can be encoded by a set, collection or library of nucleic acid sequences and said set, collection or library of nucleic acid sequences is screened for nucleic acid sequences that encode an immunoglobulin sequence that can bind to and/or have affinity for said cell-associated antigen; more specifically, the nucleic acid sequences that encode an immunoglobulin sequence that can bind to and/or have affinity for said cell-associated antigen can be purified and/or isolated, followed by expressing said immunoglobulin sequence.

According to the invention, the immunoglobulin sequence that can bind to and/or has affinity for said cell-associated antigen can be purified and/or isolated.

The invention also relates to immunoglobulin obtainable by a method as described herein, and compositions comprising the said immunoglobulin sequences, more in particular to immunoglobulin sequence that are directed against (as defined herein) ion channels and GPCRs.

In particular, the present invention relates to immunoglobulin sequences that are directed against (as defined herein) ion channels, as well as to compounds or constructs, and in particular proteins and polypeptides, that comprise or essentially consist of one or more such immunoglobulin sequences (also referred to herein as "immunoglobulin sequences of the invention", "compounds of the invention", and "polypeptides of the invention", respectively). The invention also relates to nucleic acids encoding such immunoglobulin sequences and polypeptides (also referred to herein as "nucleic acids of the invention" or "nucleotide sequences of the invention"); to methods for preparing such immunoglobulin sequences and polypeptides; to host cells expressing or capable of expressing such immunoglobulin sequences or polypeptides; to compositions, and in particular to pharmaceutical compositions, that comprise such immunoglobulin sequences, polypeptides, nucleic acids and/or host cells; and to uses of such immunoglobulin sequences or polypeptides, nucleic acids, host cells and/or compositions, in particular for prophylactic, therapeutic or diagnostic purposes, such as the prophylactic, therapeutic or diagnostic purposes mentioned herein.

BRIEF DESCRIPTION OF THE FIGURES

FIG. 6A: "DNA" prime—"cell" boost protocol; FIG. 6B: "cell" boost protocol only.

FIG. 13A: Anti-Llama IgG-1; FIG. 13B: Anti-Llama IgG-2/3.

FIGS. 19A and 19B Nanobodies 14D5, 13G9, 7H6, 13B5, no nb, Art 2.2 nb; FIGS. 19C and 19D: 4B4, 7D6, 13A7, 8G11, 8F5, 8G12, no nb, irrelevant nb, Art2.2 nb.

FIGS. 20A and 20B: Nanobodies or Nanobody constructs: 8G11, 13A7-35GS-13A7, 13A7, 8G11-35GS-8G11, irrelevant nb; FIGS. 20C and 20D: Nanobodies or Nanobody constructs: 14D5, 14D5-35GS-14D5, irrelevant nb.

DETAILED DESCRIPTION OF THE INVENTION

Figure 1A:
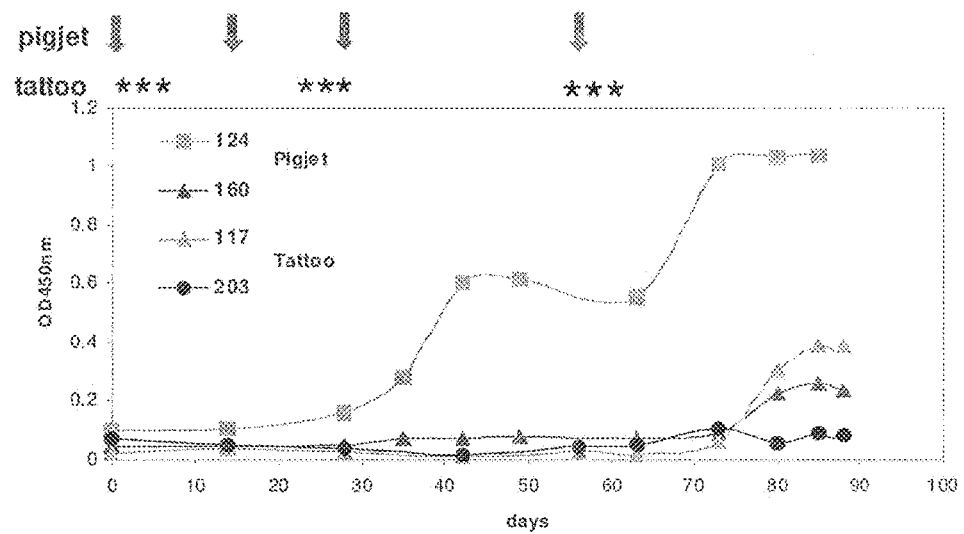
FIGS. 1A-1C: Kinetics of humoral immune response in llama following genetic vaccination with PigJet (FIGS. 1A and 1B) or Tattoo method (FIGS. 1A and 1C). Sera were tested at 1/400 dilution. Arrows indicate the moment of Jet immunizations, the Tattoo short-interval regimes are indicated by asterisks.

The present invention encompasses, but is not limited to, the subject matter of the appended claims.

A) DEFINITIONS

Unless indicated or defined otherwise, all terms used have their usual meaning in the art, which will be clear to the skilled person. Reference is for example made to the standard handbooks, such as Sambrook et al, "Molecular Cloning: A Laboratory Manual" (2nd. Ed.), Vols. 1-3, Cold Spring Harbor Laboratory Press (1989); F. Ausubel et al, eds., "Current protocols in molecular biology", Green Publishing and Wiley Interscience, New York (1987); Lewin, "Genes II", John Wiley & Sons, New York, N.Y., (1985); Old et al., "Principles of Gene Manipulation: An Introduction to Genetic Engineering", 2nd edition, University of California Press, Berkeley, Calif. (1981); Rot et al., "Immunology" (6th. Ed.), Mosby/Elsevier, Edinburgh (2001); Roitt et al., Roitt's Essential Immunology, $10^{th}$ Ed. Blackwell Publishing, UK (2001); and Janeway et al., "Immunobiology" (6th Ed.), Garland Science Publishing/Churchill Livingstone, New York (2005), as well as to the general background art cited herein;

Unless indicated otherwise, the term "immunoglobulin sequence"—whether used herein to refer to a heavy chain antibody or to a conventional 4-chain antibody—is used as a general term to include both the full-size antibody, the individual chains thereof, as well as all parts, domains or fragments thereof (including but not limited to antigen-binding domains or fragments such as $V_{HH}$ domains or $V_H/V_L$ domains, respectively). The terms antigen-binding molecules or antigen-binding protein are used interchangeably with immunoglobulin sequence, and include Nanobodies.

In one embodiment of the invention, the immunoglobulin sequences are light chain variable domain sequences (e.g. a $V_L$-sequence), or heavy chain variable domain sequences (e.g. a $V_H$-sequence); more specifically, the immunoglobulin sequences can be heavy chain variable domain sequences that are derived from a conventional four-chain antibody or heavy chain variable domain sequences that are derived from a heavy chain antibody.

According to the invention, the immunoglobulin sequences can be domain antibodies, or immunoglobulin sequences that are suitable for use as domain antibodies, single domain antibodies, or immunoglobulin sequences that are suitable for use as single domain antibodies, "dAbs", or immunoglobulin sequences that are suitable for use as dAbs, or Nanobodies, including but not limited to $V_{HH}$ sequences, and preferably are Nanobodies.

The immunoglobulin sequences provided by the invention are preferably in essentially isolated form (as defined herein), or form part of a protein or polypeptide of the invention (as defined herein), which may comprise or essentially consist of one or more immunoglobulin sequences of the invention and which may optionally further comprise one or more further immunoglobulin sequences (all optionally linked via one or more suitable linkers). For example, and without limitation, the one or more immunoglobulin sequences of the invention may be used as a binding unit in such a protein or polypeptide, which may optionally contain one or more further immunoglobulin sequences that can serve as a binding unit (i.e. against one or more other targets than cell associated antigens), so as to provide a monovalent, multivalent or multispecific polypeptide of the invention, respectively, all as described herein. Such a protein or polypeptide may also be in essentially isolated form (as defined herein).

The invention includes immunoglobulin sequences of different origin, comprising mouse, rat, rabbit, donkey, human and camelid immunoglobulin sequences. The invention also includes fully human, humanized or chimeric immunoglobulin sequences. For example, the invention comprises camelid immunoglobulin sequences and humanized camelid immunoglobulin sequences, or camelized domain antibodies, e.g. camelized Dab as described by Ward et al (see for example WO 94/04678 and Davies and Riechmann (1994 and 1996)). Moreover, the invention comprises fused immunoglobulin sequences, e.g. forming a multivalent and/or multispecific construct (for multivalent and multispecific polypeptides containing one or more $V_{HH}$ domains and their preparation, reference is also made to Conrath et al., J. Biol. Chem., Vol. 276, 10. 7346-7350, 2001, as well as to for example WO 96/34103 and WO 99/23221), and immunoglobulin sequences comprising tags or other functional moieties, e.g. toxins, labels, radiochemicals, etc., which are derivable from the immunoglobulin sequences of the present invention.

The immunoglobulin sequence and structure of an immunoglobulin sequence, in particular a Nanobody can be considered—without however being limited thereto—to be comprised of four framework regions or "FR's", which are referred to in the art and herein as "Framework region 1" or "FR1"; as "Framework region 2" or "FR2"; as "Framework region 3" or "FR3"; and as "Framework region 4" or "FR4", respectively; which framework regions are interrupted by three complementary determining regions or "CDR's", which are referred to in the art as "Complementarity Determining Region 1" or "CDR1"; as "Complementarity Determining Region 2" or "CDR2"; and as "Complementarity Determining Region 3" or "CDR3", respectively.

The total number of amino acid residues in a Nanobody can be in the region of 110-120, is preferably 112-115, and is most preferably 113. It should however be noted that parts, fragments, analogs or derivatives (as further described herein) of a Nanobody are not particularly limited as to their length and/or size, as long as such parts, fragments, analogs or derivatives meet the further requirements outlined herein and are also preferably suitable for the purposes described herein.

As used herein, the term "immunoglobulin sequences" refers to both the nucleic acid sequences coding for an immunoglobulin molecule, and the immunoglobulin polypeptide per se. Any more limiting meaning will be apparent from the particular context.

All these molecules are also referred to as "polypeptide of the invention", which is synonymous with "immunoglobulin sequences" of the invention.

In addition, the term "sequence" as used herein (for example in terms like "immunoglobulin sequence", "antibody sequence", "variable domain sequence", "$V_{HH}$ sequence" or "protein sequence"), should generally be understood to include both the relevant immunoglobulin sequence as well as nucleic acid sequences or nucleotide sequences encoding the same, unless the context requires a more limited interpretation.

In the following, reference to a "nucleic acid molecule" of the invention may either relate to the nucleic acid for genetic vaccination, or the nucleic acid encoding the immunoglobulin sequences of the invention, or both, as will be apparent from the specific context.

Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein; as well as to for example the following reviews Presta, Adv. Drug Deliv. Rev, 2006, 58 (5-6): 640-56; Levin and Weiss, Md. Biosyst. 2006, 2(1): 49-57; Irving et al., J. Immunol. Methods, 2001, 248(1-2), 31-45; Schmitz et al., Placenta, 2000, 21 Suppl. A, S106-12, Gonzales et al., Tumour Biol., 2005, 26(1), 31-43, which describe techniques for protein engineering, such as affinity maturation and other techniques for improving the specificity and other desired properties of proteins such as immunoglobulins.

The invention relates to immunoglobulin sequences that can bind to and/or have affinity for an antigen as defined herein. In the context of the present invention, "binding to and/or having affinity for" a certain antigen has the usual meaning in the art as understood e.g. in the context of antibodies and their respective antigens.

In particular embodiments of the invention, the term "binds to and/or having affinity for" means that the immunoglobulin sequence specifically interacts with an antigen, and is used interchangeably with immunoglobulin sequences "against" the said antigen.

The term "specificity" refers to the number of different types of antigens or antigenic determinants to which a particular immunoglobulin sequence, antigen-binding molecule or antigen-binding protein (such as a Nanobody or a polypeptide of the invention) can bind. The specificity of an antigen-binding protein can be determined based on affinity and/or avidity. The affinity, represented by the equilibrium constant for the dissociation of an antigen with an antigen-binding protein ($K_D$), is a measure for the binding strength between an antigenic determinant and an antigen-binding site on the antigen-binding protein: the lesser the value of the $K_D$, the stronger the binding strength between an antigenic determinant and the antigen-binding molecule (alternatively, the affinity can also be expressed as the affinity constant ($K_A$), which is $1/K_D$). As will be clear to the skilled person (for example on the basis of the further disclosure herein), affinity can be determined in a manner known per se, depending on the specific antigen of interest. Avidity is the measure of the strength of binding between an antigen-binding molecule (such as a Nanobody or polypeptide of the invention) and the pertinent antigen. Avidity is related to both the affinity between an antigenic determinant and its antigen binding site on the antigen-binding molecule and the number of pertinent binding sites present on the antigen-binding molecule. Typically, immunoglobulin sequences of the present invention (such as the immunoglobulin sequences, Nanobodies and/or polypeptides of the invention) will bind to their antigen with a dissociation constant ($K_D$) of $10^{-5}$ to $10^{-12}$ moles/liter or less, and preferably $10^{-7}$ to $10^{-12}$ moles/liter or less and more preferably $10^{-6}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles), and/or
bind to cell associated antigens as defined herein with a $k_{on}$-rate of between $10^2$ $M^{-1}s^{-1}$ to about $10^7$ $M^{-1}s^{-1}$, preferably between $10^3$ $M^{-1}s^{-1}$ and $10^7$ $M^{-1}s^{-1}$, more preferably between $10^4$ $M^{-1}s^{-1}$ and $10^7$ $M^{-1}s^{-1}$, such as between $10^5$ $M^{-1}s^{-1}$ and $10^7$ $M^{-1}s^{-1}$; and/or bind to cell associated antigens as defined herein with a $k_{off}$ rate between $1s^{-1}$ ($t_{1/2}$=0.69 s) and $10^{-6}$ $s^{-1}$ (providing a near irreversible complex with a $t_{1/2}$ of multiple days), preferably between $10^{-2}$ $s^{-1}$ and $10^{-6}$ $s^{-1}$, more preferably between $10^{-3}$ $s^{-1}$ and $10^{-6}$ $s^{-1}$, such as between $10^{-4}$ $s^{-1}$ and $10^{-6}$ $s^{-1}$.

Any $K_D$ value greater than $10^{-4}$ mol/liter (or any $K_A$ value lower than $10^4$ $M^{-1}$) liters/mol is generally considered to indicate non-specific binding.

Preferably, a monovalent immunoglobulin sequence of the invention will bind to the desired antigen with an affinity less than 500 nM, preferably less than 200 nM, more preferably less than 10 nM, such as less than 500 pM.

Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as the other techniques mentioned herein.

The dissociation constant may be the actual or apparent dissociation constant, as will be clear to the skilled person. Methods for determining the dissociation constant will be clear to the skilled person, and for example include the techniques mentioned herein. In this respect, it will also be clear that it may not be possible to measure dissociation constants of more then $10^{-4}$ moles/liter or $10^{-3}$ moles/liter (e.g., of $10^{-2}$ moles/liter). Optionally, as will also be clear to the skilled person, the (actual or apparent) dissociation constant may be calculated on the basis of the (actual or apparent) association constant ($K_A$), by means of the relationship [$K_D$=1/$K_A$].

The affinity denotes the strength or stability of a molecular interaction. The affinity is commonly given as by the $K_D$, or dissociation constant, which has units of mol/liter (or M). The affinity can also be expressed as an association constant, $K_A$, which equals 1/$K_D$ and has units of (mol/liter)$^{-1}$ (or $M^{-1}$). In the present specification, the stability of the interaction between two molecules (such as an immunoglobulin sequence, immunoglobulin sequence, Nanobody or polypeptide of the invention and its intended target) will mainly be expressed in terms of the $K_D$ value of their interaction; it being clear to the skilled person that in view of the relation $K_A$=1/$K_D$, specifying the strength of molecular interaction by its $K_D$ value can also be used to calculate the corresponding $K_A$ value. The $K_D$-value characterizes the strength of a molecular interaction also in a thermodynamic sense as it is related to the free energy (DG) of binding by the well known relation DG=RT·ln($K_D$) (equivalently DG=−RT·ln($K_A$)), where R equals the gas constant, T equals the absolute temperature and ln denotes the natural logarithm.

The $K_D$ for biological interactions, such as the binding of the immunoglobulin sequences of the invention to the cell associated antigen as defined herein, which are considered meaningful (e.g. specific) are typically in the range of $10^{-10}$M (0.1 nM) to $10^{-5}$M (10000 nM). The stronger an interaction is, the lower is its $K_D$.

The $K_D$ can also be expressed as the ratio of the dissociation rate constant of a complex, denoted as $k_{off}$, to the rate of its association, denoted $k_{on}$ (so that $K_D$=$k_{off}$/$k_{on}$ and $K_A$=$k_{on}$/$k_{off}$). The off-rate $k_{off}$ has units $s^{-1}$ (where s is the SI unit notation of second). The on-rate $k_{on}$ has units $M^{-1}s^{-1}$.

As regards immunoglobulin sequences of the invention, the on-rate may vary between $10^2$ $M^{-1}s^{-1}$ to about $10^7$ $M^{-1}s^{-1}$, approaching the diffusion-limited association rate constant for bimolecular interactions. The off-rate is related to the half-life of a given molecular interaction by the relation $t_{1/2}$=ln(2)/$k_{off}$. The off-rate of immunoglobulin sequences of the invention may vary between $10^{-6}$ $s^{-1}$ (near irreversible complex with a $t_{1/2}$ of multiple days) to 1 $s^{-1}$ ($t_{1/2}$=0.69 s).

The affinity of a molecular interaction between two molecules can be measured via different techniques known per se, such as the well known surface plasmon resonance (SPR) biosensor technique (see for example Ober et al., Intern. Immunology, 13, 1551-1559, 2001) where one molecule is immobilized on the biosensor chip and the other molecule is passed over the immobilized molecule under flow conditions yielding $k_{on}$ $k_{off}$ measurements and hence $K_D$ (or $K_A$) values. This can for example be performed using the well-known Biacore instruments.

It will also be clear to the skilled person that the measured $K_D$ may correspond to the apparent $K_D$ if the measuring process somehow influences the intrinsic binding affinity of the implied molecules for example by artefacts related to the coating on the biosensor of one molecule. Also, an apparent $K_D$ may be measured if one molecule contains more than one recognition sites for the other molecule. In such situation the measured affinity may be affected by the avidity of the interaction by the two molecules.

Another approach that may be used to assess affinity is the 2-step ELISA (Enzyme-Linked Immunosorbent Assay) procedure of Friguet et al. (J. Immunol. Methods, 77, 305-19, 1985). This method establishes a solution phase binding equilibrium measurement and avoids possible artefacts relating to adsorption of one of the molecules on a support such as plastic.

However, the accurate measurement of $K_D$ may be quite labour-intensive and as consequence, often apparent $K_D$ values are determined to assess the binding strength of two molecules. It should be noted that as long as all measurements are made in a consistent way (e.g. keeping the assay conditions unchanged) apparent $K_D$ measurements can be used as an approximation of the true $K_D$ and hence in the present document $K_D$ and apparent $K_D$ should be treated with equal importance or relevance.

Finally, it should be noted that in many situations the experienced scientist may judge it to be convenient to determine the binding affinity relative to some reference molecule. For example, to assess the binding strength between molecules A and B, one may e.g. use a reference molecule C that is known to bind to B and that is suitably labelled with a fluorophore or chromophore group or other chemical moiety, such as biotin for easy detection in an ELISA or FACS (Fluorescent activated cell sorting) or other format (the fluorophore for fluorescence detection, the chromophore for light absorption detection, the biotin for streptavidin-mediated ELISA detection). Typically, the reference molecule C is kept at a fixed concentration and the concentration of A is varied for a given concentration or amount of B. As a result an $IC_{50}$ value is obtained corresponding to the concentration of A at which the signal measured for C in absence of A is halved. Provided $K_{D\ ref}$, the $K_D$ of the reference molecule, is known, as well as the total concentration $c_{ref}$ of the reference molecule, the apparent $K_D$ for the interaction AB can be obtained from following formula: $K_D=IC_{50}/(1+c_{ref}/K_{D\ ref})$. Note that if $c_{ref}\ll K_{D\ ref}$, $K_D \approx IC_{50}$. Provided the measurement of the $IC_{50}$ is performed in a consistent way (e.g. keeping $c_{ref}$ fixed) for the binders that are compared, the strength or stability of a molecular interaction can be assessed by the $IC_{50}$ and this measurement is judged as equivalent to $K_D$ or to apparent $K_D$ throughout this text.

In the context of the present invention, "conformation dependent epitope", or "conformational epitope" denotes an epitope that comprises amino acids which are not within a single consecutive stretch of the primary sequence of the antigen. In other words, due to the secondary and/or tertiary structure of a protein target, amino acids which may be spaced apart in the primary sequence are brought into proximity to each other and thereby participate in the formation of an epitope. If for example an antigen comprises three amino acid loops, residues on each one of these loops may participate in the formation of a single epitope. The same applies to antigens comprising more than one domain or subunit. In this case, an epitope may be formed by amino acids on different domains or subunits. Complete or partial denaturing of the protein by appropriate conditions, i.e. the partial or full destruction of secondary and/or tertiary structures, will also partly or fully destroy conformational epitopes. The skilled person will understand that the precise conditions under which a conformational epitope is destroyed by denaturing a protein will depend on the nature of the protein and the specific circumstances.

In a preferred embodiment, the present invention is directed to immunoglobulin sequences against conformational epitopes. In particular, the invention concerns immunoglobulin sequences against conformational epitopes on cell-associated antigens as defined herein, which may preferably be camelid immunoglobulin sequences, including Nanobodies.

In the context of the present invention, "cell-associated an en" means antigens that are firmly anchored in or located within the membranes of a cell (including membranes of subcellular compartments and organelles), and includes antigens that have a single or multiple transmembrane regions. In other words, the term refers to antigens exhibiting membrane-dependent conformational epitopes. In particular, the term refers to antigens having conformational epitopes as defined herein. The term encompasses transmembrane antigens, transmembrane antigens with multiple membrane spanning domains such as GPCRs or ion channels. Amongst all these antigens the skilled person knows a range of druggable target antigens, which represent a preferred cell associated antigen of the present invention. The invention in particular relates to cell associated antigens wherein the conformation dependent epitope is dependent on the correct anchoring and/or location in the membrane. Thus, the invention provides immunoglobulin sequences against such conformation dependent epitopes.

In a preferred embodiment the invention relates to antigens that are integral membrane proteins having one, or more preferably multiple membrane spanning domains. These antigens will reside in and operate within a cell's plasma membrane, and/or the membranes of subcellular compartments and organelles. Many transmembrane proteins, such as transmembrane receptors comprise two or more subunits or domains, which functionally interact with one another.

Integral membrane proteins comprise three distinct parts or domains, i.e. an extracellular (or extracompartmental) domain, a transmembrane domain and an intracellular (or intracompartmental) domain. A protein having multiple transmembrane domains will typically also have multiple extra- and intra cellular/compartmental domains. For example, a seven transmembrane receptor comprise seven transmembrane domains.

Thus, the term cell associated antigen as understood herein is intended to exclude antigens that are only loosely associated, i.e. that are not firmly anchored or located within a membrane. An antigen is firmly anchored if it comprises at least one domain or part that extends into the membrane.

In one embodiment, the invention excludes antigens that have a membrane insertion via a lipid tail, but no transmembrane domain. In this instance, the conformation of the hydrophilic portion or domain of the protein will not depend on the membrane environment. It will, for example, be possible to express a recombinant protein lacking the lipid tail, which is in the proper conformation, i.e. expresses the conformational epitopes also present if the antigen is associated with the membrane via the lipid tail. Similarly, any other proteins which are only loosely associated are excluded from the invention in a particular embodiment. "Loosely associated" in this connection means proteins which exhibit their natural conformation even in the absence of membrane, i.e. their natural conformation is not dependent on the anchoring or embedding within a membrane. In a further particular embodiment, the invention excludes ART2.2.

Typical examples of cell associated antigens according to the invention comprise seven membrane domain receptors, including G-protein coupled receptors, such as the ones further described herein, Adrenergic receptor, Olfactory receptors, Receptor tyrosine kinases, such as Epidermal growth factor receptor, Insulin Receptor, Fibroblast growth factor receptors, High affinity neurotrophin receptors, and Eph Receptors, Integrins, Low Affinity Nerve Growth Factor Receptor, NMDA receptor, Several Immune receptors including Toll-like receptor, T cell receptor and CD28. Furthermore, cell associated antigens according to the invention comprise also ion channels, such as the ones further described herein, calcium channels, sodium channels, potassium channels, 2P ion channels, 6-TM ion channels, voltage-gated ion channels and/or calcium-activated potassium channels.

As used herein, the term "cell-associated antigen" is intended to include, and also refer to, any part, fragment, subunit, or domain of said cell associated antigen. Any subsection of the cell associated antigen falls within the scope of the present invention, provided it represents a conformational epitope of interest. If for example the epitope of interest is located in a binding site of a receptor, or the pore of an ion channel, any fragment(s) of the cell associated antigen capable of forming said epitope are included in the invention. Preferably, those parts, domains, fragments or subunits will be those parts of the cell associated antigen which are responsible for the membrane-dependent conformation. If for example a protein comprises several transmembrane domains, linked by extended intracellular loops, it is envisaged that such loops are in part or fully omitted, without influencing the extracellular conformational epitopes.

In particular, the present invention relates to immunoglobulin sequences directed to cell associated antigens in their natural conformation. In the context of the present invention, "natural conformation" means that the protein exhibits its secondary and/or tertiary structure, in particular its membrane dependent secondary and/or tertiary structure. In other words, the natural conformation describes the protein in a non-denatured form, and describes a conformation wherein the conformational epitopes, in particular the membrane dependent conformational epitopes, are present. Specifically, the protein will have the conformation that is present when the protein is integrated into or firmly attached to a membrane. Antigens can be obtained in their natural conformation when present in cells comprising natural or transfected cells expressing the cell-associated antigen, cell derived membrane extracts, vesicles or any other membrane derivative harbouring antigen, liposomes, or virus particles expressing the cell associated antigen. In any of these embodiments, antigen may be enriched by suitable means. Said cell-associated antigen can be expressed on any suitable cell allowing expression of the antigen in its native or natural conformation, encompassing, but not limited to Cho, Cos7, Hek293, or cells of camelid origin.

The cell associated antigen of the present invention is preferably a druggable membrane protein, in particular a druggable membrane protein having multiple membrane spanning domains. In one embodiment of the invention, the target is a GPCR or an ion channel.

Specific, non limiting examples of ion channels that represent cell associated antigens according to the present invention are provided in the following. Also listed are therapeutic effects of immunoglobulin sequences specifically recognizing such ion channels.

1. Two-P potassium channels (see Goldstein et al., Pharmacological Reviews, 57, 4, 527 (2005)), such as $K_{2P}1.1$, $K_{2P}2.1$, $K_{2P}3.1$, $K_{2P}3.1$, $K_{2P}4.1$, $K_{2P}5.1$, $K_{2P}6.1$, $K_{2P}7.1$, $K_{2P}9.1$, $K_{2P}10.1$, $K_{2P}12.1$, $K_{2P}13.1$, $K_{2P}15.1$, $K_{2P}16.1$, $K_{2P}17.1$ and $K_{2P}18.1$, which can all be screened using electrophysiological assays such as FLIPR or patch-clamp.
2. CatSper channels (see Clapham and Garbers, Pharmacological Reviews, 57, 4, 451 (2005)), such as CatSper-1 and CatSper-2 (both involved in fertility and sperm motility), CatSper-3 and CatSper-4, which can all be screened using electrophysiological assays such as FLIPR, patch-clamp or calcium imaging techniques.
3. Two-pore channels (see Clapham and Garbers, Pharmacological Reviews, 57, 4, 451 (2005)), such as TPC1 and TPC2.
4. Cyclic nucleotide-gated channels (see Hofman et al., Pharmacological Reviews, 57, 4, 455 (2005), such as CNGA-1, CNGA-2, CNGA-3, CNGA-4A, CNGB1 and CNGB3, which can be screened using techniques such as patch-clamp and calcium imaging
5. Hyperpolarization-activated cyclic nucleotide-gated channels (see Hofman et al., Pharmacological Reviews, 57, 4, 455 (2005)), such as HCN1, HCN2, HCN3, HCN4 (all regarded as promising pharmacological targets for development of drugs for cardiac arrhythmias and ischemic heart disease), which can be screened using techniques such as voltage-clamp.
6. Inwardly rectifying potassium channels (see Kubo et al., Pharmacological Reviews, 57, 4, 509 (2005)), such as $K_{ir}1.1$, $K_{ir}21$. $K_{ir}2.2$, $K_{ir}2.3$, $K_{ir}2.4$, $K_{ir}3.1$, $K_{ir}3.2$, $K_{ir}3.3$, $K_{ir}3.4$, $K_{ir}3.4$, $K_{ir}4.2$, $K_{ir}5.1$, $K_{ir}6.1$ (a target for antihypertensive agents and coronary vasodilators), $K_{ir}6.2$ (the target for pentholamine; its subunit SUR1 is a target for the treatment of diabetes and PHHI) and Kir7.1 (which is a possible site for side-effects of calcium channel blockers), which can be screened using techniques such as voltage-clamp.
7. Calcium-activated potassium channels (see Wei et al., Pharmacological Reviews, 57, 4, 463 (2005)), such as
    $K_{Ca}1.1$ - openers of which may be useful in the treatment of stroke, epilepsy, bladder over-reactivity, asthma, hypertension, gastric hypermotility and psychoses;
    $K_{Ca}2.1$ - modulators of which may be useful in the treatment of various diseases such as myotonic muscular dystrophy, gastrointestinal dysmotility, memory disorders, epilepsy, narcolepsy and alcohol intoxication. Openers of $K_{Ca}2.2$ have been proposed for cerebellar ataxia;
    $K_{Ca}2.2$ - modulators of which may be useful in the treatment of various diseases such as myotonic muscular dystrophy, gastrointestinal dysmotility, memory disorders, epilepsy, narcolepsy and alcohol intoxication. Openers of $K_{Ca}2.2$ have been proposed for cerebellar ataxia;
    $K_{Ca}2.2$ - modulators of which may be useful in the treatment of various diseases such as myotonic muscular dystrophy, gastrointestinal dysmotility, memory disorders, epilepsy, narcolepsy, hypertension and urinary incontinence;
    $K_{Ca}3.1$ - blockers of which may be useful in the treatment of sickle cell anemia, diarrhea, as immunosuppressants, EAE, the prevention of restenosis and angiogenesis, the treatment of brain injuries and the reduction of brain oedema. Openers if $K_{Ca}3.1$ have been proposed for the treatment of cystic fibrosis and COPD;
as well as $K_{Ca}4.1$, $K_{Ca}4.2$ and $K_{Ca}5.1$; all of which can be screened using electrophysiological techniques or techniques such as patch-clamp or voltage-clamp.
8. Potassium channels (see Shieh et al., Pharmacological Reviews, 57, 4, 557 (2005) and Gutman et al., Pharmacological Reviews, 57, 4, 473 (2005)), including:
    voltage-gated calcium channels such as Kv1.1, Kv1.2, Kv1.3, Kv1.4, Kv1.5, Kv1.6 and Kv.17;
    voltage- and cGMP-gated calcium channels such as Kv1.10;

-continued beta-subunits of Kv channels such as KvBeta-1, KvBeta-2 and KvBeta-3;
Shab-like channels such as Kv2.1 and Kv2.2;
Shaw-like channels such as Kv3.1, Kv3.2. Kv3.3 and Kv3.4;
Shal-like channels such as Kv4.1, Kv4.2, Kv4.3, Kv5.1, Kv6.1, Kv6.2, Kv8.1, Kv9.1, Kv9.2, Kv9.3, KH1 and KH2;
Ether-a-go-go-channels such as EAG, HERG, BEC1 and BEC2;
MinK-type channels such as MinK, MiRP1 and MiRP2;
KvLQT-type channels such as KvLQT1, KvLQT2, KvLQT3, KvLQT4, KvLQT5
Inwardly rectifying potassium channels such as those mentioned above;
Sulfonylurea receptors such as the sulfonylurea receptors 1 and 2;
Large conductance calcium-activated channels such as Slo and the Beta-subunits of $BK_{Ca}$;
Small conductance calcium-activated channels such as SK1, SK2 and SK3;
Intermediate conductance calcium-activated channels such as IKCa1;
Two-pore potassium channels such as TWIK1, TREK, TASK, TASK2, TWIK2, TOSS, TRAAK and CTBAK1;

all of which can be screened using electrophysiological techniques or techniques such as patch-clamp or voltage-clamp. Potassium channels are implicated in a wide variety of diseases and disorders such as cardiac diseases (such as arrhythmia), neuronal diseases, neuromuscular disorders, hearing and vestibular diseases, renal diseases, Alzheimer's disease. and metabolic diseases; and are targets for active compounds in these diseases. Reference is again made to the reviews by Shieh et al. and by Gutman et al. (and the further prior art cited therein) as well as to the further references cited in the present specification. Tables 3 and 4 of the Shieh review also mention a number of known openers and blockers, respectively, of various potassium channels and the disease indications for which they have been used/proposed.

9. Voltage-gated calcium channels (see Catterall et al., Pharmacological Reviews, 57, 4, 411 (2005)), such as:

$Ca_v1.2$ - modulators of which are useful as $Ca^{2+}$ antagonists;
$Ca_v1.3$ - modulators of which have been proposed for modulating the heart rate, as antidepressants and as drugs for hearing disorders;
$Ca_v2.1$ - modulators of which have been proposed as analgesics for inflammatory pain;
$Ca_v2.2$ - modulators of which have been proposed as analgesics for pain such as inflammatory pain, postsurgical pain, thermal hyperalgesia, chronic pain and mechanical allodynia;
$Ca_v3.2$ - which has been proposed as a target for epilepsy, hypertension and angina pectoris;
$Ca_v3.3$ - which has been proposed as a target for the treatment of thalamic oscillations;
and $Ca_v1.1$, $Ca_v1.4$, $Ca_v2.3$, $Ca_v3.1$,; all of which can be screened using techniques such as patch-clamp, voltage-clamp and calcium imaging.

10. Transient receptor potential (TRP) channels (see Clapham et al., Pharmacological Reviews, 57, 4, 427 (2005)) such as:
TRPC channels such as TRPC1, TRPC2, TRPC3, TRPC4, TRPC5, TRPC6 and TRPC7;
TRPV channels such as TRPV1, TRPV2, TRPV3, TRPV4, TRPV5 and TRPV6;
TRPM channels such as TRPM1, TRPM2, TRPM3, TRPM4, TRPM5, TRPM6, TRPM7 and TRPM8;
TRPA1;
TRPP channels such as PKD1,, PKD2L1 and PKD2L2, which are involved in polycystic kidney disease;
TRPML channels such as mucolipin 1, mucolipin 2 and mucolipin 3;
which can be screened using techniques such as patch-clamp and calcium imaging.

11. Voltage-gated sodium channels (see Catterall et al., Pharmacological Reviews, 57, 4, 397 (2005)), such as:

$Na_v1.1$, $Na_v1.2$ and $Na_v1.3$ - which are a target for drugs for the prevention and treatment of epilepsy and seizures;
$Na_v1.4$ - which is a target for local anaesthetics for the treatment of myotonia;
$Na_v1.5$ - which is a target for antiarrhythmic drugs;
$Na_v1.6$ - which is a target for antiepileptic and analgesic drugs;
$Na_v1.7$, $Na_v1.8$ and $Na_v1.9$ - which are potential targets for local anaesthetics;

all of which can be screened using voltage clamp or techniques involving voltage-sensitive dyes.

Ion channels and the diseases and disorders which they are associated are well known in the art. Reference is for example made to the following reviews: Goldstein et al., Pharmacological Reviews, 57, 4, 527 (2005); Yu et al., Pharmacological Reviews, 57, 4, 387 (2005); Clapham and Garbers, Pharmacological Reviews, 57, 4, 451 (2005); Hoffmann et al., Pharmacological Reviews, 57, 4, 455 (2005); Kubo et al., Pharmacological Reviews, 57, 4, 509 (2005); Wei et al., Pharmacological Reviews, 57, 4, 463 (2005); Shieh et al, Pharmacological Reviews, 57, 4, 557 (2005);

Catterall et al, Pharmacological Reviews, 57, 4, 411 (2005); Gutman et al., Pharmacological Reviews, 57, 4, 473 (2005); Clapham et al., Pharmacological Reviews, 57, 4, 427 (2005); and Catterall et al., Pharmacological Reviews, 57, 4, 397 (2005); as well as the further references cited in these reviews and the following articles and reviews: Chandy et al., Trends in Pharmacological Sciences, May 2004, 280-289; Takana and Shigenobu, J. Pharmacol. Sci., 99, 214-200 (2005); Padinjat and Andrews, Journal of Cell Science, 117, 5707-5709 (2004); Amir et al., The Journal of Pain, Vol. 7, No. 5, S1-S29 (2006); Devor, The Journal of Pain, Vol. 7, No. 15, S3-S12 (2006); Xie et al., Current Drug Discovery, April 2004, 31-33; Vianna-Jorge and Suarez-Kurtz, BioDrugs 2004, 18(5), 329-41; Garcia and Kaczorowski, Sci STKE, 2005, 302; Gopalakrishnan and Shieh, Expert Opin. Ther. Targets, 2005, 8(5), 437-58; Mannhold, Med. Res. Rev., 2004, 24(2), 213-66; Sabido-David et al., Expert Opin. Investig. Drugs, 2004, 13(1) 1249-61; and Christ, Journal of Andrology, Vol. 23, No. 5, S10-S19 (2002), and to the further prior art cited therein (all incorporated herein by reference), as well as to the table below and the further prior art cited in this application.

As can be seen from these reviews and this prior art, ion channels are generally classified on the basis of the ions that can flow through them (i.e. as calcium channels, sodium channels or potassium channels), on the basis of their composition and structure (e.g. the number and type of subunits, pores and transmembrane domains, for example 2P ion channels, 6-TM ion channels, etc.), and/or on the basis of the manner in which they are activated (e.g. voltage-gated ion channels or calcium-activated potassium channels).

Ion channels generally comprise a number of transmembrane domain subunits, linked by a combination of intracellular and extracellular loops. Reference is again made to the references and prior art cited above, as well as to Benham, Nature Biotechnology, October 2005, 1234-1235 and the further prior art cited herein.

The fact that ion channels are membrane proteins, as well as their known association with various disease states, make ion channels attractive molecular targets for pharmaceutical and veterinary compounds (i.e. for prophylaxis, therapy or diagnosis). Also, methods for screening potential pharmaceutical or veterinary compounds for activity (either as agonists, antagonists, blockers and/or openers) and/or selectivity with respect to ion channels and their biological or physiological activity are well known in the art. Some non-limiting examples of suitable techniques, depending upon the ion channel involved, include techniques such as patch clamp, voltage clamp, measuring ion flux, FLIPR, calcium imaging and electrophysiological techniques.

Specific, non limiting examples of GPCRs that represent cell associated antigens according to the present invention are provided in the following. Also listed are some exemplary therapeutic effects of immunoglobulin sequences of the present invention that are directed against these GPCRs.
Class A GPCRs
  Acetylcholine receptor (agonist),
  Muscarinic receptor (agonist),
  Muscarinic M1 receptor (agonist),
  Muscarinic M2 receptor (agonist),
  Muscarinic M3 receptor (agonist),
  Muscarinic M4 receptor (agonist),
  Muscarinic M5 receptor (agonist)
  Muscarinic receptor (partial agonist)
  Adrenoceptor (agonist),
  Alpha adrenoceptor (agonist),
  Alpha 1 adrenoceptor (agonist),
  Alpha 1A adrenoceptor (agonist),
  Alpha 1B adrenoceptor (agonist)
  Alpha 1D adrenoceptor (agonist)
  Alpha 2 adrenoceptor (agonist),
  Alpha 2A adrenoceptor (agonist),
  Alpha 2B adrenoceptor (agonist),
  Alpha 2C adrenoceptor (agonist),
  Alpha 2 adrenoceptor (partial agonist)
  Alpha 3 adrenoceptor (agonist),
  Beta adrenoceptor (agonist),
  Beta 1 adrenoceptor (agonist),
  Beta 2 adrenoceptor (agonist),
  Beta 3 adrenoceptor (agonist),
  Dopamine receptor (agonist),
  Dopamine D5 receptor (agonist)
  Dopamine D1 receptor (agonist),
  Dopamine D2 receptor (agonist),
  Dopamine D3 receptor (agonist),
  Dopamine D4 receptor (agonist),
  Histamine receptor (agonist),
  Histamine H1 receptor (agonist),
  Histamine H2 receptor (agonist),
  Histamine H3 receptor (agonist),
  Histamine H4 receptor (agonist),
  5-HT GPCR (agonist),
  5-HT 1 (agonist),
  5-HT 2 (agonist),
  5-HT 4 (agonist),
  5-HT 5a (agonist),
  5-HT 5b (agonist)
  5-HT 6 (agonist),
  5-HT 7 (agonist),
  Trace amine-associated receptor (agonist),
  Trace amine-associated receptor-1 (agonist),
  Trace amine-associated receptor-2 (agonist)
  Trace amine-associated receptor-3 (agonist)
  Trace amine-associated receptor-4 (agonist)
  Trace amine-associated receptor-5 (agonist)
  Trace amine-associated receptor-6 (agonist)
  Trace amine-associated receptor-7 (agonist)
  Trace amine-associated receptor-8 (agonist)
  Trace amine-associated receptor-9 (agonist)
  Apelin receptor (agonist),
  Cannabinoid receptor (agonist),
  Cannabinoid CB1 receptor (agonist),
  Cannabinoid CB2 receptor (agonist),
  Lysosphingolipid receptor (agonist),
  Sphingosine-1-phosphate receptor-1 (agonist),
  Lysophosphatidate-1 receptor (agonist)
  Sphingosine-1-phosphate receptor-3 (agonist),
  Lysophosphatidate-2 receptor (agonist)
  Sphingosine-1-phosphate receptor-2 (agonist)
  Sphingosine-1-phosphate receptor-4 (agonist),
  Lysophosphatidate-3 receptor (agonist)
  Sphingosine-1-phosphate receptor-5 (agonist)
  Class A hormone protein GPCR (agonist),
  FSH (agonist),
  Luteinizing hormone receptor (agonist),
  TSH (agonist),
  Leukotriene (agonist),
  Leukotriene BLT receptor (agonist),
  Cysteinyl leukotriene receptor (agonist),
  Melatonin (agonist),
  Melatonin MT1 (agonist),
  Melatonin MT2 (agonist),
  Melatonin MT3 (agonist)
  Class A nucleotide like GPCR (agonist), Adenosine receptor (agonist),
P2Y receptor (agonist),
Class A orphan GPCR (agonist),
Ghrelin (agonist),
Class A peptide GPCR (agonist),
Angiotensin receptor (agonist),
Angiotensin I receptor (agonist),
Angiotensin II receptor (agonist),
Bombesin receptor (agonist),
Bombesin BB1 receptor (agonist)
Bombesin BB2 receptor (agonist)
Bombesin bb3 receptor (agonist),
Gastrin releasing peptide ligand,
Neuromedin B ligand
Neuromedin C ligand
Bradykinin receptor (agonist),
Bradykinin B1 receptor (agonist),
Bradykinin B2 receptor (agonist),
C3a receptor (agonist),
C5a (agonist),
CCK receptor (agonist),
CCK 1 receptor (agonist),
CCK 2 receptor (agonist),
Gastrin (agonist),
Chemokine (agonist),
CC chemokine receptor (agonist),
CCR1 chemokine (agonist),
CCR2 chemokine (agonist),
CCR3 chemokine (agonist),
CCR4 chemokine (agonist),
CCR5 chemokine (agonist),
CCR6 chemokine (agonist),
CCR7 chemokine (agonist)
CCR8 chemokine (agonist),
CCR9 chemokine (agonist)
CCR10 chemokine (agonist),
CCR11 chemokine (agonist)
CX3C chemokine receptor (agonist),
CX3CR1 chemokine (agonist),
XCR1 chemokine (agonist)
CXC chemokine receptor (agonist),
CXCR1 chemokine (agonist)
CXCR3 chemokine (agonist),
CXCR4 chemokine (agonist),
CXCR5 chemokine (agonist)
Adrenomedullin receptor (agonist),
Endothelin (agonist),
Endothelin ET-A (agonist),
Endothelin ET-B (agonist),
Galanin (agonist),
Galanin GAL1 (agonist),
Galanin GAL2 (agonist),
Galanin GAL3 (agonist)
IL-9 (agonist),
KiSS-1 receptor (agonist),
Melanin concentrating hormone (agonist),
MCH receptor-1 (agonist)
MCH receptor-2 (agonist)
Melanocortin (agonist),
Melanocortin MC1 (agonist),
ACTH receptor (agonist),
Melanocortin MC3 (agonist),
Melanocortin MC4 (agonist),
Melanocortin MC5 (agonist),
NK (agonist),
NK1 (agonist),
NK2 (agonist)
NK3 (agonist), Drugs: 1
Neuropeptide Y receptor (agonist),
Neuropeptide Y1 receptor (agonist)
Neuropeptide Y2 receptor (agonist),
Neuropeptide Y4 receptor (agonist),
Neuropeptide Y5 receptor (agonist),
Neuropeptide Y6 receptor (agonist)
Neurotensin receptor (agonist),
Neurotensin NTS1 (agonist),
Neurotensin NTS2 (agonist)
Orexin & neuropeptide FF receptor (agonist),
Orexin (agonist),
Opioid (agonist),
Delta opioid (agonist),
Kappa opioid (agonist),
Mu opioid (agonist),
ORL1 receptor (agonist),
Opioid (partial agonist)
Sigma opioid (agonist),
Orexin & neuropeptide FF receptor (agonist),
Neuropeptide FF receptor (agonist),
Neuropeptide FF1 receptor (agonist)
Neuropeptide FF2 receptor (agonist),
Orexin (agonist),
Orexin-1 (agonist)
Orexin-2 (agonist)
Protease-activated receptor (agonist),
Protease-activated receptor-1 (agonist),
Protease-activated receptor-2 (agonist),
Protease-activated receptor-3 (agonist)
Protease-activated receptor-4 (agonist)
Prokineticin receptor (agonist),
Prokineticin receptor-1 (agonist),
Prokineticin receptor-2 (agonist),
Somatostatin (agonist),
Somatostatin 1 (agonist),
Somatostatin 2 (agonist),
Somatostatin 3 (agonist),
Somatostatin 4 (agonist),
Somatostatin 5 (agonist),
Urotensin II (agonist),
Vasopressin like receptor (agonist),
Oxytocin (agonist),
Vasopressin (agonist),
Vasopressin V1 (agonist),
Vasopressin V2 (agonist),
Prostanoid receptor (agonist),
DP prostanoid (agonist),
PGD2 (agonist),
EP1 prostanoid (agonist),
PGE2 (agonist),
EP2 prostanoid (agonist),
PGE2 (agonist),
EP3 prostanoid (agonist),
PGE2 (agonist),
EP4 prostanoid (agonist),
PGE2 (agonist),
FP prostanoid (agonist),
PGF2 alpha (agonist),
IP prostanoid (agonist),
Prostacyclin (agonist),
Prostanoid receptor (partial agonist)
TP prostanoid (agonist),
Thromboxane A2 (agonist)
Succinate receptor 1 (agonist)
TRH (agonist),
TRH1 (agonist)

TRH2 (agonist)
Vomeronasal type-1 receptor (agonist)
Vomeronasal type-1 receptor-1 (agonist)
Vomeronasal type-1 receptor-2 (agonist)
Vomeronasal type-1 receptor-3 (agonist)
Vomeronasal type-1 receptor-4 (agonist)
Vomeronasal type-1 receptor-5 (agonist)
Apelin receptor (modulator),
Cannabinoid receptor (modulator),
Chemokine receptor-like 1 (modulator),
Lysosphingolipid receptor (modulator),
Class A hormone protein GPCR (modulator),
Leukotriene receptor (modulator),
Melatonin receptor (modulator),
Class A nucleotide like GPCR (modulator),
Class A orphan GPCR (modulator),
PAF receptor (modulator),
Class A peptide GPCR (modulator),
Prostanoid receptor (modulator),
Succinate receptor 1 (modulator)
TRH receptor (modulator),
Vomeronasal type-1 receptor (modulator),
Class B GPCRs
  G-protein coupled receptor-3 (modulator),
  G-protein coupled receptor-3 (agonist)
  G-protein coupled receptor-3 (antagonist),
  G-protein coupled receptor-6 (modulator),
  G-protein coupled receptor-6 (agonist)
  G-protein coupled receptor-6 (antagonist),
  G-protein coupled receptor-12 (modulator),
  G-protein coupled receptor-12 (agonist)
  G-protein coupled receptor-12 (antagonist),
  G-protein coupled receptor-14 (modulator)
  G-protein coupled receptor-14 (agonist)
  G-protein coupled receptor-14 (antagonist)
  Class B GPCR (agonist),
  CRF-1 receptor (agonist)
  CRF-2 receptor (agonist),
  Calcitonin receptor (modulator),
  Calcitonin (agonist),
  Calcitonin (antagonist),
  ACTH releasing factor receptor (modulator),
  CRF-1 receptor (modulator),
  CRF-1 receptor (agonist)
  CRF-1 receptor (antagonist),
  CRF-2 receptor (modulator),
  CRF-2 receptor (agonist),
  CRF-2 receptor (antagonist),
  ACTH releasing factor (agonist),
  CRF-1 receptor (agonist)
  CRF-2 receptor (agonist),
  ACTH releasing factor (antagonist),
  CRF-1 receptor (antagonist),
  CRF-2 receptor (antagonist),
  Glucagon-like peptide receptor (modulator),
  Glucagon-like peptide 1 receptor (modulator),
  Glucagon-like peptide 2 receptor (modulator),
  Glucagon-like peptide (agonist),
  Glucagon-like peptide (antagonist),
  Glucagon receptor (modulator),
  Glucagon (agonist),
  Glucagon (antagonist),
  GHRH receptor (modulator),
  GHRH (agonist),
  Growth hormone releasing factor (antagonist),
  PACAP type I receptor (modulator),
  PACAP type I receptor (agonist),
  PACAP type I receptor (antagonist)
  PTH receptor (modulator),
  PTH-1 receptor (modulator)
  PTH-2 receptor (modulator)
  PTH (agonist),
  PTH (antagonist),
  Secretin receptor (modulator),
  Secretin (agonist),
  Secretin (antagonist)
  VIP receptor (modulator),
  VIP-1 receptor (modulator),
  VIP-2 receptor (modulator),
  VIP (agonist),
  VIP (antagonist),
Class C GPCRs
  Class C GPCR (modulator),
  Class C GPCR (agonist),
  GABA B receptor (agonist),
  Metabotropic glutamate receptor (agonist),
  Metabotropic glutamate receptor 1 (agonist),
  Metabotropic glutamate receptor 2 (agonist),
  Metabotropic glutamate receptor 3 (agonist),
  Metabotropic glutamate receptor 4 (agonist),
  Metabotropic glutamate receptor 5 (agonist),
  Metabotropic glutamate receptor 6 (agonist)
  Metabotropic glutamate receptor 7 (agonist)
  Metabotropic glutamate receptor 8 (agonist)

Preferably, said cell-associated antigen is a membrane-spanning antigen, including but not limited to an antigen selected from ion channels such as e.g. P2X7.

The skilled person will appreciate that there may be different specific three dimensional conformations that are encompassed by the term "natural conformation". If, for example, a protein has two or more different conformations whilst being in a membrane environment, all these conformations will be considered "natural conformations". This is exemplified by receptors changing their conformation by activation, e.g. the different activation states of rhodopsin induced by light, or ion channels showing a "closed" or "open" conformation. The invention encompasses immunoglobulin sequences to any one of these different natural conformations, i.e. to the different kinds of conformational epitopes that may be present.

A "nucleic acid" of the invention can be in the form of single or double stranded DNA or RNA, and is preferably in the form of double stranded DNA. For example, the nucleotide sequences of the invention may be genomic DNA, cDNA or synthetic DNA (such as DNA with a codon usage that has been specifically adapted for expression in the intended host cell or host organism).

According to one embodiment of the invention, the nucleic acid of the invention is in essentially isolated from, as defined herein.

The nucleic acid of the invention may also be in the form of, be present in and/or be part of a vector, such as for example a plasmid, cosmid or YAC, which again may be in essentially isolated form.

The nucleic acids of the invention can be prepared or obtained in a manner known per se, based on the information on the cell associated antigen or immunoglobulin sequences of the invention, and/or can be isolated from a suitable natural source. To provide analogs; nucleotide sequences encoding naturally occurring $V_{HH}$ domains can for example be subjected to site-directed mutagenesis, so at to provide a nucleic acid of the invention encoding said analog. Also, as will be clear to the skilled person, to prepare a nucleic acid of the invention, also several nucleotide sequences; such as at least one nucleotide sequence encoding a Nanobody and for example nucleic acids encoding one or more linkers can be linked together in a suitable manner.

Techniques for generating the nucleic acids of the invention will be clear to the skilled person and may for instance include, but are not limited to, automated DNA synthesis; site-directed mutagenesis; combining two or more naturally occurring and/or synthetic sequences (or two or more parts thereof), introduction of mutations that lead to the expression of a truncated expression product; introduction of one or more restriction sites (e.g. to create cassettes and/or regions that may easily be digested and/or ligated using suitable restriction enzymes), and/or the introduction of mutations by means of a PCR reaction using one or more "mismatched" primers, using for example a sequence of a naturally occurring GPCR as a template. These and other techniques will be clear to the skilled person, and reference is again made to the standard handbooks, such as Sambrook et al. and Ausubel et al., mentioned above, as well as the Examples below.

The nucleic acid of the invention may also be in the form of, be present in and/or be part of a genetic construct, as will be clear to the person skilled in the art. Such genetic constructs generally comprise at least one nucleic acid of the invention that is optionally linked to one or more elements of genetic constructs known per se, such as for example one or more suitable regulatory elements (such as a suitable promoter(s), enhancer(s), terminator(s), etc.) and the further elements of genetic constructs referred to herein. Such genetic constructs comprising at least one nucleic acid of the invention will also be referred to herein as "genetic constructs of the invention".

The genetic constructs of the invention may be DNA or RNA, and are preferably double-stranded DNA. The genetic constructs of the invention may also be in a form suitable for transformation of the intended host cell or host organism, in a form suitable for integration into the genomic DNA of the intended host cell or in a form suitable for independent replication, maintenance and/or inheritance in the intended host organism, or in a form suitable for genetic immunization. For instance, the genetic constructs of the invention may be in the form of a vector, such as for example a plasmid, cosmid, YAC, a viral vector or transposon. In particular, the vector may be an expression vector, i.e. a vector that can provide for expression in vitro and/or in vivo (e.g. in a suitable host cell, host organism and/or expression system).

In a preferred but non-limiting embodiment, a genetic construct of the invention comprises
a) at least one nucleic acid of the invention; operably connected to
b) one or more regulatory elements, such as a promoter and optionally a suitable terminator;
and optionally also
c) one or more further elements of genetic constructs known per se;
in which the terms "regulatory element", "promoter", "terminator" and "operably connected" have their usual meaning in the art (as further described herein); and in which said "further elements" present in the genetic constructs may for example be 3'- or 5'-UTR sequences, leader sequences, selection markers, expression markers/reporter genes, and/or elements that may facilitate or increase (the efficiency of) transformation or integration. These and other suitable elements for such genetic constructs will be clear to the skilled person, and may for instance depend upon the type of construct used, the intended host cell, host organism or animal to be immunized; the manner in which the nucleotide sequences of the invention of interest are to be expressed (e.g. via constitutive, transient or inducible expression); and/or the transformation/vaccination technique to be used. For example, regulatory sequences, promoters and terminators known per se for the expression and production of antibodies and antibody fragments (including but not limited to (single) domain antibodies and ScFv fragments) may be used in an essentially analogous manner.

Preferably, in the genetic constructs of the invention, said at least one nucleic acid of the invention and said regulatory elements, and optionally said one or more further elements, are "operably linked" to each other, by which is generally meant that they are in a functional relationship with each other. For instance, a promoter is considered "operably linked" to a coding sequence if said promoter is able to initiate or otherwise control/regulate the transcription and/or the expression of a coding sequence (in which said coding sequence should be understood as being "under the control of" said promoter). Generally, when two nucleotide sequences are operably linked, they will be in the same orientation and usually also in the same reading frame. They will usually also be essentially contiguous, although this may also not be required.

Preferably, the regulatory and further elements of the genetic constructs of the invention are such that they are capable of providing their intended biological function in the intended host cell or host organism.

For instance, a promoter, enhancer or terminator should be "operable" in the intended host cell or host organism, by which is meant that (for example) said promoter should be capable of initiating or otherwise controlling/regulating the transcription and/or the expression of a nucleotide sequence—e.g. a coding sequence—to which it is operably linked (as defined herein).

For some (further) non-limiting examples of the promoters, selection markers, leader sequences, expression markers and further elements that may be present/used in the genetic constructs of the invention—such as terminators, transcriptional and/or translational enhancers and/or integration factors—reference is made to the general handbooks such as Sambrook et al. and Ausubel et al. mentioned above, as well as to the examples that are given in WO 95/07463, WO 96/23810, WO 95/07463, WO 95/21191, WO 97/11094, WO 97/42320, WO 98/06737, WO 98/21355, U.S. Pat. No. 6,207,410, U.S. Pat. No. 5,693,492 and EP 1 085 089. Other examples will be clear to the skilled person. Reference is also made to the general background art cited above and the further references cited herein.

The genetic constructs of the invention may generally be provided by suitably linking the nucleotide sequence(s) of the invention to the one or more further elements described above, for example using the techniques described in the general handbooks such as Sambrook et al. and Ausubel et al., mentioned above.

Often, the genetic constructs of the invention will be obtained by inserting a nucleotide sequence of the invention in a suitable (expression) vector known per se. Some preferred, but non-limiting examples of suitable expression vectors are those used in the Examples below, as well as those mentioned herein.

The nucleic acids of the invention and/or the genetic constructs of the invention may be used to transform a host cell or host organism, i.e. for expression and/or production of the Nanobody or polypeptide of the invention, or for genetic vaccination. Suitable hosts or host cells will be clear to the skilled person, and may for example be any suitable fungal, prokaryotic or eukaryotic cell or cell line or any suitable fungal, prokaryotic or eukaryotic organism.

According to one non-limiting embodiment of the invention, the immunoglobulin sequences, Nanobody or polypeptide of the invention is glycosylated. According to another non-limiting embodiment of the invention, the immunoglobulin sequences, Nanobody or polypeptide of the invention is non-glycosylated.

In the context of the present invention, "genetic vaccination" includes any known methods or means to transfer a nucleic acid sequence, e.g. a DNA sequence, into a target animal that is suitable for inducing an immune response to a protein encoded by said nucleic acid sequence. The skilled person knows standard ways of genetic vaccination. According to the invention, genetic vaccination can be performed by a needle-free jet injection, by a ballistic method, by needle-mediated injections such as tattoo, by topical application of the DNA onto the skin in patches or by any of these administration methods followed by in vivo electroporation, and furthermore includes vaccination performed by intradermal, intramuscular or subcutaneous administration of DNA.

In the context of genetic vaccination, the term "genetic" refers to any suitable type or kind of nucleic acid molecule, e.g. as defined herein, such as DNA, RNA, cDNA, double stranded DNA, including nucleic acid molecules comprising modified nucleotides, such as PNA, wherein said nucleic acid molecule encodes the cell associated antigen as defined herein, and is suitable for causing expression in the non-human animal such that an immune response can be generated.

Examples of nucleic acid molecules comprise DNA, RNA, PNA, cDNA, double stranded DNA, as well as other forms of nucleic acid molecules comprising chemical modifications to increase e.g. stability in vivo or in vitro.

The nucleic acid molecules can be in the form of an expression vector, plasmid, or any other nucleic acid molecule or genetic construct suitable for expressing the antigen in the animal. Suitable nucleic acid molecules are known to the skilled person, and include commercially available expression vectors and plasmids. Specific, non-limiting example include the commercially available pVAX1 construct, or the eukaryotic expression vector pRc/CMV-Hbs(s) encoding the Hepatitis B small surface antigen (HBSAg) obtainable from Aldevron, which can be engineered by routine means to express the antigen of interest.

Some non-limiting examples of vectors for use in mammalian cells include: pMAMneo (Clontech), pcDNA3 (Invitrogen), pMC1neo (Stratagene), pSG5 (Stratagene), EBO-pSV2-neo (ATCC 37593), pBPV-1 (8-2) (ATCC 37110), pdBPV-MMTneo (342-12) (ATCC 37224), pRSVgpt (ATCC37199), pRSVneo (ATCC37198), pSV2-dhfr (ATCC 37146), pUCTag (ATCC 37460) and 1ZD35 (ATCC 37565), as well as viral-based expression systems, such as those based on adenovirus;

Genetic vaccination will be performed by a suitable nucleic acid or genetic construct, comprising elements suitable for expressing the target antigen in the non-human animal. Such elements will comprise elements that encode the structural information of the antigen, or parts thereof, provided that the conformational epitopes of interest are represented by this structural information. The genetic construct may also comprise elements that are responsible for the control of expression, such as suitable promoters, enhancers, terminators and other control sequences known to the skilled person. Specifically, the invention encompasses the use of promoters allowing constitutive expression after in vivo transfection. A specific, non-limiting example of a suitable promoter is the constitutive Cytomegalovirus (CMV) promoter. The skilled person knows a multitude of further suitable promoters, including, but not limited to promoters for expression in mammalian cells: human cytomegalovirus (hCMV) immediate early enhancer/promoter; human cytomegalovirus (hCMV) immediate early promoter variant that contains two tetracycline operator sequences such that the promoter can be regulated by the Tet repressor; Herpes Simplex Virus thymidine kinase (TK) promoter; Rous Sarcoma Virus long terminal repeat (RSV LTR) enhancer/promoter; elongation factor 1α (hEF-1α) promoter from human, chimpanzee, mouse or rat; the SV40 early promoter; HIV-1 long terminal repeat promoter; β-actin promoter.

The invention encompasses production of the nucleic acid molecules required for genetic vaccination in suitable quantities by methods known in the art. For example, endotoxin-low plasmid DNA can be produced using endotoxin-free Gigaprep kit (Qiagen) according to the manufacturer's instructions.

For genetic vaccination, the nucleic acid molecule as described herein may be formulated in a suitable fashion. For example, the nucleic acid molecule, such as a vector or plasmid is finally reconstituted in endotoxin-free $H_2O$, preferably LAL (limulus amaebocyte lysate) $H_2O$ (i.e. water that has been tested for endotoxin by LAL) or in endotoxin-free 0.9% NaCl in LAL $H_2O$, or another suitable buffer or solution known to the skilled person. The reconstituted nucleic acid molecule can be stored in solution in aliquots at −20° C., or alternatively can be stored in lyophilized form for reconstitution prior to use.

The nucleic acid molecule will be diluted to a suitable dilution for use in genetic vaccination, e.g. at a concentration of 0.1 to 10 mg/ml, specifically 1 to 5 mg/ml, more specifically 1 mg/mL.

For genetic vaccination, the nucleic acid molecule will be administered to the animal in a suitable fashion, as outlined herein. Specific examples of suitable methods for intradermal application of DNA comprise needle-free jet injection (Pig-jet), a tattoo method (Bins, et al., Nature Medicine 11:899-904), needle-free jet injection using the Vacci-jet (Robbins Instruments, USA), topical administration of DNA onto the skin via patches or the Helios Gene-gun (Biorad) as ballistic method to administer the DNA. All DNA administration methods can be followed by in vivo electroporation to enhance cellular transfection efficiency.

In the context of any of the above methods, the nucleic acid may be associated with a suitable carrier. For example, the nucleic acid may be associated with particles, including, but not limited to gold particles. The skilled person knows routine techniques for associating nucleic acids with suitable carriers.

In the context of the present invention, "non-human animal" includes, but is not limited to vertebrate, shark, mammal, lizard, camelid, llama, preferably camelids and most preferably llama or alpaca.

B) THE METHOD OF THE PRESENT INVENTION

The present invention relates to a method for the generation of immunoglobulin sequences that can bind to and/or have affinity for a cell-associated antigen, as defined herein. The method comprises, but is not limited, to the following steps:

a) genetic vaccination of a non-human animal with a nucleic acid encoding said cell-associated antigen or a domain or specific part of said cell associated antigen or a domain or specific part of said cell associated antigen as a genetic fusion to for example immune modulatory genetic elements or a domain or specific part of said cell associated antigen grafted on a camelid orthologue sequence; and b) optionally boosting the animal with said antigen in its natural conformation selected from cells comprising natural or transfected cells expressing the cell-associated antigen (or antigen domains or a specific part of said antigen), cell derived membrane extracts; vesicles or any other membrane derivative harbouring enriched antigen, liposomes, or virus particles expressing the cell associated antigen c) screening a set, collection or library of immunoglobulin sequences derived from said non-human animal for immunoglobulin sequences that can bind to and/or have affinity for said cell-associated antigen Thus, in general terms the method of the present invention includes genetic vaccination of a non-human animal as defined herein. In one particular embodiment, the non-human animal is a camelid.

On particular advantage of the present invention resides in the fact that it provides a robust method for generating immunoglobulin sequences that is widely applicable to a range of antigens. The method of the invention is not limited by the accessibility of protein antigen. In particular, there is no requirement for purified antigen. Advantageously, the method also excludes the need for antigen expressed on a cell, or present in a membrane environment, in that it can be performed by solely using genetic vaccination. Hence, the method of the present invention is broadly applicable to any of the antigens exemplified above, but not limited thereto. In particular, the present method is applicable to antigens for which a corresponding nucleic acid sequence is known, or can be identified by routine means.

Hence, the present invention is advantageous as compared to prior art methods that lack such robust and broad applicability. In particular there is no teaching in the art for such a robust method for the generation of immunoglobulin sequences in animals such as camelids, in particular llama.

Specifically; the present invention provides an improved method for generating immunoglobulin sequences against cell-associated antigens, which, according to one specific embodiment, is without the need for a boost with purified protein, by inducing an immune response via DNA vaccination and subsequent screening for immunoglobulin sequences that can bind the cell-associated antigen. More particularly, the present invention provides a method for the generation of immunoglobulin sequences, including Nanobodies, against a cell-associated antigen comprising the steps of:

a) Vaccination of a camelid with a nucleic acid encoding said cell-associated antigen (or antigen domains or a specific part of said antigen); and b) Screening a set, collection or library of immunoglobulin sequences derived from said camelid for immunoglobulin sequences that can bind to and/or have affinity for said cell-associated antigen.

It has also been surprisingly found, that even in cases where the serum antibody titre was lower after DNA vaccination as compared to protein or cell based immunization, the screening for specific immunoglobulin sequences provided comparable hit rates, i.e. a comparable frequency of specific immunoglobulin sequences could be obtained. Moreover, the affinity of the identified binders was high (as defined herein). This underlines the particular advantage of the present invention of resulting in a more specific high affinity immunoglobulin response, and allowing for more efficient screening and isolation of specific immunoglobulin sequences. It was unforeseeable from the prior art that such advantages can be obtained by DNA vaccination, in particular when the immunized animal exhibits a lower immune response in terms of serum antibody titre.

In an alternative embodiment, the present invention provides a method for the generation of immunoglobulin sequences, including Nanobodies, against a cell-associated antigen comprising the steps of:

a) Vaccination of a camelid with a nucleic acid encoding said cell-associated antigen (or antigen domains or a specific part of said antigen);

b) boosting the camelid with cell associated antigen in its natural conformation, e.g. by use of transfected cells expressing the cell-associated antigen (or antigen domains or a specific part of said antigen), with cell membrane extracts or with virus particles expressing the cell associated antigen, and c) Screening a set, collection or library of immunoglobulin sequences derived from said camelid for immunoglobulin sequences that can bind to and/or have affinity for said cell-associated antigen.

Vaccination

In the method of the invention, genetic vaccination suitable for inducing an immune response in the animal is performed. More specifically, the genetic vaccination must be suitable to induce an immune response as reflected in the generation of immunoglobulin sequences in the animal. The detection of an antibody response in the serum of the animal is also referred to as "serum conversion". The skilled person can monitor genetic vaccination by determining the antibody response by routine means. Thus, the skilled person can readily determine the adequate dosage and frequency that is required for inducing an appropriate antibody response.

Preferably, the genetic vaccination will induce an adequate antibody titre. The antibody titre will correspond to the number of specific antibody producing cells, which will allow the generation of immunoglobulin sequences by isolation and/or screening. However, as pointed out above, the method of the present invention allows for the successful isolation of high affinity immunoglobulin sequences even when there is only a low serum antibody titre as compared to conventional methods. For example, genetic vaccination will allow the successful isolation of high affinity immunoglobulin sequences at serum antibody titres that are e.g. 3 fold lower as compared to the serum titres obtained after a protein boost (which are comparable to antibody tires obtainable by conventional protein immunization techniques). In a particular embodiment, the serum antibody titres may be 5 fold lower, preferably 10 fold lower. Serum titres can be determined by conventional methods, including e.g. ELISA or FACS.

A further aspect of importance for the present invention is the breadth of the antibody repertoire obtained by genetic vaccination. In particular, it is one aspect of the present invention that the antibody response is directed to both linear and conformational epitopes, and importantly is directed to membrane dependent conformational epitopes.

Thus, the present invention relates to genetic vaccination suitable for obtaining an antibody response of an adequate titre and breadth in the non-human animals.

In one embodiment, the present invention may involve a single genetic vaccination at one or multiple sites of the animal. For example, a camelid may be injected in 1, 2, 3, 4, 5 or multiple sites, that may be adjacent to each other or distributed over the body of the animal in suitable locations. In a specific example, the camelid, e.g. a llama, receives genetic vaccination on up to five adjacent sites on the neck. It is self evident that the areas for genetic vaccination have to be clean and free of hair. Hence, the invention encompasses suitable means of removing hair, such as shaving and chemical means such as depilation creams or physical removal of hairs via tape.

In one aspect of the invention it has surprisingly been found that the location of administering the DNA vaccine has an influence on the obtainable immunoglobulin sequences, in particular in terms of diversity and epitope preference.

The invention encompasses repeated genetic vaccination, e.g. 2, 3, 4 or 5 sequences of genetic vaccination in suitable time intervals. Such intervals will be preferably days to weeks, e.g. 3 days to 4 weeks, more preferably 5 days to two weeks. Suitable intervals comprise, genetic vaccination on 0, 3, 7, 21, 24, 28, 56, 59 and 63 days, alternatively on 0, 14, 28 and 57 days, alternatively at days 0, 3, 7, 21, 24, 28, 56, 59 and 63, alternatively on days 0, 14, 28 and 42.

In one specific embodiment, genetic vaccination is performed on a weekly or every other week, until an adequate antibody response is elicited in the animal.

In a further specific embodiment, intradermal administration, e.g. by needle free injection, is performed on days 0, 14, 28 and 57. In another specific embodiment, the short-interval tattoo method, tattooing is performed at days 0, 3, 7, 21, 24, 28, 56, 59 and 63. A further specific example comprises immunization by needle free injection on days 0, 14, 28 and 42. In a ballistic method of genetic vaccination, the dose may be 12 shots of 1 µg DNA/mg gold at a pressure setting of up to 500-600 psi, administered at intervals of 0, 14, 28 and 42 days.

In one particular embodiment, the present invention relates to genetic vaccination using a suitable DNA administration technique followed by in vivo electroporation. It has been surprisingly found that this mode of administration is advantageous as compared to the conventional methods of genetic vaccination. For example, in vivo electroporation is advantageous in terms of vaccination efficacy, i.e. it results in a more pronounced, and/or more reliable immune response. More reliable in this context means that a lower variability in the immune response, an in particular in the number of "hits" obtainable by screening, between individual animals is observed. Moreover, the use of electroporation allows, by changing the settings of the system, to readily adapt the vaccination protocol to the required penetration depth, e.g. to select between intradermal, subcutaneous or intramuscular vaccination. Moreover, considering the relatively thick and tough skin of some animals, such as camelids, electroporation also allows for a good vaccination efficacy, and the ready adaptation to various different locations of immunization characterized by different skin properties.

The skilled person can select a suitable dose of nucleic acid molecules for genetic vaccination. For example, 0.1-10 mg nucleic acid, specifically 1-5 mg, more specifically 1 to 2 mg, or 1 mg nucleic acid can be used for one application of genetic vaccination (e.g. on day 0), resulting in a cumulative dose that depends on the number of repeat genetic vaccinations.

When a suitable antibody response has been confirmed in the animal, immunoglobulin sequences can in one embodiment of the invention be directly isolated from said animal, i.e. without protein boost, by methods as described herein.

Detection of antibody responses can be done by routine means, such as ELISA, RIA, FACS, or any other method for detecting antibodies.

Protein Boost

Alternatively, the method also includes boosting the animal with a suitable source of protein. In particular it is envisaged to boost the animal with compositions that comprise the cell associated antigen as defined herein, in particular a transmembrane antigen, in its natural conformation. Such compositions may comprise cells expressing the antigen, or fragments or derivatives of the cell, such as membrane fractions, isolated organelles, or other suitable preparations. Also envisaged are viruses, liposomes, micelles or other systems that are suitable for containing the cell associated antigen in its natural conformation.

In one aspect of the invention the antigen can be expressed on a homologous cell. For example, for immunization of a camelid, the antigen can be expressed on a camelid cell. The camelid immune system will be tolerant to the camelid cell, i.e. it will not mount an immune response to most of the antigens comprised in this cell. However, if a heterologous antigen, including but not limited to cell associated antigens as defined herein, is artificially introduced into said cell, the immune system of the animal will mount an immune response specifically directed to said antigen. This has the advantage that the immune response will be mainly directed to the antigen of interest, i.e. it will be characterized by an enhanced specificity towards this antigen. The skilled person will appreciate that this approach can be used for related species. For example, camel derived cells can be used for immunization of llama, and vice versa, in view of their close relationship.

Any suitable cell that is homologous to the animal to be immunized can be used. For example, camelid cells can be used for immunization of camelids, e.g. llama cells for immunization of llama. Suitable cells will comprise, but are not limited to, cells that are spontaneously immortal, e.g. cancer cells or undifferentiated cells, such as embryo-derived cells. Suitable cells also encompass cells immortalized artificially by known means.

Cells can advantageously be treated prior to administration to the animals; such that their proliferation in vivo is reduced or eliminated. Suitable treatments comprise, but are not limited to chemical and physical treatments. One specific example of a suitable physical treatment is irradiation with X rays such that the cells can no longer proliferate.

Any of the above cells can also be used for immunizing a non-human animal as defined herein in its own right, i.e. independent of DNA vaccination.

Preferably the protein is enriched in any of the above preparations, in order to strengthen the immune response. For example, recombinant expression in cells using highly efficient promoters can be used to increase the quantity of antigen per cell. In one embodiment, when using camelids as the non-human animal, the cells expressing the antigen of interest can be camelid derived cells, preferably immortalized camelid derived cells. The cells will be genetically modified to express the said antigen.

Moreover, the skilled person will understand that the invention also encompasses the use of an adjuvant commonly used in order to enhance an immune response in the context of vaccination. The protein preparation may also be in a physical form that enhances the immune response, such as e.g. a gel or emulsion. Specific, non-limiting examples of an adjuvant include Stimune or Specol (CEDI Diagnostics, Lelystad, The Netherlands), Freund's Complete Adjuvant, Freund's Incomplete Adjuvant, TiterMax (Gold), monophosphoryl lipid A (MPL), Alum, QuilA, CpG DNA.

The present invention comprises a single or multiple boosts with the said source of protein in its natural conformation (optionally using an adjuvant). The protein boosts will be performed at suitable intervals, which can be determined by routine means, e.g. by monitoring the immunoglobulin response in the animals.

The boost can be performed by different routes of administration, including, but not limited to, intradermal, subcutaneous, or intramuscular administration.

In one particular embodiment the present invention relates to the reduction of the number of protein administrations required in an animal to elicit a suitable immune response. Thus, the genetic vaccination-protein boost (also referred to as "prime-boost") strategy will eliminate the need for repeated protein boost of the animal. This, for one, reduces the burden on the animal, facilitates and speeds up the procedure, and reduces the amount of antigen that is necessary for raising the immunoglobulin sequences. Thus, the genetic vaccination-protein boost strategy of the present invention can surprisingly result in the same antibody titres in the blood of an animal, as a conventional method comprising multiple protein boosts, even without or if only a single protein boost is given after genetic vaccination.

A further particular advantage of a prime-boost strategy using cells as antigen source for the boost resides in the fact that the antibody response will be characterized by a particularly high specificity as compared to known approaches. In other words, because of the DNA priming, the recall immune response elicited by the cell boost will primarily be directed to the antigen of interest, and any other antigenic determinants on the cells will not significantly affect the overall immune response. Thus, the DNA prime-cell boost according to the present invention is particularly advantageous in terms of specificity, hence resulting in an advantageous "hit rate", i.e. a large number of specific immunoglobulin sequences upon screening.

Thus, in the embodiment comprising a protein boost, particular technical effects comprise the enhanced immune response. Moreover, the sequence diversity of different functional Nanobodies belonging to the same B-cell lineage will be enhanced. The boost according to the invention causes introduction of formerly unidentified amino acid substitutions compared with sequences identified after the genetic immunization only, which is an indication for boost mediated in vivo maturation.

Screening/Isolating Immunoglobulin Sequences

The genetic vaccination as described herein will induce an immune response in the animal. Then, a set, collection or library of immunoglobulin sequences is isolated from the animals. "Isolation" includes a) the separation of sequences from the animal, e.g. by sampling suitable tissues, and b) the singling out of specific sequences e.g. by screening, i.e. the isolation of "hits" of specific binders.

The skilled person is well acquainted with techniques for establishing suitable sets, collection or libraries of immunoglobulin sequences, and screening thereof for the sequences of interest. The skilled person can make general reference to the techniques described in for example WO 02/085945 and in WO 04/049794. Reference can also be made to techniques and methods described in WO 99/37681, WO 01/90190, WO 03/025020 and WO 03/035694. Alternatively, improved synthetic or semi-synthetic libraries derived from e.g. $V_{HH}$ libraries, obtained form the animals immunized in accordance with the present invention, may be used, such as $V_{HH}$ libraries obtained from $V_{HH}$ libraries by techniques such as random mutagenesis and/or CDR shuffling, as for example described in WO 00/43507.

The invention includes the isolation of material from the animal which comprises immunoglobulin sequences, such as, but not limited to, antibody producing cells. For example, peripheral blood monocytes (PBMCs) can be isolated by conventional means. Other material includes peripheral blood lymphocytes (PBLs), peripheral lymph nodes, in particular lymph nodes draining the site of immunization, the spleen, bone marrow, or other immunologically relevant materials.

In one specific, non-limiting example, B-cell containing blood samples can be collected, and peripheral blood lymphocytes (PBLs) can be purified by standard methods. For example, a density gradient centrifugation on Ficoll-Paque (Amersham Biosciences, Uppsala, Sweden) can be employed according to the manufacturer's instructions.

Any of the above described material, including e.g. PBLs isolated from the animal will comprise a multitude of immunoglobulin sequences, i.e. a set, collection or library of immunoglobulin sequences.

Amongst this multitude of immunoglobulin sequences, e.g. expressed on PBMCs, the desired immunoglobulin specificities can be directly isolated, e.g. by immunopanning of the cells.

Alternatively, nucleic acid sequences coding for the set, collection or library of immunoglobulin sequences can be isolated, transferred, and expressed on a set, collection or sample of cells or viruses.

The genetic material can be isolated and processed further by suitable means to isolate such sequences that code for the immunoglobulin sequences of the desired specificity. To this end, e.g. the nucleic acid sequences encoding the said multiplicity of immunoglobulin sequences can be extracted from the material by suitable means, and transferred into a recipient cell or virus for expression. The skilled person is familiar with suitable techniques for extraction of immunoglobulin sequences and manipulating these sequences for expression, e.g. in an expression library in cells or viruses. Some non-limiting examples comprise the generation of an expression library in e.g. *E. coli* or bacteriophages.

In one specific, non-limiting example, total RNA can be extracted from the said material. The total RNA can be converted into cDNA by known means. Using this cDNA, immunoglobulin sequences, such as e.g. the Nanobody repertoire, can be amplified by routine means, including e.g. PCR, or nested PCR methods as known in the art (see patent references above).

Nucleic acid molecules comprising immunoglobulin sequences can be digested by use of suitable restriction enzymes, optionally followed by purification e.g. by gel electrophoresis. The digested sequences can be ligated into corresponding restriction sites in a suitable genetic construct, such as a vector or plasmid. Non-limiting examples of suitable vectors include phage display vectors, e.g. pAX50, pAX50 contains the LacZ promoter, a coliphage pIII protein coding sequence, a resistance gene for ampicillin or carbenicillin, a multicloning site (harboring the SfiI and BstEII restriction sites) and a chimeric leader sequence consisting of gene3 and *Erwinia carotovora* pelB motifs. This display vector allows the production of phage particles, expressing the individual Nanobodies as a fusion protein with the geneIII product.

The ligated nucleic acid molecule can be used to obtain a library, e.g. by transformation of a suitable host organism, like *E. coli*. The skilled person knows suitable techniques of transformation, e.g. chemical methods, electroporation, and others. Thus, a library of a suitable size, e.g. 1E7 to 1E8, can be obtained.

In one embodiment, libraries can be rescued by growing the bacteria to logarithmic phase (e.g. OD600=0.5), followed by infection with helper phage to obtain recombinant phage expressing the repertoire of cloned immunoglobulin sequences on tip of the phage as a pill fusion protein, the obtained phage can be stored, e.g. after filter sterilization, for further use, e.g. at 4° C.

A set, collection or library of cells or viruses is screened for cells or viruses that express immunoglobulin sequences that can bind to and/or have affinity for said cell-associated antigen, more specifically, a nucleic acid sequence that encodes the immunoglobulin sequence that can bind to and/or has affinity for said cell-associated antigen can be purified and/or isolated from the cell or virus, followed by expression of said immunoglobulin sequence.

Thus, the present invention also encompasses suitable screening step(s), to select and isolate the immunoglobulin sequences directed to the antigen of interest (or nucleic acid sequences encoding the same) from a multitude of sequences present in the non-human animal. Such screening methods encompass all methods that are suitable for singling out a cell, virus, expression construct, or sequence that relates to the immunoglobulin sequence of interest. The skilled person is well aware of a multitude of suitable techniques, including phage display, immunopanning, etc. Of course the invention also relates to combinations of known methods. Suitable combinations will be apparent to the skilled person.

In one specific embodiment, the library of phages expressing immunoglobulin sequences can be selected by a single round, or multiple rounds of panning on a suitable source of cell-associated antigen, including, but not limited to (immobilized) cells or liposomes comprising the antigen of interest.

After a round of selection, e.g. by immunopanning, the output can be recloned as a pool into a suitable expression vector for further selection and/or processing.

According to the invention, the immunoglobulin sequence that can bind to and/or has affinity for said cell-associated antigen can be purified and/or isolated.

The skilled person can use standard techniques for production of immunoglobulins. Thus, after a cell, virus or nucleic acid sequence encoding the immunoglobulin sequence of interest has been identified by a screening method, the said immunoglobulin sequence can be produced, e.g. by means of recombinant expression. For this purpose, the cell or virus can be used directly, or the nucleic acid encoding the immunoglobulin sequence can be transferred into a suitable expression system, including a suitable host cell. Host cells include mammalian systems, such as CHO cells, eukaryotic systems such as insect cells or fungi, including e.g. *Pichia pastoris*, and prokaryotic systems such as *E. coli*. The skilled person knows suitable expression vectors and tools for use in expressing immunoglobulin sequences in these host systems.

The immunoglobulin sequences, Nanobodies and nucleic acids of the invention can be prepared in a manner known per se, as will be clear to the skilled person from the description herein. The skilled person will understand which of the specific examples are suitable for genetic vaccination, for the generation and/or screening of sets, collections or libraries of immunoglobulin sequences, or for the production of immunoglobulin sequences after selection of antigen specific sequences.

For example, the polypeptides of the invention can be prepared in any manner known per se for the preparation of antibodies and in particular for the preparation of antibody fragments (including but not limited to (single) domain antibodies and ScFv fragments).

As will be clear to the skilled person, one particularly useful method for preparing a polypeptide of the invention generally comprises the steps of:

the expression, in a suitable host cell or host organism (also referred to herein as a "host of the invention") or in another suitable expression system of a nucleic acid that encodes said Nanobody or polypeptide of the invention (also referred to herein as a "nucleic acid of the invention", this term is also used for the genetic constructs for vaccination, as will be apparent from the specific context), optionally followed by:

isolating and/or purifying the Nanobody or polypeptide of the invention thus obtained.

Moreover, the produced immunoglobulins can be purified by standard techniques, including precipitation, affinity chromatography, size exclusion chromatography, ion exchange chromatography, HPLC, filtration, and other known purification methods.

Furthermore, the immunoglobulin sequences can be further characterized by known methods, e.g. to determine their epitope specificity, binding kinetics, etc.

Immunoglobulin Sequences

The invention also relates to immunoglobulin sequences, i.e. the polypeptide molecules, obtainable by a method as described herein, and compositions comprising the said immunoglobulin sequences. Such compositions comprise compositions for research purposes as well as pharmaceutical compositions for use in therapy. The skilled person is familiar with standard techniques and formulations for therapeutic application of immunoglobulin sequences. Thus, in one aspect the method of the present invention encompasses the purification of specific immunoglobulin sequences and their formulation as a pharmaceutical composition.

The present invention provides immunoglobulin sequences in essentially isolated form, e.g. in a form that is at least 90% pure, at least 95% pure, at least 98%, at least 99%, or at least 99.99% pure. In one non-limiting embodiment, purity means that no sequences of other immunoglobulins are present in the preparation. In a further non-limiting embodiment purity means that no contaminants from the producing organism are present in the composition.

The present invention also encompasses immunoglobulin sequences that are derivatives of the immunoglobulin sequences obtainable by the methods disclosed herein. For example, the invention encompasses humanized immunoglobulin sequences obtainable by methods known in the art. Moreover, the invention encompasses camelized immunoglobulin sequences, also obtainable by methods known in the art. The invention also encompasses known structural variants of immunoglobulin sequences.

Immunoglobulin Sequences Directed Against Hepatitis B Small Surface Antigen

The present invention relates to immunoglobulin sequences that are directed against (as defined herein) Hepatitis B small surface antigens, as well as to compounds or constructs, and in particular proteins and polypeptides, that comprise or essentially consist of one or more such immunoglobulin sequences (also referred to herein as "immunoglobulin sequences of the invention", "compounds of the invention", and "polypeptides of the invention", respectively). The invention also relates to nucleic acids encoding such immunoglobulin sequences and polypeptides (also referred to herein as "nucleic acids of the invention" or "nucleotide sequences of the invention"); to methods for preparing such immunoglobulin sequences and polypeptides; to host cells expressing or capable of expressing such immunoglobulin sequences or polypeptides; to compositions, and in particular to pharmaceutical compositions, that comprise such immunoglobulin sequences, polypeptides, nucleic acids and/or host cells; and to uses of such immunoglobulin sequences or polypeptides, nucleic acids, host cells and/or compositions, in particular for prophylactic, therapeutic or diagnostic purposes, such as the prophylactic, therapeutic or diagnostic purposes mentioned herein.

Immunoglobulin Sequences Directed Against Ion Channels

The present invention relates to immunoglobulin sequences that are directed against (as defined herein) ion channels, as well as to compounds or constructs, and in particular proteins and polypeptides, that comprise or essentially consist of one or more such immunoglobulin sequences (also referred to herein as "immunoglobulin sequences of the invention", "compounds of the invention", and "polypeptides of the invention", respectively). The invention also relates to nucleic acids encoding such immunoglobulin sequences and polypeptides (also referred to herein as "nucleic acids of the invention" or "nucleotide sequences of the invention"); to methods for preparing such immunoglobulin sequences and polypeptides; to host cells expressing or capable of expressing such immunoglobulin sequences or polypeptides; to compositions, and in particular to pharmaceutical compositions, that comprise such immunoglobulin sequences, polypeptides, nucleic acids and/ or host cells; and to uses of such immunoglobulin sequences or polypeptides, nucleic acids, host cells and/or compositions, in particular for prophylactic, therapeutic or diagnostic purposes, such as the prophylactic, therapeutic or diagnostic purposes mentioned herein.

Xu et al., Nature Biotechnology, October 2005, 1289-1293 and Benham, Nature Biotechnology, October 2005, 1234-1235, describe an approach for blocking ion channels with a six-transmembrane domain structure, in which polyclonal antibodies raised in rabbits directed against a specific extracellular loop, i.e. the third extracellular region (E3), are used. However, rabbit polyclonal antibodies are not suited for therapeutic use in human beings. It is thus an object of the present invention to provide therapeutic compounds that can be used in the prevention, treatment or diagnosis of diseases and disorders that are associated with ion channels and/or with the biological and/or physiological activity of ion channels. As used herein, "prevention" and "treatment" of a disease or disorder generally include any prophylactic or therapeutic effect that benefits a subject suffering or at risk of the disease or disorder, and for example also includes alleviating or preventing one or more symptoms of the disease and preventing or slowing down the onset and/or the (further) progression of the disease In particular, it is an object of the present invention to provide such therapeutic compounds that are capable of modulating ion channels. By "modulating ion channels" is generally meant herein that the compound, upon coming into contact or otherwise suitably interacting with the ion channel (i.e. under the conditions of a suitable in vitro, cellular or in vivo assay and/or in a suitable animal model; and in particular under physiological conditions, i.e. upon suitable administration to a subject), provides an agonistic or antagonistic effect with respect to the ion channel and/or with respect to the biological and/or physiological functions associated with said ion channel.

It is another objective of the present invention to provide therapeutic compounds that can be used in the prevention, treatment and/or diagnosis of diseases and disorders that can be treated, prevented and/or diagnosed, respectively, by the use of the therapeutic compounds described herein in prophylaxis or therapy (i.e. by administering one or more of the compounds to a subject in need of such treatment, as further described herein) or for diagnostic purposes (also as further described herein). In particular, it is an objective of the present invention to provide therapeutic compounds that can be used in the prevention, treatment and/or diagnosis of diseases and disorders that can be treated, prevented and/or diagnosed, respectively, by modulating (as defined herein) at least one ion channel. It is a further objective to provide such compounds, which do not have the disadvantages that are associated with the use of polyclonal antibodies, with the use of antibodies that have been raised in rabbits, and with the use of conventional four-chain antibodies. It is also an objective of the present invention to provide methods that can be used to easily generate such compounds.

One specific, but non-limiting object of the invention is to provide proteins and/or polypeptides directed against ion channels, and to provide immunoglobulin sequences for use in such proteins or polypeptides, that have improved therapeutic and/or pharmacological properties and/or other advantageous properties (such as, for example, improved ease of preparation and/or reduced costs of goods), compared to the conventional polyclonal rabbit antibodies described by Xu et al or fragments thereof. These improved and advantageous properties will become clear from the further description herein. The above objectives are generally achieved by (the use of) the immunoglobulin sequences and compositions described herein.

The immunoglobulin sequences, polypeptides and compositions of the present invention can generally be used to modulate the opening and/or closing (or enhancing the opening and/or closing) of ion channels and/or to modulate the flow of ions through ion channels (i.e. to increase or to decrease such flow, or to partially or fully block such flow; in an irreversible manner but preferably in a reversible manner). As such, the polypeptides and compositions of the present invention can generally be used to modulate the biological functions, pathways, responses, effects, mechanisms and actions in which ion channels and/or the flow of ions through ion channels are involved. In particular, the polypeptides and compositions of the invention may be used to reduce or inhibit (i.e. fully or partially, and in an irreversible manner but preferably in a reversible manner) the flow of ions through ion channels. As such, the immunoglobulin sequences, polypeptides and compositions of the present invention can generally act as (full or partial) blockers and/or as (full an partial) openers of ion channels (again in a an irreversible manner but preferably in a reversible manner) and/or as agonists or as antagonists of ion channels and/or of the biological functions, pathways, responses, effects, mechanisms and actions in which ion channels and/or the flow of ions through ion channels are involved. As such, the polypeptides and compositions of the present invention can be used for the prevention and treatment (as defined herein) of diseases and disorders associated with ion channels. Generally, "diseases and disorders associated with ion channels" can be defined as diseases and disorders that can be prevented and/or treated, respectively, by suitably administering to a subject in need thereof (i.e. having the disease or disorder or at least one symptom thereof and/or at risk of attracting or developing the disease or disorder) either a polypeptide or composition of the invention (and in particular, of a pharmaceutically active amount thereof) and/or a known active principle active against ion channels. Examples of such diseases and disorders associated with ion channels will be clear to the skilled person based on the disclosure herein, and for example include the diseases and disorders mentioned in the prior art cited herein, depending on the ion channel(s) to which the immunoglobulin sequence or compound/polypeptide of the invention is directed. Thus, without being limited thereto, the immunoglobulin sequences and polypeptides of the invention can for example be used to prevent and/or to treat all diseases and disorders that are currently being prevented or treated with active principles that can modulate ion channels, such as those mentioned in the prior art cited above. It is also envisaged that the polypeptides of the invention can be used to prevent and/or to treat all diseases and disorders for which treatment with such active principles is currently being developed, has been proposed, or will be proposed or developed in future. In addition, it is envisaged that, because of their favourable properties as further described herein, the polypeptides of the present invention may be used for the prevention and treatment of other diseases and disorders than those for which these known active principles are being used or will be proposed or developed; and/or that the polypeptides of the present invention may provide new methods and regimens for treating the diseases and disorders described herein.

Other applications and uses of the immunoglobulin sequences and polypeptides of the invention will become clear to the skilled person from the further disclosure herein. In general, the invention provides immunoglobulin sequences that are directed against (as defined herein) and/or can specifically bind (as defined herein) to ion channels; as well as compounds and constructs, and in particular proteins and polypeptides, that comprise at least one such immunoglobulin sequence. More in particular, the invention provides immunoglobulin sequences can bind to ion channels with an affinity (suitably measured and/or expressed as a $K_D$-value (actual or apparent), a $K_A$-value (actual or apparent), a $k_{on}$-rate and/or a $k_{off}$ rate, or alternatively as an $IC_{50}$ value, as further described herein) that is as defined herein; as well as compounds and constructs, and in particular proteins and polypeptides, that comprise at least one such immunoglobulin sequence.

In particular, immunoglobulin sequences and polypeptides of the invention are preferably such that they:
  bind to ion channels with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles);
and/or such that they:
  bind to ion channels with a $k_{on}$-rate of between $10^2$ $M^{-1}s^{-1}$ to about $10^7$ $M^{-1}s^{-1}$, preferably between $10^3$ $M^{-1}s^{-1}$ and $10^7$ $M^{-1}s^{-1}$, more preferably between $10^4$ $M^{-1}s^{-1}$ and $10^7$ $M^{-1}s^{-1}$, such as between $10^5$ $M^{-1}s^{-1}$ and $10^7$ $M^{-1}s^{-1}$;
and/or such that they:
  bind to ion channels with a $k_{off}$ rate between $1s^{-1}$ ($t_{1/2}$=0.69 s) and $10^{-6}$ $s^{-1}$ (providing a near irreversible complex with a $t_{1/2}$ of multiple days), preferably between $10^{-2}$ $s^{-1}$ and $10^{-6}$ $s^{-1}$, more preferably between $10^{-3}$ $s^{-1}$ and $10^{-6}$ $s^{-1}$, such as between $10^{-4}$ $s^{-1}$ and $10^{-6}$ $s^{-1}$.

Preferably, a monovalent immunoglobulin sequence of the invention (or a polypeptide that contains only one immunoglobulin sequence of the invention) is preferably such that it will bind to ion channels with an affinity less than 500 nM, preferably less than 200 nM, more preferably less than 10 nM, such as less than 500 pM. Some preferred IC50 values for binding of the immunoglobulin sequences or polypeptides of the invention to ion channels will become clear from the further description and examples herein. For binding to ion channels, an immunoglobulin sequence of the invention will usually contain within its immunoglobulin sequence one or more amino acid residues or one or more stretches of amino acid residues (i.e. with each "stretch" comprising two or amino acid residues that are adjacent to each other or in dose proximity to each other, i.e. in the primary or tertiary structure of the immunoglobulin sequence) via which the immunoglobulin sequence of the invention can bind to on channels, which amino acid residues or stretches of amino acid residues thus form the "site" for binding to ion channels (also referred to herein as the "antigen binding site").

The immunoglobulin sequences provided by the invention are preferably in essentially isolated form (as defined herein), or form part of a protein or polypeptide of the invention (as defined herein), which may comprise or essentially consist of one or more immunoglobulin sequences of the invention and which may optionally further comprise one or more further immunoglobulin sequences (all optionally linked via one or more suitable linkers). For example, and without limitation, the one or more immunoglobulin sequences of the invention may be used as a binding unit in such a protein or polypeptide, which may optionally contain one or more further immunoglobulin sequences that can serve as a binding unit (i.e. against one or more other targets than ion channels), so as to provide a monovalent, multivalent or multispecific polypeptide of the invention, respectively, all as described herein. Such a protein or polypeptide may also be in essentially isolated form (as defined herein).

The immunoglobulin sequences and polypeptides of the invention as such preferably essentially consist of a single amino acid chain that is not linked via disulphide bridges to any other immunoglobulin sequence or chain (but that may or may not contain one or more intramolecular disulphide bridges. For example, it is known that Nanobodies—as described herein—may sometimes contain a disulphide bridge between CDR3 and CDR1 or FR2). However, it should be noted that one or more immunoglobulin sequences of the invention may be linked to each other and/or to other immunoglobulin sequences (e.g. via disulphide bridges) to provide peptide constructs that may also be useful in the invention (for example Fab' fragments, F(ab')$_2$ fragments, ScFv constructs, "diabodies" and other multispecific constructs. Reference is for example made to the review by Holliger and Hudson, Nat Biotechnol. 2005 September; 23(9):1126-36)). Generally, when an immunoglobulin sequence of the invention (or a compound, construct or polypeptide comprising the same) is intended for administration to a subject (for example for therapeutic and/or diagnostic purposes as described herein), it is preferably either an immunoglobulin sequence that does not occur naturally in said subject; or, when it does occur naturally in said subject, in essentially isolated form (as defined herein).

It will also be clear to the skilled person that for pharmaceutical use, the immunoglobulin sequences of the invention (as well as compounds, constructs and polypeptides comprising the same) are preferably directed against human ion channels; whereas for veterinary purposes, the immunoglobulin sequences and polypeptides of the invention are preferably directed against ion channels from the species to be treated, or at least cross-reactive with ion channels from the species to be treated.

Furthermore, an immunoglobulin sequence of the invention may optionally, and in addition to the at least one binding site for binding against ion channels, contain one or more further binding sites for binding against other antigens, proteins or targets.

The efficacy of the immunoglobulin sequences and polypeptides of the invention, and of compositions comprising the same, can be tested using any suitable in vitro assay, cell-based assay, in vivo assay and/or animal model known per se, or any combination thereof, depending on the specific disease or disorder involved. Suitable assays and animal models will be clear to the skilled person, and for example include the assays and animal models referred to in the reviews and prior art cited herein.

Also, according to the invention, immunoglobulin sequences and polypeptides that are directed against ion channels from a first species of warm-blooded animal may or may not show cross-reactivity with ion channels from one or more other species of warm-blooded animal. For example, immunoglobulin sequences and polypeptides directed against human ion channels may or may not show cross reactivity with ion channels from one or more other species of primates (such as, without limitation, mouse, monkeys from the genus *Macaca* (such as, and in particular, cynomolgus monkeys (*Macaca fascicularis*) and/or rhesus monkeys (*Macaca mulatta*)) and baboon (*Papio ursinus*)) and/or with ion channels from one or more species of animals that are often used in animal models for diseases (for example mouse, rat, rabbit, pig or dog), and in particular in animal models for diseases and disorders associated with ion channels (such as the species and animal models mentioned herein). In this respect, it will be clear to the skilled person that such cross-reactivity, when present, may have advantages from a drug development point of view, since it allows the immunoglobulin sequences and polypeptides against human ion channels to be tested in such disease models.

More generally, immunoglobulin sequences and polypeptides of the invention that are cross-reactive with ion channels from multiple species of mammal will usually be advantageous for use in veterinary applications, since it will allow the same immunoglobulin sequence or polypeptide to be used across multiple species. Thus, it is also encompassed within the scope of the invention that immunoglobulin sequences and polypeptides directed against ion channels from one species of animal (such as immunoglobulin sequences and polypeptides against human ion channels) can be used in the treatment of another species of animal, as long as the use of the immunoglobulin sequences and/or polypeptides provide the desired effects in the species to be treated.

The immunoglobulin sequences of the invention (as well as polypeptides comprising the same) are preferably such that they are capable of modulating (as defined herein) an ion channel. In particular, the immunoglobulin sequences of the invention (as well as polypeptides comprising the same) are preferably such that they are capable of (fully or partially) blocking an ion channel. By "partially or fully blocking", respectively, of an ion channel by a compound is meant that the modulation of the ion channel by the immunoglobulin sequence or polypeptide results in a reduced flow of ions through the channel (i.e. compared to the flow of ions through the ion channel when there is no interaction between the immunoglobulin sequence/polypeptide and the ion channel, as determined by a suitable assay, such as those described herein) or essentially no flow of ions through the channel, respectively, irrespective of the specific mechanism via which the ion channel is blocked by the immunoglobulin sequence or polypeptide. For example, and without limitation, the immunoglobulin sequence or polypeptide may partially or fully block the ion channel directly by binding to an epitope of the ion channel (or of at least one subunit thereof) such that the flow of ions through the channel is fully or partially blocked (e.g. by steric hindrance or steric interactions); or indirectly, for example via interaction with one or more extracellular parts, regions, domain or loops of the ion channel or by affecting the (possible) confirmation(s) of the ion channel, or by limiting the extent and/or rate by which the ion channel can undergo conformational changes.

An immunoglobulin sequence or polypeptide of the invention that is a blocker of an ion channel is preferably such that it reduces the flow of ions through the channel by at least 1%, preferably at least 5%, such as at least 10%, fore example 25% or more or even 50% or more and up to 75% or even more than 90% or more, compared to the flow of ions through the ion channel when there is no interaction between the immunoglobulin sequence/polypeptide and the ion channel, as determined by a suitable assay, such as those described herein.

An immunoglobulin sequence or polypeptide of the invention that is a opener of an ion channel is preferably such that it increases the flow of ions through the channel by at least 1%, preferably at least 5%, such as at least 10%, fore example 25% or more or even 50% or more and up to 75% or even more than 90% or more, compared to the flow of ions through the ion channel when there is no interaction between the immunoglobulin sequence/polypeptide and the ion channel, as determined by a suitable assay, such as those described herein.

An immunoglobulin sequence or polypeptide of the invention that is an agonists of an ion channel and/or of the biological function(s) or response(s) associated therewith is preferably such that it increases the desired biological function or response by at least 1%, preferably at least 5%, such as at least 10%, fore example 25% or more or even 50% or more and up to 75% or even more than 90% or more, compared to the biological function or response when there is no interaction between the immunoglobulin sequence/polypeptide and the on channel, as determined by a suitable assay, such as those described herein.

An immunoglobulin sequence or polypeptide of the invention that is an antagonists of an ion channel and/or of the biological function(s) or response(s) associated therewith is preferably such that it decreases the desired biological function or response by at least 1%, preferably at least 5%, such as at least 10%, fore example 25% or more or even 50% or more and up to 75% or even more than 90% or more, compared to the biological function or response when there is no interaction between the immunoglobulin sequence/polypeptide and the ion channel, as determined by a suitable assay, such as those described herein.

Immunoglobulin sequences or polypeptides of the invention that are blockers or openers of ion channels (or enhance blockers or openers) and/or that are agonists or antagonists of ion channels or the biological function(s) or response(s) associated therewith may provide their desired activity in an irreversible manner, but preferably do so in a reversible manner.

The present invention is in its broadest sense also not particularly limited to or defined by a specific antigenic determinant, epitope, part, domain, subunit or confirmation (where applicable) of ion channels against which the immunoglobulin sequences and polypeptides of the invention are directed.

The immunoglobulin sequences and polypeptides of the invention may be directed against any desired ion channel, and may in particular be directed against an ion channel that has at least one extracellular domain. More in particular, but without limitation, the immunoglobulin sequences and polypeptides of the invention may be directed against any desired ion channel that has at least one transmembrane domain, more in particular at least two transmembrane domains, such as at least four transmembrane domains (e.g., the 4-TM ion channels) or six or more transmembrane domains (e.g. the 6-TM ion channels). Examples of such ion channels will be clear to the skilled person based on the prior art cited herein. Reference is for example made to the reviews from Goldstein et al., Yu et al., Clapham and Garbers, Hoffmann et al., Kubo et al., Wei et al., Shieh et al. (see for example FIG. 2 on page 559), Catterall et al, Gutman et al., Clapham et al., Catterall et al. cited above. As further described herein, the immunoglobulin sequences and polypeptides of the invention may for example be directed against the extracellular parts of such transmembrane domains and in particular against the extracellular loops/repeats that connect such transmembrane domains (reference is for example again made to FIG. 2 on page 559 of Shieh et al. and to FIG. 1 on page 1290 of Xu et al, supra, which schematically show such extracellular loops of 2-TM, 4-TM and 6-TM ion channels).

In one preferred, but non-limiting aspect, the immunoglobulin sequences and polypeptides of the invention are directed against 6-TM ion channels (such as, without limitation, the Kv-ion channels mentioned above (e.g. from Kv1.1 to Kv9.3, the KvLQT ion channels, Slo and $IK_{Ca}10$), and in particular against one of the extracellular loops/repeats that connect the transmembrane domains of such 6-TM ion channels, such as the E1, E2, and in particular E3 loop, or the region between 85 and 86 of repeats 2, 3 and 4.

However, according to a specific aspect of the invention, an immunoglobulin sequence or polypeptide of the invention may be directed against (as defined herein) an ion channel that is expressed on the surface of a cell and/or against at least one extracellular region, domain, loop or other extracellular epitope of an ion channel.

In particular, according to this aspect, an immunoglobulin sequence or polypeptide of the invention is directed against (as defined herein) at least one extracellular region, domain, loop or other extracellular epitope of an ion channel; and is preferably further such that said immunoglobulin sequence or polypeptide of the invention is capable of modulating (as defined herein) said ion channel. More in particular, according to this aspect, an immunoglobulin sequence or polypeptide of the invention is directed against (as defined herein) at least one extracellular region, domain, loop or other extracellular epitope of an ion channel; and is preferably further such that said immunoglobulin sequence or polypeptide of the invention is capable of (fully or partially) blocking said ion channel.

According to this aspect of the invention, the immunoglobulin sequence or polypeptide of the invention may be directed against any suitable extracellular part, region, domain, loop or other extracellular epitope, but is preferably directed against one of the extracellular parts of the transmembrane domains or more preferably against one of the extracellular loops that link the transmembrane domains. More in particular, when the ion channel is a 6-TM channel, the protein or polypeptide (and in particular at least one of the immunoglobulin sequences present therein) may be directed against the extracellular E3 loop that linking the transmembrane domains (and/or may have been raised against the extracellular E3 loop and/or against synthetic or semi-synthetic peptides that are derived from or based on the sequence of the extracellular E3 loop).

Other suitable extracellular parts, regions, domains, loops or epitopes may be derived by Kyte-Doolittle analysis of the immunoglobulin sequence of the pertinent ion channel; by aligning ion channels belonging to the same (sub)families and identifying the various transmembrane domains and extracellular parts, regions, domain or loops (including the E3 loop); by TMAP-analysis; or by any suitable combination thereof. The invention also relates to immunoglobulin sequences and (as further defined herein) that are directed against such extracellular parts, regions, domains, loops or epitopes (and/or that have been raised against parts or fragments of the immunoglobulin sequence that comprise such extracellular parts, regions, domains, loops or epitopes and/or against synthetic or semi-synthetic peptides that are derived from or based on such extracellular parts, regions, domains, loops or epitopes).

In particular, immunoglobulin sequences and polypeptides of the invention are preferably such that they:

bind to an extracellular part, region, domain, loop or other extracellular epitope of an ion channel (as described herein) with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles);

and/or such that they:

bind to an extracellular part, region, domain, loop or other extracellular epitope of an ion channel (as described herein) with a $k_{on}$-rate of between $10^2$ $M^{-1}s^{-1}$ to about $10^7$ $M^{-1}s^{-1}$, preferably between $10^3$ $M^{-1}s^{-1}$ and $10^7$ $M^{-1}s^{-1}$, more preferably between $10^4$ $M^{-1}s^{-1}$ and $10^7$ $M^{-1}s^{-1}$, such as between $10^5 M^{-1}s^{-1}$ and $10^7$ $M^{-1}s^{-1}$;

and/or such that they:

bind to an extracellular part, region, domain, loop or other extracellular epitope of an ion channel (as described herein) with a $k_{off}$ rate between $1s^{-1}$ ($t_{1/2}$=0.69 s) and $10^{-8}$ $s^{-1}$ (providing a near irreversible complex with a $t_{1/2}$ of multiple days), preferably between $10^{-2}$ $s^{-1}$ and $10^{-6}$ $s^{-1}$, more preferably between $10^{-3}$ $s^{-1}$ and $10^{-8}$ $s^{-1}$, such as between $10^{-4}$ $s^{-1}$ and $10^{-6}$ $s^{-1}$.

Preferably, a monovalent immunoglobulin sequence of the invention (or a polypeptide that contains only one immunoglobulin sequence of the invention) is preferably such that it will bind to bind to an extracellular part, region, domain, loop or other extracellular epitope of an ion channel (as described herein) with an affinity less than 500 nM, preferably less than 200 nM, more preferably less than 10 nM, such as less than 500 pM.

Some preferred 1050 values for binding of the immunoglobulin sequences or polypeptides of the invention to bind to an extracellular part, region, domain, loop or other extracellular epitope of an ion channel (as described herein) will become clear from the further description and examples herein.

Also, according to this aspect, any multivalent or multispecific (as defined herein) polypeptides of the invention may also be suitably directed against two or more different extracellular parts, regions, domains, loops or other extracellular epitopes on the same antigen, for example against two different extracellular loops, against two different extracellular parts of the transmembrane domains or against one extracellular loops and one extracellular loop. Such multivalent or multispecific polypeptides of the invention may also have (or be engineered and/or selected for) increased avidity and/or improved selectivity for the desired ion channel, and/or for any other desired property or combination of desired properties that may be obtained by the use of such multivalent or multispecific polypeptides.

An immunoglobulin sequence or polypeptide of the invention may also be said to be "directed against" (as further defined herein) a peptide antigen when it is directed against said peptide antigen per se, for example in a standard assay for determining the binding (i.e. the specificity, affinity, $K_D$, $K_A$, $k_{on}$ or $k_{off}$ of such binding; all as described herein) of the immunoglobulin sequence or polypeptide of the invention against the peptide antigen, using the peptide antigen of the invention as such (instead of, for example, the peptide antigen as part of a larger protein or polypeptide, for example as part of an ion channel present on the surface of a cell). Techniques for determining the binding of immunoglobulin sequences or polypeptides to small peptides will be clear to the skilled person, and for example include the techniques described herein.

An immunoglobulin sequence or polypeptide of the invention may also be said to be "directed against" (as further defined herein) a peptide antigen when it has been screened against, selected using and/or raised against (i.e. by suitably immunizing a mammal, as further described herein) said peptide antigen. Techniques for raising immunoglobulin sequences and polypeptides of the invention against a peptide antigen of the invention, and for screening or selecting immunoglobulin sequences and polypeptides of the invention for binding against a peptide antigen of the invention, will be clear to the skilled person, for example based on the further disclosure herein.

Generally, it is expected that immunoglobulin sequences an polypeptides of the invention that are directed against a peptide antigen of the invention per se, and/or that have been screened against, selected using and/or raised against a peptide antigen of the invention, will also be able to bind (and in particular, to specifically bind, as defined herein) to a peptide antigen of the invention that forms part of an ion channel (or at least one subunit thereof) that is present on the surface of a cell. Thus, the peptide antigens of the invention may find particular use in methods for generating immunoglobulin sequences and polypeptides of the invention (as defined herein); and such methods and uses form further aspects of the invention.

For example, such a method may comprise one of the following steps or a suitable combination of both of the following steps:

a) a step of suitably immunizing a Camelid with a suitable antigen that comprises the desired extracellular part, region, domain, loop or other extracellular epitope(s), such that an immune response against the desired extracellular part, region, domain, loop or other extracellular epitope(s) is raised. The antigen may be any suitable antigen that is capable of raising an immune response against the desired extracellular part, region, domain, loop or other extracellular epitope(s); such as, for example and without limitation, whole cells that have the desired extracellular part, region, domain, loop or other extracellular epitope(s) on their surface, cell wall fragments thereof or any other suitable preparation derived from such cells, vesicles that have the desired extracellular part, region, domain, loop or other extracellular epitope(s) on their surface, a subunit or fragment of a subunit of an ion channel that comprises the desired extracellular part, region, domain, loop or other extracellular epitope(s), or a synthetic or semi-synthetic peptide that comprises and/or is based on (the immunoglobulin sequence of) the desired extracellular part, region, domain, loop or other extracellular epitope(s);

and/or b) a step of screening for affinity and/or binding for the desired extracellular part, region, domain, loop or other extracellular epitope(s). This may for example be performed by screening a set, collection or library of cells that express heavy chain antibodies on their surface (e.g. B-cells obtained from a suitably immunized Camelid), by screening of a (naïve or immune) library of VHH sequences or Nanobody sequences, or by screening of a (naïve or immune) library of nucleic acid sequences that encode VHH sequences or Nanobody sequences; which may all be performed in a manner known per se, for which reference is made to the further disclosure and prior art mentioned herein;

and which method may optionally further comprise one or more other suitable steps known per se, such as, for example and without limitation, a step of affinity maturation, a step of expressing the desired immunoglobulin sequence, a step of screening for binding and/or for activity against the desired antigen (in this case, the ion channel), a step of determining the desired immunoglobulin sequence or nucleotide sequence, a step of introducing one or more humanizing substitutions (e.g. as further described herein), a step of formatting in a suitable multivalent and/or multispecific format, a step of screening for the desired biological and/or physiological properties (i.e. using a suitable assay, such as those described herein); and/or any suitable combination of one or more of such steps, in any suitable order.

Such methods and the immunoglobulin sequences obtained via such methods, as well as proteins and polypeptides comprising or essentially consisting of the same, form further aspects of this invention.

In a preferred embodiment, the immunoglobulin sequence or polypeptide of the invention is a "monoclonal" immunoglobulin sequence or polypeptide, by which is meant that at least each of the one or more immunoglobulin sequences directed against the ion channel that are present in said protein or polypeptide (and preferably all of the immunoglobulin sequences that are present in said protein or polypeptide) are "monoclonal" as commonly understood by the skilled person. In this respect, it should however be noted that, as further described herein, the present invention explicitly covers multivalent or multispecific proteins that comprise two or more immunoglobulin sequences (and in particular monoclonal immunoglobulin sequences) that are directed against different parts, regions, domains, loops or epitopes of the same ion channel, and in particular against different extracellular parts, regions, domains, loops or epitopes of the same ion channel.

In another aspect, the invention relates to a protein or polypeptide that comprises or essentially consist of at least one immunoglobulin sequence of the invention, or of at least one part, fragment, analog, variant or derivative of an immunoglobulin sequence of the invention, wherein said protein or polypeptide is capable of modulating (as defined herein) an ion channel. Preferably, said protein or polypeptide is capable of fully or partially blocking (as defined herein) an ion channel.

The protein or polypeptides described herein are preferably directed against an ion channel that is expressed on the surface of a cell and/or against at least one extracellular region, domain, loop or other extracellular epitope of an ion channel, more preferably against at least one extracellular loop of an ion channel. In one specific aspect, when the ion channel is an ion channel with six transmembrane domains (6-TM), the protein or polypeptide is preferably directed against the extracellular E3 loop. The proteins or polypeptides described herein may also be directed against a peptide antigen of the invention.

In one specific aspect, the invention relates to a protein or polypeptide that comprises or essentially consist of at least one immunoglobulin sequence of the invention, or of at least one part, fragment, analog, variant or derivative of an immunoglobulin sequence of the invention, wherein at least one of the immunoglobulin sequences of the invention (or at least one of the parts, fragments, analogs, variants or derivatives of the immunoglobulin sequence of the invention) present in protein or polypeptide is directed against an ion channel. Preferably, at least one of the immunoglobulin sequences of the invention (or at least one of the parts, fragments, analogs, variants or derivatives of the immunoglobulin sequence of the invention) present in protein or polypeptide is capable of modulating an ion channel, and more preferably of fully or partially blocking an ion channel. Also, preferably, at least one of the immunoglobulin sequences of the invention (or at least one of the parts, fragments, analogs, variants or derivatives of the immunoglobulin sequence of the invention) present in protein or polypeptide is directed against at least one extracellular region, domain, loop or other extracellular epitope of an ion channel, and in particular against one extracellular loop of an ion channel. In one specific aspect, when the ion channel is an ion channel with six transmembrane domains (6-TM), at least one of the immunoglobulin sequences of the invention present in the protein or polypeptide is preferably directed against the extracellular E3 loop.

The proteins or polypeptides described herein may comprise or essentially consist of a single immunoglobulin sequence of the invention (or part, fragment, analog, variant or derivative of an immunoglobulin sequence of the invention), or alternatively of at least two (such as two, three, four or more) immunoglobulin sequences of the invention (or parts, fragments, analogs, variants or derivatives of an immunoglobulin sequence of the invention), which are optionally suitably linked via one or more suitable linkers (as described herein). Suitable examples of such linkers will be clear to the person skilled in the art, for example on the basis of the further disclosure herein.

In one aspect of the invention, when a protein or polypeptide comprises at least two immunoglobulin sequences of the invention, at least two of the immunoglobulin sequences of the invention (or parts, fragments, analogs, variants or derivatives of an immunoglobulin sequence of the invention) present in the protein or polypeptide are directed against the same ion channel. For example, at least two of the immunoglobulin sequences of the invention (or parts, fragments, analogs, variants or derivatives of an immunoglobulin sequence of the invention) present in the protein or polypeptide may directed against different extracellular regions, domains, loops or other extracellular epitopes of the same ion channel. However, preferably at least one (or at least two) of the immunoglobulin sequences of the invention (or parts, fragments, analogs, variants or derivatives of an immunoglobulin sequence of the invention) present in the protein or polypeptide is directed against at least one extracellular loop of the ion channel.

When a protein or polypeptide of the invention comprises or essentially consists of at least two immunoglobulin sequences of the invention (or parts, fragments, analogs, variants or derivatives of an immunoglobulin sequence of the invention), it may comprise at least two different immunoglobulin sequences of the invention (or parts, fragments, analogs, variants or derivatives of an immunoglobulin sequence of the invention), and/or comprise at least two identical immunoglobulin sequences of the invention (or parts, fragments, analogs, variants or derivatives of an immunoglobulin sequence of the invention).

In one specific aspect, when a protein or polypeptide of the invention comprises or essentially consists of at least two immunoglobulin sequences of the invention (or parts, fragments, analogs, variants or derivatives of an immunoglobulin sequence of the invention), it may comprise at least one immunoglobulin sequence of the invention (or part, fragment, analog, variant or derivative of an immunoglobulin sequence of the invention) that is directed against a protein, polypeptide or other antigen different from an ion channel.

In another aspect, the invention relates to an immunoglobulin sequence of the invention, or part, fragment, analog, variant or derivative of an immunoglobulin sequence of the invention that is capable of modulating an ion channel. Preferably, said immunoglobulin sequence of the invention is capable of fully or partially blocking (as defined herein) an ion channel.

The immunoglobulin sequences of the invention described herein are preferably directed against at least one extracellular region, domain, loop or other extracellular epitope of an ion channel, more preferably against at least one extracellular loop of an ion channel. In one specific aspect, when the ion channel is an ion channel with six transmembrane domains (6-TM), the immunoglobulin sequence of the invention is preferably directed against the extracellular E3 loop.

It is also within the scope of the invention that, where applicable, an immunoglobulin sequence of the invention can bind to two or more antigenic determinants, epitopes, parts, domains, subunits or confirmations of ion channels. In such a case, the antigenic determinants, epitopes, parts, domains or subunits of ion channels to which the immunoglobulin sequences and/or polypeptides of the invention bind may be essentially the same (for example, if ion channels contains repeated structural motifs or occurs in a multimeric form) or may be different (and in the latter case, the immunoglobulin sequences and polypeptides of the invention may bind to such different antigenic determinants, epitopes, parts, domains, subunits of ion channels with an affinity and/or specificity which may be the same or different). Also, for example, when ion channels exists in an activated conformation and in an inactive conformation, the immunoglobulin sequences and polypeptides of the invention may bind to either one of these confirmation, or may bind to both these confirmations (i.e. with an affinity and/or specificity which may be the same or different). Also, for example, the immunoglobulin sequences and polypeptides of the invention may bind to a conformation of ion channels in which it is bound to a pertinent ligand, may bind to a conformation of ion channels in which it not bound to a pertinent ligand, or may bind to both such conformations (again with an affinity and/or specificity which may be the same or different).

It is also expected that the immunoglobulin sequences and polypeptides of the invention will generally bind to all naturally occurring or synthetic analogs, variants, mutants, alleles, parts and fragments of ion channels; or at least to those analogs, variants, mutants, alleles, parts and fragments of ion channels that contain one or more antigenic determinants or epitopes that are essentially the same as the antigenic determinant(s) or epitope(s) to which the immunoglobulin sequences and polypeptides of the invention bind in ion channels (e.g. in wild-type ion channels). Again, in such a case, the immunoglobulin sequences and polypeptides of the invention may bind to such analogs, variants, mutants, alleles, parts and fragments with an affinity and/or specificity that are the same as, or that are different from (i.e. higher than or lower than), the affinity and specificity with which the immunoglobulin sequences of the invention bind to (wild-type) ion channels. It is also included within the scope of the invention that the immunoglobulin sequences and polypeptides of the invention bind to some analogs, variants, mutants, alleles, parts and fragments of ion channels, but not to others.

When ion channels exists in a monomeric form and in one or more multimeric forms, it is within the scope of the invention that the immunoglobulin sequences and polypeptides of the invention only bind to ion channels in monomeric form, only bind to ion channels in multimeric form, or bind to both the monomeric and the multimeric form. Again, in such a case, the immunoglobulin sequences and polypeptides of the invention may bind to the monomeric form with an affinity and/or specificity that are the same as, or that are different from (i.e. higher than or lower than), the affinity and specificity with which the immunoglobulin sequences of the invention bind to the multimeric form.

Also, when ion channels can associate with other proteins or polypeptides to form protein complexes (e.g. with multiple subunits), it is within the scope of the invention that the immunoglobulin sequences and polypeptides of the invention bind to ion channels in its non-associated state, bind to ion channels in its associated state, or bind to both. In all these cases, the immunoglobulin sequences and polypeptides of the invention may bind to such multimers or associated protein complexes with an affinity and/or specificity that may be the same as or different from (i.e. higher than or lower than) the affinity and/or specificity with which the immunoglobulin sequences and polypeptides of the invention bind to ion channels in its monomeric and non-associated state.

Also, as will be clear to the skilled person, proteins or polypeptides that contain two or more immunoglobulin sequences directed against ion channels may bind with higher avidity to ion channels than the corresponding monomeric immunoglobulin sequence(s). For example, and without limitation, proteins or polypeptides that contain two or more immunoglobulin sequences directed against different epitopes of ion channels may (and usually will) bind with higher avidity than each of the different monomers, and proteins or polypeptides that contain two or more immunoglobulin sequences directed against ion channels may (and usually will) bind also with higher avidity to a multimer of ion channels.

Generally, immunoglobulin sequences and polypeptides of the invention will at least bind to those forms of ion channels (including monomeric, multimeric and associated forms) that are the most relevant from a biological and/or therapeutic point of view, as will be clear to the skilled person. It is also within the scope of the invention to use parts, fragments, analogs, mutants, variants, alleles and/or derivatives of the immunoglobulin sequences and polypeptides of the invention, and/or to use proteins or polypeptides comprising or essentially consisting of one or more of such parts, fragments, analogs, mutants, variants, alleles and/or derivatives, as long as these are suitable for the uses envisaged herein. Such parts, fragments, analogs, mutants, variants, alleles and/or derivatives will usually contain (at least part of) a functional antigen-binding site for binding against ion channels; and more preferably will be capable of specific binding to ion channels, and even more preferably capable of binding to ion channels with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein. Some non-limiting examples of such parts, fragments, analogs, mutants, variants, alleles, derivatives, proteins and/or polypeptides will become clear from the further description herein. Additional fragments or polypeptides of the invention may also be provided by suitably combining (i.e. by linking or genetic fusion) one or more (smaller) parts or fragments as described herein.

In one specific, but non-limiting aspect of the invention, which will be further described herein, such analogs, mutants, variants, alleles, derivatives have an increased half-life in serum (as further described herein) compared to the immunoglobulin sequence from which they have been derived. For example, an immunoglobulin sequence of the invention may be linked (chemically or otherwise) to one or more groups or moieties that extend the half-life (such as PEG), so as to provide a derivative of an immunoglobulin sequence of the invention with increased half-life.

In one specific, but non-limiting aspect, the immunoglobulin sequence of the invention may be an immunoglobulin sequence that comprises an immunoglobulin fold or may be an immunoglobulin sequence that, under suitable conditions (such as physiological conditions) is capable of forming an immunoglobulin fold (i.e. by folding). Reference is inter alia made to the review by Halaby et al., J. (1999) Protein Eng. 12, 563-71. Preferably, when properly folded so as to form an immunoglobulin fold, such an immunoglobulin sequence is capable of specific binding (as defined herein) to ion channels; and more preferably capable of binding to ion channels with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein. Also, parts, fragments, analogs, mutants, variants, alleles and/or derivatives of such immunoglobulin sequences are preferably such that they comprise an immunoglobulin fold or are capable for forming, under suitable conditions, an immunoglobulin fold.

In particular, but without limitation, the immunoglobulin sequences of the invention may be immunoglobulin sequences that essentially consist of 4 framework regions (FR1 to FR4 respectively) and 3 complementarity determining regions (CDR1 to CDR3 respectively); or any suitable fragment of such an immunoglobulin sequence (which will then usually contain at least some of the amino acid residues that form at least one of the CDR's, as further described herein).

In such an immunoglobulin sequence of the invention, the framework sequences may be any suitable framework sequences, and examples of suitable framework sequences will be clear to the skilled person, for example on the basis the standard handbooks and the further disclosure and prior art mentioned herein.

The framework sequences are preferably (a suitable combination of) immunoglobulin framework sequences or framework sequences that have been derived from immunoglobulin framework sequences (for example, by humanization or camelization). For example, the framework sequences may be framework sequences derived from a light chain variable domain (e.g. a $V_L$-sequence) and/or from a heavy chain variable domain (e.g. a $V_H$-sequence). In one particularly preferred aspect, the framework sequences are either framework sequences that have been derived from a $V_{HH}$-sequence (in which said framework sequences may optionally have been partially or fully humanized) or are conventional $V_H$ sequences that have been camelized (as defined herein).

The framework sequences are preferably such that the immunoglobulin sequence of the invention is a domain antibody (or an immunoglobulin sequence that is suitable for use as a domain antibody); is a single domain antibody (or an immunoglobulin sequence that is suitable for use as a single domain antibody); is a "dAb" (or an immunoglobulin sequence that is suitable for use as a dAb); or is a Nanobody™ (including but not limited to $V_{HH}$ sequence). Again, suitable framework sequences will be clear to the skilled person, for example on the basis the standard handbooks and the further disclosure and prior art mentioned herein.

In particular, the framework sequences present in the immunoglobulin sequences of the invention may contain one or more of Hallmark residues (as defined herein), such that the immunoglobulin sequence of the invention is a Nanobody™. Some preferred, but non-limiting examples of (suitable combinations of) such framework sequences will become clear from the further disclosure herein.

Again, as generally described herein for the immunoglobulin sequences of the invention, it is also possible to use suitable fragments (or combinations of fragments) of any of the foregoing, such as fragments that contain one or more CDR sequences, suitably flanked by and/or linked via one or more framework sequences (for example, in the same order as these CDR's and framework sequences may occur in the full-sized immunoglobulin sequence from which the fragment has been derived). Such fragments may also again be such that they comprise or can form an immunoglobulin fold, or alternatively be such that they do not comprise or cannot form an immunoglobulin fold.

In one specific aspect, such a fragment comprises a single CDR sequence as described herein (and in particular a CDR3 sequence), that is flanked on each side by (part of) a framework sequence (and in particular, part of the framework sequence(s) that, in the immunoglobulin sequence from which the fragment is derived, are adjacent to said CDR sequence. For example, a CDR3 sequence may be preceded by (part of) a FR3 sequence and followed by (part of) a FR4 sequence).

Such a fragment may also contain a disulphide bridge, and in particular a disulphide bridge that links the two framework regions that precede and follow the CDR sequence, respectively (for the purpose of forming such a disulphide bridge, cysteine residues that naturally occur in said framework regions may be used, or alternatively cysteine residues may be synthetically added to or introduced into said framework regions). For a further description of these "Expedite fragments", reference is again made to WO 03/050531, as well as to WO 2009/127691.

The immunoglobulin sequences of the invention may in particular be an immunoglobulin sequence or a suitable fragment thereof, and more in particular be an immunoglobulin variable domain sequence or a suitable fragment thereof, such as light chain variable domain sequence (e.g. a $V_L$-sequence) or a suitable fragment thereof; or a heavy chain variable domain sequence (e.g. a $V_H$-sequence) or a suitable fragment thereof. When the immunoglobulin sequence of the invention is a heavy chain variable domain sequence, it may be a heavy chain variable domain sequence that is derived from a conventional four-chain antibody (such as, without limitation, a $V_H$ sequence that is derived from a human antibody) or be a so-called $V_{HH}$-sequence (as defined herein) that is derived from a so-called "heavy chain antibody" (as defined herein).

However, it should be noted that the invention is not limited as to the origin of the immunoglobulin sequence of the invention (or of the nucleotide sequence of the invention used to express it), nor as to the way that the immunoglobulin sequence or nucleotide sequence of the invention is (or has been) generated or obtained. Thus, the immunoglobulin sequences of the invention may be naturally occurring immunoglobulin sequences (from any suitable species) or synthetic or semi-synthetic immunoglobulin sequences. In a specific but non-limiting aspect of the invention, the immunoglobulin sequence is a naturally occurring immunoglobulin sequence (from any suitable species) or a synthetic or semi-synthetic immunoglobulin sequence, including but not limited to "humanized" (as defined herein) immunoglobulin sequences (such as partially or fully humanized mouse or rabbit immunoglobulin sequences, and in particular partially or fully humanized $V_{HH}$ sequences or Nanobodies), "camelized" (as defined herein) immunoglobulin sequences, as well as immunoglobulin sequences that have been obtained by techniques such as affinity maturation (for example, starting from synthetic, random or naturally occurring immunoglobulin sequences), CDR grafting, veneering, combining fragments derived from different immunoglobulin sequences, PCR assembly using overlapping primers, and similar techniques for engineering immunoglobulin sequences well known to the skilled person; or any suitable combination of any of the foregoing. Reference is for example made to the standard handbooks, as well as to the further description and prior art mentioned herein.

Similarly, the nucleotide sequences of the invention may be naturally occurring nucleotide sequences or synthetic or semi-synthetic sequences, and may for example be sequences that are isolated by PCR from a suitable naturally occurring template (e.g. DNA or RNA isolated from a cell), nucleotide sequences that have been isolated from a library (and in particular, an expression library), nucleotide sequences that have been prepared by introducing mutations into a naturally occurring nucleotide sequence (using any suitable technique known per se, such as mismatch PCR), nucleotide sequence that have been prepared by PCR using overlapping primers, or nucleotide sequences that have been prepared using techniques for DNA synthesis known per se.

In particular, the immunoglobulin sequence of the invention may be a Nanobody™ (as defined herein) or a suitable fragment thereof. [Note: Nanobody™, Nanobodies™ and Nanoclone™ are trademarks of Ablynx N.V.] Such Nanobodies directed against ion channels will also be referred to herein as "Nanobodies of the invention". For a general description of Nanobodies, reference is made to the further description below, as well as to the prior art cited herein. In this respect, it should however be noted that this description and the prior art mainly described Nanobodies of the so-called "$V_H 3$ class" (i.e. Nanobodies with a high degree of sequence homology to human germline sequences of the $V_H 3$ class such as DP-47, DP-51 or DP-29), which Nanobodies form a preferred aspect of this invention. It should however be noted that the invention in its broadest sense generally covers any type of Nanobody directed against ion channels, and for example also covers the Nanobodies belonging to the so-called "V$_H$4 class" (i.e. Nanobodies with a high degree of sequence homology to human germline sequences of the V$_H$4 class such as DP-78), as for example described in the U.S. provisional application 60/792,279 by Ablynx N.V. entitled "DP-78-like Nanobodies" filed on Apr. 14, 2006.

Generally, Nanobodies (in particular V$_{HH}$ sequences and partially humanized Nanobodies) can in particular be characterized by the presence of one or more "Hallmark residues" (as described herein) in one or more of the framework sequences (again as further described herein). Thus, generally, a Nanobody can be defined as an immunoglobulin sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which one or more of the Hallmark residues are as further defined herein.

In particular, a Nanobody can be an immunoglobulin sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which the framework sequences are as further defined herein.

In particular, a Nanobody can be an immunoglobulin sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which the framework sequences are as further defined herein.

More in particular, a Nanobody can be an immunoglobulin sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:

i) preferably one or more of the amino acid residues at positions 11, 37, 44, 45, 47, 83, 84, 103, 104 and 108 according to the Kabat numbering are chosen from the Hallmark residues mentioned in Table B-2 below;

and in which:

ii) said immunoglobulin sequence has at least 80% amino acid identity with at least one of the immunoglobulin sequences of SEQ ID NO's: 1 to 22, in which for the purposes of determining the degree of amino acid identity, the amino acid residues that form the CDR sequences (indicated with X in the sequences of SEQ ID NO's: 1 to 22) are disregarded.

In these Nanobodies, the CDR sequences are generally as further defined herein.

Thus, the invention also relates to such Nanobodies that can bind to (as defined herein) and/or are directed against an ion channel, to suitable fragments thereof, as well as to polypeptides that comprise or essentially consist of one or more of such Nanobodies and/or suitable fragments.

SEQ ID NO's: 705 to 788, more preferably SEQ ID NO's 726 to 750, 753 to 758, 762 to 764, 772 to 773, 775, or 778 to 780 (see Table A-1) give the immunoglobulin sequences of a number of V$_{HH}$ sequences that have been raised against an ion channel.

TABLE A-1

Preferred VHH sequences or Nanobody sequences (also referred herein as a sequence with a particular name or SEQ ID NO: X, wherein X is a number referring to the relevant immunoglobulin sequence):

| Name | SEQ ID NO: X, wherein X = | P2X7 function | Family | IMMUNGLOBULIN SEQUENCE |
|---|---|---|---|---|
| P2X7PMP2C4 | 705 | binder | 1 | EVQLVESGGDVVQAGGSLRLSCLASGFT FDDYAIGWFRQAPGKEREGISCISSTGNV FYADSVKGRFTISSDKEKNTLYLQMNSLK PEDTAVYHCAAGHFTVDSGKVLLRTDISS WGQGTQVTVSS |
| P2X7PMP2A6 | 706 | Binder | 1 | EVQLVESGGDVVQAGGSLRLSCLASGFT FDDYAIGWFRQAPGKEREGISCISSTGNV FYADSVKGRFTISSDKEKNTLYLQMNSLE PEDTAVYHCAAGHFTVDSGKVLLRTDISS WGQGTQVTVSS |
| P2X7PMP4D5 | 707 | Binder | 1 | EMQLVESGGDVVQAGGSLRLSCLASGFT FDDYAIGWFRQAPGKEREGISCISSTGNV FYADSVKGRFTISSDKEKNTLYLQMNSLK PEDTAVYHCAAGHFTVDSGKVLLRTDISS WGQGTQVTVSS |
| P2X7PMP20E8 | 708 | Binder | 1 | EVQLVESGGDVVQAGGSLRLSCLASGFT FDDYAIGWFRQAPGKEREGISCISSTGNV FYADSVKGRFTISSDKEKNTLYLQMNSLK PGDTAVYHCAAGHFTVDSGKVLLRTDISS WGQGTQVTVSS |
| P2X7PMP16H8 | 709 | Binder | 1 | EVQLVESGGDVVQAGGSLRLSCLASGFT FDDYAIGWFRQAPGKEREGISCISSTGNV FYADSVKGRLTISSDKEKNTLYLQMNSLK |

TABLE A-1-continued

Preferred VHH sequences or Nanobody sequences (also referred herein as a sequence with a particular name or SEQ ID NO: X, wherein X is a number referring to the relevant immunoglobulin sequence):

| Name | SEQ ID NO: X, wherein X = | P2X7 function | Family | IMMUNGLOBULIN SEQUENCE |
|---|---|---|---|---|
| | | | | PEDTAVYHCAAGHFTVDSGKVLLRTDISSWGQGTQVTVSS |
| P2X7PMP16B10 | 710 | Binder | 1 | EVQLVESGGDVVQAGGSLRLSCLASGFTFDDYAIGWFRQAPGKEREGISCISSTGNVFYADSVKGRFTISSDKEKNTLYLQMDSLKPEDTAVYHCAAGHFTVDSGKVLLRTDISSWGQGTQVTVSS |
| P2X7PMP4G6 | 711 | binder | 1 | EVQLVESGGDVVQAGGSLRLSCLASGFTFDDYAIGWFRQAPGKEREGISCISSTGNVFYADSVKGRFTISSDKEKNTLYLQMNSLKPEDTAVYHCAAGHFTVDSGKVLLRTDVSSWGQGTQVTVSS |
| P2X7PMP1A8 | 712 | Binder | 2 | EVQLVESGGGLVQTGGSLRLSCAASGFTLDDYAIAWFRQAPGKEREGVSILSSIGKTFYADSVKDRFSITADGAKTTVFLQMNSLKPGDTAIYYCVAGHFVYNDGAISLNTARGSGFWGQGAQVTVSS |
| P2X7PMP1C9 | 713 | Binder | 2 | EVQLVESGGGLVQTGGSLRLSCAASGFTLDDYAIAWFRQAPGKEREGVSILSSIGKTFYADSVKDRFSITADGAKTTVFLQMNSLKPEDTAIYYCVAGHFVYNDGAISLNTARGSGFWGQGAQVTVSS |
| P2X7PMP20B10 | 714 | Binder | 2 | EVQLVESGGGLVQTGGSLRLSCAASGFTLDDYAIAWFRQAPGKEREGVSILSSIGKTFYADSVKDRFSITADGAKTTVFLQMNSLKPEDTAIYYCVAGHFVYNDGAISLNTARGSGFWGQGTQVTVSS |
| P2X7PMP20C9 | 715 | Binder | 2 | EVQLVESGGGLVQTGGSLRLSCAASGFTLDDYAIAWFRQAPGKEREGVSILSSIGKTFYADSAKDRFSITADGAKTTVFLQMNSLKPEDTAIYYCVAGHFVYNDGAISLNTARGSGFWGQGTQVTVSS |
| P2X7PMP5A1 | 716 | Binder | 3 | EVQLVESGGGLVQAGGSLRLSCAASERTYSMGWFRQAPGKEREFVAGSGWDGIPTRYADSVKGRLTISRDNAKNTVSLQMSGLKPEDTAIYYCATGTSVYHYQYWGQGTQVTVSS |
| P2X7PMP5B1 | 717 | binder | 3 | EVQLVESGGGLVQAGGSLRLSCAASERTYSMGWFRQAPGKEREFVAGSGWDGIPTRYADSVKGRFTISRDNAKNTVSLQMSGLKPEDTAIYYCATGTSVYHYQYRGQGTQVTVSS |
| P2X7PMP11G1 | 718 | Binder | 3 | EVQLVESGGGLVQAGGSLRLSCAASERTYSMGWFRRAPGKEREFVAGSGWDGIPTRYADSVKGRFTISRDNAKNTVSLQMSGLKPEDTAIYYCATGTSVYHYQYWGQGTQVTVSS |
| P2X7PMP11A1 | 719 | Binder | 3 | EVQLVESGGGLVQAGGSLRLSCAASERTYSVGWFRQAPGKEREFVAGSGWDGTPTRYADSVKGRFTISRDNAKNTVSLQMSGLKPEDTAIYYCATGTSVYHYQYWGQGTQVTVSS |
| P2X7PMP7E2 | 720 | Binder | 3 | EVQLVESGGGLVQAGGSLRLSCAAPERTYSMGWFRQAPGKEREFVAGSGWDGIPTRYADSVKGRFTISRDNAKNTVSLQMSGLKPEDTAIYYCATGTSVYHYQYWGQGTQVTVSS |

TABLE A-1-continued

Preferred VHH sequences or Nanobody sequences (also referred herein as a sequence with a particular name or SEQ ID NO: X, wherein X is a number referring to the relevant immunoglobulin sequence):

| Name | SEQ ID NO: X, wherein X = | P2X7 function | Family | IMMUNGLOBULIN SEQUENCE |
|---|---|---|---|---|
| P2X7PMP5F1 | 721 | Binder | 3 | EVQLVESGGGLVQAGGSLRLSCAASERT YSMGWFRQAPGKEREFVAGSGWDGIPT RYADSVKGRFTISRDNAKNTVSLQMSGL KPEDTAIYYCATGTSVYHYQYWGQGTQV TVSS |
| P2X7PMP7F3 | 722 | Binder | 3 | EVQLVESRGGLVQAGGSLRLSCAASERT YSMGWFRQAPGKEREFVAGSGWDGIPT RYADSVKSRFTISRDNAKNTVSLQMSGLK PEDTAIYYCATGTSVYHYQYWGQGTQVT VSS |
| P2X7PMP13B2 | 723 | binder | 3 | EVQLVESGGGLVQAGGSLRLSCAASERT YSMGWFRQAPGKEREFVAGSGWDGIPT RYADSVKGRFTISRDNAKNAVSLQMSGL KPEDTAIYYCATGTSVYHYQYWGQGTQV TVSS |
| P2X7PMP11D3 | 724 | Binder | 3 | EVQLVESGGGLVQPGGSLRLSCAASERT YSMGWFRQAPGKEREFVAGSGWDGIPT RYADSVKGRFTISRDNAKNTVSLQMSGL KPEDTAIYYCATGTSVYHYQYWGQGTQV TVSS |
| P2X7PMP7F1 | 725 | Binder | 3 | EVQLVESGGGLVQAGGSLRLSCAASERT YSMGWFRQAPGKEREFVAGSGWDGIPT RYADSVKGRFTISRDNAKSTVSLQMSGL KPEDTAIYYCATGTSVYHYQYWGQGTQV TVSS |
| P2X7PMP4B4 | 726 | Enhancer | 4 | EVQLVESGGGLVQAGGSLRLSCAASGRT VSDYGMGWFRQAPGKLREFVASINWSGI YTRYIDSVEGRFTISRDNTKNTLYLQMNN LKAEDTAVYYCAYFLGPNWYSNYGRPSS YDFYGQGTQVTVSS |
| P2X7PMP19A7 | 727 | Enhancer | 4 | KVQLVESGGGLVQAGGSLRLSCAASGRT VSDYGMGWFRQAPGKLREFVASINWSGI YTRYIDSVEGRFTISRDNTKNTLYLQMNN LRAEDTAVYYCAYFLGPNWYSNYGRPSS YDFYGQGTQVTVSS |
| P2X7PMP19A8 | 728 | Enhancer | 4 | EVQLMESGGGLVQAGGSLRLSCAASGR TVSDYGMGWFRQAPGKLREFVASINWS GIYTRYIDSVEGRFTISRDNTKNTLYLQMN NLKAEDTAVYYCAYFLGPNWYSNYGRPS SYDFYGQGTQVTVSS |
| P2X7PMP19D12 | 729 | Enhancer | 4 | EVQLVESGGGLVQAGGSLRLSCAASGRT VSDYGMGWFRQAPGKLREFVASINWSGI YTRYIDSVEGRFTISRDNTKNTLYLQMNN LKAEDTAVYYCAYFLGPNWYSNYGRPSS YGFYGQGTQVTVSS |
| P2X7PMP20B8 | 730 | Enhancer | 4 | EVQLVESGGGLVQAGGSLRLSCAASGRT VSDYGMGWFRQAPGKECEFVASINWSG TYTRYIDSVEGRFTISRDNTENTLYLQMN NLKAEDTAVYYCAYFLGPNWYSDYGRPS SYDFYGQGTQVTVSS |
| P2X7PMP4G4 | 731 | Enhancer | 4 | EVQLMESGGGLVQAGGPLRLSCAASGR TVSDYGMGWFRQAPGKEREFVASINWS GTYTRYIDSVEGRFTISRDNTENTLYLQM NNLKAEDTAVYYCAYFLGPNWYSDYGRP SSYDFYGQGTQVTVSS |
| P2X7PMP8G11 | 732 | Blocker | 5, 1 | AVQLVESGGGLVQAGGSLRLSCAASGNF FRVNTMAWYRQAPGKQRELVADITRGDR TNYADTVNGRFTISRDNVRNTVYLQMNG |

TABLE A-1-continued

Preferred VHH sequences or Nanobody sequences (also referred herein as a sequence with a particular name or SEQ ID NO: X, wherein X is a number referring to the relevant immunoglobulin sequence):

| Name | SEQ ID NO: X, wherein X = | P2X7 function | Family | IMMUNGLOBULIN SEQUENCE |
|---|---|---|---|---|
| | | | | LRPEDTAAYYCYAVIELGVLEPRDYWGQGTQVTVSS |
| P2X7PMP6A11 | 733 | Blocker | 5, 2 | EVQLVESGGGLVQAGGSLRLSCAASGNFFRVNTMAWYRQAPGKQRELVADITRGDRTNYADTVNGRFTISRDNVRNTVYLQMNGLKPEDTAAYYCYARIELGVLEPRDYWGQGTQVTVSS |
| P2X7PMP8E6 | 734 | Blocker | 5, 2 | EVQLVESGGGLVQAGGPLRLSCAASGNFFRVNTMAWYRQAPGKQRELVADITRGDRTNYADTVNGRFTISRDNVRNTVYLQMNGLKPEDTAAYYCYARIELGVLEPRDYWGQGTQVTVSS |
| P2X7PMP12A11 | 735 | Blocker | 5, 2 | EVQLVESGGGLVQAGGSLRLSCAASGSFFRVNNMAWYRQAPGKQRELVADITRGDRTNYADSVNGRFTISRDNVRNTVYLQMNGLKPEDTAVYYCYARIELGVLEPRDYWGQGTQVTVSS |
| P2X7PMP14F6 | 736 | Blocker | 5, 2 | EVQLVESGGGLVQAGGPLRLSCAASGSFFRVNNMAWYRQAPGKQRELVADITRGDRTNYADSVNGRFTISRDNVRNTVYLQMNGLKPEDTAVYYCYARIELGVLEPRDYWGQGTQVTVSS |
| P2X7PMP8B4 | 737 | Blocker | 5, 2 | EVQLVESGGGLVQAGGSLRLSCAASGNFFRVNTMAWYRQAPGKQRELVADITRGDRTNYADTVNGRFTISRDNVRNTVYLQMNSLKPEDTAAYYCYARIELGVLEPRDYWGQGTQVTVSS |
| P2X7PMP14G4 | 738 | Blocker | 5, 2 | EVQLVESGGGLVQAGGSLGLSCAASGNFFRVNTMAWYRQAPGKQRELVADITRGDRTNYADTVNGRFTISRDNVRNTVYLQMNGLKPEDTAAYYCYARIELGVLEPRDYWGQGTQVTVSS |
| P2X7PMP8H5 | 739 | Blocker | 5, 2 | EMQLVESGGGLVQAGGSLRLSCAASGNFFRVNTMAWYRQAPGKQRELVADITRGDRTNYADTVNGRFTISRDNVRNTVYLQMNGLKPEDTAAYYCYARIELGVLEPRDYWGQGTQVTVSS |
| P2X7PMP14F10 | 740 | Blocker | 5, 2 | EVQLVESGGGLVQAGGSLRLLCAASGSFFRVNNMAWYRQAPGKQRELVADITRGDRTNYADSVNGRFTISRDNVRNTVYLQMNGLKPEDTAVYSCYARIELGILEPRDYWGQGTQVTVSS |
| P2X7PMP8A11 | 741 | Blocker | 5, 2 | EVQLVESGGGLVQAGGSLRLSCAASGSFFRVNNMAWYRQAPGKQRELVADITRGDRTNYADSVNGRFTISRDNVRNTVYLQMDGLKPEDTAVYYCYARIELGVLVPRDYWGQGTQVTVSS |
| P2X7PMP8H6 | 742 | Blocker | 5, 2 | EVQLVESGGGLVQAGGSLRLSCAASGSFFRVNNMAWYRQAPGKQRELVADITRGDRTNYADSVNGRFTISRDNVRNTVYLQMNGLKPEDTAVYYCYARIELGPLVPRDYWGQGTQVTVSS |
| P2X7PMP8F5 | 743 | Blocker | 5, 2 | EVQLVKSGGGLVQAGGSLRLSCAASGSFFRVNNMAWYRQAPGKQRELVADITRGDRTNYADSVNGRFTISRDNVRNTVYLQMNGLKPEDTAVYYCYARIELGPLVPRDYWGQGTQVTVSS |

TABLE A-1-continued

Preferred VHH sequences or Nanobody sequences (also referred herein as a sequence with a particular name or SEQ ID NO: X, wherein X is a number referring to the relevant immunoglobulin sequence):

| Name | SEQ ID NO: X, wherein X = | P2X7 function | Family | IMMUNGLOBULIN SEQUENCE |
|---|---|---|---|---|
| P2X7PMP8G12 | 744 | Blocker | 5, 3 | KVQLVESGGGLVQAGGSLRLSCAASGSFFRVNNMAWYRQGPGKQRELVADITRGDRTNYADSVNGRFTISRDNVRNTVYLQMNGLKPEDTAVYYCYATIELGVLEPRDYWGQGTQVTVSS |
| P2X7PMP8B12 | 745 | Blocker | 5, 3 | EVQLVESGGGLVQAGGSLRLSCAASGSFFRVNVMAWYRQGPGKQRELVADITRGDRTNYADSVNGRFTISRDNVRNTVYLQMNGLKPEDTAVYYCYATIELGVLEPRDYWGQGTQVTVSS |
| P2X7PMP14G11 | 746 | Blocker | 5, 3 | EVQLVESGGGLVKPGGSLRLSCAASGSFFRVNNMAWYRQGPGKQRELVADITRGDRTNYADSVNGRFTISRDNVRNTVYLQMNGLKPEDTAVYYCYATIELGVLEPRDYWGQGTQVTVSS |
| P2X7PMP8C12 | 747 | Blocker | 5, 3 | EVQLVESGGGLVQAGGSLRLSCAASGSFFRVNNMAWYRQAPGKQRELVADITRGDRTNYADSVNGRFTISRDNVRNTVYLQMNGLKPEDTAVYYCYATIELGVLEPRDYWGQGTQVTVSS |
| P2X7PMP8H10 | 748 | Blocker | 5, 3 | EVQLVESGGGLVQAGGSLRLSCAASGSFFRVNNMAWYRQGPGKQRELVADITRGDRTNYADSVNGRFTISRDNVRNTVYLQMNGLKPEDTAVYYCYATIELGVLEPRDYWGQGTQVTVSS |
| P2X7PMP8D10 | 749 | Blocker | 5, 3 | EVQLVESGGGLVQPGGSLRLSCAASGSFFRVNNMAWYRQAPGKQRELVADITRGDRTNYADSVNGRFTISRDNVRNTVYLQMNGLKPEDTAVYYCYATIELGVLEPRDYWGQGTQVTVSS |
| P2X7PMP8H4 | 750 | Blocker | 5, 3 | EVQLVESGGGLVQAGGSLRLSCAASGSFFRVNNMAWYRQGPGKQRELVADITRGDRTNYADSVNGRFTISRDNVRNTVYLQMDGLKPEDTAVYYCYATIELGVLVPRDYWGQGTQVTVSS |
| P2X7PMP18D12 | 751 | Binder | 6 | EVQLVESGGDLVQAGGSLKLSCVVSGVTFDDGTIGWFRQAPGKEREGIACISRVDGTTYYRDSVKGRFTVSSDSAKTTVNLQMNSLKPEDTAVYYCAADYASLCTIETGYGSLYDYWGRGTQVTVSS |
| P2X7PMP4B3 | 752 | Binder | 6 | EVQLVESGGDLVQAGGSLKLSCVVSGVTFDDGTIGWFRQAPGKEREGIACISRVDGTTYYRDSVKGRFTVSSDSAKTTVNLQMNSLKPEDTAVYYCAADYASLCTIETGYGSLYDYWGKGTQVTVSS |
| P2X7PMP8C7 | 753 | Partial Blocker | 7 | EMQLVESGGGLVQAGGSLRLSCAASGRTFSSLAMGWLRQAPGKEREFVSGISRGGTSTYYADSVKGRFTISRDNAKNTMYLQMNSLKPEDTAVYYCAGSPVLSIVLDTRGLEYWGQGTQVTVSS |
| P2X7PMP8E7 | 754 | Partial Blocker | 7 | EVQLVESGGGLVQAGGSLRLSCAASGRTFSSLAMGWLRQAPGKEREFVSGISRGGTSTYYADSVKGRFTISRDNAKNTMYLQMNSLKPEDTAVYYCAGSPVLSIVLDTRGLEYWGQGTQVTVSS |
| P2X7PMP6D7 | 755 | Partial Blocker | 7 | EVQLVESGGGLVQAGGSLRLSCAASGRTFSSLAMGWLRQAPGKEREFVSGISRGGTSTYYADSVKGRLTISRDNAKNTMYLQMN |

TABLE A-1-continued

Preferred VHH sequences or Nanobody sequences (also referred herein as a sequence with a particular name or SEQ ID NO: X, wherein X is a number referring to the relevant immunoglobulin sequence):

| Name | SEQ ID NO: X, wherein X = | P2X7 function | Family | IMMUNGLOBULIN SEQUENCE |
|---|---|---|---|---|
| | | | | SLKPEDTAVYYCAGSPVLSIVLDTRGLEY WGQGTQVTVSS |
| P2X7PMP7D6 | 756 | Enhancer | 8 | EVQLVESGGGLVQAGGSLRLSCAASGRT FGSSPVGWFRQAPGKERDFVATISWNG VDTHYLDSVKGRFTISRDNAKNTVHLQM HILKPEDTALYYCAASTSGSVYLPYRVYQ YDSWGQGTQVTVSS |
| P2X7PMP7E8 | 757 | Enhancer | 8 | EVQLVESGGGLVQAGGSLRLSCAASGRT FSSSPVGWFRQAPGKERDFVATISWNGV DTHYLDSVKGRFTISRDNALNTVHLQMHI LKPEDTALYYCAASTSGSAYLPYRVYQYD SWGQGTQVTVSS |
| P2X7PMP7F5 | 758 | Enhancer | 8 | EVQLVESGGGLVQAGGSLRLSCAASGRT FSSSPVGWFRQAPGKERDFVATISWNGV DTHYLDSVKGRFTISRDNALNTVHLQMHI LKPEDTALYYCAASTSGSAYLPYRVHQY DSWGQGTQVTVSS |
| P2X7PMP7F9 | 759 | Binder | 9 | EVQLVESGGGLVQAGASLRVSCAASART GSYTMGWFRQAPGKEREFVSTISWNGA STVYADSVKGRFTISRDNAKNTVSLQMN SLKPEDTAVYYCAGSISSYSSRWQDDYE YWGQGTQVTVSS |
| P2X7PMP7A4 | 760 | Binder | 9 | EVQLVESGGGLVQAGGSLRVSCAASART GSYSMGWFRQAPGKEREFVSTISWNGA DTVYADSVKGRFTISRDNAKDTVYLQMN SLKPEDTAVYYCAGSITSYVSTWQHDYE YWGQGTQVTVSS |
| P2X7PMP7B4 | 761 | Binder | 10 | EVQLVESGGGLVQAGGSLRLSCAASGRN FGSYTMAWFRQAPGKGREFVSTINWSG GDTDYADSVKGRFTISRDNAKNTVYLQM DSLKPEDTAVYYCAAGLEYMSTIRYTYEY WGQGTQVTVSS |
| P2X7PMP7H6 | 762 | Blocker | 11 | EVQLVESGGGLVQPGGSLRLSCVVSGS MYRIDNMGWYRQAPGKQRELVATVRG DITNYADSVKGRFTIGRDNAKNTVYLQMN SLKPADTAVYYCNIDSYIIGAGVRDYWGR GTQVTVSS |
| P2X7PMP7G5 | 763 | Enhancer | 12 | EVQLVESGGGLVQSGGSLRLSCAGSGFS YYIIGWFRQAPGKEREEVSCIRVTDGSTY YTNSVKGRFTMSRDNAENTVYLQMNSLK PEDTAVYSCATECQRWAYPNRIGARGQ GTQVTVSS |
| P2X7PMP13F4 | 764 | Enhancer | 12 | EVQLVESGGGLVQSGGSLRLSCAGSGFS YYIIGWFRQAPGKEREEVSCIRVTDGSTY HTNSVKGRFTMSRDNAENTVYLQMNSLK PEDTAVYSCATECQRWAYPNRIGARGQ GTQVTVSS |
| P2X7PMP7D8 | 765 | Binder | 13 | EVQLVESGGGLVQPGGSLRLSCAASGLT LEYYNIGWFRQAPGKEREGVACIDWTEG STFYVDSVKGRFTISTDNAKNTVYLHMNS LEPEDTAVYYCAAGWGRVITVQHMCADR SLFTSWGQGTQVTVSS |
| P2X7PMP13B8 | 766 | Binder | 13 | EVQLVESGGGLVQPGGSLRLSCAASGLT LTYYNIGWFRQAPGKEREGVSCIDWTDG TTFYADSVKGRFTISTDNAKNTVYLHLNS LEPEDTAVYYCAAGWGRVMTVQHMCAD RSLFTSWGQGTQVTVSS |

TABLE A-1-continued

Preferred VHH sequences or Nanobody sequences (also referred herein as a sequence with a particular name or SEQ ID NO: X, wherein X is a number referring to the relevant immunoglobulin sequence):

| Name | SEQ ID NO: X, wherein X = | P2X7 function | Family | IMMUNGLOBULIN SEQUENCE |
|---|---|---|---|---|
| P2X7PMP7D5 | 767 | Binder | 14 | EVQLVESGGGLVQAGDSLRLSCAASGRTFSSVAVGWFRQAPGKERDFVAWISWSGDSTYYADSVKGRFTASRDNVNNTVYLQMNSLKPEDTADYYCAAAWKYDRASYDFPEAYDYWGQGTQVTVSS |
| P2X7PMP16D9 | 768 | Binder | 15 | EVQLVESGGGLVQAGGSLRLSCAASPGTFSSFNMGWFRQTPGKEREFVAATSWSDISTYYADSVKGRFTISRDNAKNTVTLEMNSLKPEDTAVYYCAAGYYRGGYLGYRLTLEGSYDVWGQGTQVTVSS |
| P2X7PMP1G6 | 769 | Binder | 15 | EVQLVESGGGLVQAGGSLRLSCAASPGAFSSFNMGWFRQTPGKEREFVAATSWSDISTYYADSVKGRFTISRDNAKNTVTLEMNSLKPEDTAVYYCAAGYYRGGYLGYRLTLEGSYDVWGQGTQVTVSS |
| P2X7PMP19E3 | 770 | Binder | 15 | EMQLVESGGGLVQAGGSLRLSCAASPGTFSSFNMGWFRQTPGKEREFVAATSWSDISTYYADSVKGRFTISRDNAKNTVTLEMNSLKPEDTAVYYCAAGYYRGGYLGYRLTLEGSYDVWGQGTQVTVSS |
| P2X7PMP19C2 | 771 | Binder | 15 | EVQLVKSGGGLVQAGGSLRLSCAASPGTFSSFNMGWFRQTPGKEREFVAATSWSDISTYYADSVKGRFTISRDNAKNTVTLEMNSLKPEDTAVYYCAAGYYRGGYLGYRLTLEGSYDVWGQGTQVTVSS |
| P2X7PMP6B7 | 772 | Partial Blocker | 16 | EVQLVESGGGLVQAGGSLRLSCVVSGRTFSAMGWFRQAPGKEREFVATVGWNPMNSYYGDSVKGRFTIFRDNAKNTVYLQMNSLKPEDTAVYYCAGSGSLLDVTSEAVYTDWGQGTQVTVSS |
| P2X7PMP14D5 | 773 | Enhancer | 17 | KVQLVESGGGLVQAGGSLRLSCAASGSPISSYAMGWYRQAPGKPRELVARIYTGGTAWYEDSVKGRFTISRDNAQNTVYLQMNLKSEDTAVYYCHGRVRYDYWGQGTQVTVSS |
| P2X7PMP13G5 | 774 | Binder | 18 | EVQLVESGGGLVQAGGSLRLSCAASDRTFGSSAMGWFRQAPGKDRDFVAAISWSGSSTHYADSVKGRFTISRDNAKNTMYLQMNSLKPADTAVYTCAASRRAYLPAKVGEYDFWGQGTQVTVSS |
| P2X7PMP13B5 | 775 | Partial Blocker | 19 | EVQLVESGGGLVQAGDSLRLSCAASGRTFSSYAMGWFRQAPGKEREFVAAISLSGSMTYYADSMKGRFTISRDNAKNTVYLQMNSLKPEDTAVYYCAAEELGDLGYLAYRYDYWGQGTQVTVSS |
| P2X7PMP13F6 | 776 | Binder | 20 | EVQLVESGGGLVQPGGSLRLSCAASGFTFSTNIMTWVRQAPGKGLEWISTINSGGGTTTYADSVRGRFTISRDNAKNMLYLQMSSLKPEDTALYYCITPRGVKGRGTQVTVSS |
| P2X7PMP13G4 | 777 | Binder | 21 | EVQLVESGGGLVQAGGSLRLSCAASDRTFGSSTMGWFRQPPGKNREFVATIAWSATTTHYADAVKGRFTVSRDNALNTVYLQMNSLKPEDTAVYYCAATLTWLGIHEYEYNTWGQGTQVTVSS |
| P2X7PMP13A7 | 778 | Blocker | 22 | EVQLVESGGGLVQPGESLRLSCTASRFMLDYYDIGWFRQAPGKEREGVSCRFTNDGSTAYADSVKGRFTISRDIVKHTVYLQMNS |

TABLE A-1-continued

Preferred VHH sequences or Nanobody sequences (also referred herein as a sequence with a particular name or SEQ ID NO: X, wherein X is a number referring to the relevant immunoglobulin sequence):

| Name | SEQ ID NO: X, wherein X = | P2X7 function | Family | IMMUNGLOBULIN SEQUENCE |
|---|---|---|---|---|
| | | | | LQPEDTAVYYCAAGPLTKRRQCVPGDFS MDFWGEGTLVTVSS |
| P2X7PMP13E9 | 779 | Blocker | 22 | EVQLVESGGGLVQPGESLRLSCTASRFD LDYYDIAWFRQAPGKEREGVSCSFTNDG STYYADSVKGRFTMSRNNDHRTVYLQMT SLQPEDTAVYTCAVGPLTRRRQCVPGDF SMDFWGEGTLVTVSS |
| P2X7PMP13G9 | 780 | Blocker | 23 | EVQLVESGGGLVQAGGSLRLSCVASGRT FSILTMGWFRQAPGKEREFVAAISGIGAIH YADSVKGRFTLSRDNARNTVSLHMNSLK PEDTAVYYCAAKANYESPSRETSYAYWG QGTQVTVSS |
| P2X7PMP20H9 | 781 | Binder | 24 | EVQLVESGGRVMQTGGSLRLSCAASGH TFNDYSMGWFRQAPGKELEFLAGINWSG MSTWYADSVKDRFTISRDNNKNTVFLQM NSLEPGDTAVYYCAARQWISTIILTAPSQY DYWGQGTQVTVSS |
| P2X7PMP20A11 | 782 | Binder | 24 | EVQLVESGGRVMQTGGSLRLSCAASGH TFNDYNMGWFRQAPGKELEFLAGINWS GMSTWYADSVKDRFTISRDNNKNTVFLQ MNSLEPGDTAVYYCAARQWISTIILTAPS QYDYWGQGTQVTVSS |
| P2X7PMP18C1 | 783 | Binder | 25 | EVQLVESGGDLVQPGGSLRLSCVASGFA LEEHAIGWFRQAPGKEREGVSLSSYLGA AYYATSVKGRFTISRDNAKNTVTLQMNSL KPEDTAVYYCARGHFTYDDGRITIRSVDY WGKGTLVTVSS |
| P2X7PMP18A7 | 784 | Binder | 25 | EVQLVESGGDLVQPGGSLRLSCVASGFA LEEHAIGWFRQAPGKEREGVSLSSYVGA VYYATSVKGRFTISRDNAKNTVYLQMNSL KPEDTAVYYCARGHFTYDDGRISIRSVDH WGKGTLVTVSS |
| P2X7PMP19H4 | 785 | Binder | 26 | EVQLVESGGGLVQAGGSLRLSCVASGRT LSTAVMGWFRQAPGKERGLVAMISWSG SMTYYAKSVKGRFTISRDNAKNTMYLQM NSLKPEDTAVYYCAADMGGGPPDGDAM PRLSSGMDYWGKGTLVTVSS |
| P2X7PMP16G3 | 786 | Binder | 27 | EVQLVESGGGLVQAGGSLRLSCAASGND FARFSIDAMGWYRQAPGKQRELVATVTE DGTKNYADSVKGRATISRDDANNSMYLE MNTLKPEDTAVYYCKMGGLIDGAAPYEF WGRGTQVTVSS |
| P2X7PMP15C7 | 787 | Binder | 28 | EMQLVESGGGWVQAGGSLRLSCASSGS IFSAGAMGWYRQPAGKQRELVADITLGG STNYADSVKGRFTISRDNAKNAVFLQMN SLKPEDTAVYYCNGLINTFARKIPRYAWG QGTQVTVSS |
| P2X7PMP16F5 | 788 | Binder | 29 | EVQLVESGGGLVQAGGSLRLSCAASGPT TFGRYTMGWFRQAPGREREFVAAISWIG GRTYYVDVVKGRFTISRDNAKKMVYLQM NSLKPDDTAVYHCAAAFQALGSPREYDY WGQGTQVTVSS |

In particular, the invention in some specific aspects provides:

immunoglobulin sequences that are directed against (as defined herein) an ion channel and that have at least 80%, preferably at least 85%, such as 90% or 95% or more sequence identity with at least one of the immunoglobulin sequences of SEQ ID NO's: 705 to 788, more preferably SEQ ID NO's 726 to 750, 753 to 758, 762 to 764, 772 to 773, 775, or 778 to 780, more preferably SEQ ID NO's 726 to 750, 753 to 758, 762 to 764, 772 to 773, 775, or 778 to 780 (see Table A-1). These immunoglobulin sequences may further be such that they neutralize binding of the cognate ligand to an ion channel; and/or compete with the cognate ligand for binding to an ion channel; and/or are directed against an interaction site (as defined herein) on an ion channel (such as the ligand binding site);

immunoglobulin sequences that cross-block (as defined herein) the binding of at least one of the immunoglobulin sequences of SEQ ID NO's: 705 to 788, more preferably SEQ ID NO's 726 to 750, 753 to 758, 762 to 764, 772 to 773, 775, or 778 to 780, more preferably SEQ ID NO's 726 to 750, 753 to 758, 762 to 764, 772 to 773, 775, or 778 to 780 (see Table A-1) to an ion channel and/or that compete with at least one of the immunoglobulin sequences of SEQ ID NO's: 705 to 788, more preferably SEQ ID NO's 726 to 750, 753 to 758, 762 to 764, 772 to 773, 775, or 778 to 780, more preferably SEQ ID NO's 726 to 750, 753 to 758, 762 to 764, 772 to 773, 775, or 778 to 780 (see Table A-1) for binding to an ion channel. Again, these immunoglobulin sequences may further be such that they neutralize binding of the cognate ligand to an ion channel; and/or compete with the cognate ligand for binding to an ion channel; and/or are directed against an interaction site (as defined herein) on an ion channel (such as the ligand binding site);

which immunoglobulin sequences may be as further described herein (and may for example be Nanobodies); as well as polypeptides of the invention that comprise one or more of such immunoglobulin sequences (which may be as further described herein, and may for example be bispecific and/or biparatopic polypeptides as described herein), and nucleic acid sequences that encode such immunoglobulin sequences and polypeptides. Such immunoglobulin sequences and polypeptides do not include any naturally occurring ligands.

Accordingly, some particularly preferred Nanobodies of the invention are Nanobodies which can bind (as further defined herein) to and/or are directed against to an ion channel and which:

i) have at least 80% amino acid identity with at least one of the immunoglobulin sequences of SEQ ID NO's: 705 to 788, more preferably SEQ ID NO's 726 to 750, 753 to 758, 762 to 764, 772 to 773, 775, or 778 to 780, more preferably SEQ ID NO's 726 to 750, 753 to 758, 762 to 764, 772 to 773, 775, or 778 to 780 (see Table A-1), in which for the purposes of determining the degree of amino acid identity, the amino acid residues that form the CDR sequences are disregarded. In this respect, reference is also made to Table B-1, which lists the framework 1 sequences (SEQ ID NO's: 126 to 207), framework 2 sequences (SEQ ID NO's: 290 to 371), framework 3 sequences (SEQ ID NO's: 454 to 535) and framework 4 sequences (SEQ ID NO's: 618 to 699) of the Nanobodies of SEQ ID NO's: 705 to 788, more preferably SEQ ID NO's 726 to 750, 753 to 758, 762 to 764, 772 to 773, 775, or 778 to 780, more preferably SEQ ID NO's 726 to 750, 753 to 758, 762 to 764, 772 to 773, 775, or 778 to 780 (see Table A-1) (with respect to the amino acid residues at positions 1 to 4 and 27 to 30 of the framework 1 sequences, reference is also made to the comments made below. Thus, for determining the degree of amino acid identity, these residues are preferably disregarded);

and in which:

ii) preferably one or more of the amino acid residues at positions 11, 37, 44, 45, 47, 83, 84, 103, 104 and 108 according to the Kabat numbering are chosen from the Hallmark residues mentioned in Table B-2 below.

In these Nanobodies, the CDR sequences are generally as further defined herein.

Again, such Nanobodies may be derived in any suitable manner and from any suitable source, and may for example be naturally occurring $V_{HH}$ sequences (i.e. from a suitable species of Camelid) or synthetic or semi-synthetic immunoglobulin sequences, including but not limited to "humanized" (as defined herein) Nanobodies, "camelized" (as defined herein) immunoglobulin sequences (and in particular camelized heavy chain variable domain sequences), as well as Nanobodies that have been obtained by techniques such as affinity maturation (for example, starting from synthetic, random or naturally occurring immunoglobulin sequences), CDR grafting, veneering, combining fragments derived from different immunoglobulin sequences, PCR assembly using overlapping primers, and similar techniques for engineering immunoglobulin sequences well known to the skilled person; or any suitable combination of any of the foregoing as further described herein. Also, when a Nanobody comprises a $V_{HH}$ sequence, said Nanobody may be suitably humanized, as further described herein, so as to provide one or more further (partially or fully) humanized Nanobodies of the invention. Similarly, when a Nanobody comprises a synthetic or semi-synthetic sequence (such as a partially humanized sequence), said Nanobody may optionally be further suitably humanized, again as described herein, again so as to provide one or more further (partially or fully) humanized Nanobodies of the invention.

In particular, humanized Nanobodies may be immunoglobulin sequences that are as generally defined for Nanobodies in the previous paragraphs, but in which at least one amino acid residue is present (and in particular, in at least one of the framework residues) that is and/or that corresponds to a humanizing substitution (as defined herein). Some preferred, but non-limiting humanizing substitutions (and suitable combinations thereof) will become clear to the skilled person based on the disclosure herein. In addition, or alternatively, other potentially useful humanizing substitutions can be ascertained by comparing the sequence of the framework regions of a naturally occurring $V_{HH}$ sequence with the corresponding framework sequence of one or more closely related human $V_H$ sequences, after which one or more of the potentially useful humanizing substitutions (or combinations thereof) thus determined can be introduced into said $V_{HH}$ sequence (in any manner known per se, as further described herein) and the resulting humanized $V_{HH}$ sequences can be tested for affinity for the target, for stability, for ease and level of expression, and/or for other desired properties. In this way, by means of a limited degree of trial and error, other suitable humanizing substitutions (or suitable combinations thereof) can be determined by the skilled person based on the disclosure herein. Also, based on the foregoing, (the framework regions of) a Nanobody may be partially humanized or fully humanized.

In a preferred but non-limiting aspect, the invention relates to a Nanobody (as defined herein) against ion channels such as e.g. P2X7, which consists of 4 framework regions (FR1 to FR4 respectively) and 3 complementarity determining regions (CDR1 to CDR3 respectively), in which:

CDR1 is chosen from the group consisting of:

a) the immunoglobulin sequences of SEQ ID NO's: 208 to 289;

b) immunoglobulin sequences that have at least 80% amino acid identity with at least one of the immunoglobulin sequences of SEQ ID NO's: 208 to 289;
c) immunoglobulin sequences that have 3, 2, or 1 amino acid difference with at least one of the immunoglobulin sequences of SEQ ID NO's: 208 to 289;

and/or
CDR2 is chosen from the group consisting of:
d) the immunoglobulin sequences of SEQ ID NO's: 372 to 453;
e) immunoglobulin sequences that have at least 80% amino acid identity with at least one of the immunoglobulin sequences of SEQ ID NO's: 372 to 453;
f) immunoglobulin sequences that have 3, 2, or 1 amino acid difference with at least one of the immunoglobulin sequences of SEQ ID NO's: 372 to 453;

and/or
CDR3 is chosen from the group consisting of:
g) the immunoglobulin sequences of SEQ ID NO's: 536 to 617;
h) immunoglobulin sequences that have at least 80% amino acid identity with at least one of the immunoglobulin sequences of SEQ ID NO's: 536 to 617;
i) immunoglobulin sequences that have 3, 2, or 1 amino acid difference with at least one of the immunoglobulin sequences of SEQ ID NO's: 536 to 617;

or any suitable fragment of such an immunoglobulin sequence.

In particular, according to this preferred but non-limiting aspect, the invention relates to a Nanobody (as defined herein) against ion channels such as e.g. P2X7, which consists of 4 framework regions (FR1 to FR4 respectively) and 3 complementarity determining regions (CDR1 to CDR3 respectively), in which:
CDR1 is chosen from the group consisting of:
a) the immunoglobulin sequences of SEQ ID NO's: 208 to 289;
b) immunoglobulin sequences that have at least 80% amino acid identity with at least one of the immunoglobulin sequences of SEQ ID NO's: 208 to 289;
c) immunoglobulin sequences that have 3, 2, or 1 amino acid difference with at least one of the immunoglobulin sequences of SEQ ID NO's: 208 to 289;

and
CDR2 is chosen from the group consisting of:
d) the immunoglobulin sequences of SEQ ID NO's: 372 to 453;
e) immunoglobulin sequences that have at least 80% amino acid identity with at least one of the immunoglobulin sequences of SEQ ID NO's: 372 to 453;
f) immunoglobulin sequences that have 3, 2, or 1 amino acid difference with at least one of the immunoglobulin sequences of SEQ ID NO's: 372 to 453;

and
CDR3 is chosen from the group consisting of:
g) the immunoglobulin sequences of SEQ ID NO's: 536 to 617;
h) immunoglobulin sequences that have at least 80% amino acid identity with at least one of the immunoglobulin sequences of SEQ ID NO's: 536 to 617;
i) immunoglobulin sequences that have 3, 2, or 1 amino acid difference with at least one of the immunoglobulin sequences of SEQ ID NO's: 536 to 617;

or any suitable fragment of such an immunoglobulin sequences.

As generally mentioned herein for the immunoglobulin sequences of the invention, when a Nanobody of the invention contains one or more CDR1 sequences according to b) and/or c):
i) any amino acid substitution in such a CDR according to b) and/or c) is preferably, and compared to the corresponding CDR according to a), a conservative amino acid substitution (as defined herein);

and/or
ii) the CDR according to b) and/or c) preferably only contains amino acid substitutions, and no amino acid deletions or insertions, compared to the corresponding CDR according to a);

and/or
iii) the CDR according to b) and/or c) may be a CDR that is derived from a CDR according to a) by means of affinity maturation using one or more techniques of affinity maturation known per se.

Similarly, when a Nanobody of the invention contains one or more CDR2 sequences according to e) and/or f):
i) any amino acid substitution in such a CDR according to e) and/or f) is preferably, and compared to the corresponding CDR according to d), a conservative amino acid substitution (as defined herein);

and/or
ii) the CDR according to e) and/or f) preferably only contains amino acid substitutions, and no amino acid deletions or insertions, compared to the corresponding CDR according to d);

and/or
iii) the CDR according to e) and/or f) may be a CDR that is derived from a CDR according to d) by means of affinity maturation using one or more techniques of affinity maturation known per se.

Also, similarly, when a Nanobody of the invention contains one or more CDR3 sequences according to h) and/or i):
i) any amino acid substitution in such a CDR according to h) and/or i) is preferably, and compared to the corresponding CDR according to g), a conservative amino acid substitution (as defined herein);

and/or
ii) the CDR according to h) and/or i) preferably only contains amino acid substitutions, and no amino acid deletions or insertions, compared to the corresponding CDR according to g);

and/or
iii) the CDR according to h) and/or i) may be a CDR that is derived from a CDR according to g) by means of affinity maturation using one or more techniques of affinity maturation known per se.

It should be understood that the last three paragraphs generally apply to any Nanobody of the invention that comprises one or more CDR1 sequences, CDR2 sequences and/or CDR3 sequences according to b), c), e), f), h) or i), respectively.

Of the Nanobodies of the invention, Nanobodies comprising one or more of the CDR's explicitly listed above are particularly preferred; Nanobodies comprising two or more of the CDR's explicitly listed above are more particularly preferred; and Nanobodies comprising three of the CDR's explicitly listed above are most particularly preferred.

Some particularly preferred, but non-limiting combinations of CDR sequences, as well as preferred combinations of CDR sequences and framework sequences, are mentioned in Table B-1 below, which lists the CDR sequences and framework sequences that are present in a number of preferred (but non-limiting) Nanobodies of the invention. As will be clear to the skilled person, a combination of CDR1, CDR2 and CDR3 sequences that occur in the same clone (i.e. CDR1, CDR2 and CDR3 sequences that are mentioned on the same line in Table B-1) will usually be preferred (although the invention in its broadest sense is not limited thereto, and also comprises other suitable combinations of the CDR sequences mentioned in Table B-1). Also, a combination of CDR sequences and framework sequences that occur in the same clone (i.e. CDR sequences and framework sequences that are mentioned on the same line in Table B-1) will usually be preferred (although the invention in its broadest sense is not limited thereto, and also comprises other suitable combinations of the CDR sequences and framework sequences mentioned in Table B-1, as well as combinations of such CDR sequences and other suitable framework sequences, e.g. as further described herein).

Also, in the Nanobodies of the invention that comprise the combinations of CDR's mentioned in Table B-1, each CDR can be replaced by a CDR chosen from the group consisting of immunoglobulin sequences that have at least 80%, preferably at least 90%, more preferably at least 95%, even more preferably at least 99% sequence identity (as defined herein) with the mentioned CDR's; in which:

i) any amino acid substitution in such a CDR is preferably, and compared to the corresponding CDR sequence mentioned in Table B-1, a conservative amino acid substitution (as defined herein);

and/or ii) any such CDR sequence preferably only contains amino acid substitutions, and no amino acid deletions or insertions, compared to the corresponding CDR sequence mentioned in Table B-1;

and/or iii) any such CDR sequence is a CDR that is derived by means of a technique for affinity maturation known per se, and in particular starting from the corresponding CDR sequence mentioned in Table B-1.

However, as will be clear to the skilled person, the (combinations of) CDR sequences, as well as (the combinations of) CDR sequences and framework sequences mentioned in Table B-1 will generally be preferred.

TABLE B-1

Preferred combinations of CDR sequences, preferred combinations of framework sequences, and preferred combinations of framework and CDR sequences. ("ID" refers to the SEQ ID NO as used herein)

| ID FR1 | ID CDR1 | ID FR2 | ID CDR2 | ID FR3 | ID CDR3 | ID FR4 |
|---|---|---|---|---|---|---|
| 126 EVQLVESGGDVVQAGGSLRLSCLASGFTFD | 208 DYAIG | 290 WFRQAPGKEREGIS | 372 CISSTGNVFYADSVKG | 454 RFTISSDKEKNTLYLQMNSLKPEDTAVYHCAA | 536 GHFTVDSGKVLLRTDISS | 618 WGQGTQVTVSS |
| 127 EVQLVESGGDVVQAGGSLRLSCLASGFTFD | 209 DYAIG | 291 WFRQAPGKEREGIS | 373 CISSTGNVFYADSVKG | 455 RFTISSDKEKNTLYLQMNSLEPEDTAVYHCAA | 537 GHFTVDSGKVLLRTDISS | 619 WGQGTQVTVSS |
| 128 EMQLVESGGDVVQAGGSLRLSCLASGFTFD | 210 DYAIG | 292 WFRQAPGKEREGIS | 374 CISSTGNVFYADSVKG | 456 RFTISSDKEKNTLYLQMNSLKPEDTAVYHCAA | 538 GHFTVDSGKVLLRTDISS | 620 WGQGTQVTVSS |
| 129 EVQLVESGGDVVQAGGSLRLSCLASGFTFD | 211 DYAIG | 293 WFRQAPGKEREGIS | 375 CISSTGNVFYADSVKG | 457 RFTISSDKEKNTLYLQMNSLKPGDTAVYHCAA | 539 GHFTVDSGKVLLRTDISS | 621 WGQGTQVTVSS |
| 130 EVQLVESGGDVVQAGGSLRLSCLASGFTFD | 212 DYAIG | 294 WFRQAPGKEREGIS | 376 CISSTGNVFYADSVKG | 458 RLTISSDKEKNTLYLQMNSLKPEDTAVYHCAA | 540 GHFTVDSGKVLLRTDISS | 622 WGQGTQVTVSS |
| 131 EVQLVESGGDVVQAGGSLRLSCLASGFTFD | 213 DYAIG | 295 WFRQAPGKEREGIS | 377 CISSTGNVFYADSVKG | 459 RFTISSDKEKNTLYLQMDSLKPEDTAVYHCAA | 541 GHFTVDSGKVLLRTDISS | 623 WGQGTQVTVSS |
| 132 EVQLVESGGDVVQAGGSLRLSCLASGFTFD | 214 DYAIG | 296 WFRQAPGKEREGIS | 378 CISSTGNVFYADSVKG | 460 RFTISSDKEKNTLYLQMNSLKPEDTAVYHCAA | 542 GHFTVDSGKVLLRTDVSS | 624 WGQGTQVTVSS |
| 133 EVQLVESGGGLVQTGGSLRLSCAASGFTLD | 215 DYAIA | 297 WFRQAPGKEREGVS | 379 ILSSIGKTFYADSVKD | 461 RFSITADGAKTTVFLQMNSLKPGDTAIYYCVA | 543 GHFVYNDGAISLNTARGSF | 625 WGQGAQVTVSS |
| 134 EVQLVESGGGLVQTGGSLRLSCAASGFTLD | 216 DYAIA | 298 WFRQAPGKEREGVS | 380 ILSSIGKTFYADSVKD | 462 RFSITADGAKTTVFLQMNSLKPEDTAIYYCVA | 544 GHFVYNDGAISLNTARGSF | 626 WGQGAQVTVSS |

TABLE B-1-continued

Preferred combinations of CDR sequences, preferred combinations of framework sequences, and preferred combinations of framework and CDR sequences.
("ID" refers to the SEQ ID NO as used herein)

| ID FR1 | ID CDR1 | ID FR2 | ID CDR2 | ID FR3 | ID CDR3 | ID FR4 |
|---|---|---|---|---|---|---|
| 135 EVQLVESGGGLVQTGGSLRLSCAASGFTLD | 217 DYAIA | 299 WFRQAPGKEREGVS | 381 ILSSIGKTFYADSVKD | 463 RFSITADGAKTTVFLQMNSLKPEDTAIYYCVA | 545 GHFVYNDGAISLNTARGSGF | 627 WGQGTQVTVSS |
| 136 EVQLVESGGGLVQTGGSLRLSCAASGFTLD | 218 DYAIA | 300 WFRQAPGKEREGVS | 382 ILSSIGKTFYADSAKD | 464 RFSITADGAKTTVFLQMNSLKPEDTAIYYCVA | 546 GHFVYNDGAISLNTARGSGF | 628 WGQGTQVTVSS |
| 137 EVQLVESGGGLVQAGGSLRLSCAASERTYS | 219 MG | 301 WFRQAPGKEREFVA | 383 GSGWDGIPTRYADSVKG | 465 RLTISRDNAKNTVSLQMSGLKPEDTAIYYCAT | 547 GTSVYHYQY | 629 WGQGTQVTVSS |
| 138 EVQLVESGGGLVQAGGSLRLSCAASERTYS | 220 MG | 302 WFRRAPGKEREFVA | 384 GSGWDGIPTRYADSVKG | 466 RFTISRDNAKNTVSLQMSGLKPEDTAIYYCAT | 548 GTSVYHYQY | 630 WGQGTQVTVSS |
| 139 EVQLVESGGGLVQAGGSLRLSCAASERTYS | 221 VG | 303 WFRQAPGKEREFVA | 385 GSGWDGTPTRYADSVKG | 467 RFTISRDNAKNTVSLQMSGLKPEDTAIYYCAT | 549 GTSVYHYQY | 631 WGQGTQVTVSS |
| 140 EVQLVESGGGLVQAGGSLRLSCAAPERTYS | 222 MG | 304 WFRQAPGKEREFVA | 386 GSGWDGIPTRYADSVKG | 468 RFTISRDNAKNTVSLQMSGLKPEDTAIYYCAT | 550 GTSVYHYQY | 632 WGQGTQVTVSS |
| 141 EVQLVESGGGLVQAGGSLRLSCAASERTYS | 223 MG | 305 WFRQAPGKEREFVA | 387 GSGWDGIPTRYADSVKG | 469 RFTISRDNAKNTVSLQMSGLKPEDTAIYYCAT | 551 GTSVYHYQY | 633 WGQGTQVTVSS |
| 142 EVQLVESRGGLVQAGGSLRLSCAASERTYS | 224 MG | 306 WFRQAPGKEREFVA | 388 GSGWDGIPTRYADSVKS | 470 RFTISRDNAKNTVSLQMSGLKPEDTAIYYCAT | 552 GTSVYHYQY | 634 WGQGTQVTVSS |
| 143 EVQLVESGGGLVQAGGSLRLSCAASERTYS | 225 MG | 307 WFRQAPGKEREFVA | 389 GSGWDGIPTRYADSVKG | 471 RFTISRDNAKNAVSLQMSGLKPEDTAIYYCAT | 553 GTSVYHYQY | 635 WGQGTQVTVSS |
| 144 EVQLVESGGGLVQPGGSLRLSCAASERTYS | 226 MG | 308 WFRQAPGKEREFVA | 390 GSGWDGIPTRYADSVKG | 472 RFTISRDNAKNTVSLQMSGLKPEDTAIYYCAT | 554 GTSVYHYQY | 636 WGQGTQVTVSS |
| 145 EVQLVESGGGLVQAGGSLRLSCAASERTYS | 227 MG | 309 WFRQAPGKEREFVA | 391 GSGWDGIPTRYADSVKG | 473 RFTISRDNAKSTVSLQMSGLKPEDTAIYYCAT | 555 GTSVYHYQY | 637 WGQGTQVTVSS |
| 146 KVQLVESGGGLVQAGGSLRLSCAASGRTVS | 228 DYGMG | 310 WFRQAPGKLREFVA | 392 SINWSGIYTRYIDSVEG | 474 RFTISRDNTKNTLYLQMNNLRAEDTAVYYCAY | 556 FLGPNWYSNYGRPSSYDF | 638 YGQGTQVTVSS |
| 147 EVQLMESGGGLVQAGGSLRLSCAASGRTVS | 229 DYGMG | 311 WFRQAPGKLREFVA | 393 SINWSGIYTRYIDSVEG | 475 RFTISRDNTKNTLYLQMNNLKAEDTAVYYCAY | 557 FLGPNWYSNYGRPSSYDF | 639 YGQGTQVTVSS |
| 148 EVQLVESGGGLVQAGGSLRLSCAASGRTVS | 230 DYGMG | 312 WFRQAPGKLREFVA | 394 SINWSGIYTRYIDSVEG | 476 RFTISRDNTKNTLYLQMNNLKAEDTAVYYCAY | 558 FLGPNWYSNYGRPSSYGF | 640 YGQGTQVTVSS |

TABLE B-1-continued

Preferred combinations of CDR sequences, preferred combinations of framework sequences, and preferred combinations of framework and CDR sequences.
("ID" refers to the SEQ ID NO as used herein)

| ID FR1 | ID CDR1 | ID FR2 | ID CDR2 | ID FR3 | ID CDR3 | ID FR4 |
|---|---|---|---|---|---|---|
| 149 EVQLVESG GGLVQAGG SLRLSCAAS GRTVS | 231 DYGMG | 313 WFRQAPGKE CEFVA | 395 SINWSGTYTRYIDSVEG | 477 RFTISRDNTENTLYLQ MNNLKAEDTAVYYCAY | 559 FLGPNWYSD YGRPSSYDF | 641 YGQGTQ VTVSS |
| 150 EVQLMESG GGLVQAGG PLRLSCAAS GRTVS | 232 DYGMG | 314 WFRQAPGKE REFVA | 396 SINWSGTYTRYIDSVEG | 478 RFTISRDNTENTLYLQ MNNLKAEDTAVYYCAY | 560 FLGPNWYSD YGRPSSYDF | 642 YGQGTQ VTVSS |
| 151 AVQLVESG GGLVQAGG SLRLSCAAS GNFFR | 233 VNTMA | 315 WYRQAPGKQ RELVA | 397 DITRGDRTNYADTVNG | 479 RFTISRDNVRNTVYL QMNGLRPEDTAAYY CYA | 561 VIELGVLEPRDY | 643 WGQGT QVTVSS |
| 152 EVQLVESG GGLVQAGG SLRLSCAAS GNFFR | 234 VNTMA | 316 WYRQAPGKQ RELVA | 398 DITRGDRTNYADTVNG | 480 RFTISRDNVRNTVYL QMNGLKPEDTAAYY CYA | 562 RIELGVLEPR DY | 644 WGQGT QVTVSS |
| 153 EVQLVESG GGLVQAGG PLRLSCAAS GNFFR | 235 VNTMA | 317 WYRQAPGKQ RELVA | 399 DITRGDRTNYADTVNG | 481 RFTISRDNVRNTVYL QMNGLKPEDTAAYY CYA | 563 RIELGVLEPR DY | 645 WGQGT QVTVSS |
| 154 EVQLVESG GGLVQAGG SLRLSCAAS GSFFR | 236 VNNMA | 318 WYRQAPGKQ RELVA | 400 DITRGDRTNYADSVNG | 482 RFTISRDNVRNTVYL QMNGLKPEDTAVYY CYA | 564 RIELGVLEPR DY | 646 WGQGT QVTVSS |
| 155 EVQLVESG GGLVQAGG PLRLSCAAS GSFFR | 237 VNNMA | 319 WYRQAPGKQ RELVA | 401 DITRGDRTNYADSVNG | 483 RFTISRDNVRNTVYL QMNGLKPEDTAVYY CYA | 565 RIELGVLEPR DY | 647 WGQGT QVTVSS |
| 156 EVQLVESG GGLVQAGG SLRLSCAAS GNFFR | 238 VNTMA | 320 WYRQAPGKQ RELVA | 402 DITRGDRTNYADTVNG | 484 RFTISRDNVRNTVYL QMNSLKPEDTAAYY CYA | 566 RIELGVLEPR DY | 648 WGQGT QVTVSS |
| 157 EVQLVESG GGLVQAGG SLGLSCAAS GNFFR | 239 VNTMA | 321 WYRQAPGKQ RELVA | 403 DITRGDRTNYADTVNG | 485 RFTISRDNVRNTVYL QMNGLKPEDTAAYY CYA | 567 RIELGVLEPR DY | 649 WGQGT QVTVSS |
| 158 EMQLVESG GGLVQAGG SLRLSCAAS GNFFR | 240 VNTMA | 322 WYRQAPGKQ RELVA | 404 DITRGDRTNYADTVNG | 486 RFTISRDNVRNTVYL QMNGLKPEDTAAYY CYA | 568 RIELGVLEPR DY | 650 WGQGT QVTVSS |
| 159 EVQLVESG GGLVQAGG SLRLLCAAS GSFFR | 241 VNNMA | 323 WYRQAPGKQ RELVA | 405 DITRGDRTNYADSVNG | 487 RFTISRDNVRNTVYL QMNGLKPEDTAVYS CYA | 569 RIELGILEPRDY | 651 WGQGT QVTVSS |
| 160 EVQLVESG GGLVQAGG SLRLSCAAS GSFFR | 242 VNNMA | 324 WYRQAPGKQ RELVA | 406 DITRGDRTNYADSVNG | 488 RFTISRDNVRNTVYL QMDGLKPEDTAVYY CYA | 570 RIELGVLVPR DY | 652 WGQGT QVTVSS |
| 161 EVQLVESG GGLVQAGG SLRLSCAAS GSFFR | 243 VNNMA | 325 WYRQAPGKQ RELVA | 407 DITRGDRTNYADSVNG | 489 RFTISRDNVRNTVYL QMNGLKPEDTAVYY CYA | 571 RIELGPLVPR DY | 653 WGQGT QVTVSS |
| 162 EVQLVKSG GGLVQAGG SLRLSCAAS GSFFR | 244 VNNMA | 326 WYRQAPGKQ RELVA | 408 DITRGDRTNYADSVNG | 490 RFTISRDNVRNTVYL QMNGLKPEDTAVYY CYA | 572 RIELGPLVPR DY | 654 WGQGT QVTVSS |

TABLE B-1-continued

Preferred combinations of CDR sequences, preferred combinations of framework sequences, and preferred combinations of framework and CDR sequences.
("ID" refers to the SEQ ID NO as used herein)

| ID FR1 | ID CDR1 | ID FR2 | ID CDR2 | ID FR3 | ID CDR3 | ID FR4 |
|---|---|---|---|---|---|---|
| 163 KVQLVESGGGLVQAGGSLRLSCAASGSFFR | 245 VNNMA | 327 WYRQGPGKQRELVA | 409 DITRGDRTNYADSVNG | 491 RFTISRDNVRNTVYLQMNGLKPEDTAVYYCYA | 573 TIELGVLEPRDY | 655 WGQGTQVTVSS |
| 164 EVQLVESGGGLVQAGGSLRLSCAASGSFFR | 246 VNVMA | 328 WYRQGPGKQRELVA | 410 DITRGDRTNYADSVNG | 492 RFTISRDNVRNTVYLQMNGLKPEDTAVYYCYA | 574 TIELGVLEPRDY | 656 WGQGTQVTVSS |
| 165 EVQLVESGGGLVKPGGSLRLSCAASGSFFR | 247 VNNMA | 329 WYRQGPGKQRELVA | 411 DITRGDRTNYADSVNG | 493 RFTISRDNVRNTVYLQMNGLKPEDTAVYYCYA | 575 TIELGVLEPRDY | 657 WGQGTQVTVSS |
| 166 EVQLVESGGGLVQAGGSLRLSCAASGSFFR | 248 VNNMA | 330 WYRQAPGKQRELVA | 412 DITRGDRTNYADSVNG | 494 RFTISRDNVRNTVYLQMNGLKPEDTAVYYCYA | 576 TIELGVLEPRDY | 658 WGQGTQVTVSS |
| 167 EVQLVESGGGLVQAGGSLRLSCAASGSFFR | 249 VNNMA | 331 WYRQGPGKQRELVA | 413 DITRGDRTNYADSVNG | 495 RFTISRDNVRNTVYLQMNGLKPEDTAVYYCYA | 577 TIELGVLEPRDY | 659 WGQGTQVTVSS |
| 168 EVQLVESGGGLVQPGGSLRLSCAASGSFFR | 250 VNNMA | 332 WYRQAPGKQRELVA | 414 DITRGDRTNYADSVNG | 496 RFTISRDNVRNTVYLQMNGLKPEDTAVYYCYA | 578 TIELGVLEPRDY | 660 WGQGTQVTVSS |
| 169 EVQLVESGGGLVQAGGSLRLSCAASGSFFR | 251 VNNMA | 333 WYRQGPGKQRELVA | 415 DITRGDRTNYADSVNG | 497 RFTISRDNVRNTVYLQMDGLKPEDTAVYYCYA | 579 TIELGVLVPRDY | 661 WGQGTQVTVSS |
| 170 EVQLVESGGDLVQAGGSLKLSCVVSGVTFD | 252 DGTIG | 334 WFRQAPGKEREGIA | 416 CISRVDGTTYYRDSVKG | 498 RFTVSSDSAKTTVNLQMNSLKPEDTAVYYCAA | 580 DYASLCTIETGYGSLYDY | 662 WGRGTQVTVSS |
| 171 EVQLVESGGDLVQAGGSLKLSCVVSGVTFD | 253 DGTIG | 334 WFRQAPGKEREGIA | 417 CISRVDGTTYYRDSVKG | 499 RFTVSSDSAKTTVNLQMNSLKPEDTAVYYCAA | 581 DYASLCTIETGYGSLYDY | 663 WGKGTQVTVSS |
| 172 EMQLVESGGGLVQAGGSLRLSCAASGRTFS | 254 SLAMG | 336 WLRQAPGKEREFVS | 418 GISRGGTSTYYADSVKG | 500 RFTISRDNAKNTMYLQMNSLKPEDTAVYYCAG | 582 SPVLSIVDTRGLEY | 664 WGQGTQVTVSS |
| 173 EVQLVESGGGLVQAGGSLRLSCAASGRTFS | 255 SLAMG | 337 WLRQAPGKEREFVS | 419 GISRGGTSTYYADSVKG | 501 RFTISRDNAKNTMYLQMNSLKPEDTAVYYCAG | 583 SPVLSIVDTRGLEY | 665 WGQGTQVTVSS |
| 174 EVQLVESGGGLVQAGGSLRLSCAASGRTFS | 256 SLAMG | 338 WLRQAPGKEREFVS | 420 GISRGGTSTYYADSVKG | 502 RLTISRDNAKNTMYLQMNSLKPEDTAVYYCAG | 584 SPVLSIVDTRGLEY | 666 WGQGTQVTVSS |
| 175 EVQLVESGGGLVQAGGSLRLSCAASGRTFG | 257 SSPVG | 339 WFRQAPGKERDFVA | 421 TISWNGVDTHYLDSVKG | 503 RFTISRDNAKNTVHLQMHILKPEDTALYYCAA | 585 STSGSVYLPYRVYQYDS | 667 WGQGTQVTVSS |
| 176 EVQLVESGGGLVQAGGSLRLSCAASGRTFS | 258 SSPVG | 340 WFRQAPGKERDFVA | 422 TISWNGVDTHYLDSVKG | 504 RFTISRDNALNTVHLQMHILKPEDTALYYCAA | 586 STSGSAYLPYRVYQYDS | 668 WGQGTQVTVSS |
| 177 EVQLVESGGGLVQAGG | 259 SSPVG | 341 WFRQAPGKERDFVA | 423 TISWNGVDTHYLDSVKG | 505 RFTISRDNALNTVHLQMHILKPEDTALYYC | 587 STSGSAYLPYRVHQYDS | 669 WGQGTQVTVSS |

TABLE B-1-continued

Preferred combinations of CDR sequences, preferred combinations of framework sequences, and preferred combinations of framework and CDR sequences.
("ID" refers to the SEQ ID NO as used herein)

| ID FR1 | ID CDR1 | ID FR2 | ID CDR2 | ID FR3 | ID CDR3 | ID FR4 |
|---|---|---|---|---|---|---|
| SLRLSCAAS GRTFS | | | | AA | | |
| 178 EVQLVESG GGLVQAGA SLRVSCAAS ARTGS | 260 YTMG | 342 WFRQAPGKE REFVS | 424 TISWNGASTVYADSVKG | 506 RFTISRDNAKNTVSL QMNSLKPEDTAVYY CAG | 588 SISSYSSRWQ DDYEY | 670 WGQGT QVTVSS |
| 179 EVQLVESG GGLVQAGG SLRVSCAAS ARTGS | 261 YSMG | 343 WFRQAPGKE REFVS | 425 TISWNGADTVYADSVKG | 507 RFTISRDNAKDTVYL QMNSLKPEDTAVYY CAG | 589 SITSYVSTWQ HDYEY | 671 WGQGT QVTVSS |
| 180 EVQLVESG GGLVQAGG SLRLSCAAS GRNFG | 262 SYTMA | 344 WFRQAPGKG REFVS | 426 TINWSGGDTDYADSVKG | 508 RFTISRDNAKNTVYL QMDSLKPEDTAVYY CAA | 590 GLEYMSTIRY TYEY | 672 WGQGT QVTVSS |
| 181 EVQLVESG GGLVQPGG SLRLSCVVS GSMYR | 263 IDNMG | 345 WYRQAPGKQ RELVA | 427 TVTRGDITNYADSVKG | 509 RFTIGRDNAKNTVYL QMNSLKPADTAVYY CNI | 591 DSYIIGAGVRDY | 673 WGRGT QVTVSS |
| 182 EVQLVESG GGLVQSGG SLRLSCAGS GFSYY | 264 IIG | 346 WFRQAPGKE REEVS | 428 CIRVTDGSTYYTNSVKG | 510 RFTMSRDNAENTVYL QMNSLKPEDTAVYS CAT | 592 ECQRWAYPN RIGA | 674 RGQGT QVTVSS |
| 183 EVQLVESG GGLVQSGG SLRLSCAGS GFSYY | 265 IIG | 347 WFRQAPGKE REEVS | 429 CIRVTDGSTYHTNSVKG | 511 RFTMSRDNAENTVYL QMNSLKPEDTAVYS CAT | 593 ECQRWAYPN RIGA | 675 RGQGT QVTVSS |
| 184 EVQLVESG GGLVQPGG SLRLSCAAS GLTLE | 266 YYNIG | 348 WFRQAPGKE REGVA | 430 CIDWTEGSTFYVDSVKG | 512 RFTISTDNAKNTVYLH MNSLEPEDTAVYYCAA | 594 GWGRVITVQH MCADRSLFTS | 676 WGQGT QVTVSS |
| 185 EVQLVESG GGLVQPGG SLRLSCAAS GLTLT | 267 YYNIG | 349 WFRQAPGKE REGVS | 431 CIDWTDGTTFYADSVKG | 513 RFTISTDNAKNTVYLH LNSLEPEDTAVYYCAA | 595 GWGRVMTVQ HMCADRSLFTS | 677 WGQGT QVTVSS |
| 186 EVQLVESG GGLVQAGD SLRLSCAAS GRTFS | 268 SVAVG | 350 WFRQAPGKE RDFVA | 432 WISWSGDSTYYADSVKG | 514 RFTASRDNVNNTVYL QMNLKPEDTADYY CAA | 596 AWKYDRASY DFPEAYDY | 678 WGQGT QVTVSS |
| 187 EVQLVESG GGLVQAGG SLRLSCAAS PGTFS | 269 SFNMG | 351 WFRQTPGKE REFVA | 433 ATSWSDISTYYADSVKG | 515 RFTISRDNAKNTVTLE MNSLKPEDTAVYYCAA | 597 GYYRGGYLG YRLTLEGSYDV | 679 WGQGT QVTVSS |
| 188 EVQLVESG GGLVQAGG SLRLSCAAS PGAFS | 270 SFNMG | 352 WFRQTPGKE REFVA | 434 ATSWSDISTYYADSVKG | 516 RFTISRDNAKNTVTLE MNSLKPEDTAVYYCAA | 598 GYYRGGYLG YRLTLEGSYDV | 680 WGQGT QVTVSS |
| 189 EMQLVESG GGLVQAGG SLRLSCAAS PGTFS | 271 SFNMG | 353 WFRQTPGKE REFVA | 435 ATSWSDISTYYADSVKG | 517 RFTISRDNAKNTVTLE MNSLKPEDTAVYYCAA | 599 GYYRGGYLG YRLTLEGSYDV | 681 WGQGT QVTVSS |
| 190 EVQLVKSG GGLVQAGG SLRLSCAAS PGTFS | 272 SFNMG | 354 WFRQTPGKE REFVA | 436 ATSWSDISTYYADSVKG | 518 RFTISRDNAKNTVTLE MNSLKPEDTAVYYCAA | 600 GYYRGGYLG YRLTLEGSYDV | 682 WGQGT QVTVSS |
| 191 EVQLVESG GGLVQAGG SLRLSCVVS GRTFS | 273 AMG | 355 WFRQAPGKE REFVA | 437 TVGWNPMNSYYGDSVKG | 519 RFTIFRDNAKNTVYL QMNSLKPEDTAVYY CAG | 601 SGSLLDVTSE AVYTD | 683 WGQGT QVTVSS |

TABLE B-1-continued

Preferred combinations of CDR sequences, preferred combinations of framework sequences, and preferred combinations of framework and CDR sequences.
("ID" refers to the SEQ ID NO as used herein)

| ID FR1 | ID CDR1 | ID FR2 | ID CDR2 | ID FR3 | ID CDR3 | ID FR4 |
|---|---|---|---|---|---|---|
| 192 KVQLVESGGGLVQAGGSLRLSCAASGSPIS | 274 SYAMG | 356 WYRQAPGKPRELVA | 438 RIYTGGTAWYEDSVKG | 520 RFTISRDNAQNTVYLQMNSLKSEDTAVYYCHG | 602 RVRYDY | 684 WGQGTQVTVSS |
| 193 EVQLVESGGGLVQAGGSLRLSCAASDRTFG | 275 SSAMG | 357 WFRQAPGKDRDFVA | 439 AISWSGSSTHYADSVKG | 521 RFTISRDNAKNTMYLQMNSLKPADTAVYTCAA | 603 SRRAYLPAKVGEYDF | 685 WGQGTQVTVSS |
| 194 EVQLVESGGGLVQAGDSLRLSCAASGRTFS | 276 SYAMG | 358 WFRQAPGKEREFVA | 440 AISLSGSMTYYADSMKG | 522 RFTISRDNAKNTVYLQMNSLKPEDTAVYYCAA | 604 EELGDGLGYLAYRYDY | 686 WGQGTQVTVSS |
| 195 EVQLVESGGGLVQPGGSLRLSCAASGFTFS | 277 TNIMT | 359 WVRQAPGKGLEWIS | 441 TINSGGGTTTYADSVRG | 523 RFTISRDNAKNMLYLQMSSLKPEDTALYYCIT | 605 PRGV | 687 KGRGTQVTVSS |
| 196 EVQLVESGGGLVQAGGSLRLSCAASDRTFG | 278 SSTMG | 360 WFRQPPGKNREFVA | 442 TIAWSATTTHYADAVKG | 524 RFTVSRDNALNTVYLQMNSLKPEDTAVYYCAA | 606 TLTWLGIHEYEYNT | 688 WGQGTQVTVSS |
| 197 EVQLVESGGGLVQPGESLRLSCTASRFMLD | 279 YYDIG | 361 WFRQAPGKEREGVS | 443 CRFTNDGSTAYADSVKG | 525 RFTISRDIVKHTVYLQMNSLQPEDTAVYYCAA | 607 GPLTKRRQCVPGDFSMDF | 689 WGEGTLVTVSS |
| 198 EVQLVESGGGLVQPGESLRLSCTASRFDLD | 280 YYDIA | 362 WFRQAPGKEREGVS | 444 CSFTNDGSTYYADSVKG | 526 RFTMSRNNDHRTVYLQMTSLQPEDTAVYTCAV | 608 GPLTRRRQCVPGDFSMDF | 690 WGEGTLVTVSS |
| 199 EVQLVESGGGLVQAGGSLRLSCVASGRTFS | 281 ILTMG | 363 WFRQAPGKEREFVA | 445 AISGIGAIHYADSVKG | 527 RFTLSRDNARNTVSLHMNSLKPEDTAVYYCAA | 609 KANYESPSRETSYAY | 691 WGQGTQVTVSS |
| 200 EVQLVESGGRVMQTGGSLRLSCAASGHTFN | 282 DYSMG | 364 WFRQAPGKELEFLA | 446 GINWSGMSTWYADSVKD | 528 RFTISRDNNKNTVFLQMNSLEPGDTAVYYCAA | 610 RQWISTIILTAPSQYDY | 692 WGQGTQVTVSS |
| 201 EVQLVESGGRVMQTGGSLRLSCAASGHTFN | 283 DYNMG | 365 WFRQAPGKELEFLA | 447 GINWSGMSTWYADSVKD | 529 RFTISRDNNKNTVFLQMNSLEPGDTAVYYCAA | 611 RQWISTIILTAPSQYDY | 693 WGQGTQVTVSS |
| 202 EVQLVESGGDLVQPGGSLRLSCVASGFALE | 284 EHAIG | 366 WFRQAPGKEREGVS | 448 LSSYLGAAYYATSVKG | 530 RFTISRDNAKNTVTLQMNSLKPEDTAVYYCAR | 612 GHFTYDDGRITIRSVDY | 694 WGKGTLVTVSS |
| 203 EVQLVESGGDLVQPGGSLRLSCVASGFALE | 285 EHAIG | 367 WFRQAPGKEREGVS | 449 LSSYVGAVYYATSVKG | 531 RFTISRDNAKNTVYLQMNSLKPEDTAVYYCAR | 613 GHFTYDDGRISIRSVDH | 695 WGKGTLVTVSS |
| 204 EVQLVESGGGLVQAGGSLRLSCVASGRTLS | 286 TAVMG | 368 WFRQAPGKERGLVA | 450 MISWSGSMTYYAKSVKG | 532 RFTISRDNAKNTMYLQMNSLKPEDTAVYYCAA | 614 DMGGGPPDGDAMPRLSSGMDY | 696 WGKGTLVTVSS |
| 205 EVQLVESGGGLVQAGGSLRLSCAASGNDFA | 287 RFSIDAMG | 369 WYRQAPGKQRELVA | 451 TVTEDGTKNYADSVKG | 533 RATISRDDANNSMYLEMNTLKPEDTAVYYCKM | 615 GGLIDGAAPYEF | 697 WGRGTQVTVSS |

TABLE B-1-continued

Preferred combinations of CDR sequences, preferred combinations of framework sequences, and preferred combinations of framework and CDR sequences.
("ID" refers to the SEQ ID NO as used herein)

| ID FR1 | ID CDR1 | ID FR2 | ID CDR2 | ID FR3 | ID CDR3 | ID FR4 |
|---|---|---|---|---|---|---|
| 206 EMQLVESG GGWVQAG GSLRLSCAS SGSIFS | 288 AGAMG | 370 WYRQPAGKQ RELVA | 452 DITLGGSTNYADSVKG | 534 RFTISRDNAKNAVFL QMNSLKPEDTAVYY CNG | 616 LINTFARKIPR YA | 698 WGQGT QVTVSS |
| 207 EVQLVESG GGLVQAGG SLRLSCAAS GPTTF | 289 GRYTMG | 371 WFRQAPGRE REFVA | 453 AISWIGGRTYYVDVVKG | 535 RFTISRDNAKKMVYL QMNSLKPDDTAVYH CAA | 617 AFQALGSPRE YDY | 699 WGQGT QVTVSS |

Thus, in the Nanobodies of the invention, at least one of the CDR1, CDR2 and CDR3 sequences present is suitably chosen from the group consisting of the CDR1, CDR2 and CDR3 sequences, respectively, listed in Table B-1; or from the group of CDR1, CDR2 and CDR3 sequences, respectively, that have at least 80%, preferably at least 90%, more preferably at least 95%, even more preferably at least 99% "sequence identity" (as defined herein) with at least one of the CDR1, CDR2 and CDR3 sequences, respectively, listed in Table B-1; and/or from the group consisting of the CDR1, CDR2 and CDR3 sequences, respectively, that have 3, 2 or only 1 "amino acid difference(s)" (as defined herein) with at least one of the CDR1, CDR2 and CDR3 sequences, respectively, listed in Table B-1.

In this context, by "suitably chosen" is meant that, as applicable, a CDR1 sequence is chosen from suitable CDR1 sequences (i.e. as defined herein), a CDR2 sequence is chosen from suitable CDR2 sequences (i.e. as defined herein), and a CDR3 sequence is chosen from suitable CDR3 sequence (i.e. as defined herein), respectively. More in particular, the CDR sequences are preferably chosen such that the Nanobodies of the invention bind to ion channels such as e.g. P2X7 with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein.

In particular, in the Nanobodies of the invention, at least the CDR3 sequence present is suitably chosen from the group consisting of the CDR3 sequences listed in Table B-1 or from the group of CDR3 sequences that have at least 80%, preferably at least 90%, more preferably at least 95%, even more preferably at least 99% sequence identity with at least one of the CDR3 sequences listed in Table B-1; and/or from the group consisting of the CDR3 sequences that have 3, 2 or only 1 amino acid difference(s) with at least one of the CDR3 sequences listed in Table B-1.

Preferably, in the Nanobodies of the invention, at least two of the CDR1, CDR2 and CDR3 sequences present are suitably chosen from the group consisting of the CDR1, CDR2 and CDR3 sequences, respectively, listed in Table B-1 or from the group consisting of CDR1, CDR2 and CDR3 sequences, respectively, that have at least 80%, preferably at least 90%, more preferably at least 95%, even more preferably at least 99% sequence identity with at least one of the CDR1, CDR2 and CDR3 sequences, respectively, listed in Table B-1; and/or from the group consisting of the CDR1, CDR2 and CDR3 sequences, respectively, that have 3, 2 or only 1 "amino acid difference(s)" with at least one of the CDR1, CDR2 and CDR3 sequences, respectively, listed in Table B-1.

In particular, in the Nanobodies of the invention, at least the CDR3 sequence present is suitably chosen from the group consisting of the CDR3 sequences listed in Table B-1 or from the group of CDR3 sequences that have at least 80%, preferably at least 90%, more preferably at least 95%, even more preferably at least 99% sequence identity with at least one of the CDR3 sequences listed in Table B-1, respectively; and at least one of the CDR1 and CDR2 sequences present is suitably chosen from the group consisting of the CDR1 and CDR2 sequences, respectively, listed in Table B-1 or from the group of CDR1 and CDR2 sequences, respectively, that have at least 80%, preferably at least 90%, more preferably at least 95%, even more preferably at least 99% sequence identity with at least one of the CDR1 and CDR2 sequences, respectively, listed in Table B-1; and/or from the group consisting of the CDR1 and CDR2 sequences, respectively, that have 3, 2 or only 1 amino acid difference(s) with at least one of the CDR1 and CDR2 sequences, respectively, listed in Table B-1.

Most preferably, in the Nanobodies of the invention, all three CDR1, CDR2 and CDR3 sequences present are suitably chosen from the group consisting of the CDR1, CDR2 and CDR3 sequences, respectively, listed in Table B-1 or from the group of CDR1, CDR2 and CDR3 sequences, respectively, that have at least 80%, preferably at least 90%, more preferably at least 95%, even more preferably at least 99% sequence identity with at least one of the CDR1, CDR2 and CDR3 sequences, respectively, listed in Table B-1; and/or from the group consisting of the CDR1, CDR2 and CDR3 sequences, respectively, that have 3, 2 or only 1 amino acid difference(s) with at least one of the CDR1, CDR2 and CDR3 sequences, respectively, listed in Table B-1.

Even more preferably, in the Nanobodies of the invention, at east one of the CDR1, CDR2 and CDR3 sequences present is suitably chosen from the group consisting of the CDR1, CDR2 and CDR3 sequences, respectively, listed in Table B-1. Preferably, in this aspect, at least one or preferably both of the other two CDR sequences present are suitably chosen from CDR sequences that have at least 80%, preferably at least 90%, more preferably at least 95%, even more preferably at least 99% sequence identity with at least one of the corresponding CDR sequences, respectively, listed in Table B-1; and/or from the group consisting of the CDR sequences that have 3, 2 or only 1 amino acid difference(s) with at least one of the corresponding sequences, respectively, listed in Table B-1.

In particular, in the Nanobodies of the invention, at least the CDR3 sequence present is suitably chosen from the group consisting of the CDR3 listed in Table B-1. Preferably, in this aspect, at least one and preferably both of the CDR1 and CDR2 sequences present are suitably chosen from the groups of CDR1 and CDR2 sequences, respectively, that have at least 80%, preferably at least 90%, more preferably at least 95%, even more preferably at least 99% sequence identity with the CDR1 and CDR2 sequences, respectively, listed in Table B-1; and/or from the group consisting of the CDR1 and CDR2 sequences, respectively, that have 3, 2 or only 1 amino acid difference(s) with at least one of the CDR1 and CDR2 sequences, respectively, listed in Table B-1.

Even more preferably, in the Nanobodies of the invention, at least two of the CDR1, CDR2 and CDR3 sequences present are suitably chosen from the group consisting of the CDR1, CDR2 and CDR3 sequences, respectively, listed in Table B-1. Preferably, in this aspect, the remaining CDR sequence present is suitably chosen from the group of CDR sequences that have at least 80%, preferably at least 90%, more preferably at least 95%, even more preferably at least 99% sequence identity with at least one of the corresponding CDR sequences listed in Table B-1; and/or from the group consisting of CDR sequences that have 3, 2 or only 1 amino acid difference(s) with at least one of the corresponding sequences listed in Table B-1

In particular, in the Nanobodies of the invention, at least the CDR3 sequence is suitably chosen from the group consisting of the CDR3 sequences listed in Table B-1, and either the CDR1 sequence or the CDR2 sequence is suitably chosen from the group consisting of the CDR1 and CDR2 sequences, respectively, listed in Table B-1. Preferably, in this aspect, the remaining CDR sequence present is suitably chosen from the group of CDR sequences that have at least 80%, preferably at least 90%, more preferably at least 95%, even more preferably at least 99% sequence identity with at least one of the corresponding CDR sequences listed in Table B-1; and/or from the group consisting of CDR sequences that have 3, 2 or only 1 amino acid difference(s) with the corresponding CDR sequences listed in Table B-1.

Even more preferably, in the Nanobodies of the invention, all three CDR1, CDR2 and CDR3 sequences present are suitably chosen from the group consisting of the CDR1, CDR2 and CDR3 sequences, respectively, listed in Table B-1. Also, generally, the combinations of CDR's listed in Table B-1 (i.e. those mentioned on the same line in Table B-1) are preferred. Thus, it is generally preferred that, when a CDR in a Nanobody of the invention is a CDR sequence mentioned in Table B-1 or is suitably chosen from the group of CDR sequences that have at least 80%, preferably at least 90%, more preferably at least 95%, even more preferably at least 99% sequence identity with a CDR sequence listed in Table B-1; and/or from the group consisting of CDR sequences that have 3, 2 or only 1 amino acid difference(s) with a CDR sequence listed in Table B-1 that at least one and preferably both of the other CDR's are suitably chosen from the CDR sequences that belong to the same combination in Table B-1 (i.e. mentioned on the same line in Table B-1) or are suitably chosen from the group of CDR sequences that have at least 80%, preferably at least 90%, more preferably at least 95%, even more preferably at least 99% sequence identity with the CDR sequence(s) belonging to the same combination and/or from the group consisting of CDR sequences that have 3, 2 or only 1 amino acid difference(s) with the CDR sequence(s) belonging to the same combination. The other preferences indicated in the above paragraphs also apply to the combinations of CDR's mentioned in Table B-1.

Thus, by means of non-limiting examples, a Nanobody of the invention can for example comprise a CDR1 sequence that has more than 80% sequence identity with one of the CDR1 sequences mentioned in Table B-1, a CDR2 sequence that has 3, 2 or 1 amino acid difference with one of the CDR2 sequences mentioned in Table B-1 (but belonging to a different combination), and a CDR3 sequence.

Some preferred Nanobodies of the invention may for example comprise: (1) a CDR1 sequence that has more than 80% sequence identity with one of the CDR1 sequences mentioned in Table B-1; a CDR2 sequence that has 3, 2 or 1 amino acid difference with one of the CDR2 sequences mentioned in Table B-1 (but belonging to a different combination); and a CDR3 sequence that has more than 80% sequence identity with one of the CDR3 sequences mentioned in Table B-1 (but belonging to a different combination); or (2) a CDR1 sequence that has more than 80% sequence identity with one of the CDR1 sequences mentioned in Table B-1; a CDR2 sequence, and one of the CDR3 sequences listed in Table B-1; or (3) a CDR1 sequence; a CDR2 sequence that has more than 80% sequence identity with one of the CDR2 sequence listed in Table B-1; and a CDR3 sequence that has 3, 2 or 1 amino acid differences with the CDR3 sequence mentioned in Table B-1 that belongs to the same combination as the CDR2 sequence.

Some particularly preferred Nanobodies of the invention may for example comprise: (1) a CDR1 sequence that has more than 80% sequence identity with one of the CDR1 sequences mentioned in Table B-1; a CDR2 sequence that has 3, 2 or 1 amino acid difference with the CDR2 sequence mentioned in Table B-1 that belongs to the same combination; and a CDR3 sequence that has more than 80% sequence identity with the CDR3 sequence mentioned in Table B-1 that belongs to the same combination; (2) a CDR1 sequence; a CDR 2 listed in Table B-1 and a CDR3 sequence listed in Table B-1 (in which the CDR2 sequence and CDR3 sequence may belong to different combinations).

Some even more preferred Nanobodies of the invention may for example comprise: (1) a CDR1 sequence that has more than 80% sequence identity with one of the CDR1 sequences mentioned in Table B-1; the CDR2 sequence listed in Table B-1 that belongs to the same combination; and a CDR3 sequence mentioned in Table B-1 that belongs to a different combination; or (2) a CDR1 sequence mentioned in Table B-1; a CDR2 sequence that has 3, 2 or 1 amino acid differences with the CDR2 sequence mentioned in Table B-1 that belongs to the same combination; and a CDR3 sequence that has more than 80% sequence identity with the CDR3 sequence listed in Table B-1 that belongs to the same or a different combination.

Particularly preferred Nanobodies of the invention may for example comprise a CDR1 sequence mentioned in Table B-1, a CDR2 sequence that has more than 80% sequence identity with the CDR2 sequence mentioned in Table B-1 that belongs to the same combination; and the CDR3 sequence mentioned in Table B-1 that belongs to the same combination. In the most preferred Nanobodies of the invention, the CDR1, CDR2 and CDR3 sequences present are suitably chosen from one of the combinations of CDR1, CDR2 and CDR3 sequences, respectively, listed in Table B-1.

According to another preferred, but non-limiting aspect of the invention (a) CDR1 has a length of between 1 and 12 amino acid residues, and usually between 2 and 9 amino acid residues, such as 5, 6 or 7 amino acid residues; and/or (b) CDR2 has a length of between 13 and 24 amino acid residues, and usually between 15 and 21 amino acid residues, such as 16 and 17 amino acid residues; and/or (c) CDR3 has a length of between 2 and 35 amino acid residues, and usually between 3 and 30 amino acid residues, such as between 6 and 23 amino acid residues.

In another preferred, but non-limiting aspect, the invention relates to a Nanobody in which the CDR sequences (as defined herein) have more than 80%, preferably more than 90%, more preferably more than 95%, such as 99% or more sequence identity (as defined herein) with the CDR sequences of at least one of the immunoglobulin sequences of SEQ ID NO's: 705 to 788, more preferably SEQ ID NO's 726 to 750, 753 to 758, 762 to 764, 772 to 773, 775, or 778 to 780, more preferably SEQ ID NO's 726 to 750, 753 to 758, 762 to 764, 772 to 773, 775, or 778 to 780, more preferred SEQ ID NO's 732, 773 or 778 (see Table A-1).

Generally, Nanobodies with the above CDR sequences may be as further described herein, and preferably have framework sequences that are also as further described herein. Thus, for example and as mentioned herein, such Nanobodies may be naturally occurring Nanobodies (from any suitable species), naturally occurring $V_{HH}$ sequences (i.e. from a suitable species of Camelid) or synthetic or semi-synthetic immunoglobulin sequences or Nanobodies, including but not limited to partially humanized Nanobodies or $V_{HH}$ sequences, fully humanized Nanobodies or $V_{HH}$ sequences, camelized heavy chain variable domain sequences, as well as Nanobodies that have been obtained by the techniques mentioned herein.

Thus, in one specific, but non-limiting aspect, the invention relates to a humanized Nanobody, which consists of 4 framework regions (FR1 to FR4 respectively) and 3 complementarity determining regions (CDR1 to CDR3 respectively), in which CDR1 to CDR3 are as defined herein and in which said humanized Nanobody comprises at least one humanizing substitution (as defined herein), and in particular at least one humanizing substitution in at least one of its framework sequences (as defined herein).

In another preferred, but non-limiting aspect, the invention relates to a Nanobody in which the CDR sequences have at least 70% amino acid identity, preferably at least 80% amino acid identity, more preferably at least 90% amino acid identity, such as 95% amino acid identity or more or even essentially 100% amino acid identity with the CDR sequences of at least one of the immunoglobulin sequences of SEQ ID NO's: 705 to 788, more preferably SEQ ID NO's 726 to 750, 753 to 758, 762 to 764, 772 to 773, 775, or 778 to 780, more preferably SEQ ID NO's 726 to 750, 753 to 758, 762 to 764, 772 to 773, 775, or 778 to 780, more preferred SEQ ID NO's 732, 773 or 778 (see Table A-1). This degree of amino acid identity can for example be determined by determining the degree of amino acid identity (in a manner described herein) between said Nanobody and one or more of the sequences of SEQ ID NO's: 705 to 788, more preferably SEQ ID NO's 726 to 750, 753 to 758, 762 to 764, 772 to 773, 775, or 778 to 780, more preferred SEQ ID NO's 732, 773 or 778 (see Table A-1), in which the amino acid residues that form the framework regions are disregarded. Such Nanobodies can be as further described herein.

In another preferred, but non-limiting aspect, the invention relates to a Nanobody with an immunoglobulin sequence that is chosen from the group consisting of SEQ ID NO's: 705 to 788, more preferably SEQ ID NO's 726 to 750, 753 to 758, 762 to 764, 772 to 773, 775, or 778 to 780, more preferred SEQ ID NO's 732, 773 or 778 (see Table A-1) or from the group consisting of from immunoglobulin sequences that have more than 80%, preferably more than 90%, more preferably more than 95%, such as 99% or more sequence identity (as defined herein) with at least one of the immunoglobulin sequences of SEQ ID NO's: 705 to 788, more preferably SEQ ID NO's 726 to 750, 753 to 758, 762 to 764, 772 to 773, 775, or 778 to 780, more preferred SEQ ID NO's 732, 773 or 778 (see Table A-1).

Another preferred, but non-limiting aspect of the invention relates to humanized variants of the Nanobodies of SEQ ID NO's: 705 to 788, more preferably SEQ ID NO's 726 to 750, 753 to 758, 762 to 764, 772 to 773, 775, or 778 to 780, more preferred SEQ ID NO's 732, 773 or 778 (see Table A-1), that comprise, compared to the corresponding native $V_{HH}$ sequence, at least one humanizing substitution (as defined herein), and in particular at least one humanizing substitution in at least one of its framework sequences (as defined herein).

The polypeptides of the invention comprise or essentially consist of at least one Nanobody of the invention. Some preferred, but non-limiting examples of polypeptides of the invention are given in SEQ ID NO's: 789 to 791 (see Table A-3).

TABLE A-3

(if applicable): Preferred polypeptide or compound sequences (also referred herein as a sequence with a particular name or SEQ ID NO: X, wherein X is a number referring to the relevant immunoglobulin sequence):

| Name | P2X7 function | SEQ ID NO: X, wherein X = | Immunoglobulin sequence |
|---|---|---|---|
| 14D5-35GS-14D5 | Enhancer (see example 3.11&3.12) | 789 | EVQLVESGGGLVQAGGSLRLSCAASGSPISSY AMGWYRQAPGKPRELVARIYTGGTAWYEDSV KGRFTISRDNAQNTVYLQMNSLKSEDTAVYYC HGRVRYDYWGQGTQVTVSSGGGGSGGGGS GGGGSGGGGSGGGGSGGGGSGGGGSEVQL VESGGGLVQAGGSLRLSCAASGSPISSYAMG WYRQAPGKPRELVARIYTGGTAWYEDSVKGR FTISRDNAQNTVYLQMNSLKSEDTAVYYCHGR VRYDYWGQGTQVTVSS |
| 13A7-35GS-13A7 | Blocker (see example 3.11&3.12) | 790 | EVQLVESGGGLVQPGESLRLSCTASRFMLDYY DIGWFRQAPGKEREGVSCRFTNDGSTAYADS VKGRFTISRDIVKHTVYLQMNSLQPEDTAVYYC AAGPLTKRRQCVPGDFSMDFWGEGTLVTVSS |

TABLE A-3-continued (if applicable): Preferred polypeptide or compound
sequences (also referred herein as a sequence with a
particular name or SEQ ID NO: X, wherein X is a number
referring to the relevant immunoglobulin sequence):

| Name | P2X7 function | SEQ ID NO: X, wherein X = | Immunoglobulin sequence |
|---|---|---|---|
| | | | GGGGSGGGGSGGGGSGGGGSGGGGSGGG GSGGGGSEVQLVESGGGLVQPGESLRLSCTA SRFMLDYYDIGWFRQAPGKEREGVSCRFTND GSTAYADSVKGRFTISRDIVKHTVYLQMNSLQP EDTAVYYCAAGPLTKRRQCVPGDFSMDFWGE GTLVTVSS |
| 8G11-35GS-8G11 | Blocker (see example 3.11&3.12) | 791 | EVQLVESGGGLVQAGGSLRLSCAASGNFFRV NTMAWYRQAPGKQRELVADITRGDRTNYADT VNGRFTISRDNVRNTVYLQMNGLRPEDTAAYY CYAVIELGVLEPRDYWGQGTQVTVSSGGGGS GGGGSGGGGSGGGGSGGGGSGGGGSGGG GSEVQLVESGGGLVQAGGSLRLSCAASGNFF RVNTMAWYRQAPGKQRELVADITRGDRTNYA DTVNGRFTISRDNVRNTVYLQMNGLRPEDTAA YYCYAVIELGVLEPRDYWGQGTQVTVSS |

It will be clear to the skilled person that the Nanobodies that are mentioned herein as "preferred" (or "more preferred", "even more preferred", etc.) are also preferred (or more preferred, or even more preferred, etc.) for use in the polypeptides described herein. Thus, polypeptides that comprise or essentially consist of one or more "preferred" Nanobodies of the invention will generally be preferred, and polypeptides that comprise or essentially consist of one or more "more preferred" Nanobodies of the invention will generally be more preferred.

Generally, proteins or polypeptides that comprise or essentially consist of a single Nanobody (such as a single Nanobody of the invention) will be referred to herein as "monovalent" proteins or polypeptides or as "monovalent constructs". Proteins and polypeptides that comprise or essentially consist of two or more Nanobodies (such as at least two Nanobodies of the invention or at least one Nanobody of the invention and at least one other Nanobody) will be referred to herein as "multivalent" proteins or polypeptides or as "multivalent constructs", and these may provide certain advantages compared to the corresponding monovalent Nanobodies of the invention. Some non-limiting examples of such multivalent constructs will become clear from the further description herein.

According to one specific, but non-limiting aspect, a polypeptide of the invention comprises or essentially consists of at least two Nanobodies of the invention, such as two or three Nanobodies of the invention. As further described herein, such multivalent constructs can provide certain advantages compared to a protein or polypeptide comprising or essentially consisting of a single Nanobody of the invention, such as a much improved avidity for ion channels such as e.g. P2X7. Such multivalent constructs will be clear to the skilled person based on the disclosure herein; some preferred, but non-limiting examples of such multivalent Nanobody constructs are the constructs of SEQ ID NO's: 789 to 791.

According to another specific, but non-limiting aspect, a polypeptide of the invention comprises or essentially consists of at least one Nanobody of the invention and at least one other binding unit (i.e. directed against another epitope, antigen, target, protein or polypeptide), which is preferably also a Nanobody. Such proteins or polypeptides are also referred to herein as "multispecific" proteins or polypeptides or as 'multispecific constructs", and these may provide certain advantages compared to the corresponding monovalent Nanobodies of the invention (as will become clear from the further discussion herein of some preferred, but-nonlimiting multispecific constructs). Such multispecific constructs will be clear to the skilled person based on the disclosure herein; some preferred, but non-limiting examples of such multispecific Nanobody constructs are the constructs of SEQ ID NO's: 789 to 791.

According to yet another specific, but non-limiting aspect, a polypeptide of the invention comprises or essentially consists of at least one Nanobody of the invention, optionally one or more further Nanobodies, and at least one other immunoglobulin sequence (such as a protein or polypeptide) that confers at least one desired property to the Nanobody of the invention and/or to the resulting fusion protein. Again, such fusion proteins may provide certain advantages compared to the corresponding monovalent Nanobodies of the invention. Some non-limiting examples of such immunoglobulin sequences and of such fusion constructs will become clear from the further description herein.

It is also possible to combine two or more of the above aspects, for example to provide a trivalent bispecific construct comprising two Nanobodies of the invention and one other Nanobody, and optionally one or more other immunoglobulin sequences. Further non-limiting examples of such constructs, as well as some constructs that are particularly preferred within the context of the present invention, will become clear from the further description herein.

In the above constructs, the one or more Nanobodies and/or other immunoglobulin sequences may be directly linked to each other and/or suitably linked to each other via one or more linker sequences. Some suitable but non-limiting examples of such linkers will become clear from the further description herein.

In one specific aspect of the invention, a Nanobody of the invention or a compound, construct or polypeptide of the invention comprising at least one Nanobody of the invention may have an increased half-life, compared to the corresponding immunoglobulin sequence of the invention. Some preferred, but non-limiting examples of such Nanobodies, compounds and polypeptides will become clear to the skilled person based on the further disclosure herein, and for example comprise u Nanobodies sequences or polypeptides of the invention that have been chemically modified to increase the half-life thereof (for example, by means of pegylation); immunoglobulin sequences of the invention that comprise at least one additional binding site for binding to a serum protein (such as serum albumin, see for example EP 0 368 684 B1, page 4); or polypeptides of the invention that comprise at least one Nanobody of the invention that is linked to at least one moiety (and in particular at least one immunoglobulin sequence) that increases the half-life of the Nanobody of the invention. Examples of polypeptides of the invention that comprise such half-life extending moieties or immunoglobulin sequences will become clear to the skilled person based on the further disclosure herein; and for example include, without limitation, polypeptides in which the one or more Nanobodies of the invention are suitable linked to one or more serum proteins or fragments thereof (such as serum albumin or suitable fragments thereof) or to one or more binding units that can bind to serum proteins (such as, for example, Nanobodies or (single) domain antibodies that can bind to serum proteins such as serum albumin, serum immunoglobulins such as IgG, or transferrin); polypeptides in which a Nanobody of the invention is linked to an Fc portion (such as a human Fc) or a suitable part or fragment thereof; or polypeptides in which the one or more Nanobodies of the invention are suitable linked to one or more small proteins or peptides that can bind to serum proteins (such as, without limitation, the proteins and peptides described in WO 91/01743, WO 01/45746, WO 02/076489 and to the US provisional application of Ablynx N.V. entitled "Peptides capable of binding to serum proteins" of Ablynx N.V. filed on Dec. 5, 2006 (see also PCT/EP/2007/063348).

Again, as will be clear to the skilled person, such Nanobodies, compounds, constructs or polypeptides may contain one or more additional groups, residues, moieties or binding units, such as one or more further immunoglobulin sequences and in particular one or more additional Nanobodies (i.e. not directed against ion channels such as e.g. P2X7), so as to provide a tri- of multispecific Nanobody construct.

Generally, the Nanobodies of the invention (or compounds, constructs or polypeptides comprising the same) with increased half-life preferably have a half-life that is at least 1.5 times, preferably at least 2 times, such as at least 5 times, for example at least 10 times or more than 20 times, greater than the half-life of the corresponding immunoglobulin sequence of the invention per se. For example, the Nanobodies, compounds, constructs or polypeptides of the invention with increased half-life may have a half-life that is increased with more than 1 hours, preferably more than 2 hours, more preferably more than 6 hours, such as more than 12 hours, or even more than 24, 48 or 72 hours, compared to the corresponding immunoglobulin sequence of the invention per se.

In a preferred, but non-limiting aspect of the invention, such Nanobodies, compound, constructs or polypeptides of the invention exhibit a serum half-life in human of at least about 12 hours, preferably at least 24 hours, more preferably at least 48 hours, even more preferably at least 72 hours or more. For example, compounds or polypeptides of the invention may have a half-life of at least 5 days (such as about 5 to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

In another one aspect of the invention, a polypeptide of the invention comprises one or more (such as two or preferably one) Nanobodies of the invention linked (optionally via one or more suitable linker sequences) to one or more (such as two and preferably one) immunoglobulin sequences that allow the resulting polypeptide of the invention to cross the blood brain barrier. In particular, said one or more immunoglobulin sequences that allow the resulting polypeptides of the invention to cross the blood brain barrier may be one or more (such as two and preferably one) Nanobodies, such as the Nanobodies described in WO 02/057445, of which FC44 (SEQ ID NO: 189 of WO 06/040153) and FC5 (SEQ ID NO: 190 of WO 06/040154) are preferred examples.

In particular, polypeptides comprising one or more Nanobodies of the invention are preferably such that they:
bind to ion channels such as e.g. P2X7 with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles);
and/or such that they:
bind to ion channels such as e.g. P2X7 with a $k_{on}$-rate of between $10^2$ $M^{-1}s^{-1}$ to about $10^7$ $M^{-1}s^{-1}$, preferably between $10^3$ $M^{-1}s^{-1}$ and $10^7$ $M^{-1}s^{-1}$, more preferably between $10^4$ $M^{-1}s^{-1}$ and $10^7$ $M^{-1}s^{-1}$, such as between $10^5$ $M^{-1}s^{-1}$ and $10^7$ $M^{-1}s^{-1}$;
and/or such that they:
bind to ion channels such as e.g. P2X7 with a $k_{off}$ rate between 1 $s^{-1}$ ($t_{1/2}$=0.69 s) and $10^{-6}$ $s^{-1}$ (providing a near irreversible complex with a $t_{1/2}$ of multiple days), preferably between $10^{-2}$ $s^{-1}$ and $10^{-5}$ $s^{-1}$, more preferably between $10^{-3}$ $s^{-1}$ and $10^{-6}$ $s^{-1}$, such as between $10^{-4}$ $s^1$ and $10^{-6}$ $s^{-1}$.

Preferably, a polypeptide that contains only one immunoglobulin sequence of the invention is preferably such that it will bind to ion channels such as e.g. P2X7 with an affinity less than 500 nM, preferably less than 200 nM, more preferably less than 10 nM, such as less than 500 µM. In this respect, it will be clear to the skilled person that a polypeptide that contains two or more Nanobodies of the invention may bind to ion channels such as e.g. P2X7 with an increased avidity, compared to a polypeptide that contains only one immunoglobulin sequence of the invention.

Some preferred $IC_{50}$ values for binding of the immunoglobulin sequences or polypeptides of the invention to ion channels such as e.g. P2X7 will become clear from the further description and examples herein.

Other polypeptides according to this preferred aspect of the invention may for example be chosen from the group consisting of immunoglobulin sequences that have more than 80%, preferably more than 90%, more preferably more than 95%, such as 99% or more "sequence identity" (as defined herein) with one or more of the immunoglobulin sequences of SEQ ID NO's: 789 to 791 (see Table A-3), in which the Nanobodies comprised within said immunoglobulin sequences are preferably as further defined herein.

Another aspect of this invention relates to a nucleic acid that encodes an immunoglobulin sequence of the invention (such as a Nanobody of the invention) or a polypeptide of the invention comprising the same. Again, as generally described herein for the nucleic acids of the invention, such a nucleic acid may be in the form of a genetic construct, as defined herein.

In another aspect, the invention relates to host or host cell that expresses or that is capable of expressing an immunoglobulin sequence (such as a Nanobody) of the invention and/or a polypeptide of the invention comprising the same; and/or that contains a nucleic acid of the invention. Some preferred but non-limiting examples of such hosts or host cells will become clear from the further description herein.

Another aspect of the invention relates to a product or composition containing or comprising at least one immunoglobulin sequence of the invention, at least one polypeptide of the invention and/or at least one nucleic acid of the invention, and optionally one or more further components of such compositions known per se, i.e. depending on the intended use of the composition. Such a product or composition may for example be a pharmaceutical composition (as described herein), a veterinary composition or a product or composition for diagnostic use (as also described herein). Some preferred but non-limiting examples of such products or compositions will become clear from the further description herein.

The invention further relates to methods for preparing or generating the immunoglobulin sequences, compounds, constructs, polypeptides, nucleic acids, host cells, products and compositions described herein. Some preferred but non-limiting examples of such methods will become clear from the further description herein.

The invention further relates to applications and uses of the immunoglobulin sequences, compounds, constructs, polypeptides, nucleic acids, host cells, products and compositions described herein, as well as to methods for the prevention and/or treatment for diseases and disorders associated with ion channels such as e.g. P2X7. Some preferred but non-limiting applications and uses will become clear from the further description herein.

Other aspects, embodiments, advantages and applications of the invention will also become clear from the further description hereinbelow. Generally, it should be noted that the term Nanobody as used herein in its broadest sense is not limited to a specific biological source or to a specific method of preparation. For example, as will be discussed in more detail below, the Nanobodies of the invention can generally be obtained by any of the techniques (1) to (8) mentioned on pages 61 and 62 of WO 08/020079, or any other suitable technique known per se. One preferred class of Nanobodies corresponds to the $V_{HH}$ domains of naturally occurring heavy chain antibodies directed against ion channels such as e.g. P2X7. As further described herein, such $V_{HH}$ sequences can generally be generated or obtained by suitably immunizing a species of Camelid with ion channels such as e.g. P2X7 (i.e. so as to raise an immune response and/or heavy chain antibodies directed against ion channels such as e.g. P2X7), by obtaining a suitable biological sample from said Camelid (such as a blood sample, serum sample or sample of B-cells), and by generating $V_{HH}$ sequences directed against ion channels such as e.g. P2X7, starting from said sample, using any suitable technique known per se. Such techniques will be clear to the skilled person and/or are further described herein.

Alternatively, such naturally occurring $V_{HH}$ domains against ion channels such as e.g. P2X7, can be obtained from naïve libraries of Camelid $V_{HH}$ sequences, for example by screening such a library using ion channels such as e.g. P2X7, or at least one part, fragment, antigenic determinant or epitope thereof using one or more screening techniques known per se. Such libraries and techniques are for example described in WO 99/37681, WO 01/90190, WO 03/025020 and WO 03/035694. Alternatively, improved synthetic or semi-synthetic libraries derived from naïve $V_{HH}$ libraries may be used, such as $V_{HH}$ libraries obtained from naïve $V_{HH}$ libraries by techniques such as random mutagenesis and/or CDR shuffling, as for example described in WO 00/43507.

Thus, in another aspect, the invention relates to a method for generating Nanobodies, that are directed against ion channels such as e.g. P2X7. In one aspect, said method at least comprises the steps of:

a) providing a set, collection or library of Nanobody sequences; and
b) screening said set, collection or library of Nanobody sequences for Nanobody sequences that can bind to and/or have affinity for ion channels such as e.g. P2X7; and
c) isolating the Nanobody or Nanobodies that can bind to and/or have affinity for ion channels such as e.g. P2X7.

In such a method, the set, collection or library of Nanobody sequences may be a naïve set, collection or library of Nanobody sequences; a synthetic or semi-synthetic set, collection or library of Nanobody sequences; and/or a set, collection or library of Nanobody sequences that have been subjected to affinity maturation.

In a preferred aspect of this method, the set, collection or library of Nanobody sequences may be an immune set, collection or library of Nanobody sequences, and in particular an immune set, collection or library of $V_{HH}$ sequences, that have been derived from a species of Camelid that has been suitably immunized with ion channels such as e.g. P2X7 or with a suitable antigenic determinant based thereon or derived therefrom, such as an antigenic part, fragment, region, domain, loop or other epitope thereof. In one particular aspect, said antigenic determinant may be an extracellular part, region, domain, loop or other extracellular epitope(s).

In the above methods, the set, collection or library of Nanobody or $V_{HH}$ sequences may be displayed on a phage, phagemid, ribosome or suitable micro-organism (such as yeast), such as to facilitate screening. Suitable methods, techniques and host organisms for displaying and screening (a set, collection or library of) Nanobody sequences will be clear to the person skilled in the art, for example on the basis of the further disclosure herein. Reference is also made to WO 03/054016 and to the review by Hoogenboom in Nature Biotechnology, 23, 9, 1105-1116 (2005).

In another aspect, the method for generating Nanobody sequences comprises at least the steps of:

a) providing a collection or sample of cells derived from a species of Camelid that express immunoglobulin sequences;
b) screening said collection or sample of cells for (i) cells that express an immunoglobulin sequence that can bind to and/or have affinity for ion channels such as e.g. P2X7; and (ii) cells that express heavy chain antibodies, in which substeps (i) and (ii) can be performed essentially as a single screening step or in any suitable order as two separate screening steps, so as to provide at least one cell that expresses a heavy chain antibody that can bind to and/or has affinity for ion channels such as e.g. P2X7; and
c) either (i) isolating from said cell the $V_{HH}$ sequence present in said heavy chain antibody; or (ii) isolating from said cell a nucleic acid sequence that encodes the $V_{HH}$ sequence present n said heavy chain antibody, followed by expressing said $V_{HH}$ domain.

In the method according to this aspect, the collection or sample of cells may for example be a collection or sample of B-cells. Also, in this method, the sample of cells may be derived from a Camelid that has been suitably immunized with ion channels such as e.g. P2X7 or a suitable antigenic determinant based thereon or derived therefrom, such as an antigenic part, fragment, region, domain, loop or other epitope thereof. In one particular aspect, said antigenic determinant may be an extracellular part, region, domain, loop or other extracellular epitope(s).

The above method may be performed in any suitable manner, as will be clear to the skilled person. Reference is for example made to EP 0 542 810, WO 05/19824, WO 04/051268 and WO 04/106377. The screening of step b) is preferably performed using a flow cytometry technique such as FACS. For this, reference is for example made to Lieby et al., Blood, Vol. 97, No. 12, 3820. Particular reference is made to the so-called "Nanoclone™" technique described in International application WO 06/079372 by Ablynx N.V.

In another aspect, the method for generating an immunoglobulin sequence directed against ion channels such as e.g. P2X7 may comprise at least the steps of:
a) providing a set, collection or library of nucleic acid sequences encoding heavy chain antibodies or Nanobody sequences;
b) screening said set, collection or library of nucleic acid sequences for nucleic acid sequences that encode a heavy chain antibody or a Nanobody sequence that can bind to and/or has affinity for ion channels such as e.g. P2X7; and
c) isolating said nucleic acid sequence, followed by expressing the $V_{HH}$ sequence present in said heavy chain antibody or by expressing said Nanobody sequence, respectively.

In such a method, the set, collection or library of nucleic acid sequences encoding heavy chain antibodies or Nanobody sequences may for example be a set, collection or library of nucleic acid sequences encoding a naïve set, collection or library of heavy chain antibodies or $V_{HH}$ sequences; a set, collection or library of nucleic acid sequences encoding a synthetic or semi-synthetic set, collection or library of Nanobody sequences; and/or a set, collection or library of nucleic acid sequences encoding a set, collection or library of Nanobody sequences that have been subjected to affinity maturation.

In a preferred aspect of this method, the set, collection or library of nucleic acid sequences may be an immune set, collection or library of nucleic acid sequences encoding heavy chain antibodies or $V_{HH}$ sequences derived from a Camelid that has been suitably immunized with ion channels such as e.g. P2X7 or with a suitable antigenic determinant based thereon or derived therefrom, such as an antigenic part, fragment, region, domain, loop or other epitope thereof. In one particular aspect, said antigenic determinant may be an extracellular part, region, domain, loop or other extracellular epitope(s).

In the above methods, the set, collection or library of nucleotide sequences may be displayed on a phage, phagemid, ribosome or suitable micro-organism (such as yeast), such as to facilitate screening. Suitable methods, techniques and host organisms for displaying and screening (a set, collection or library of) nucleotide sequences encoding immunoglobulin sequences will be clear to the person skilled in the art, for example on the basis of the further disclosure herein. Reference is also made to WO 03/054016 and to the review by Hoogenboom in Nature Biotechnology, 23, 9, 1105-1116 (2005).

As will be clear to the skilled person, the screening step of the methods described herein can also be performed as a selection step. Accordingly the term "screening" as used in the present description can comprise selection, screening or any suitable combination of selection and/or screening techniques. Also, when a set, collection or library of sequences is used, it may contain any suitable number of sequences, such as 1, 2, 3 or about 5, 10, 50, 100, 500, 1000, 5000, $10^4$, $10^5$, $10^6$, $10^7$, $10^8$ or more sequences.

Also, one or more or all of the sequences in the above set, collection or library of immunoglobulin sequences may be obtained or defined by rational, or semi-empirical approaches such as computer modelling techniques or biostatics or datamining techniques.

Furthermore, such a set, collection or library can comprise one, two or more sequences that are variants from one another (e.g. with designed point mutations or with randomized positions), compromise multiple sequences derived from a diverse set of naturally diversified sequences (e.g. an immune library)), or any other source of diverse sequences (as described for example in Hoogenboom et al, Nat Biotechnol 23:1105, 2005 and Binz et al, Nat Biotechnol 2005, 23:1247). Such set, collection or library of sequences can be displayed on the surface of a phage particle, a ribosome, a bacterium, a yeast cell, a mammalian cell, and linked to the nucleotide sequence encoding the immunoglobulin sequence within these carriers. This makes such set, collection or library amenable to selection procedures to isolate the desired immunoglobulin sequences of the invention. More generally, when a sequence is displayed on a suitable host or host cell, it is also possible (and customary) to first isolate from said host or host cell a nucleotide sequence that encodes the desired sequence, and then to obtain the desired sequence by suitably expressing said nucleotide sequence in a suitable host organism. Again, this can be performed in any suitable manner known per se, as will be clear to the skilled person.

Yet another technique for obtaining $V_{HH}$ sequences or Nanobody sequences directed against ion channels such as e.g. P2X7 involves suitably immunizing a transgenic mammal that is capable of expressing heavy chain antibodies (i.e. so as to raise an immune response and/or heavy chain antibodies directed against ion channels such as e.g. P2X7), obtaining a suitable biological sample from said transgenic mammal that contains (nucleic acid sequences encoding) said $V_{HH}$ sequences or Nanobody sequences (such as a blood sample, serum sample or sample of B-cells), and then generating $V_{HH}$ sequences directed against ion channels such as e.g. P2X7, starting from said sample, using any suitable technique known per se (such as any of the methods described herein or a hybridoma technique). For example, for this purpose, the heavy chain antibody-expressing mice and the further methods and techniques described in WO 02/085945, WO 04/049794 and WO 06/008548 and Janssens et al., Proc. Natl. Acad. Sci. USA. 2006 Oct. 10; 103(41):15130-5 can be used. For example, such heavy chain antibody expressing mice can express heavy chain antibodies with any suitable (single) variable domain, such as (single) variable domains from natural sources (e.g. human (single) variable domains, Camelid (single) variable domains or shark (single) variable domains), as well as for example synthetic or semi-synthetic (single) variable domains.

The invention also relates to the $V_{HH}$ sequences or Nanobody sequences that are obtained by the above methods, or alternatively by a method that comprises the one of the above methods and in addition at least the steps of determining the nucleotide sequence or immunoglobulin sequence of said $V_{HH}$ sequence or Nanobody sequence; and of expressing or synthesizing said $V_{HH}$ sequence or Nanobody sequence in a manner known per se, such as by expression in a suitable host cell or host organism or by chemical synthesis.

As mentioned herein, a particularly preferred class of Nanobodies of the invention comprises Nanobodies with an immunoglobulin sequence that corresponds to the immunoglobulin sequence of a naturally occurring $V_{HH}$ domain, but that has been "humanized", i.e. by replacing one or more amino acid residues in the immunoglobulin sequence of said naturally occurring $V_{HH}$ sequence (and in particular in the framework sequences) by one or more of the amino acid residues that occur at the corresponding position(s) in a $V_H$ domain from a conventional 4-chain antibody from a human being (e.g. indicated above), as further described on, and using the techniques mentioned on, page 63 of WO 08/020079. Another particularly preferred class of Nanobodies of the invention comprises Nanobodies with an immunoglobulin sequence that corresponds to the immunoglobulin sequence of a naturally occurring $V_H$ domain, but that has been "camelized", i.e. by replacing one or more amino acid residues in the immunoglobulin sequence of a naturally occurring $V_H$ domain from a conventional 4-chain antibody by one or more of the amino acid residues that occur at the corresponding position(s) in a $V_{HH}$ domain of a heavy chain antibody, as further described on, and using the techniques mentioned on, page 63 of WO 08/020079.

Other suitable methods and techniques for obtaining the Nanobodies of the invention and/or nucleic acids encoding the same, starting from naturally occurring $V_H$ sequences or preferably $V_{HH}$ sequences, will be clear from the skilled person, and may for example include the techniques that are mentioned on page 64 of WO 08/00279 As mentioned herein, Nanobodies may in particular be characterized by the presence of one or more "Hallmark residues" (as described herein) in one or more of the framework sequences.

Thus, according to one preferred, but non-limiting aspect of the invention, a Nanobody in its broadest sense can be generally defined as a polypeptide comprising:

a) an immunoglobulin sequence that is comprised of four framework regions/sequences interrupted by three complementarity determining regions/sequences, in which the amino acid residue at position 108 according to the Kabat numbering is Q;

and/or:

b) an immunoglobulin sequence that is comprised of four framework regions/sequences interrupted by three complementarity determining regions/sequences, in which the amino acid residue at position 45 according to the Kabat numbering is a charged amino acid (as defined herein) or a cysteine residue, and position 44 is preferably an E;

and/or:

c) an immunoglobulin sequence that is comprised of four framework regions/sequences interrupted by three complementarity determining regions/sequences, in which the amino acid residue at position 103 according to the Kabat numbering is chosen from the group consisting of P, R and S, and is in particular chosen from the group consisting of R and S.

Thus, in a first preferred, but non-limiting aspect, a Nanobody of the invention may have the structure
FR1-CDR1-FR2-CDR2-FR3-CDR3-FR4
in which FR1 to FR4 refer to framework regions 1 to 4, respectively, and in which CDR1 to CDR3 refer to the complementarity determining regions 1 to 3, respectively, and in which a) the amino acid residue at position 108 according to the Kabat numbering is Q; and/or in which:

b) the amino acid residue at position 45 according to the Kabat numbering is a charged amino acid or a cysteine and the amino acid residue at position 44 according to the Kabat numbering is preferably E;

and/or in which:

c) the amino acid residue at position 103 according to the Kabat numbering is chosen from the group consisting of P, R and S, and is in particular chosen from the group consisting of R and S;

and in which:

d) CDR1, CDR2 and CDR3 are as defined herein, and are preferably as defined according to one of the preferred aspects herein, and are more preferably as defined according to one of the more preferred aspects herein.

In particular, a Nanobody in its broadest sense can be generally defined as a polypeptide comprising:

a) an immunoglobulin sequence that is comprised of four framework regions/sequences interrupted by three complementarity determining regions/sequences, in which the amino acid residue at position 108 according to the Kabat numbering is Q;

and/or:

b) an immunoglobulin sequence that is comprised of four framework regions/sequences interrupted by three complementarity determining regions/sequences, in which the amino acid residue at position 44 according to the Kabat numbering is E and in which the amino acid residue at position 45 according to the Kabat numbering is an R;

and/or:

c) an immunoglobulin sequence that is comprised of four framework regions/sequences interrupted by three complementarity determining regions/sequences, in which the amino acid residue at position 103 according to the Kabat numbering is chosen from the group consisting of P, R and S, and is in particular chosen from the group consisting of R and S.

Thus, according to a preferred, but non-limiting aspect, a Nanobody of the invention may have the structure
FR1-CDR1-FR2-CDR2-FR3-CDR3-FR4
in which FR1 to FR4 refer to framework regions 1 to 4, respectively, and in which CDR1 to CDR3 refer to the complementarity determining regions 1 to 3, respectively, and in which a) the amino acid residue at position 108 according to the Kabat numbering is Q;

and/or in which:

b) the amino acid residue at position 44 according to the Kabat numbering is E and in which the amino acid residue at position 45 according to the Kabat numbering is an R;

and/or in which:

c) the amino acid residue at position 103 according to the Kabat numbering is chosen from the group consisting of P, R and 5, and is in particular chosen from the group consisting of R and S;

and in which:

d) CDR1, CDR2 and CDR3 are as defined herein, and are preferably as defined according to one of the preferred aspects herein, and are more preferably as defined according to one of the more preferred aspects herein.

In particular, a Nanobody against ion channels such as e.g. P2X7 according to the invention may have the structure:
FR1-CDR1-FR2-CDR2-FR3-CDR3-FR4
in which FR1 to FR4 refer to framework regions 1 to 4, respectively, and in which CDR1 to CDR3 refer to the complementarity determining regions 1 to 3, respectively, and in which
a) the amino acid residue at position 108 according to the Kabat numbering is Q;
and/or in which:
b) the amino acid residue at position 44 according to the Kabat numbering is E and in which the amino acid residue at position 45 according to the Kabat numbering is an R;
and/or in which:
c) the amino acid residue at position 103 according to the Kabat numbering is chosen from the group consisting of P, R and S, and is in particular chosen from the group consisting of R and S;
and in which:
d) CDR1, CDR2 and CDR3 are as defined herein, and are preferably as defined according to one of the preferred aspects herein, and are more preferably as defined according to one of the more preferred aspects herein.

In particular, according to one preferred, but non-limiting aspect of the invention, a Nanobody can generally be defined as a polypeptide comprising an immunoglobulin sequence that is comprised of four framework regions/sequences interrupted by three complementarity determining regions/sequences, in which;
a-1) the amino acid residue at position 44 according to the Kabat numbering is chosen from the group consisting of A, G, E, D, G, Q, R, S, L; and is preferably chosen from the group consisting of G, E or Q; and
a-2) the amino acid residue at position 45 according to the Kabat numbering is chosen from the group consisting of L, R or C; and is preferably chosen from the group consisting of L or R; and
a-3) the amino acid residue at position 103 according to the Kabat numbering is chosen from the group consisting of W, R or S; and is preferably W or R, and is most preferably W;
a-4) the amino acid residue at position 108 according to the Kabat numbering is Q; or in which:
b-1) the amino acid residue at position 44 according to the Kabat numbering is chosen from the group consisting of E and Q; and
b-2) the amino acid residue at position 45 according to the Kabat numbering is R;
and
b-3) the amino acid residue at position 103 according to the Kabat numbering is chosen from the group consisting of W, R and S; and is preferably W;
b-4) the amino acid residue at position 108 according to the Kabat numbering is chosen from the group consisting of Q and L; and is preferably Q;
or in which:
c-1) the amino acid residue at position 44 according to the Kabat numbering is chosen from the group consisting of A, G, E, D, Q, R, S and L; and is preferably chosen from the group consisting of G, E and Q; and
c-2) the amino acid residue at position 45 according to the Kabat numbering is chosen from the group consisting of L, R and C; and is preferably chosen from the group consisting of L and R; and c-3) the amino acid residue at position 103 according to the Kabat numbering is chosen from the group consisting of P, R and S; and is in particular chosen from the group consisting of R and S; and
c-4) the amino acid residue at position 108 according to the Kabat numbering is chosen from the group consisting of Q and L; is preferably Q;
and in which
d) CDR1, CDR2 and CDR3 are as defined herein, and are preferably as defined according to one of the preferred aspects herein, and are more preferably as defined according to one of the more preferred aspects herein.

Thus, in another preferred, but non-limiting aspect, a Nanobody of the invention may have the structure
FR1-CDR1-FR2-CDR2-FR3-CDR3-FR4
in which FR1 to FR4 refer to framework regions 1 to 4, respectively, and in which CDR1 to CDR3 refer to the complementarity determining regions 1 to 3, respectively, and in which:
a-1) the amino acid residue at position 44 according to the Kabat numbering is chosen from the group consisting of A, G, E, D, G, Q, R, S, L; and is preferably chosen from the group consisting of G, E or Q;
and in which:
a-2) the amino acid residue at position 45 according to the Kabat numbering is chosen from the group consisting of L, R or C; and is preferably chosen from the group consisting of L or R;
and in which:
a-3) the amino acid residue at position 103 according to the Kabat numbering is chosen from the group consisting of W, R or S; and is preferably W or R, and is most preferably W;
and in which
a-4) the amino acid residue at position 108 according to the Kabat numbering is Q;
and in which:
d) CDR1. CDR2 and CDR3 are as defined herein, and are preferably as defined according to one of the preferred aspects herein, and are more preferably as defined according to one of the more preferred aspects herein.

In another preferred, but non-limiting aspect, a Nanobody of the invention may have the structure
FR1-CDR1-FR2-CDR2-FR3-CDR3-FR4
in which FR1 to FR4 refer to framework regions 1 to 4, respectively, and in which CDR1 to CDR3 refer to the complementarity determining regions 1 to 3, respectively, and in which:
b-1) the amino acid residue at position 44 according to the Kabat numbering is chosen from the group consisting of E and Q;
and in which:
b-2) the amino acid residue at position 45 according to the Kabat numbering is R;
and in which:
b-3) the amino acid residue at position 103 according to the Kabat numbering is chosen from the group consisting of W, R and S; and is preferably W;
and in which:
b-4) the amino acid residue at position 108 according to the Kabat numbering is chosen from the group consisting of Q and L; and is preferably Q;
and in which:
d) CDR1, CDR2 and CDR3 are as defined herein, and are preferably as defined according to one of the preferred aspects herein, and are more preferably as defined according to one of the more preferred aspects herein.

In another preferred, but non-limiting aspect, a Nanobody of the invention may have the structure
FR1-CDR1-FR2-CDR2-FR3-CDR3-FR4
in which FR1 to FR4 refer to framework regions 1 to 4, respectively, and in which CDR1 to CDR3 refer to the complementarity determining regions 1 to 3, respectively, and in which:
c-1) the amino acid residue at position 44 according to the Kabat numbering is chosen from the group consisting of A, G, E, D, Q, R, S and L; and is preferably chosen from the group consisting of G, E and Q;
and in which:
c-2) the amino acid residue at position 45 according to the Kabat numbering is chosen from the group consisting of L, R and C; and is preferably chosen from the group consisting of L and R;
and in which:
c-3) the amino acid residue at position 103 according to the Kabat numbering is chosen from the group consisting of P, R and S; and is in particular chosen from the group consisting of R and S;
and in which:
c-4) the amino acid residue at position 108 according to the Kabat numbering is chosen from the group consisting of Q and L; is preferably Q;
and in which:
d) CDR1, CDR2 and CDR3 are as defined herein, and are preferably as defined according to one of the preferred aspects herein, and are more preferably as defined according to one of the more preferred aspects herein.

Two particularly preferred, but non-limiting groups of the Nanobodies of the invention are those according to a) above; according to (a-1) to (a-4) above; according to b) above; according to (b-1) to (b-4) above; according to (c) above; and/or according to (c-1) to (c-4) above, in which either:
i) the amino acid residues at positions 44-47 according to the Kabat numbering form the sequence GLEW (or a GLEW-like sequence as described herein) and the amino acid residue at position 108 is Q;
or in which:
ii) the amino acid residues at positions 43-46 according to the Kabat numbering form the sequence KERE or KQRE (or a KERE-like sequence as described) and the amino acid residue at position 108 is Q or L, and is preferably Q.

Thus, in another preferred, but non-limiting aspect, a Nanobody of the invention may have the structure
FR1-CDR1-FR2-CDR2-FR3-CDR3-FR4
in which FR1 to FR4 refer to framework regions 1 to 4, respectively, and in which CDR1 to CDR3 refer to the complementarity determining regions 1 to 3, respectively; and in which:
i) the amino acid residues at positions 44-47 according to the Kabat numbering form the sequence GLEW (or a GLEW-like sequence as defined herein) and the amino acid residue at position 108 is Q;
and in which:
ii) CDR1, CDR2 and CDR3 are as defined herein, and are preferably as defined according to one of the preferred aspects herein, and are more preferably as defined according to one of the more preferred aspects herein.

In another preferred, but non-limiting aspect, a Nanobody of the invention may have the structure
FR1-CDR1-FR2-CDR2-FR3-CDR3-FR4
in which FR1 to FR4 refer to framework regions 1 to 4, respectively, and in which CDR1 to CDR3 refer to the complementarity determining regions 1 to 3, respectively, and in which:
i) the amino acid residues at positions 43-46 according to the Kabat numbering form the sequence KERE or KQRE (or a KERE-like sequence) and the amino acid residue at position 108 is Q or L, and is preferably Q;
and in which:
ii) CDR1, CDR2 and CDR3 are as defined herein, and are preferably as defined according to one of the preferred aspects herein, and are more preferably as defined according to one of the more preferred aspects herein.

In the Nanobodies of the invention in which the amino acid residues at positions 43-46 according to the Kabat numbering form the sequence KERE or KQRE, the amino acid residue at position 37 is most preferably F. In the Nanobodies of the invention in which the amino acid residues at positions 44-47 according to the Kabat numbering form the sequence GLEW, the amino acid residue at position 37 is chosen from the group consisting of Y, H, I, L, V or F, and is most preferably V.

Thus, without being limited hereto in any way, on the basis of the amino acid residues present on the positions mentioned above, the Nanobodies of the invention can generally be classified on the basis of the following three groups:
i) The "GLEW-group": Nanobodies with the immunoglobulin sequence GLEW at positions 44-47 according to the Kabat numbering and Q at position 108 according to the Kabat numbering. As further described herein, Nanobodies within this group usually have a V at position 37, and can have a W, P, R or S at position 103, and preferably have a W at position 103. The GLEW group also comprises some GLEW-like sequences such as those mentioned in Table B-2 below. More generally, and without limitation, Nanobodies belonging to the GLEW-group can be defined as Nanobodies with a G at position 44 and/or with a W at position 47, in which position 46 is usually E and in which preferably position 45 is not a charged amino acid residue and not cysteine;
ii) The "KERE-group": Nanobodies with the immunoglobulin sequence KERE or KQRE (or another KERE-like sequence) at positions 43-46 according to the Kabat numbering and Q or L at position 108 according to the Kabat numbering. As further described herein, Nanobodies within this group usually have a F at position 37, an L or F at position 47; and can have a W, P, R or S at position 103, and preferably have a W at position 103. More generally, and without limitation, Nanobodies belonging to the KERE-group can be defined as Nanobodies with a K, Q or R at position 44 (usually K) in which position 45 is a charged amino acid residue or cysteine, and position 47 is as further defined herein;
iii) The "103 P, R, S-group": Nanobodies with a P, R or S at position 103. These Nanobodies can have either the immunoglobulin sequence GLEW at positions 44-47 according to the Kabat numbering or the immunoglobulin sequence KERE or KQRE at positions 43-46 according to the Kabat numbering, the latter most preferably in combination with an F at position 37 and an L or an F at position 47 (as defined for the KERE-group); and can have Q or L at position 108 according to the Kabat numbering, and preferably have Q.

Also, where appropriate, Nanobodies may belong to (i.e. have characteristics of) two or more of these classes. For example, one specifically preferred group of Nanobodies has GLEW or a GLEW-like sequence at positions 44-47; P, R or S (and in particular R) at position 103; and Q at position 108 (which may be humanized to L).

More generally, it should be noted that the definitions referred to above describe and apply to Nanobodies in the form of a native (i.e. non-humanized) $V_{HH}$ sequence, and that humanized variants of these Nanobodies may contain other amino acid residues than those indicated above (i.e. one or more humanizing substitutions as defined herein). For example, and without limitation, in some humanized Nanobodies of the GLEW-group or the 103 P, R, S-group, Q at position 108 may be humanized to 108L. As already mentioned herein, other humanizing substitutions (and suitable combinations thereof) will become clear to the skilled person based on the disclosure herein. In addition, or alternatively, other potentially useful humanizing substitutions can be ascertained by comparing the sequence of the framework regions of a naturally occurring $V_{HH}$ sequence with the corresponding framework sequence of one or more closely related human $V_H$ sequences, after which one or more of the potentially useful humanizing substitutions (or combinations thereof) thus determined can be introduced into said $V_{HH}$ sequence (in any manner known per se, as further described herein) and the resulting humanized $V_{HH}$ sequences can be tested for affinity for the target, for stability, for ease and level of expression, and/or for other desired properties. In this way, by means of a limited degree of trial and error, other suitable humanizing substitutions (or suitable combinations thereof) can be determined by the skilled person based on the disclosure herein. Also, based on the foregoing, (the framework regions of) a Nanobody may be partially humanized or fully humanized.

Thus, in another preferred, but non-limiting aspect, a Nanobody of the invention may be a Nanobody belonging to the GLEW-group (as defined herein), and in which CDR1, CDR2 and CDR3 are as defined herein, and are preferably as defined according to one of the preferred aspects herein, and are more preferably as defined according to one of the more preferred aspects herein.

In another preferred, but non-limiting aspect, a Nanobody of the invention may be a Nanobody belonging to the KERE-group (as defined herein), and CDR1, CDR2 and CDR3 are as defined herein, and are preferably as defined according to one of the preferred aspects herein, and are more preferably as defined according to one of the more preferred aspects herein.

Thus, in another preferred, but non-limiting aspect, a Nanobody of the invention may be a Nanobody belonging to the 103 P, ft S-group (as defined herein), and in which CDR1, CDR2 and CDR3 are as defined herein, and are preferably as defined according to one of the preferred aspects herein, and are more preferably as defined according to one of the more preferred aspects herein.

Also, more generally and in addition to the 108Q, 43E/ 44R and 103 P, R, S residues mentioned above, the Nanobodies of the invention can contain, at one or more positions that in a conventional $V_H$ domain would form (part of) the $V_H/V_L$ interface, one or more amino acid residues that are more highly charged than the amino acid residues that naturally occur at the same position(s) in the corresponding naturally occurring $V_H$ sequence, and in particular one or more charged amino acid residues (as mentioned in Table A-2 on page 48 of the International application WO 08/020079). Such substitutions include, but are not limited to, the GLEW-like sequences mentioned in Table B-2 below; as well as the substitutions that are described in the International Application WO 00/29004 for so-called "microbodies", e.g. so as to obtain a Nanobody with Q at position 108 in combination with KLEW at positions 44-47. Other possible substitutions at these positions will be clear to the skilled person based upon the disclosure herein. In one aspect of the Nanobodies of the invention, the amino acid residue at position 83 is chosen from the group consisting of L, M, S, V and W; and is preferably L. Also, in one aspect of the Nanobodies of the invention, the amino acid residue at position 83 is chosen from the group consisting of R, K, N, E, G, I, T and Q; and is most preferably either K or E (for Nanobodies corresponding to naturally occurring $V_{HH}$ domains) or R (for "humanized" Nanobodies, as described herein). The amino acid residue at position 84 is chosen from the group consisting of P, A, R, S, D T, and V in one aspect, and is most preferably P (for Nanobodies corresponding to naturally occurring $V_{HH}$ domains) or R (for "humanized" Nanobodies, as described herein). Furthermore, in one aspect of the Nanobodies of the invention, the amino acid residue at position 104 is chosen from the group consisting of G and D; and is most preferably G.

Collectively, the amino acid residues at positions 11, 37, 44, 45, 47, 83, 84, 103, 104 and 108, which in the Nanobodies are as mentioned above, will also be referred to herein as the "Hallmark Residues". The Hallmark Residues and the amino acid residues at the corresponding positions of the most closely related human $V_H$ domain, $V_H3$, are summarized in Table B-2.

Some especially preferred but non-limiting combinations of these Hallmark Residues as occur in naturally occurring $V_E$ domains are mentioned in Table B-3. For comparison, the corresponding amino acid residues of the human $V_H3$ called DP-47 have been indicated in italics.

TABLE B-2

Hallmark Residues in Nanobodies

| Position | Human $V_H3$ | Hallmark Residues |
|---|---|---|
| 11 | L, V; predominantly L | L, S, V, M, W, F, T, Q, E, A, R, G, K, Y, N, P, I; preferably L |
| 37 | V, I, F; usually V | F$^{(1)}$, Y, V, L, A, H, S, I, W, C, N, G, D, T, P, preferably F$^{(1)}$ or Y |
| 44$^{(8)}$ | G | E$^{(3)}$, Q$^{(3)}$, G$^{(2)}$, D, A, K, R, L, P, S, V, H, T, N, W, M, I; preferably G$^{(2)}$, E$^{(3)}$ or Q$^{(3)}$; most preferably G$^{(2)}$ or Q$^{(3)}$. |
| 45$^{(8)}$ | L | L$^{(2)}$, R$^{(3)}$, P, H, F, G, Q, S, E, T, Y, C, I, D, V; preferably L$^{(2)}$ or R$^{(3)}$ |
| 47$^{(8)}$ | W, Y | F$^{(1)}$, L$^{(1)}$ or W$^{(2)}$ G, I, S, A, V, M, R, Y, E, P, T, C, H, K, Q, N, D; preferably W$^{(2)}$, L$^{(1)}$ or F$^{(1)}$ |
| 83 | R or K; usually R | R, K$^{(5)}$, T, E$^{(5)}$, Q, N, S, I, V, G, M, L, A, D, Y, H; preferably K or R; most preferably K |
| 84 | A, T, D; predominantly A | P$^{(5)}$, S, H, L, A, V, I, T, F, D, R, Y, N, Q, G, E; preferably P |
| 103 | W | W$^{(4)}$, R$^{(6)}$, G, S, K, A, M, Y, L, F, T, N, V, Q, P$^{(6)}$, E, C; preferably W |
| 104 | G | G, A, S, T, D, P, N, E, C, L; preferably G |
| 108 | L, M or T; predominantly L | Q, L$^{(7)}$, R, P, E, K, S, T, M, A, H; preferably Q or L$^{(7)}$ |

Notes:
$^{(1)}$In particular, but not exclusively, in combination with KERE or KQRE at positions 43-46.
$^{(2)}$Usually as GLEW at positions 44-47.
$^{(3)}$Usually as KERE or KQRE at positions 43-46, e.g. as KEREL, KEREF, KQREL, KQREF, KEREG, KQREW or KQREG at positions 43-47. Alternatively, also sequences such as TERE (for example TEREL), TQRE (for example TQREL), KECE (for example KECEL or KECER), KQCE (for example KQCEL), RERE (for example REREG), RQRE (for example RQREL, RQREF or RQREW), QERE (for example QEREG), QQRE, (for example QQREW, QQREL or QQREF), KGRE (for example KGREG), KDRE (for example KDREV) are possible. Some other possible, but less preferred sequences include for example DECKL and NVCEL.
$^{(4)}$With both GLEW at positions 44-47 and KERE or KQRE at positions 43-46.
$^{(5)}$Often as KP or EP at positions 83-84 of naturally occurring $V_{HH}$ domains.
$^{(6)}$In particular, but not exclusively, in combination with GLEW at positions 44-47.
$^{(7)}$With the proviso that when positions 44-47 are GLEW, position 108 is always Q in (non-humanized) $V_{HH}$ sequences that also contain a W at 103.
$^{(8)}$The GLEW group also contains GLEW-like sequences at positions 44-47, such as for example GVEW, EPEW, GLER, DQEW, DLEW, GIEW, ELEW, GPEW, EWLP, GPER, GLER and ELEW.

TABLE B-3

Some preferred but non-limiting combinations of Hallmark Residues in naturally occurring Nanobodies. For humanization of these combinations, reference is made to the specification.

|  | 11 | 37 | 44 | 45 | 47 | 83 | 84 | 103 | 104 | 108 |
|---|---|---|---|---|---|---|---|---|---|---|
| DP-47 (human) | M | V | G | L | W | R | A | W | G | L |
| "KERE" group | L | F | E | R | L | K | P | W | G | Q |
|  | L | F | E | R | F | E | P | W | G | Q |
|  | L | F | E | R | F | K | P | W | G | Q |
|  | L | Y | Q | R | L | K | P | W | G | Q |
|  | L | F | L | R | V | K | P | Q | G | Q |
|  | L | F | Q | R | L | K | P | W | G | Q |
|  | L | F | E | R | F | K | P | W | G | Q |
| "GLEW" group | L | V | G | L | W | K | S | W | G | Q |
|  | M | V | G | L | W | K | P | R | G | Q |

In the Nanobodies, each amino acid residue at any other position than the Hallmark Residues can be any amino acid residue that naturally occurs at the corresponding position (according to the Kabat numbering) of a naturally occurring $V_{HH}$ domain.

Such amino acid residues will be clear to the skilled person. Tables B-4 to B-7 mention some non-limiting residues that can be present at each position (according to the Kabat numbering) of the FR1, FR2, FR3 and FR4 of naturally occurring $V_{HH}$ domains. For each position, the amino acid residue that most frequently occurs at each position of a naturally occurring $V_{HH}$ domain (and which is the most preferred amino acid residue for said position in a Nanobody) is indicated in bold; and other preferred amino acid residues for each position have been underlined (note: the number of amino acid residues that are found at positions 26-30 of naturally occurring $V_{HH}$ domains supports the hypothesis underlying the numbering by Chothia (supra) that the residues at these positions already form part of CDR1).

In Tables B-4-B-7, some of the non-limiting residues that can be present at each position of a human $V_H3$ domain have also been mentioned. Again, for each position, the amino acid residue that most frequently occurs at each position of a naturally occurring human $V_H3$ domain is indicated in bold; and other preferred amino acid residues have been underlined.

For reference only, Tables B-4-B-7 also contain data on the $V_{HH}$ entropy ("$V_{HH}$ Ent.") and $V_{HH}$ variability ("$V_{HH}$ Var.") at each amino acid position for a representative sample of 7732 $V_{HH}$ sequences (including a.o. data kindly provided by David Lutje Hulsing and Prof. Theo Verrips of Utrecht University). The values for the $V_{HH}$ entropy and the $V_{HH}$ variability provide a measure for the variability and degree of conservation of amino acid residues between the 7732 $V_{HH}$ sequences analyzed: low values (i.e. <1, such as <0.5) indicate that an amino acid residue is highly conserved between the $V_{HH}$ sequences (i.e. little variability). For example, the G at position 9 and the W at position 36 have values for the $V_{HH}$ entropy of 0.01 and 0 respectively, indicating that these residues are highly conserved and have little variability (and in case of position 36 is W in all 7732 sequences analysed), whereas for residues that form part of the CDR's generally values of 1.5 or more are found (data not shown). Note that the data represented below support the hypothesis that the amino acid residues at positions 27-30 and maybe even also at positions 93 and 94 already form part of the CDR's (although the invention is not limited to any specific hypothesis or explanation, and as mentioned above, herein the numbering according to Kabat is used). For a general explanation of sequence entropy, sequence variability and the methodology for determining the same, see Oliveira et al., PROTEINS: Structure, Function and Genetics, 52: 544-552 (2003).

TABLE B-4

Non-limiting examples of amino acid residues in FR1 (for the footnotes, see the footnotes to Table B-2)

| Pos. | Human $V_H3$ | Camelid $V_{HH}$'s | $V_{HH}$ Ent. | $V_{HH}$ Var. |
|---|---|---|---|---|
| 1 | E, Q | E, Q, K, D, A, G, R | 0.47 | 5 |
| 2 | V | V, M, A, E, L | 0.04 | 1 |
| 3 | Q | Q, K, P, H, F, R | 0.04 | 1 |
| 4 | L | L, M, Q, P, R, F, V | 0.02 | 1 |
| 5 | V, L | V, Q, M, E, A, L, P, K, R | 0.35 | 3 |
| 6 | E | E, A, Q, D, K, H | 0.21 | 5 |
| 7 | S, T | S, F, L, W, T | 0.05 | 2 |
| 8 | G, R | G, R, E, V | 0.04 | 1 |
| 9 | G | G, R, V, A | 0.01 | 1 |
| 10 | G, V | G, D, R, S, K, E, A, Q, N, T, V | 0.22 | 4 |
| 11 |  | Hallmark residue: L, S, V, M, W, F, T, Q, E, A, R, G, K, Y, N, P, I; preferably L | 0.35 | 4 |
| 12 | V, I | V, A, L, M, E, G, T | 0.11 | 2 |
| 13 | Q, K, R | Q, L, R, H, P, E, K, T, S, V, D, G, A, N, M | 0.46 | 3 |
| 14 | P | A, P, T, V, S, D, F, N, I, E, L, R, G, Y, Q, H | 0.92 | 5 |
| 15 | G | G, E | 0 | 1 |
| 16 | G, R | G, D, E, A, S, N, V, R, K, T, P, C, L | 0.47 | 4 |
| 17 | S | S, F, P, Y, T, A, C, R, N | 0.14 | 2 |
| 18 | L | L, V, R, M, P, Q, S, A, T, K, H | 0.06 | 1 |
| 19 | R, K | R, T, K, S, N, G, A, I, L, Q, F, E, V, M | 0.36 | 4 |
| 20 | L | L, F, V, I, P, H, S | 0.18 | 3 |
| 21 | S | S, A, T, P, F, V, H, D, R, L, I, G | 0.13 | 3 |
| 22 | C | C, W | 0 | 1 |
| 23 | A, T | A, V, T, E, S, L, G, I, K, Q, R, D, F, N, P, M | 0.88 | 5 |
| 24 | A | A, D, V, T, H, Y, P, G, S, F, L, I, N, Q, E, R | 0.78 | 9 |
| 25 | S | S, P, T, A, F, L, N, Y, R, H, D, V, I, W, G, K, Q, C | 0.2 | 2 |

TABLE B-4-continued

Non-limiting examples of amino acid residues in FR1 (for the footnotes, see the footnotes to Table B-2)

| Pos. | Human $V_H3$ | Camelid $V_{HH}$'s | $V_{HH}$ Ent. | $V_{HH}$ Var. |
|---|---|---|---|---|
| 26 | G | G, E, R, V, T, A, S, K, D, L, I, Q, N, F, Y, M, W, P, H | 0.45 | 6 |
| 27 | F | R, F, S, P, L, G, I, N, T, D, H, V, E, A, Y, K, M, Q, W, C | 1.89 | 12 |
| 28 | T | T, I, S, A, P, F, D, N, V, R, M, L, G, Y, K, E, H, W, Q | 1.29 | 12 |
| 29 | F, V | F, L, S, V, I, A, W, Y, G, D, R, T, P, N, E, M, H, Q, K, C | 1.23 | 11 |
| 30 | S, D, G | S, D, N, G, R, T, A, E, I, Y, K, V, H, L, F, W, M, P, C, Q | 1.55 | 12 |

TABLE B-5

Non-limiting examples of amino acid residues in FR2 (for the footnotes, see the footnotes to Table B-2)

| Pos. | Human $V_H3$ | Camelid $V_{HH}$'s | $V_{HH}$ Ent. | $V_{HH}$ Var. |
|---|---|---|---|---|
| 36 | W | W | 0 | 1 |
| 37 | | Hallmark residue: $F^{(1)}$, Y, V, L, A, H, S, I, W, C, N, G, D, T, P, preferably $F^{(1)}$ or Y | 1.1 | 7 |
| 38 | R | R, H, C, P, Y, L, V | 0.01 | 1 |
| 39 | Q | Q, E, R, H, L, A, S, K, P, V, T, D | 0.22 | 3 |
| 40 | A | A, V, T, P, G, S, D, I, L, R, N, F, Y, C, E, H | 0.55 | 6 |
| 41 | P, S, T | P, S, A, L, T, Q, R, V, D, G, I, H | 0.18 | 3 |
| 42 | G | G, E, A, R, D, V, W, T, Q, K, L, N, H, M | 0.1 | 2 |
| 43 | K | K, N, Q, E, R, T, L, S, M, D, G, A, V, H, I, F, P | 0.45 | 7 |
| 44 | | Hallmark residue: $E^{(3)}$, $Q^{(3)}$, $G^{(2)}$, D, A, K, R, L, P, S, V, H, T, N, W, M, I; preferably $G^{(2)}$, $E^{(3)}$ or $Q^{(3)}$; most preferably $G^{(2)}$ or $Q^{(3)}$. | 1.11 | 4 |
| 45 | | Hallmark residue: $L^{(2)}$, $R^{(3)}$, P, H, F, G, Q, S, E, T, Y, C, I, D, V; preferably $L^{(2)}$ or $R^{(3)}$ | 0.56 | 3 |
| 46 | E, V | E, D, A, Q, V, M, K, T, G, R, S, N, I, L, F | 0.42 | 4 |
| 47 | | Hallmark residue: $F^{(1)}$, $L^{(1)}$ or $W^{(2)}$ G, I, S, A, V, M, R, Y, E, P, T, C, H, K, Q, N, D; preferably $W^{(2)}$, $L^{(1)}$ or $F^{(1)}$ | 1.64 | 11 |
| 48 | V | V, I, L, A, T, Q, F, M, G, E, R | 0.35 | 5 |
| 49 | S, A, G | A, S, G, T, V, L, C, I, F, P, E, Y, M, D, R | 0.89 | 5 |

TABLE B-6

Non-limiting examples of amino acid residues in FR3 (for the footnotes, see the footnotes to Table B-2)

| Pos. | Human $V_H3$ | Camelid $V_{HH}$'s | $V_{HH}$ Ent. | $V_{HH}$ Var. |
|---|---|---|---|---|
| 66 | R | R | 0 | 1 |
| 67 | F | F, S, L, V, I, C, A, Y, M, G | 0.1 | 1 |
| 68 | T | T, A, S, I, F, V, P, N, G, R, K, M, D, L, W, Q | 0.34 | 4 |
| 69 | I | I, V, M, T, L, A, F, P, S, G, N | 0.5 | 5 |
| 70 | S | S, T, A, F, P, V, Y, L, D, G, N, H, W, E, C | 0.22 | 4 |
| 71 | R | R, S, K, G, T, I, W, A, N, V, E, L, M, F, D, Q, C | 0.61 | 7 |
| 72 | D, E | D, N, E, G, V, A, H, L, S, T, I, Q, F, P, Y, R | 0.34 | 4 |
| 73 | N, D, G | N, D, S, K, I, Y, G, T, H, R, A, V, F, L, E, M, P, C | 0.65 | 9 |
| 74 | A, S | A, T, V, S, F, G, D, P, N, I, R, L, Y, H, E, Q, K, W, M | 0.8 | 8 |
| 75 | K | K, N, E, R, Q, A, G, T, M, S, L, D, V, W, Y, I | 0.71 | 6 |
| 76 | N, S | N, K, S, R, D, T, H, G, E, A, Y, I, M, Q, L, W, P, F, V | 0.66 | 7 |

TABLE B-6-continued

Non-limiting examples of amino acid residues in FR3 (for the footnotes, see the footnotes to Table B-2)

| Pos. | Human V$_H$3 | Camelid V$_{HH}$'s — Amino acid residue(s) | V$_{HH}$ Ent. | V$_{HH}$ Var. |
|---|---|---|---|---|
| 77 | S, T, I | T, A, M, S, R, I, V, L, P, E, N, K, G, W, Q | 0.72 | 7 |
| 78 | L, A | V, L, A, M, I, G, T, F, W, Q, S, E, N, H | 1.11 | 6 |
| 79 | Y, H | Y, F, D, S, H, N, T, A, L, W, V, C, G, E, I, P, R | 0.68 | 8 |
| 80 | L | L, M, V, P, F | 0.05 | 2 |
| 81 | Q | Q, E, R, H, L, D, T, G, K, P, A, I, S, N, Y, V, M | 0.38 | 4 |
| 82 | M | M, I, L, V, A, T, S, K | 0.12 | 3 |
| 82a | N, G | N, S, D, T, E, H, K, I, A, G, R, Y, L, V, F, Q | 0.77 | 5 |
| 82b | S | S, N, T, G, H, D, R, A, K, I, M, V, F, E, P, Y, C, L | 0.72 | 8 |
| 82c | L | L, V, M, P, A, T, G | 0.08 | 2 |
| 83 | Hallmark residue: R, K$^{(5)}$, T, E$^{(5)}$, Q, N, S, I, V, G, M, L, A, D, Y, H; preferably K or R; most preferably K | | 0.66 | 6 |
| 84 | Hallmark residue: P$^{(5)}$, S, H, L, A, V, I, T, F, D, R, Y, N, Q, G, E; preferably P | | 0.85 | 7 |
| 85 | E, G | E, D, G, A, Q, V, S, N, K, T, R, L | 0.27 | 3 |
| 86 | D | D, E, G, N | 0.02 | 1 |
| 87 | T, M | T, S, A, M, R, P, K, E | 0.15 | 3 |
| 88 | A | A, G, S, D, N, T, P, V | 0.23 | 2 |
| 89 | V, L | V, I, L, E, A, R, T, D, F, M, N, S, K, G, Q, H | 0.71 | 7 |
| 90 | Y | Y, H, F, N | 0 | 1 |
| 91 | Y, H | Y, F, R, S, H, T, I, V, L, N, D, C, Q, W, A, E, M | 0.6 | 7 |
| 92 | C | C, R, P | 0 | 1 |
| 93 | A, K, T | A, N, T, K, G, V, R, Y, S, H, W, L, F, Q, M, I, E, C, D | 1.33 | 10 |
| 94 | K, R, T | A, K, V, T, R, L, G, S, D, Q, I, M, F, Y, N, E, H, P, C, W | 1.55 | 12 |

TABLE B-7

Non-limiting examples of amino acid residues in FR4 (for the footnotes, see the footnotes to Table B-2)

| Pos. | Human V$_H$3 | Camelid V$_{HH}$'s — Amino acid residue(s) | V$_{HH}$ Ent. | V$_{HH}$ Var. |
|---|---|---|---|---|
| 103 | Hallmark residue: W$^{(4)}$, R$^{(6)}$, G, S, K, A, M, Y, L, F, T, N, V, Q, P$^{(6)}$, E, C; preferably W | | 0.54 | 6 |
| 104 | Hallmark residue: G, A, S, T, D, P, N, E, C, L; preferably G | | 0.13 | 3 |
| 105 | Q, R | Q, K, H, R, P, E, L, T, N, S, V, A, M, G | 0.52 | 5 |
| 106 | G | G, R, E | 0 | 1 |
| 107 | T | T, Q, I, A, S, N, R, V, D | 0.24 | 3 |
| 108 | Hallmark residue: Q, L$^{(7)}$, R, P, E, K, S, T, M, A, H; preferably Q or L$^{(7)}$ | | 0.3 | 4 |
| 109 | V | V, I, L | 0 | 1 |
| 110 | T | T, S, N, A, I, F | 0.01 | 1 |
| 111 | V | V, I, A | 0.01 | 1 |
| 112 | S | S, T, P, F, A | 0.01 | 1 |
| 113 | S | S, T, A, L, P, F, E, V | 0.04 | 1 |

Thus, in another preferred, but not limiting aspect, a Nanobody of the invention can be defined as an immunoglobulin sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:

i) one or more of the amino acid residues at positions 11, 37, 44, 45, 47, 83, 84, 103, 104 and 108 according to the Kabat numbering are chosen from the Hallmark residues mentioned in Table B-2;

and in which:

ii) CDR1, CDR2 and CDR3 are as defined herein, and are preferably as defined according to one of the preferred aspects herein, and are more preferably as defined according to one of the more preferred aspects herein.

The above Nanobodies may for example be V$_{HH}$ sequences or may be humanized Nanobodies. When the above Nanobody sequences are V$_{HH}$ sequences, they may be suitably humanized, as further described herein. When the Nanobodies are partially humanized Nanobodies, they may optionally be further suitably humanized, again as described herein.

In particular, a Nanobody of the invention can be an immunoglobulin sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:

i) (preferably) one or more of the amino acid residues at positions 11, 37, 44, 45, 47, 83, 84, 103, 104 and 108 according to the Kabat numbering are chosen from the Hallmark residues mentioned in Table B-2 (it being understood that $V_{HH}$ sequences will contain one or more Hallmark residues; and that partially humanized Nanobodies will usually, and preferably, [still] contain one or more Hallmark residues [although it is also within the scope of the invention to provide—where suitable in accordance with the invention—partially humanized Nanobodies in which all Hallmark residues, but not one or more of the other amino acid residues, have been humanized]; and that in fully humanized Nanobodies, where suitable in accordance with the invention, all amino acid residues at the positions of the Hallmark residues will be amino acid residues that occur in a human $V_H 3$ sequence. As will be clear to the skilled person based on the disclosure herein that such $V_{HH}$ sequences, such partially humanized Nanobodies with at least one Hallmark residue, such partially humanized Nanobodies without Hallmark residues and such fully humanized Nanobodies all form aspects of this invention);

and in which:

ii) said immunoglobulin sequence has at least 80% amino acid identity with at least one of the immunoglobulin sequences of SEQ ID NO's: 1 to 22, in which for the purposes of determining the degree of amino acid identity, the amino acid residues that form the CDR sequences (indicated with X in the sequences of SEQ ID NO's: 1 to 22) are disregarded;

and in which:

iii) CDR1, CDR2 and CDR3 are as defined herein, and are preferably as defined according to one of the preferred aspects herein, and are more preferably as defined according to one of the more preferred aspects herein.

The above Nanobodies may for example be $V_{HH}$ sequences or may be humanized Nanobodies. When the above Nanobody sequences are $V_{HH}$ sequences, they may be suitably humanized, as further described herein. When the Nanobodies are partially humanized Nanobodies, they may optionally be further suitably humanized, again as described herein.

TABLE B-8

Representative immunoglobulin sequences for Nanobodies of the KERE, GLEW and P, R, S 103 group. The CDR's are indicated with XXXX

| | | |
|---|---|---|
| KERE sequence no. 1 | SEQ ID NO: 1 | EVQLVESGGGLVQPGGSLRLSCAASGIPFSXXXXXWFRQAPGK QRDSVAXXXXXXRFTISRDNAKNTVYLQMNSLKPEDTAVYRCYFX XXXXXWGQGTQVTVSS |
| KERE sequence no. 2 | SEQ ID NO: 2 | QVKLEESGGGLVQAGGSLRLSCVGSGRTFSXXXXXWFRLAPG KEREFVAXXXXXXRFTISRDTASNRGYLHMNNLTPEDTAVYYCAA XXXXXWGQGTQVTVSS |
| KERE sequence no. 3 | SEQ ID NO: 3 | AVQLVDSGGGLVQAGDSLKLSCALTGGAFTXXXXXWFRQTPG REREFVAXXXXXXRFTISRDNAKNMVYLRMNSLIPEDAAVYSCAA XXXXXWGQGTLVTVSS |
| KERE sequence no. 4 | SEQ ID NO: 4 | QVQLVESGGGLVEAGGSLRLSCTASESPFRXXXXXWFRQTSG QEREFVAXXXXXXRFTISRDDAKNTVWLHGSTLKPEDTAVYYCAA XXXXXWGQGTQVTVSS |
| KERE sequence no. 5 | SEQ ID NO: 5 | AVQLVESGGGLVQGGGSLRLACAASERIFDXXXXXWYRQGPG NERELVAXXXXXXRFTISMDYTKQTVYLHMNSLRPEDTGLYYCKI XXXXXWGQGTQVTVSS |
| KERE sequence no. 6 | SEQ ID NO: 6 | DVKFVESGGGLVQAGGSLRLSCVASGFNFDXXXXXWFRQAPG KEREEVAXXXXXXRFTISSEKDKNSVYLQMNSLKPEDTALYICAG XXXXXWGRGTQVTVSS |
| KERE sequence no. 7 | SEQ ID NO: 7 | QVRLAESGGGLVQSGGSLRLSCVASGSTYTXXXXXWYRQYPG KQRALVAXXXXXXRFTIARDSTKDTFCLQMNNLKPEDTAVYYCYA XXXXXWGQGTQVTVSS |
| KERE sequence no. 8 | SEQ ID NO: 8 | EVQLVESGGGLVQAGGSLRLSCAASGFTSDXXXXXWFRQAPG KPREGVSXXXXXXRFTISTDNAKNTVHLLMNRVNAEDTALYYCAV XXXXXWGRGTRVTVSS |
| KERE sequence no. 9 | SEQ ID NO: 9 | QVQLVESGGGLVQPGGSLRLSCQASGDISTXXXXXWYRQVPG KLREFVAXXXXXXRFTISGDNAKRAIYLQMNNLKPDDTAVYYCNR XXXXXWGQGTQVTVSP |
| KERE sequence no. 10 | SEQ ID NO: 10 | QVPVVESGGGLVQAGDSLRLFCAVPSFTSTXXXXXWFRQAPGK EREFVAXXXXXXRFTISRNATKNTLTLRMDSLKPEDTAVYYCAAX XXXXXWGQGTQVTVSS |
| KERE sequence no. 11 | SEQ ID NO: 11 | EVQLVESGGGLVQAGDSLRLFCTVSGGTASXXXXXWFRQAPG EKREFVAXXXXXXRFTIARENAGNMVYLQMNNLKPDDTALYTCAA XXXXXWGRGTQVTVSS |

TABLE B-8-continued

Representative immunoglobulin sequences for Nanobodies of the KERE, GLEW and P, R, S 103 group. The CDR's are indicated with XXXX

| | | |
|---|---|---|
| KERE sequence no. 12 | SEQ ID NO: 12 | AVQLVESGGDSVQPGDSQTLSCAASGRTNSXXXXXWFRQAPG KERVFLAXXXXXRFTISRDSAKNMMYLQMNNLKPQDTAVYYCA AXXXXXWGQGTQVTVSS |
| KERE sequence no. 13 | SEQ ID NO: 13 | AVQLVESGGGLVQAGGSLRLSCVVSGLTSSXXXXXWFRQTPW QERDFVAXXXXXRFTISRDNYKDTVLLEMNFLKPEDTAIYYCAAX XXXXWGQGTQVTVSS |
| KERE sequence no. 14 | SEQ ID NO: 14 | AVQLVESGGGLVQAGASLRLSCATSTRTLDXXXXXWFRQAPGR DREFVAXXXXXRFTVSRDSAENTVALQMNSLKPEDTAVYYCAA XXXXXWGQGTRVTVSS |
| KERE sequence no. 15 | SEQ ID NO: 15 | QVQLVESGGGLVQPGGSLRLSCTVSRLTAHXXXXXWFRQAPG KEREAVSXXXXXRFTISRDYAGNTAFLQMDSLKPEDTGVYYCAT XXXXXWGQGTQVTVSS |
| KERE sequence no. 16 | SEQ ID NO: 16 | EVQLVESGGELVQAGGSLKLSCTASGRNFVXXXXXWFRRAPG KEREFVAXXXXXRFTVSRDNGKNTAYLRMNSLKPEDTADYYCA VXXXXXLGSGTQVTVSS |
| GLEW sequence no. 1 | SEQ ID NO: 17 | AVQLVESGGGLVQPGGSLRLSCAASGFTFSXXXXXWVRQAPG KVLEWVSXXXXXRFTISRDNAKNTLYLQMNSLKPEDTAVYYCVK XXXXXGSQGTQVTVSS |
| GLEW sequence no. 2 | SEQ ID NO: 18 | EVQLVESGGGLVQPGGSLRLSCVCVSSGCTXXXXXWVRQAPG KAEEWVSXXXXXRFKISRDNAKKTLYLQMNSLGPEDTAMYYCQ RXXXXXRGQGTQVTVSS |
| GLEW sequence no. 3 | SEQ ID NO: 19 | EVQLVESGGGLALPGGSLTLSCVFSGSTFSXXXXXWVRHTPGK AEEWVSXXXXXRFTISRDNAKNTLYLEMNSLSPEDTAMYYCGR XXXXXRSKGIQVTVSS |
| P, R, S 103 sequence no. 1 | SEQ ID NO: 20 | AVQLVESGGGLVQAGGSLRLSCAASGRTFSXXXXXWFRQAPG KEREFVAXXXXXRFTISRDNAKNTVYLQMNSLKPEDTAVYYCAA XXXXXRGQGTQVTVSS |
| P, R, S 103 sequence no. 2 | SEQ ID NO: 21 | DVQLVESGGDLVQPGGSLRLSCAASGFSFDXXXXXWLRQTPG KGLEWVGXXXXXRFTISRDNAKNMLYLHLNNLKSEDTAVYYCR RXXXXXLGQGTQVTVSS |
| P, R, S 103 sequence no. 3 | SEQ ID NO: 22 | EVQLVESGGGLVQPGGSLRLSCVCVSSGCTXXXXXWVRQAPG KAEEWVSXXXXXRFKISRDNAKKTLYLQMNSLGPEDTAMYYCQ RXXXXXRGQGTQVTVSS |

In particular, a Nanobody of the invention of the KERE group can be an immunoglobulin sequence with the (general) structure
FR1-CDR1-FR2-CDR2-FR3-CDR3-FR4
in which:
i) the amino acid residue at position 45 according to the Kabat numbering is a charged amino acid (as defined herein) or a cysteine residue, and position 44 is preferably an E;
and in which:
ii) FR1 is an immunoglobulin sequence that has at least 80% amino acid identity with at least one of the following immunoglobulin sequences:

TABLE B-9

Representative FW1 sequences for Nanobodies of the KERE-group.

| | | |
|---|---|---|
| KERE FW1 sequence no. 1 | SEQ ID NO: 23 | QVQRVESGGGLVQAGGSLRLSCAASG RTSS |
| KERE FW1 sequence no. 2 | SEQ ID NO: 24 | QVQLVESGGGLVQTGDSLSLSCSASG RTFS |
| KERE FW1 sequence no. 3 | SEQ ID NO: 25 | QVKLEESGGGLVQAGDSLRLSCAATG RAFG |
| KERE FW1 sequence no. 4 | SEQ ID NO: 26 | AVQLVESGGGLVQPGESLGLSCVASG RDFV |
| KERE FW1 sequence no. 5 | SEQ ID NO: 27 | EVQLVESGGGLVQAGGSLRLSCEVLG RTAG |
| KERE FW1 sequence no. 6 | SEQ ID NO: 28 | QVQLVESGGGWVQPGGSLRLSCAASE TILS |
| KERE FW1 sequence no. 7 | SEQ ID NO: 29 | QVQLVESGGGTVQPGGSLNLSCVASG NTFN |
| KERE FW1 sequence no. 8 | SEQ ID NO: 30 | EVQLVESGGGLAQPGGSLQLSCSAPG FTLD |
| KERE FW1 sequence no. 9 | SEQ ID NO: 31 | AQELEESGGGLVQAGGSLRLSCAASG RTFN | and in which:
iii) FR2 is an immunoglobulin sequence that has at least 80% amino acid identity with at least one of the following immunoglobulin sequences:

TABLE B-10

Representative FW2 sequences for Nanobodies of the KERE-group.

| | | |
|---|---|---|
| KERE FW2 sequence no. 1 | SEQ ID NO: 41 | WFRQAPGKEREFVA |
| KERE FW2 sequence no. 2 | SEQ ID NO: 42 | WFRQTPGREREFVA |
| KERE FW2 sequence no. 3 | SEQ ID NO: 43 | WYRQAPGKQREMVA |
| KERE FW2 sequence no. 4 | SEQ ID NO: 44 | WYRQGPGKQRELVA |
| KERE FW2 sequence no. 5 | SEQ ID NO: 45 | WIRQAPGKEREGVS |
| KERE FW2 sequence no. 6 | SEQ ID NO: 46 | WFREAPGKEREGIS |
| KERE FW2 sequence no. 7 | SEQ ID NO: 47 | WYRQAPGKERDLVA |
| KERE FW2 sequence no. 8 | SEQ ID NO: 48 | WFRQAPGKQREEVS |
| KERE FW2 sequence no. 9 | SEQ ID NO: 49 | WFRQPPGKVREFVG | and in which:

iv) FR3 is an immunoglobulin sequence that has at least 80% amino acid identity with at least one of the following immunoglobulin sequences:

TABLE B-11

Representative FW3 sequences for Nanobodies of the KERE-group.

| | | |
|---|---|---|
| KERE FW3 sequence no. 1 | SEQ ID NO: 50 | RFTISRDNAKNTVYLQMNSLKPEDTAVYRCYF |
| KERE FW3 sequence no. 2 | SEQ ID NO: 51 | RFAISRDNNKNTGYLQMNSLEPEDTAVYYCAA |
| KERE FW3 sequence no. 3 | SEQ ID NO: 52 | RFTVARNNAKNTVNLEMNSLKPEDTAVYYCAA |
| KERE FW3 sequence no. 4 | SEQ ID NO: 53 | RFTISRDIAKNTVDLLMNNLEPEDTAVYYCAA |
| KERE FW3 sequence no. 5 | SEQ ID NO: 54 | RLTISRDNAVDTMYLQMNSLKPEDTAVYYCAA |
| KERE FW3 sequence no. 6 | SEQ ID NO: 55 | RFTISRDNAKNTVYLQMDNVKPEDTAIYYCAA |
| KERE FW3 sequence no. 7 | SEQ ID NO: 56 | RFTISKDSGKNTVYLQMTSLKPEDTAVYYCAT |
| KERE FW3 sequence no. 8 | SEQ ID NO: 57 | RFTISRDSAKNMMYLQMNNLKPQDTAVYYCAA |
| KERE FW3 sequence no. 9 | SEQ ID NO: 58 | RFTISRENDKSTVYLQLNSLKPEDTAVYYCAA |
| KERE FW3 sequence no. 10 | SEQ ID NO: 59 | RFTISRDYAGNTAYLQMNSLKPEDTGVYYCAT | and in which:

v) FR4 is an immunoglobulin sequence that has at least 80% amino acid identity with at least one of the following immunoglobulin sequences:

TABLE B-12

Representative FW4 sequences for Nanobodies of the KERE-group.

| | | |
|---|---|---|
| KERE FW4 sequence no. 1 | SEQ ID NO: 60 | WGQGTQVTVSS |
| KERE FW4 sequence no. 2 | SEQ ID NO: 61 | WGKGTLVTVSS |
| KERE FW4 sequence no. 3 | SEQ ID NO: 62 | RGQGTRVTVSS |
| KERE FW4 sequence no. 4 | SEQ ID NO: 63 | WGLGTQVTISS | and in which:

vi) CDR1, CDR2 and CDR3 are as defined herein, and are preferably as defined according to one of the preferred aspects herein, and are more preferably as defined according to one of the more preferred aspects herein.

In the above Nanobodies, one or more of the further Hallmark residues are preferably as described herein (for example, when they are $V_{HH}$ sequences or partially humanized Nanobodies).

Also, the above Nanobodies may for example be $V_{HH}$ sequences or may be humanized Nanobodies. When the above Nanobody sequences are $V_{HH}$ sequences, they may be suitably humanized, as further described herein. When the Nanobodies are partially humanized Nanobodies, they may optionally be further suitably humanized, again as described herein.

With regard to framework 1, it will be clear to the skilled person that, when an immunoglobulin sequence as outlined above is generated by expression of a nucleotide sequence, the first four immunoglobulin sequences (i.e. amino acid residues 1-4 according to the Kabat numbering) may often be determined by the primer(s) that have been used to generate said nucleic acid. Thus, for determining the degree of amino acid identity, the first four amino acid residues are preferably disregarded.

Also, with regard to framework 1, and although amino acid positions 27 to 30 are according to the Kabat numbering considered to be part of the framework regions (and not the CDR's), it has been found by analysis of a database of more than 1000 $V_{HH}$ sequences that the positions 27 to 30 have a variability (expressed in terms of $V_{HH}$ entropy and $V_{HH}$ variability—see Tables B-4 to B-7) that is much greater than the variability on positions 1 to 26. Because of this, for determining the degree of amino acid identity, the amino acid residues at positions 27 to 30 are preferably also disregarded.

In view of this, a Nanobody of the KERE class may be an immunoglobulin sequence that is comprised of four framework regions/sequences interrupted by three complementarity determining regions/sequences, in which:

i) the amino acid residue at position 45 according to the Kabat numbering is a charged amino acid (as defined herein) or a cysteine residue, and position 44 is preferably an E;

and in which:

ii) FR1 is an immunoglobulin sequence that, on positions 5 to 26 of the Kabat numbering, has at least 80% amino acid identity with at least one of the following immunoglobulin sequences:

TABLE B-13

Representative FW1 sequences (amino acid residues 5 to 26) for Nanobodies of the KERE-group.

| | | |
|---|---|---|
| KERE FW1 sequence no. 10 | SEQ ID NO: 32 | VESGGGLVQPGGSLRLSCAASG |
| KERE FW1 sequence no. 11 | SEQ ID NO: 33 | VDSGGGLVQAGDSLKLSCALTG |
| KERE FW1 sequence no. 12 | SEQ ID NO: 34 | VDSGGGLVQAGDSLRLSCAASG |
| KERE FW1 sequence no. 13 | SEQ ID NO: 35 | VDSGGGLVEAGGSLRLSCQVSE |
| KERE FW1 sequence no. 14 | SEQ ID NO: 36 | QDSGGGSVQAGGSLKLSCAASG |
| KERE FW1 sequence no. 15 | SEQ ID NO: 37 | VQSGGRLVQAGDSLRLSCAASE |
| KERE FW1 sequence no. 16 | SEQ ID NO: 38 | VESGGTLVQSGDSLKLSCASST |
| KERE FW1 sequence no. 17 | SEQ ID NO: 39 | MESGGDSVQSGGSLTLSCVASG |
| KERE FW1 sequence no. 18 | SEQ ID NO: 40 | QASGGGLVQAGGSLRLSCSASV | and in which:
iii) FR2, FR3 and FR4 are as mentioned herein for FR2, FR3 and FR4 of Nanobodies of the KERE-class;
and in which:
iv) CDR1, CDR2 and CDR3 are as defined herein, and are preferably as defined according to one of the preferred aspects herein, and are more preferably as defined according to one of the more preferred aspects herein.

The above Nanobodies may for example be $V_{HH}$ sequences or may be humanized Nanobodies. When the above Nanobody sequences are $V_{HH}$ sequences, they may be suitably humanized, as further described herein. When the Nanobodies are partially humanized Nanobodies, they may optionally be further suitably humanized, again as described herein.

A Nanobody of the GLEW class may be an immunoglobulin sequence that is comprised of four framework regions/sequences interrupted by three complementarity determining regions/sequences, in which
i) preferably, when the Nanobody of the GLEW-class is a non-humanized Nanobody, the amino acid residue in position 108 is Q;
ii) FR1 is an immunoglobulin sequence that has at least 80% amino acid identity with at least one of the following immunoglobulin sequences:

TABLE B-14

Representative FW1 sequences for Nanobodies of the GLEW-group.

| | | |
|---|---|---|
| GLEW FW1 sequence no. 1 | SEQ ID NO: 64 | QVQLVESGGGLVQPGGSLRLSCAASGFTFS |
| GLEW FW1 sequence no. 2 | SEQ ID NO: 65 | EVHLVESGGGLVRPGGSLRLSCAAFGFIFK |
| GLEW FW1 sequence no. 3 | SEQ ID NO: 66 | QVKLEESGGGLAQPGGSLRLSCVASGFTFS |
| GLEW FW1 sequence no. 4 | SEQ ID NO: 67 | EVQLVESGGGLVQPGGSLRLSCVCVSSGCT |

TABLE B-14-continued

Representative FW1 sequences for Nanobodies of the GLEW-group.

| | | |
|---|---|---|
| GLEW FW1 sequence no. 5 | SEQ ID NO: 68 | EVQLVESGGGLALPGGSLTLSCVFSGSTFS | and in which:
iii) FR2 is an immunoglobulin sequence that has at least 80% amino acid identity with at least one of the following immunoglobulin sequences:

TABLE B-15

Representative FW2 sequences for Nanobodies of the GLEW-group.

| | | |
|---|---|---|
| GLEW FW2 sequence no. 1 | SEQ ID NO: 72 | WVRQAPGKVLEWVS |
| GLEW FW2 sequence no. 2 | SEQ ID NO: 73 | WVRRPPGKGLEWVS |
| GLEW FW2 sequence no. 3 | SEQ ID NO: 74 | WVRQAPGMGLEWVS |
| GLEW FW2 sequence no. 4 | SEQ ID NO: 75 | WVRQAPGKEPEWVS |
| GLEW FW2 sequence no. 5 | SEQ ID NO: 76 | WVRQAPGKDQEWVS |
| GLEW FW2 sequence no. 6 | SEQ ID NO: 77 | WVRQAPGKAEEWVS |
| GLEW FW2 sequence no. 7 | SEQ ID NO: 78 | WVRQAPGKGLEWVA |
| GLEW FW2 sequence no. 8 | SEQ ID NO: 79 | WVRQAPGRATEWVS | and in which:
iv) FR3 is an immunoglobulin sequence that has at least 80% amino acid identity with at least one of the following immunoglobulin sequences:

TABLE B-16

Representative FW3 sequences for Nanobodies of the GLEW- group.

| | | |
|---|---|---|
| GLEW FW3 sequence no. 1 | SEQ ID NO: 80 | RFTISRDNAKNTLYLQMNSLKPEDTAVYYCVK |
| GLEW FW3 sequence no. 2 | SEQ ID NO: 81 | RFTISRDNARNTLYLQMDSLIPEDTALYYCAR |
| GLEW FW3 sequence no. 3 | SEQ ID NO: 82 | RFTSSRDNAKSTLYLQMNDLKPEDTALYYCAR |
| GLEW FW3 sequence no. 4 | SEQ ID NO: 83 | RFIISRDNAKNTLYLQMNSLGPEDTAMYYCQR |
| GLEW FW3 sequence no. 5 | SEQ ID NO: 84 | RFTASRDNAKNTLYLQMNSLKSEDTARYYCAR |
| GLEW FW3 sequence no. 6 | SEQ ID NO: 85 | RFTISRDNAKNTLYLQMDDLQSEDTAMYYCGR | and in which:
v) FR4 is an immunoglobulin sequence that has at least 80% amino acid identity with at least one of the following immunoglobulin sequences:

TABLE B-17

Representative FW4 sequences for Nanobodies of the GLEW-group.

| | | |
|---|---|---|
| GLEW FW4 sequence no. 1 | SEQ ID NO: 86 | GSQGTQVTVSS |
| GLEW FW4 sequence no. 2 | SEQ ID NO: 87 | LRGGTQVTVSS |
| GLEW FW4 sequence no. 3 | SEQ ID NO: 88 | RGQGTLVTVSS |
| GLEW FW4 sequence no. 4 | SEQ ID NO: 89 | RSRGIQVTVSS |
| GLEW FW4 sequence no. 5 | SEQ ID NO: 90 | WGKGTQVTVSS |
| GLEW FW4 sequence no. 6 | SEQ ID NO: 91 | WGQGTQVTVSS | and in which:

vi) CDR1, CDR2 and CDR3 are as defined herein, and are preferably as defined according to one of the preferred aspects herein, and are more preferably as defined according to one of the more preferred aspects herein.

In the above Nanobodies, one or more of the further Hallmark residues are preferably as described herein (for example, when they are $V_{HH}$ sequences or partially humanized Nanobodies).

With regard to framework 1, it will again be clear to the skilled person that, for determining the degree of amino acid identity, the amino acid residues on positions 1 to 4 and 27 to 30 are preferably disregarded.

In view of this, a Nanobody of the GLEW class may be an immunoglobulin sequence that is comprised of four framework regions/sequences interrupted by three complementarity determining regions/sequences, in which:

i) preferably, when the Nanobody of the GLEW-class is a non-humanized Nanobody, the amino acid residue in position 108 is Q;

and in which:

ii) FR1 is an immunoglobulin sequence that, on positions 5 to 26 of the Kabat numbering, has at least 80% amino acid identity with at least one of the following immunoglobulin sequences:

TABLE B-18

Representative FW1 sequences (amino acid residues 5 to 26) for Nanobodies of the KERE-group.

| | | |
|---|---|---|
| GLEW FW1 sequence no. 6 | SEQ ID NO: 69 | VESGGGLVQPGGSLRLSCAASG |
| GLEW FW1 sequence no. 7 | SEQ ID NO: 70 | EESGGGLAQPGGSLRLSCVASG |
| GLEW FW1 sequence no. 8 | SEQ ID NO: 71 | VESGGGLALPGGSLTLSCVFSG | and in which:

iii) FR2, FR3 and FR4 are as mentioned herein for FR2, FR3 and FR4 of Nanobodies of the GLEW-class;

and in which:

iv) CDR1. CDR2 and CDR3 are as defined herein, and are preferably as defined according to one of the preferred aspects herein, and are more preferably as defined according to one of the more preferred aspects herein.

The above Nanobodies may for example be $V_{HH}$ sequences or may be humanized Nanobodies. When the above Nanobody sequences are $V_{HH}$ sequences, they may be suitably humanized, as further described herein. When the Nanobodies are partially humanized Nanobodies, they may optionally be further suitably humanized, again as described herein. In the above Nanobodies, one or more of the further Hallmark residues are preferably as described herein (for example, when they are $V_{HH}$ sequences or partially humanized Nanobodies).

A Nanobody of the P, R, S 103 class may be an immunoglobulin sequence that is comprised of four framework regions/sequences interrupted by three complementarity determining regions/sequences, in which i) the amino acid residue at position 103 according to the Kabat numbering is different from W;

and in which:

ii) preferably the amino acid residue at position 103 according to the Kabat numbering is P, R or 5, and more preferably R;

and in which:

iii) FR1 is an immunoglobulin sequence that has at least 80% amino acid identity with at least one of the following immunoglobulin sequences:

TABLE B-19

Representative FW1 sequences for Nanobodies of the P, R, S 103-group.

| | | |
|---|---|---|
| P, R, S 103 FW1 sequence no. 1 | SEQ ID NO: 92 | AVQLVESGGGLVQAGGSLRLSCAAS GRTFS |
| P, R, S 103 FW1 sequence no. 2 | SEQ ID NO: 93 | QVQLQESGGGMVQPGGSLRLSCAA SGFDFG |
| P, R, S 103 FW1 sequence no. 3 | SEQ ID NO: 94 | EVHLVESGGGLVRPGGSLRLSCAAF GFIFK |
| P, R, S 103 FW1 sequence no. 4 | SEQ ID NO: 95 | QVQLAESGGGLVQPGGSLKLSCAAS RTIVS |
| P, R, S 103 FW1 sequence no. 5 | SEQ ID NO: 96 | QEHLVESGGGLVDIGGSLRLSCAASE RIFS |
| P, R, S 103 FW1 sequence no. 6 | SEQ ID NO: 97 | QVKLEESGGGLAQPGGSLRLSCVAS GFTFS |
| P, R, S 103 FW1 sequence no. 7 | SEQ ID NO: 98 | EVQLVESGGGLVQPGGSLRLSCVCV SSGCT |
| P, R, S 103 FW1 sequence no. 8 | SEQ ID NO: 99 | EVQLVESGGGLALPGGSLTLSCVFS GSTFS | and in which iv) FR2 is an immunoglobulin sequence that has at least 80% amino acid identity with at least one of the following immunoglobulin sequences:

TABLE B-20

Representative FW2 sequences for Nanobodies of the P, R, S 103-group.

| | | |
|---|---|---|
| P, R, S 103 FW2 sequence no. 1 | SEQ ID NO: 102 | WFRQAPGKEREFVA |
| P, R, S 103 FW2 sequence no. 2 | SEQ ID NO: 103 | WVRQAPGKVLEWVS |
| P, R, S 103 FW2 sequence no. 3 | SEQ ID NO: 104 | WVRRPPGKGLEWVS |
| P, R, S 103 FW2 sequence no. 4 | SEQ ID NO: 105 | WIRQAPGKEREGVS |

TABLE B-20-continued

Representative FW2 sequences for
Nanobodies of the P, R, S 103-group.

| | | |
|---|---|---|
| P, R, S 103 FW2 sequence no. 5 | SEQ ID NO: 106 | WVRQYPGKEPEWVS |
| P, R, S 103 FW2 sequence no. 6 | SEQ ID NO: 107 | WFRQPPGKEHEFVA |
| P, R, S 103 FW2 sequence no. 7 | SEQ ID NO: 108 | WYRQAPGKRTELVA |
| P, R, S 103 FW2 sequence no. 8 | SEQ ID NO: 109 | WLRQAPGQGLEWVS |
| P, R, S 103 FW2 sequence no. 9 | SEQ ID NO: 110 | WLRQTPGKGLEWVG |
| P, R, S 103 FW2 sequence no. 10 | SEQ ID NO: 111 | WVRQAPGKAEEFVS | and in which:
v) FR3 is an immunoglobulin sequence that has at least 80% amino acid identity with at least one of the following immunoglobulin sequences:

TABLE B-21

Representative FW3 sequences for
Nanobodies of the P, R, S 103-group.

| | | |
|---|---|---|
| P, R, S 103 FW3 sequence no. 1 | SEQ ID NO: 112 | RFTISRDNAKNTVYLQMNSLKPEDTAVYYCAA |
| P, R, S 103 FW3 sequence no. 2 | SEQ ID NO: 113 | RFTISRDNARNTLYLQMDSLIPEDTALYYCAR |
| P, R, S 103 FW3 sequence no. 3 | SEQ ID NO: 114 | RFTISRDNAKNEMYLQMNNLKTEDTGVYWCGA |
| P, R, S 103 FW3 sequence no. 4 | SEQ ID NO: 115 | RFTISSDSNRNMIYLQMNNLKPEDTAVYYCAA |
| P, R, S 103 FW3 sequence no. 5 | SEQ ID NO: 116 | RFTISRDNAKNMLYLHLNNLKSEDTAVYYCRR |
| P, R, S 103 FW3 sequence no. 6 | SEQ ID NO: 117 | RFTISRDNAKKTVYLRLNSLNPEDTAVYSCNL |
| P, R, S 103 FW3 sequence no. 7 | SEQ ID NO: 118 | RFKISRDNAKKTLYLQMNSLGPEDTAMYYCQR |
| P, R, S 103 FW3 sequence no. 8 | SEQ ID NO: 119 | RFTVSRDNGKNTAYLRMNSLKPEDTADYYCAV | and in which:
vi) FR4 is an immunoglobulin sequence that has at least 80% amino acid identity with at least one of the following immunoglobulin sequences:

TABLE B-22

Representative FW4 sequences for
Nanobodies of the P, R, S 103-group.

| | | |
|---|---|---|
| P, R, S 103 FW4 sequence no. 1 | SEQ ID NO: 120 | RGQGTQVTVSS |
| P, R, S 103 FW4 sequence no. 2 | SEQ ID NO: 121 | LRGGTQVTVSS |
| P, R, S 103 FW4 sequence no. 3 | SEQ ID NO: 122 | GNKGTLVTVSS |
| P, R, S 103 FW4 sequence no. 4 | SEQ ID NO: 123 | SSPGTQVTVSS |

TABLE B-22-continued

Representative FW4 sequences for
Nanobodies of the P, R, S 103-group.

| | | |
|---|---|---|
| P, R, S 103 FW4 sequence no. 5 | SEQ ID NO: 124 | SSQGTLVTVSS |
| P, R, S 103 FW4 sequence no. 6 | SEQ ID NO: 125 | RSRGIQVTVSS | and in which:
vii) CDR1, CDR2 and CDR3 are as defined herein, and are preferably as defined according to one of the preferred aspects herein, and are more preferably as defined according to one of the more preferred aspects herein.

In the above Nanobodies, one or more of the further Hallmark residues are preferably as described herein (for example, when they are $V_{HH}$ sequences or partially humanized Nanobodies).

With regard to framework 1, it will again be clear to the skilled person that, for determining the degree of amino acid identity, the amino acid residues on positions 1 to 4 and 27 to 30 are preferably disregarded.

In view of this, a Nanobody of the P, R, S 103 class may be an immunoglobulin sequence that is comprised of four framework regions/sequences interrupted by three complementarity determining regions/sequences, in which:
i) the amino acid residue at position 103 according to the Kabat numbering is different from W;
and in which:
ii) preferably the amino acid residue at position 103 according to the Kabat numbering is P, R or S, and more preferably R;
and in which:
iii) FR1 is an immunoglobulin sequence that, on positions 5 to 26 of the Kabat numbering, has at least 80% amino acid identity with at least one of the following immunoglobulin sequences:

TABLE B-23

Representative FW1 sequences (amino acid residues
5 to 26) for Nanobodies of the P, R, S 103-group.

| | | |
|---|---|---|
| P, R, S 103 FW1 sequence no. 9 | SEQ ID NO: 100 | VESGGGLVQAGGSLRLSCAASG |
| P, R, S 103 FW1 sequence no. 10 | SEQ ID NO: 101 | AESGGGLVQPGGSLKLSCAASR | and in which:
iv) FR2, FR3 and FR4 are as mentioned herein for FR2, FR3 and FR4 of Nanobodies of the P, R, S 103 class;
and in which:
v) CDR1, CDR2 and CDR3 are as defined herein, and are preferably as defined according to one of the preferred aspects herein, and are more preferably as defined according to one of the more preferred aspects herein.

The above Nanobodies may for example be $V_{HH}$ sequences or may be humanized Nanobodies. When the above Nanobody sequences are $V_{HH}$ sequences, they may be suitably humanized, as further described herein. When the Nanobodies are partially humanized Nanobodies, they may optionally be further suitably humanized, again as described herein.

In the above Nanobodies, one or more of the further Hallmark residues are preferably as described herein (for example, when they are $V_{HH}$ sequences or partially humanized Nanobodies).

In another preferred, but non-limiting aspect, the invention relates to a Nanobody as described above, in which the CDR sequences have at least 70% amino acid identity, preferably at least 80% amino acid identity, more preferably at least 90% amino acid identity, such as 95% amino acid identity or more or even essentially 100% amino acid identity with the CDR sequences of at least one of the immunoglobulin sequences of SEQ ID NO's: 705 to 788, more preferably SEQ ID NO's 726 to 750, 753 to 758, 762 to 764, 772 to 773, 775, or 778 to 780, more preferred SEQ ID NO's 732, 773 or 778 (see Table A-1). This degree of amino acid identity can for example be determined by determining the degree of amino acid identity (in a manner described herein) between said Nanobody and one or more of the sequences of SEQ ID NO's: 705 to 788, more preferably SEQ ID NO's 726 to 750, 753 to 758, 762 to 764, 772 to 773, 775, or 778 to 780, more preferred SEQ ID NO's 732, 773 or 778 (see Table A-1), in which the amino acid residues that form the framework regions are disregarded. Such Nanobodies can be as further described herein.

As already mentioned herein, another preferred but non-limiting aspect of the invention relates to a Nanobody with an immunoglobulin sequence that is chosen from the group consisting of SEQ ID NO's: 705 to 788, more preferably SEQ ID NO's 726 to 750, 753 to 758, 762 to 764, 772 to 773, 775, or 778 to 780, more preferred SEQ ID NO's 732, 773 or 778 (see Table A-1) or from the group consisting of from immunoglobulin sequences that have more than 80%, preferably more than 90%, more preferably more than 95%, such as 99% or more sequence identity (as defined herein) with at least one of the immunoglobulin sequences of SEQ ID NO's: 705 to 788, more preferably SEQ ID NO's 726 to 750, 753 to 758, 762 to 764, 772 to 773, 775, or 778 to 780, more preferred SEQ ID NO's 732, 773 or 778 (see Table A-1).

Also, in the above Nanobodies:
i) any amino acid substitution (when it is not a humanizing substitution as defined herein) is preferably, and compared to the corresponding immunoglobulin sequence of SEQ ID NO's: 705 to 788, more preferably SEQ ID NO's 726 to 750, 753 to 758, 762 to 764, 772 to 773, 775, or 778 to 780, more preferred SEQ ID NO's 732, 773 or 778 (see Table A-1), a conservative amino acid substitution, (as defined herein);
and/or:
ii) its immunoglobulin sequence preferably contains either only amino acid substitutions, or otherwise preferably no more than 5, preferably no more than 3, and more preferably only 1 or 2 amino acid deletions or insertions, compared to the corresponding immunoglobulin sequence of SEQ ID NO's: 705 to 788, more preferably SEQ ID NO's 726 to 750, 753 to 758, 762 to 764, 772 to 773, 775, or 778 to 780, more preferred SEQ ID NO's 732, 773 or 778 (see Table A-1);
and/or
iii) the CDR's may be CDR's that are derived by means of affinity maturation, for example starting from the CDR's of to the corresponding immunoglobulin sequence of SEQ ID NO's: 705 to 788, more preferably SEQ ID NO's 726 to 750, 753 to 758, 762 to 764, 772 to 773, 775, or 778 to 780, more preferred SEQ ID NO's 732, 773 or 778 (see Table A-1).

Preferably, the CDR sequences and FR sequences in the Nanobodies of the invention are such that the Nanobodies of the invention (and polypeptides of the invention comprising the same):

bind to ion channels such as e.g. P2X7 with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles);

and/or such that they:
bind to ion channels such as e.g. P2X7 with a $k_{on}$-rate of between $10^2$ $M^{-1}s^{-1}$ to about $10^7$ $M^{-1}s^{-1}$, preferably between $10^3$ $M^{-1}s^{-1}$ and $10^7$ $M^{-1}s^{-1}$, more preferably between $10^4$ $M^{-1}s^{-1}$ and $10^7$ $M^{-1}s^{-1}$, such as between $10^5$ $M^{-1}s^{-1}$ and $10^7$ $M^{-1}s^{-1}$;

and/or such that they:
bind to ion channels such as e.g. P2X7 with a $k_{off}$ rate between 1 $s^{-1}$ ($t_{1/2}$=0.69 s) and $10^{-6}$ $s^{-1}$ (providing a near irreversible complex with a $t_{1/2}$ of multiple days), preferably between $10^2$ $s^{t1}$ and $10^6$ $s^1$ more preferably between $10^{t3}$ $s^{t1}$ and $10^{-6}$ $s^{-1}$, such as between $10^{-4}$ $s^{-1}$ and $10^{-6}$ $s^{-1}$.

Preferably, CDR sequences and FR sequences present in the Nanobodies of the invention are such that the Nanobodies of the invention will bind to ion channels such as e.g. P2X7 with an affinity less than 500 nM, preferably less than 200 nM, more preferably less than 10 nM, such as less than 500 pM.

According to one non-limiting aspect of the invention, a Nanobody may be as defined herein, but with the proviso that it has at least "one amino acid difference" (as defined herein) in at least one of the framework regions compared to the corresponding framework region of a naturally occurring human $V_H$ domain, and in particular compared to the corresponding framework region of DP-47. More specifically, according to one non-limiting aspect of the invention, a Nanobody may be as defined herein, but with the proviso that it has at least "one amino acid difference" (as defined herein) at at least one of the Hallmark residues (including those at positions 108, 103 and/or 45) compared to the corresponding framework region of a naturally occurring human $V_H$ domain, and in particular compared to the corresponding framework region of DP-47. Usually, a Nanobody will have at least one such amino acid difference with a naturally occurring $V_H$ domain in at least one of FR2 and/or FR4, and in particular at at least one of the Hallmark residues in FR2 and/or FR4 (again, including those at positions 108, 103 and/or 45).

Also, a humanized Nanobody of the invention may be as defined herein, but with the proviso that it has at least "one amino acid difference" (as defined herein) in at least one of the framework regions compared to the corresponding framework region of a naturally occurring $V_{HH}$ domain. More specifically, according to one non-limiting aspect of the invention, a humanized Nanobody may be as defined herein, but with the proviso that it has at least "one amino acid difference" (as defined herein) at at least one of the Hallmark residues (including those at positions 108, 103 and/or 45) compared to the corresponding framework region of a naturally occurring $V_{HH}$ domain. Usually, a humanized Nanobody will have at least one such amino acid difference with a naturally occurring $V_{HH}$ domain in at least one of FR2 and/or FR4, and in particular at at least one of the Hallmark residues in FR2 and/or FR4 (again, including those at positions 108, 103 and/or 45).

As will be clear from the disclosure herein, it is also within the scope of the invention to use natural or synthetic analogs, mutants, variants, alleles, homologs and orthologs (herein collectively referred to as "analogs") of the Nanobodies of the invention as defined herein, and in particular analogs of the Nanobodies of SEQ ID NO's 705 to 788, more preferably SEQ ID NO's 726 to 750, 753 to 758, 762 to 764, 772 to 773, 775, or 778 to 780, more preferred SEQ ID NO's 732, 773 or 778 (see Table A-1). Thus, according to one aspect of the invention, the term "Nanobody of the invention" in its broadest sense also covers such analogs.

Generally, in such analogs, one or more amino acid residues may have been replaced, deleted and/or added, compared to the Nanobodies of the invention as defined herein. Such substitutions, insertions or deletions may be made in one or more of the framework regions and/or in one or more of the CDR's. When such substitutions, insertions or deletions are made in one or more of the framework regions, they may be made at one or more of the Hallmark residues and/or at one or more of the other positions in the framework residues, although substitutions, insertions or deletions at the Hallmark residues are generally less preferred (unless these are suitable humanizing substitutions as described herein).

By means of non-limiting examples, a substitution may for example be a conservative substitution (as described herein) and/or an amino acid residue may be replaced by another amino acid residue that naturally occurs at the same position in another $V_{HH}$ domain (see Tables B-4 to B-7 for some non-limiting examples of such substitutions), although the invention is generally not limited thereto. Thus, any one or more substitutions, deletions or insertions, or any combination thereof, that either improve the properties of the Nanobody of the invention or that at least do not detract too much from the desired properties or from the balance or combination of desired properties of the Nanobody of the invention (i.e. to the extent that the Nanobody is no longer suited for its intended use) are included within the scope of the invention. A skilled person will generally be able to determine and select suitable substitutions, deletions or insertions, or suitable combinations of thereof, based on the disclosure herein and optionally after a limited degree of routine experimentation, which may for example involve introducing a limited number of possible substitutions and determining their influence on the properties of the Nanobodies thus obtained.

For example, and depending on the host organism used to express the Nanobody or polypeptide of the invention, such deletions and/or substitutions may be designed in such a way that one or more sites for post-translational modification (such as one or more glycosylation sites) are removed, as will be within the ability of the person skilled in the art. Alternatively, substitutions or insertions may be designed so as to introduce one or more sites for attachment of functional groups (as described herein), for example to allow site-specific pegylation (again as described herein).

As can be seen from the data on the $V_{HH}$ entropy and $V_{HH}$ variability given in Tables B-4 to B-7 above, some amino acid residues in the framework regions are more conserved than others. Generally, although the invention in its broadest sense is not limited thereto, any substitutions, deletions or insertions are preferably made at positions that are less conserved. Also, generally, amino acid substitutions are preferred over amino acid deletions or insertions.

The analogs are preferably such that they can bind to ion channels such as e.g. P2X7 with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein for the Nanobodies of the invention.

The analogs are preferably also such that they retain the favourable properties the Nanobodies, as described herein.

Also, according to one preferred aspect, the analogs have a degree of sequence identity of at least 70%, preferably at least 80%, more preferably at least 90%, such as at least 95% or 99% or more; and/or preferably have at most 20, preferably at most 10, even more preferably at most 5, such as 4, 3, 2 or only 1 amino acid difference (as defined herein), with one of the Nanobodies of SEQ ID NOs: 705 to 788, more preferably SEQ ID NO's 726 to 750, 753 to 758, 762 to 764, 772 to 773, 775, or 778 to 780, more preferred SEQ ID NO's 732, 773 or 778 (see Table A-1).

Also, the framework sequences and CDR's of the analogs are preferably such that they are in accordance with the preferred aspects defined herein. More generally, as described herein, the analogs will have (a) a Q at position 108; and/or (b) a charged amino acid or a cysteine residue at position 45 and preferably an E at position 44, and more preferably E at position 44 and R at position 45; and/or (c) P, R or S at position 103.

One preferred class of analogs of the Nanobodies of the invention comprise Nanobodies that have been humanized (i.e. compared to the sequence of a naturally occurring Nanobody of the invention). As mentioned in the background art cited herein, such humanization generally involves replacing one or more amino acid residues in the sequence of a naturally occurring $V_{HH}$ with the amino acid residues that occur at the same position in a human $V_H$ domain, such as a human $V_H3$ domain. Examples of possible humanizing substitutions or combinations of humanizing substitutions will be clear to the skilled person, for example from the Tables herein, from the possible humanizing substitutions mentioned in the background art cited herein, and/or from a comparison between the sequence of a Nanobody and the sequence of a naturally occurring human $V_H$ domain.

The humanizing substitutions should be chosen such that the resulting humanized Nanobodies still retain the favourable properties of Nanobodies as defined herein, and more preferably such that they are as described for analogs in the preceding paragraphs. A skilled person will generally be able to determine and select suitable humanizing substitutions or suitable combinations of humanizing substitutions, based on the disclosure herein and optionally after a limited degree of routine experimentation, which may for example involve introducing a limited number of possible humanizing substitutions and determining their influence on the properties of the Nanobodies thus obtained.

Generally, as a result of humanization, the Nanobodies of the invention may become more "humanlike", while still retaining the favorable properties of the Nanobodies of the invention as described herein. As a result, such humanized Nanobodies may have several advantages, such as a reduced immunogenicity, compared to the corresponding naturally occurring $V_{HH}$ domains. Again, based on the disclosure herein and optionally after a limited degree of routine experimentation, the skilled person will be able to select humanizing substitutions or suitable combinations of humanizing substitutions which optimize or achieve a desired or suitable balance between the favourable properties provided by the humanizing substitutions on the one hand and the favourable properties of naturally occurring $V_{HH}$ domains on the other hand.

The Nanobodies of the invention may be suitably humanized at any framework residue(s), such as at one or more Hallmark residues (as defined herein) or at one or more other framework residues (i.e. non-Hallmark residues) or any suitable combination thereof. One preferred humanizing substitution for Nanobodies of the "P, R, S-103 group" or the "KERE group" is Q108 into L108. Nanobodies of the "GLEW class" may also be humanized by a Q108 into L108 substitution, provided at least one of the other Hallmark residues contains a camelid (camelizing) substitution (as defined herein). For example, as mentioned above, one particularly preferred class of humanized Nanobodies has GLEW or a GLEW-like sequence at positions 44-47; P, R or S (and in particular R) at position 103, and an L at position 108.

The humanized and other analogs, and nucleic acid sequences encoding the same, can be provided in any manner known per se, for example using one or more of the techniques mentioned on pages 103 and 104 of WO 08/020079.

As mentioned there, it will be also be clear to the skilled person that the Nanobodies of the invention (including their analogs) can be designed and/or prepared starting from human $V_H$ sequences (i.e. immunoglobulin sequences or the corresponding nucleotide sequences), such as for example from human $V_H3$ sequences such as DP-47, DP-51 or DP-29, i.e. by introducing one or more camelizing substitutions (i.e. changing one or more amino acid residues in the immunoglobulin sequence of said human $V_H$ domain into the amino acid residues that occur at the corresponding position in a $V_{HH}$ domain), so as to provide the sequence of a Nanobody of the invention and/or so as to confer the favourable properties of a Nanobody to the sequence thus obtained. Again, this can generally be performed using the various methods and techniques referred to in the previous paragraph, using an immunoglobulin sequence and/or nucleotide sequence for a human $V_H$ domain as a starting point.

Some preferred, but non-limiting camelizing substitutions can be derived from Tables B-4-B-7. It will also be clear that camelizing substitutions at one or more of the Hallmark residues will generally have a greater influence on the desired properties than substitutions at one or more of the other amino acid positions, although both and any suitable combination thereof are included within the scope of the invention. For example, it is possible to introduce one or more camelizing substitutions that already confer at least some the desired properties, and then to introduce further camelizing substitutions that either further improve said properties and/or confer additional favourable properties. Again, the skilled person will generally be able to determine and select suitable camelizing substitutions or suitable combinations of camelizing substitutions, based on the disclosure herein and optionally after a limited degree of routine experimentation, which may for example involve introducing a limited number of possible camelizing substitutions and determining whether the favourable properties of Nanobodies are obtained or improved (i.e. compared to the original $V_{11}$ domain).

Generally, however, such camelizing substitutions are preferably such that the resulting an immunoglobulin sequence at least contains (a) a Q at position 108; and/or (b) a charged amino acid or a cysteine residue at position 45 and preferably also an E at position 44, and more preferably E at position 44 and R at position 45; and/or (c) P, R or S at position 103; and optionally one or more further camelizing substitutions. More preferably, the camelizing substitutions are such that they result in a Nanobody of the invention and/or in an analog thereof (as defined herein), such as in a humanized analog and/or preferably in an analog that is as defined in the preceding paragraphs.

Nanobodies can also be derived from $V_H$ domains by the incorporation of substitutions that are rare in nature, but nonetheless, structurally compatible with the VH domain fold. For example, but without being limiting, these substitutions may include on or more of the following: Gly at position 35, Ser, Val or Thr at position 37, Ser, Thr, Arg, Lys, His, Asp or Glu at position 39, Glu or His at position 45, Trp, Leu, Val, Ala, Thr, or Glu at position 47, S or R at position 50. (Barthelemy et al. J Biol Chem. 2008 Feb. 8; 283(6): 3639-54. Epub 2007 Nov. 28)

As will also be clear from the disclosure herein, it is also within the scope of the invention to use parts or fragments, or combinations of two or more parts or fragments, of the Nanobodies of the invention as defined herein, and in particular parts or fragments of the Nanobodies of SEQ ID NO's: 705 to 788, more preferably SEQ ID NO's 726 to 750, 753 to 758, 762 to 764, 772 to 773, 775, or 778 to 780, more preferred SEQ ID NO's 732, 773 or 778 (see Table A-1). Thus, according to one aspect of the invention, the term "Nanobody of the invention" in its broadest sense also covers such parts or fragments.

Generally, such parts or fragments of the Nanobodies of the invention (including analogs thereof) have immunoglobulin sequences in which, compared to the immunoglobulin sequence of the corresponding full length Nanobody of the invention (or analog thereof), one or more of the amino acid residues at the N-terminal end, one or more amino acid residues at the C-terminal end, one or more contiguous internal amino acid residues, or any combination thereof, have been deleted and/or removed.

The parts or fragments are preferably such that they can bind to ion channels such as e.g. P2X7 with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein for the Nanobodies of the invention.

Any part or fragment is preferably such that it comprises at least 10 contiguous amino acid residues, preferably at least 20 contiguous amino acid residues, more preferably at least 30 contiguous amino acid residues, such as at least 40 contiguous amino acid residues, of the immunoglobulin sequence of the corresponding full length Nanobody of the invention.

Also, any part or fragment is such preferably that it comprises at least one of CDR1, CDR2 and/or CDR3 or at least part thereof (and in particular at least CDR3 or at least part thereof). More preferably, any part or fragment is such that it comprises at least one of the CDR's (and preferably at least CDR3 or part thereof) and at least one other CDR (i.e. CDR1 or CDR2) or at least part thereof, preferably connected by suitable framework sequence(s) or at least part thereof. More preferably, any part or fragment is such that it comprises at least one of the CDR's (and preferably at least CDR3 or part thereof) and at least part of the two remaining CDR's, again preferably connected by suitable framework sequence(s) or at least part thereof.

According to another particularly preferred, but non-limiting aspect, such a part or fragment comprises at least CDR3, such as FR3, CDR3 and FR4 of the corresponding full length Nanobody of the invention, i.e. as for example described in the International application WO 03/050531 (Lasters et al.).

As already mentioned above, it is also possible to combine two or more of such parts or fragments (i.e. from the same or different Nanobodies of the invention), i.e. to provide an analog (as defined herein) and/or to provide further parts or fragments (as defined herein) of a Nanobody of the invention. It is for example also possible to combine one or more parts or fragments of a Nanobody of the invention with one or more parts or fragments of a human $V_H$ domain.

According to one preferred aspect, the parts or fragments have a degree of sequence identity of at least 50%, preferably at least 60%, more preferably at least 70%, even more preferably at least 80%, such as at least 90%, 95% or 99% or more with one of the Nanobodies of SEQ ID NOs 705 to 788, more preferably SEQ ID NO's 726 to 750, 753 to 758, 762 to 764, 772 to 773, 775, or 778 to 780, more preferred SEQ ID NO's 732, 773 or 778 (see Table A-1).

The parts and fragments, and nucleic acid sequences encoding the same, can be provided and optionally combined in any manner known per se. For example, such parts or fragments can be obtained by inserting a stop codon in a nucleic acid that encodes a full-sized Nanobody of the invention, and then expressing the nucleic acid thus obtained in a manner known per se (e.g. as described herein). Alternatively, nucleic acids encoding such parts or fragments can be obtained by suitably restricting a nucleic acid that encodes a full-sized Nanobody of the invention or by synthesizing such a nucleic acid in a manner known per se. Parts or fragments may also be provided using techniques for peptide synthesis known per se.

The invention in its broadest sense also comprises derivatives of the Nanobodies of the invention. Such derivatives can generally be obtained by modification, and in particular by chemical and/or biological (e.g. enzymatical) modification, of the Nanobodies of the invention and/or of one or more of the amino acid residues that form the Nanobodies of the invention.

Examples of such modifications, as well as examples of amino acid residues within the Nanobody sequence that can be modified in such a manner (i.e. either on the protein backbone but preferably on a side chain), methods and techniques that can be used to introduce such modifications and the potential uses and advantages of such modifications will be clear to the skilled person.

For example, such a modification may involve the introduction (e.g. by covalent linking or in an other suitable manner) of one or more functional groups, residues or moieties into or onto the Nanobody of the invention, and in particular of one or more functional groups, residues or moieties that confer one or more desired properties or functionalities to the Nanobody of the invention. Example of such functional groups will be clear to the skilled person.

For example, such modification may comprise the introduction (e.g. by covalent binding or in any other suitable manner) of one or more functional groups that increase the half-life, the solubility and/or the absorption of the Nanobody of the invention, that reduce the immunogenicity and/or the toxicity of the Nanobody of the invention, that eliminate or attenuate any undesirable side effects of the Nanobody of the invention, and/or that confer other advantageous properties to and/or reduce the undesired properties of the Nanobodies and/or polypeptides of the invention; or any combination of two or more of the foregoing. Examples of such functional groups and of techniques for introducing them will be clear to the skilled person, and can generally comprise all functional groups and techniques mentioned in the general background art cited hereinabove as well as the functional groups and techniques known per se for the modification of pharmaceutical proteins, and in particular for the modification of antibodies or antibody fragments (including ScFv's and single domain antibodies), for which reference is for example made to Remington's Pharmaceutical Sciences, 16th ed., Mack Publishing Co., Easton, Pa. (1980). Such functional groups may for example be linked directly (for example covalently) to a Nanobody of the invention, or optionally via a suitable linker or spacer, as will again be clear to the skilled person.

One of the most widely used techniques for increasing the half-life and/or reducing the immunogenicity of pharmaceutical proteins comprises attachment of a suitable pharmacologically acceptable polymer, such as poly(ethyleneglycol) (PEG) or derivatives thereof (such as methoxypoly(ethyleneglycol) or mPEG). Generally, any suitable form of pegylation can be used, such as the pegylation used in the art for antibodies and antibody fragments (including but not limited to (single) domain antibodies and ScFv's); reference is made to for example Chapman, Nat. Biotechnol., 54, 531-545 (2002); by Veronese and Harris, Adv. Drug Deliv. Rev. 54, 453-456 (2003), by Harris and Chess, Nat. Rev. Drug. Discov., 2, (2003) and in WO 04/060965. Various reagents for pegylation of proteins are also commercially available, for example from Nektar Therapeutics, USA.

Preferably, site-directed pegylation is used, in particular via a cysteine-residue (see for example Yang et al., Protein Engineering, 16, 10, 761-770 (2003). For example, for this purpose, PEG may be attached to a cysteine residue that naturally occurs in a Nanobody of the invention, a Nanobody of the invention may be modified so as to suitably introduce one or more cysteine residues for attachment of PEG, or an immunoglobulin sequence comprising one or more cysteine residues for attachment of PEG may be fused to the N- and/or C-terminus of a Nanobody of the invention, all using techniques of protein engineering known per se to the skilled person.

Preferably, for the Nanobodies and proteins of the invention, a PEG is used with a molecular weight of more than 5000, such as more than 10,000 and less than 200,000, such as less than 100,000; for example in the range of 20,000-80,000.

Another, usually less preferred modification comprises N-linked or O-linked glycosylation, usually as part of co-translational and/or post-translational modification, depending on the host cell used for expressing the Nanobody or polypeptide of the invention.

Yet another modification may comprise the introduction of one or more detectable labels or other signal-generating groups or moieties, depending on the intended use of the labelled Nanobody. Suitable labels and techniques for attaching, using and detecting them will be clear to the skilled person, and for example include, but are not limited to, the fluorescent labels, phosphorescent labels, chemiluminescent labels, bioluminescent labels, radio-isotopes, metals, metal chelates, metallic cations, chromophores and enzymes, such as those mentioned on page 109 of WO 08/020079. Other suitable labels will be clear to the skilled person, and for example include moieties that can be detected using NMR or ESR spectroscopy.

Such labelled Nanobodies and polypeptides of the invention may for example be used for in vitro, in vivo or in situ assays (including immunoassays known per se such as ELISA, RIA, EIA and other "sandwich assays", etc.) as well as in vivo diagnostic and imaging purposes, depending on the choice of the specific label.

As will be clear to the skilled person, another modification may involve the introduction of a chelating group, for example to chelate one of the metals or metallic cations referred to above. Suitable chelating groups for example include, without limitation, diethyl-enetriaminepentaacetic acid (DTPA) or ethylenediaminetetraacetic acid (EDTA).

Yet another modification may comprise the introduction of a functional group that is one part of a specific binding pair, such as the biotin-(strept)avidin binding pair. Such a functional group may be used to link the Nanobody of the invention to another protein, polypeptide or chemical compound that is bound to the other half of the binding pair, i.e. through formation of the binding pair. For example, a Nanobody of the invention may be conjugated to biotin, and linked to another protein, polypeptide, compound or carrier conjugated to avidin or streptavidin. For example, such a conjugated Nanobody may be used as a reporter, for example in a diagnostic system where a detectable signal-producing agent is conjugated to avidin or streptavidin. Such binding pairs may for example also be used to bind the Nanobody of the invention to a carrier, including carriers suitable for pharmaceutical purposes. One non-limiting example are the liposomal formulations described by Cao and Suresh, Journal of Drug Targeting, 8, 4, 257 (2000). Such binding pairs may also be used to link a therapeutically active agent to the Nanobody of the invention.

For some applications, in particular for those applications in which it is intended to kill a cell that expresses the target against which the Nanobodies of the invention are directed (e.g. in the treatment of cancer), or to reduce or slow the growth and/or proliferation such a cell, the Nanobodies of the invention may also be linked to a toxin or to a toxic residue or moiety. Examples of toxic moieties, compounds or residues which can be linked to a Nanobody of the invention to provide—for example—a cytotoxic compound will be clear to the skilled person and can for example be found in the prior art cited above and/or in the further description herein. One example is the so-called ADEPT™ technology described in WO 03/055527.

Other potential chemical and enzymatical modifications will be clear to the skilled person. Such modifications may also be introduced for research purposes (e.g. to study function-activity relationships). Reference is for example made to Lundblad and Bradshaw, Biotechnol. Appl. Biochem., 26, 143-151 (1997).

Preferably, the derivatives are such that they bind to on channels such as e.g. P2X7 with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein for the Nanobodies of the invention.

As mentioned above, the invention also relates to proteins or polypeptides that essentially consist of or comprise at least one Nanobody of the invention. By "essentially consist of" is meant that the immunoglobulin sequence of the polypeptide of the invention either is exactly the same as the immunoglobulin sequence of a Nanobody of the invention or corresponds to the immunoglobulin sequence of a Nanobody of the invention which has a limited number of amino acid residues, such as 1-20 amino acid residues, for example 1-10 amino acid residues and preferably 1-6 amino acid residues, such as 1, 2, 3, 4, 5 or 6 amino acid residues, added at the amino terminal end, at the carboxy terminal end, or at both the amino terminal end and the carboxy terminal end of the immunoglobulin sequence of the Nanobody.

Said amino acid residues may or may not change, alter or otherwise influence the (biological) properties of the Nanobody and may or may not add further functionality to the Nanobody. For example, such amino acid residues:

- can comprise an N-terminal Met residue, for example as result of expression in a heterologous host cell or host organism.
- may form a signal sequence or leader sequence that directs secretion of the Nanobody from a host cell upon synthesis. Suitable secretory leader peptides will be clear to the skilled person, and may be as further described herein. Usually, such a leader sequence will be linked to the N-terminus of the Nanobody, although the invention in its broadest sense is not limited thereto;
- may form a sequence or signal that allows the Nanobody to be directed towards and/or to penetrate or enter into specific organs, tissues, cells, or parts or compartments of cells, and/or that allows the Nanobody to penetrate or cross a biological barrier such as a cell membrane, a cell layer such as a layer of epithelial cells, a tumor including solid tumors, or the blood-brain-barrier. Examples of such immunoglobulin sequences will be clear to the skilled person and include those mentioned in paragraph c) on page 112 of WO 08/020079.
- may form a "tag", for example an immunoglobulin sequence or residue that allows or facilitates the purification of the Nanobody, for example using affinity techniques directed against said sequence or residue. Thereafter, said sequence or residue may be removed (e.g. by chemical or enzymatical cleavage) to provide the Nanobody sequence (for this purpose, the tag may optionally be linked to the Nanobody sequence via a cleavable linker sequence or contain a cleavable motif). Some preferred, but non-limiting examples of such residues are multiple histidine residues, glutathione residues and a myc-tag (see for example SEQ ID NO:31 of WO 06/12282).
- may be one or more amino acid residues that have been functionalized and/or that can serve as a site for attachment of functional groups. Suitable amino acid residues and functional groups will be clear to the skilled person and include, but are not limited to, the amino acid residues and functional groups mentioned herein for the derivatives of the Nanobodies of the invention.

DNA Vaccination in Camelids

DNA vaccination has been widely used for inducing immune responses in experimental animals, such as rats, mice and rabbits (see e.g. Tang et al., Nature, 1992; Nagata et al., J. Immunol. Methods, 2003; Bins et al., Nature Med. 2005; Bins et al, J. Immunol., 2007; Kilpatrick et al., Hybridoma, 1998). However, DNA vaccination of larger animals has been considered difficult, if not impossible. In particular, reports on DNA vaccination of camelids are scarce. The report by Koch Nolte et al., 2007, describes a lengthy and cumbersome procedure requiring no less than 8 rounds of DNA vaccination, at 6-12 week intervals, in combination with a further two rounds of protein boost. It is one objective of the present invention to provide an improved method for DNA vaccination of large animals, in particular camelids.

a) Generation of Immunoglobulin Sequences without Protein Boost

In a particular embodiment, the present invention relates to a method for generating immunoglobulin sequences in a non-human animal, specifically in a camelid, more specifically a llama, by genetic vaccination, without protein boost.

It has previously been demonstrated in non-camelids, e.g. in mice, that polyclonal serum antibody responses can be obtained after DNA vaccination, without boost with a protein antigen (e.g. Bins et al., Nature Medicine, 2005; Bins et al., J. Immunol. 2007). However, it is known that such polyclonal antibody responses are not sufficient to efficiently generate antigen specific monoclonal antibodies (Nagata et al., 2003). The authors report a specific hybridoma yield that was "almost negligible" (0.0-1.3/10E8 spleen cells) in mice in the absence of a protein boost.

It is generally known that genetic vaccination of larger animals, in particular camelids, is far less efficient in eliciting an immune response as compared to mice. The production of immunoglobulin sequences by use of genetic vaccination in camelids has therefore been considered impossible.

Koch-Nolte et al. 2007 describe the immunization of a llama with a DNA-prime protein boost strategy for obtaining single domain antibodies against ecto-ADP-ribosyltransferase ART2.2. This procedure, however, was characterized by low efficiency and required extensive boosting. More specifically, a llama received four intradermal gene gun immunizations with an expression vector encoding ART2.2 at 6 to 12 week intervals (12 shots of 1 µg DNA/mg gold at a pressure setting of 300 psi). Four subsequent boost DNA immunizations and a further two protein boosts were required using recombinant ART2.2, in order to obtain a satisfactory immune response. Overall, this procedure extends over several months prior to achieving a suitable immune response in the animal, and necessitates multiple protein boosts.

In view of this prior art teaching, it is a surprising finding of the present invention that by using the methods as described herein, a suitable immune response can be achieved in camelids, in particular llamas, without a protein boost. In other words, genetic vaccination alone can suffice to induce an immune response that is adequate for the generation of immunoglobulin sequences by subsequent screening. In particular it has surprisingly been found that even if the serum antibody response is low as compared to conventional immunization strategies, the DNA vaccination alone suffices to achieve good "hit-rates", i.e. to obtain antigen specific immunoglobulin sequences at an acceptable frequency.

b) Generation of Antibody Responses to Cell Associated Antigens

As outlined in the introductory section, the art does not provide for adequate means to generate antibody responses to antigens which are cell associated as defined herein, in particular to transmembrane antigens.

The present invention is based on the surprising finding that by genetic vaccination of suitable non-human animals, in particular camelids, preferably llamas, antibody responses can be generated, which are characterized by an improved breadth of the repertoire as well as an improved specificity as compared to prior art attempts.

Cell-associated antigens, more specifically those with single or multiple transmembrane domains, are difficult to purify in their natural conformation. In order to obtain immunoglobulin sequences, including Nanobodies, against native epitopes, it is crucial to administer the target antigen to the llama in its native conformation. For these cell-associated antigens, immunization with whole cells functionally expressing the antigen is the preferred strategy (as was done e.g. in WO 05/044858; WO 07/042289; U.S. 61/004,332). The main disadvantage of whole cell immunizations is the fact that many other antigens (cell surface markers) are also presented to the immune system of the animal, which results in a highly diluted target specific immune response. To increase the specificity, elaborate and technically complex prime-boost strategies have to be devised. To the extent any of these steps includes the use of denatured protein or peptides, the resulting antibody response will be biased to the disadvantage of conformational epitopes. Therefore, the breadth of the obtainable spectrum of immunoglobulin sequences will be limited. Moreover, solely cell-based approaches, i.e. approaches which use cells expressing the target antigen for immunization, will be characterized by poor specificity of the immunoglobulin sequences, rendering an efficient isolation of immunoglobulin sequences of interest impossible.

Koch-Nolte et al. 2007 describe the immunization of one llama with a DNA-prime protein boost strategy for obtaining single domain antibodies against ecto-ADP-ribosyltransferase ART2.2.

Ecto-ADP-ribosyltransferase ART2.2 is a Gpi anchored protein, characterized by a membrane insertion via a lipid tail but without a transmembrane domain. For this protein, correctly folded purified protein could be prepared for the boost. Therefore a boost could be done with the purified protein. As indicated above, purified protein of cell-associated antigens that are anchored within, or located in the membrane can not be obtained in a purified form in their natural conformation. Any purified preparations will have lost the membrane dependent conformational epitopes. And therefore, a boost with purified protein from these cell-associated antigens is not possible.

In the context of transmembrane proteins, and in particular proteins with multiple transmembrane domains, conformational epitopes, and in particular membrane-dependent conformational epitopes are of particular interest as targets for immunoglobulin sequences. For example, the pore of an ion channel represents a target of primary therapeutic importance. However, by use of conventional approaches, it is nearly impossible to generate immunoglobulin sequences that recognize such a target. To stay with the example, the pore region of an ion channel is formed by multiple membrane spanning domains, and possibly even multiple subunits of the channel. It is near impossible to provide peptides for the generation of immunoglobulin sequences binding to this pore region. Moreover, because the protein will only exhibit its natural conformation in the membrane environment, purified ion channel protein cannot be used for immunization.

The present invention provides for the generation of immunoglobulin sequences to such kind of conformational epitope, and excludes the need for boost with purified protein.

In the invention it is envisaged that after genetic vaccination (which provides for the necessary specificity of the immune response), an animal can be boosted with e.g. cells expressing the protein in its natural conformation, i.e. embedded/anchored in the membrane. Even though these cells will express a multitude of antigens, the immunological recall response will only occur for the antigen that has been delivered by genetic vaccination. Thus, priming the animal with genetic vaccination allows a boost with protein in its natural conformation, even if the protein is non-purified, e.g. in the context of a cell expressing the protein, but nevertheless obtaining a highly specific repertoire of immunoglobulin sequences.

In a preferred embodiment, the invention relates to the generation of immunoglobulin sequences in camelids, in particular llama. The antibody response of these animals is characterized by the existence of immunoglobulin sequences that can extend into, and specifically bind to grooves or crevices on a target antigen. This is of particular importance and benefit in the case of conformational epitopes of cell associated antigens Thus, in one specific embodiment the present invention relates to the use of genetic vaccination of camelids, to raise immunoglobulin sequences against conformational epitopes of cell-associated antigens, in particular antigens exhibiting one or multiple membrane spanning domains.

The general principles of the present invention as set forth above will now be exemplified by reference to specific preferred aspects, experiments and claims. However, the invention is not to be understood as being limited thereto.

The entire contents of all of the references (including literature references, issued patents, published patent applications, and co-pending patent applications) cited throughout this application are hereby expressly incorporated by reference.

Preferred Aspects:

Aspect A-1: An immunoglobulin sequence that is directed against and/or that can specifically bind to ion channels such as e.g. P2X7.

Aspect A-2: An immunoglobulin sequence according to aspect A-1, that is in essentially isolated form.

Aspect A-3: An immunoglobulin sequence according to aspect A-1 or A-2, for administration to a subject, wherein said immunoglobulin sequence does not naturally occur in said subject.

Aspect A-4: An immunoglobulin sequence that can specifically bind to ion channels such as e.g. P2X7 with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter. Such an immunoglobulin sequence may in particular be an immunoglobulin sequence according to any of the preceding aspects.

Aspect A-5: An immunoglobulin sequence that can specifically bind to ion channels such as e.g. P2X7 with a rate of association ($k_{on}$-rate) of between $10^2$ $M^{-1}s^{-1}$ to about $10^7$ $M^{-1}s^{-1}$, preferably between $10^3$ $M^{-1}s^{-1}$ and $10^7$ $M^{-1}s^{-1}$, more preferably between $10^4$ $M^{-1}s^{-1}$ and $10^7 M^{-1}s^{-1}$, such as between $10^5$ $M^{-1}s^{-1}$ and $10^7$ $M^{-1}s^{-1}$. Such an immunoglobulin sequence may in particular be an immunoglobulin sequence according to any of the preceding aspects.

Aspect A-6: An immunoglobulin sequence that can specifically bind to ion channels such as e.g. P2X7 with a rate of dissociation ($k_{off}$ rate) between 1 $s^{-1}$ and $10^{-6}$ $s^{-1}$, preferably between $10^{-2}$ $s^{-1}$ and $10^{-6}$ $s^{-1}$, more preferably between $10^{-3}$ $s^{-1}$ and $10^{-6}$ $s^{-1}$, such as between $10^{-4}$ $s^{-1}$ and $10^{-6}$ $s^{-1}$. Such an immunoglobulin sequence may in particular be an immunoglobulin sequence according to any of the preceding aspects.

Aspect A-7: An immunoglobulin sequence that can specifically bind to ion channels such as e.g. P2X7 with an affinity less than 500 nM, preferably less than 200 nM, more preferably less than 10 nM, such as less than 500 pM. Such an immunoglobulin sequence may in particular be an immunoglobulin sequence according to any of the preceding aspects.

Aspect A-8: An immunoglobulin sequence according to any of the preceding aspects, that is a naturally occurring immunoglobulin sequence (from any suitable species) or a synthetic or semi-synthetic immunoglobulin sequence.

Aspect A-9: An immunoglobulin sequence according to any of the preceding aspects, that comprises an immunoglobulin fold or that under suitable conditions is capable of forming an immunoglobulin fold.

Aspect A-10: An immunoglobulin sequence according to any of the preceding aspects, that essentially consists of 4 framework regions (FR1 to FR4 respectively) and 3 complementarity determining regions (CDR1 to CDR3 respectively).

Aspect A-11: An immunoglobulin sequence according to any of the preceding aspects, that is an immunoglobulin sequence.

Aspect A-12: An immunoglobulin sequence according to any of the preceding aspects, that is a naturally occurring immunoglobulin sequence (from any suitable species) or a synthetic or semi-synthetic immunoglobulin sequence.

Aspect A-13: An immunoglobulin sequence according to any of the preceding aspects that is a humanized immunoglobulin sequence, a camelized immunoglobulin sequence or an immunoglobulin sequence that has been obtained by techniques such as affinity maturation.

Aspect A-14: An immunoglobulin sequence according to any of the preceding aspects, that essentially consists of a light chain variable domain sequence (e.g. a VL-sequence); or of a heavy chain variable domain sequence (e.g. a VH-sequence).

Aspect A-15: An immunoglobulin sequence according to any of the preceding aspects, that essentially consists of a heavy chain variable domain sequence that is derived from a conventional four-chain antibody or that essentially consist of a heavy chain variable domain sequence that is derived from heavy chain antibody.

Aspect A-16: An immunoglobulin sequence according to any of the preceding aspects, that essentially consists of a domain antibody (or an immunoglobulin sequence that is suitable for use as a domain antibody), of a single domain antibody (or an immunoglobulin sequence that is suitable for use as a single domain antibody), of a "dAb" (or an immunoglobulin sequence that is suitable for use as a dAb) or of a Nanobody (including but not limited to a VHH sequence).

Aspect A-17: An immunoglobulin sequence according to any of the preceding aspects, that essentially consists of a Nanobody.

Aspect A-18: An immunoglobulin sequence according to any of the preceding aspects, that essentially consists of a Nanobody that
  i) has at least 80% amino acid identity with at least one of the An immunoglobulin sequences of SEQ ID NO's: 1 to 22, in which for the purposes of determining the degree of amino acid identity, the amino acid residues that form the CDR sequences are disregarded; and in which:
  ii) preferably one or more of the amino acid residues at positions 11, 37, 44, 45, 47, 83, 84, 103, 104 and 108 according to the Kabat numbering are chosen from the Hallmark residues mentioned in Table B-2.

Aspect A-19: An immunoglobulin sequence according to any of the preceding aspects, that essentially consists of a polypeptide that
  i) has at least 80% amino acid identity with at least one of the immunoglobulin sequences of SEQ ID NO's: 789 to 791, in which for the purposes of determining the degree of amino acid identity, the amino acid residues that form the CDR sequences are disregarded; and in which:
  ii) preferably one or more of the amino acid residues at positions 11, 37, 44, 45, 47, 83, 84, 103, 104 and 108 according to the Kabat numbering are chosen from the Hallmark residues mentioned in Table B-2.

Aspect A-20: An immunoglobulin sequence according to any of the preceding aspects, that essentially consists of a Nanobody that i) has at least 80% amino acid identity with at least one of the immunoglobulin sequences of SEQ ID NO's: 705 to 788, more preferably SEQ ID NO's 726 to 750, 753 to 758, 762 to 764, 772 to 773, 775, or 778 to 780, more preferred SEQ ID NO's 732, 773 or 778, in which for the purposes of determining the degree of amino acid identity, the amino acid residues that form the CDR sequences are disregarded;

and in which:

ii) preferably one or more of the amino acid residues at positions 11, 37, 44, 45, 47, 83, 84, 103, 104 and 108 according to the Kabat numbering are chosen from the Hallmark residues mentioned in Table B-2.

Aspect A-21: An immunoglobulin sequence according to any of the preceding aspects, that essentially consists of a humanized Nanobody.

Aspect A-22: An immunoglobulin sequence according to any of the preceding aspects, that in addition to the at least one binding site for binding against ion channels such as e.g. P2X7, contains one or more further binding sites for binding against other antigens, proteins or targets.

CDR-Based Aspects

Aspect B-1: An immunoglobulin sequence that is directed against and/or that can specifically bind ion channels such as e.g. P2X7, and that comprises one or more stretches of amino acid residues chosen from the group consisting of:
a) the immunoglobulin sequences of SEQ ID NO's: 208 to 289;
b) immunoglobulin sequences that have at least 80% amino acid identity with at least one of the immunoglobulin sequences of SEQ ID NO's: 208 to 289;
c) immunoglobulin sequences that have 3, 2, or 1 amino acid difference with at least one of the immunoglobulin sequences of SEQ ID NO's: 208 to 289;
d) the immunoglobulin sequences of SEQ ID NO's: 372 to 453;
e) immunoglobulin sequences that have at least 80% amino acid identity with at least one of the immunoglobulin sequences of SEQ ID NO's: 372 to 453;
f) immunoglobulin sequences that have 3, 2, or 1 amino acid difference with at least one of the immunoglobulin sequences of SEQ ID NO's: 372 to 453;
g) the immunoglobulin sequences of SEQ ID NO's: 536 to 617;
h) immunoglobulin sequences that have at least 80% amino acid identity with at least one of the immunoglobulin sequences of SEQ ID NO's: 536 to 617;
i) immunoglobulin sequences that have 3, 2, or 1 amino acid difference with at least one of the immunoglobulin sequences of SEQ ID NO's: 536 to 617;
or any suitable combination thereof.

Such an immunoglobulin sequence may in particular be an immunoglobulin sequence according to any of the aspects A-1 to A-22.

Aspect B-2: An immunoglobulin sequence according to aspect B-1, in which at least one of said stretches of amino acid residues forms part of the antigen binding site for binding against ion channels such as e.g. P2X7.

Aspect B-3: An immunoglobulin sequence that is directed against and/or that can specifically bind ion channels such as e.g. P2X7 and that comprises two or more stretches of amino acid residues chosen from the group consisting of:
a) the immunoglobulin sequences of SEQ ID NO's: 208 to 289;
b) immunoglobulin sequences that have at least 80% amino acid identity with at least one of the immunoglobulin sequences of SEQ ID NO's: 208 to 289;
c) immunoglobulin sequences that have 3, 2, or 1 amino acid difference with at least one of the immunoglobulin sequences of SEQ ID NO's: 208 to 289;
d) the immunoglobulin sequences of SEQ ID NO's: 372 to 453;
e) immunoglobulin sequences that have at least 80% amino acid identity with at least one of the immunoglobulin sequences of SEQ ID NO's: 372 to 453;
f) immunoglobulin sequences that have 3, 2, or 1 amino acid difference with at least one of the immunoglobulin sequences of SEQ ID NO's: 372 to 453;
g) the immunoglobulin sequences of SEQ ID NO's: 536 to 617;
h) immunoglobulin sequences that have at least 80% amino acid identity with at least one of the immunoglobulin sequences of SEQ ID NO's: 536 to 617;
i) immunoglobulin sequences that have 3, 2, or 1 amino acid difference with at least one of the immunoglobulin sequences of SEQ ID NO's: 536 to 617;

such that (i) when the first stretch of amino acid residues corresponds to one of the immunoglobulin sequences according to a), b) or c), the second stretch of amino acid residues corresponds to one of the immunoglobulin sequences according to d), e), f), g), h) or i); (ii) when the first stretch of amino acid residues corresponds to one of the immunoglobulin sequences according to d), e) or f), the second stretch of amino acid residues corresponds to one of the immunoglobulin sequences according to a), b), c), g), h) or i); or (iii) when the first stretch of amino acid residues corresponds to one of the immunoglobulin sequences according to g), h) or i), the second stretch of amino acid residues corresponds to one of the immunoglobulin sequences according to a), b), c), d), e) or f).

Such an immunoglobulin sequence may in particular be an immunoglobulin sequence according to any of the aspects A-1 to A-22, B-1 or B-2.

Aspect B-4: An immunoglobulin sequence according to aspect B-3, in which the at least two stretches of amino acid residues forms part of the antigen binding site for binding against ion channels such as e.g. P2X7.

Aspect B-5: An immunoglobulin sequence that is directed against and/or that can specifically bind on channels such as e.g. P2X7 and that comprises three or more stretches of amino acid residues, in which the first stretch of amino acid residues is chosen from the group consisting of:
a) the immunoglobulin sequences of SEQ ID NO's: 208 to 289;
b) immunoglobulin sequences that have at least 80% amino acid identity with at least one of the immunoglobulin sequences of SEQ ID NO's: 208 to 289;
c) immunoglobulin sequences that have 3, 2, or 1 amino acid difference with at least one of the immunoglobulin sequences of SEQ ID NO's: 208 to 289;

the second stretch of amino acid residues is chosen from the group consisting of:
d) the immunoglobulin sequences of SEQ ID NO's: 372 to 453;
e) immunoglobulin sequences that have at least 80% amino acid identity with at least one of the immunoglobulin sequences of SEQ ID NO's: 372 to 453;
f) immunoglobulin sequences that have 3, 2, or 1 amino acid difference with at least one of the immunoglobulin sequences of SEQ ID NO's: 372 to 453;

and the third stretch of amino acid residues is chosen from the group consisting of:

g) the immunoglobulin sequences of SEQ ID NO's: 536 to 617;
h) immunoglobulin sequences that have at least 80% amino acid identity with at least one of the immunoglobulin sequences of SEQ ID NO's: 536 to 617;
i) immunoglobulin sequences that have 3, 2, or 1 amino acid difference with at least one of the immunoglobulin sequences of SEQ ID NO's: 536 to 617.

Such an immunoglobulin sequence may in particular be an immunoglobulin sequence according to any of the aspects A-1 to A-22 and/or B-1 to B-4.

Aspect B-6: An immunoglobulin sequence according to aspect B-5, in which the at least three stretches of amino acid residues forms part of the antigen binding site for binding against ion channels such as e.g. P2X7.

Aspect B-7: An immunoglobulin sequence that is directed against and/or that can specifically bind ion channels such as e.g. P2X7 in which the CDR sequences of said immunoglobulin sequence have at least 70% amino acid identity, preferably at least 80% amino acid identity, more preferably at least 90% amino acid identity, such as 95% amino acid identity or more or even essentially 100% amino acid identity with the CDR sequences of at least one of the immunoglobulin sequences of SEQ ID NO's: 705 to 788, more preferably SEQ ID NO's 726 to 750, 753 to 758, 762 to 764, 772 to 773, 775, or 778 to 780, more preferred SEQ ID NO's 732, 773 or 778. Such an immunoglobulin sequence may in particular be an immunoglobulin sequence according to any of the aspects A-1 to A-22 and/or B-1 to B-6.

Aspect C-1: An immunoglobulin sequence that is directed against ion channels such as e.g. P2X7 and that cross-blocks the binding of at least one of the immunoglobulin sequences of SEQ ID NO's: 705 to 788, more preferably SEQ ID NO's 726 to 750, 753 to 758, 762 to 764, 772 to 773, 775, or 778 to 780, more preferred SEQ ID NO's 732, 773 or 778 to ion channels such as e.g. P2X7. Such an immunoglobulin sequence may in particular be an immunoglobulin sequence according to any of the aspects A-1 to A-22 and/or according to aspects B-1 to B-7. Also, preferably, such an immunoglobulin sequence is able to specifically bind to ion channels such as e.g. P2X7.

Aspect C-2: An immunoglobulin sequence that is directed against ion channels such as e.g. P2X7 and that is cross-blocked from binding to ion channels such as e.g. P2X7 by at least one of the immunoglobulin sequences of SEQ ID NO's: 705 to 788, more preferably SEQ ID NO's 726 to 750, 753 to 758, 762 to 764, 772 to 773, 775, or 778 to 780, more preferred SEQ ID NO's 732, 773 or 778. Such an immunoglobulin sequence may in particular be an immunoglobulin sequence according to any of the aspects A-1 to A-22 and/or according to aspects B-1 to B-7. Also, preferably, such an immunoglobulin sequence is able to specifically bind to ion channels such as e.g. P2X7.

Aspect C-3: An immunoglobulin sequence according to any of aspects C-1 or C-2, wherein the ability of said immunoglobulin sequence to cross-block or to be cross-blocked is detected in a Biacore assay.

Aspect C-4: An immunoglobulin sequence according to any of aspects C-1 to C-3 wherein the ability of said immunoglobulin sequence to cross-block or to be cross-blocked is detected in an ELISA assay.

Aspect D-1: An immunoglobulin sequence according to any of aspects B-1 to B-7 or C-1 to C-7, that is in essentially isolated form.

Aspect D-2: An immunoglobulin sequence according to any of aspects B-1 to B-7, C-1 to C-7, and/or D1 for administration to a subject, wherein said immunoglobulin sequence does not naturally occur in said subject.

Aspect D-3: An immunoglobulin sequence according to any of aspects B-1 to B-7, C-1 to C-7, and/or D1 to D-2 that can specifically bind to ion channels such as e.g. P2X7 with a dissociation constant ($K_D$) of $10^{-5}$ to $10^{-12}$ moles/liter or less, and preferably $10^{-7}$ to $10^{-12}$ moles/liter or less and more preferably $10^{-5}$ to $10^{-12}$ moles/liter.

Aspect D-4: An immunoglobulin sequence according to any of aspects B-1 to B-7, C-1 to C-7, and/or D-1 to D-3 that can specifically bind to ion channels such as e.g. P2X7 with a rate of association ($k_{on}$-rate) of between 102 $M^{-1}s^{-1}$ to about $10^7$ $M^{-1}s^{-1}$, preferably between $10^3$ $M^{-1}s^{-1}$ and $10^7$ $M^{-1}s^{-1}$, more preferably between $10^4$ $M^{-1}s^{-1}$ and $10^7$ $M^{-1}s^{-1}$, such as between $10^5$ $M^{-1}s^{-1}$ and $10^7$ $M^{-1}s^{-1}$.

Aspect D-5: An immunoglobulin sequence according to any of aspects B-1 to B-7, C-1 to C-7, and/or D-1 to D-4 that can specifically bind to ion channels such as e.g. P2X7 with a rate of dissociation ($k_{off}$ rate) between 1 $s^{-1}$ and $10^{-6}$ $s^{-1}$ preferably between $10^{-2}$ $s^{-1}$ and $10^{-6}$ $s^{-1}$, more preferably between $10^{-3}$ $s^{-1}$ and $10^{-6}$ $s^{-1}$, such as between $10^{-4}$ $s^{-1}$ and $10^{-6}$ $s^{-1}$.

Aspect D-6: An immunoglobulin sequence according to any of aspects B-1 to B-7, C-1 to C-7, and/or D-1 to D-5 that can specifically bind to ion channels such as e.g. P2X7 with an affinity less than 500 nM, preferably less than 200 nM, more preferably less than 10 nM, such as less than 500 pM.

The immunoglobulin sequences according to aspects D-1 to D-6 may in particular be an immunoglobulin sequence according to any of the aspects A-1 to A-22.

Aspect E-1: An immunoglobulin sequence according to any of aspects B-1 to B-7, C-1 to C-7 and/or D1 to D-6, that is a naturally occurring immunoglobulin sequence (from any suitable species) or a synthetic or semi-synthetic immunoglobulin sequence.

Aspect E-2: An immunoglobulin sequence according to any of aspects B-1 to B-7, C-1 to C-7, D1 to D-6, and/or E-1 that comprises an immunoglobulin fold or that under suitable conditions is capable of forming an immunoglobulin fold.

Aspect E-3: An immunoglobulin sequence according to any of aspects B-1 to B-7, C-1 to C-7, D1 to D-6, and/or D-1 or D-2, that is an immunoglobulin sequence.

Aspect E-4: An immunoglobulin sequence according to any of aspects B-1 to B-7, C-1 to C-7, D1 to D-6, and/or E-1 to E-3, that is a naturally occurring immunoglobulin sequence (from any suitable species) or a synthetic or semi-synthetic immunoglobulin sequence.

Aspect E-5: An immunoglobulin sequence according to any of aspects B-1 to B-7, C-1 to C-7, D1 to D-6, and/or E-1 to E-4 that is a humanized immunoglobulin sequence, a camelized immunoglobulin sequence or an immunoglobulin sequence that has been obtained by techniques such as affinity maturation.

Aspect E-6: An immunoglobulin sequence according to any of aspects B-1 to B-7, C-1 to C-7, D1 to D-6, and/or E-1 to E-5 that essentially consists of a light chain variable domain sequence (e.g. a $V_L$-sequence); or of a heavy chain variable domain sequence (e.g. a $V_H$-sequence).

Aspect E-7: An immunoglobulin sequence according to any of aspects B-1 to B-7, C-1 to C-7, D1 to D-6, and/or E-1 to E-6, that essentially consists of a heavy chain variable domain sequence that is derived from a conventional four-chain antibody or that essentially consist of a heavy chain variable domain sequence that is derived from heavy chain antibody.

Aspect E-8: An immunoglobulin sequence according to any of aspects B-1 to B-7, C-1 to C-7, D1 to D-6, and/or E-1 to E-7, that essentially consists of a domain antibody (or an immunoglobulin sequence that is suitable for use as a domain antibody), of a single domain antibody (or an immunoglobulin sequence that is suitable for use as a single domain antibody), of a "dAb" (or an immunoglobulin sequence that is suitable for use as a dAb) or of a Nanobody (including but not limited to a $V_{HH}$ sequence).

Aspect E-9: An immunoglobulin sequence according to any of aspects B-1 to B-7, C-1 to C-7, D1 to D-6, and/or E1 to E-8 that essentially consists of a Nanobody.

Aspect E-10: An immunoglobulin sequence according to any of aspects B-1 to B-7, C-1 to C-7, D1 to D-6, and/or E-1 to E-9 that essentially consists of a Nanobody that
i) has at least 80% amino acid identity with at least one of the immunoglobulin sequences of SEQ ID NO's: 1 to 22, in which for the purposes of determining the degree of amino acid identity, the amino acid residues that form the CDR sequences are disregarded;
and in which:
ii) preferably one or more of the amino acid residues at positions 11, 37, 44, 45, 47, 83, 84, 103, 104 and 108 according to the Kabat numbering are chosen from the Hallmark residues mentioned in Table B-2.

Aspect E-11: An immunoglobulin sequence according to any of aspects B-1 to B-7, C-1 to C-7, D1 to D-6, and/or E1 to E-10, that essentially consists of a Nanobody that
i) has at least 80% amino acid identity with at least one of the An immunoglobulin sequences of SEQ ID NO's: 705 to 788, more preferably SEQ ID NO's 726 to 750, 753 to 758, 762 to 764, 772 to 773, 775, or 778 to 780, more preferred SEQ ID NO's 732, 773 or 778, in which for the purposes of determining the degree of amino acid identity, the amino acid residues that form the CDR sequences are disregarded;
and in which:
ii) preferably one or more of the amino acid residues at positions 11, 37, 44, 45, 47, 83, 84, 103, 104 and 108 according to the Kabat numbering are chosen from the Hallmark residues mentioned in Table B-2.

Aspect E-12: An immunoglobulin sequence according to any of aspects B-1 to B-7, C-1 to C-7, D1 to D-6, and/or E-1 to E-11 that essentially consists of a humanized Nanobody.

Aspect E-13: An immunoglobulin sequence according to any of the aspects B-1 to B-7, C-1 to C-7, D1 to D-6, and/or E1 to E-11, that in addition to the at least one binding site for binding formed by the CDR sequences, contains one or more further binding sites for binding against other antigens, proteins or targets.

The immunoglobulin sequences according to aspects E-1 to E-13 may in particular be an immunoglobulin sequence according to any of the aspects A-1 to A-22.

Framework+CDR's Aspects

Aspect F-1: An immunoglobulin sequence that essentially consists of 4 framework regions (FR1 to FR4, respectively) and 3 complementarity determining regions (CDR1 to CDR3, respectively), in which:
CDR1 is chosen from the group consisting of:
a) the immunoglobulin sequences of SEQ ID NO's: 208 to 289;
b) immunoglobulin sequences that have at least 80% amino acid identity with at least one of the immunoglobulin sequences of SEQ ID NO's: 208 to 289;
c) immunoglobulin sequences that have 3, 2, or 1 amino acid difference with at least one of the immunoglobulin sequences of SEQ ID NO's: 208 to 289;
and/or
CDR2 is chosen from the group consisting of:
d) the immunoglobulin sequences of SEQ ID NO's: 372 to 453;
e) immunoglobulin sequences that have at least 80% amino acid identity with at least one of the immunoglobulin sequences of SEQ ID NO's: 372 to 453;
f) immunoglobulin sequences that have 3, 2, or 1 amino acid difference with at least one of the immunoglobulin sequences of SEQ ID NO's: 372 to 453;
and/or
CDR3 is chosen from the group consisting of:
g) the immunoglobulin sequences of SEQ ID NO's: 536 to 617;
h) immunoglobulin sequences that have at least 80% amino acid identity with at least one of the immunoglobulin sequences of SEQ ID NO's: 536 to 617;
i) immunoglobulin sequences that have 3, 2, or 1 amino acid difference with at least one of the immunoglobulin sequences of SEQ ID NO's: 536 to 617.

Such an immunoglobulin sequence is preferably directed against ion channels such as e.g. P2X7 and/or an immunoglobulin sequence that can specifically bind to ion channels such as e.g. P2X7. Also, such an immunoglobulin sequence is preferably an immunoglobulin sequence according to any of the aspects A-1 to A-22, C-1 to C-7, D1 to D-6 and/or E1 to E-13.

Aspect F-2: An immunoglobulin sequence that essentially consists of 4 framework regions (FR1 to FR4, respectively) and 3 complementarity determining regions (CDR1 to CDR3, respectively), in which:
CDR1 is chosen from the group consisting of:
a) the immunoglobulin sequences of SEQ ID NO's: 208 to 289;
b) immunoglobulin sequences that have at least 80% amino acid identity with at least one of the immunoglobulin sequences of SEQ ID NO's: 208 to 289;
c) immunoglobulin sequences that have 3, 2, or 1 amino acid difference with at least one of the immunoglobulin sequences of SEQ ID NO's: 208 to 289;
and
CDR2 is chosen from the group consisting of:
d) the immunoglobulin sequences of SEQ ID NO's: 372 to 453;
e) immunoglobulin sequences that have at least 80% amino acid identity with at least one of the immunoglobulin sequences of SEQ ID NO's: 372 to 453;
f) immunoglobulin sequences that have 3, 2, or 1 amino acid difference with at least one of the immunoglobulin sequences of SEQ ID NO's: 372 to 453;
and
CDR3 is chosen from the group consisting of:
g) the immunoglobulin sequences of SEQ ID NO's: 536 to 617;
h) immunoglobulin sequences that have at least 80% amino acid identity with at least one of the immunoglobulin sequences of SEQ ID NO's: 536 to 617;
i) immunoglobulin sequences that have 3, 2, or 1 amino acid difference with at least one of the immunoglobulin sequences of SEQ ID NO's: 536 to 617.

Such an immunoglobulin sequence is preferably directed against ion channels such as e.g. P2X7 and/or an immunoglobulin sequence that can specifically bind to ion channels such as e.g. P2X7. Also, such an immunoglobulin sequence is preferably an immunoglobulin sequence according to any of the aspects A-1 to A-22, C-1 to C-7, D1 to D-6 and/or E1 to E-13.

Aspect F-3: An immunoglobulin sequence according to any of aspects F-1 and F-2, in which the CDR sequences of said immunoglobulin sequence have at least 70% amino acid identity, preferably at least 80% amino acid identity, more preferably at least 90% amino acid identity, such as 95% amino acid identity or more or even essentially 100% amino acid identity with the CDR sequences of at least one of the immunoglobulin sequences of SEQ ID NO's: 705 to 788, more preferably SEQ ID NO's 726 to 750, 753 to 758, 762 to 764, 772 to 773, 775, or 778 to 780, more preferred SEQ ID NO's 732, 773 or 778.

Such an immunoglobulin sequence is preferably directed against ion channels such as e.g. P2X7 and/or an immunoglobulin sequence that can specifically bind to ion channels such as e.g. P2X7. Also, such an immunoglobulin sequence is preferably an immunoglobulin sequence according to any of the aspects A-1 to A-22, C-1 to C-7, D1 to D-6 and/or E-1 to E-13.

Aspect F-4: An immunoglobulin sequence according to any of aspects F-1 to F-3 that is directed against ion channels such as e.g. P2X7 and that cross-blocks the binding of at least one of the immunoglobulin sequences according to any of aspects the immunoglobulin sequences of SEQ ID NO's: 705 to 788, more preferably SEQ ID NO's 726 to 750, 753 to 758, 762 to 764, 772 to 773, 775, or 778 to 780, more preferred SEQ ID NO's 732, 773 or 778.

Aspect F-5: An immunoglobulin sequence according to any of aspects F-1 to F-3 that is directed against ion channels such as e.g. P2X7 and that is cross-blocked from binding to ion channels such as e.g. P2X7 by at least one of the immunoglobulin sequences of SEQ ID NO's: 705 to 788, more preferably SEQ ID NO's 726 to 750, 753 to 758, 762 to 764, 772 to 773, 775, or 778 to 780, more preferred SEQ ID NO's 732, 773 or 778.

Aspect F-6: Immunoglobulin sequence according to any of aspects F-4 or F-5 wherein the ability of said immunoglobulin sequence to cross-block or to be cross-blocked is detected in a Biacore assay.

Aspect F-7: Immunoglobulin sequence according to any of aspects F4 or F-5 wherein the ability of said immunoglobulin sequence to cross-block or to be cross-blocked is detected in an ELISA assay.

Aspect F-8: An immunoglobulin sequence according to any of aspects F-1 to F-7, that is in essentially isolated form.

Aspect F-9: An immunoglobulin sequence according to any of aspects F-1 to F-8, for administration to a subject, wherein said an immunoglobulin sequence does not naturally occur in said subject.

Aspect F-10: An immunoglobulin sequence according to any of aspects F-1 to F-9, that can specifically bind to ion channels such as e.g. P2X7 with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter.

Aspect F-11: An immunoglobulin sequence according to any of aspects F-1 to F-10, that can specifically bind to ion channels such as e.g. P2X7 with a rate of association ($k_{on}$-rate) of between $10^2$ $M^{-1}s^{-1}$ to about $10^7$ $M^{-1}s^{-1}$, preferably between $10^3$ $M^{-1}s^{-1}$ and $10^7$ $M^{-1}s^{-1}$, more preferably between $10^4$ $M^{-1}s^{-1}$ and $10^7$ $M^{-1}s^{-1}$, such as between $10^5$ $M^{-1}s^{-1}$ and $10^7$ $M^{-1}s^{-1}$.

Aspect F-12: An immunoglobulin sequence according to any of aspects F-1 to F-11, that can specifically bind to ion channels such as e.g. P2X7 with a rate of dissociation ($k_{off}$ rate) between $1$ $s^{-1}$ and $10^{-6}$ $s^{-1}$ preferably between $10^{-2}$ $s^{-1}$ and $10^{-6}$ $s^1$, more preferably between $10^{-3}$ $s^{-1}$ and $10^{-6}$ $s^{-1}$, such as between $10^{-4}$ $s^{-1}$ and $10^{-6}$ $s^{-1}$.

Aspect F-13: An immunoglobulin sequence according to any of aspects F-1 to F-12, that can specifically bind to ion channels such as e.g. P2X7 with an affinity less than 500 nM, preferably less than 200 nM, more preferably less than 10 nM, such as less than 500 μM.

Aspect F-14: An immunoglobulin sequence according to any of aspects F-1 to F-13, that is a naturally occurring immunoglobulin sequence (from any suitable species) or a synthetic or semi-synthetic immunoglobulin sequence.

Aspect F-15: An immunoglobulin sequence according to any of aspects F-1 to F-14, that comprises an immunoglobulin fold or that under suitable conditions is capable of forming an immunoglobulin fold.

Aspect F-16: An immunoglobulin sequence according to any of aspects F-1 to F-15, that is an immunoglobulin sequence.

Aspect F-17: An immunoglobulin sequence according to any of aspects F-1 to F-16, that is a naturally occurring immunoglobulin sequence (from any suitable species) or a synthetic or semi-synthetic immunoglobulin sequence.

Aspect F-18: An immunoglobulin sequence according to any of aspects F-1 to F-17, that is a humanized immunoglobulin sequence, a camelized immunoglobulin sequence or an immunoglobulin sequence that has been obtained by techniques such as affinity maturation.

Aspect F-19: An immunoglobulin sequence according to any of aspects F-1 to F-19, that essentially consists of a light chain variable domain sequence (e.g. a $V_L$-sequence); or of a heavy chain variable domain sequence (e.g. a $V_H$-sequence).

Aspect F-20: An immunoglobulin sequence according to any of aspects F-1 to F-19, that essentially consists of a heavy chain variable domain sequence that is derived from a conventional four-chain antibody or that essentially consist of a heavy chain variable domain sequence that is derived from heavy chain antibody.

Aspect F-21: An immunoglobulin sequence according to any of aspects F-1 to F-20, that essentially consists of a domain antibody (or an immunoglobulin sequence that is suitable for use as a domain antibody), of a single domain antibody (or an immunoglobulin sequence that is suitable for use as a single domain antibody), of a "dAb" (or an immunoglobulin sequence that is suitable for use as a dAb) or of a Nanobody (including but not limited to a $V_{HH}$ sequence).

Aspect F-22: An immunoglobulin sequence according to any of aspects F-1 to F-21, that essentially consists of a Nanobody.

Aspect F-23: An immunoglobulin sequence according to any of aspects F-1 to F-22, that essentially consists of a Nanobody that
i) has at least 80% amino acid identity with at least one of the immunoglobulin sequences of SEQ ID NO's: 1 to 22, in which for the purposes of determining the degree of amino acid identity, the amino acid residues that form the CDR sequences are disregarded;
and in which:
ii) preferably one or more of the amino acid residues at positions 11, 37, 44, 45, 47, 83, 84, 103, 104 and 108 according to the Kabat numbering are chosen from the Hallmark residues mentioned in Table B-2.

Aspect F-24: An immunoglobulin sequence according to any of aspects F-1 to F-23, that essentially consists of a Nanobody that
i) has at least 80% amino acid identity with at least one of the immunoglobulin sequences of SEQ ID NO's: 705 to 788, more preferably SEQ ID NO's 726 to 750, 753 to 758, 762 to 764, 772 to 773, 775, or 778 to 780, more preferred SEQ ID NO's 732, 773 or 778, in which for the purposes of determining the degree of amino acid identity, the amino acid residues that form the CDR sequences are disregarded;
and in which:
ii) preferably one or more of the amino acid residues at positions 11, 37, 44, 45, 47, 83, 84, 103, 104 and 108 according to the Kabat numbering are chosen from the Hallmark residues mentioned in Table B-2.

Aspect F-25: An immunoglobulin sequence according to any of aspects F-1 to F-24, that essentially consists of a humanized Nanobody.

Aspect G-1: An immunoglobulin sequence according to any of the preceding aspects, that in addition to the at least one binding site formed by the CDR sequences, contains one or more further binding sites for binding against another antigen, protein or target.

Aspect H-1: Nanobody that is directed against and/or that can specifically bind to ion channels such as e.g. P2X7.

Aspect H-2: Nanobody according to aspect H-1, that is in essentially isolated form.

Aspect H-3: Nanobody according to any of aspects H-1 to H-2, that can specifically bind to ion channels such as e.g. P2X7 with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter.

Aspect H-4: Nanobody according to any of aspects H-1 to H-3, that can specifically bind to ion channels such as e.g. P2X7 with a rate of association ($k_{on}$-rate) of between $10^2$ $M^{-1}s^{-1}$ to about $10^7$ $M^{-1}s^{-1}$, preferably between $10^3$ $M^{-1}s^{-1}$ and $10^7$ $M^{-1}s^{-1}$, more preferably between $10^4$ $M^{-1}s^{-1}$ and $10^7$ $M^{-1}s^{-1}$, such as between $10^5$ $M^{-1}s^{-1}$ and $10^7$ $M^{-1}s^{-1}$.

Aspect H-5: Nanobody according to any of aspects H-1 to H-4, that can specifically bind to ion channels such as e.g. P2X7 with a rate of dissociation ($k_{off}$ rate) between 1 $s^{-1}$ and $10^{-6}$ $s^{-1}$ preferably between $10^{-2}$ $s^{-1}$ and $10^{-6}$ $s^{-1}$, more preferably between $10^{-6}$ $s^{-1}$ and $10^{-6}$ $s^{-1}$, such as between $10^{-4}$ $s^{-1}$ and $10^{-6}$ $s^{-1}$.

Aspect H-6: Nanobody according to any of aspects H-1 to H-5, that can specifically bind to on channels such as e.g. P2X7 with an affinity less than 500 nM, preferably less than 200 nM, more preferably less than 10 nM, such as less than 500 µM.

Aspect H-7: Nanobody according to any of aspects H-1 to H-6, that is a naturally occurring Nanobody (from any suitable species) or a synthetic or semi-synthetic Nanobody.

Aspect H-8: Nanobody according to any of aspects to H-1 to H-7, that is a $V_{HH}$ sequence, a partially humanized $V_{HH}$ sequence, a fully humanized $V_{HH}$ sequence, a camelized heavy chain variable domain or a Nanobody that has been obtained by techniques such as affinity maturation.

Aspect H-9: Nanobody according to any of aspects H-1 to H-8, that
i) has at least 80% amino acid identity with at least one of the An immunoglobulin sequences of SEQ ID NO's: 1 to 22, in which for the purposes of determining the degree of amino acid identity, the amino acid residues that form the CDR sequences are disregarded;
and in which:
ii) preferably one or more of the amino acid residues at positions 11, 37, 44, 45, 47, 83, 84, 103, 104 and 108 according to the Kabat numbering are chosen from the Hallmark residues mentioned in Table B-2.

Aspect H-10: Nanobody according to any of aspects H-1 to H-9, that
i) has at least 80% amino acid identity with at least one of the An immunoglobulin sequences of SEQ ID NO's: 705 to 788, more preferably SEQ ID NO's 726 to 750, 753 to 758, 762 to 764, 772 to 773, 775, or 778 to 780, more preferred SEQ ID NO's 732, 773 or 778, in which for the purposes of determining the degree of amino acid identity, the amino acid residues that form the CDR sequences are disregarded;
and in which:
ii) preferably one or more of the amino acid residues at positions 11, 37, 44, 45, 47, 83, 84, 103, 104 and 108 according to the Kabat numbering are chosen from the Hallmark residues mentioned in Table B-2.

Aspect H-11: Nanobody according to any of aspects H-1 to H-10, in which:
CDR1 is chosen from the group consisting of:
a) the immunoglobulin sequences of SEQ ID NO's: 208 to 289;
b) immunoglobulin sequences that have at least 80% amino acid identity with at least one of the immunoglobulin sequences of SEQ ID NO's: 208 to 289;
c) immunoglobulin sequences that have 3, 2, or 1 amino acid difference with at least one of the immunoglobulin sequences of SEQ ID NO's: 208 to 289;
and/or
CDR2 is chosen from the group consisting of:
d) the immunoglobulin sequences of SEQ ID NO's: 372 to 453;
e) immunoglobulin sequences that have at least 80% amino acid identity with at least one of the immunoglobulin sequences of SEQ ID NO's: 372 to 453;
f) immunoglobulin sequences that have 3, 2, or 1 amino acid difference with at least one of the immunoglobulin sequences of SEQ ID NO's: 372 to 453;
and/or
CDR3 is chosen from the group consisting of:
g) the immunoglobulin sequences of SEQ ID NO's: 536 to 617;
h) immunoglobulin sequences that have at least 80% amino acid identity with at least one of the immunoglobulin sequences of SEQ ID NO's: 536 to 617;
i) immunoglobulin sequences that have 3, 2, or 1 amino acid difference with at least one of the immunoglobulin sequences of SEQ ID NO's: 536 to 617.

Aspect H-12: Nanobody according to any of aspects H-1 to H-11, in which:
CDR1 is chosen from the group consisting of:
a) the immunoglobulin sequences of SEQ ID NO's: 208 to 289;
b) immunoglobulin sequences that have at least 80% amino acid identity with at least one of the immunoglobulin sequences of SEQ ID NO's: 208 to 289;

c) immunoglobulin sequences that have 3, 2, or 1 amino acid difference with at least one of the immunoglobulin sequences of SEQ ID NO's: 208 to 289;
and
CDR2 is chosen from the group consisting of:
d) the immunoglobulin sequences of SEQ ID NO's: 372 to 453;
e) immunoglobulin sequences that have at least 80% amino acid identity with at least one of the immunoglobulin sequences of SEQ ID NO's: 372 to 453;
f) immunoglobulin sequences that have 3, 2, or 1 amino acid difference with at least one of the immunoglobulin sequences of SEQ ID NO's: 372 to 453;
and
CDR3 is chosen from the group consisting of:
g) the immunoglobulin sequences of SEQ ID NO's: 536 to 617;
h) immunoglobulin sequences that have at least 80% amino acid identity with at least one of the immunoglobulin sequences of SEQ ID NO's: 536 to 617;
i) immunoglobulin sequences that have 3, 2, or 1 amino acid difference with at least one of the immunoglobulin sequences of SEQ ID NO's: 536 to 617.

Aspect H-13: Nanobody according to any of aspects H-1 to H-12, in which the CDR sequences have at least 70% amino acid identity, preferably at least 80% amino acid identity, more preferably at least 90% amino acid identity, such as 95% amino acid identity or more or even essentially 100% amino acid identity with the CDR sequences of at least one of the immunoglobulin sequences of SEQ ID NO's: 705 to 788, more preferably SEQ ID NO's 726 to 750, 753 to 758, 762 to 764, 772 to 773, 775; or 778 to 780, more preferred SEQ ID NO's 732, 773 or 778.

Aspect H-14: Nanobody according to any of aspects H-1 to H-13, which is a partially humanized Nanobody.

Aspect H-15: Nanobody according to any of aspects H-1 to H-14, which is a fully humanized Nanobody.

Aspect H-16: Nanobody according to any of aspects H-1 to H-15, that is chosen from the group consisting of SEQ ID NO's: 705 to 788, more preferably SEQ ID NO's 726 to 750, 753 to 758, 762 to 764, 772 to 773, 775, or 778 to 780, more preferred SEQ ID NO's 732, 773 or 778 or from the group consisting of from immunoglobulin sequences that have more than 80%, preferably more than 90%, more preferably more than 95%, such as 99% or more sequence identity (as defined herein) with at least one of the immunoglobulin sequences of SEQ ID NO's: 705 to 788, more preferably SEQ ID NO's 726 to 750, 753 to 758, 762 to 764, 772 to 773, 775, or 778 to 780, more preferred SEQ ID NO's 732, 773 or 778.

Aspect H-17: Nanobody according to any of aspects H-1 to H-16, which is a humanized Nanobody.

Aspect H-18: Nanobody according to any of aspects H-1 to H-17, that is chosen from the group consisting of SEQ ID NO's: 705 to 788, more preferably SEQ ID NO's 726 to 750, 753 to 758, 762 to 764, 772 to 773, 775, or 778 to 780, more preferred SEQ ID NO's 732, 773.

Aspect H-19: Nanobody directed against ion channels such as e.g. P2X7 that cross-blocks the binding of at least one of the immunoglobulin sequences of SEQ ID NO's: 705 to 788, more preferably SEQ ID NO's 726 to 750, 753 to 758, 762 to 764, 772 to 773, 775, or 778 to 780, more preferred SEQ ID NO's 732, 773 or 778 to ion channels such as e.g. P2X7.

Aspect H-20: Nanobody directed against ion channels such as e.g. P2X7 that is cross-blocked from binding to ion channels such as e.g. P2X7 by at least one of the immunoglobulin sequences of SEQ ID NO's: 705 to 788, more preferably SEQ ID NO's 726 to 750, 753 to 758, 762 to 764, 772 to 773, 775, or 778 to 780, more preferred SEQ ID NO's 732, 773 or 778.

Aspect H-21: Nanobody according to any of aspects H-19 or H-20 wherein the ability of said Nanobody to cross-block or to be cross-blocked is detected in a Biacore assay.

Aspect H-22: Nanobody according to any of aspects H-19 to H-21 wherein the ability of said Nanobody to cross-block or to be cross-blocked is detected in an ELISA assay.

Polypeptides.

Aspect K-1: Polypeptide that comprises or essentially consists of one or more immunoglobulin sequences according to any of aspects A-1 to A-22, B-1 to B-7, C-1 to C-4, D-1 to D-6, E-1 to E-13, F-1 to F-25 or G-1 and/or one or more Nanobodies according to any of aspects H-1 to H-22, and optionally further comprises one or more peptidic linkers.

Aspect K-2: Polypeptide according to aspect K-1, in which said one or more binding units are immunoglobulin sequences.

Aspect K-3: Polypeptide according to any of aspects K-1 or K-2, in which said one or more other groups, residues, moieties or binding units are chosen from the group consisting of domain antibodies, immunoglobulin sequences that are suitable for use as a domain antibody, single domain antibodies, immunoglobulin sequences that are suitable for use as a single domain antibody, "dAb"'s, immunoglobulin sequences that are suitable for use as a dAb, or Nanobodies.

Aspect K-4: Polypeptide according to any of aspects K-1 to K-3, in which said one or more immunoglobulin sequences of the invention are immunoglobulin sequences.

Aspect K-5: Polypeptide according to any of aspects K-1 to K-4, in which said one or more immunoglobulin sequences of the invention are chosen from the group consisting of domain antibodies, immunoglobulin sequences that are suitable for use as a domain antibody, single domain antibodies, immunoglobulin sequences that are suitable for use as a single domain antibody, "dAb"'s, immunoglobulin sequences that are suitable for use as a dAb, or Nanobodies.

Aspect K-6: Polypeptide according to any of aspects K-1 to K-5, that comprises or essentially consists of one or more Nanobodies according to any of aspects H-1 to H-22 and in which said one or more other binding units are Nanobodies.

Aspect K-7: Polypeptide according to any of aspects K-1 to K-6, wherein at least one binding unit is a multivalent construct.

Aspect K-8: Polypeptide according to any of aspects K-1 to K-8, wherein at least one binding unit is a multiparatopic construct.

Aspect K-9: Polypeptide according to any of aspects K-1 to K-8, wherein at least one binding unit is a multispecific construct.

Aspect K-10: Polypeptide according to any of aspects K-1 to K-9, which has an increased half-life, compared to the corresponding immunoglobulin sequence according to any of aspects A-1 to A-22, B-1 to B-7, C-1 to C-4, D-1 to D-6, E-1 to E-13, F-1 to F-25 or G-1 per se or Nanobody according to any of aspects H-1 to H-22 per se, respectively.

Aspect K-11: Polypeptide according to aspect K-10, in which said one or more other binding units provide the polypeptide with increased half-life, compared to the corresponding immunoglobulin sequence according to any of aspects A-1 to A-22, B-1 to B-7, C-1 to C-4, D-1 to D-6, E-1 to E-13, F-1 to F-25 or G-1 per se or Nanobody according to any of aspects H-1 to H-22 per se, respectively.

Aspect K-12: Polypeptide according to aspect K-10 or K-11, in which said one or more other binding units that provide the polypeptide with increased half-life is chosen from the group consisting of serum proteins or fragments thereof, binding units that can bind to serum proteins, an Fc portion, and small proteins or peptides that can bind to serum proteins.

Aspect K-13: Polypeptide according to any of aspects K-10 to K-12, in which said one or more other binding units that provide the polypeptide with increased half-life is chosen from the group consisting of human serum albumin or fragments thereof.

Aspect K-14: Polypeptide according to any of aspect K-10 to K-13, in which said one or more other binding units that provides the polypeptide with increased half-life are chosen from the group consisting of binding units that can bind to serum albumin (such as human serum albumin) or a serum immunoglobulin (such as IgG).

Aspect K-15: Polypeptide according to any of aspects K-10 to K-14, in which said one or more other binding units that provides the polypeptide with increased half-life are chosen from the group consisting of domain antibodies, immunoglobulin sequences that are suitable for use as a domain antibody, single domain antibodies, immunoglobulin sequences that are suitable for use as a single domain antibody, "dAb"'s, immunoglobulin sequences that are suitable for use as a dAb, or Nanobodies that can bind to serum albumin (such as human serum albumin) or a serum immunoglobulin (such as IgG).

Aspect K-16: Polypeptide according to aspect K-10 to K-15, in which said one or more other binding units that provides the polypeptide with increased half-life is a Nanobody that can bind to serum albumin (such as human serum albumin) or a serum immunoglobulin (such as IgG).

Aspect K-17: Polypeptide according to any of aspects K-10 to K-16, that has a serum half-life that is at least 1.5 times, preferably at least 2 times, such as at least 5 times, for example at least 10 times or more than 20 times, greater than the half-life of the corresponding immunoglobulin sequence according to any of aspects A-1 to A-22, B-1 to B-7, C-1 to C-4, D-1 to D-6, E-1 to E-13, F-1 to F-25 or G-1 per se or Nanobody according to any of aspects H-1 to H-22 per se, respectively.

Aspect K-18: Polypeptide according to any of aspects K-10 to K-17, that has a serum half-life that is increased with more than 1 hours, preferably more than 2 hours, more preferably more than 6 hours, such as more than 12 hours, or even more than 24, 48 or 72 hours, compared to the corresponding immunoglobulin sequence according to any of aspects A-1 to A-22, B-1 to B-7, C-1 to C-4, D-1 to D-6, E-1 to E-13, F-1 to F-25 or G-1 per se or Nanobody according to any of aspects H-1 to H-22 per se, respectively.

Aspect K-19: Polypeptide according to any of aspects K-1 to K-18, that has a serum half-life in human of at least about 12 hours, preferably at least 24 hours, more preferably at least 48 hours, even more preferably at least 72 hours or more; for example, of at least 5 days (such as about 5 to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

Compound or Construct.

Aspect L-1: Compound or construct, that comprises or essentially consists of one or more immunoglobulin sequences according to any of aspects A-1 to A-22, B-1 to B-7, C-1 to C-4, D-1 to D-6, E-1 to E-13, F-1 to F-25 or G-1 and/or one or more Nanobodies according to any of aspects H-1 to H-22, and optionally further comprises one or more other groups, residues, moieties or binding units, optionally linked via one or more linkers.

Aspect L-2: Compound or construct according to aspects L-1, in which said one or more other groups, residues, moieties or binding units are immunoglobulin sequences.

Aspect L-3: Compound or construct according to aspect L1 or L-2, in which said one or more linkers, if present, are one or more immunoglobulin sequences.

Aspect L-4: Compound or construct according to any of aspects L1 to L-3, in which said one or more other groups, residues, moieties or binding units are immunoglobulin sequences.

Aspect L-5: Compound or construct according to any of aspects L1 to L4, in which said one or more other groups, residues, moieties or binding units are chosen from the group consisting of domain antibodies, immunoglobulin sequences that are suitable for use as a domain antibody, single domain antibodies, immunoglobulin sequences that are suitable for use as a single domain antibody, "dAb"'s, immunoglobulin sequences that are suitable for use as a dAb, or Nanobodies.

Aspect L-6: Compound or construct according to any of aspects L1 to L-5, in which said one or more immunoglobulin sequences of the invention are immunoglobulin sequences.

Aspect L-7: Compound or construct according to any of aspects L-1 to L-6, in which said one or more immunoglobulin sequences of the invention are chosen from the group consisting of domain antibodies, immunoglobulin sequences that are suitable for use as a domain antibody, single domain antibodies, immunoglobulin sequences that are suitable for use as a single domain antibody, "dAb"'s, immunoglobulin sequences that are suitable for use as a dAb, or Nanobodies.

Aspect L-8: Compound or construct, that comprises or essentially consists of one or more Nanobodies according to any of aspects H-1 to H-22 and in which said one or more other groups, residues, moieties or binding units are Nanobodies.

Aspect L-9: Compound or construct according to any of aspects L-1 to L-9, which is a multivalent construct.

Aspect L-10: Compound or construct according to any of aspects L-1 to L-10, which is a multispecific construct.

Aspect L-11: Compound or construct according to any of aspects L-1 to L-10, which has an increased half-life, compared to the corresponding immunoglobulin sequence according to any of aspects A-1 to A-22, B-1 to B-7. C-1 to C-4, D-1 to D-6, E-1 to E-13, F-1 to F-25 or G-1 per se or Nanobody according to any of aspects H-1 to H-22 per se, respectively.

Aspect L-12: Compound or construct according to aspect L-1 to L-11, in which said one or more other groups, residues, moieties or binding units provide the compound or construct with increased half-life, compared to the corresponding immunoglobulin sequence according to any of aspects A-1 to A-22, B-1 to B-7, C-1 to C-4, D-1 to D-6, E-1 to E-13, F-1 to F-25 or G-1 per se or Nanobody according to any of aspects H-1 to H-22 per se, respectively.

Aspect L-13: Compound or construct according to aspect L-12, in which said one or more other groups, residues, moieties or binding units that provide the compound or construct with increased half-life is chosen from the group consisting of serum proteins or fragments thereof, binding units that can bind to serum proteins, an Fc portion, and small proteins or peptides that can bind to serum proteins.

Aspect L-14: Compound or construct according to aspect L-12 or L-13, in which said one or more other groups, residues, moieties or binding units that provide the compound or construct with increased half-life is chosen from the group consisting of human serum albumin or fragments thereof.

Aspect L-15: Compound or construct according to any of aspects L-12 to L-14, in which said one or more other groups, residues, moieties or binding units that provides the compound or construct with increased half-life are chosen from the group consisting of binding units that can bind to serum albumin (such as human serum albumin) or a serum immunoglobulin (such as IgG).

Aspect L-16: Compound or construct according to any of aspects L-12 to L-14, in which said one or more other groups, residues, moieties or binding units that provides the compound or construct with increased half-life are chosen from the group consisting of domain antibodies, immunoglobulin sequences that are suitable for use as a domain antibody, single domain antibodies, immunoglobulin sequences that are suitable for use as a single domain antibody, "dAb"'s, immunoglobulin sequences that are suitable for use as a dAb, or Nanobodies that can bind to serum albumin (such as human serum albumin) or a serum immunoglobulin (such as IgG).

Aspect L-17: Compound or construct according to any of aspects L-12 to L-14, in which said one or more other groups, residues, moieties or binding units that provides the compound or construct with increased half-life is a Nanobody that can bind to serum albumin (such as human serum albumin) or a serum immunoglobulin (such as IgG).

Aspect L-18: Compound or construct according to any of aspects L-12 to L-17, that has a serum half-life that is at least 1.5 times, preferably at least 2 times, such as at least 5 times, for example at least 10 times or more than 20 times, greater than the half-life of the corresponding immunoglobulin sequence according to any of aspects A-1 to A-22, B-1 to B-7, C-1 to C-4, D-1 to 0-6, E-1 to E-13, F-1 to F-25 or G-1 per se or Nanobody according to any of aspects H-1 to H-22 per se, respectively.

Aspect L19: Compound or construct according to any of aspects L-12 to L-18 that has a serum half-life that is increased with more than 1 hours, preferably more than 2 hours, more preferably more than 6 hours, such as more than 12 hours, or even more than 24, 48 or 72 hours, compared to the corresponding immunoglobulin sequence according to any of aspects A-1 to A-22, B-1 to B-7, C-1 to C-4, D-1 to 0-6, E-1 to E-13, F-1 to F-25 or G-1 per se or Nanobody according to any of aspects H-1 to H-22 per se, respectively.

Aspect L-20: Compound or construct according to any of aspects L-12 to L-19, that has a serum half-life in human of at least about 12 hours, preferably at least 24 hours, more preferably at least 48 hours, even more preferably at least 72 hours or more; for example, of at least 5 days (such as about 5 to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

Aspect L-21: Monovalent construct, comprising or essentially consisting of one immunoglobulin sequence according to any of aspects A-1 to A-22, B-1 to B-7, C-1 to C-4, D-1 to 0-6, E-1 to E-13, F-1 to F-25 or G-1 and/or one Nanobody according to any of aspects H-1 to H-22.

Aspect L-22: Monovalent construct according to aspect L-21, in which said immunoglobulin sequence of the invention is chosen from the group consisting of domain antibodies, immunoglobulin sequences that are suitable for use as a domain antibody, single domain antibodies, immunoglobulin sequences that are suitable for use as a single domain antibody, "dAb"'s, immunoglobulin sequences that are suitable for use as a dAb, or Nanobodies.

Aspect L-23: Monovalent construct, comprising or essentially consisting of one Nanobody according to any of aspects H-1 to H-22.

Nucleic Acid

Aspect M-1: Nucleic acid or nucleotide sequence, that encodes an immunoglobulin sequence according to any of aspects A-1 to A-22, B-1 to B-7, C-1 to C-4, D-1 to D-6, E-1 to E-13, F-1 to F-25 or G-1, a Nanobody according to any of aspects H-1 to H-22.

Aspect M-2: Nucleic acid or nucleotide sequence, that encodes a compound or construct according to any of above aspects.

Host Cell

Aspect N-1: Host or host cell that expresses, or that under suitable circumstances is capable of expressing, an immunoglobulin sequence according to any of aspects A-1 to A-22, B-1 to B-7, C-1 to C-4, D-1 to D-6, E-1 to E-13, F-1 to F-25 or G-1, a Nanobody according to any of aspects H-1 to H-22, a polypeptide according to any of aspects K-1 to K-19, a compound or construct according to any of aspects L-1 to L-21 that is such that it can be obtained by expression of a nucleic acid or nucleotide sequence encoding the same, or a monovalent construct according to any of aspects L-22 or L-23; and/or that comprises a nucleic acid or nucleotide sequence according to aspect M-1 or a genetic construct according to aspect M-2.

Compositions

Aspect O-1: Composition comprising at least one immunoglobulin sequence according to any of aspects A-1 to A-22, B-1 to B-7, C-1 to C-4, D-1 to D-6, E-1 to E-13, F-1 to F-25 or G-1, Nanobody according to any of aspects H-1 to H-22, polypeptide according to any of aspects K-1 to K-19, compound or construct according to any of aspects L-1 to L-21, monovalent construct according to any of aspects L-22 or L-23, or nucleic acid or nucleotide sequence according to aspects M-1 or M-2.

Aspect O-2: Composition according to aspect O-1, which is a pharmaceutical composition.

Aspect O-3: Composition according to aspect O-2, which is a pharmaceutical composition, that further comprises at least one pharmaceutically acceptable carrier, diluent or excipient and/or adjuvant, and that optionally comprises one or more further pharmaceutically active polypeptides and/or compounds.

Making of Agent and Composition of the Invention

Aspect P-1: Method for producing an immunoglobulin sequence according to any of aspects A-1 to A-22, B-1 to B-7, C-1 to C-4, D-1 to D-6, E-1 to E-13, F-1 to F-25 or G-1, a Nanobody according to any of aspects H-1 to H-22, a polypeptide according to any of aspects K-1 to K-19, a compound or construct according to any of aspects L-1 to L-21 that is such that it can be obtained by expression of a nucleic acid or nucleotide sequence encoding the same, or a monovalent construct according to any of aspects L-22 or L-23, said method at least comprising the steps of:
a) expressing, in a suitable host cell or host organism or in another suitable expression system, a nucleic acid or nucleotide sequence according to aspect M-1, or a genetic construct according to aspect M-2;
optionally followed by:
b) isolating and/or purifying the immunoglobulin sequence according to any of aspects A-1 to A-22, B-1 to B-7, C-1 to C-4, 0-1 to D-6, E-1 to E-13, F-1 to F-25 or G-1, a Nanobody according to any of aspects H-1 to H-22, a polypeptide according to any of aspects K-1 to K-19, a compound or construct according to any of aspects L-1 to L-21, or a monovalent construct according to any of aspects L-22 or L-23 thus obtained.

Aspect P-2: Method for producing an immunoglobulin sequence according to any of aspects A-1 to A-22, B-1 to B-7, C-1 to C-4, 0-1 to 0-6, E-1 to E-13, F-1 to F-25 or G-1, a Nanobody according to any of aspects H-1 to H-22, a polypeptide according to any of aspects K-1 to K-19, a compound or construct according to any of aspects L-1 to L-21 that is such that it can be obtained by expression of a nucleic acid or nucleotide sequence encoding the same, or a monovalent construct according to any of aspects L-22 or L-23, said method at least comprising the steps of:
a) cultivating and/or maintaining a host or host cell according to aspect . . . under conditions that are such that said host or host cell expresses and/or produces at least one immunoglobulin sequence according to any of aspects A-1 to A-22, B-1 to B-7, C-1 to C-4, D-1 to 0-6, E-1 to E-13, F-1 to F-25 or G-1, Nanobody according to any of aspects H-1 to H-22, a polypeptide according to any of aspects K-1 to K-19, a compound or construct according to any of aspects L-1 to L-21, or monovalent construct according to any of aspects L-22 or L-23;
optionally followed by:
b) isolating and/or purifying the immunoglobulin sequence according to any of aspects A-1 to A-22, B-1 to B-7, C-1 to C-4, 0-1 to D-6, E-1 to E-13, F-1 to F-25 or G-1, Nanobody according to any of aspects H-1 to H-22, a polypeptide according to any of aspects K-1 to K-19, a compound or construct according to any of aspects L-1 to L-21, or monovalent construct according to any of aspects L-22 or L-23 thus obtained.

Method of Screening
Aspect Q-1: Method for screening immunoglobulin sequences directed against ion channels such as e.g. P2X7 that comprises at least the steps of:
a) providing a set, collection or library of nucleic acid sequences encoding immunoglobulin sequences;
b) screening said set, collection or library of nucleic acid sequences for nucleic acid sequences that encode an immunoglobulin sequence that can bind to and/or has affinity for ion channels such as e.g. P2X7 and that is cross-blocked or is cross blocking a Nanobody of the invention, e.g. SEQ ID NO: 705 to 788, more preferably SEQ ID NO's 726 to 750, 753 to 758, 762 to 764, 772 to 773, 775, or 778 to 780, more preferred SEQ ID NO's 732, 773 or 778 (Table A-1) or a polypeptide or construct of the invention, e.g. SEQ ID NO: 789 to 791 (see Table A-3); and
c) isolating said nucleic acid sequence, followed by expressing said immunoglobulin sequence.

Use of Binding Agent of the Invention
Aspect R-1: Method for the prevention and/or treatment of at least one [insert diseases and disorders], said method comprising administering, to a subject in need thereof, a pharmaceutically active amount of at least one immunoglobulin sequence according to any of aspects A-1 to A-22, B-1 to B-7, C-1 to C-4, D-1 to D-6, E1 to E-13, F-1 to F-25 or G-1, Nanobody according to any of aspects H-1 to H-22, polypeptide according to any of aspects K-1 to K-19, compound or construct according to any of aspects L-1 to L-21, monovalent construct according to any of aspects L-22 or L-23; or composition according to aspect O-2 or 0-3.

Aspect R-2: Method for the prevention and/or treatment of at least one disease or disorder that is associated with ion channels such as e.g. P2X7, with its biological or pharmacological activity, and/or with the biological pathways or signalling in which ion channels such as e.g. P2X7 is involved, said method comprising administering, to a subject in need thereof, a pharmaceutically active amount of at least one immunoglobulin sequence according to any of aspects A-1 to A-22, B-1 to B-7. C-1 to C-4, D-1 to D-6, E-1 to E-13, F-1 to F-25 or G-1, Nanobody according to any of aspects H-1 to H-22, polypeptide according to any of aspects K-1 to K-19, compound or construct according to any of aspects L-1 to L-21, monovalent construct according to any of aspects L-22 or L-23; or composition according to aspect O-2 or 0-3.

Aspect R-3: Method for the prevention and/or treatment of at least one disease or disorder that can be prevented and/or treated by administering, to a subject in need thereof, at least one immunoglobulin sequence according to any of aspects A-1 to A-22, B-1 to B-7, C-1 to C-4, D-1 to D-6, E-1 to E-13, F-1 to F-25 or G-1, Nanobody according to any of aspects H-1 to H-22, polypeptide according to any of aspects K-1 to K-19, compound or construct according to any of aspects L-1 to L-21, monovalent construct according to any of aspects L-22 or L-23; or composition according to aspect O-2 or O-3, said method comprising administering, to a subject in need thereof, a pharmaceutically active amount of at least one at least one immunoglobulin sequence according to any of aspects A-1 to A-22, B-1 to B-7, C-1 to C-4, D-1 to D-6, E-1 to E-13, F-1 to F-25 or G-1, Nanobody according to any of aspects H-1 to H-22, polypeptide according to any of aspects K-1 to K-19, compound or construct according to any of aspects L-1 to L-21, monovalent construct according to any of aspects L-22 or L-23; or composition according to aspect O-2 or O-3.

Aspect R-4: Method for immunotherapy, said method comprising administering, to a subject in need thereof, a pharmaceutically active amount of at least one immunoglobulin sequence according to any of aspects A-1 to A-22, B-1 to B-7, C-1 to C-4, D-1 to D-6, E-1 to E-13, F-1 to F-25 or G-1, Nanobody according to any of aspects H-1 to H-22, polypeptide according to any of aspects K-1 to K-19, compound or construct according to any of aspects L-1 to L-21, monovalent construct according to any of aspects L-22 or L-23; or composition according to aspect O-2 or O-3.

Aspect R-5: Use of an immunoglobulin sequence according to any of aspects A-1 to A-22, B-1 to B-7, C-1 to C-4, D-1 to D-6, E-1 to E-13, F-1 to F-25 or G-1, a Nanobody according to any of aspects H-1 to H-22, a polypeptide according to any of aspects K-1 to K-19, a compound or construct according to any of aspects L-1 to L-21, or a monovalent construct according to any of aspects L-22 or L-23 in the preparation of a pharmaceutical composition for prevention and/or treatment of at least one [insert diseases and disorders]; and/or for use in one or more of the methods according to aspects R-1 to R-3.

Aspect R-6: Immunoglobulin sequence according to any of aspects A-1 to A-22, B-1 to B-7, C-1 to C-4, D-1 to D-6, E-1 to E-13, F-1 to F-25 or G-1, Nanobody according to any of aspects H-1 to H-22, polypeptide according to any of aspects K-1 to K-19, compound or construct according to any of aspects L-1 to L-21, monovalent construct according to any of aspects L-22 or L-23; or composition according to aspect O-2 or O-3 for the prevention and/or treatment of at least one disease or disorder in which an ion channel plays a role or is implicated.

Fragment Aspects

Aspect S-1: Part or fragment of an immunoglobulin sequence according to any of aspects A-1 to A-22, B-1 to B-7, C-1 to C-4, D-1 to D-6, E-1 to E-13, F-1 to F-25 or G-1, or of a Nanobody according to any of aspects H-1 to H-22.

Aspect S-2: Part or fragment according to aspect S-1, that can specifically bind to ion channels such as e.g. P2X7.

Aspect S-3: Part of fragment according to any of aspects S-1 or S-2, that can specifically bind to ion channels such as e.g. P2X7 with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter.

Aspect S-4: Part or fragment according to any of aspects S-1 to S-3, that can specifically bind to ion channels such as e.g. P2X7 with a rate of association ($k_{on}$-rate) of between $10^2$ $M^{-1}s^{-1}$ to about $10^7$ $M^{-1}s^{-1}$, preferably between $10^3$ $M^{-1}s^{-1}$ and $10^7$ $M^{-1}s^{-1}$, more preferably between $10^4$ $M^{-1}s^{-1}$ and $10^7$ $M^{-1}s^{-1}$, such as between $10^5$ $M^{-1}s^{-1}$ and $10^7$ $M^{-1}s^{-1}$.

Aspect S-5: Part or fragment according to any of aspects S-1 to S-4, that can specifically bind to ion channels such as e.g. P2X7 with a rate of dissociation ($k_{off}$-rate) between 1 $s^{-1}$ and $10^{-6}$ $s^{-1}$ preferably between $10^{-2}$ $s^{-1}$ and $10^{-6}$ $s^{-1}$, more preferably between $10^{-3}$ $s^{-1}$ and $10^{-6}$ $s^{-1}$, such as between $10^{-4}$ $s^{-1}$ and $10^{-6}$ $s^{-1}$.

Aspect S-6: Compound or construct, that comprises or essentially consists of one or more parts or fragments according to any of aspects S-1 to S-4, and optionally further comprises one or more other groups, residues, moieties or binding units, optionally linked via one or more linkers.

Aspect 3-7: Compound or construct according to aspect S-6, in which said one or more other groups, residues, moieties or binding units are immunoglobulin sequences.

Aspect S-8: Compound or construct according to aspect S-6 or S-7, in which said one or more linkers, if present, are one or more immunoglobulin sequences.

Aspect 3-9: Nucleic acid or nucleotide sequence, that encodes a part or fragment according to any of aspects S-1 to S-7 or a compound or construct according to aspect S-8.

Aspect 3-10: Composition, comprising at least one part or fragment according to any of aspects S-1 to 3-7, compound or construct according to any of aspects 3-6 to S-8, or nucleic acid or nucleotide sequence according to aspect S-9.

Derivatives Aspects

Aspect T-1: Derivative of an immunoglobulin sequence according to any of aspects A-1 to A-22, B-1 to B-7, C-1 to C-4, D-1 to 0-6, E-1 to E-13, F-1 to F-25 or G-1, or of a Nanobody according to any of aspects H-1 to H-22.

Aspect T-2: Derivative according to aspect T-1, that can specifically bind to ion channels such as e.g. P2X7.

Aspect T-3: Derivative according to any of aspects T-1 or T-2, that can specifically bind to ion channels such as e.g. P2X7 with a dissociation constant ($K_D$) of $10^{-5}$ to $10^{-12}$ moles/liter or less, and preferably $10^{-7}$ to $10^{-12}$ moles/liter or less and more preferably $10^{-6}$ to $10^{-12}$ moles/liter.

Aspect T-4: Derivative according to any of aspects T-1 to T-3, that can specifically bind to ion channels such as e.g. P2X7 with a rate of association ($k_{on}$-rate) of between $10^2$ $M^{-1}s^{-1}$ to about $10^7$ $M^{-1}s^{-1}$, preferably between $10^3$ $M^{-1}s^{-1}$ and $10^7$ $M^{-1}s^{-1}$, more preferably between $10^4$ $M^{-1}s^{-1}$ and $10^7$ $M^{-1}s^{-1}$, such as between $10^5$ $M^{-1}s^{-1}$ and $10^7$ $M^{-1}s^{-1}$.

Aspect T-5: Derivative according to any of aspects T-1 to T-4, that can specifically bind to ion channels such as e.g. P2X7 with a rate of dissociation ($k_{off}$-rate) between 1 $s^{-1}$ and $10^{-6}$ $s^{-1}$ preferably between $10^{-2}$ $s^{-1}$ and $10^{-6}$ s-more preferably between $10^{-3}$ $s^{-1}$ and $10^6$ $s^{-1}$, such as between and $10^4$ $s^{-1}$ and $10^{-6}$ $s^{-1}$.

Aspect T-6: Derivative of a polypeptide according to any of aspects K-1 to K-19 or compound or construct according to any of aspects L-1 to L-23.

Aspect T-7: Derivative according to aspect T-6, that can specifically bind to ion channels such as e.g. P2X7.

Aspect T-8: Derivative according to any of aspects T-6 or T-7, that can specifically bind to ion channels such as e.g. P2X7 with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter.

Aspect T-9: Derivative according to any of aspects T-6 to T-8, that can specifically bind to ion channels such as e.g. P2X7 with a rate of association ($k_{on}$-rate) of between $10^2$ $M^{-1}s^{-1}$ to about $10^7$ $M^{-1}s^{-1}$, preferably between $10^3$ $M^{-1}s^{-1}$ and $10^7$ $M^{-1}s^{-1}$, more preferably between $10^4$ $M^{-1}s^{-1}$ and $10^7$ $M^{-1}s^{-1}$, such as between $10^5$ $M^{-1}s^{-1}$ and $10^7$ $M^{-1}s^{-1}$.

Aspect T-10: Derivative according to any of aspects T-6 to T-9, that can specifically bind to ion channels such as e.g. P2X7 with a rate of dissociation ($k_{off}$-rate) between 1 $s^{-1}$ and $10^{-6}$ $s^{-1}$ preferably between $10^{-2}$ $s^{-1}$ and $10^{-6}$ $s^{-1}$, more preferably between $10^{-3}$ $s^{-1}$ and $10^{-6}$ $s^1$, such as between $10^{-4}$ $s^{-1}$ and $10^{-6}$ $s^{-1}$.

Aspect T-11: Derivative according to any of aspects T-1 to T-10, that has a serum half-life that is at least 1.5 times, preferably at least 2 times, such as at least 5 times, for example at least 10 times or more than 20 times, greater than the half-life of the corresponding immunoglobulin sequence according to any of aspects A-1 to A-22, B-1 to B-7, C-1 to C-4, D-1 to D-6, E-1 to E-13, F-1 to F-25 or G-1 per se, Nanobody according to any of aspects H-1 to H-22 per se, polypeptide according to any of aspects K-1 to K-19 or compound or construct according to any of aspects L-1 to L-23 per se.

Aspect T-12: Derivative according to any of aspects T-1 to T-11, that has a serum half-life that is increased with more than 1 hours, preferably more than 2 hours, more preferably more than 6 hours, such as more than 12 hours, or even more than 24, 48 or 72 hours, compared to the corresponding immunoglobulin sequence according to any of aspects A-1 to A-22, B-1 to B-7, C-1 to C-4, D-1 to D-6, E-1 to E-13, F-1 to F-25 or G-1 per se, Nanobody according to any of aspects H-1 to H-23 per se, polypeptide according to any of aspects K-1 to K-19 or compound or construct according to any of aspects L-1 to L-23 per se, respectively.

Aspect T-13: Derivative according to any of aspects T-1 to T-12, that has a serum half-life in human of at least about 12 hours, preferably at least 24 hours, more preferably at least 48 hours, even more preferably at least 72 hours or more; for example, at least 5 days (such as about 5 to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

Aspect T-14: Derivative according to any of aspects T-1 to T-13, that is a pegylated derivative.

Aspect T-15: Compound or construct, that comprises or essentially consists of one or more derivatives according to any of aspects T-1 to T-14, and optionally further comprises one or more other groups, residues, moieties or binding units, optionally linked via one or more linkers.

Aspect T-16: Compound or construct according to aspect T-15, in which said one or more other groups, residues, moieties or binding units are immunoglobulin sequences.

Aspect T-17: Compound or construct according to aspect T-16, in which said one or more linkers, if present, are one or more immunoglobulin sequences.

Aspect T-18: Nucleic acid encoding a compound or construct according to aspect T-16 or T-17.

Aspect T-19: Composition, comprising at least one derivative to any of aspects T-1 to T-14, compound or construct according to any of aspects T-15 to T-17, or nucleic acid or nucleotide sequence according to aspect T-18.

Particularly Preferred Aspects

1. Method for the generation of immunoglobulin sequences that can bind to and/or have affinity for a cell-associated antigen comprising the steps of:
   a) genetic vaccination of a non-human animal with a nucleic acid encoding said cell-associated antigen or a domain or specific part of said cell associated antigen; and
   b) optionally boosting the animal with said antigen in its natural conformation selected from cells comprising natural or transfected cells expressing the cell-associated antigen, cell derived membrane extracts, vesicles or any other membrane derivative harbouring enriched antigen, liposomes, or virus particles expressing the cell associated antigen
   c) screening a set, collection or library of immunoglobulin sequences derived from said non-human animal for immunoglobulin sequences that can bind to and/or have affinity for said cell-associated antigen.

2. The method according to aspect 1, wherein said cell-associated antigen is selected from transmembrane antigens, including transmembrane antigens with multiple spanning domains, including but not limited to GPCRs or ion channels.

3. The method according to aspect 1 or 2, wherein said non-human animal is selected from vertebrates such as sharks, lizard, and mammals, more specifically camelids such as llama and alpaca.

4. The method according to any one of aspects 1 to 3, wherein the non-human animal is a camelid or llama.

5. The method according to any one of aspects 1 to 4, wherein said immunoglobulin sequences are light chain variable domain sequences, or heavy chain variable domain sequences.

6. The method according to aspect 5, wherein the immunoglobulin sequences are heavy chain variable domain sequences that are derived from a conventional four-chain antibody or heavy chain variable domain sequences that are derived from a heavy chain antibody.

7. The method according to any one of aspects 1 to 6, wherein the immunoglobulin sequences are domain antibodies, or immunoglobulin sequences that are suitable for use as domain antibodies, single domain antibodies, or immunoglobulin sequences that are suitable for use as single domain antibodies, "dAbs", or immunoglobulin sequences that are suitable for use as dAbs, or Nanobodies, including but not limited to $V_{HH}$ sequences or immunoglobulin sequences that are suitable for use as Nanobodies.

8. The method according to aspect 7, wherein the immunoglobulin sequences are Nanobodies.

9. The method according to any one of aspects 1 to 8, wherein vaccination is performed by a needle-free jet injection, by a ballistic method, by needle-mediated injections such as Tattoo, by topical application or by any DNA administration method followed by in vivo electroporation.

10. The method according to any one of aspects 1 to 9, wherein vaccination is performed by intradermal, intramuscular or subcutaneous administration of DNA.

11. The method according to any one of aspects 1 to 10, wherein the set, collection or library of immunoglobulin sequences is obtained from the blood, lymph node, spleen, bone marrow or any tissue harbouring cells encoding these immunoglobulin sequences of said non-human mammal.

12. The method according to any one of aspects 1 to 11, wherein said cell-associated antigen is expressed on any cell which allows expressing of the target in its native conformation such as but not limiting to a cell selected from Cho, Cos7, Hek293, or camelid derived cells such as Llama derived or Alpaca derived cell.

13. The method according to any one of aspects 1 to 12, wherein said cell-associated antigen is a membrane-spanning antigen such as e.g. a GPCR and/or ion channel.

14. The method according to any one of aspects 1 to 13, wherein said antigen is selected from CXCR7, CXCR4 and/or P2X7.

15. The method according to any of aspects 1 to 14, wherein the set, collection or library of immunoglobulin sequences is expressed on a set, collection or sample of cells or viruses and said set, collection or sample of cells is screened for cells that express an immunoglobulin sequence that can bind to and/or have affinity for said cell-associated antigen.

16. The method according to aspect 15, wherein a nucleic acid sequence that encodes the immunoglobulin sequence that can bind to and/or has affinity for said cell-associated antigen is purified and/or isolated from the cell or virus, followed by expression of said immunoglobulin sequence.

17. The method according to any of aspects 1 to 16, wherein the set, collection or library of immunoglobulin sequences is encoded by a set, collection or library of nucleic acid sequences and said set, collection or library of nucleic acid sequences is screened for nucleic acid sequences that encode an immunoglobulin sequence that can bind to and/or has affinity for said cell-associated antigen.

18. The method according to aspect 17, wherein the nucleic acid sequences that encode an immunoglobulin sequence that can bind to and/or has affinity for said cell-associated antigen are purified and/or isolated, followed by expressing said immunoglobulin sequence.
19. The method according to any one of aspects 1 to 18, wherein the immunoglobulin sequence that can bind to and/or has affinity for said cell-associated antigen is purified and/or is isolated.
20. Immunoglobulin obtainable by a method of any one of aspects 1 to 19.
21. Immunoglobulin directed against an ion channel obtainable by a method of any one of aspects 1 to 19.
22. Immunoglobulin according to aspect 21, wherein the immunoglobulin is an antagonist (partial or full) of an ion channel.
23. Immunoglobulin according to aspect 21, wherein the immunoglobulin is an agonist (partial or full) of an ion channel.
24. Immunoglobulin directed against P2X7 by a method of any one of aspects 1 to 19.
25. Composition comprising the immunoglobulin sequence according to any of aspect 20 to 24.

EXAMPLES

Example 1. Genetic Immunization of Llamas and Identification of Immunoglobulin Sequences Using the Hepatitis B Small Surface Antigen as a Model Antigen Target specific camelid immunoglobulin sequences were identified following DNA vaccination. Hepatitis B small surface antigen was chosen as a model antigen, as this protein has been widely used to induce humoral immune responses in animals following genetic immunization.

Example 1.1. Generation and Preparation of Plasmid for Genetic Immunization

Eukaryotic expression vector pRc/CMV-Hbs(s) encoding the Hepatitis B small surface antigen (HBSAg) is obtained from Aldevron. Expression is under control of the constitutive Cytomegalovirus (CMV) promoter. The sequence of the resulting construct as been verified by sequence analysis.
Plasmid DNA is produced using Endotoxin-free Gigaprep kit (Qiagen) according to the manufacturer's instructions. The vector DNA is finally reconstituted at a concentration of 1 mg/mL in endotoxin-free LAL H$_2$O or in endotoxin-free 0.9% NaCl in LAL H$_2$O. Plasmid is stored in aliquots at −20° C. Prior to use the plasmid DNA solution is centrifuged to remove possible aggregates.

Figure 1B:
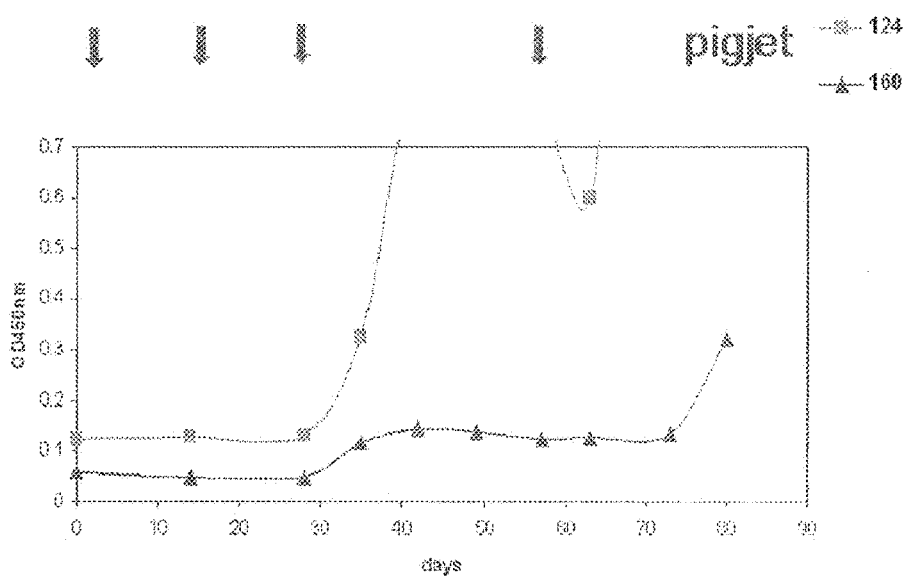
Figure 1C:
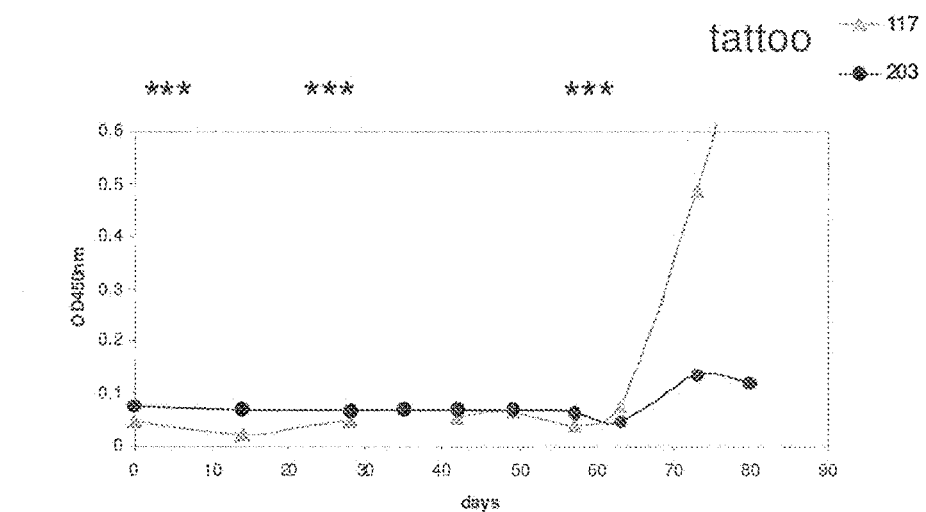

Example 1.2. Induction of a Humoral Immune Response in Camelids Via Genetic Immunization Following Distinct Methods of DNA Administration After approval of the Ethical Committee of the Faculty of Veterinary Medicine (University Ghent, Belgium), four llamas (124, 160, 117 and 203) were immunized using two genetic immunization methods to induce an antigen specific humoral response. For both methods, DNA was applied intradermally (ID). The first DNA administration method consisted of needle-free jet injection, the second followed a tattoo method (Bins et al. 2005. Nature Medicine 11:899-904).
Prior to the application of the DNA, an area of the llama skin of approximately 200-240 cm$^2$ is shaved above the shoulder-blade, the skin is treated with commercial depilation cream (Veet) for 2 minutes to chemically remove all remaining hair and part of the stratum corneum, and the shaved area is thoroughly cleaned by rinsing with water. For the first method, DNA is administrated into the skin using the Pig-jet device (Endoscopic)(llamas 124 and 160). A multi-nozzle head allows to distribute the DNA solution simultaneously over five adjacent spots of 0.04 ml each, leaving injection blebs or papulae in the skin for a couple of hours. Each dose (1 mg DNA) the llama received (days 0, 14, 28 and 57) thus resulted in 25 injection blebs. For the short-interval tattoo method, a short-interval regimen was used. Llamas 117 and 203 are anaesthetized, and the area of DNA application is divided into three parts for tattooing at days 0, 3, 7 (interval 1), 21, 24, 28 (interval 2), 56, 59 and 63 (interval 3). One mg/ml droplets of DNA are applied and tattooed into the skin using a commercial tattoo device (magnum 9 formation needle) at 0.5 mm depth during at least 10 minutes per session over a surface of approximately 80 cm$^2$. The dose of administered DNA is 1.33 mg (interval 1 and 2) and 4 mg (interval 3). From all llamas, small blood samples are collected at regular intervals during the immunization to monitor serum conversion via ELISA.
To verify whether the llamas induced a HBsAg specific humoral immune response after DNA vaccination, an ELISA was executed with a 400-fold dilution of pre-immune and immune sera. In brief, 1 µg/ml recombinant HBsAg (Aldevron) is immobilized overnight at 4° C. in a 96-well Maxisorp plate (Nunc). Wells are blocked with a casein solution (1% in PBS). After addition of the serum dilution, specifically bound immunoglobulins were detected using a goat anti-llama-IgG horseradish peroxidase conjugate (Bethyl Lab. Inc., Montgomery, Tex.). Results depicted in FIGS. 1A-1C demonstrate that for the jet injection method for both llamas (124 and 160) a clear target specific serum conversion is detected (day 0 vs day 80) although with variable magnitudes (FIGS. 1A and 1B). After the third cycle of tattooing, a similar trend is demonstrated for llama 117 and 203, although the magnitude of the response is lower compared to jet injection (FIGS. 1A and 1C).

Figure 2:
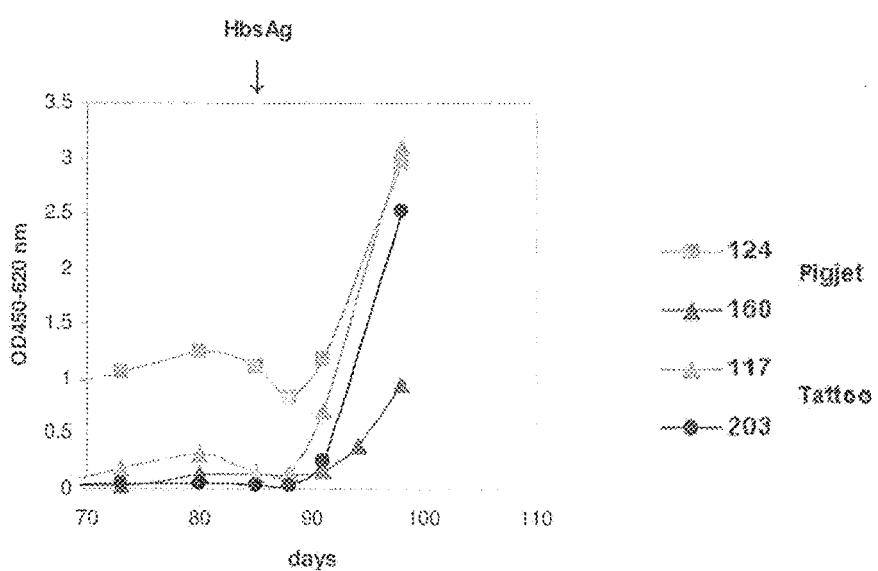
FIG. 2: Strong secondary serum response observed in DNA vaccinated llamas after single HBsAg protein boost.
Figure 3:
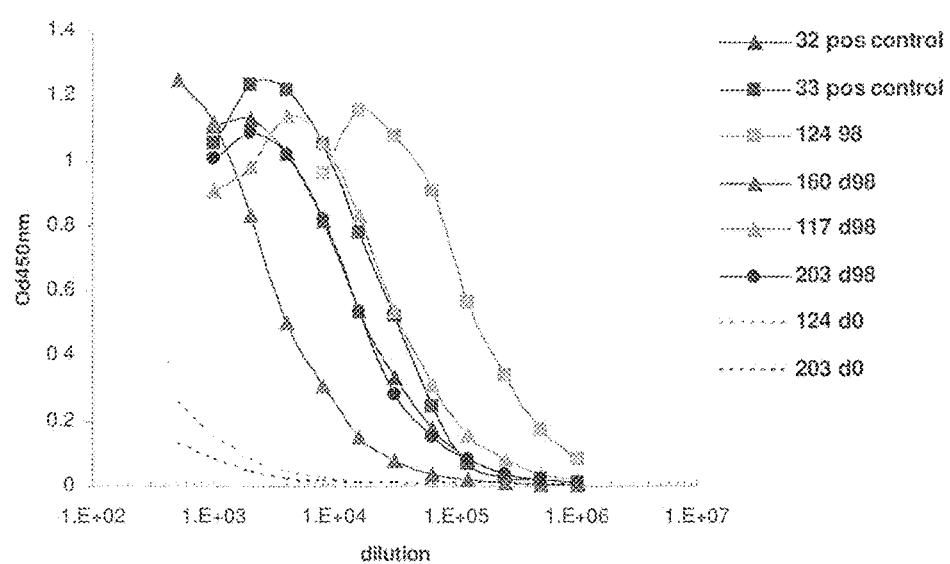
FIG. 3. Humoral immune responses obtained via "DNA" prime—"protein" boost protocol (llamas 124, 160, 117, 203) versus protein immunizations (llamas 32 and 33).
Figure 4:
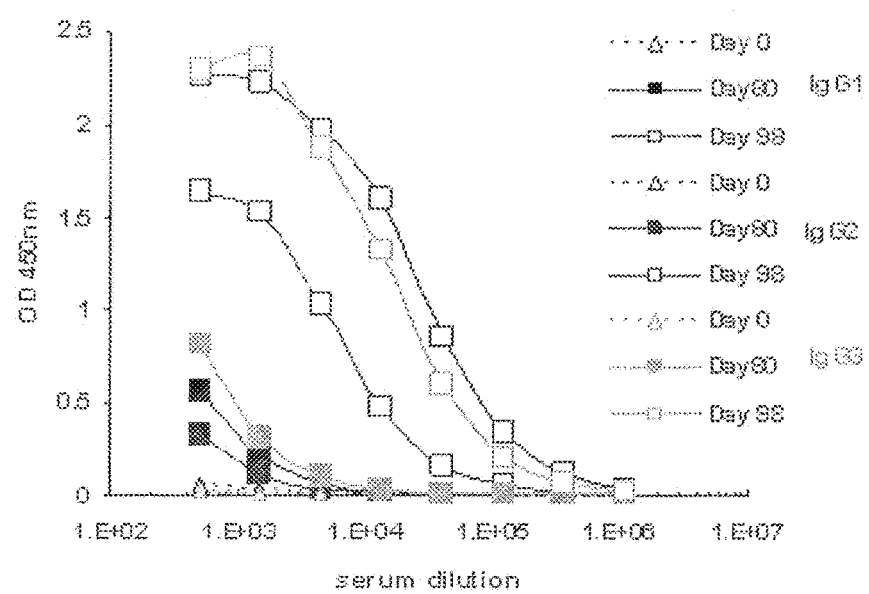
FIG. 4. Heavy chain antibody (IgG2 and 3)-mediated antibody response against HBsAg (llama 124).

Example 1.3. Boosting the DNA Primed Camelids with HBsAg Protein Increased Antigen Specific Serum Conversion, Including Heavy Chain Antibody Mediated Responses At day 85, a single boost with 50 µg purified HBsAg using Stimune (CEDI Diagnostics, Lelystad, The Netherlands) as adjuvant was administered intramuscularly (IM) into the neck of all four llamas, and small serum samples were collected. Evaluation of the immune response for all four animals was performed via ELISA as described in the previous example and showed that a single HBsAg boost induced a strong secondary response for all four animals (FIG. 2). Following this "DNA" prime-"protein" boost approach, similar antigen specific serum titers were generated as compared to an immunization method where only HBsAg protein has been injected (llamas 32 and 33; six weekly IM neck injections; dose of 100-50 µg protein/injection using Stimune as adjuvant). Results are shown in FIG. 3. The antibody response was mounted both by the conventional and the heavy chain antibody expressing B-cell repertoires, since bound llama immunoglobulins were detected with monoclonal antibodies specifically recognizing the llama IgG1 conventional antibodies or the heavy-chain only llama IgG2 and IgG3 antibodies (FIG. 4)(Daley et al., Clin Diagn Lab Immunol. 2005 March; 12(3):380-6).

Example 1.4. Priming the Immune Response in Camelids Against HBsAg with DNA is Sufficient to Identify In Vivo Matured Antigen Specific Nanobodies B-cell containing 150 mL blood samples were collected from llama 124 and 117 (the llamas showing highest serum conversion following Pig-jet and Tattoo DNA application, respectively) between the last DNA administration and the HBsAg protein boost. Subsequently, peripheral blood lymphocytes (PBLs) were purified by a density gradient centrifugation on Ficoll-Paque (Amersham Biosciences, Uppsala, Sweden) according to the manufacturer's instructions.

Total RNA was extracted and cDNA was prepared to amplify the Nanobody repertoire via nested PCR as previously described (e.g. WO 02/085945 and WO 04/049794). The PCR products were digested with SfiI (introduced via nested PCR in the FR1 primer region) and BstEII (restriction site naturally occurring in FR4) and following gel electrophoresis, the DNA fragment of approximately 350 bps was purified from gel. 330 ng of amplified Nanobody repertoire was ligated into the corresponding restriction sites of one μg of SfiI-BstEII digested phage display vector (pAX50) to obtain a library after electroporation of Escherichia coli TG1. pAX50 contains the LacZ promoter, a coliphage pIII protein coding sequence, a resistance gene for ampicillin or carbenicillin, a multicloning site (harboring the SfiI and BstEII restriction sites) and a chimeric leader sequence consisting of gene3 and Erwinia carotovora pelB motifs. This display vector allows the production of phage particles, expressing the individual Nanobodies as a fusion protein with a c-Myc, a His6-tag and with the geneIII product. The size of the libraries derived from llama 124 and 117 immune tissues was $1\times10^8$ and $3\times10^7$ CFUs respectively. As a library quality control, the percentage of insert of correct size was determined as 91 and 100%, respectively, by a colony PCR using the M13 reverse and a geneIII primer on 24 randomly picked colonies of each library.

Libraries were rescued by growing the bacteria to logarithmic phase ($OD_{500}$=0.5), followed by infection with helper phage to obtain recombinant phage expressing the repertoire of cloned Nanobodies on tip of the phage as a pIII fusion protein. Phage was stored after filter sterilization at 4° C. for further use.

HBsAg specific Nanobodies were selected after a single round of panning as follows. Recombinant HBsAg (Aldevron) was directly immobilized on Maxisorp 96-well plates (Nunc, Wiesbaden, Germany) at 500 and 50 ng per well. After 2-hour incubation with the phage libraries and extensive washing, bound phage was eluted with trypsin (1 mg/ml) during 15 minutes at room temperature. Protease activity was inhibited by adding 5 μl of 16 mM ABSF protease inhibitor to the 100 μl of phage eluate. In all selection conditions, a higher number of eluted phage from a HBsAg immobilized well was observed when comparing to the number of eluted phage eluted from a non-HBsAg coated well, indicating an enrichment for HBsAg specific Nanobodies. The output from each selection was re-infected in logarithmically grown E. coli TG1 for 30 minutes at 37° C. and appropriate dilutions were grown overnight on solid medium (LB containing 2% glucose and ampicillin) to obtain single colonies. Individual colonies were picked from HBsAg enriched selection outputs and grown in 96 deep-well plates (1 ml volume) and induced by adding IPTG for Nanobody expression. Periplasmic extracts (PEs) were prepared in a volume of 80 μl according to standard methods.

In total 10-fold dilutions of 188 PEs (94 for llama 124 and 94 for llama 117 derived PE) were screened for specific binding to solid-phase coated HBsAg via ELISA, using mouse anti-Myc monoclonal antibody and subsequent step anti-mouse-HRP conjugated detection antibodies. Periplasmic extracts showing minimal 2 fold signal above background (non-coated well) were scored as positive and corresponding Nanobody clones were sequenced. For libraries 124 and 117, 68% and 4% of the clones scored positive, respectively. Following sequence analysis, 5 HBsAg specific Nanobody families were identified (3 from llama 124 and 2 from llama 117; SEQ IDs Table 1.1) with representative family examples HBSAGPMP2E7 (family 1), HBSAGPMP2E12 (family 2) and HBSAGPMP2A4 (family 3) from llama 124 and HBSAGPMP1C6 (family 4) and HBSAGPMP1E11 (family 5) from llama 117.

Example 1.5. Nanobodies Isolated from DNA Vaccinated Llamas Show Similar Off-Rates to Those Identified from Protein Immunized Llamas Plasma-derived HBsAg particles (Biodesign) were immobilized on surface plasmon resonance CM5 sensor chips (BIAcore) at a density of 11000 RUs. Regeneration of the chip surface was performed with a five second flow of 0.1 M HCl at a flow rate of 45 μl/minute. Periplasmic Nanobody extracts were injected to evaluate the off-rates (Biacore). Data were double referenced by subtraction of the curves on the reference channel and of a blank running buffer injection. Processed curves were evaluated by fitting a 1:1 dissociation model onto the binding curves in the Biacore T100 Evaluation software v1.1.1 and Biaevaluation software v4.1. Off-rates of HBSAGPMP2E7, HBSAGPMP2E12 were calculated as 8.8E-4 s−1 and 1.3E-3 s$^{-1}$, respectively. These off-rates were similar to those obtained for the HBsAg specific Nanobodies identified after selection on libraries obtained from llama 32 and 33 (off-rates between 6.0E-2 and 1.7E-3 s$^{-1}$) (Serruys et al. 2009 Hepatology 49(1):39-49), indicating that the affinities of the Nanobodies obtained via genetic immunization do not differ from Nanobodies identified via protein immunization.

TABLE 1.1

Sequences:

| Name | SEQ ID NO: | Immunoglobulin sequence |
|---|---|---|
| PHbsAgPMP2E7 | 700 | EVQLVESGGGLLQAGGSLRLSCAASERAFIIYG KAWFRQAPGKEREFVAGINWNGGDLHYADSVK GRFTISRDNTNNVVYLQMNSLKSEDTAVYYCAV RRGTAYETDVSSYEWGTQVTVSS |
| PHbsAgPMP2E12 | 701 | EVQLVESGGGLVQAGGSLRLSCAASGRSISEYA MGWFRQAPGQEREFVASISTSGGSTTYADSVK GRFIISRDNAKNTVYLQMNSLKPEDTAVYYCAR YNGWMYYAGTMGVHFGQGTQVTVSS |
| PHbsAgPMP2A4 | 702 | EVQLVESGGGLVQPGGSLRLSCAASGSIDSINR MGWYRQAPGKQRELVASSTSGGSTDYADSVK GRFTISRDNAKNTVYLQMNSLKPEDTAVYYCNF RGSYYSGYGDYWGKGTLVTVSS |

TABLE 1.1-continued

Sequences:

| Name | SEQ ID NO: | Immunoglobulin sequence |
|---|---|---|
| PHbsAgPMP1C6 | 703 | KVQLVESGGGWVRTGGSMRLSCAASGRTSSG SAMGWFRQAPGKERVFVAAISWGGAYTDYADS VKGRFTISRDNWRNTVDLQMNNLKPEDTAVYY CADGGSTWYEPTESDFGSWGQGTQVTVSS |
| PHbsAgPMP1E11 | 704 | EVQLVESGGGLVQPGGSLRLSCAASGSRDRLN VMGWYRQAPGKERDLVATMTAGGSTNYADSV KGRFTISRDIANMVYLQMNSLKPEDTAVYYCNGI TASWYSGSYNYNNYWGQGTQVTVSS |

Example 2. Identification of Nanobodies Against G-Protein Coupled Receptors Via Genetic Immunization In order to demonstrate the feasibility of genetic immunization for membrane bound targets carrying multiple transmembrane domains, the human chemokine receptor CXCR4 was chosen as first example.

Example 2.1. Generation of a CXCR4-Encoding Vector Suitable for Genetic Immunization Human chemokine receptor CXCR4 encoding cDNA (NM_003467) was purchased from Open Biosystems. After PCR-mediated introduction of restriction sites NheI (5' end) and XhoI (3' end), the amplicon was cloned into the corresponding sites of pVAX-1 (Invitrogen) and pCDNA3.1 (Invitrogen). The sequence integrity of the resulting pVAX1-CXCR4 and pCDNA3.1-CXCR4 was verified by sequence analysis. The vector pVAX1 was designed to be used for genetic immunization, and harbors the human cytomegalovirus (CMV) promoter. pVAX1 allows high-copy number replication in E. coli, transient high-level expression of the protein of interest in most mammalian cells both in vitro and in vivo. Milligram amounts of endotoxin-free pVAX1-CXCR4 plasmid was produced, dissolved to a concentration of 2 mg/mL in 0.9% saline in LAL H2O and stored at −20° C.

Example 2.2. pVAX1-CXCR4 Transfected Cells Express Functional CXCR4 Receptor

Figure 5A:
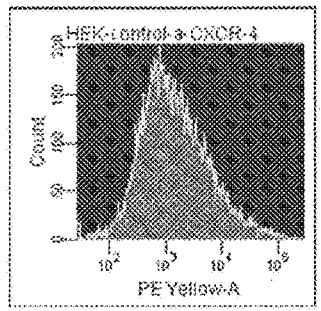
FIGS. 5A and 5B. CXCR4 specific staining of HEK293 cells following pVAX-hCXCR4 transfection and camelid after pcDNA3.1-hCXCR4 transfection.
Figure 5A:
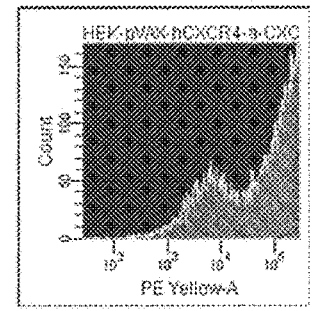

To verify the functional expression of human CXCR4, the endotoxin-free pVAX1-CXCR4 plasmid was transiently transfected into HEK293 cells using Eugene (Roche) to monitor in vitro extracellular expression via flow cytometry. Human CXCR4 specific monoclonal antibody 12G5 (R&D Systems MAB170) followed by PE-labeled goat anti-mouse IgG detecting antibody (Jackson ImmunoResearch Inc. Cat. Nr. 115-115-164) were used as the detection antibodies. Following this method, a 38-fold fluorescence intensity shift of the transfected pVAX1-hCXCR4/HEK293 over non-transfected HEK293 cells was shown (FIG. 5A). The presence of functional CXCR4 at the cell surface was confirmed by binding of its biotinylated ligand CXCL12/SDF-1α (R&D Systems, Human CXCL12/SDF-1 alpha Biotinylated Fluorokine Kit NNS00) to CXCR4-transfected HEK293 but not parental HEK293 cells, following the manufacturers procedure (not shown).

Example 2.3. Generation of Stably Transfected CXCR4 Camelid Cells

Figure 5B:
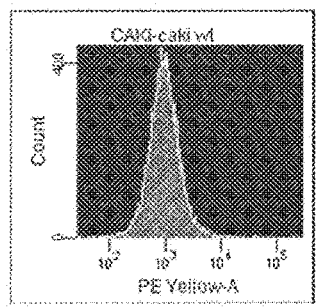
Figure 5B:
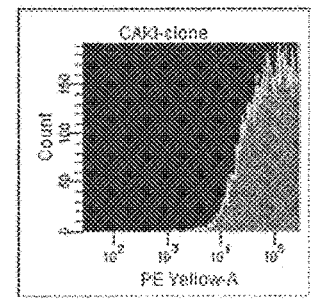

For the generation of stable CXCR4 cell lines, pCDNA3.1-hCXCR4 plasmid was transfected into immortalized camel kidney (CAKI) cells (Nguyen et al. 2001. Adv. Immunol. 79: 261-296). Individual transfected cells showing high expression density indicated by fluorescent staining with the 12G5 antibody (as described in example 2.2) were cloned by deposition of single cells in microtiter plate wells (FACSAria I with ACDU, Becton Dickinson). After outgrowth of clonal cell lines in medium containing selection antibiotics and confirmation of CXCR4 expression via flow cytometry (as in example 2.2), multiple homogenous stable CXCR4 CAKI transfectants were obtained. One clone showing a fluorescence shift of 114-fold over the non-transfected camelid cells, indicating high levels of CXCR4 membrane expression, was selected for further experiments (FIG. 5B).

Figure 6A:
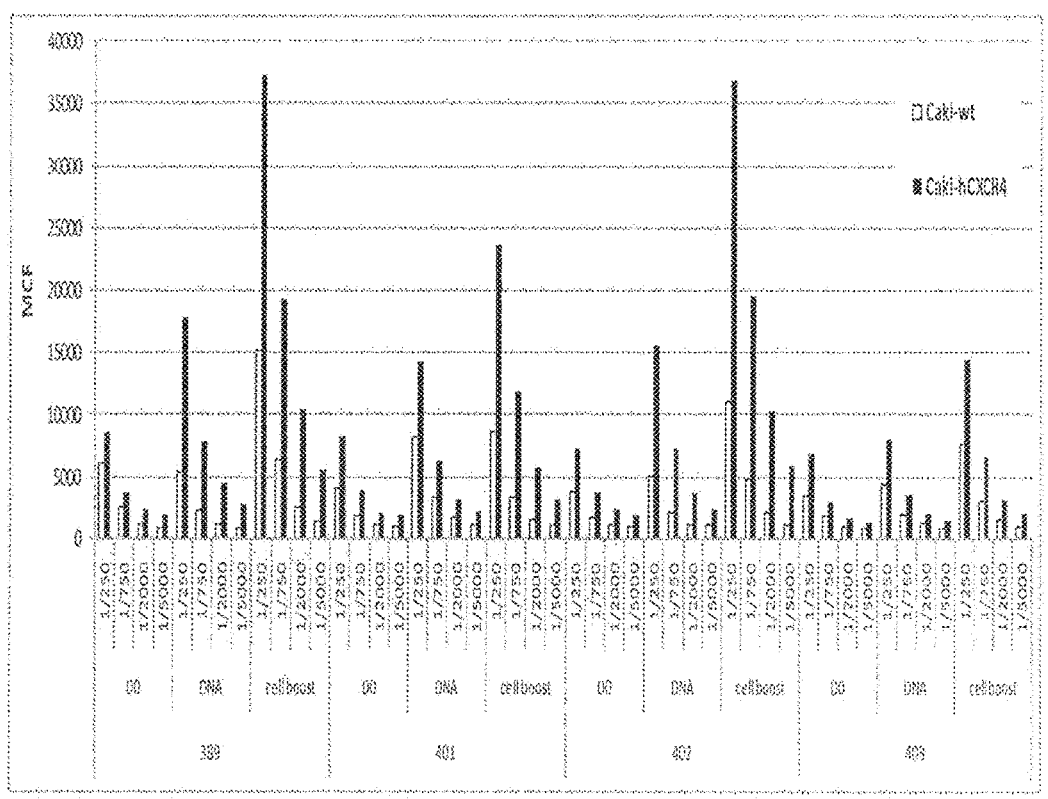
FIGS. 6A and 6B. CXCR4 specific serum conversion in llamas via genetic immunization.
Figure 6B:
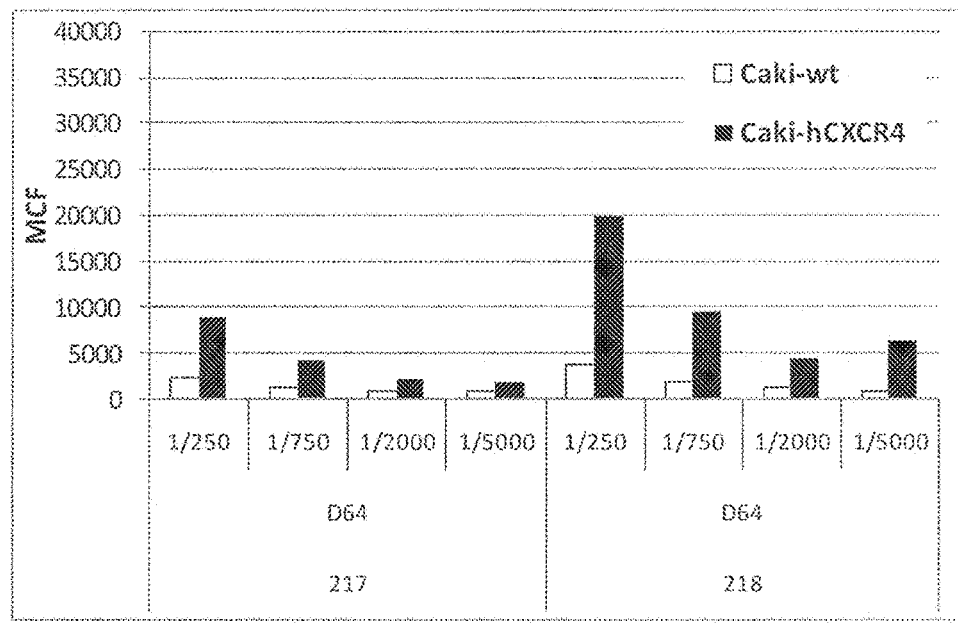

Example 2.4. Intradermal Delivery of pVAX1-CXCR4 is Sufficient to Induce a Detectable Target Specific Humoral Immune Response in Llama After approval by the ethical committee of the Faculty of Veterinary Medicine, University Ghent, Belgium, four llamas (llama 389, 401, 402 and 403) were assigned for genetic immunization. Immediately prior to the administration of the CXCR4 encoding DNA, a skin area of 250 cm$^2$ covering the llama shoulder-blade was shaved and all remaining hair tissue was removed by application of commercial depilation cream as described in Example 1.2. DNA dissolved into 0.9% saline was administered into the bald skin by needle-free jet injection using the automatic dermojet named Vaccijet (Akra DermoJet France) using a 3 nozzle head. For all four DNA administrations (day 0, 14, 28 and 42), two mg DNA per llama was applied, distributed over multiple adjacent spots. Successful intradermal (ID) application of the DNA containing liquid is indicated by the formation of superficial liquid containing blebs or papulae on the skin for a couple of hours. Of each llama, a pre-immune 10-ml serum sample and distinct serum samples during the genetic vaccination procedure were collected to monitor the antigen specific humoral response. Binding of llama immunoglobulins present in the 250- to 5000-fold diluted pre-immune samples (day 0) and immune serum sample (day 53; collected 11 days after the fourth DNA application) were scored for differential staining of CXCR4 transfected camelid versus non-transfected camelid cells via flow cytometry. Detection of cell bound llama total IgG (conventional+heavy-chain antibody) was detected via goat anti-llama IgG (Cat nr A160-100; Bethyl) followed by secondary staining with PE-conjugated donkey anti-goat IgG (Jackson ImmunoResearch Laboratories Cat nr. 115-115-164). Except for llama 403, a clear increase in mean cell fluorescence (MCF) was observed for all day 53 immune sera on CXCR4-transfected CAKI cells as compared to the pre-immune level (for minimally three dilutions tested), while MCF values of non-transfected CAKI cells stained similarly remained low (FIGS. 6A and 6B). This indicated that following ID genetic immunizations, 3 out of 4 llamas showed a specific humoral response against the native target conformation.

Example 2.5. Genetic Immunization Followed by a Single Cell Boost Significantly Increases CXCR4 Specific Serum Conversion Camelid cells were chosen as the immunogen cell background to direct the immune response towards CXCR4, anticipating reduced immunogenicity of camelid cell surface markers in llama due to high overall sequence similarity, as compared to human or rodent host cell backgrounds. Cultured CXCR4 expressing camelid cells (example 2.3) were freshly harvested and washed twice with D-PBS to remove all culture medium contaminants. Cells were resuspended in 2 mL D-PBS and stored on ice during transfer to the animal facilities. Llamas 389, 401, 402 and 403 were subcutaneously (SC) injected with 2E7 hCXCR4 transfected camelid cells, minimally three weeks after the final DNA administration. Eleven days after the cell boost, an immune blood sample was collected from each llama and CXCR4 serum titer was determined as described in example 2.4. For all four llamas (at 250 to 2250 fold serum dilutions), increased MCF values were detected on CXCR4 transfected camelid cells compared to serum sample obtained after DNA administration alone (day 53), while the serum binding to untransfected camelid cells was only slightly increased in three animals. These results indicate that the single cell boost resulted in an increased CXCR4 response magnitude for all four llamas (FIGS. 6A and 6B and Table 2.1). In parallel to the four genetic immunized llamas, the serum titer was determined on day 62 samples collected from llamas 217 and 218 (FIGS. 6A and 6B and Table 2.1). These llamas were immunized with six CXCR4-HEK293 cell injections (1-4E7 cells per dose) at weekly intervals (described in patent WO/2009/138519A1). Only one of the two llamas (218) showed a strong serum response to CXCR4-expressing cells compared to the untransfected control cells (n=2; one representative example shown). The detected MCF values indicated that the executed genetic immunization procedure (DNA+cell boost) generates a similar or better target specific titer magnitude compared to a full cell immunization

TABLE 2.1

Discovery overview of CXCR4 specific Nanobody B-cell lineages.

| Llama ID | Immunogen | CXCR4 response (FACS) | Library | Selection conditions | Specificity screening Hit-rate (ELISA) | Number of CXCR4 specific Nanobody families (some of which are displacing ligand) |
|---|---|---|---|---|---|---|
| 389 | DNA | + | DNA | R1: 10U | 18% (8/45) | 5 |
|  |  |  |  | R2: 10U | 9% (4/45) |  |
|  |  |  |  | R2: 1U | 13% (6/45) |  |
|  | hCXCR4/camelid cells | ++ | PB | R1: 10U | 4% (2/45) | 3 |
|  |  |  |  | R2: 10U | 76% (34/45) |  |
|  |  |  |  | R2: 1U | 78% (35/45) |  |
| 401 | DNA | + | DNA | R1: 10U | 0% (0/45) | 3 |
|  |  |  |  | R2: 10U | 2% (1/45) |  |
|  |  |  |  | R2: 1U | 4% (2/45) |  |
|  | hCXCR4/camelid cells | ++ | PB | R1: 10U | 22% (10/45) | 3 |
|  |  |  |  | R2: 10U | 89% (40/45) |  |
|  |  |  |  | R2: 1U | 76% (34/45) |  |
| 402 | DNA | + | DNA | R1: 10U | 0% (0/45) | 4 |
|  |  |  |  | R2: 10U | 16% (7/45) |  |
|  |  |  |  | R2: 1U | 7% (3/45) |  |
|  | hCXCR4/camelid cells | ++ | PB | R1: 10U | 36% (16/45) | 22 |
|  |  |  |  | R2: 10U | 67% (30/45) |  |
|  |  |  |  | R2: 1U | 67% (30/45) |  |
| 403 | DNA | − | DNA | R1: 10U | 4% (2/45) | 6 |
|  |  |  |  | R2: 10U | 31% (14/45) |  |
|  |  |  |  | R2: 1U | 27% (12/45) |  |
|  | hCXCR4/camelid cells | + | PB | R1: 10U | 7% (3/45) | 4 |
|  |  |  |  | R2: 10U | 51% (23/45) |  |
|  |  |  |  | R2: 1U | 44% (20/45) |  |
| 217 | hCXCR4/Hek293 cells | + | Cells | R1: 10U | 4% (2/45) | 10 |
|  |  |  |  | R2: 10U | 89% (40/45) |  |
|  |  |  |  | R2: 1U | 78% (35/45) |  |
| 218 | hCXCR4/Hek293 cells | + | Cells | R1: 10U | 7% (3/45) | 15 |
|  |  |  |  | R2: 10U | 93% (42/45) |  |
|  |  |  |  | R2: 1U | 96% (43/45) |  |

Example 2.6. Genetic Immunization is Sufficient to Identify CXCR4 Specific Nanobodies From llamas 389, 401, 402, 403, four 150 ml blood samples were collected 3 and 9 days following the last DNA administration (encoded PBL1 and PBL2, respectively) and 4 and 8 days after the cell boost (PBL3 and PBL4, respectively). Additionally, a biopsy of the palpable bow lymph node (LN) was collected from each llama via local surgery three to four days after the cell boost. Peripheral blood lymphocytes were purified from PBL1-4 samples by density gradient centrifugation on Ficoll-Paque as described in Example 1.4. From all lymphocyte harboring immune tissues total RNA was extracted and used as template to prepare cDNA (as described in example 1.4). For each genetic immunized llama, 2 separate libraries were generated (Table 2.2): one library derived from pooled PBL1+2 cDNA ('DNA' library) and a second one derived from pooled PBL3+4 and LN (post boost or 'PB' library).

TABLE 2.2

Genetic distance of five in vivo matured CXCR4 Nanobody families versus parental V-germline sequences.

| Nanobody Family | Nanobody family originated from Llama | Library (number of Nanobody variants) | Average target interaction potency (MCF ratio; FACS) | Average target interaction potency (absorption ratio; ELISA) | Average number of nt mutations versus parental V-germline[1] | Average number of AA mutations versus parental V-germline[1] |
|---|---|---|---|---|---|---|
| A | 389 | DNA (1) | 46 | 14 | 19 | 10 |
|   |     | PB (16) | 553 | 33 | 26 | 12 |
| B | 389 | DNA (1) | 105 | 7 | 17 | 12 |
|   |     | PB (3) | 261 | 11 | 19 | 13 |
| C | 389 | DNA (2) | 505 | 43.5 | 5.5 | 5 |
|   |     | PB (6) | 556 | 87.3 | 13 | 9 |
| D | 402 | DNA (1) | 755 | 56 | 21 | 15 |
|   |     | PB (7) | 671 | 73 | 22 | 14.6 |
| E | 403 | DNA (2) | 381 | 20.5 | 17 | 10.5 |
|   |     | PB (2) | 412 | 10.5 | 18 | 11.5 |

[1]Any change, including a deletion or an addition are considered to calculate the number of mutations.

Though the polyclonal serum responses detected via flow cytometry indicate the presence of target specific llama antibodies against native CXCR4, the magnitude of the titer is not necessarily predictive for i) the anti-CXCR4 heavy-chain antibody mediated clonal diversity, ii) the affinity of monoclonal Nanobodies for the target and iii) of the response width, e.g. the CXCR4 epitopes covered by the individual Nanobodies. CXCR4-specific Nanobodies were identified via phage display in order to characterize these on a monoclonal level. Parallel selections were performed on each of the eight DNA and PB libraries, and on two additional libraries generated from cell immunized llamas. Libraries were generated similarly in a similar manner from pooled cDNA derived from PBL1+2, collected 4 and 8 days after the final cell injection.

To select CXCR4 specific Nanobodies, recombinant phage was rescued from all ten libraries as described under example 1.4. In a first selection round, 10 units of 96-well Maxisorp plate (Nunc) immobilized membrane vesicles derived from CXCR4 transfected HEK293 cells were blocked with low-fat milk powder (Marvell 4% in PBS). After 2 hours of incubation with rescued phage, trypsin elution (1 mg/ml) was allowed for 15 minutes at room temperature subsequent to 15 PBS washes. Protease activity was immediately neutralized by applying 0.8 mM protease inhibitor ABSF. All phage outputs were infected into logarithmically grown E. coli TG1 cells and were plated on agar plates (LB+Amp+2% glucose) for analysis of individual Nanobody clones. The round 1 phage outputs were rescued and a second selection round on 10 or 1 units of plate-immobilized CXCR4 membrane vesicles was performed. Enrichment was calculated as the ratio between the number of phage eluted from CXCR4 membrane vesicles versus those eluted from non-transfected HEK293 control membrane vesicles. For 8 out of 10 libraries, round two outputs showed enrichments >5 (data not shown). The round 2 phage outputs selected on 10 or 1 units plate immobilized hCXCR4 membrane vesicles were infected into TG1 cells and were plated on agar plates (LB+Amp+2% glucose). Forty five individual clones of each output selected on CXCR4 Membrane vesicles (round 1 and round 2) were grown in 1-ml 96-deep-well plates and periplasmic extracts (PEs) were prepared as described under example 1.4.

Figure 7:
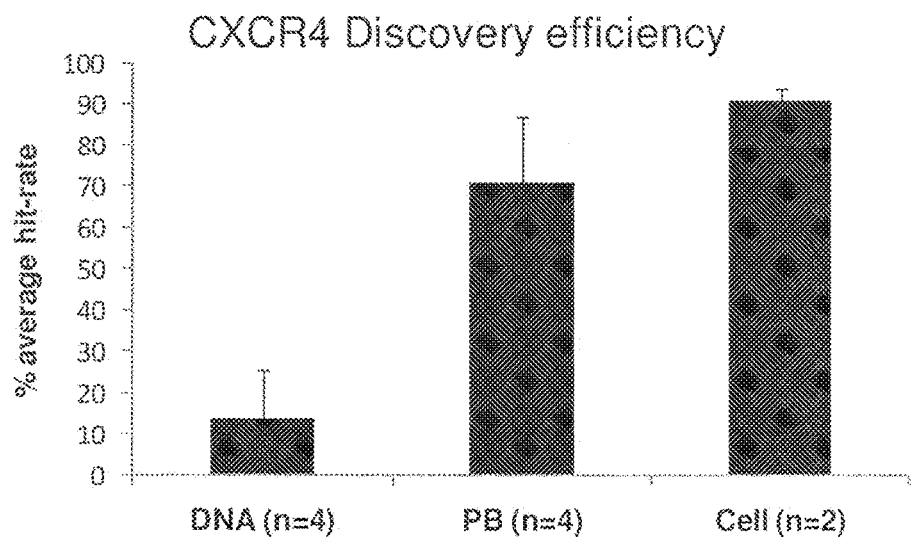
FIG. 7. hCXCR4 specific Nanobody discovery efficiency from 'DNA', 'PB' or 'cell' repertoires (number of libraries).

CXCR4 specificity was determined via two screening assays using two different receptor formats. In a first method, two units of CXCR4 Membrane vesicles were immobilized per well on 96-well Maxisorp plates by overnight coating at 4° C. Following blocking with 4% Marvel in PBS, 10-fold diluted PE was added and bound Nanobody (harbouring a c-Myc tag) was detected via sequential mouse anti-Myc and rabbit anti-mouse-HRP detection. 501 Nanobodies, showing a minimally 5-fold increased ELISA signal on hCXCR4 membrane vesicles over control membrane vesicles, were considered to be CXCR4 specific. The corresponding average ratios of the two types of negative control PEs, one generated from TG-1 expressing an irrelevant Nanobody and another from TG-1 containing an empty expression vector, were 1.1±0.8 and 1.2±0.7, respectively. Resulting from this screening method, hit-rates for each selection output were calculated and are summarized in Table 2.1. Based on the average hit-rates on round 2 selection outputs (10 U membrane vesicles) following the different immunization strategies, discovery efficiencies were calculated as 14, 71 and 91% for 'DNA', 'PB' and 'cell' repertoires, respectively (FIG. 7). Even in absence of a detectable heavy chain antibody (HcAb) titer to CXCR4 (Table 2.1), target specific Nanobodies were identified, as indicated by hit-rates of 4 to 31% after one and two rounds of selection on llama 403 DNA library, respectively. The hit-rates indicate that after the single cell boost, a single round of selection was sufficient to identify CXCR4 specific Nanobodies from all HcAb llama repertoires (hit-rates in Table 2.1 between 4 and 36%).

All 501 CXCR4 specific Nanobodies were sequenced and redundant Nanobodies (identical AA sequence) were removed. This resulted in the identification of 171 unique sequences, belonging to 70 distinct Nanobody B-cell lineages (Table 2.1). Nanobodies belong to the same B-cell lineage or family when their CDR3 region show high amino acid sequence similarity and are of the same length. The CDR3 is anticipated to contribute mostly to the antigen interaction and consequently Nanobodies belonging to the same family are assumed to bind the same epitope. The average number of CXCR4 specific Nanobody families identified per llama is 12.5 after cell immunizations (217, 218) and 11.2 via DNA immunization (DNA+cell boost; 389, 401, 402 and 403), respectively. The number of Nanobody amino acid sequence variants (minimally 1 AA residue mutation) belonging to one Nanobody family was in the range of 1 to maximally 17 family variants.

CXCR4 specific binding was confirmed in a secondary screening assay measuring Nanobody binding to cells expressing human CXCR4 via flow cytometry. Hereto, five-fold diluted PEs were incubated with parental or CXCR4 transfected camelid cells (2×10⁵ cells) and Nanobody binding was measured via mouse anti-Myc (Serotec MCA2200) and subsequent anti-mouse IgG-PE (Jackson ImmunoResearch Laboratories 115-115-164) detection antibodies. For all samples, the ratio of the MCF value on CXCR-4 expressing cells to the MCF on untransfected control cells was calculated. While an irrelevant Nanobody consistently showed a ratio <2.4, a ratio >10 was detected for 61 Nanobody families (at least one family member), thereby confirming specificity of these families for native CXCR4. Of the remaining nine Nanobody families, seven families consisting of a single member (7 families) showed a ratio <3, despite absorbance ratios of 5-10 fold measured in ELISA on Membrane vesicles. For the remaining two Nanobody families (2 families; all single member families) the absorbance ratios (ELISA) were 144 and 70, respectively, while the MCF ratios (FACS) were 2.2 and 2.3, respectively.

Example 2.7. Intradermal DNA Administration as Immunization Method is Sufficient to Identify Nanobodies Modulating SDF-1-CXCR4 Receptor Interaction Subsequent to the screening for CXCR4 specificity (determined via ELISA or FACS), all 171 CXCR4 specific Nanobody variants were tested for their ability to block the interaction of the ligand SDF-1 with its receptor to identify receptor function modulating Nanobodies (as described in patent WO/2009/138519A1). In brief, 40 µM of [$^{125}$I] SDF-1 ligand (in-house labelled) was allowed to bind 2 µg of hCXCR4/HEK293 membrane extracts in presence or absence of Nanobody competitor ten-fold dilution of a PE (produced as described in example 1.4). After incubation for 1 hour at 4° C., membrane extracts were washed and the total amount of bound ligand radioactive counts per minute (cpm) was determined. Aspecific binding of the radiolabelled ligand to the membrane extracts (non-CXCR4 related) was determined by addition of excess unlabelled SDF-1 (100 nM) to compete all radio-ligand from the CXCR4 receptor. The aspecific binding value for each plate was subtracted from the total binding (cpm in absence of NB) and the cpm values obtained for each Nanobody, and % residual [$^{125}$I] SDF-1 binding ($SDF_{res}$) in presence of Nanobody was calculated. A number of Nanobody families scored as ligand displacer were identified (Table 2.1), showing that ligand competing Nanobodies were identified from each immunization strategy (representing repertoires DNA, PB and cell).

Example 2.8. Epitope Mapping of Nanobodies Identified after the Different Immunization Strategies A selection of target specific Nanobodies (competitors and binders) from each immunization strategy will be recloned in an expression vector allowing expression and purification of soluble Nanobody fused to a His6 and Myc tag for further characterization. Expression will occur in *E. coli* after IPTG induction at 37° C. After spinning the cell cultures, periplasmic extracts will be prepared by freeze-thawing the pellets and resuspension in dPBS. These extracts are used as starting material for immobilized metal affinity chromatography (IMAC). Nanobodies will be eluted from the column using 250 mM imidazole and subsequently desalted towards dPBS. Purity and integrity of all Nanobodies will be verified by polyacrylamide gel electrophoresis (SDS-PAGE), while the presence of tags will be verified by western blotting.

To determine whether the DNA vaccination strategy (DNA only or followed by cell boost) results in the identification of Nanobodies against different epitopes compared to the Nanobodies identified after the cell immunization strategy, a number of epitope binning assays will be implemented. These are: binding to the CXCR4 N-terminal peptide corresponding to AA residues 1-14 (ELISA), binding to CXCR4 mutant receptors in which point-mutations within the N-terminus and the extracellular loop regions have been introduced, or binding to mutated CXCR4 such as N-terminally truncated hCXCR4 receptor or CXCR4 chimeras in which the N-terminus or extracellular loops have been individually replaced by the sequence of a related GPCR. Alternatively, epitope mapping will be performed using competition experiments of our panel of purified Nanobodies with distinct CXCR4-specific compounds, including i) monoclonal antibodies or Fab fragments of which the epitope has been described (Carnec et al. 2005, J. Vir. 1930-33) such as 4G10 (Santa Cruz, SC53534) which binds to the linear N-terminus, ii) small molecule inhibitors, such as the antagonist AMD3100 (Sigma A5602), and iii) other Nanobodies labeled with a fluorescent marker or biotin.

Figure 8:
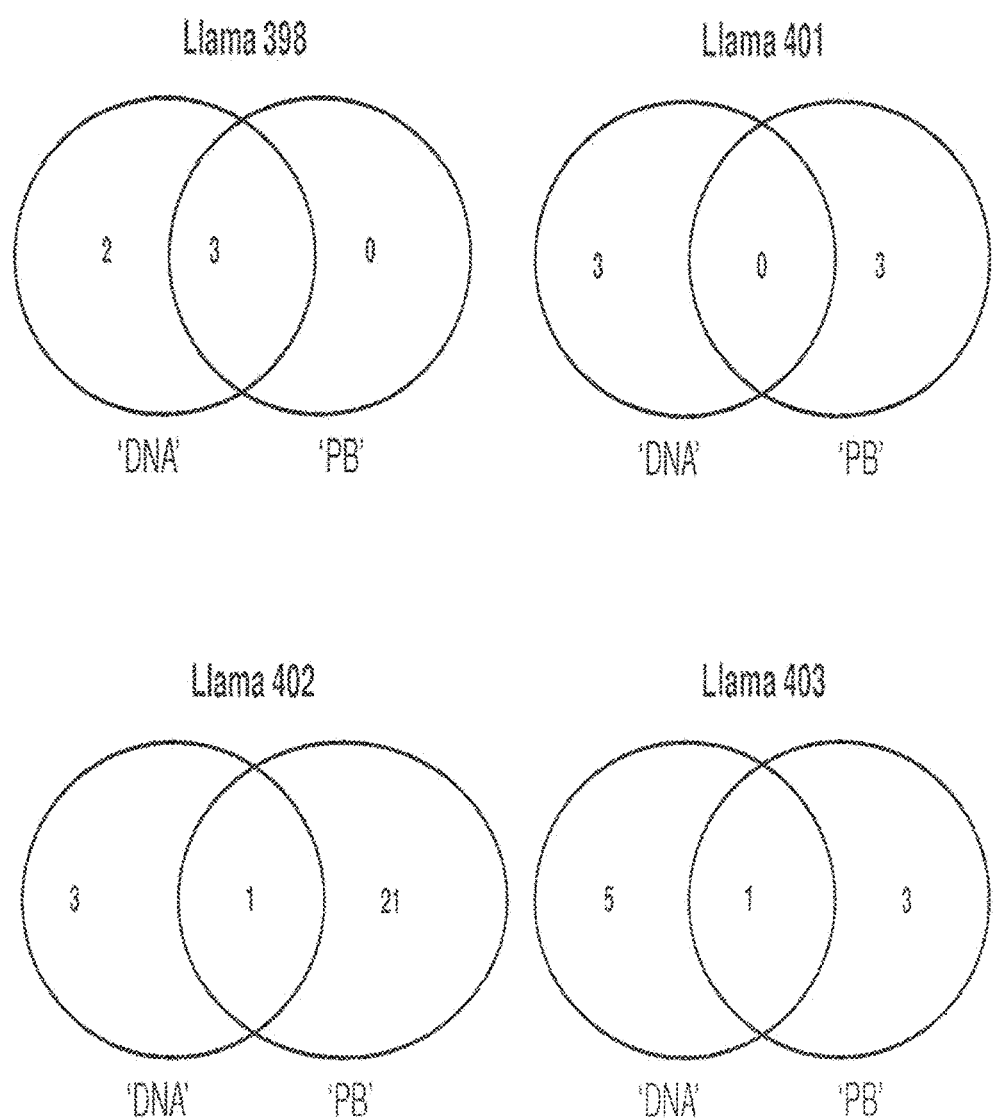
FIG. 8. Complementary target specific Nanobody repertoires obtained after genetic immunization (DNA) and single cell boost (PB). Numbers of repertoire specific Nanobody families are depicted.

Example 2.9. Cell Boost Following Genetic Immunization Generates a Different Nanobody Repertoire From llamas 389, 401, 402 and 403, 45 CXCR4 specific Nanobody families were identified consisting of 123 Nanobody sequence variants (out of 225 sequenced). Each of these 123 variants was assigned to the 'DNA' libraries or the 'PB' library (no variant with identical AA sequence was obtained from both libraries). Only for five of these 45 families (11.1% of the total family diversity), Nanobody variants belonging to the same family were identified from the 'DNA' and 'PB' libraries derived from the same animal (Table 2.2). These five families comprise 42 different Nanobody variants, corresponding to 34% of the non-redundant clones. The remaining Nanobody repertoire (76%) is identified either from the 'DNA' library or from the 'PB' library indicating that the cell boost following to genetic immunization caused in vivo maturation of a Nanobody repertoire not readily identified via panning of a library generated after genetic immunization only (FIG. 8). Genetic immunization only results in a different Nanobody repertoire, indicating that repertoire may be lost after the cell boost.

Example 2.10. The Average Potency of the 'DNA' Repertoire is Lower than that of the 'PB' and 'Cell' Repertoire The previous example indicates that only a limited number of families has been identified from both 'DNA' and 'PB' libraries. In order to verify what the effect is of the cell boost for this repertoire subset, we scored in vivo maturation by i) calculating the genetic distance versus the parental V-gene germline sequence (in number of amino acid or nucleotide mutations; excluding the D- and J-gene segments encoding the CDR3 and FR4 region) for each variant within the specific Nanobody family and ii) by comparing Nanobody variant potencies. For the calculation of the genetic distance, we assumed a proportional introduction of amplification errors for all libraries (a proofreading polymerase has been used to limit the number of mutations caused by the Nanobody repertoire cloning method including amplification via PCR). For three of these five families, the 'B' originating Nanobodies showed on average 12, 13 and 9 AA mutations (or 26, 19 and 13 nt mutations) versus the parental V-gene germline sequence, while respectively 10, 12 and 5 (or 19, 17 and 5.5 on the nt level) for the Nanobodies derived from the 'DNA' library, which suggests that on average the 'B' originating Nanobodies are more distant from the parental V-gene germline (hence more matured) than the 'DNA' originating Nanobodies. For these three families, the higher degree of maturation of the 'PB' Nanobodies is also reflected in the average binding potency (MCF ratio as described in example 2.6) of the 'PB' versus 'DNA' originating Nanobodies being respectively 553 vs 46, 261 vs 105, 556 vs 505 for 3 families respectively (FACS results but trend is confirmed in ELISA, see Table 2.2).

Figure 9A:
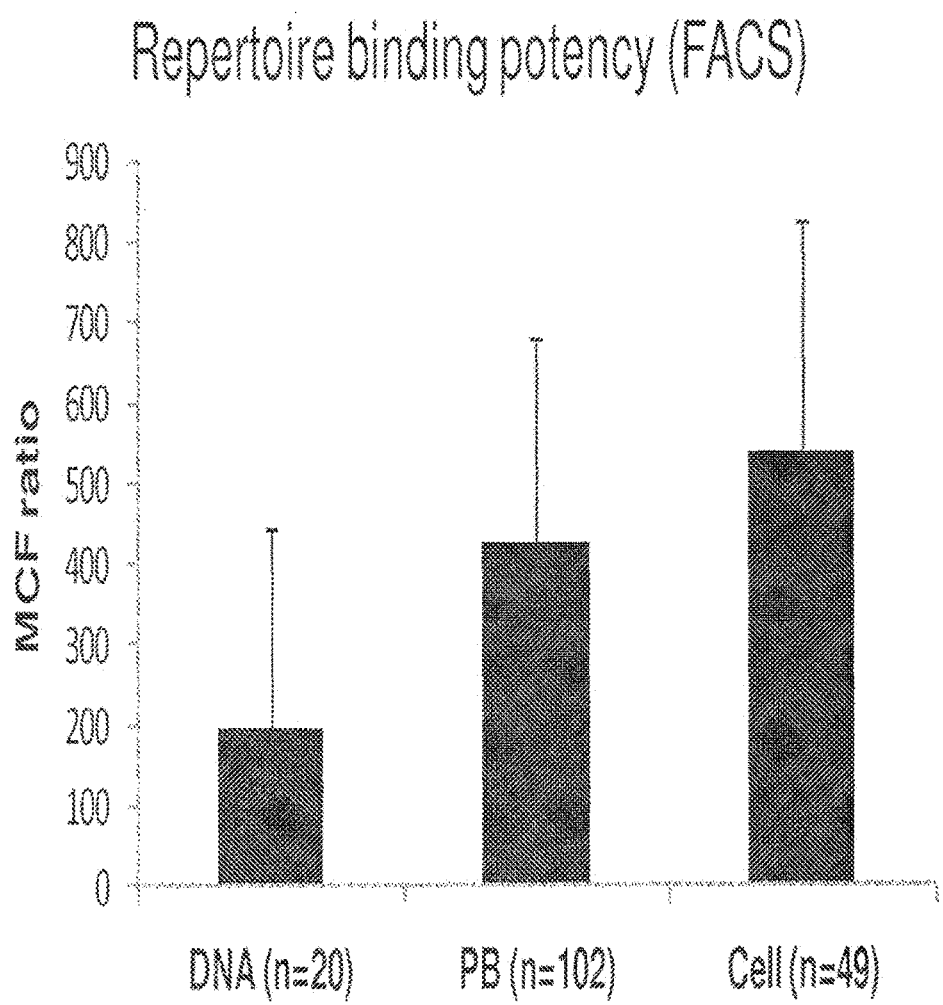
FIGS. 9A and 9B. Average binding potencies determined via FACS (FIG. 9A) or ELISA (FIG. 9B) of CXCR4-specific Nanobody repertoire after primary screening identified after genetic immunization ('DNA'), subsequent single cell boost ('PB') or after complete cell immunization ('cell') (number of individual Nanobodies).
Figure 9B:
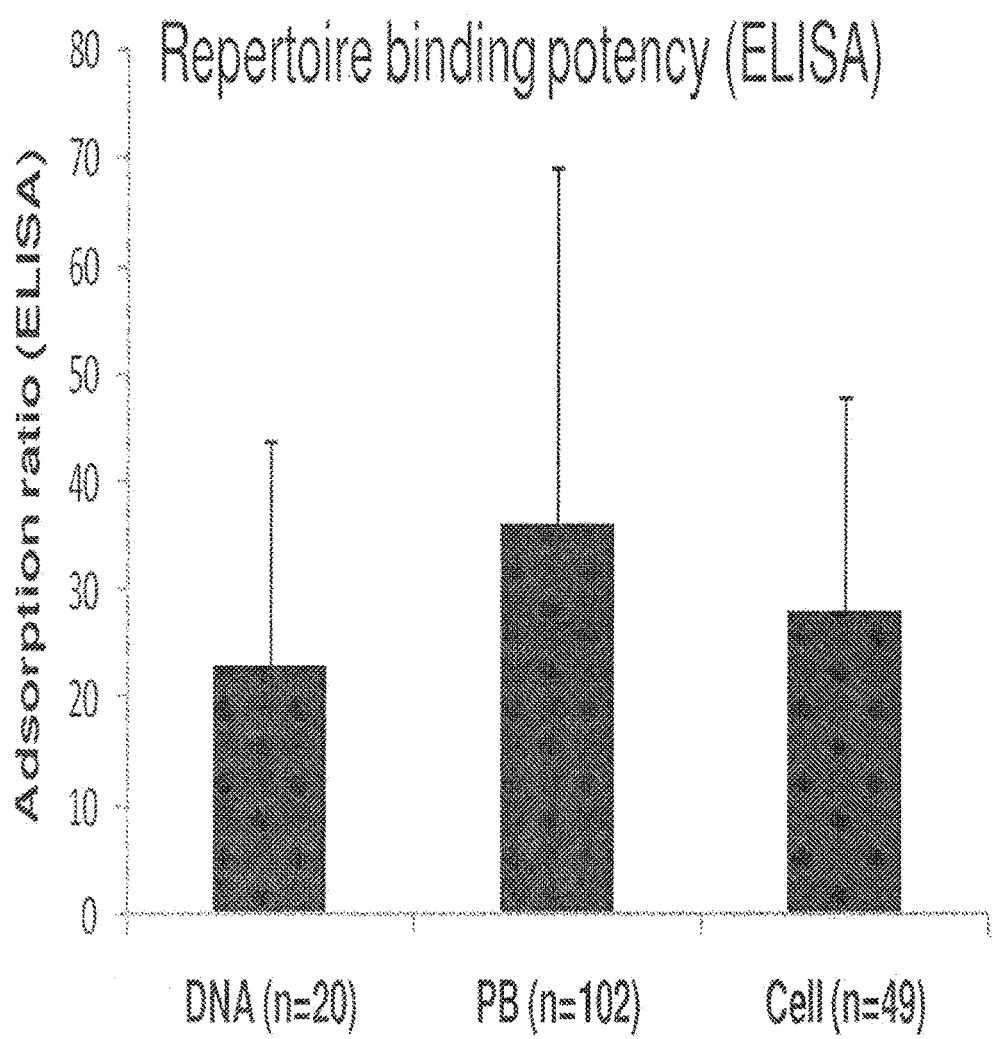

When analyzing concentration dependent target binding for all 122 unique Nanobodies from llama 389, 401, 402 and 403 (20 and 102 Nanobody variants originating respectively from the 'DNA' and 'PB' libraries), the average MCF ratios (FACS) were 427 and 196 for the Nanobodies originating from 'PB' and 'DNA' libraries, respectively (FIGS. 9A and 9B). The corresponding number calculated from the 49 Nanobody variants originating from 'cell' libraries (llamas 217 or 218) is 538. This trend is confirmed via the numbers generated by the ELISA assay: the average adsorption ratios (calculated as described under example 2.6) were 36.2 and 23 for the Nanobodies originating from 'PB' and 'DNA' libraries, respectively. The corresponding number calculated from the 49 Nanobody variants originating from 'cell' libraries (llamas 217 or 218) is 28. This suggests that the average genetic distance of the Nanobody variants originating from the 'DNA' libraries are more closely related to the parental germline sequence than those Nanobodies identified from 'PB' libraries, hence considered as being less matured. Moreover, when analyzing the average binding potencies of the three repertoires, the 'DNA' repertoire appears less potent than the 'PB' repertoire, the latter being similarly potent to the 'cell' repertoire (FIGS. 9A and 9B).

For the fourth family however, surprisingly, the variants obtained from the 'DNA' library suggested an equal to higher degree of in vivo maturation compared to the Nanobodies identified from the 'PB' libraries (Table 2.2). The 'DNA' originating clone from this family shows 15 AA (or 21 nt) mutations compared to the V-germline and the corresponding average value for the 'PB' originating Nanobodies is 14.6 (AA) or 21.7 (nt). This is also reflected in the average potencies in the FACS assay of the 'DNA' and 'PB' Nanobodies, being 755 and 671, respectively. For the fifth family, maturation of the 'DNA' and 'PB' libraries is scored as highly similar since no consistent ranking between the 'DNA' and 'PB' originating Nanobodies is detected following the 4 analysis methods (AA or nt mutations, FACS and ELISA).

Although there is no statistically significant difference between average binding potencies of the three different repertoires, the average potency of the 'PB' repertoire is similar to the one obtained from the 'cell' libraries, which are higher than this of the 'DNA' repertoire. On the monoclonal level however, Nanobodies with similar binding potencies have been identified after genetic immunization only compared to those identified after cell boost or a cell immunization.

Example 3. Identification of Nanobodies Against a Ligand-Operated Ion Channel

As a second example to demonstrate the feasibility of genetic immunization for membrane bound targets carrying multiple transmembrane domains, the mouse purinoceptor P2X7 was chosen.

P2X7 is a ligand-gated ion channel, which is activated by high concentrations of exogeneous ATP or by NAD-dependent ADP-ribosylation. The functional channel is formed by three P2X7 protein subunits, each consisting of two membrane-spanning regions and a single extracellular loop of 285 AA residues. Activation of the purinoceptor induces a conformational change, leading to the formation of a large non-selective pore, ultimately causing membrane blebbing and apoptosis.

Genetic immunization with P2X7 has previously been demonstrated to successfully raise polyclonal and monoclonal anti-P2X7 antibodies in rabbits and rats (Adriouch et al, 2005. Cell Immun 236, 72-77). Here we demonstrate the identification of P2X7-specific Nanobodies that modulate the ligand-induced P2X7 activation following genetic immunization.

Example 3.1. Induction of a Humoral Response in Llama to mP2X7 Via Genetic Immunization Using a Ballistic Method Gene gun immunization has been shown to be an efficient method of intradermal DNA delivery for the induction of a humoral response in a various range of animals, including mouse, bovine and llama (Koch-Nolte 2007, Faseb. J. 21, 3490-3499). This ballistic administration method delivers DNA coated gold microparticles to the highly immune competent skin tissue under high pressure, immediately targeting and transfecting immune effector cells present in the dermis such as the Langerhans antigen presenting cells. This results in increased in vivo transfection efficiency and consequently a sustained antigen presentation considered to stimulate the induction of humoral immune responses.

Three llamas (407, 414 and 417) were immunized with mouse P2X7 (mP2X7) encoding DNA. The device used for the DNA delivery was the Helios Gene-gun (Biorad). Endotoxin-free mP2X7-expression plasmid pCDNA6.1-mP2X7 (Adriouch et al. 2005, Cell Immun 236, 72-77) was coated onto 1 µm gold particles (Biorad, cat nr. 1652263) following the manufacturer's instructions. Llama skin in the neck region was prepared as in example 1.2. Each llama received four antigen doses with administration intervals of two weeks. Each dose consisted of 12 shots of plasmid-conjugated gold particles (1 µg of DNA conjugated onto 0.5 mg gold particles per shot) applied with a pressure setting at 600 psi into the skin. Three weeks after the final genetic immunization, all llamas received a single boost with $2 \times 10^7$ mP2X7-transfected Hek293 cells. At regular intervals, blood samples were collected to monitor the induction of the humoral immune response over time. For the isolation of B-cell tissues, blood was collected from these animals 3 and 9 days after the fourth DNA immunization (PBL1 and PBL2), and 4 and 8 days after the cell boost (PBL3 and PBL4). A biopsy of the palpable lymph node (LN) in the bow area was taken 4 days after the cell boost.

Another three llamas (413, 415 and 416) were immunized subcutaneously in the bow area with $2 \times 10^7$ stably transfected mP2X7 Hek293 cells (Adriouch et al. 2005, Cell Immun 236, 72-77) for four times with two week intervals. Blood was collected from these animals 4 days and 8 days after the fourth immunization and a LN biopsy was taken 4 days after the fourth immunization.

Figure 10:
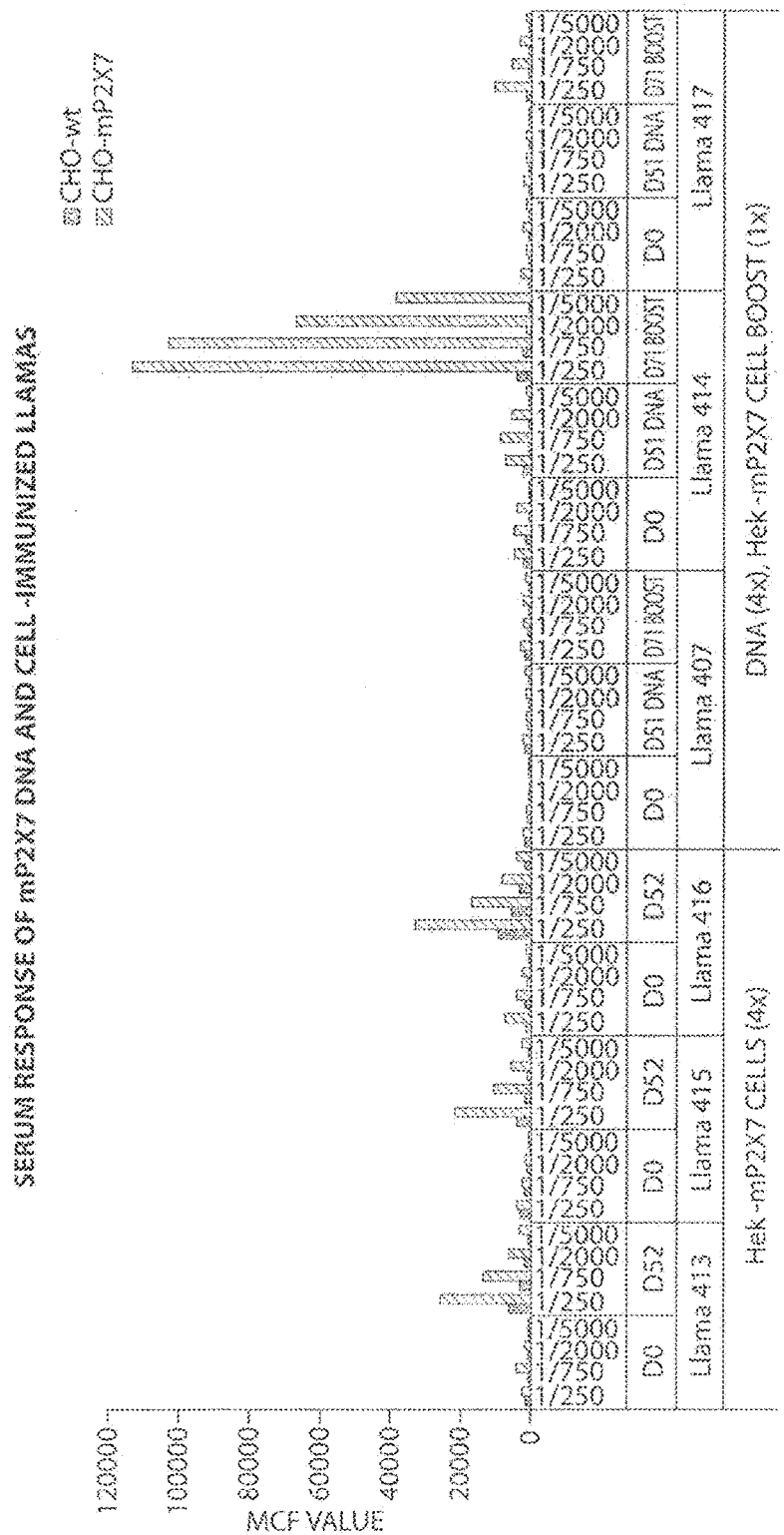
FIG. 10. mP2X7-specific serum conversion in llamas via genetic immunization.

The serum response was monitored for mP2X7 reactivity via flow cytometry using untransfected and mP2X7-transfected CHO cells similarly as described in example 2.4. For the DNA immunized llamas, the mP2X7 serum conversion was compared between the pre-immune serum sample (day 0), a serum sample collected after the final DNA immunization (day 51, PBL2) and one after the cell boost (day 71, PBL4). For the llamas immunized via four cell injections, mP2X7 specific titers were compared between the pre-immune and an immune sample collected at day 52. FIG. 10 shows the total IgG (conventional and heavy-chain antibody) immune response of all six mP2X7 immunized llamas. Except for llama 407, a clear increase in mean cell fluorescence (MCF) of mP2X7-transfected CHO cells was observed with the day 71 immune serum sample collected after the cell boost, compared to the pre-immune level (for minimally three dilutions tested). MCF values against non-transfected CHO cells remain low. Following the genetic immunization procedure (DNA priming followed by single cell boost), two out of three llamas showed a specific humoral response against the native target conformation. All three animals having received multiple cell injections show detectable mP2X7 specific serum titers (day 52). The background response against irrelevant CHO cell surface antigens is higher in these animals than in those immunized via genetic immunization (DNA+cell boost).

Figure 11:
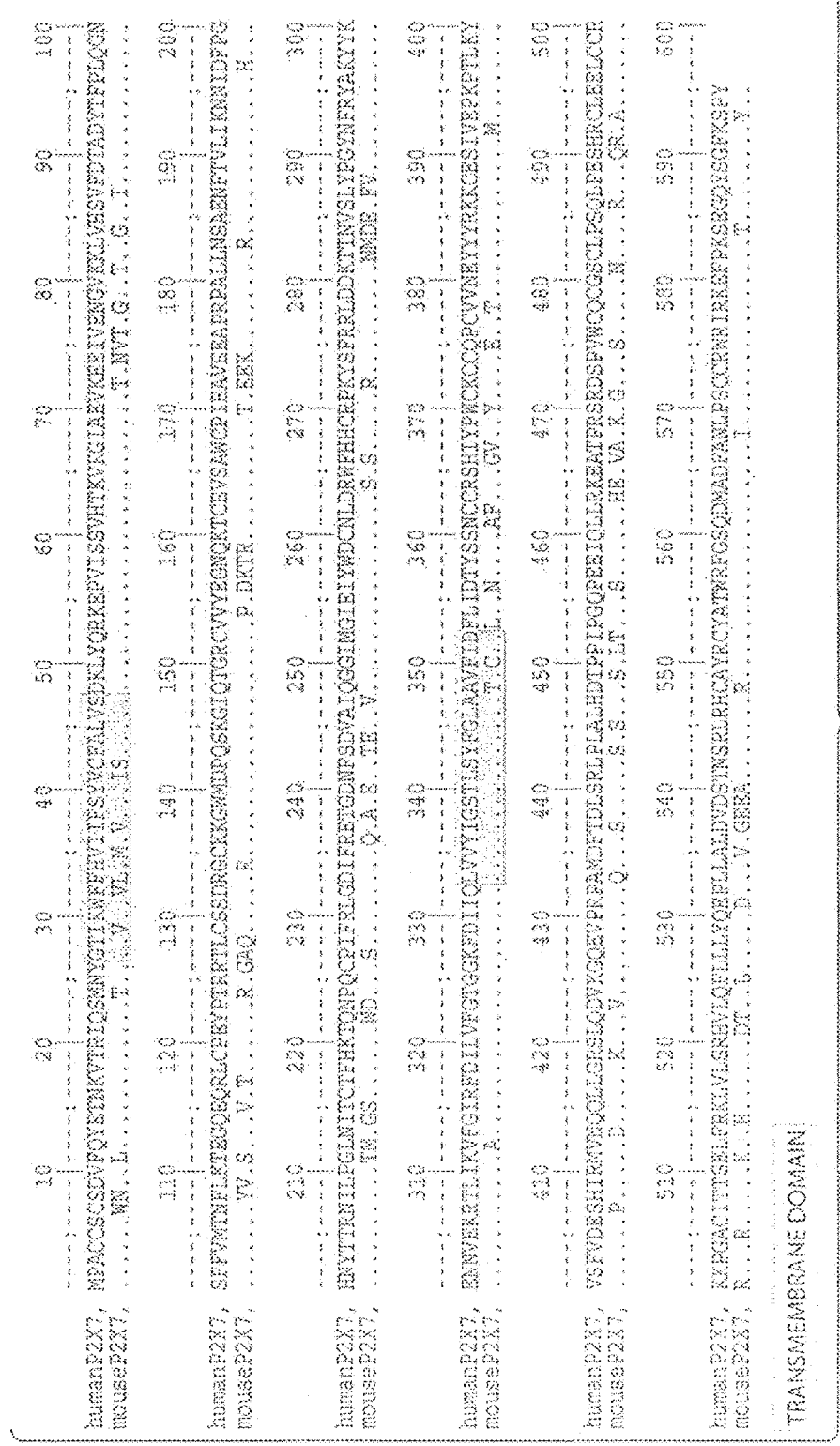
FIG. 11. Sequence alignment of human P2X7 and mouse mP2X7. The human P2X7 amino acid sequence is SEQ ID NO: 792 and the mouse P2X7 amino acid sequence is SEQ ID NO: 793.

Example 3.2. Genetic Cocktail Immunization of Human and Mouse P2X7 Using Gene Gun One benefit of genetic immunization is the versatility to generate immune response against multiple targets simply by administering different target encoding genes to the same animal. Cocktail immunizations can also be used to bias the immune response to a specific conformation. As example of cocktail immunizations, we chose human (h) and mP2X7, orthologues which share 80.5% overall sequence identity as illustrated in FIG. 11, for Gene gun DNA immunization of llamas. In addition, to allow induction of an immune response to the P2X7 channel in its open conformation, two modifications to the immunization strategy described in example 3.1 were made. At first, a cocktail immunization was applied with a mixture of plasmids encoding for mP2X7 and mArt2.2, which is a known activator of P2X7 by mediating ADP-ribosylation. Second, prior to the cell boost the P2X7-transfected Hek293 cells were treated with ATP to activate the channel, after which cells were fixed using paraformaldehyde to preserve the open conformation.

Two llamas (405 and 418) were immunized simultaneously with both h and mP2X7 using genetic immunization with the Gene gun. A mixture of endotoxin-free pCDNA6.1-mP2X7 and pCDNA6.1-mArt2.2 (1:10 ratio) was conjugated to 1 μm gold particles. Similarly, the pCDNA6.1-hP2X7 plasmid encoding hP2X7 was conjugated to 1 μm gold particles. Genetic immunization was performed as described under example 3.1 (1 μg/0.5 mg/shot). The left flank of the neck was used for immunization with mP2X7/mArt2.2-conjugates, while the right flank was used for immunization with hP2X7 conjugates. Three weeks after the fourth DNA immunization, both llamas were boosted simultaneously with $2 \times 10^7$ ATP-treated, fixed mP2X7-Hek293 cells (left side) and hP2X7-Hek293 cells (right side). A second boost was given at the left side after 3 days with $2 \times 10^7$ ATP-treated, fixed hP2X7-Hek293 cells. For the isolation of B-cell tissues, blood was collected from these animals 3 and 9 days after the fourth DNA immunization (PBL1 and PBL2), and 4 and 8 days after the first cell boost (PBL3 and PBL4). A LN biopsy was taken from the bow area at the left side 3 days after the first cell boost.

Figure 12:
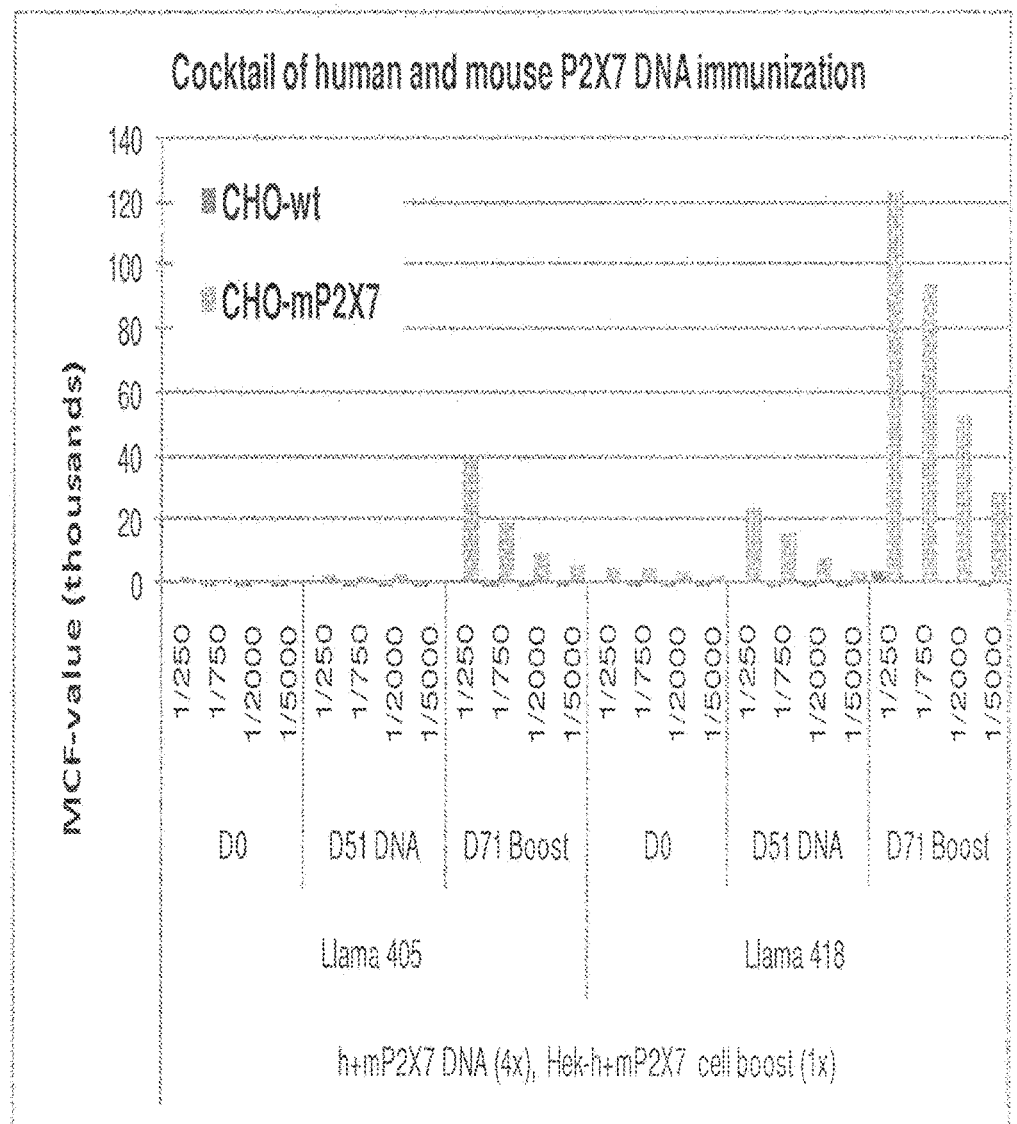
FIG. 12. mP2X7-specific serum conversion in llamas via genetic cocktail immunization.

The total IgG serum titer response to mP2X7 of both llamas was monitored in flow cytometry using untransfected and mP2X7-transfected cells, as described in example 3.1. Hereto the pre-immune serum sample (day 0) was compared to samples taken after DNA immunization (day 51, PBL2) and the respective cell boost (day 71, PBL4). Llama 418 shows a clear total IgG immune response to mP2X7 after DNA immunization, which is further enhanced after the cell boost, while llama 405 only shows mP2X7 reactivity after the cell boost (FIG. 12). For both llamas, the MCF values on untransfected CHO cells remain low. The serum reactivity to human P2X7 was not determined. In conclusion, after genetic immunization and subsequent cell boost 4 out of 5 llamas show clear mP2X7 serum responses.

Figure 13A:
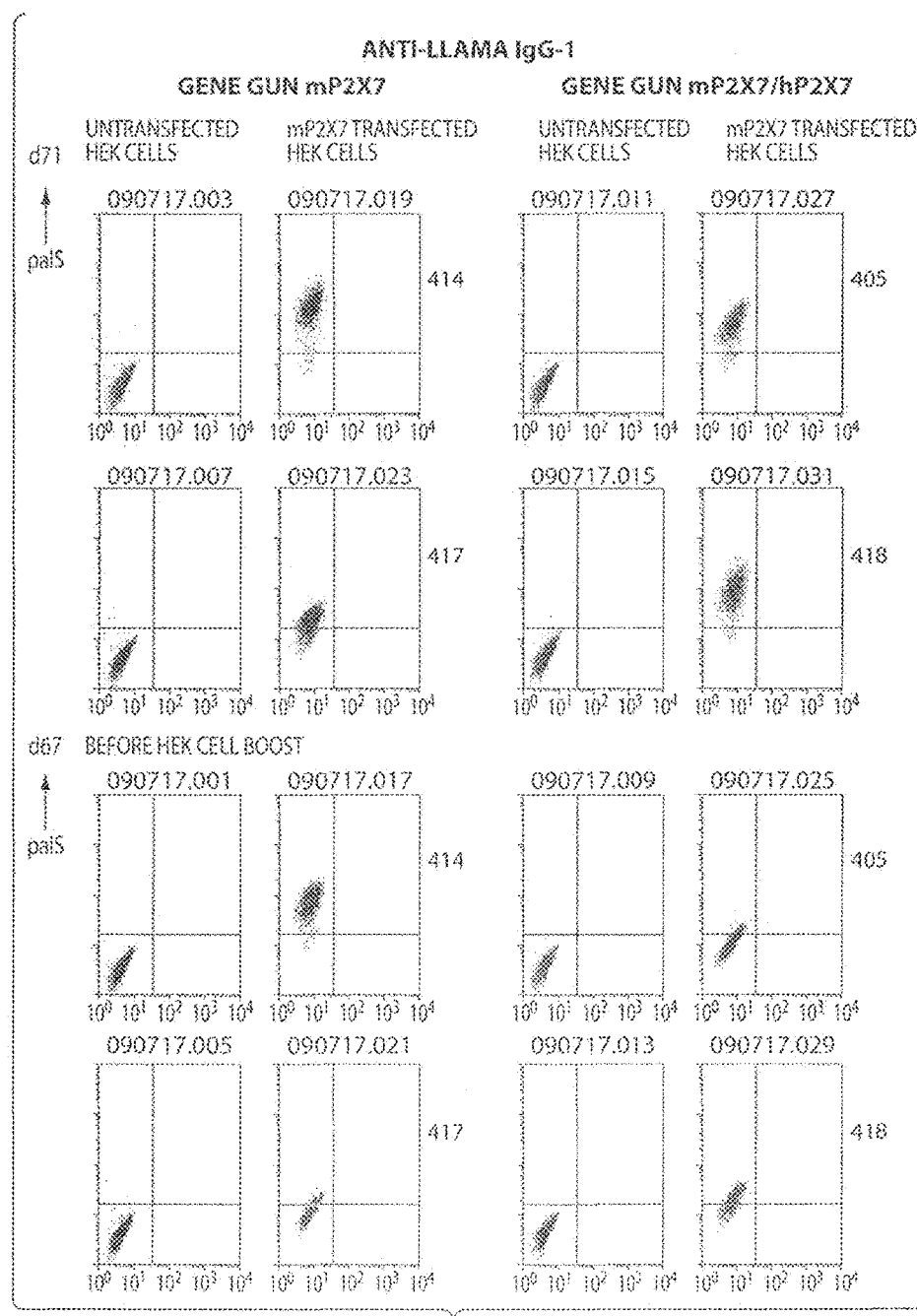
FIGS. 13A and 13B. Pre-adsorbed immune sera contain mP2X7-specific heavy-chain antibodies after genetic immunization.
Figure 13B:
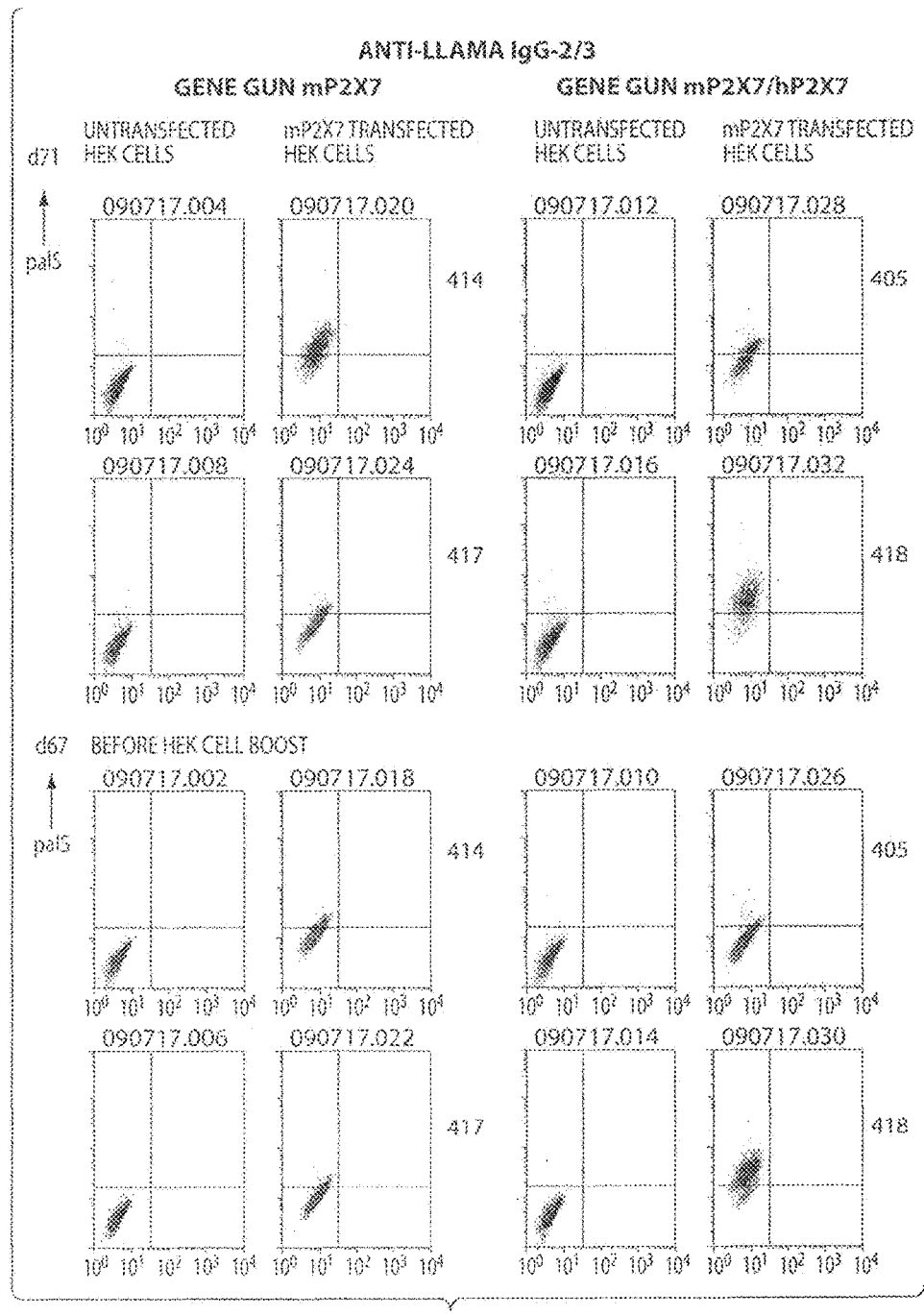

Example 3.3. Induction of a Heavy-Chain Antibody Response after Genetic Immunization In addition, the induction of a heavy-chain antibody (HcAb) mediated mP2X7-specific response was monitored by FACS using llama IgG isotype-specific monoclonal antibodies on stable Hek293-mP2X7 transfectants. To test this setup, dilutions of llama sera (1/200 for DNA-immunized llamas and 1/1000 for cell-immunized llamas) were pre-adsorbed on $1 \times 10^7$ WT Hek293 cells at room temperature for 1 hour to deplete for cell background antibodies. Next, $5 \times 10^5$ Hek293-mP2X7 or untransfected Hek293 cells were incubated with 0.1 mL of the pre-adsorbed sera for 0.5 hour at 4° C. (to prevent internalization), after which bound HcAbs were detected by a mixture of mouse-anti-llama IgG2 and IgG3 antibodies (Daley et el. 2005. Clin Diagn Lab Immunol 12:380-386) followed by anti-mouse IgG-PE (Jackson ImmunoResearch) staining. Binding of conventional llama antibodies was detected using anti-llama IgG1. As control for mP2X7 staining, the rat mAb Hano43 was included (Adriouch et al. 2005, Cell Immun 236, 72-77). mP2X7 specific IgG serum titers of Hek293-mP2X7 immunized llamas could not be determined due to high levels of Hek293 cell background binding, while no such high background was observed for DNA-immunized llama 407. FIGS. 13A and 13B show the conventional antibody (FIG. 13A) and HcAb mediated (FIG. 13B) serum response after genetic immunization with mP2X7 (llama 414 and 417) or the cocktail of m and hP2X7 (llama 405 and 418). After DNA vaccination only, sera of llamas 414 and 418 showed a clear MCF shift on mP2X7 transfected Hek293 cells vs non-transfected WT Hek293 cells for the conventional Ab-mediated response, confirming the serum conversions detected via total IgG (in example 3.1 and 3.2). The cell boost induced a moderate (llama 417) to clear (llamas 405, 414 and 418) conventional Ab mediated MCF shift on mP2X7 transfected Hek293 cells vs non-transfected WT Hek293 cells. A moderate HcAb response was detected for llamas 414 and 418 before the cell boost, which was enhanced for llama 414 by the cell boost (compare day 71 and day 67 sera). In contrast, there was only little if any detectable heavy chain serum response for llamas 405 and 417 (FIG. 13B). In conclusion, in two out of five llamas, genetic immunization resulted in a detectable HcAb response to mP2X7 after cell boost.

Example 3.4. Library Construction

Peripheral blood mononuclear cells were prepared from blood samples using Ficoll-Hypaque according to the manufacturer's (Amersham Bioscience) instructions. Next, total RNA was extracted from these cells as well as from the LN biopsy and used as starting material for RT-PCR to amplify Nanobody encoding gene fragments (example 1.4). For the five DNA immunized llamas 405, 407, 414, 417 and 418, cDNA obtained from PBL1 and PBL2 after DNA immunizations only were used to generate 'DNA' libraries, while the cDNA from PBL3, PBL4 and LN was used to construct post-boost (PB) libraries. For the llamas immunized with Hek293-mP2X7 cells, cDNA obtained from PBL1, PBL2 and LN was used for the generation of libraries. Fragments corresponding to the variable domain of the HcAb repertoire were cloned into phagemid vector derived from pUC119 which contains the LacZ promoter, a E. coli phage pIII protein coding sequence, a resistance gene for ampicillin or carbenicillin, a multicloning site and the gene3 leader sequence. In frame with the Nanobody coding sequence, the vector codes for a C-terminal c-myc tag and a (His)$_6$ tag. In total 13 phage libraries were generated, designated 405-DNA; 405-PB, 407-DNA, 407-PB, 414-DNA, 414-PB, 417-DNA, 417-PB, 418-DNA 418-PB, 413-cell, 415-cell, and 416-cell. The size of the resulting phage libraries was estimated between 0.12-2.5×10$^8$ clones with insert percentages between 83-100% Phage was prepared according to standard methods and stored at 4° C. for further use.

Example 35. Nanobody Selection on mP2X7-Expressing Cells Using Phage Display

To identify Nanobodies recognizing the mP2X7 purinoceptor in its native conformation, selections were performed on whole cells expressing mP2X7 using all 10 libraries generated from animals after DNA vaccination and three libraries generated from the cell-immunized llamas. In order to compare the characteristics of the monoclonal Nanobodies identified via different immunization methods, selections on all libraries were performed in parallel. In a first round of selection, CHO cells transfected with mP2X7 or untransfected CHO cells (5×10$^6$ per library) were blocked with blocking buffer (10% fetal bovine serum (FBS) and 2% Marvel in PBS) for 30 minutes at 4° C. As preblocking step, all phage inputs were incubated in blocking buffer for 30 minutes at 4° C. Cells were incubated with the phage under slow rotation at 4° C., then spun down and washed three times with blocking buffer and twice more using PBS. Cell-bound phage were eluted using trypsin, as in example 1.4. All phage outputs were infected into logarithmically growing E. coli TG1 cells and plated on agar plates (LB+Amp+2% glucose) for analysis of individual Nanobody clones. Enrichment was calculated as the ratio between the number of phage eluted from mP2X7-CHO cells versus those eluted from non-transfected CHO cells in parallel selections. First selection round enrichments higher than 3-fold could only be observed for 413 and 414 libraries, the PB library of the latter even showing an enrichment >200-fold. Round 1 mP2X7/CHO selected phage outputs were rescued and used for a second selection round on mouse Yac-1 cells, which endogenously express mP2X7. The change in cellular background was done to reduce the selection of phage binding to irrelevant cell background markers. Essentially the same procedure was followed as for round 1. Since no control cells were available for this second round, relative enrichments were calculated by taking the ratio of the round 2 to round 1 outputs. From the DNA libraries, only for 407 and 417 enrichments were detected (ratio of 6 and 97, respectively). For the PB repertoire, 3 out of 5 libraries showed enrichments above 10, while for 407 a moderate 3-fold enrichment was observed. No further enrichment was seen for PB library 414, which may be due to the already high antigen specific phage enrichment during the first selection round. From the cell-immunized libraries, only 413 showed a moderate 3-fold enrichment. Forty five to 48 individual clones of each selection output (round 1 and round 2) were grown in 96-well formats and phage were prepared for subsequent screening, as described under example 1.

Example 3.6. Screening for mP2X7-Specific Nanobodies

P2X7 specificity was at first determined by phage ELISA on untransfected and mP2X7-transfected CHO cells. Cells were seeded in 96-well culture plates at density of 4×10$^4$ cells per well in 0.2 ml of DMEM medium containing 10% FBS supplemented with penicillin and streptomycin (100 U/ml and 100 µg/ml, respectively) and incubated for 24 hours at 37° C. in a 5% CO$_2$ atmosphere. Sub-confluent cells were rinsed with PBS and fixed using 4% paraformaldehyde in PBS for 10 minutes at RT. Fixed cells were washed three times with PBS, and blocked with 2% BSA in PBS for 2 hours. Following blocking, 10-fold diluted culture supernatant containing phage was added and incubated for 1 hour. Cell-bound phage was detected via mouse anti-M13-HRP-conjugate (GE Healthcare, Cat nr. E2886). Rat mAb Hano43 was used as positive control. 523 out of 1506 screened individual clones derived from all selection rounds showed a minimally 2-fold increased ELISA signal on mP2X7-CHO cells relative to control CHO cells. Hit-rates after primary screening of DNA, PB, and cell libraries are shown in table 3.1.

Figure 14:
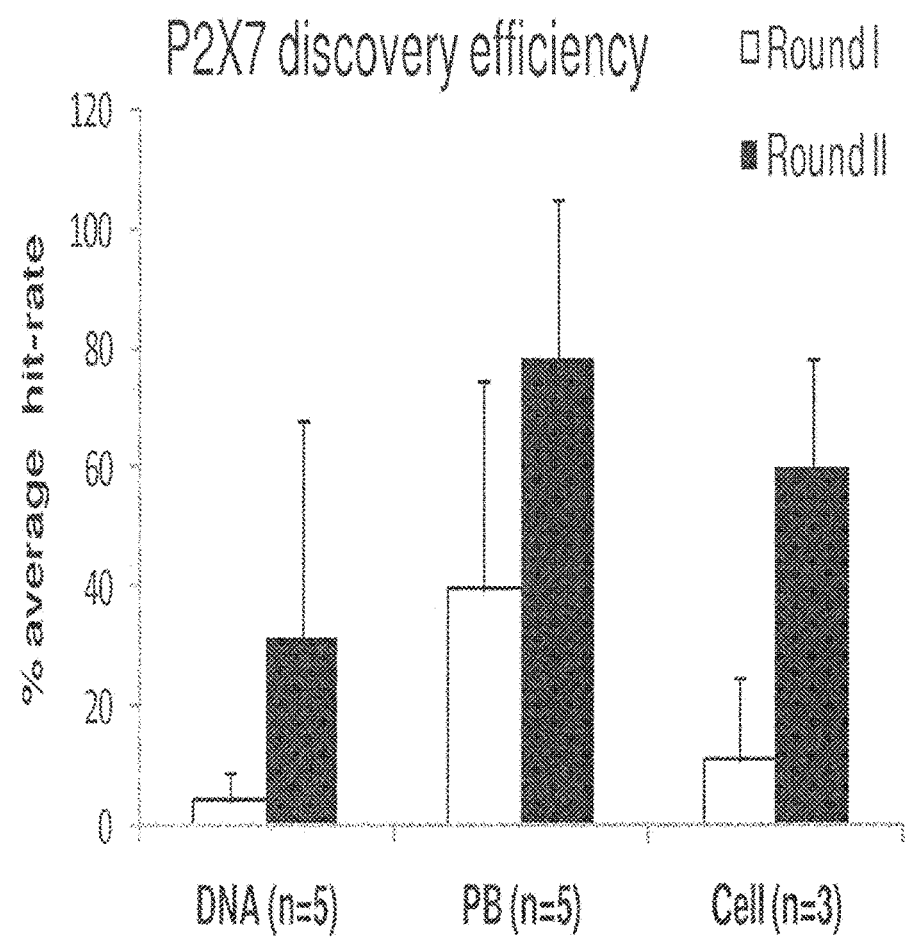
FIG. 14. mP2X7 specific Nanobody discovery efficiency from 'DNA', 'PB' or 'cell' repertoires (number of libraries).

Based on the average hit-rates on round 1 and 2 selection outputs on repertoires generated after the different immunization strategies (DNA, PB, cell), discovery efficiencies were calculated as 4, 40 and 11 (round 1 outputs) or 31, 78, and 60% (round 2 outputs) for 'DNA', 'PB' and 'cell' repertoires, respectively (FIG. 14). This indicated that the proportion of mP2X7 binding Nanobodies in the different repertoires was higher for 'PB' and 'cell' than for 'DNA'. For cDNA immunized animals, a good correlation between serum titer and hit-rate after two selection rounds was observed for PB libraries from llamas 405, 418 and 414, with hit-rates ranging from >48% after round 1 and >90% after round 2. For comparison, the hit-rates observed with libraries from cell immunization ranged between 40-73% after two selection rounds. Despite the absence of a detectable serum titer in Hamas 407 and 417 after DNA immunization (FIG. 10), the hit-rate of the corresponding DNA libraries was 25% and 87%, respectively, after 2 selection rounds. As shown previously for CXCR4, this indicates DNA vaccination is sufficient to identify mP2X7-specific Nanobodies via the phage display technology, even in the absence of a detectable target-specific serum conversion.

Example 3.7. Sequence Diversity of mP2X7-Binding Clones

Figure 15:
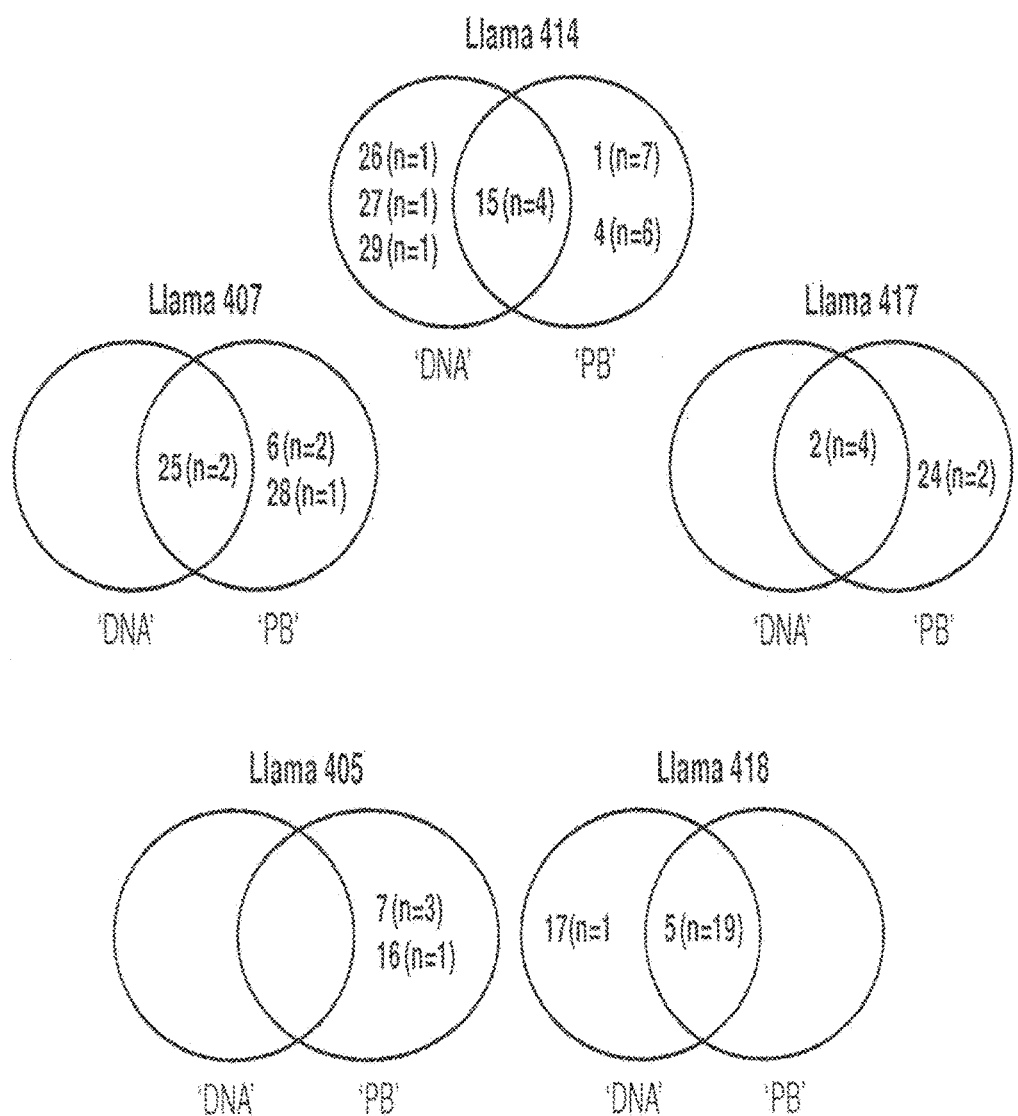
FIG. 15. Sequence diversity of Nanobodies identified after primary screening for mP2X7. DNA: DNA immunization; PB: DNA immunization followed by post boost.
Figure 22:
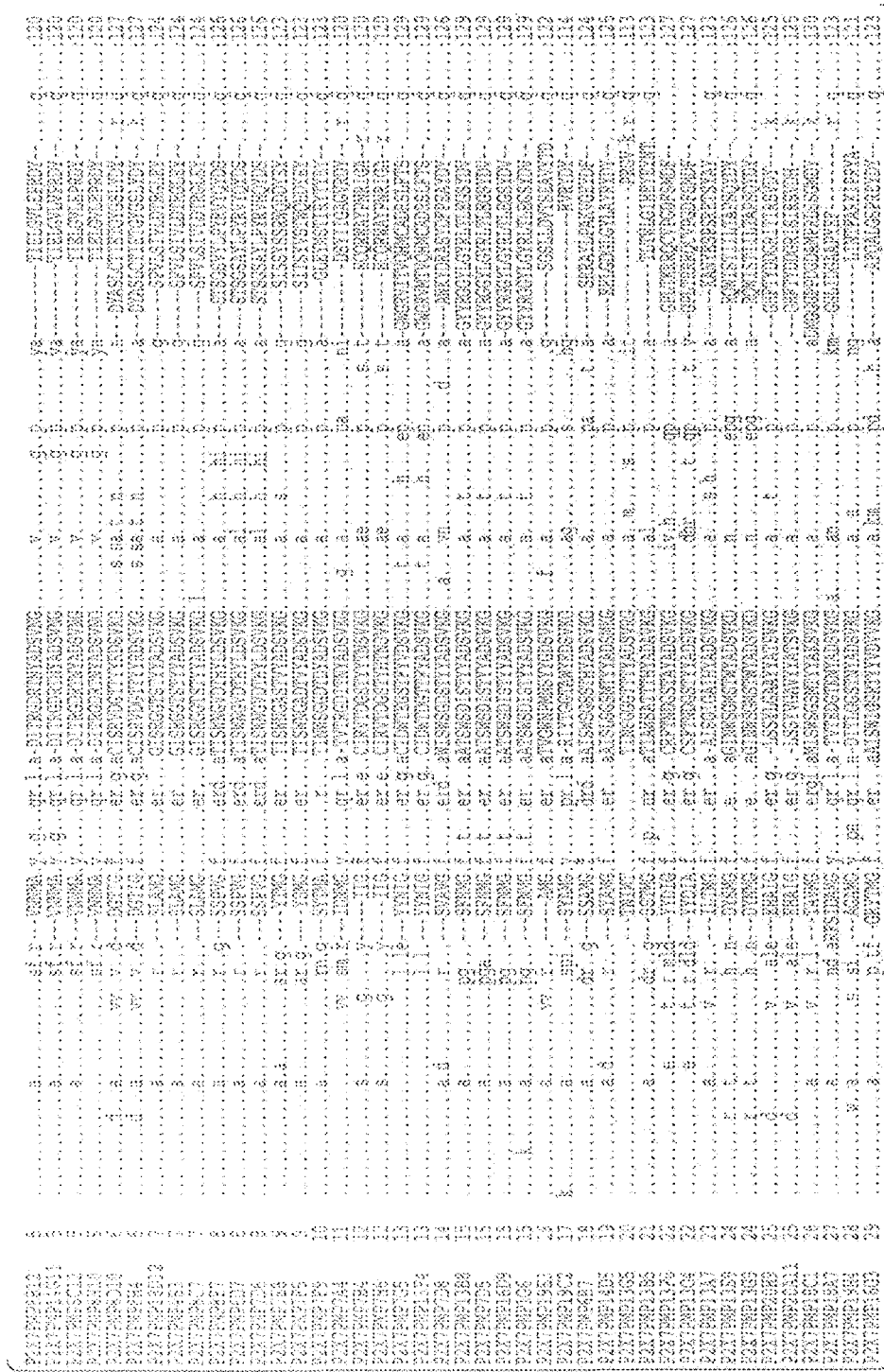
FIG. 22. Sequence alignment of 84 non-redundant mP2X7-selected Nanobodies to human germline sequence VH3-23/JH5 (SEQ ID NOs:705-786).

The sequences of all mP2X7 binders in the primary screening was analysed. Out of 523 Nanobody clones, 84 unique clones were identified that could be categorised into 29 different sequence families (FIG. 22). The number of Nanobody amino acid sequence variants belonging to the same family is summarized in FIG. 15. Respectively 15 and 14 families have been identified after DNA vaccination (DNA+PB) and cell immunization, resulting in an average diversity of 3 families after DNA+cell boost immunization method and 4.7 after the cell immunization strategy. Four mP2X7 families were identified that comprised family variants from both DNA and PB libraries, i.e. families 2, 15, 25 and 5 (FIG. 14). Two of these clones, 16D9 (family 15, llama 414) and 6A11 (family 5, llama 418), were identified from both the DNA and PB repertoire. However, as shown earlier for CXCR4, most families were identified exclusively in the 'DNA' (4 out of 15 families) or the 'PB' libraries (7 out of 15 families). This indicates that the cell boost following genetic immunizations caused in vivo maturation of a Nanobody repertoire not readily identified in a library generated after genetic immunizations only (Table 3.1).

rinsed and cell-bound fluorescence was detected by means of flow cytometry. Alternatively, sequential staining of 10-fold diluted PE with anti-myc FITC-conjugated antibodies was done after incubation with the cells. For members of

TABLE 3.1

Screening hit rates after mP2X7 genetic and cell immunization.

| Llama ID | Immunization strategy | Library | Serum titer FACS (total IgG) | Primary screening hit-rate (%) R1 | R2 | NB families identified |
|---|---|---|---|---|---|---|
| 407 | DNA (4x) | DNA | − | 0.0 | 11.1 | 25 |
|  | mP2X7/HEK (1x) | PB | − | 2.2 | 39.1 | 6, 25, 28 |
| 414 | DNA (4x) | DNA | +/− | 6.7 | 11.1 | 15, 26, 27, 29 |
|  | mP2X7/HEK (1x) | PB | ++ | 73.9 | 93.5 | 1, 4, 15 |
| 417 | DNA (4x) | DNA | − | 11.1 | 86.7 | 2 |
|  | mP2X7/HEK (1x) | PB | +/− | 2.2 | 60.9 | 2, 24 |
| 405 | Cocktail DNA (4x) | DNA | − | 0.0 | 0.0 | — |
|  | m + hP2X7/HEK (1x) | PB | + | 47.9 | 97.9 | 7, 16 |
| 418 | Cocktail DNA (4x) | DNA | + | 2.1 | 50.0 | 5, 17 |
|  | m + hP2X7/HEK (1x) | PB | ++ | 70.8 | 100.0 | 5 |
| 413 | mP2X7/HEK (4x) | Cell | + | 27.1 | 72.9 | 3 |
| 415 | mP2X7/HEK (4x) | Cell | + | 2.1 | 68.8 | 8, 10, 11, 12, 14, 18, 19, 20, 21 |
| 416 | mP2X7/HEK (4x) | Cell | + | 4.2 | 39.6 | 9, 13, 22, 23 |

Figure 16:
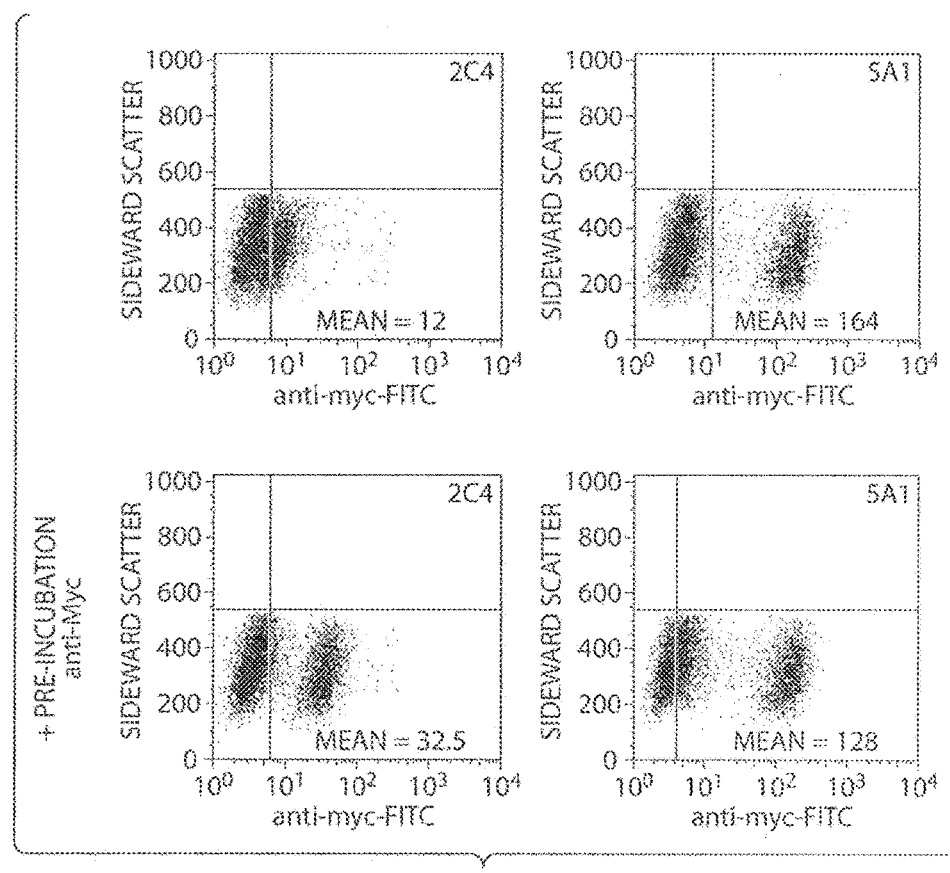
FIG. 16. Representative example of periplasmatic extracts of clones 2C4 and 5A1 with and without preincubation with anti-Myc-antibodies for binding to mP2X7-expressing Hek293 and control WT Hek293 cells.
Figure 17:
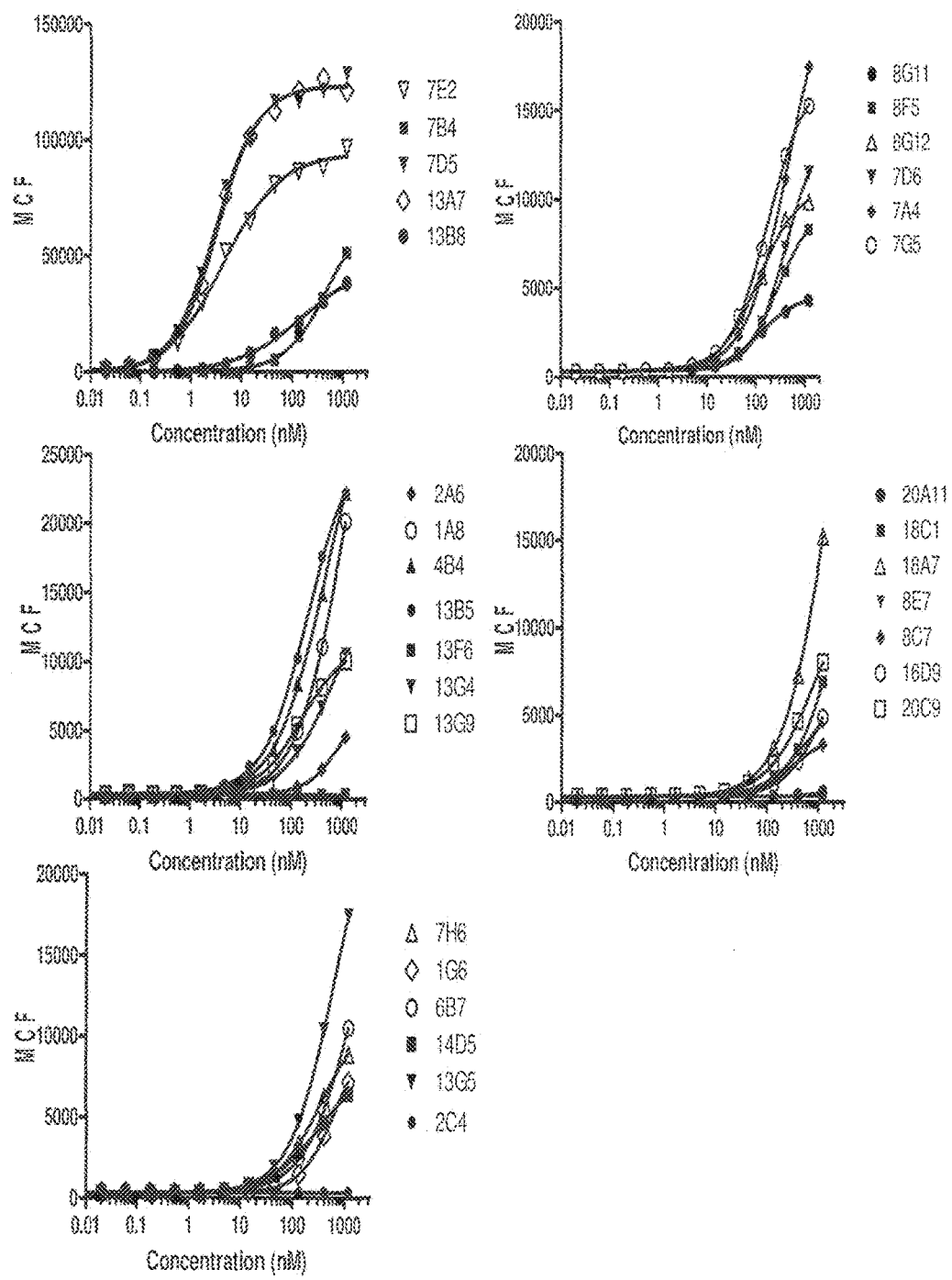
FIG. 17. Titration curve of Nanobodies from 24 different families for binding to mP2X7-Cho cells.

Example 3.8. Confirmation of Specificity and Ranking of mP2X7-Binding Clones for Selection of Representative Clones for Each Family All non-redundant mP2X7-specific clones were re-arrayed in 96-well plates for the production of PEs in 1 mL 96-deep-well plates, as described in example 1. To confirm that the mP2X7 specific Nanobodies identified after screening for binding to fixed cells can also bind native mP2X7, PE of all non-redundant clones were analysed for direct binding to mP2X7-Hek293 cells in FACS using the myc-tag for detection. Ten-fold diluted PE were pre-incubation with 0.5 µg anti-myc FITC-conjugated antibodies (AbD Serotec, cat no. MCA2200F) (creating pseudo-bivalent Nanobodies in order to increase binding strength) in 0.1 ml PBS/10% FCS for 45 minutes at 4° C. PE dilutions were incubated with a mixture of Hek293-mP2X7 and untransfected cells (5×10$^5$ of each) for 0.5 hour at 4° C., after which the cells were Nanobody family 1, 2, 4, 5, 25 (from DNA/PB libraries) and 10 and 11 (from cell immunization libraries), a clear avidity benefit was seen, indicating that the epitopes of these Nanobodies are still readily accessible for pseudo-dimerized Nanobodies. The effect of pre-incubation for Nanobodies 2C4 (family 1) and 5A1 (family 3) is illustrated in FIG. 16. Of each family, the best binder was selected for further characterization. Families 6, 26-29 only showed low binding to mP2X7-expressing cells, even after pre-incubation with anti-Myc antibodies and were thus excluded from further characterization. From families with unique clones derived from both DNA and PB libraries (families 2, 5, 15, and 25), at least two representatives were selected to allow comparison of DNA and PB-derived clones. In turn, this would allow determining the possible contribution of the cell boost on potencies and affinities of the respective Nanobodies. The panel of selected Nanobodies for further characterization is depicted in FIG. 17 and Table 3.2.

TABLE 3.2

Characterization of mP2X7-specific Nanobodies.

| | | | | | | Titration NB | | Titration ligand | |
|---|---|---|---|---|---|---|---|---|---|
| Clone | Family | Llama | Library | P2X7 function | Fold Cho P2X7/wt (phage ELISA) | IC50 (nM) against 100 uM ATP n = 2 | IC50 (nM) against 20 uM NAD n = 2 | ATP IC50 (mM) by 2 mM NB n = 1 | NAD IC50 (mM) by 22 mM NB n = 1 |
| 2C4 | 1 | 414 | PB | | 4 | | | | |
| 2A6 | 1 | 414 | PB | | 8 | | | | |
| 1A8 | 2 | 417 | DNA | | 20 | | | | |
| 20C9 | 2 | 417 | PB | | 11 | | | | |
| 7E2 | 3 | 413 | Cell | | 25 | | | | |

TABLE 3.2-continued

Characterization of mP2X7-specific Nanobodies.

| Clone | Family | Llama | Library | P2X7 function | Fold Cho P2X7/wt (phage ELISA) | Titration NB IC50 (nM) against 100 uM ATP n = 2 | Titration NB IC50 (nM) against 20 uM NAD n = 2 | Titration ligand ATP IC50 (mM) by 2 mM NB n = 1 | Titration ligand NAD IC50 (mM) by 22 mM NB n = 1 |
|---|---|---|---|---|---|---|---|---|---|
| 4B4 | 4 | 414 | PB | enhancer | 19 | | | 47 | 5 |
| 8G11 | 5 | 418 | PB | block | 26 | 37 | 68 | 389 | >540 |
| 8F5 | 5 | 418 | DNA | block | 16 | 350 | 579 | 171 | partial |
| 8G12 | 5 | 418 | PB | block | 36 | 55 | 82 | 290 | >540 |
| 8C7 | 7 | 405 | PB | part.block | 21 | 386* | 4000* | | |
| 8E7 | 7 | 405 | PB | part.block | 16 | 576* | 4000* | | |
| 7D6 | 8 | 415 | Cell | enhancer | 18 | | | | |
| 7A4 | 9 | 415 | Cell | | 32 | | | | |
| 7B4 | 10 | 415 | Cell | | 23 | | | | |
| 7H6 | 11 | 415 | Cell | block | 23 | 122.6 | 208.3 | 494 | >540 |
| 7G5 | 12 | 415 | Cell | enhancer | 30 | | | | |
| 13B8 | 13 | 416 | Cell | | 24 | | | | |
| 7D5 | 14 | 415 | Cell | | 14 | | | | |
| 1G6 | 15 | 414 | DNA | | 12 | | | | |
| 16D9 | 15 | 414 | DNA, PB | | 7 | | | | |
| 6B7 | 16 | 405 | PB | part.block | 24 | | | | |
| 14D5 | 17 | 418 | DNA | enhancer | 8 | | | 16 | 2 |
| 13G5 | 18 | 415 | Cell | | 35 | | | | |
| 13B5 | 19 | 415 | Cell | part.block | 28 | 436 | 3653 | 200 | partial |
| 13F6 | 20 | 415 | Cell | | 20 | | | | |
| 13G4 | 21 | 415 | Cell | | 56 | | | | |
| 13A7 | 22 | 416 | Cell | block | 25 | 6 | 11 | 565 | >540 |
| 13G9 | 23 | 416 | Cell | block | 17 | 35 | 136 | 469 | >540 |
| 20A11 | 24 | 417 | PB | | 11 | | | | |
| 18C1 | 25 | 407 | DNA | | 18 | | | | |
| 18A7 | 25 | 407 | PB | | 14 | | | | |

*Nanobodies were tested n = 1

Example 3.9. Production and Purification of mP2X7-Specific Nanobodies

The encoding sequences of the selected Nanobodies were recloned in an expression vector derived from pUC119 which contained the LacZ promoter, a resistance gene for kanamycin, a multicloning site and the OmpA signal peptide sequence (as described in example 2.8). In frame with the Nanobody coding sequence, the vector coded for a C-terminal c-myc tag and a (His)6 tag. Expression occurred in E. coli TG-1 cells as c-myc, $His_6$-tagged proteins in a culture volume of 250 mL. Expression was induced by addition of 1 mM IPTG and allowed to continue for 3 hours at 37° C. After spinning the cell cultures, periplasmic extracts were prepared by freeze-thawing the pellets and resuspension in dPBS. These extracts were used as starting material for immobilized metal affinity chromatography (MAC) using Histrap FF crude columns (GE Healthcare, Uppsala, Sweden). Nanobodies® were eluted from the column with 250 mM imidazole and subsequently desalted towards dPBS. Purity and integrity of all Nanobodies was verified by polyacrylamide gel electrophoresis (SDS-PAGE), while the presence of tags was verified by western blotting using anti-His antibodies for detection.

Example 3.10. None of the Mouse P2X7 Nanobodies are Cross-Reactive to Human P2X7 or to P2X4

Concentration dependant mP2X7 binding of purified Nanobodies was analysed using stable mP2X7-expressing CHO cells in FACS. Serial dilutions of Nanobodies ranging from 1.2 uM to 6.7 µM were prepared and incubated with $2 \times 10^5$ cells in 0.1 ml dPBS supplemented with 10% FBS (FACS buffer) for 0.5 hour at 4° C. Next, cells were washed three times, and bound Nanobody was detected using mouse anti-Myc (Serotec MCA2200) and subsequent staining with anti-mouse IgG-PE (Jackson ImmunoResearch Laboratories 115-115-164). As positive control, hybridoma supernatant of the rat Hano43 antibody was used, which was visualized by anti-rat IgG-PE (Jackson ImmunoResearch Laboratories 112-116-143). Results are depicted in FIG. 17. The maximum MCF value obtained with an irrelevant control Nanobody ranged between 314 and 355 (concentrations between 1.2 µM to 6.7 µM). For Nanobodies 7D5 (family 14), 13A7 (family 22) and 7E2 (family 3), $EC_{50}$ values are 3, 3.4 and 4.3 nM, respectively. For all other Nanobodies tested, no sigmoidal curve was obtained and consequently no $EC_{50}$ values could be determined (FIG. 17). Of note, the strongest binding Nanobodies were all derived from the three llamas immunized with Hek293-P2X7 cells. For all Nanobodies specific binding was confirmed, except for 2C4, 20A11 and 13F6 for which no MCF value above 600 were detected.

Second, the specificity of Nanobodies of all 24 families was determined by analysis of cross-reactive binding to Hek293 cells expressing the human orthologue of P2X7, and CHO cells expressing hP2X4, another member of the P2X purinoceptor family (Möller et al Purinergic Signal 3:359-366, 2007). Of each Nanobody 250 ng (final concentration of 147 nM) was pre-incubated with anti-Myc-FITC conjugated antibodies, following the same procedure as described in example 3.7 except that no untransfected Hek cells were included. As positive controls, antibodies L4 (specific for hP2X7, Buell et al. Blood 15: 3521-3528) and CR29 (specific for hP2X4, Möller et al Purinergic Signal 3:359-366, 2007) were used, while an irrelevant Nanobody was included as negative control. None of the Nanobodies was found to bind hP2X7-Hek293 or hP2X4-expressing CHO cells. Despite the fact that some Nanobodies were isolated from llamas immunized with both h and mP2X7 (Families 5, 7, 16, and 17), none of these were cross-reactive to hP2X7.

Example 3.11. Identification of Nanobodies which Enhance or Block mP2X7 Receptor Function All purified Nanobodies from 24 different families were analysed for their ability to modulate the functional activity of the mP2X7 purinoceptor. Activation of P2X7 occurs by extracellular ATP (direct activation) or NAD-dependent ADP-ribosylation (indirect activation) and results in calcium release, exposure of phosphatidyl serine and shedding of CD62L, ultimately leading to apoptosis (Scheuplein et al. 2009, J. Immun. 182(5):2898-908). Ligand-induced CD62L-shedding was used to determine whether Nanobodies could interfere with mP2X7 function.

Figure 18:
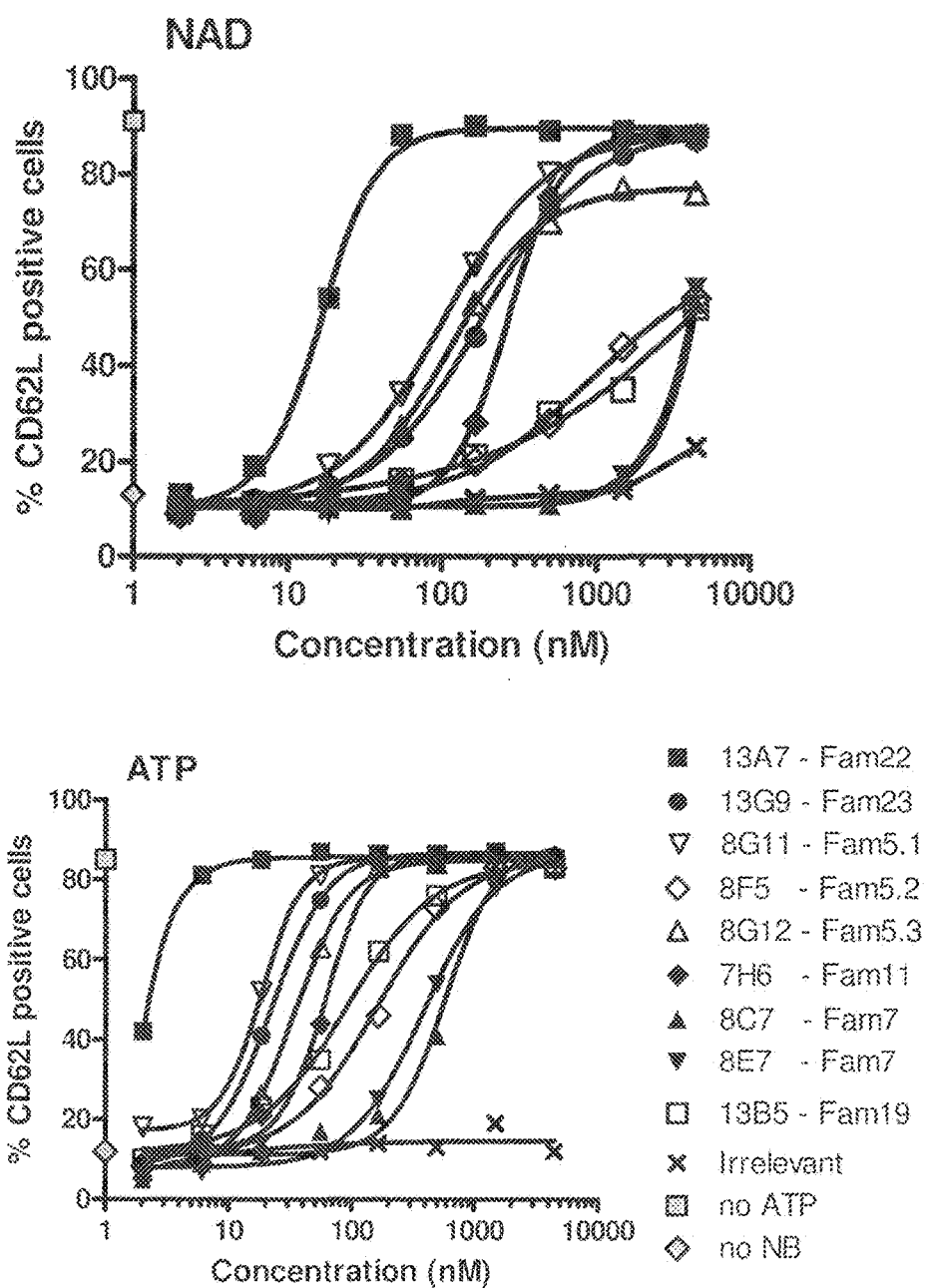
FIG. 18. Dose-dependent inhibition by Nanobodies of ligand-induced CD62L shedding on Yac-1 cells expressing mP2X7.
Figure 19A:
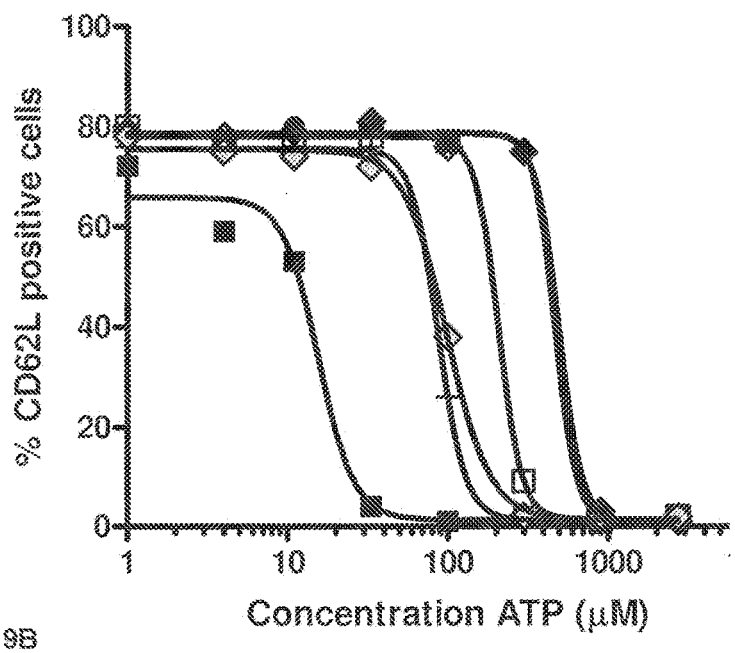
FIGS. 19A-19D. Titration of nucleotides in mP2X7-mediated CD62L-ectodomain shedding with fixed concentration of Nanobodies (2 μM).
Figure 19B:
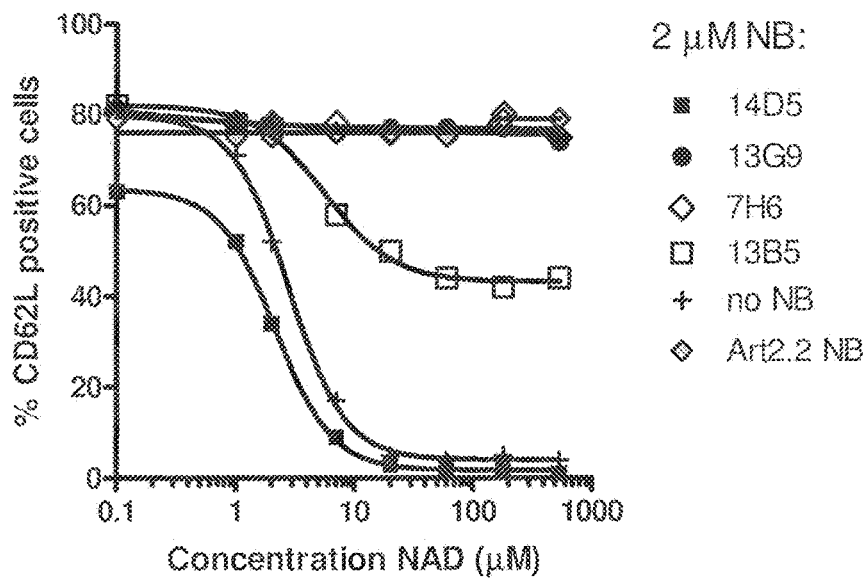
Figure 19C:
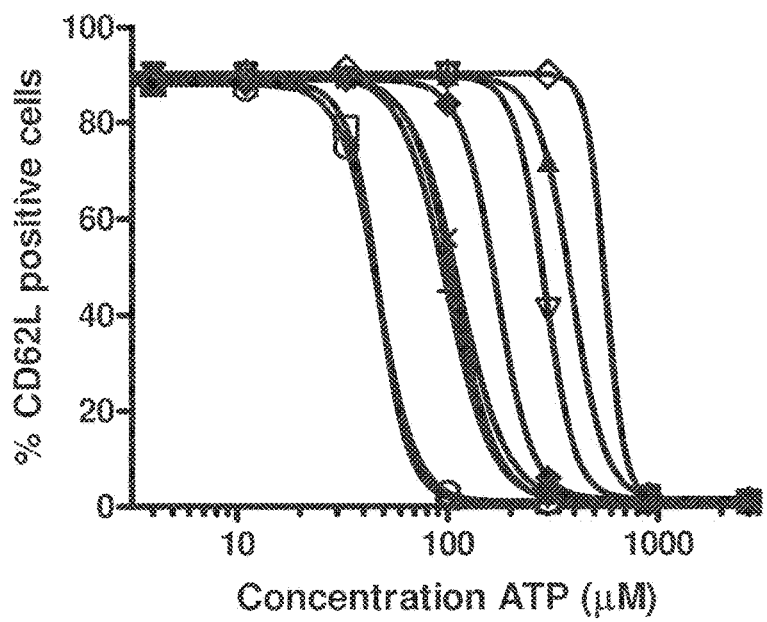
Figure 19D:
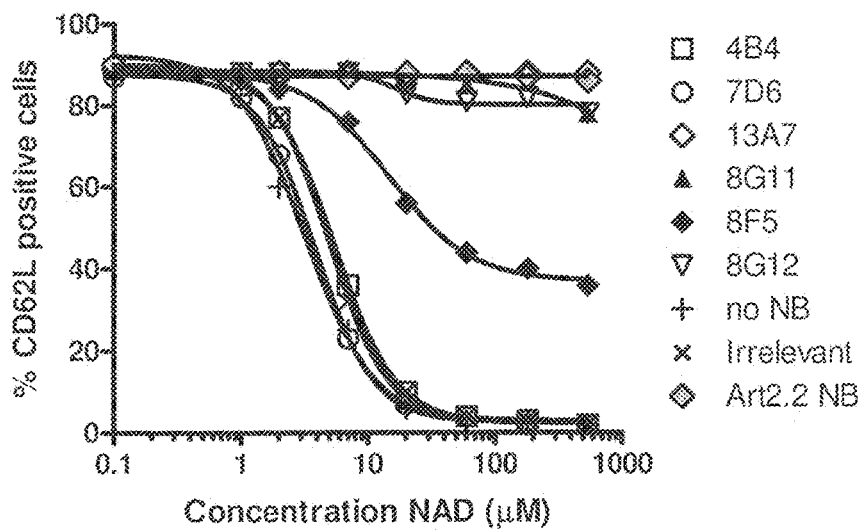
Figure 20A:
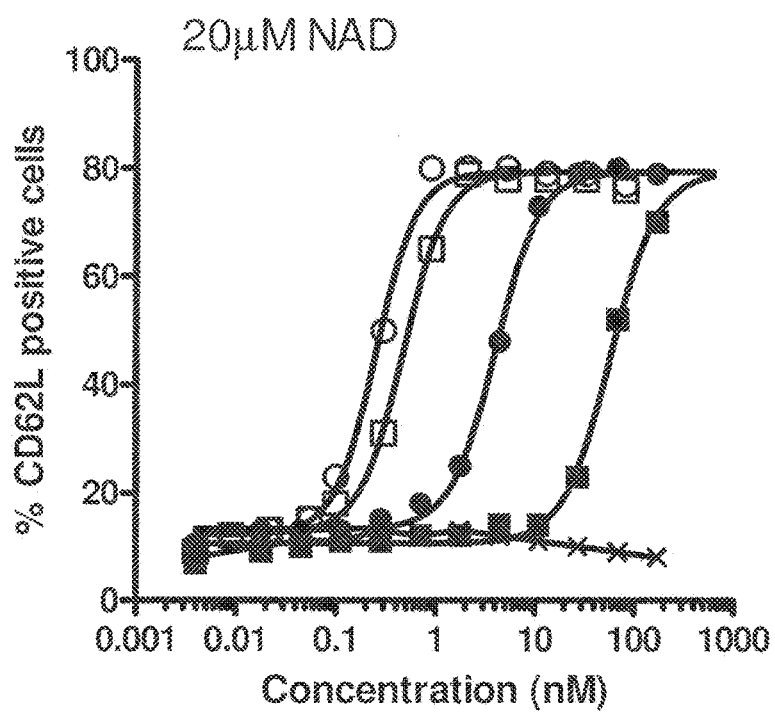
FIGS. 20A-20D. Bivalent Nanobodies of 13A7 (cell), 8O11 (PB) and 14D5 (DNA) show enhanced potencies in blocking or enhancing mP2X7 function.
Figure 20B:
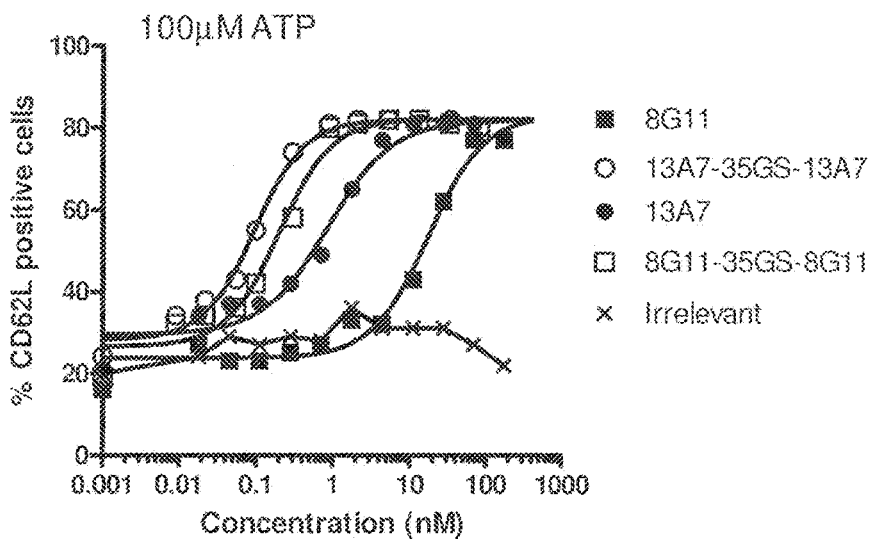
Figure 20C:
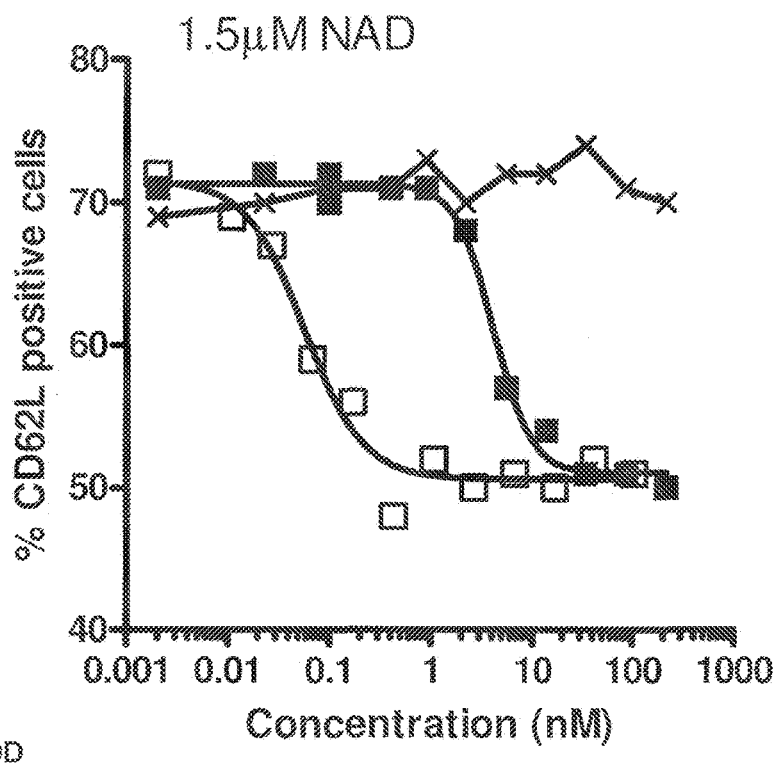
Figure 20D:
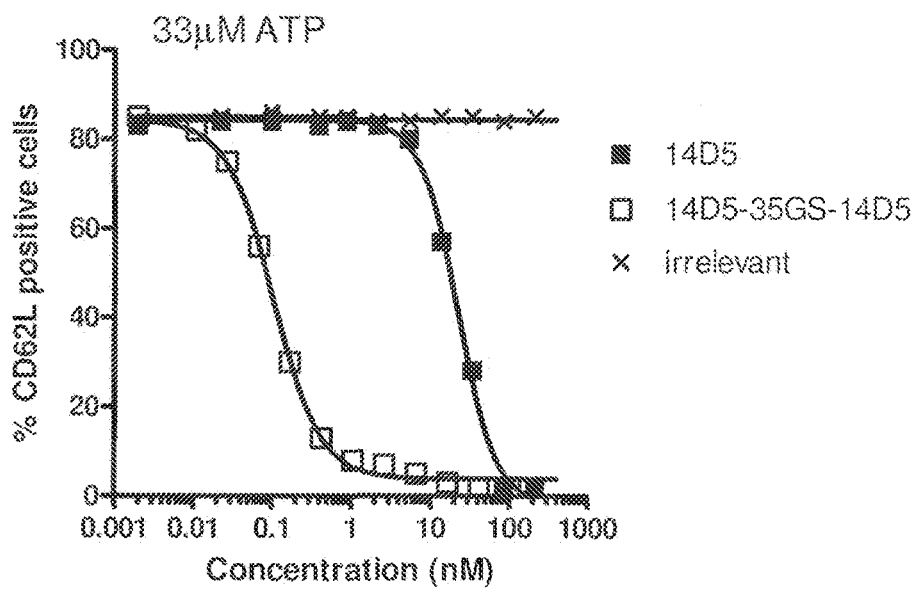

In a first approach, $5 \times 10^5$ Yac-1 cells (endogenously expressing mP2X7) were incubated with a single concentration of Nanobodies (5 µg, final concentration of 2 µM), in RPMI supplemented with 10% FBS for 15 minutes at RT. Subsequently the P2X7 ion channel was activated by addition of ATP to a final concentration of 100 µM, or NAD to a final concentration of 20 µM, followed by further incubation of the cell suspension for 20 minutes at 37° C. Previous titration experiments indicated that these ligand concentrations induced maximal CD62L-ectodomain cleavage. Cells were washed and the presence of cell-surface CD62L was detected in FACS using anti-CD62L-PE conjugated antibodies (BD Pharmingen, cat no. 553151). The percentage of CD62L-positively stained cells was taken as measure for modulation of P2X7 function. As controls, no Nanobody or irrelevant control Nanobody were included, which resulted in CD62L-shedding by 80-98% of cells, i.e. 2-20% of cells remaining CD62L positive, depending on the ligand and individual experiment. A Nanobody was considered a mP2×7 blocker when the percentage of cells remaining CD62L positive was more than 3-fold the value obtained with the irrelevant Nanobody. Ten Nanobodies, representing seven families (families 5, 7, 11, 16, 19, 22, and 23), blocked both ATP and NAD induced CD62L shedding, with the two Nanobodies of family 7 lying just above the threshold. Furthermore, two Nanobodies belonging to families 16 and 19 appeared to block the NAD-induced but not the ATP-induced response, suggesting these may selectively target the NAD-dependent ADP-ribosylation site on mP2X7 (Adriouch et al. FASEB J 22:861-869, 2008). In order to confirm inhibitory capacities, as well as to rank the Nanobody blocking potencies in the ATP and NAD mediated CD62L shedding assays, 9 out of these 10 Nanobodies were tested in serial dilutions in two parallel experiments. A representative example is shown in FIG. 18. Inhibition of P2X7 function could be confirmed for all blockers in both ligand mediated assays and IC50 values are presented in Table 3.2. The suggested NAD-selectivity for family 19 Nanobody 13B5 was not confirmed. Based on blocking potency, Nanobodies can be ranked as follows: 13A7>8G11, 13G9, 8G12>7H6>13B5, 8F5>8C7, 8E7.

To verify if Nanobodies by themselves could activate the mP2X7 channel, cells were also incubated with 2 µM Nanobodies without subsequent ligand treatment. None of the tested monovalent Nanobodies was able to directly activate mP2X7. However, for certain Nanobodies an increase in CD62L ectodomain shedding was observed after nucleotide treatment, suggesting that these clones may facilitate the gating of mP2X7. Enhancement of ATP- and NAD-induced P2X7 activation was verified using sub-optimal ligand concentrations: below 100 µM for ATP and below 20 µM for NAD. Yac-1 cells were treated with a fixed concentration of Nanobody (2 µM) and next stimulated with increasing concentrations of ATP (1-2700 µM) or NAD (1-540 µM). In case of ATP, three Nanobodies were found to clearly enhance the CD62L shedding in the following order of efficacy: 14D5>4B4=7D6 (FIGS. 19A-19D). For NAD the enhancement was less apparent.

Blocking Nanobodies were also tested in the same assays (at a fixed concentration of Nanobody vs. increasing concentrations of ligand). At the highest concentration of NAD tested (540 µM), most blockers were still maximally inhibiting cleavage, with the exception of 13B5 and 8F5 which reached a plateau around 60% inhibition (FIGS. 19A-19D). Based on the titration curve obtained with ATP the following ranking in blockers could be made; 13A7, 13G9, 7H6>8G11, 8G12>8F5, 13B5 (Table 3.2). Comparing the three family 5 Nanobodies, both clones derived from the PB libraries (8G11 and 8G12) were superior blockers to the clone from the DNA library (8F5).

Receptor modulating Nanobodies (blockers and enhancers) were identified from all three repertoires 'DNA', 'PB' or 'Cell' with the most potent blacker, 13A7, (IC50s of 6 nM and 11 nM in ATP and NAD assay, respectively) identified from a 'Cell' library. In contrast, the most potent enhancer, 14D5, was identified from a 'DNA' library.

Example 3.12. Multivalent Nanobodies with Improved Receptor Modulation Potencies Bivalent Nanobody constructs, consisting of a head-to-tail genetic fusion of two identical Nanobody sequences connected by a 35 amino acid GlySer linker were generated from the functional blocking Nanobodies, 13A7 (family 22, Cell) and 8G11 (family 5, PB), as well as from partial agonist 14D5 (family 17, DNA). Constructs were made by means of separate PCR reactions (one for the N-terminal, and one for the C-terminal Nanobody subunit) using different sets of primers encompassing specific restriction sites. An expression vector derived from pUC119 was used which contained the LacZ promoter, a resistance gene for kanamycin and the OmpA signal peptide sequence. Directly downstream of the signal peptide a multiple cloning site was present for Nanobody insertion, followed by a 35Gly-Ser linker encoding DNA sequence and a second multiple cloning site for cloning of a second Nanobody sequence. In frame with the resulting Nanobody-35Gly-Ser-Nanobody coding sequence, the vector coded for a C-terminal c-myc tag and a (His)6 tag. After verification of the nucleotide sequences, all three bivalent mP2X7 Nanobody constructs were expressed and purified. Production was done in *E. coli* TG1 cells, followed by purification from the periplasmic fraction via the His-tag by IMAC and desalting, essentially as described in example 3.9.

The potencies of monovalent and bivalent 14D5 in enhancing mP2X7 activity were compared by measuring the enhancement of CD62L-ectodomain shedding at suboptimal nucleotide concentrations (33 µM ATP, 1.5 µM NAD), where no ectodomain shedding occurs in Yac-1 cells (as described in example 3.11). The increase in potency of bivalent 14D5 vs. monovalent 14D5 was approximately 220-fold for shedding induced by ATP ($EC_{50}$ of 0.1 vs. 22.6 nM) and 40-fold for NAD ($EC_{50}$ 0.06 vs. 4.1 nM). In the absence of ligand, neither monovalent nor bivalent 14D5 could induce gating of P2X7.

As illustrated in FIGS. 20A-20D, the potencies of the two blocking Nanobodies 13A7 and 8G11 were determined at 100 μM ATP and 20 μM NAD, respectively. Bivalents of 13A7 and 8G11 had potencies in the sub-nanomolar range for both ATP and NAD. The potency increase of bivalent 13A7 vs. monovalent 13A7 was only moderate, with a 23 fold increase in case of NAD and a 9-fold increase in case of ATP-induced shedding ($IC_{50}$ bivalent 0.1 nM for ATP, and 0.3 nM for NAD). For 8G11 the potency increase from mono- to bivalent was much stronger, with 146-fold (NAD) and 84-fold (ATP)($IC_{50}$ bivalent 0.2 nM for ATP, and 0.52 nM for NAD).

Example. 3.13

Nanobodies Map to Different Epitopes on the mP2X7 Trimer

Recently, the crystal structure of zebrafish purinoceptor P2X4 was published (Kawate et al. 2009. Nature 460:592-598). Based on the available P2X4 structure (pdb3I5D and pdb3H9V with resolutions at 3.5 and 3.1 Å, respectively), a model for mP2X7 was built using homology modeling software (Modeler built in Discovery Studio, Accelrys). The sequence identity between zebrafish P2X4 and mP2X7 comprises 49% in the extracellular region. First, the sequence of the mouse P2X7 was aligned with the sequence of the known P2X4 structure. The sequence alignment takes care of a proper positioning of the gaps between the 2 sequences and of the conserved disulfide bonds. Second, the 3D coordinates of the known P2X4 structure are used to predict those of the unknown mP2X7. A probability density function (pdf) describes the restraints on the geometric features and is used to evaluate the 3D model. Out of an existing panel of mP2X7 arginine mutants that show extracellular mP2X7 expression to a similar level as mP2X7 WT, seven mutants were selected (Adriouch et al. 2008, FASEB J 22:861-869, Schwarz et al. Purinergic Signal 5:151-161, 2009). According to the generated model, these seven mutants represent six structurally dispersed regions on the mP2X7 molecule; mutant R125A (site I; R125 residue critical for NAD mediated ribosylation), R294A (site I; cleft located residue critical for ATP binding), R206A (site II; gain-of-function mutant located near the interface of two mP2X7 interacting monomers); R151A (site III; critical residue for binding anti-mP2X7 mAb Hano44; Adriouch et al. 2008, FASEB J 22:861-869); R178A (site IV); R230A (site V); R53K (site VI; residue located near the transmembrane domain at the interface of two mP2X7 interacting monomers). In order to determine whether binding of the Nanobodies to mP2X7 might be affected by these substitutions, 24 purified Nanobodies representing different families were evaluated for binding to non-transfected Hek293 cells and Hek293 cells transiently transfected with WT or mutant mP2X7 receptors. For flow cytometric assays, detection of Nanobodies was performed via anti-Myc and subsequent goat anti-mouse-PE conjugate, while an estimation of P2X7 expression densities was obtained via staining with rat monoclonal Hano43 followed by secondary anti-rat-PE conjugate. After normalization of expression densities over the different transient transfectants (WT mP2X7 and 7 mutants) by subtraction of background binding to Hek293 cells, residual binding of the different Nanobodies at 1 μM were calculated.

A reduction of binding >90% was only detected for six Nanobodies, all to the mutant R151A: Nanobody 7H6 (cell, 415, fam 11), 7D5 (cell, 415, fam 14), 6B7 (PB, 405, fam 16), 7E2 (cell, 413, fam 3), 8O11 (PB, 418, fam 5), 8O12 (PB, 418, fam 5). This implicates that all other Nanobodies are not critically dependent on Arg151 for binding, either because they bind to separate regions, or that these Nanobodies do not bind to the Arg residue within their footprint. As expected, mP2X7 specific rat antibody Hano44 did not show any binding to R151A mutant.

Example 3.14. The Average Potency of the 'DNA' Repertoire is Comparable to that of the 'PB' but Lower than that of the 'Cell' Repertoire Only four families were identified from both 'DNA' and 'PB' libraries. We scored in vivo maturation for each variant within the specific Nanobody family relative to the closest related Llama V-germline sequence (comprising of FR1 to FR3) as in example 2.10 and compared Nanobody variant potencies (Table 3.3). For family 2, 5, 15 and 25, the 'PB' originating Nanobodies showed on average 19.5, 16.5, 10 and 14 AA mutations versus the parental V-gene germline sequence, while respectively 19.5, 17, 10.3 and 15 for the Nanobodies derived from the 'DNA' library, which argues for equal maturation of the 'DNA' and 'PB' originating Nanobodies. When the sequences of the CDR3 regions of DNA and PB derived family members are compared, an increase in diversity in the PB relative to the DNA sequences is observed only for families 5 and 25.

TABLE 3.3

Genetic distance of in vivo matured Nanobodies versus parental V-germline sequences.

| Nanobody family (llama) | Nanobody variant within family | Llama germ-line | Library | Target interaction potency | | Number of AA mutations versus parental V-germline[1] | Number of AA in CDR3 different to DNA-clone |
|---|---|---|---|---|---|---|---|
| | | | | MFI FACS (pre-Myc incubation) | (absorption ratio; ELISA) | | |
| 2 (417) | 1C9 | VHH1e | DNA | 19 | 6 | 19 | 0 |
| | 1A8 | | DNA | 18 | 21 | 20 | 0 |
| | 20C9 | | PB | 97 | 11 | 20 | 0 |
| | 20B10 | | PB | 85 | 8 | 19 | 0 |
| 5 (418) | 14F6 | VHH2a/b | DNA | nd | 15 | 16 | 0 |
| | 8B4 | | DNA | 71 | 13 | 17 | 0 |
| | 8H5 | | DNA | 24 | 12 | 18 | 0 |
| | 6A11 | | DNA + PB | 53 | 17 | 18 | 0 |
| | 8E6 | | DNA | 69 | 12 | 19 | 0 |
| | 14G4 | | DNA | nd | 34 | 19 | 0 |

TABLE 3.3-continued

Genetic distance of in vivo matured Nanobodies versus parental V-germline sequences.

| Nano-body family (llama) | Nanobody variant within family | Llama germ-line | Library | Target interaction potency | | Number of AA mutations versus parental V-germline[1] | Number of AA in CDR3 different to DNA-clone |
|---|---|---|---|---|---|---|---|
| | | | | MFI FACS (pre-Myc incubation) | (absorption ratio; ELISA) | | |
| | 8F5 | | DNA | 143 | 16 | 15 | 2 |
| | 8H6 | | DNA | 43 | 17 | 15 | 2 |
| | 8H4 | | DNA | 65 | 27 | 17 | 2 |
| | 14F10 | | PB | nd | 19 | 17 | 1 |
| | 14G11 | | PB | nd | 30 | 18 | 2 |
| | 8G11 | | PB | 166 | 26 | 19 | 1 |
| | 8G12 | | PB | 166 | 36 | 16 | 1 |
| | 8D10 | | PB | 94 | 18 | 16 | 1 |
| | 8H10 | | PB | 94 | 19 | 16 | 1 |
| | 8B12 | | PB | 93 | 38 | 16 | 1 |
| | 8C12 | | PB | 89 | 28 | 15 | 1 |
| | 6H10 | | PB | 44 | 7 | 15 | 0 |
| | 8A11 | | PB | 17 | 11 | 16 | 1 |
| 15 (414) | 16D9 | VHH-3 | DNA + PB | 53 | 7 | 10 | 0 |
| | 19C2 | | DNA | 64 | 18 | 10 | 0 |
| | 19E3 | | DNA | 55 | 8 | 10 | 0 |
| | 1G6 | | DNA | 11 | 12 | 11 | 0 |
| 25 (407) | 18C1 | VHH-1e | DNA | 63 | 18 | 15 | 0 |
| | 18A7 | | PB | 69 | 14 | 14 | 2 |

[1]Any change, including a deletion or an addition are considered to calculate the number of mutations.

Figure 21:
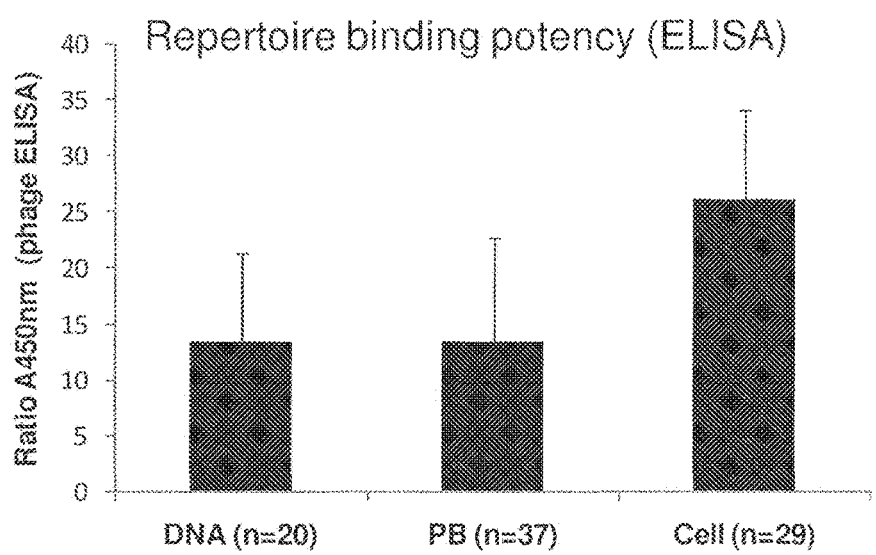
FIG. 21. Average binding potencies determined via ELISA of mP2X7 specific Nanobody repertoire identified after genetic immunization ('DNA'), subsequent single cell boost ('PB') or after complete cell immunization ('cell') (number of unique Nanobodies).

The average adsorption ratios (ELISA) of 20, 37 and 29 Nanobody variants originating respectively from the 'DNA', 'PB' and 'Cell' repertoires, are 13, 13 and 26, respectively (FIG. 21), indicating superiority of 'Cell' originating Nanobodies for this target. These observations are also reflected at the monoclonal Nanobody level, as both most potent binders (13A7, 7D5 and 7E2, example 3.10) the most potent blocker (13A7) were identified from the 'Cell' repertoire. However, when considering individual families, for family 5 (but not the others) a clear increase is observed in average potency of the PB versus the DNA repertoire (23 vs 18 adsorption ratios, and 95 vs. 66 mean fluorescence intensity FACS). This suggests that affinity maturation occurred as result of the cell boost in this family. In the other three families, the cell boost did not improve potency. In the ranking of the potencies of the functional Nanobodies, however, the most potent enhancer 14D5 originates from the DNA repertoire, while the second best blocker was derived from family 5 from the PB repertoire. Both families were identified from llama 418, which was the llama showing the strongest HcAb mediated serum response after DNA immunization (FIG. 13B).

Example 3.15. Genetic Immunizations with a Cocktail of Targets Allow Identification of Nanobodies Specific for Each Individual Target Immunization of outbred animals such as llama resulted in highly variable target specific humoral response magnitudes between the individual animals. This effect is even more pronounced after genetic immunization with low immunogenic cell surface expressed receptors containing multiple transmembrane domains such as GPCRs and ion channels (examples 2.4 and 3.1). It is expected that a detectable HcAb mediated target specific response will at least increase the efficiency of the discovery. Consequently, genetic immunization of outbred animals with target cocktails of any type (cell bound and non-cell bound molecules) would be favourable: a higher number of animals increases the chances to identify more target responders (of high magnitude) without burdening the availability. As an example of cocktail DNA vaccination, we immunized two llamas (405 and 418) with two ion channels P2X7 of mouse and human origin as described under example 3.2. Since the amino acid identity between mouse and human P2X7 is sufficiently different (80.5% sequence identity) and all mouse P2X7 identified Nanobodies lack cross-reactivity with human P2X7 (example 3.10), mouse and human P2X7 can be utilised as relevant target examples to demonstrate the cocktail genetic immunization approach.

In order to identify hP2X7 specific Nanobodies, cell based selections were performed to enrich for hP2X7 specific Nanobodies essentially as described under example 3. Selections were performed on pooled 'DNA' (PBL1+2) and 'PB' (PBL2+PBL3+LN) libraries from each llama 405 and 418 to maintain all diversity, but keeping the libraries separate per animal. Stable hP2X7 transfected YAC-1 cells and hP2X7-Art2.2-transfected CHO cells were used for the first and second round of selection, respectively. After the second selection round, the enrichment was calculated as the ratio of the number of eluted phage from hP2X7 transfected cells versus non transfected CHO cells. Enrichment was 15- and 7-fold for libraries from llamas 405 and 418, respectively, indicating the presence of hP2X7 Nanobodies and suggesting successful identification of Nanobodies against both ion channels.

After infection of *E. coli* TG1 with phage outputs after hP2X7 selection, individual clones will be picked and periplasmic extracts will be prepared as in example 1.4. The periplasmic extracts will be used to determine specificity for human P2X7 via flow cytometry, similarly as performed for mouse P2X7 (example 3.5). Periplasmic extracts showing clear staining on a hP2X7 transfected cell line (such as CHO or HEK293), while not above background on an identical parental cell line transfected with mouse P2X7 or the same non-transfected WT cell line, will be considered to be specific for hP2X7. hP2X7 specificity will be confirmed in a dose-dependent way using purified Nanobody via the same method to determine EC50s.

Example 4.1. Induction of a Humoral CXCR7 Specific Serum Titer Following Genetic Immunization of Llama Using the Helios Gene-Gun As a second GPCR example to identify target specific Nanobodies after genetic immunization, the chemokine receptor CXCR7 was chosen. Human CXCR7 encoding cDNA was cloned in pVAX1 and plasmid DNA purified as described in example 2.1. After transfection, the pVAX1-CXCR7 construct showed expression of native CXCR7 at the cell surface, confirmed by differential staining of CXCR7 transfected versus parental WT cells following a similar detection method to the one described in example 2.2 (data not shown).

Four llamas (391, 395, 396 and 397) were immunized via intradermal jet injection as described in example 2.4. A single $2 \times 10^7$ cells CAKI/hCXCR7 injection was administered 42 to 56 days after the fourth DNA immunization. Three llamas (385, 387 and 404) were immunized with 4 injections of $2 \times 10^7$ stably transfected CXCR7/HEK293 cells with 14-day intervals. The CXCR7 specific serum IgG titer was determined similarly as in example 2.4 using pre-immune and immune serum samples after DNA vaccination and after the single cell boost. None of the seven llamas showed a CXCR7 specific humoral response following the two immunization regimes.

Figure 23:
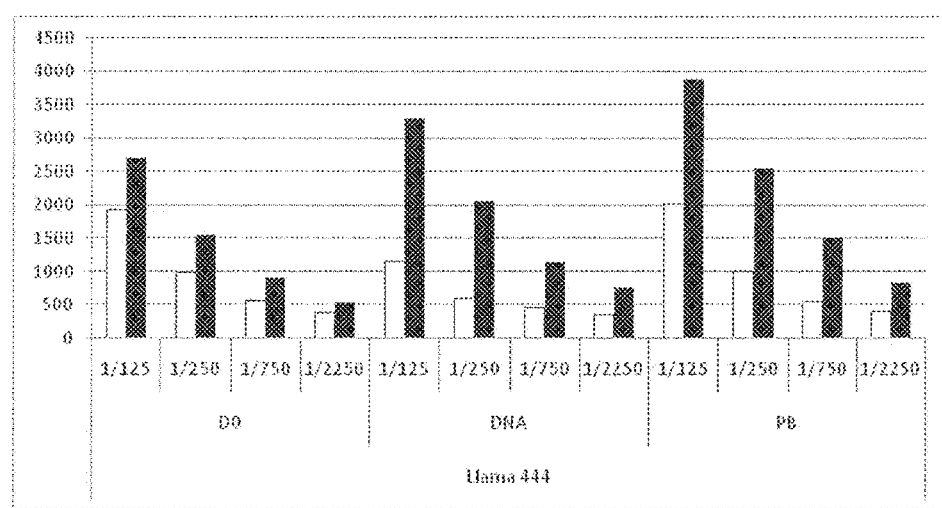
FIG. 23. CXCR7 specific serum conversion in llamas via Gene Gun genetic immunization. White or black bars represent the MCF values generated on CXCR7 transfected or non-transfected HEK293 WT cells.

In another immunization experiment, four llamas (434, 439, 441 and 444) were genetically immunized using a Helios Gene-gun as described under example 3. In short, 4 doses of DNA were applied (24 shots per dose) at two-weekly intervals followed by a single cell boost of CAKI transfected CXCR7 cells (2E7 cells). A pre-immune blood sample; one 8 days after the fourth DNA administration and a final blood sample 8 days after the single cell boost was collected from each llama and the target specific serum titer was determined via FACS as described under example 2.4. Out of four llamas immunized, only a single llama (444) showed a moderate though consistently increased MCF with the 'DNA' and post-cell boost serum sample on CXCR7-transfected HEK293 cells compared to the pre-immune level for all dilutions tested (FIG. 23). In parallel, four llamas (435, 436, 437, 440) were immunized with CXCR7-transfected CAKI cells by four cell injections ($2 \times 10^7$ cells per injection) at intervals of 2 weeks. Contrary to llama 444, none of the latter four llamas showed a detectable CXCR7 serum titer.

Figure 24:
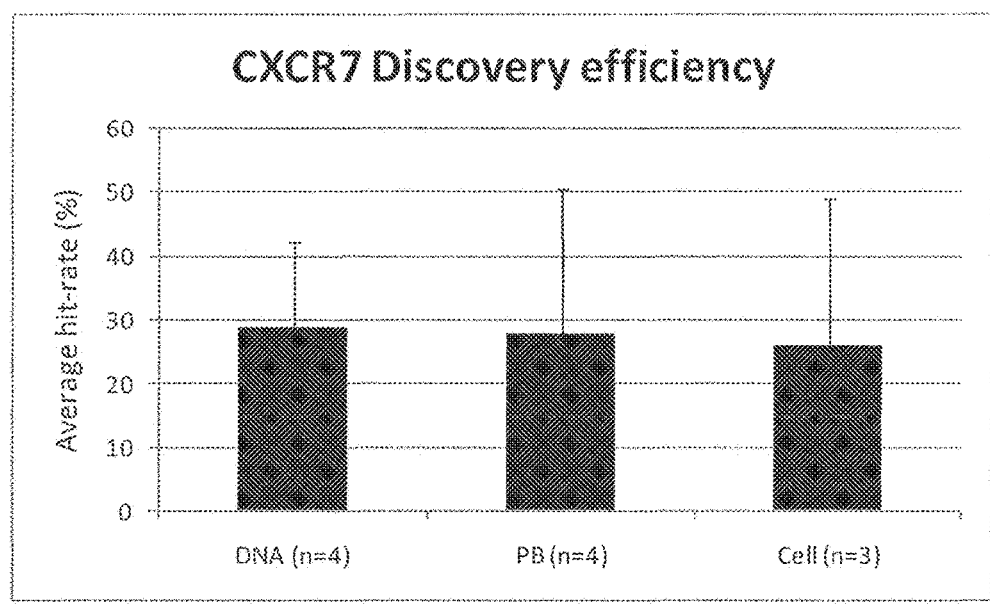
FIG. 24. CXCR7 specific Nanobody discovery efficiency from 'DNA', 'PB' or 'cell' repertoires (number of libraries).

Example 4.2. Identification of Target Specific Nanobodies in Absence of a Detectable CXCR7 Specific Serum Conversion Libraries were constructed from immune tissues collected after the genetic immunization and after the cell boost (DNA and PB repertoire, respectively) for each of the llamas 391, 395, 396 and 397. Three additional libraries were constructed from the cell immunized llamas 385, 387 and 404. An overview of the libraries is summarized in Table 4.1. Phage display selections were performed with all 11 libraries on 10 (selection round 1 and round 2) and 1 (selection round 2) units of CXCR7 Membrane vesicles as described before (example 2.6). 853 clones from all round 2 selection outputs were screened (between 31 and 155 individual clones per library); results are summarized in Table 4.1. CXCR7 specificity was determined via phage ELISA on 2 units of CXCR7 Membrane vesicles applying 10-fold dilutions of phage supernatant prepared from a 1 mL culture. 234 Nanobodies, showing a minimally 2-fold increased ELISA signal on hCXCR7 Membrane vesicles over non-transfected control Membrane vesicles, were considered to be CXCR7 specific. Round 2 hit-rates per animal and repertoire are summarized in Table 4.1, ranging from 4 to 61%. Based on the average hit-rates on round 2 selection outputs following the different immunization strategies, discovery efficiencies were calculated as 29, 28 and 26% for 'DNA', 'PB' and 'cell' repertoires, respectively (FIG. 24). Even in absence of a detectable HcAb titer to CXCR7, target specific Nanobodies were identified from all immunization strategies (DNA, PB, cell). All 234 CXCR7 specific Nanobodies were sequenced and redundant Nanobodies (identical AA sequence) were removed. This resulted in the identification of 78 unique sequences, belonging to 46 distinct Nanobody B-cell lineages (Table 4.1). The number of variants (minimally 1 AA residue difference) identified within a family ranged between 1 and 12. The average number of CXCR7 specific Nanobody families identified per llama is 5.3 after cell immunizations (385, 387, 404) and 7.5 via DNA immunization (DNA+cell boost; 391, 395, 396, 397), respectively, showing that for this target, genetic immunization (DNA+PB) resulted in a higher Nanobody family diversity as compared to the diversity obtained via cell immunizations.

TABLE 4.1

Discovery overview of CXCR7 specific Nanobody families.

| Llama ID | Immunogen | CXCR7 response (FACS) | Library | Specificity screening Hit-rate (ELISA) | Number of different CXCR7 specific Nanobody families (of which some are displacing) |
|---|---|---|---|---|---|
| 391 | DNA | — | DNA | 26% (12/46) | 4 |
|  | CXCR7/CAKI | — | PB | 18% (8/44) | 2 |
| 395 | DNA | — | DNA | 45% (62/138) | 6 |
|  | CXCR7/CAKI | — | PB | 29% (9/31) | 4 |
| 396 | DNA | — | DNA | 17% (8/46) | 3 |
|  | CXCR7/CAKI | — | PB | 61% (22/36) | 2 |
| 397 | DNA | — | DNA | 17% (24/138) | 6 |
|  | CXCR7/CAKI | — | PB | 10% (4/42) | 3 |

TABLE 4.1-continued

Discovery overview of CXCR7 specific Nanobody families.

| Llama ID | Immunogen | CXCR7 response (FACS) | Library | Specificity screening Hit-rate (ELISA) | Number of different CXCR7 specific Nanobody families (of which some are displacing) |
|---|---|---|---|---|---|
| 385 | CXCR7/Hek293 | — | Cells | 46% (71/155) | 7 |
| 387 | CXCR7/Hek293 | — | Cells | 4% (2/45) | 2 |
| 404 | CXCR7/Hek293 | — | Cells | 9% (12/132) | 7 |

To identify receptor function modulating Nanobodies, an SDF-1 ligand displacement assay was performed using CXCR7/HEK293 membrane extracts similarly as described for CXCR4 (example 2.7). Nanobodies showing a clear reduction in residual [$^{125}$I]-SDF-1 binding to CXCR7/HEK293 membrane extracts were considered to be ligand competitors. The number of Nanobody families scored as ligand displacer are illustrated in Table 4.1, showing that ligand competing Nanobodies were identified irrespective of the immunization strategy (represented by repertoires DNA, PB and cell).

Figure 25:
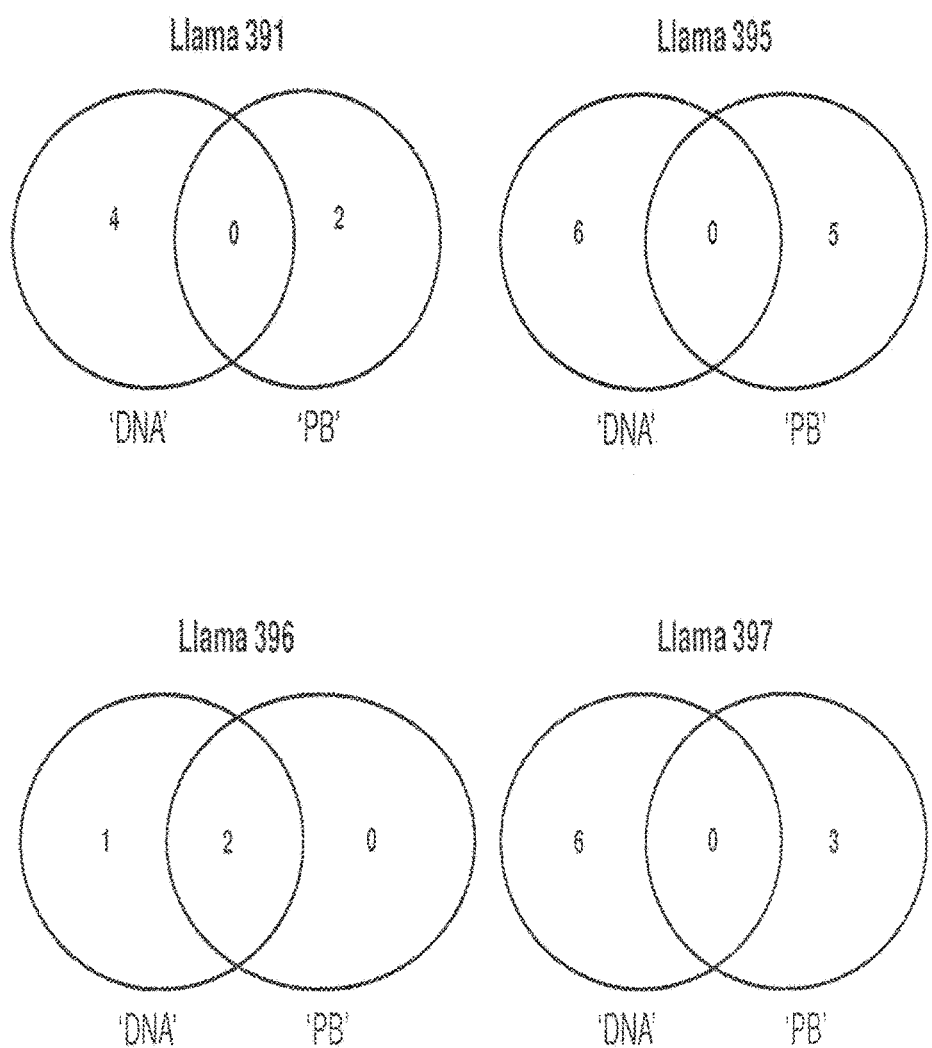
FIG. 25. Complementary target specific Nanobody repertoires obtained after genetic immunization (DNA) and single cell boost (PB). Numbers of repertoire specific Nanobody families are depicted.

Example 4.3. Cell Boost Following Genetic Immunization Generates a Different Nanobody Repertoire From llamas 391, 395, 396 and 397, 29 CXCR7 specific Nanobody families were identified consisting of 55 Nanobody sequence variants (out of 234 sequenced). Two families contained minimally 1 identical variant could be identified both in the DNA and the PB repertoire of llama 396, in contrasts to the findings in examples 2 (CXCR4) and 3 (P2X7). Only for 2 of these 29 families (7% of the total family diversity), Nanobody variants belonging to the same family were identified from the 'DNA' and 'PB' library (Table 4.1 and FIG. 25), again suggesting that the Nanobody repertoire after DNA vaccination (DNA) or cell boost (PB) is different. Genetic immunization only results in a different Nanobody repertoire, indicating that a part of the repertoire is not identified or lost after the cell boost.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

All of the references described herein are incorporated by reference, in particular for the teaching that is referenced hereinabove.

The invention claimed is:

1. An immunoglobulin that specifically binds to P2X7, which consists of 4 framework regions (FR1 to FR4 respectively) and 3 complementarity determining regions (CDR1 to CDR3 respectively), in which:
   CDR1 is the amino acid sequence of SEQ ID NO: 279;
   CDR2 is the amino acid sequence of SEQ ID NO: 443; and
   CDR3 is the amino acid sequence of SEQ ID NO: 607.

2. The immunoglobulin according to claim 1, wherein the immunoglobulin has at least 80% amino acid identity with the framework regions of the amino acid sequence of SEQ ID NO: 778.

3. An immunoglobulin that specifically binds to P2X7, that consists of SEQ ID NO: 778.

4. A polypeptide comprising an immunoglobulin according to claim 1.

5. A polypeptide comprising at least two immunoglobulins, wherein at least one of the at least two immunoglobulins is the immunoglobulin according to claim 1.

6. The polypeptide according to claim 5, wherein the polypeptide has at least 80% amino acid identity with the framework regions of the amino acid sequence of SEQ ID NO: 790.

7. A polypeptide that specifically binds to P2X7, that consists of SEQ ID NO: 790.

8. An immunoglobulin that specifically binds to P2X7, wherein the immunoglobulin has at least 80% amino acid identity with the framework regions of the amino acid sequence of SEQ ID NO: 778, and wherein one or more of the amino acid residues at positions 11, 37, 44, 45, 47, 83, 84, 103, 104 and 108 according to the Kabat numbering are chosen from the Hallmark residues listed in Table B-2.

9. The polypeptide according to claim 5, wherein the polypeptide has at least 90% amino acid identity with the framework regions of the amino acid sequence of SEQ ID NO: 790.

10. The polypeptide according to claim 5, wherein the polypeptide has at least 95% amino acid identity with the framework regions of the amino acid sequence of SEQ ID NO: 790.

11. The polypeptide according to claim 5, wherein the polypeptide has at least 99% amino acid identity with the framework regions of the amino acid sequence of SEQ ID NO: 790.

\* \* \* \* \*